(12) United States Patent
Arimori et al.

(10) Patent No.: US 9,554,576 B2
(45) Date of Patent: Jan. 31, 2017

(54) TETRAZOLINONE COMPOUNDS AND THEIR USE AS PESTICIDES

(71) Applicant: SUMITOMO CHEMICAL COMPANY, LIMITED, Tokyo (JP)

(72) Inventors: Sadayuki Arimori, Takarazuka (JP); Takayuki Shioda, Takarazuka (JP)

(73) Assignee: SUMITOMO CHEMICAL COMPANY, LIMITED, Tokyo (JP)

( * ) Notice: Subject to any disclaimer, the term of this patent is extended or adjusted under 35 U.S.C. 154(b) by 0 days.

(21) Appl. No.: 15/063,121

(22) Filed: Mar. 7, 2016

(65) Prior Publication Data

US 2016/0183529 A1 Jun. 30, 2016

Related U.S. Application Data

(63) Continuation of application No. 14/424,952, filed as application No. PCT/JP2013/077009 on Sep. 27, 2013, now Pat. No. 9,314,023.

(30) Foreign Application Priority Data

Sep. 28, 2012 (JP) .................... 2012-216039
Dec. 25, 2012 (JP) .................... 2012-280708

(51) Int. Cl.
*A01N 43/713* (2006.01)
*C07D 257/04* (2006.01)
*C07D 403/12* (2006.01)

(52) U.S. Cl.
CPC ........... *A01N 43/713* (2013.01); *C07D 257/04* (2013.01); *C07D 403/12* (2013.01)

(58) Field of Classification Search
CPC ........................ A01N 43/713; C07D 257/04
See application file for complete search history.

(56) References Cited

U.S. PATENT DOCUMENTS

| 5,605,920 | A | 2/1997 | Goto et al. |
| 6,583,090 | B1 | 6/2003 | Gewehr et al. |
| 2012/0015980 | A1 | 1/2012 | Fischer et al. |
| 2015/0031733 | A1 | 1/2015 | Yoshimoto et al. |
| 2015/0051171 | A1 | 2/2015 | Yoshimoto et al. |

FOREIGN PATENT DOCUMENTS

| CN | 1138574 A | 12/1996 |
| CN | 1798738 A | 7/2006 |
| DE | 19900571 A1 | 7/1999 |
| JP | 9-208565 A | 8/1997 |
| WO | WO 96/36229 A1 | 11/1996 |
| WO | WO 99/46246 A1 | 9/1999 |
| WO | WO 2004/092140 A1 | 10/2004 |
| WO | WO 2011/157654 A1 | 12/2011 |
| WO | WO 2013/092224 A1 | 6/2013 |
| WO | WO 2014/051161 A1 | 4/2014 |
| WO | WO 2014/084223 A1 | 6/2014 |
| WO | WO 2014/104268 A1 | 7/2014 |
| WO | WO 2014/104382 A1 | 7/2014 |
| WO | WO 2014/104384 A1 | 7/2014 |
| WO | WO 2014/175465 A1 | 10/2014 |

OTHER PUBLICATIONS

European Office Action for Application No. 13779397.2 dated May 18, 2016.
The International Preliminary Report on Patentability and a Written Opinion of the International Searching Authority of International Application No. PCT/JP2013/077009 issued on Mar. 31, 2015.
CAS Record, DN No. 159:160272, Dec. 6, 2012.
Chinese Office Action for Application No. 201380050698.1 dated Oct. 20, 2015 with English language translation.
STN RN No. 1445337-59-6, entered into STN on Jul. 18, 2013.
STN RN No. 243141-11-9, entered into STN on Oct. 1, 1999.
Chinse Office Action for Application No. 2013380050698.1 dated Apr. 8, 2016 with English language translation.

*Primary Examiner* — Michael Barker
*Assistant Examiner* — Karen Cheng
(74) *Attorney, Agent, or Firm* — Birch, Stewart, Kolasch & Birch, LLP

(57) ABSTRACT

The present invention provides a compound having an excellent efficacy for controlling pests. A tetrazolinone compound of formula (1):

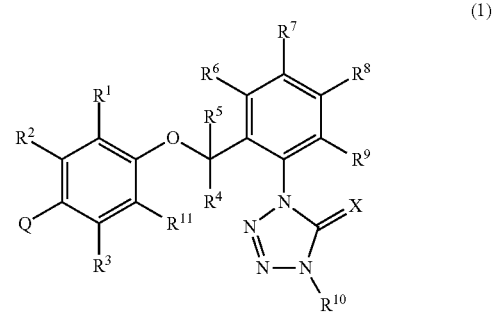

shows an excellent controlling efficacy on pests.

7 Claims, No Drawings

TETRAZOLINONE COMPOUNDS AND THEIR USE AS PESTICIDES

This application is a Continuation of copending Application Ser. No. 14/424,952, filed on Feb. 27, 2015 which was filed as PCT International Application No. PCT/JP2013/077009 on Sep. 27, 2013, which claims the benefit under 35 U.S.C. §119(a) to Patent Application Nos. 2012-216039, filed in Japan on Sep. 28, 2012 and 2012-280708, filed in Japan on Dec. 25, 2012, all of which are hereby expressly incorporated by reference into the present application.

TECHNICAL FIELD

The present invention relates to tetrazolinone compounds and its use.

BACKGROUND ART

Heretofore, various drugs for controlling pests have been widely developed and provides in practice use, but in some cases, these drugs may not exert enough efficacy.

Also, as compounds having tetrazolinone ring, 1-{2-{2-chloro-4-(3,5-dimethyl-pyrazole-1-yl)-phenoxymethyl}-phenyl}-4-methyl-1,4-dihydrotetrazole-5-one represented by the following formula (A):

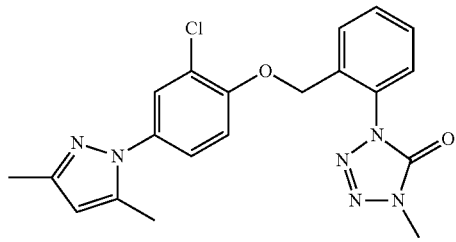

(A)

have been known (see Patent Document 1).

CITATION LIST

Patent Document

Patent Document 1: WO 1999/46246 pamphlet

SUMMARY OF THE INVENTION

An object of the present invention is to provide a compound having an excellent efficacy for controlling pests.

The present inventors have intensively studied to find that compounds having an excellent efficacy for controlling pests and as a result, found that a tetrazolinone compound of the following formula (I) has an excellent efficacy for controlling pests, which thus have completed the present invention.

Specifically, the present invention includes the following [1] to [18].

[1] A tetrazolinone compound of a formula (1):

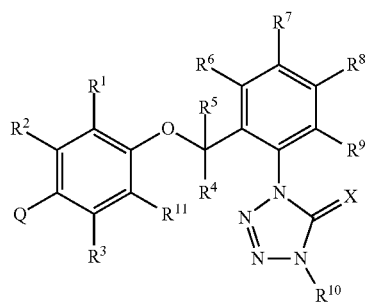

(1)

[wherein

Q represents a group selected from the following group: Q1, Q2, Q3 or Q4:

Q;

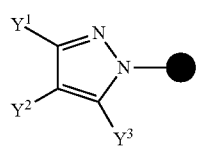

Q1

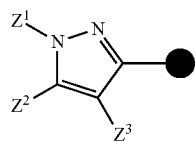

Q1

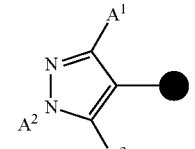

Q3

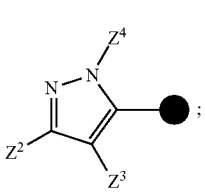

Q4

;

$R^1$, $R^2$, $R^3$ and $R^{11}$ represent independently of each other a hydrogen atom, a halogen atom, a cyano group, a nitro group, an amino group, a hydroxy group, a thiol group, an C2-C6 alkenyl group, a C2-C6 haloalkenyl group, an C2-C6 alkynyl group, a C2-C6 haloalkynyl group, an C1-C6 alkoxy group, a C1-C6 haloalkoxy group, an C1-C8 alkylamino group, a C1-C8 haloalkylamino group, an C1-C6 alkylthio group, a C1-C6 haloalkylthio group, an C1-C6 alkylsulfinyl group, a C1-C6 haloalkylsulfinyl group, an C1-C6 alkylsulfonyl group, a C1-C6 haloalkylsulfonyl group, a pentafluorosulfanyl group, a C3-C9 trialkylsilyl group, an C2-C6 alkylcarbonyl group, an C2-C6 alkoxycarbonyl group, an C2-C8 alkylaminocarbonyl group, an C1-C6 alkyl group optionally having one or more groups selected from Group P¹ or an C3-C6 cycloalkyl group optionally having one or more groups selected from Group P¹;

R⁴ and R⁵ represent independently of each other a hydrogen atom, a halogen atom or an C1-C3 alkyl group;

R⁶ represents a C3-C6 cycloalkyl group, an C2-C4 alkynyl group, a C2-C4 haloalkynyl group, a C1-C4 haloalkoxy group, an C1-C4 alkythio group, an C1-C4 alkylsulfinyl group, an C1-C4 alkylsulfonyl group, a C1-C4 haloalkylthio group, a C1-C4 haloalkylsulfinyl group, a C1-C4 haloalkylsulfonyl group, an C1-C6 alkylamino group, a C1-C6 haloalkylamino group or a C3-C6 halocycloalkyl group;

R⁷, R⁸ and R⁹ represent independently of each other a hydrogen atom, a halogen atom, an C1-C3 alkyl group, a C1-C3 haloalkyl group, an C2-C3 alkenyl group, a C2-C3 haloalkenyl group or an C1-C3 alkoxy group;

R¹⁰ represents an C1-C3 alkyl group, a C1-C3 haloalkyl group, an C2-C3 alkenyl group, a C2-C3 haloalkenyl group, an C2-C3 alkynyl group, a C2-C3 haloalkynyl group, a C3-C5 cycloalkyl group or a C3-C5 halocycloalkyl group;

X represents an oxygen atom or a sulfur atom;

A¹ and A³ represent independently of each other a hydrogen atom, a halogen atom, a cyano group, a nitro group, an amino group, a hydroxy group, a thiol group, an C2-C6 alkenyl group, a C2-C6 haloalkenyl group, an C2-C6 alkynyl group, a C2-C6 haloalkynyl group, an C1-C6 alkoxy group, a C1-C6 haloalkoxy group, an C1-C8 alkylamino group, a C1-C8 haloalkylamino group, an C1-C6 alkylthio group, a C1-C6 haloalkylthio group, an C1-C6 alkylsulfinyl group, a C1-C6 haloalkylsulfinyl group, an C1-C6 alkylsulfonyl group, a C1-C6 haloalkylsulfonyl group, a pentafluorosulfanyl group, a C3-C9 trialkylsilyl group, an C2-C6 alkylcarbonyl group, an C2-C6 alkoxycarbonyl group, an C2-C8 alkylaminocarbonyl group, an C1-C6 alkyl group optionally having one or more groups selected from Group P¹, or a C3-C6 cycloalkyl group optionally having one or more groups selected from Group P¹;

A², Z¹ and Z⁴ represent independently of each other a hydrogen atom, an amino group, an C3-C6 alkenyl group, a C3-C6 haloalkenyl group, an C3-C6 alkynyl group, a C3-C6 haloalkynyl group, an C1-C6 alkylsulfinyl group, a C1-C6 haloalkylsulfinyl group, an C1-C6 alkylsulfonyl group, a C1-C6 haloalkylsulfonyl group, a C3-C6 cycloalkylsulfonyl group, a C3-C6 halocycloalkylsulfonyl group, an C2-C8 alkylaminosulfonyl group, a C2-C8 haloalkylaminosulfonyl group, a C3-C9 trialkylsilyl group, an C2-C6 alkylcarbonyl group, an C2-C6 alkoxycarbonyl group, an C2-C8 alkylaminocarbonyl group, a C4-C7 cycloalkylmethyl group, an C1-C6 alkyl group optionally having one or more groups selected from Group P¹ or a C3-C6 cycloakyl group optionally having one or more groups selected from Group P¹;

Y¹, Y², Y³, Z² and Z³ represent independently of each other a hydrogen atom, a halogen atom, a cyano group, a nitro group, an amino group, a hydroxy group, a thiol group, an aldehyde group, an C2-C6 alkenyl group, a C2-C6 haloalkenyl group, an C2-C6 alkynyl group, a C2-C6 haloalkynyl group, an C1-C6 alkoxy group, a C1-C6 haloalkoxy group, an C3-C6 alkenyloxy group, a C3-C6 haloalkenyloxy group, an C3-C6 alkynyloxy group, a C3-C6 haloalkynyloxy group, an C3-C6 alkenylthio group, an C3-C6 alkynylthio group, a C3-C6 haloalkenylthio group, a C3-C6 haloalkynylthio group, an C1-C8 alkylamino group, a C1-C8 haloalkylamino group, an C1-C6 alkylthio group, a C1-C6 haloalkylthio group, an C1-C6 alkylsulfinyl group, a C1-C6 haloalkylsulfinyl group, an C1-C6 alkylsulfonyl group, a C1-C6 haloalkylsulfonyl group, an C2-C8 alkylaminosulfonyl group, a pentaflurosulfanyl group, a C3-C9 trialkylsilyl group, an C2-C6 alkylcarbonyl group, an C2-C6 alkoxycarbonyl group, an aminocarbonyl group, an C2-C8 alkylaminocarbonyl group, an C1-C6 alkyl group optionally having one or more groups selected from Group P¹ or a C3-C6 cycloalkyl group optionally having one or more groups selected from Group P¹; or Y¹ and Y² may combine each other together with the carbon atom to which they are attached to form a five-, six- or seven-membered saturated ring, said saturated ring may optionally contain one or more oxygen atoms or sulfur atoms as the ring-constituent atom, and the saturated ring may optionally have one or more substituents selected from Group P¹; or Y² and Y³ may combine each other together with the carbon atom to which they are attached to form a five-, six- or seven-membered saturated ring, said saturated ring may optionally contain one or more oxygen atoms or sulfur atoms as the ring-constituent atom, and the saturated ring may optionally have one or more substituents selected from Group P¹; or Z¹ and Z² may combine each other together with the carbon atom or nitrogen atom to which they are attached to form a five-, six- or seven-membered saturated ring, said the saturated ring may optionally contain one or more oxygen atoms, nitrogen atoms or sulfur atoms as the ring-constituent atom, and the saturated ring may optionally have one or more substituents selected from Group P¹); or Z² and Z³ may combine each other together with the carbon atom to which they are attached to form a five-, six- or seven-membered saturated ring, said saturated ring may optionally contain one or more oxygen atoms, nitrogen atoms or sulfur atoms as the ring-constituent atom, and the saturated ring may optionally have one or more substituents selected from Group P¹); and Group P¹: a group consisting of a halogen atom, a cyano group, a C3-C6 cycloalkyl group, a C3-C6 halocycloalkyl group, an C1-C4 alkoxy group, a C1-C4 haloalkoxy group, an C1-C4 alkylthio group or a C1-C4 haloalkylthio group].

[2] The tetrazolinone compound according to [1] wherein Q represents Q1.

[3] The tetrazolinone compound according to [1] wherein Q represents Q2.

[4] The tetrazolinone compound according to [1] wherein Q represents Q3.

[5] The tetrazolinone compound according to [1] wherein Q represents Q4.

[6] The tetrazolinone compound according to any one of [1] to [5], wherein

R¹ represents an C1-C3 alkyl group, a halogen atom, a C1-C3 haloalkyl group, an C2-C3 alkynyl group, a C2-C3 haloalkynyl group, a C3-C5 cycloalkyl group, a C3-C5 halocycloalkyl group, an C1-C3 alkoxy group or a C1-C3 haloalkoxy group;

R², R⁴, R⁵, R⁷, R⁸, R⁹ and R¹¹ represent a hydrogen atom;

R³ represents a hydrogen atom, a halogen atom, an C1-C3 alkyl group or a C1-C3 haloalkyl group;

R⁶ represents a C3-C6 cycloalkyl group, an C2-C4 alkynyl group, a C2-C4 haloalkynyl group, a C1-C4 haloalkoxy group, an C1-C4 alkythio group, a C1-C4 haloalkylthio group or a C3-C6 halocycloalkyl group;

R¹⁰ represents a methyl group; and

X represents an oxygen atom.

[7] The tetrazolinone compound according to any one of [1], [2] or [6],
wherein
$Y^1$ and $Y^2$ may combine each other together with the carbon atom to which they are attached to form a five- or six-membered saturated ring;
$Y^2$ and $Y^3$ may combine each other together with the carbon atom to which they are attached to form a five- or six-membered saturated ring;
when each of $Y^1$, $Y^2$ and $Y^3$ does not form the five- or six-membered saturated ring,
$Y^1$ represents a hydrogen atom, an C1-C6 alkyl group, a C1-C6 haloalkyl group, a C3-C6 cycloalkyl group or a C3-C6 halocycloalkyl group;
$Y^2$ represents a hydrogen atom, a halogen atom, an C1-C6 alkyl group, a C1-C6 haloalkyl group, an C2-C6 alkynyl group, an C1-C6 alkoxy group, a C1-C6 haloalkoxy group, a C3-C6 cycloalkyl group or a C3-C6 halocycloalkyl group;
$Y^3$ represents a hydrogen atom, an C1-C4 alkyl group or a C1-C4 haloalkyl group.

[8] The tetrazolinone compound according to any one of [1], [3] or [6],
wherein
$Z^1$ represents an C1-C6 alkyl group, a C1-C6 haloalkyl group, an C3-C6 alkynyl group, a C3-C6 haloalkynyl group, a C3-C6 cycloalkyl group, a C3-C6 halocycloalkyl group or a C4-C7 cycloalkylmethyl group;
$Z^2$ represents a hydrogen atom, a halogen atom, an C1-C6 alkyl group, a C1-C6 haloalkyl group, an C1-C6 alkoxy group, a C1-C6 haloalkoxy group, a C3-C6 cycloalkyl group or a C3-C6 halocycloalkyl group; alternatively,
$Z^1$ and $Z^2$ may combine each other together with the carbon atom or the nitrogen atom to which they are attached to form a five- or six-membered saturated ring; and
$Z^3$ represents a hydrogen atom, a halogen atom, an C1-C4 alkyl group or a C1-C4 haloalkyl group.

[9] The tetrazolinone compound according to any one of [1], [2], [6] or [7], wherein
$Y^1$ and $Y^2$ connect to each other to represent —CH$_2$—CH$_2$—CH$_2$—CH$_2$—, which combines together with the carbon atoms to which $Y^1$ and $Y^2$ are attached to form a six-membered ring;
$Y^2$ and $Y^3$ connect to each other to represent —CH$_2$—CH$_2$—CH$_2$—CH$_2$—, which combines together with the carbon atoms to which $Y^2$ and $Y^3$ are attached to form a six-membered ring;
when each of $Y^1$, $Y^2$ and $Y^3$ does not form the six-membered saturated ring,
$Y^1$ represents a hydrogen atom, an C1-C3 alkyl group, a C1-C3 haloalkyl group or a cyclopropyl group;
$Y^2$ represents a hydrogen atom, an C1-C3 alkyl group, a C1-C3 haloalkyl group, a cyano group or an C1-C3 alkoxy group; and
$Y^3$ represents a hydrogen atom or a methyl group.

[10] The tetrazolinone compound according to any one of [1], [3] or [6],
wherein
$Z^1$ represents an C1-C6 alkyl group;
$Z^2$ represents a hydrogen atom, a halogen atom, an C1-C6 alkyl group, a C1-C6 haloalkyl group, a cyano group, an C1-C6 alkoxy group or a C1-C6 alkylthio group; and
$Z^3$ represents a hydrogen atom, a halogen atom or an C1-C4 alkyl group.

[11] The tetrazolinone compound according to any one of [1], [3] or [6],
wherein
$Z^1$ represents an C1-C3 alkyl group;
$Z^2$ represents a hydrogen atom, a chlorine atom, a methoxy group, an ethoxy group, a methylthio group, a cyano group, a trifluoromethyl group or an C1-C3 alkyl group; and
$Z^3$ represents a hydrogen atom, a halogen atom or a methyl group.

[12] The tetrazolinone compound according to any one of [1], [3], [6] or [8],
wherein
$Z^1$ represents an C1-C3 alkyl group;
$Z^2$ represents a hydrogen atom, a chlorine atom, a methoxy group, a methylthio group, a trifluoromethyl group a cyano group, or an C1-C3 alkyl group; and
$Z^3$ represents a hydrogen atom, a chlorine atom or a methyl group.

[13] The tetrazolinone compound according to any one of [1] to [12],
wherein
$R^1$ represents a methyl group, an ethyl group, a chlorine atom, a bromine atom or a trifluoromethyl group;
$R^3$ represents a hydrogen atom or a methyl group; and
$R^6$ represents a cyclopropyl group, an ethynyl group, a difluoromethoxy group or a methylthio group.

[14] A tetrazolinone compound of a formula (2):

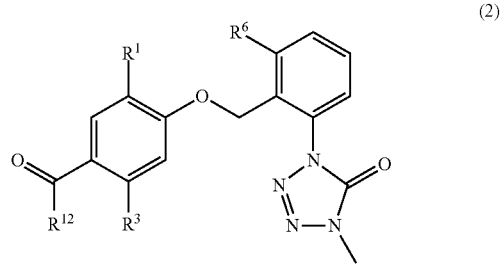

[wherein
$R^1$ represents a methyl group, an ethyl group, a chlorine atom, a bromine atom, a trifluoromethyl group or a cyclopropyl group;
$R^3$ represents a hydrogen atom or a methyl group;
$R^6$ represents a cyclopropyl group, a difluoromethoxy group, an ethynyl group or a methylthio group; and
$R^{12}$ represents an C1-C6 alkyl group, a C1-C6 haloalkyl group, a C3-C6 cycloalkyl group or a C1-C6 halocycloalkyl group].

[15] The tetrazolinone compound according to [14],
wherein
$R^1$ represents a methyl group, an ethyl group, a chlorine atom or a bromine atom;
$R^3$ represents a hydrogen atom or a methyl group;
$R^6$ represents a cyclopropyl group; and
$R^{12}$ represents a methyl group, an ethyl group or a cyclopropyl group.

[16] An agent for controlling pests comprising the tetrazolinone compound according to any one of [1] to [15].

[17] A method for controlling pests comprising applying an effective amount of the tetrazolinone compound according to any one of [1] to [15] to plant or soil.

[18] Use of the tetrazolinone compound according to any one of [1] to [15] for controlling pests.

The present invention can control pests.

DESCRIPTION OF EMBODIMENTS

The compound of the present invention (hereinafter, sometimes referred to as "the present compound") is a tetrazolinone compound of a formula (1):

A tetrazolinone compound of a formula (1):

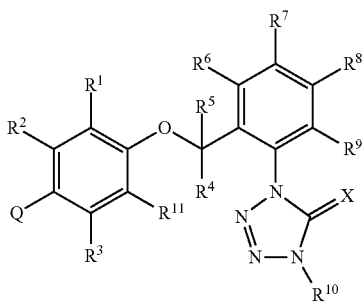

[wherein
Q represents a group selected from the following group: Q1, Q2, Q3 or Q4:
Q;

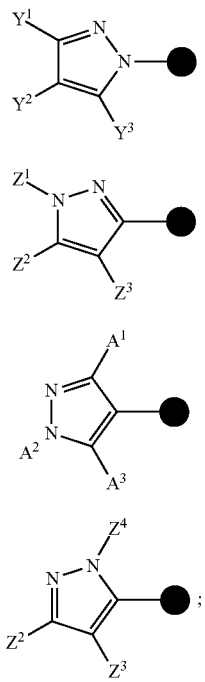

$R^1$, $R^2$, $R^3$ and $R^{11}$ represent independently of each other a hydrogen atom, a halogen atom, a cyano group, a nitro group, an amino group, a hydroxy group, a thiol group, an C2-C6 alkenyl group, a C2-C6 haloalkenyl group, an C2-C6 alkynyl group, a C2-C6 haloalkynyl group, an C1-C6 alkoxy group, a C1-C6 haloalkoxy group, an C1-C8 alkylamino group, a C1-C8 haloalkylamino group, an C1-C6 alkylthio group, a C1-C6 haloalkylthio group, an C1-C6 alkylsulfinyl group, a C1-C6 haloalkylsulfinyl group, an C1-C6 alkylsulfonyl group, a C1-C6 haloalkylsulfonyl group, a pentafluorosulfanyl group, a C3-C9 trialkylsilyl group, an C2-C6 alkylcarbonyl group, an C2-C6 alkoxycarbonyl group, an C2-C8 alkylaminocarbonyl group, an C1-C6 alkyl group optionally having one or more groups selected from Group $P^1$ or an C3-C6 cycloalkyl group optionally having one or more groups selected from Group $P^1$;

$R^4$ and $R^5$ represent independently of each other a hydrogen atom, a halogen atom or an C1-C3 alkyl group;
$R^6$ represents a C3-C6 cycloalkyl group, an C2-C4 alkynyl group, a C2-C4 haloalkynyl group, a C1-C4 haloalkoxy group, an C1-C4 alkythio group, an C1-C4 alkylsulfinyl group, an C1-C4 alkylsulfonyl group, a C1-C4 haloalkylthio group, a C1-C4 haloalkylsulfinyl group, a C1-C4 haloalkylsulfonyl group, an C1-C6 alkylamino group, a C1-C6 haloalkylamino group or a C3-C6 halocycloalkyl group;
$R^7$, $R^8$ and $R^9$ represent independently of each other a hydrogen atom, a halogen atom, an C1-C3 alkyl group, a C1-C3 haloalkyl group, an C2-C3 alkenyl group, a C2-C3 haloalkenyl group or an C1-C3 alkoxy group;
$R^{10}$ represents an C1-C3 alkyl group, a C1-C3 haloalkyl group, an C2-C3 alkenyl group, a C2-C3 haloalkenyl group, an C2-C3 alkynyl group, a C2-C3 haloalkynyl group, a C3-C5 cycloalkyl group or a C3-C5 halocycloalkyl group;
X represents an oxygen atom or a sulfur atom;
$A^1$ and $A^3$ represent independently of each other a hydrogen atom, a halogen atom, a cyano group, a nitro group, an amino group, a hydroxy group, a thiol group, an C2-C6 alkenyl group, a C2-C6 haloalkenyl group, an C2-C6 alkynyl group, a C2-C6 haloalkynyl group, an C1-C6 alkoxy group, a C1-C6 haloalkoxy group, an C1-C8 alkylamino group, a C1-C8 haloalkylamino group, an C1-C6 alkylthio group, a C1-C6 haloalkylthio group, an C1-C6 alkylsulfinyl group, a C1-C6 haloalkylsulfinyl group, an C1-C6 alkylsulfonyl group, a C1-C6 haloalkylsulfonyl group, a pentafluorosulfanyl group, a C3-C9 trialkylsilyl group, an C2-C6 alkylcarbonyl group, an C2-C6 alkoxycarbonyl group, an C2-C8 alkylaminocarbonyl group, an C1-C6 alkyl group optionally having one or more groups selected from Group $P^1$, or a C3-C6 cycloalkyl group optionally having one or more groups selected from Group $P^1$;
$A^2$, $Z^1$ and $Z^4$ represent independently of each other a hydrogen atom, an amino group, an C3-C6 alkenyl group, a C3-C6 haloalkenyl group, an C3-C6 alkynyl group, a C3-C6 haloalkynyl group, an C1-C6 alkylsulfinyl group, a C1-C6 haloalkylsulfinyl group, an C1-C6 alkylsulfonyl group, a C1-C6 haloalkylsulfonyl group, a C3-C6 cycloalkylsulfonyl group, a C3-C6 halocycloalkylsulfonyl group, an C2-C8 alkylaminosulfonyl group, a C2-C8 haloalkylaminosulfonyl group, a C3-C9 trialkylsilyl group, an C2-C6 alkylcarbonyl group, an C2-C6 alkoxycarbonyl group, an C2-C8 alkylaminocarbonyl group, a C4-C7 cycloalkylmethyl group, an C1-C6 alkyl group optionally having one or more groups selected from Group $P^1$ or a C3-C6 cycloakyl group optionally having one or more groups selected from Group $P^1$;
$Y^1$, $Y^2$, $Y^3$, $Z^2$ and $Z^3$ represent independently of each other a hydrogen atom, a halogen atom, a cyano group, a nitro group, an amino group, a hydroxy group, a thiol group, an aldehyde group, an C2-C6 alkenyl group, a C2-C6 haloalkenyl group, an C2-C6 alkynyl group, a C2-C6 haloalkynyl group, an C1-C6 alkoxy group, a C1-C6 haloalkoxy group, an C3-C6 alkenyloxy group, a C3-C6 haloalkenyloxy group, an C3-C6 alkynyloxy group, a C3-C6 haloalkynyloxy group, an C3-C6 alkenylthio group, an C3-C6 alkynylthio group, a C3-C6 haloalkenylthio group, a C3-C6 haloalkynylthio group, an C1-C8 alkylamino group, a C1-C8 haloalkylamino group, an C1-C6 alkylthio group, a C1-C6 haloalkylthio group, an C1-C6 alkylsulfinyl group, a C1-C6 haloalkylsulfinyl group, an C1-C6 alkylsulfonyl group, a C1-C6 haloakylsulfonyl group, an C2-C8 alkylaminosulfonyl group, a pentaflurosulfanyl group, a C3-C9 trialkylsilyl group, an C2-C6 alkylcarbonyl group, an C2-C6 alkoxycarbonyl group, an aminocarbonyl group, an C2-C8 alkylaminocarbonyl group, an C1-C6 alkyl group optionally having one or more groups selected from Group P¹ or a C3-C6 cycloalkyl group optionally having one or more groups selected from Group P¹; or Y¹ and Y² may combine each other together with the carbon atom to which they are attached to form a five-, six- or seven-membered saturated ring, said saturated ring may optionally contain one or more oxygen atoms or sulfur atoms as the ring-constituent atom, and the saturated ring may optionally have one or more substituents selected from Group P¹; or Y² and Y³ may combine each other together with the carbon atom to which they are attached to form a five-, six- or seven-membered saturated ring, said saturated ring may optionally contain one or more oxygen atoms or sulfur atoms as the ring-constituent atom, and the saturated ring may optionally have one or more substituents selected from Group P¹; or Z¹ and Z² may combine each other together with the carbon atom or nitrogen atom to which they are attached to form a five-, six- or seven-membered saturated ring, said saturated ring may optionally contain one or more oxygen atoms, nitrogen atoms or sulfur atoms as the ring-constituent atom, and the saturated ring may optionally have one or more substituents selected from Group P¹); or Z² and Z³ may combine each other together with the carbon atom or nitrogen atom to which they are attached to form a five-, six- or seven-membered saturated ring, said saturated ring may optionally contain one or more oxygen atoms, nitrogen atoms or sulfur atoms as the ring-constituent atom, and the saturated ring may optionally have one or more substituents selected from Group P¹); and Group P¹: a group consisting of a halogen atom, a cyano group, a C3-C6 cycloalkyl group, a C3-C6 halocycloalkyl group, an C1-C4 alkoxy group, a C1-C4 haloalkoxy group, an C1-C4 alkylthio group or a C1-C4 haloalkylthio group].

Also, in the present invention a tetrazolinone compound represented by a formula (2):

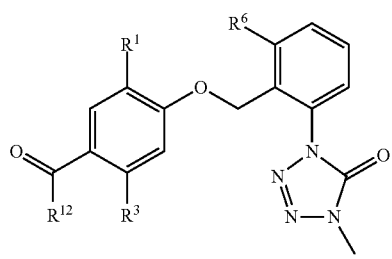

(2)

[wherein
R¹ represents a methyl group, an ethyl group, a chlorine atom, a bromine atom, a trifluoromethyl group or a cyclopropyl group;
R³ represents a hydrogen atom or a methyl group;
R⁶ represents a cyclopropyl group, an difluoromethoxy group, an ethynyl group or a methylthio group; and
R¹² represents an C1-C6 alkyl group, a C1-C6 haloalkyl group, a C3-C6 cycloalkyl group or a C1-C6 halocycloalkyl group]
is also included, which is used in a preparation of the present compound and has an excellent efficacy for controlling pests.

Hereinafter, the present invention is explained in detail.

The substituent to be used herein is specifically described below.

The term "halogen atom" includes, for example, a fluorine atom, a chlorine atom, a bromine atom and an iodine atom.

The term "C1-C6 alkyl group" represents a straight or branched alkyl group of one to six carbon atoms, and includes, for example, a methyl group, an ethyl group, a propyl group, an isopropyl group, a butyl group, an isobutyl group, a sec-butyl group, a tert-butyl group, a pentyl group and a hexyl group.

The term "C1-C4 alkyl group" represents a straight or branched alkyl group of one to four carbon atoms, and includes, for example, a methyl group, an ethyl group, a propyl group, an isopropyl group, a butyl group, an isobutyl group, a sec-butyl group and a tert-butyl group.

The term "C1-C3 alkyl group" includes, for example, a methyl group, an ethyl group, a propyl group and an isopropyl group.

The term "C1-C6 haloalkyl group" represents a group wherein at least one hydrogen atom of the straight or branched C1-C6 alkyl group is substituted with a halogen atom, and includes, for example, a monofluoromethyl group, a monochloromethyl group, a dichloromethyl group, a difluoromethyl group, a trifluoromethyl group, a trichloromethyl group, a tribromomethyl group, a 2,2,2-trifluoroethyl group, a 2,2,2-trichloroethyl group, a pentafluoroethyl group, a chlorofluoromethyl group, a dichlorofluoromethyl group, a chlorodifluoromethyl group, a 2,2-difluoroethyl group, a 2-chloro-2-fluoroethyl group, a 2-chloro-2,2-difluoroethyl group, a 2,2-dichloro-2-fluoroethyl group, a 2-fluoropropyl group, a 3-fluoropropyl group, a 2,2-difluoropropyl group, a 3,3,3-trifluoropropyl group, a 3-(fluoromethyl)-2-fluoroethyl group, a 4-fluorobutyl group, and a 2,2-difluorohexyl group. The halogen atom that can be substituted for a hydrogen atom includes a fluorine atom, a chlorine atom, a bromine atom and an iodine atom.

The term "C1-C4 haloalkyl group" represents a group wherein at least one hydrogen atom of the straight or branched C1-C4 alkyl group is substituted with a halogen atom, and includes, for example, a monofluoromethyl group, a monochloromethyl group, a dichloromethyl group, a difluoromethyl group, a trifluoromethyl group, a trichloromethyl group, a tribromomethyl group, a 2,2,2-trifluoroethyl group, a 2,2,2-trichloroethyl group, a pentafluoroethyl group, a chlorofluoromethyl group, a dichlorofluoromethyl group, a chlorodifluoromethyl group, a 2,2-difluoroethyl group, a 2-chloro-2-fluoroethyl group, a 2-chloro-2,2-difluoroethyl group, a 2,2-dichloro-2-fluoroethyl group, a 2-fluoropropyl group, a 3-fluoropropyl group, a 2,2-difluoropropyl group, a 3,3,3-trifluoropropyl group, a 3-(fluoromethyl)-2-fluoroethyl group, and a 4-fluorobutyl group. The halogen atom that can be substituted for a hydrogen atom includes a fluorine atom, a chlorine atom, a bromine atom and an iodine atom.

The term "C1-C3 haloalkyl group" represents a group wherein at least one hydrogen atom of the straight or branched C1-C3 alkyl group is substituted with a halogen atom, and includes, for example, a chloromethyl group, a dichloromethyl group, a fluoromethyl group, a difluoromethyl group, a chlorofluoromethyl group, a dichlorofluoromethyl group, a chlorodifluoromethyl group, a trifluoromethyl group, a trichloromethyl group, a tribromomethyl group, a 2-fluoroethyl group, a 2,2-difluoroethyl group, a 2,2,2-trifluoroethyl group, a 2-chloroethyl group, a 2,2-dichloroethyl group, a 2,2,2-trichloroethyl group, a pentafluoroethyl group, a pentachloroethyl group, a 2-chloro-2-fluoroethyl group, a 2-chloro-2,2-difluoroethyl group, a 2-fluoropropyl group, a 3-fluoropropyl group, a 2,2-difluoropropyl group, a 2,3-difluoropropyl group, a 3,3,3-trifluoropropyl group, a heptafluoropropyl group and a 1-(fluoromethyl)-2-fluoroethyl group.

The term "C3-C6 cycloalkyl group" represents a cyclic alkyl group of three to six carbon atoms, and encompasses a cycloalkyl group having an alkyl group, and includes, for example, a cyclopropyl group, a cyclobutyl group, a cyclopentyl group, a cyclohexyl group, a 1-methylcyclopropyl group, a 2-methylcyclopropyl group, a 2,2-dimethylcyclopropyl group and a 2,3-dimethylcyclopropyl group.

The term "C3-C5 cycloalkyl group" represents a cyclic alkyl group of three to five carbon atoms, and encompasses a cycloalkyl group having an alkyl group, and includes, for example, a cyclopropyl group, a cyclobutyl group, a cyclopentyl group, a 1-methylcyclopropyl group, a 2-methylcyclopropyl group, a 2,2-dimethylcyclopropyl group and a 2,3-dimethylcyclopropyl group.

The term "C3-C4 cycloalkyl group" represents a cyclic alkyl group of three to four carbon atoms, and encompasses a cycloalkyl group having an alkyl group, and includes, for example, a cyclopropyl group, a cyclobutyl group and a 1-methylcyclopropyl group.

The term "C4-C7 cycloalkylmethyl group" represents a methyl group having a cyclic alkyl of four to seven carbon atoms, and the cyclic alkyl group may further optionally contain alkyl group(s), and the number of carbon atom of the cycloalkylmethyl group is four to seven. The C4-C7 cycloalkyl group includes, for example, a cyclopropylmethyl group, a cyclobutylmethyl group, a cyclopentylmethyl group, a cyclohexylmethyl group, a 1-methylcyclopropylmethyl group, a 2-methylcyclopropylmethyl group and a 2,2-dimethylcyclopropylmethyl group.

The term "C3-C6 halocycloalkyl group" represents a group wherein at least one hydrogen atom of the C3-C6 cycloalkyl group is substituted with a halogen atom, and includes, for example a 1-fluorocyclopropyl group, a 2-fluorocyclopropyl group, a 2,2-difluorocyclopropyl group, a 1-chlorocyclopropyl group, a 2-chloro-2-fluorocyclopropyl group, a 2,2-dichlorocyclopropyl group, a 2,2-dibromocyclopropyl group, a 2,2-difluoro-1-methylcyclopropyl group, a 2,2-dichloro-1-methylcyclopropyl group, a 2,2-dibromo-1-methylcyclopropyl group, a 1-(trifluoromethyl)cyclopropyl group, a 2,2,3,3-tetrafluorocyclobutyl group, a 1-fluorocyclobutyl group, a 1-chlorocyclobutyl group, a 2-chlorocyclopentyl group, a 3-chlorocyclopentyl group, a 3,3-difluorocyclopentyl group, a 1-fluorocyclohexyl group, a 2,2-difluorocyclohexyl group, a 3,3-difluorocyclohexyl group and a 4,4-difluorocyclohexyl group. The halogen atom that can be substituted for a hydrogen atom includes a fluorine atom, a chlorine atom, a bromine atom and an iodine atom.

The term "C3-C5 halocycloalkyl group" represents a group wherein at least one hydrogen atom of the C3-C5 cycloalkyl group is substituted with a halogen atom, and includes, for example a 1-fluorocyclopropyl group, a 2-fluorocyclopropyl group, a 2,2-difluorocyclopropyl group, a 1-chlorocyclopropyl group, a 2-chloro-2-fluorocyclopropyl group, a 2,2-dichlorocyclopropyl group, a 2,2-dibromocyclopropyl group, a 2,2-difluoro-1-methylcyclopropyl group, a 2,2-dichloro-1-methylcyclopropyl group, a 2,2-dibromo-1-methylcyclopropyl group, a 1-(trifluoromethyl)cyclopropyl group, a 2,2,3,3-tetrafluorocyclobutyl group, a 2-chlorocyclopentyl group and a 3-chlorocyclopentyl group. The halogen atom that can be substituted for a hydrogen atom includes a fluorine atom, a chlorine atom, a bromine atom and an iodine atom.

The term "C3-C4 halocycloalkyl group" represents a group wherein at least one hydrogen atom of the C3-C4 cycloalkyl group is substituted with a halogen atom, and includes, for example a 2-fluorocyclopropyl group, a 2,2-difluorocyclopropyl group, a 2-chloro-2-fluorocyclopropyl group, a 2,2-dichlorocyclopropyl group, a 2,2-dibromocyclopropyl group, a 2,2-difluoro-1-methylcyclopropyl group, a 2,2-dichloro-1-methylcyclopropyl group, a 2,2-dibromo-1-methylcyclopropyl group, a 1-(trifluoromethyl)cyclopropyl group, a 2,2,3,3-tetrafluorocyclobutyl group and a 2,2,3,3-tetrafluorocyclobutyl group. The halogen atom that can be substituted for a hydrogen atom includes a fluorine atom, a chlorine atom, a bromine atom and an iodine atom.

The term "C2-C6 alkenyl group" represents a straight or branched alkenyl group of two to six carbon atoms, and includes, for example, a vinyl group, a 1-propenyl group, an isopropenyl group, a 2-propenyl group, a 1-butenyl group, a 1-methyl-1-propenyl group, a 2-butenyl group, a 1-methyl-2-propenyl group, a 3-butenyl group, a 2-methyl-1-propenyl group, a 2-methyl-2-propenyl group, a 1,3-butadienyl group, a 1-pentenyl group, an 1-ethyl-2-propenyl group, a 2-pentenyl group, a 1-methyl-1-butenyl group, a 3-pentenyl group, a 1-methyl-2-butenyl group, a 4-pentenyl group, a 1-methyl-3-butenyl group, a 3-methyl-1-butenyl group, a 1,2-dimethyl-2-propenyl group, a 1,1-dimethyl-2-propenyl group, a 2-methyl-2-butenyl group, a 3-methyl-2-butenyl group, a 1,2-dimethyl-1-propenyl group, a 2-methyl-3-butenyl group, a 3-methyl-3-butenyl group, a 1,3-pentadienyl group, a 1-vinyl-2-propenyl group, a 1-hexenyl group and a 5-hexenyl group.

A term "C2-C6 haloalkenyl group" represents a group wherein at least one hydrogen atom of the straight or branched C2-C6 alkenyl group is substituted with a halogen atom, and includes, for example, a 2-chlorovinyl group, a 2-bromovinyl group, an 2-iodovinyl group, a 3-chloro-2-propenyl group, a 3-bromo-2-propenyl group, a 1-chloromethylvinyl group, a 2-bromo-1-methylvinyl group, a 1-trifluoromethylvinyl group, a 3,3,3-trichloro-1-propenyl group, a 3-bromo-3,3-difluoro-1-propenyl group, a 2,3,3,3-tetrachloro-1-propenyl group, a 1-trifluoromethyl-2,2-difluorovinyl group, a 2-chloro-2-propenyl group, a 3,3-difluoro-2-propenyl group, a 2,3,3-trichloro-2-propenyl group, a 4-bromo-3-chloro-3,4,4-trifluoro-1-butenyl group, a 1-bromomethyl-2-propenyl group, a 3-chloro-2-butenyl group, a 4,4,4-trifluoro-2-butenyl group, a 4-bromo-4,4-difluoro-2-butenyl group, a 3-bromo-3-butenyl group, a 3,4,4-trifluoro-3-butenyl group, a 3,4,4-tribromo-3-butenyl group, a 3-bromo-2-methyl-2-propenyl group, a 3,3-difluoro-2-methyl-2-propenyl group, a 3,3,3-trifluoro-2-methyl-1-propenyl group, a 3-chloro-4,4,4-trifluoro-2-butenyl group, a 3,3,3-trifluoro-1-methyl-1-propenyl group, a 3,4,4-trifluoro-1,3-butadienyl group, a 3,4-dibromo-1-pentenyl group, a 4,4-difluoro-3-methyl-3-butenyl group, a 3,3,4,4,5,5,5-heptafluoro-1-pentenyl group, a 5,5-difluoro-4-pentenyl group, a 4,5,5-trifluoro-4-pentenyl group, a 3,4,4,4-tetrafluoro-3-trifluoromethyl-1-butenyl group, a 4,4,4-trifluoro-3-methyl-2-butenyl group, a 3,5,5-trifluoro-2,4-pentadienyl group, a 4,4,5,5,6,6,6-heptafluoro-2-hexenyl group, a 3,4,4,5,5,5-hexafluoro-3-trifluoromethyl-1-pentenyl group, a 4,5,5,5-tetrafluoro-4-trifluoromethyl-2-pentenyl group and a 5-bromo-4,5,5-trifluoro-4-trifluoromethyl-2-pentenyl group. The halogen atom that can be substituted for a hydrogen atom includes a fluorine atom, a chlorine atom, a bromine atom and an iodine atom.

The term "C3-C6 alkenyl group" represents a straight or branched alkenyl group of three to six carbon atoms, and includes, for example, a 2-propenyl group, a 2-butenyl group, a 1-methyl-2-propenyl group, a 3-butenyl group, a 2-methyl-2-propenyl group, an 1-ethyl-2-propenyl group, a 2-pentenyl group, a 3-pentenyl group, a 1-methyl-2-butenyl group, a 4-pentenyl group, a 1-methyl-3-butenyl group, a 1,2-dimethyl-2-propenyl group, a 1,1-dimethyl-2-propenyl group, a 2-methyl-2-butenyl group, a 3-methyl-2-butenyl group, a 2-methyl-3-butenyl group, a 3-methyl-3-butenyl group, a 1-vinyl-2-propenyl group, a 2-hexenyl group, a 3-hexenyl group, a 4-hexenyl group and a 5-hexenyl group.

A term "C3-C6 haloalkenyl group" represents a group wherein at least one hydrogen atom of the straight or branched C3-C6 alkenyl group is substituted with a halogen atom, and includes, for example, a 3-chloro-2-propenyl group, a 3-bromo-2-propenyl group, a 2-chloro-2-propenyl group, a 3,3-difluoro-2-propenyl group, a 2,3,3-trichloro-2-propenyl group, a 1-bromomethyl-2-propenyl group, a 3-chloro-2-butenyl group, a 4,4,4-trifluoro-2-butenyl group, a 4-bromo-4,4-difluoro-2-butenyl group, a 3-bromo-3-butenyl group, a 3,4,4-trifluoro-3-butenyl group, a 3,4,4-tribromo-3-butenyl group, a 3-bromo-2-methyl-2-propenyl group, a 3,3-difluoro-2-methyl-2-propenyl group, a 3-chloro-4,4,4-trifluoro-2-butenyl group, a 3,4-dibromo-1-pentenyl group, a 4,4-difluoro-3-methyl-3-butenyl group, a 5,5-difluoro-4-pentenyl group, a 4,5,5-trifluoro-4-pentenyl group, a 4,4,4-trifluoro-3-methyl-2-butenyl group, a 3,5,5-trifluoro-2,4-pentadienyl group, a 4,4,5,5,6,6,6-heptafluoro-2-hexenyl group, a 4,5,5,5-tetrafluoro-4-trifluoromethyl-2-pentenyl group and a 5-bromo-4,5,5-trifluoro-4-trifluoromethyl-2-pentenyl group. The halogen atom that can be substituted for a hydrogen atom includes a fluorine atom, a chlorine atom, a bromine atom and an iodine atom.

The term "C2-C3 alkenyl group" includes, for example, a vinyl group, a 1-propenyl group, an isopropenyl group and a 2-propenyl group.

A term "C2-C3 haloalkenyl group" represents a group wherein at least one hydrogen atom of the straight or branched C2-C3 alkenyl group is substituted with a halogen atom, and includes, for example, a 2-chlorovinyl group, a 2-bromovinyl group, an 2-iodovinyl group, a 3-chloro-2-propenyl group, a 3-bromo-2-propenyl group, a 1-chloromethylvinyl group, a 2-bromo-1-methylvinyl group, a 1-trifluoromethylvinyl group, a 3,3,3-trichloro-1-propenyl group, a 3-bromo-3,3-difluoro-1-propenyl group, a 2,3,3,3-tetrachloro-1-propenyl group, a 1-trifluoromethyl-2,2-difluorovinyl group, a 2-chloro-2-propenyl group, a 3,3-difluoro-2-propenyl group and a 2,3,3-trichloro-2-propenyl group.

The term "C2-C6 alkynyl group" represents an alkynyl group of two to six carbon atoms which may be straight or branched and includes, for example, an ethynyl group, a propargyl group, a 1-butyne-3-yl group, a 3-methyl-1-butyne-3-yl group, a 2-butynyl group, a 3-butynyl group, a 2-pentynyl group, a 3-pentynyl group, a 4-pentynyl group, a 1-hexynyl group and a 5-hexynyl group.

The term "C2-C6 haloalkynyl group" represents a group wherein at least one hydrogen atom of the straight or branched C2-C6 alkynyl group is substituted with a halogen atom, and includes, for example, a fluoroethynyl group, a 3-fluoro-2-propynyl group, a 3-chloro-2-propynyl group, a 3-bromo-2-propynyl group, an 3-iodo-2-propynyl group, a 3-chloro-1-propynyl group, a 5-chloro-4-pentynyl group, a 3,3,3-trifluoro-1-propynyl group, a 3,3-difluoro-1-propynyl group, a 4,4,4-trifluoro-2-butynyl group, a perfluoro-2-butynyl group, a perfluoro-2-pentynyl group, a perfluoro-3-pentynyl group and a perfluoro-1-hexynyl group. The halogen atom that can be substituted for a hydrogen atom includes a fluorine atom, a chlorine atom, a bromine atom and an iodine atom.

The term "C3-C6 alkynyl group" represents an alkynyl group of three to six carbon atoms which may be straight or branched, and includes, for example, a 2-propynyl group, a 1-butyne-3-yl group, a 3-methyl-1-butyne-3-yl group, a 2-butynyl group, a 3-butynyl group, a 2-pentynyl group, a 3-pentynyl group, a 4-pentynyl group, a 1-hexynyl group and a 5-hexynyl group. The halogen atom that can be substituted for a hydrogen atom includes a fluorine atom, a chlorine atom, a bromine atom and an iodine atom.

The term "C3-C6 haloalkynyl group" represents a group wherein at least one hydrogen atom of the straight or branched C3-C6 alkynyl group is substituted with a halogen atom, and includes, for example, a 3-chloro-2-propynyl group, a 3-bromo-2-propynyl group, an 3-iodo-2-propynyl group, a 5-chloro-4-pentynyl group, a 4,4,4-trifluoro-2-butynyl group, a perfluoro-2-butynyl group, a perfluoro-2-pentynyl group and a perfluoro-3-pentynyl group. The halogen atom that can be substituted for a hydrogen atom includes a fluorine atom, a chlorine atom, a bromine atom and an iodine atom.

The term "C3-C4 alkynyl group" includes, for example, a 2-propynyl group, a 2-butynyl group and a 3-butynyl group.

The term "C2-C3 alkynyl group" includes, for example, an ethynyl group, a 1-propynyl group and a 2-propynyl group.

The term "C2-C4 alkynyl group" includes, for example, an ethynyl group, a 1-propynyl group, a 2-propynyl group, a 1-butynyl group and a 2-butynyl group.

The term "C2-C4 haloalkynyl group" includes, for example, 3,3,3-trifluoropropynyl group, a 3,3-difluoropropynyl group, a 3,3,3-trifluorobutynyl group, 4,4,4-trifluoro-2-butynyl group and a 3,3-difluoro-butynyl group.

The term "C2-C3 haloalkynyl group" includes, for example, a fluoroethynyl group, a 3-fluoro-2-propynyl group, a 3-chloro-2-propynyl group, a 3-bromo-2-propynyl group, an 3-iodo-2-propynyl group, a 3-chloro-1-propynyl group, a 3,3,3-trifluoro-1-propynyl group and a 3,3-difluoro-1-propynyl group.

The term "C1-C6 alkoxy group" represents an alkoxy group of one to six carbon atoms which may be straight or branched, and includes, for example, a methoxy group, an ethoxy group, a propyloxy group, an isopropyloxy group, a butyloxy group, an isobutyloxy group, a sec-butyloxy group, a tert-butyloxy group, a pentyloxy group, an isoamyloxy group, a neopentyloxy group, a 2-pentyloxy group, a 3-pentyloxy group, a 2-methylbutyloxy group, a hexyloxy group, an isohexyloxy group, a 3-methylpentyloxy group and a 4-methylpentyloxy group.

The term "C1-C4 alkoxy group" represents an alkoxy group of one to four carbon atoms which may be straight or branched, and includes, for example, a methoxy group, an ethoxy group, a propyloxy group, an isopropyloxy group, a butyloxy group, an isobutyloxy group, a sec-butyloxy group and a tert-butyloxy group.

The term "C1-C3 alkoxy group" includes, for example, a methoxy group, an ethoxy group, a propyloxy group and an isopropyloxy group.

The term "C1-C2 alkoxy group" includes, for example, a methoxy group and an ethoxy group.

The term "C1-C6 haloalkoxy group" represents a group wherein at least one hydrogen atom of the straight or branched C1-C6 alkoxy group is substituted with a halogen atom, and includes, for example, a trifluoromethoxy group, a trichloromethoxy group, a chloromethoxy group, a dichloromethoxy group, a fluoromethoxy group, a difluoromethoxy group, a chlorofluoromethoxy group, a dichlorofluoromethoxy group, a chlorodifluoromethoxy group, a pentafluoroethoxy group, a pentachloroethoxy group, a 2,2,2-trichloroethoxy group, a 2,2,2-trifluoroethoxy group, a 2,2,2-tribromoethoxy group, a 2,2,2-triiodoethoxy group, a 2-fluoroethoxy group, a 2-chloroethoxy group, a 2,2-difluoroethoxy group, a 2-chloro-2-fluoroethoxy group, a 2-chloro-2,2-difluoroethoxy group, a heptafluoropropoxy group, a heptachloropropoxy group, a heptabromopropoxy group, a heptaiodopropoxy group, a 3,3,3-trifluoropropoxy group, a 3,3,3-trichloropropoxy group, a 3,3,3-tribromopropoxy group, a 3,3,3-triiodopropoxy group, a 2-fluoropropoxy group, a 3-fluoropropoxy group, a 2,2-difluoropropoxy group, a 2,3-difluoropropoxy group, a 2-chloropropoxy group, a 3-chloropropoxy group, a 2,3-dichloropropoxy group, a 2-bromopropoxy group, a 3-bromopropoxy group, a 3,3,3-trifluoropropoxy group, a nonafluorobutoxy group, a nonachlorobutoxy group, a nonabromobutoxy group, a nonaiodobutoxy group, a perfluoropentyloxy group, a perchloropentyloxy group, a perbromopentyloxy group, a perfluorohexyloxy group, a perchlorohexyloxy group, a perbromohexyloxy group and a periodohexyloxy group. The halogen atom that can be substituted for a hydrogen atom includes a fluorine atom, a chlorine atom, a bromine atom and an iodine atom.

The term "C1-C4 haloalkoxy group" represents a group wherein at least one hydrogen atom of the straight or branched C1-C4 alkoxy group is substituted with a halogen atom, and includes, for example, a trifluoromethoxy group, a trichloromethoxy group, a chloromethoxy group, a dichloromethoxy group, a fluoromethoxy group, a difluoromethoxy group, a chlorofluoromethoxy group, a dichlorofluoromethoxy group, a chlorodifluoromethoxy group, a pentafluoroethoxy group, a pentachloroethoxy group, a 2,2,2-trichloroethoxy group, a 2,2,2-trifluoroethoxy group, a 2,2,2-tribromoethoxy group, a 2,2,2-triiodoethoxy group, a 2-fluoroethoxy group, a 2-chloroethoxy group, a 2,2-difluoroethoxy group, a 2,2,2-trifluoroethoxy group, a 2-chloro-2-fluoroethoxy group, a 2-chloro-2,2-difluoroethoxy group, a heptafluoropropoxy group, a heptachloropropoxy group, a heptabromopropoxy group, a heptaiodopropoxy group, a 3,3,3-trifluoropropoxy group, a 3,3,3-trichloropropoxy group, a 3,3,3-tribromopropoxy group, a 3,3,3-triiodopropoxy group, a 2-fluoropropoxy group, a 3-fluoropropoxy group, a 2,2-difluoropropoxy group, a 2,3-difluoropropoxy group, a 2-chloropropoxy group, a 3-chloropropoxy group, a 2,3-dichloropropoxy group, a 2-bromopropoxy group, a 3-bromopropoxy group, a 2,3,3-trifluoropropoxy group, a nonafluorobutoxy group, a nonachlorobutoxy group, a nonabromobutoxy group and a nonaiodobutoxy group. The halogen atom that can be substituted for a hydrogen atom includes a fluorine atom, a chlorine atom, a bromine atom and an iodine atom.

The term "C1-C3 haloalkoxy group" represents a group wherein at least one hydrogen atom of the straight or branched C1-C3 alkoxy group is substituted with a halogen atom, and includes, for example, a trifluoromethoxy group, a trichloromethoxy group, a chloromethoxy group, a dichloromethoxy group, a fluoromethoxy group, a difluoromethoxy group, a chlorofluoromethoxy group, a dichlorofluoromethoxy group, a chlorodifluoromethoxy group, a pentafluoroethoxy group, a pentachloroethoxy group, a 2,2,2-trichloroethoxy group, a 2,2,2-trifluoroethoxy group, a 2,2,2-tribromoethoxy group, a 2,2,2-triiodoethoxy group, a 2-fluoroethoxy group, a 2-chloroethoxy group, a 2,2-difluoroethoxy group, a 2,2,2-trifluoroethoxy group, a 2-chloro-2-fluoroethoxy group, a 2-chloro-2,2-difluoroethoxy group, a heptafluoropropoxy group, a heptachloropropoxy group, a heptabromopropoxy group, a heptaiodopropoxy group, a 3,3,3-trifluoropropoxy group, a 3,3,3-trichloropropoxy group, a 3,3,3-tribromopropoxy group, a 3,3,3-triiodopropoxy group, a 2-fluoropropoxy group, a 3-fluoropropoxy group, a 2,2-difluoropropoxy group, a 2,3-difluoropropoxy group, a 2-chloropropoxy group, a 3-chloropropoxy group, a 2,3-dichloropropoxy group, a 2-bromopropoxy group, a 3-bromopropoxy group and a 3,3,3-trifluoropropoxy group. The halogen atom that can be substituted for a hydrogen atom includes a fluorine atom, a chlorine atom, a bromine atom and an iodine atom.

The term "C1-C2 haloalkoxy group" represents a group wherein at least one hydrogen atom of the straight or branched C1-C2 alkoxy group is substituted with a halogen atom, and includes, for example, a trifluoromethoxy group, a trichloromethoxy group, a chloromethoxy group, a dichloromethoxy group, a fluoromethoxy group, a difluoromethoxy group, a chlorofluoromethoxy group, a dichlorofluoromethoxy group, a chlorodifluoromethoxy group, a pentafluoroethoxy group, a pentachloroethoxy group, a 2,2,2-trichloroethoxy group, a 2,2,2-trifluoroethoxy group, a 2,2,2-tribromoethoxy group, a 2,2,2-triiodoethoxy group, a 2-fluoroethoxy group, a 2-chloroethoxy group, a 2,2-difluoroethoxy group, a 2,2,2-trifluoroethoxy group, a 2-chloro-2-fluoroethoxy group and a 2-chloro-2,2-difluoroethoxy group. The halogen atom that can be substituted for a hydrogen atom includes a fluorine atom, a chlorine atom, a bromine atom and an iodine atom.

The term "C1-C6 alkylthio group" represents an alkylthio group of one to six carbon atoms which may be straight or branched, and includes, for example, a methylthio group, an ethylthio group, a propylthio group, an isopropylthio group, a butylthio group, a sec-butylthio group, a tert-butylthio group, a pentylthio group, an isopentylthio group, a neopentylthio group, a hexylthio group, an isohexylthio group and a sec-hexylthio group.

The term "C1-C6 haloalkylthio group" represents a group wherein at least one hydrogen atom of the straight or branched C1-C6 alkylthio group is substituted with a halogen atom, and includes, for example, a monofluoromethylthio group, a difluoromethylthio group, a trifluoromethylthio group, a trichloromethylthio group, a tribromomethylthio group, a triiodomethylthio group, a chlorofluoromethylthio group, a pentafluoroethylthio group, a pentachloroethylthio group, a pentabromoethylthio group, a pentaiodoethylthio group, a 2,2,2-trichloroethylthio group, a 2,2,2-trifluoroethylthio group, a 2,2,2-tribromoethylthio group, a 2,2,2-triiodoethylthio group, a 2,2-difluoroethylthio group, a heptafluoropropylthio group, a heptachloropropylthio group, a heptabromopropylthio group, a heptaiodopropylthio group, a 3,3,3-trifluoropropylthio group, a 3,3,3-trichloropropylthio group, a 3,3,3-tribromopropylthio group, a 3,3,3-triiodopropylthio group, a 2,2-difluoropropylthio group, a 2,3,3-trifluoropropylthio group, a nonafluorobutylthio group, a nonachlorobutylthio group, a nonabromobutylthio group, a nonaiodobutylthio group, a perfluoropentylthio group, a perchloropentylthio group, a perbromopentylthio group, a perfluorohexylthio group, a perchlorohexylthio group, a perbromohexylthio group and a periodohexylthio group. The halogen atom that can be substituted for a hydrogen atom includes a fluorine atom, a chlorine atom, a bromine atom and an iodine atom.

The term "C1-C4 alkylthio group" includes, for example, a methylthio group, an ethylthio group, a propylthio group, an isopropylthio group, a butylthio group, an isobutylthio group and a tert-butylthio group.

The term "C1-C2 alkylthio group" includes, for example, a methylthio group and an ethylthio group.

The term "C1-C4 haloalkylthio group" represents a group wherein at least one hydrogen atom of the straight or branched C1-C4 alkylthio group is substituted with a halogen atom, and includes, for example, a monofluoromethylthio group, a difluoromethylthio group, a trifluoromethylthio group, a trichloromethylthio group, a tribromomethylthio group, a triiodomethylthio group, a chlorofluoromethylthio group, a pentafluoroethylthio group, a pentachloroethylthio group, a pentabromoethylthio group, a pentaiodoethylthio group, a 2,2,2-trichloroethylthio group, a 2,2,2-trifluoroethylthio group, a 2,2,2-tribromoethylthio group, a 2,2,2-triiodoethylthio group and a 2,2-difluoroethylthio group. The halogen atom that can be substituted for a hydrogen atom includes a fluorine atom, a chlorine atom, a bromine atom and an iodine atom.

The term "C3-C6 alkenyloxy group" represents a straight or branched alkenyloxy group of three to six carbon atoms, and includes, for example, a 2-propenyloxy group, a 2-butenyloxy group, a 1-methyl-2-propenyloxy group, a 3-butenyloxy group, a 2-methyl-2-propenyloxy group, a 2-pentenyloxy group, a 3-pentenyloxy group, a 4-pentenyloxy group, a 1-methyl-3-butenyloxy group, a 1,2-dimethyl-2-propenyloxy group, a 1,1-dimethyl-2-propenyloxy group, a 2-methyl-2-butenyloxy group, a 3-methyl-2-butenyloxy group, a 2-methyl-3-butenyloxy group, a 3-methyl-3-butenyloxy group, a 1-vinyl-2-propenyloxy group and a 5-hexenyloxy group.

The term "C3-C6 haloalkenyloxy group" represents a group wherein at least one hydrogen atom of the straight or branched C3-C6 alkenyloxy group is substituted with a halogen atom, and includes, for example, a 3-chloro-2-propenyloxy group, a 3-bromo-2-propenyloxy group, a 3-bromo-3,3-difluoro-1-propenyloxy group, a 2,3,3,3-tetrachloro-1-propenyloxy group, a 2-chloro-2-propenyloxy group, a 3,3-difluoro-2-propenyloxy group, a 2,3,3-trichloro-2-propenyloxy group, a 3,3-dichloro-2-propenyloxy group, a 3,3-dibromo-2-propenyloxy group, a 3-fluoro-3-chloro-2-propenyloxy group, a 4-bromo-3-chloro-3,4,4-trifluoro-1-butenyloxy group, a 1-bromomethyl-2-propenyloxy group, a 3-chloro-2-butenyloxy group, a 4,4,4-trifluoro-2-butenyloxy group, a 4-bromo-4,4-difluoro-2-butenyloxy group, a 3-bromo-3-butenyloxy group, a 3,4,4-trifluoro-3-butenyloxy group, a 3,4,4-tribromo-3-butenyloxy group, a 3-bromo-2-methyl-2-propenyloxy group, a 3,3-difluoro-2-methyl-2-propenyloxy group, a 3-chloro-4,4,4-trifluoro-2-butenyloxy group, a 4,4-difluoro-3-methyl-3-butenyloxy group, a 5,5-difluoro-4-pentenyloxy group, a 4,5,5-trifluoro-4-pentenyloxy group, a 4,4,4-trifluoro-3-methyl-2-butenyloxy group, a 3,5,5-trifluoro-2,4-pentadienyloxy group, a 4,4,5,5,6,6,6-heptafluoro-2-hexenyloxy group, a 4,5,5,5-tetrafluoro-4-trifluoromethyl-2-pentenyloxy group and a 5-bromo-4,5,5-trifluoromethyl-2-pentenyloxy group. The halogen atom that can be substituted for a hydrogen atom includes a fluorine atom, a chlorine atom, a bromine atom and an iodine atom.

The term "C3-C6 alkynyloxy group" represents a straight or branched alkynyloxy group of three to six carbon atoms, and includes, for example, a 2-propynyloxy group, a 1-butyne-3-yloxy group, a 3-methyl-1-butyne-3-yloxy group, a 2-butynyloxy group, a 3-butynyloxy group, a 2-penthynyloxy group, a 3-penthynyloxy group, a 4-penthynyloxy group and a 5-hexynyloxy group.

The term "C3-C6 haloalkynyloxy group" represents a group wherein at least one hydrogen atom of the straight or branched C3-C6 alkynyloxy group is substituted with a halogen atom, and includes, for example, a 3-chloro-2-propynyloxy group, a 3-bromo-2-propynyloxy group, an 3-iodo-2-propynyloxy group, a 5-chloro-4-pentynyloxy group, a 4,4,4-trifluoro-2-butynyloxy group, a perfluoro-2-butynyloxy group, a perfluoro-3-butynyloxy group, a perfluoro-2-pentynyloxy group, a perfluoro-3-pentynyloxy group, a perfluoro-4-pentynyloxy group and a perfluoro-5-hexynyloxy group. The halogen atom that can be substituted for a hydrogen atom includes a fluorine atom, a chlorine atom, a bromine atom and an iodine atom.

The term "C3-C6 alkenylthio group" represents a straight or branched alkenylthio group of three to six carbon atoms, and includes, for example, a 2-propenylthio group, a 2-butenylthio group, a 1-methyl-2-propenylthio group, a 3-butenylthio group, a 2-methyl-2-propenylthio group, a 2-pentenylthio group, a 3-pentenylthio group, a 4-pentenylthio group, a 1-methyl-3-butenylthio group, a 1,2-dimethyl-2-propenylthio group, a 1,1-dimethyl-2-propenylthio group, a 2-methyl-2-butenylthio group, a 3-methyl-2-butenylthio group, a 2-methyl-3-butenylthio group, a 3-methyl-3-butenylthio group, a 1-vinyl-2-propenylthio group and a 5-hexenylthio group.

The term "C3-C6 haloalkenythio group" represents a group wherein at least one hydrogen atom of the straight or branched C3-C6 alkynythio group is substituted with a halogen atom, and includes, for example, a 3-chloro-2-propenylthio group, a 3-bromo-2-propenylthio group, a 3-bromo-3,3-difluoro-1-propenylthio group, a 2,3,3,3-tetrachloro-1-propenylthio group, a 2-chloro-2-propenylthio group, a 3,3-difluoro-2-propenylthio group, a 2,3,3-trichloro-2-propenylthio group, a 3,3-dichloro-2-propenylthio group, a 3,3-dibromo-2-propenylthio group, a 3-fluoro-3-chloro-2-propenylthio group, a 4-bromo-3-chloro-3,4,4-trifluoro-1-butenylthio group, a 1-bromomethyl-2-propenylthio group, a 3-chloro-2-butenylthio group, a 4,4,4-trifluoro-2-butenylthio group, a 4-bromo-4,4-difluoro-2-butenylthio group, a 3-bromo-3-butenylthio group, a 3,4,4-trifluoro-3-butenylthio group, a 3,4,4-tribromo-3-butenylthio group, a 3-bromo-2-methyl-2-propenylthio group, a 3,3-difluoro-2-methyl-2-propenylthio group, a 3-chloro-4,4,4-trifluoro-2-butenylthio group, a 4,4-difluoro-3-methyl-3-butenylthio group, a 5,5-difluoro-4-pentenylthio group, a 4,5,5-trifluoro-4-pentenylthio group, a 4,4,4-trifluoromethyl-3-methyl-2-butenylthio group, a 3,5,5-trifluoro-2,4-pentadienylthio group, a 4,4,5,5,6,6,6-heptafluoro-2-hexenylthio group, a 4,5,5,5-tetrafluoro-4-trifluoromethyl-2-pentenylthio group and a 5-bromo-4,5,5-trifluoro-4-trifluoromethyl-2-pentenylthio group. The halogen atom that can be substituted for a hydrogen atom includes a fluorine atom, a chlorine atom, a bromine atom and an iodine atom.

The term "C3-C6 alkynythio group" represents a straight or branched alkynylthio group of three to six carbon atoms, and includes, for example, a propargylthio group, a 1-butyne-3-ylthio group, a 3-methyl-1-butyne-3-ylthio group, a 2-butynylthio group, a 3-butynylthio group, a 2-pentynylthio group, a 3-pentynylthio group, a 4-pentynylthio group and a 5-hexynylthio group.

The term of "C3-C6 haloalkynythio group" represents a group wherein at least one hydrogen atom of the straight or branched C3-C6 alkynythio group is substituted with a halogen atom, and includes, for example, a 3-chloro-2-propynylthio group, a 3-bromo-2-propynylthio group, an 3-iodo-2-propynylthio group, a 5-chloro-4-pentynylthio group, a 4,4,4-trifluoro-2-butynylthio group, a perfluoro-2-butynylthio group, a perfluoro-3-butynylthio group, a perfluoro-2-pentynylthio group, a perfluoro-3-pentynylthio group, a perfluoro-4-pentynylthio group and a perfluoro-5-hexynylthio group. The halogen atom that can be substituted for a hydrogen atom includes a fluorine atom, a chlorine atom, a bromine atom and an iodine atom.

The term "C1-C8 alkylamino group" represents an amino group having the straight or branched C1-C8 alkyl group wherein one or two hydrogen atom(s) on the nitrogen atom of the alkyl group is substituted with the straight and/or branched C1-C4 alkyl group which may be same or different from each other, and includes, for example, a methylamino group, an ethylamino group, a propylamino group, an isopropylamino group, a N,N-dimethylamino group, a N,N-diethylamino group, an N-ethyl-N-methylamino group, a butylamino group, a pentylamino group, a hexylamino group, a N,N-dibutylamino group and a N-sec-butyl-N-methylamino group.

The term "C1-C6 alkylamino group" represents an amino group containing the straight or branched C1-C6 alkyl group and includes, for example, a N-methylamino group, an N-ethylamino group, a N-propylamino group, an N-isopropylamino group, a N,N-dimethylamino group, a N,N-diethylamino group, an N-ethyl-N-methylamino group, a N-butylamino group, a N-pentylamino group, a N-hexylamino group, a N,N-dibutylamino group and a N-sec-butyl-N-methylamino group.

The term "C1-C8 haloalkylamino group" represents a group wherein at least one hydrogen atom of the C1-C8 alkylamino group is substituted with a halogen atom, and includes, for example, a N-trifluoroethylamino group, a N,N-di-trifluoroethylamino group, a N,N-di-trichloroethylamino group and a N-pentafluoropropylamino group. The halogen atom that can be substituted for a hydrogen atom includes a fluorine atom, a chlorine atom, a bromine atom and an iodine atom.

The term "C1-C6 haloalkylamino group" represents a group wherein at least one hydrogen atom of the C1-C6 alkylamino group is substituted with a halogen atom, and includes, for example, a N-trifluoroethylamino group, a N,N-di-trifluoroethylamino group, a N,N-di-trichloroethylamino group and a N-pentafluoropropylamino group. The halogen atom that can be substituted for a hydrogen atom includes a fluorine atom, a chlorine atom, a bromine atom and an iodine atom.

The term "C2-C6 alkylcarbonyl group" represents an alkylcarbonyl group of two to six carbon atoms having a straight or branched C1-C5 alkyl group, and includes, for example, a methylcarbonyl group, an ethylcarbonyl group, a propylcarbonyl group, an isopropylcarbonyl group, a pivaloyl group, a butylcarbonyl group and a pentylcarbonyl group.

The term "C2-C6 alkoxycarbonyl group" represents an alkoxycarbonyl group of two to six carbon atoms having a straight or branched C1-C5 alkyl group, and includes, for example, a methoxycarbonyl group, an ethoxycarbonyl group, a propyloxycarbonyl group, an isopropyloxycarbonyl group, a butyloxycarbonyl group, an isobutyloxycarbonyl group, a sec-butyloxycarbonyl group, a tert-butyloxycarbonyl group, a pentyloxycarbonyl group, an isoamyloxycarbonyl group, a neopentyloxycarbonyl group, a 2-pentyloxycarbonyl group, a 3-pentyloxycarbonyl group and a 2-methylbutyloxycarbonyl group.

The term "C2-C8 alkylaminocarbonyl group" represents an aminocarbonyl group having the straight or branched C1-C7 alkylamino group wherein one or two hydrogen atom(s) on the nitrogen atom of the alkyl group is substituted with the straight and/or branched C1-C4 alkyl group which may be same or different from each other, and includes, for example, a methylaminocarbonyl group, an ethylaminocarbonyl group, a propylaminocarbonyl group, an isopropylaminocarbonyl group, a butylaminocarbonyl group, a N,N-dimethylaminocarbonyl group, a N,N-diethylaminocarbonyl group, a N,N-dipropylaminocarbonyl group and a N,N-diisopropylaminocarbonyl group.

The term "C3-C9 trialkylsilyl group" represents a trialkylsilyl group of three to nine carbon atoms having a straight or branched C3-C9 trialkyl group, and includes, for example, a trimethylsilyl group, a tert-butyldimethylsilyl group, a triethylsilyl group, an isopropyldimethylsilyl group and a triisopropylsilyl group.

The term "C1-C6 alkylsulfonyl group" represents an alkylsulfonyl group having a straight or branched C1-C6 alkyl group, and includes, for example, a methylsulfonyl group, an ethylsulfonyl group, a propylsulfonyl group, an isopropylsulfonyl group, a butylsulfonyl group, an isobutylsulfonyl group, a sec-butylsulfonyl group, a pentylsulfonyl group, an isoamylsulfonyl group, a neopentylsulfonyl group, a 2-pentylsulfonyl group, a 3-pentylsulfonyl group, a 2-methylbutylsulfonyl group, a hexylsulfonyl group, an isohexylsulfonyl group, a 3-methylpentylsulfonyl group and a 4-methylpentylsulfonyl group.

The term "C1-C4 alkylsulfonyl group" represents an alkylsulfonyl group having a straight or branched C1-C4 alkyl group, and includes, for example, a methylsulfonyl group, an ethylsulfonyl group, a propylsulfonyl group and an isopropylsulfonyl group.

The term "C1-C6 haloalkylsulfonyl group" represents a group wherein at least one hydrogen atom of the straight or branched C1-C6 alkylsulfonyl group is substituted with a halogen atom, and includes, for example, a trifluoromethylsulfonyl group, a trichloromethylsulfonyl group, a tribromomethylsulfonyl group, a triiodomethylsulfonyl group, a pentafluoroethylsulfonyl group, a pentachloroethylsulfonyl group, a pentabromoethylsulfonyl group, a pentaiodoethylsulfonyl group, a 2,2,2-trichloroethylsulfonyl group, a 2,2,2-trifluoroethylsulfonyl group, a 2,2,2-tribromoethylsulfonyl group, a 2,2,2-triiodoethylsulfonyl group, a heptafluoropropylsulfonyl group, a heptachloropropylsulfonyl group, a heptabromopropylsulfonyl group, a heptaiodopropylsulfonyl group, a 3,3,3-trifluoropropylsulfonyl group, a 3,3,3-trichloropropylsulfonyl group, a 3,3,3-tribromopropylsulfonyl group, a 3,3,3-triiodopropylsulfonyl group, a nonafluorobutylsulfonyl group, a nonachlorobutylsulfonyl group, a nonabromobutylsulfonyl group, a nonaiodobutylsulfonyl group, a perfluoropentylsulfonyl group, a perchloropentylsulfonyl group, a perbromopentylsulfonyl group, a perfluorohexylsulfonyl group, a perchlorohexylsulfonyl group, a perbromohexylsulfonyl group and a periodohexylsulfonyl group. The halogen atom that can be substituted for a hydrogen atom includes a fluorine atom, a chlorine atom, a bromine atom and an iodine atom.

The term "C1-C4 haloalkylsulfonyl group" represents a group wherein at least one hydrogen atom of the straight or branched C1-C4 alkylsulfonyl group is substituted with a halogen atom, and includes, for example, a trifluoromethylsulfonyl group, a trichloromethylsulfonyl group, a tribromomethylsulfonyl group, a triiodomethylsulfonyl group, a pentafluoroethylsulfonyl group, a pentachloroethylsulfonyl group, a pentabromoethylsulfonyl group, a pentaiodoethylsulfonyl group, a 2,2,2-trichloroethylsulfonyl group, a 2,2,2-trifluoroethylsulfonyl group, a 2,2,2-tribromoethylsulfonyl group, a 2,2,2-triiodoethylsulfonyl group, a heptafluoropropylsulfonyl group, a heptachloropropylsulfonyl group, a heptabromopropylsulfonyl group, a heptaiodopropylsulfonyl group, a 3,3,3-trifluoropropylsulfonyl group, a 3,3,3-trichloropropylsulfonyl group, a 3,3,3-tribromopropylsulfonyl group and a 3,3,3-triiodopropylsulfonyl group.

The halogen atom that can be substituted for a hydrogen atom includes a fluorine atom, a chlorine atom, a bromine atom and an iodine atom.

The term "C3-C6 cycloalkylsulfonyl group" represents a cyclic alkylsulfonyl group of three to six carbon atoms, and includes, for example, a cyclopropylsulfonyl group, a cyclobutylsulfonyl group, a cyclopentylsulfonyl group, a cyclohexylsulfonyl group, a 1-methylcyclopropylsulfonyl group and a 2,2-dimethylcyclopropylsulfonyl group.

The term "C3-C6 halocycloalkylsulfonyl group" represents a group wherein at least one hydrogen atom of the C3-C6 cyclic alkylsulfonyl group is substituted with a halogen atom, and includes, for example, a 2-fluorocyclopropylsulfonyl group, a 2,2-difluorocyclopropylsulfonyl group, a 2-chloro-2-fluorocyclopropylsulfonyl group, a 2,2-dichlorocyclopropylsulfonyl group, a 2,2-dibromocyclopropylsulfonyl group, a 2,2-difluoro-1-methylcyclopropylsulfonyl group, a 2,2-dichloro-1-methylcyclopropylsulfonyl group, a 2,2-dibromo-1-methylcyclopropylsulfonyl group, a 1-(trifluoromethyl)cyclopropylsulfonyl group, a 2,2,3,3-tetraflurocyclobutylsulfonyl group, a 2-chlorocyclohexylsulfonyl group, a 4,4-difluorocyclohexylsulfonyl group and a 4-chlorocycohexylsulfonyl group. The halogen atom that can be substituted for a hydrogen atom includes a fluorine atom, a chlorine atom, a bromine atom and an iodine atom.

The term "C2-C8 alkylaminosulfonyl group" represents an aminosulfonyl group having the straight or branched C2-C8 alkylamino group wherein one or two hydrogen atom(s) on the nitrogen atom of the alkyl group is substituted with the straight and/or branched C1-C4 alkyl group which may be same or different from each other, and includes, for example, a methylaminosulfonyl group, an ethylaminosulfonyl group, a propylaminosulfonyl group, an isopropylaminosulfonyl group, a butylaminosulfonyl group, a N,N-dimethylaminosulfonyl group, a N,N-diethylaminosulfonyl group, a N,N-dipropylaminosulfonyl group, a N,N-diisopropylaminosulfonyl group, a pentylaminosulfonyl group and a hexylaminosulfonyl group.

The term "C2-C8 haloalkylaminosulfonyl group" represents a group wherein at least one hydrogen atom of the straight or branched C1-C8 alkylaminosulfonyl group is substituted with a halogen atom, and includes, for example, a 2,2,2-trifluoroethylaminosulfonyl group, a N,N-di-(2,2,2-trifluoroethyl)aminosulfonyl group, a N,N-di-(2,2,2-trichloroethyl)aminosulfonyl group and a pentafluoropropylaminosulfonyl group. The halogen atom that can be substituted for a hydrogen atom includes a fluorine atom, a chlorine atom, a bromine atom and an iodine atom.

The term "C1-C6 alkylsulfinyl group" represents a straight or branched alkylsulfinyl group of one to six carbon atoms, and includes, for example, a methylsulfinyl group, an ethylsulfinyl group, a propylsulfinyl group, an isopropylsulfinyl group, a butylsulfinyl group, an isobutylsulfinyl group, a sec-butylsulfinyl group, a pentylsulfinyl group, an isoamylsulfinyl group, a neopentylsulfinyl group, a 2-pentylsulfinyl group, a 3-pentylsulfinyl group, a 2-methylbutylsulfinyl group, a hexylsulfinyl group, an isohexylsulfinyl group, a 3-methylpentylsulfinyl group and a 4-methylpentylsulfinyl group.

The term "C1-C4 alkylsulfinyl group" represents a straight or branched alkylsulfinyl group of one to four carbon atoms, and includes, for example, a methylsulfinyl group, an ethylsulfinyl group, a propylsulfinyl group, an isopropylsulfinyl group, a butylsulfinyl group, an isobutylsulfinyl group and a sec-butylsulfinyl group.

The term "C1-C6 haloalkylsulfinyl group" represents a group wherein at least one hydrogen atom of the straight or branched C1-C6 alkylsulfinyl group is substituted with a halogen atom, and includes, for example, a trifluoromethylsulfinyl group, a trichloromethylsulfinyl group, a tribromomethylsulfinyl group, a triiodomethylsulfinyl group, a pentafluoroethylsulfinyl group, a pentachloroethylsulfinyl group, a pentabromoethylsulfinyl group, a pentaiodoethylsulfinyl group, a 2,2,2-trichloroethylsulfinyl group, a 2,2,2-trifluoroethylsulfinyl group, a 2,2,2-tribromoethylsulfinyl group, a 2,2,2-triiodoethylsulfinyl group, a heptafluoropropylsulfinyl group, a heptachloropropylsulfinyl group, a heptabromopropylsulfinyl group, a heptaiodopropylsulfinyl group, a 3,3,3-trifluoropropylsulfinyl group, a 3,3,3-trichloropropylsulfinyl group, a 3,3,3-tribromopropylsulfinyl group, a 3,3,3-triiodopropylsulfinyl group, a nonafluorobutylsulfinyl group, a nonachlorobutylsulfinyl group, a nonabromobutylsulfinyl group, a nonaiodobutylsulfinyl group, a per fluoropentylsulfinyl group, a perchloropentylsulfinyl group, a perbromopentylsulfinyl group, a perfluorohexylsulfinyl group, a perchlorohexylsulfinyl group, a perbromohexylsulfinyl group and a periodohexylsulfinyl group. The halogen atom that can be substituted for a hydrogen atom includes a fluorine atom, a chlorine atom, a bromine atom and an iodine atom.

The term "C1-C4 haloalkylsulfinyl group" represents a group wherein at least one hydrogen atom of the straight or branched C1-C4 alkylsulfinyl group is substituted with a halogen atom, and includes, for example, a trifluoromethylsulfinyl group, a trichloromethylsulfinyl group, a tribromomethylsulfinyl group, a triiodomethylsulfinyl group, a pentafluoroethylsulfinyl group, a pentachloroethylsulfinyl group, a pentabromoethylsulfinyl group, a pentaiodoethylsulfinyl group, a 2,2,2-trichloroethylsulfinyl group, a 2,2,2-trifluoroethylsulfinyl group, a 2,2,2-tribromoethylsulfinyl group, a 2,2,2-triiodoethylsulfinyl group, a heptafluoropropylsulfinyl group, a heptachloropropylsulfinyl group, a heptabromopropylsulfinyl group, a heptaiodopropylsulfinyl group, a 3,3,3-trifluoropropylsulfinyl group, a 3,3,3-trichloropropylsulfinyl group, a 3,3,3-tribromopropylsulfinyl group, a 3,3,3-triiodopropylsulfinyl group, a nonafluorobutylsulfinyl group, a nonachlorobutylsulfinyl group, a nonabromobutylsulfinyl group and a nonaiodobutylsulfinyl group. The halogen atom that can be substituted for a hydrogen atom includes a fluorine atom, a chlorine atom, a bromine atom and an iodine atom.

The term "C1-C6 alkyl group optionally having one or more groups selected from Group $P^1$" represents an C1-C6 alkyl group wherein a hydrogen atom being attached to the carbon atom may be optionally substituted with one or more atom or group selected from Group $P^1$, and when said C1-C6 alkyl group has two or more atoms or groups selected from Group $P^1$, the atoms or groups selected from Group $P^1$ may be same or different from each other.

Examples of the C1-C6 alkyl group optionally having one or more groups selected from Group $P^1$ includes a trifluoromethyl group, a trichloromethyl group, a tribromomethyl group, a 2,2,2-trifluoroethyl group, a 2,2,2-trichloroethyl group, a 3,3,3-trifluoropropyl group, a difluoromethyl group, a 2,2-difluoroethyl group, a 1,1-difluoroethyl group, a pentafluoroethyl group, a heptafluoroisopropyl group, a 1,1,2,2-tetrafluoroethyl group, a 2,2,3,3,3-pentafluoropropyl group, a 2,2,3,3,3-pentafluorobutyl group, a cyclopropylmethyl group, a cyclopropylethyl group, a cyclopropylpropyl group, a cyclopropylbutyl group, a cyclopropylpentyl group, a cyclopropylhexyl group, a cyclobutylmethyl group, a cyclobutylethyl group, a cyclobutylpropyl group, a cyclobutylbutyl group, a cyclopentylmethyl group, a cyclopentylethyl group, a cyclopentylpropyl group, a cyclohexylethyl group, a cyclohexylpropyl group, a 1-fluorocyclopropylmethyl group, a 1-fluorocyclopropylethyl group, a 1-fluorocyclopropylpropyl group, a 2,2-difluorocyclopropylmethyl group, a 2,2-difluorocyclopropylethyl group, a 2,2-di fluorocyclopropylpropyl group, a pentafluorocyclopropylmethyl group, a pentafluorocyclopropylethyl group, a pentafluorocyclopropylpropyl group, a 1-chlorocyclopropylmethyl group, a 1-chlorocyclopropylethyl group, a 1-chlorocyclopropylpropyl group, a 2,2-dichlorocyclopropylmethyl group, a 2,2-dichlorocyclopropylethyl group, a 2,2-dichlorocyclopropylpropyl group, a pentachlorocyclopropylmethyl group, a pentachlorocyclopropylethyl group, a pentachlorocyclopropylpropyl group, a 1-fluorocyclobutylmethyl group, a 1-fluorocyclobutylethyl group, a 1-fluorocyclobutylpropyl group, a 2,2-difluorocyclobutylmethyl group, a 2,2-difluorocyclobutylethyl group, a 2,2-difluorocyclobutylpropyl group, a 1-chlorocyclobutylmethyl group, a 1-chlorocyclobutylethyl group, a 1-chlorocyclobutylpropyl group, a 2,2-dichlorocyclobutylmethyl group, a 2,2-dichlorocyclobutylethyl group, a 2,2-dichlorocyclobutylpropyl group, a 1-fluorocyclopentylmethyl group, a 1-fluorocyclopentylethyl group, a 1-fluorocyclopentylpropyl group, a 2,2-difluorocyclopentylmethyl group, a 2,2-difluorocyclopentylethyl group, a 2,2-difluorocyclopentylpropyl group, a 3,3-difluorocyclopentylmethyl group, a 3,3-difluorocyclopentylethyl group, a 3,3-difluorocyclopentylpropyl group, a 1-chlorocyclopentylmethyl group, a 1-chlorocyclopentylethyl group, a 1-chlorocyclopentylpropyl group, a 2,2-dichlorocyclopentylmethyl group, a 2,2-dichlorocyclopentylethyl group, a 2,2-dichlorocyclopentylpropyl group, a 3,3-dichlorocyclopentylmethyl group, a 3,3-dichlorocyclopentylethyl group, a 3,3-dichlorocyclopentylpropyl group, a 1-fluorocyclohexylmethyl group, a 1-fluorocyclohexylethyl group, a 1-fluorocyclohexylpropyl group, a 2,2-difluorocyclohexylmethyl group, a 2,2-difluorocyclohexylethyl group, a 2,2-difluorocyclohexylpropyl group, a 3,3-difluorocyclohexylmethyl group, a 3,3-difluorocyclohexylethyl group, a 3,3-difluorocyclohexylpropyl group, a 4,4-difluorocyclohexylmethyl group, a 4,4-difluorocyclohexylethyl group, a 4,4-difluorocyclohexylpropyl group, a 1-chlorocyclohexylmethyl group, a 1-chlorocyclohexylethyl group, a 1-chlorocyclohexylpropyl group, a 2,2-dichlorocyclohexylmethyl group, a 2,2-dichlorocyclohexylethyl group, a 2,2-dichlorocyclohexylpropyl group, a 3,3-dichlorocyclohexylmethyl group, a 3,3-dichlorocyclohexylethyl group, a 3,3-dichlorocyclohexylpropyl group, a methoxymethyl group, an ethoxymethyl group, an isopropoxymethyl group, a tert-butoxymethyl group, a 2-methoxyethyl group, an 2-ethoxyethyl group, a 2-tert-butoxyethyl group, a 3-methoxypropyl group, an 3-ethoxypropyl group, a trifluoromethoxymethyl group, a 2-trifluoromethoxyethyl group, a 3-trifluoromethoxypropyl group, a 4-trifluoromethoxybutyl group, a difluoromethoxymethyl group, a 2-difluoromethoxyethyl group, a 2-pentafluoroethoxyethyl group, a 3-pentafluoroethoxypropyl group, a 1,1,2,2-tetrafluoroethoxymethyl group, a 2-(1,1,2,2-tetrafluoroethoxy)-ethyl group, a methylthiomethyl group, a 2-methylthioethyl group, a 3-methylthiopropyl group, an ethylthiomethyl group, an 2-ethylthioethyl group, an 3-ethylthiopropyl group, a tert-butylthiomethyl group, a 2-(tert-butylthio)-ethyl group, a 3-(tert-butylthio)-propyl group, a trifluoromethylthiomethyl group, a 2-trifluoromethylthioethyl group, a trifluoromethylthiopropyl group, a cyanomethyl group, a 2-cyanoethyl group, a 3-cyanopropyl group, a 1-cyanoethyl group, a 2-cyano-2-methylethyl group and a 2-cyano-2-methylpropyl group and the others.

The term "C3-C6 cycloalkyl group optionally having one or more groups selected from Group $P^1$" represents an C3-C6 cycloalkyl group wherein a hydrogen atom being attached to the carbon atom may be optionally substituted with one or more atom or group selected from Group $P^1$, and when said C3-C6 alkyl group has two or more atoms or groups selected from Group $P^1$, the atoms or groups selected from Group $P^1$ may be same or different from each other.

Examples of the C3-C6 cycloalkyl group optionally having one or more groups selected from Group $P^1$ include a 1-fluorocyclopropyl group, a 2,2-difluorocyclopropyl group, a 1-chloro-2-fluorocyclopropyl group, a 2,2-dichlorocyclopropyl group, a 2,2-dibromocyclopropyl group, a 2,2-difluoro-1-methylcyclopropyl group, a 2,2-dichloro-1-methylcyclopropyl group, a 2,2-dibromo-1-methylcyclopropyl group, a 2,2,3,3-tetrafluorocyclobutyl group, a 2,2,3,3-tetrafluorocyclobutyl group, a 2-chlorocyclopentyl group, a 3-chlorocyclopentyl group, a 3,3-difluorocyclopentyl group, a 1-fluorocyclohexyl group, a 2,2-difluorocyclohexyl group, a 3,3-difluorocyclohexyl group, a 4,4-difluorocyclohexyl group, a 1-cyclopropylcyclopropyl group, a 2-cyclopropylcyclopropyl group, a 2,2-bis-cyclopropylcyclopropyl group, a 2,3-bis-cyclopropylcyclopropyl group, a 1-cyclopropylcyclobutyl group, a 1-cyclobutylcyclobutyl group, a 2-cyclopropylcyclobutyl group, a 1-cyclopropylcyclopentyl group, a 2-cyclopropylcyclopentyl group, a 1-(1-fluorocyclopropyl)-cyclopropyl group, a 1-(2,2-difluorocyclopropyl)-cyclopropyl group, a 1-(1-chlorocyclopropyl)-cyclopropyl group, a 1-(2,2-dichlorocyclopropyl)-cyclopropyl group, a 1-methoxycyclopropyl group, a 1-methoxycyclobutyl group, a 1-methoxycyclopentyl group, a 1-methoxycyclohexyl group, a 2-methoxycyclopropyl group, a 2-methoxycyclobutyl group, a 2-methoxycyclopentyl group, a 2-methoxycyclohexyl group, an 2-ethoxycyclopropyl group, an 2-ethoxycyclobutyl group, an 2-ethoxycyclopentyl group, an 2-ethoxycyclohexyl group, an 1-ethoxycyclopropyl group, an 1-ethoxycyclobutyl group, an 1-ethoxycyclopentyl group, an 1-ethoxycyclohexyl group, an 1-isopropoxycyclopropyl group, an 1-isopropoxycyclobutyl group, an 1-isopropoxycyclopentyl group, an 1-isopropoxycyclohexyl group, a 1-trifluoromethoxycyclopropyl group, a 2-trifluoromethoxycyclopropyl group, a 1-difluoromethoxycyclopropyl group, a 2-difluoromethoxycyclopropyl group, a 1-(2,2-difluoroethoxy)-cyclopropyl group, a 2-(2,2-difluoroethoxy)-cyclopropyl group, a 1-methylthiocyclopropyl group, an 1-ethylthiocyclopropyl group, a 2-methylthiocyclopropyl group, an 2-ethylthiocyclopropyl group, a 1-trifluoromethylthiocyclopropyl group, a 2-trifluoromethylthiocyclopropyl group, a 1-cyanocyclopropyl group, a 2-cyanocyclopropyl group and a 2,2-dicyanocyclopropyl group and the others.

$Y^1$ and $Y^2$ may combine each other together with the carbon atom to which they are attached to form a five-, six- or seven-membered saturated ring, and the saturated ring may optionally contain one or more oxygen atoms or sulfur atoms as the ring-constituent atom, and the saturated ring may optionally have one or more groups selected from Group $P^1$ as substituent. Examples of Q1 include the following structures:

Q1;

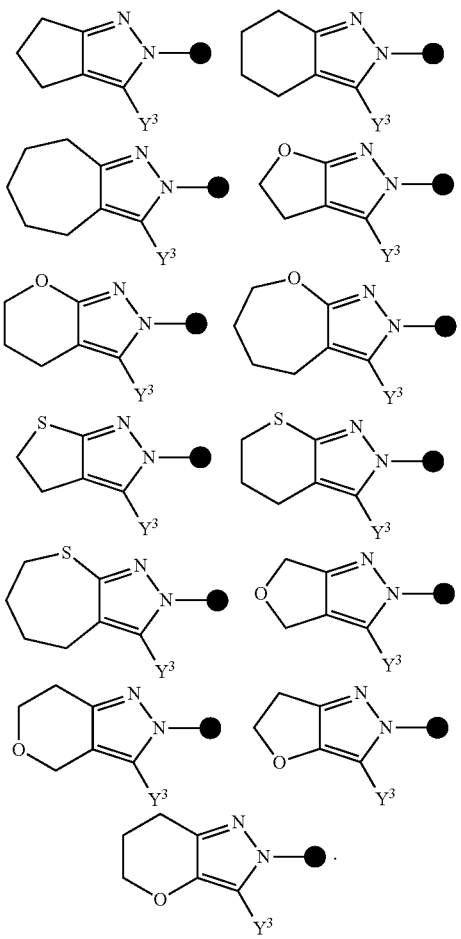

In terms of a convenience of production, preferred Q1 includes the following structures:
Q1;

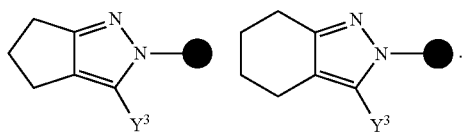

More preferred Q1 includes the following structure:
Q1;

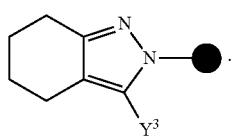

Y² and Y³ may combine each other together with the carbon atom to which they are attached to form a five-, six- or seven-membered saturated ring, and the saturated ring may optionally contain one or more oxygen atoms or sulfur atoms as the ring-constituent atom, and the saturated ring may optionally have one or more groups selected from Group P¹ as substituent. Examples of Q1 include the following structures:
Q1;

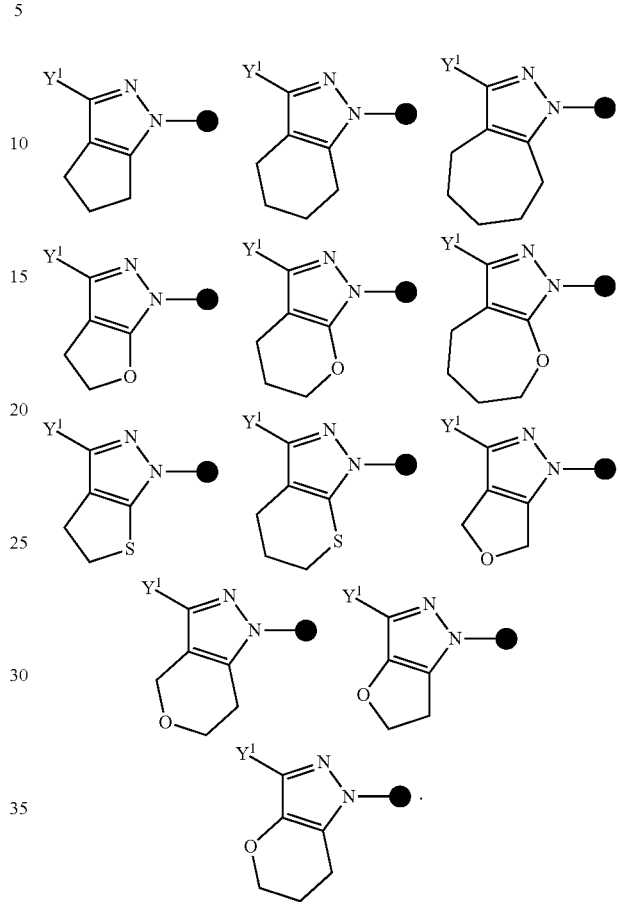

In terms of a convenience of production, preferred Q1 includes the following structures:
Q1;

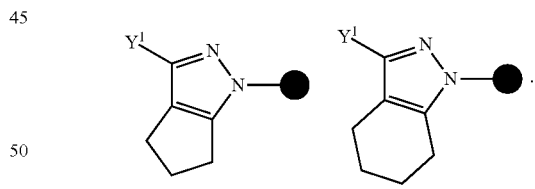

More preferred Q1 includes the following structure:
Q1;

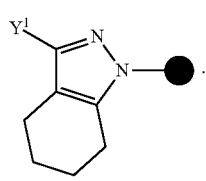

Z¹ and Z² may combine each other together with the carbon atom to which they are attached to form a five-, six- or seven-membered saturated ring, and the saturated ring may optionally contain one or more oxygen atoms or sulfur atoms as the ring-constituent atom, and the saturated ring may optionally have one or more groups selected from Group P¹ as substituent. Examples of Q2 include the following structures:

Q2;

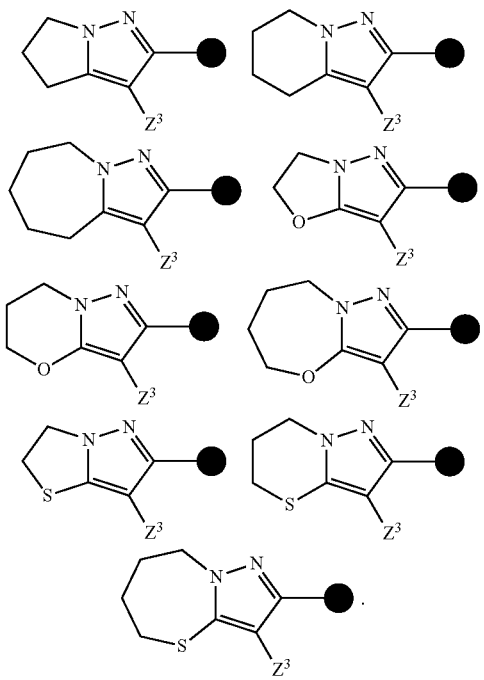

In terms of a convenience of production, preferred Q2 includes the following structures:

Q2;

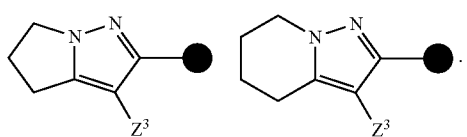

More preferred Q2 includes the following structures:

Q2;

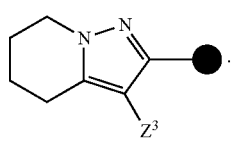

$Z^2$ and $Z^3$ may combine each other together with the carbon atom to which they are attached to form a five-, six- or seven-membered saturated ring, and the saturated ring may optionally contain one or more oxygen atoms, sulfur atoms or nitrogen atoms as the ring-constituent atom, and the saturated ring may optionally have one or more substituents selected from Group P¹ as substituent. Examples of Q2 include the following structures:

Q2;

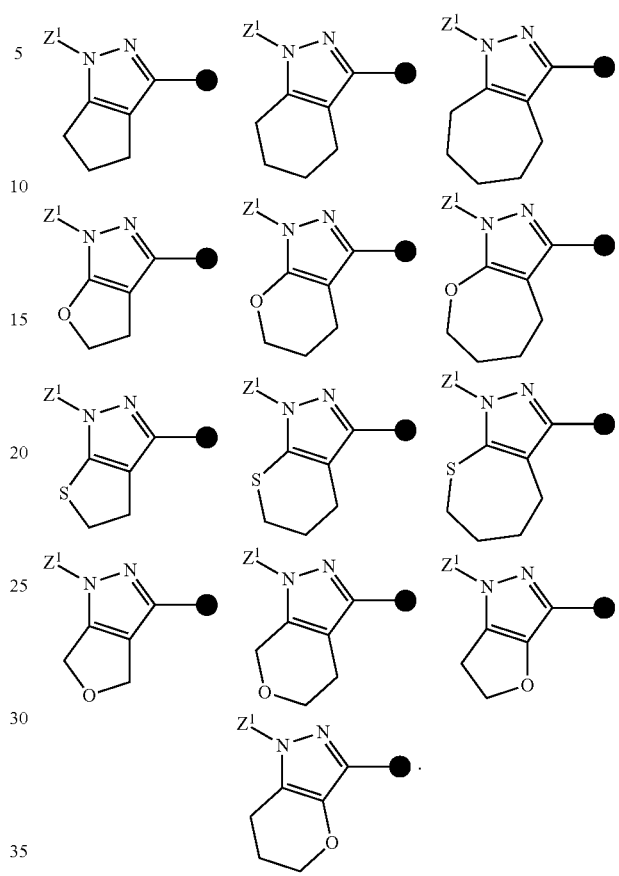

Examples of an embodiment of the present compound include the compounds of the formula (1) wherein the substituents represent the following ones.

a compound of the formula (1) wherein $R^1$ represents a methyl group, an ethyl group, a propyl group or a butyl group;

a compound of the formula (1) wherein $R^1$ represents an ethynyl group, a 1-propynyl group, a 2-propynyl group, a 1-butynyl group or a 2-butynyl group;

a compound of the formula (1) wherein $R^1$ represents a cyclopropyl group;

a compound of the formula (1) wherein $R^1$ represents a trifluoromethyl group;

a compound of the formula (1) wherein $R^1$ represents a fluorine atom, a chlorine atom, a bromine atom or an iodine atom;

a compound of the formula (1) wherein $R^2$ represents a hydrogen atom or a fluorine atom;

a compound of the formula (1) wherein $R^4$ represents a hydrogen atom or a fluorine atom;

a compound of the formula (1) wherein $R^5$ represents a hydrogen atom or a fluorine atom;

a compound of the formula (1) wherein $R^7$ represents a hydrogen atom or a fluorine atom;

a compound of the formula (1) wherein $R^8$ represents a hydrogen atom or a fluorine atom;

a compound of the formula (1) wherein $R^9$ represents a hydrogen atom or a fluorine atom;

a compound of the formula (1) wherein $R^{11}$ represents a hydrogen atom or a fluorine atom;

a compound of the formula (1) wherein $R^2$ represents a hydrogen atom;

a compound of the formula (1) wherein $R^4$ represents a hydrogen atom;

a compound of the formula (1) wherein $R^5$ represents a hydrogen atom;

a compound of the formula (1) wherein $R^7$ represents a hydrogen atom;

a compound of the formula (1) wherein $R^8$ represents a hydrogen atom;

a compound of the formula (1) wherein $R^9$ represents a hydrogen atom;

a compound of the formula (1) wherein $R^{11}$ represents a hydrogen atom;

a compound of the formula (1) wherein $R^6$ represents an ethynyl group or a 1-propynyl group;

a compound of the formula (1) wherein $R^6$ represents 3-fluoropropionyl group, a 3-chloropropynyl group, 3-bromopropynyl group, an 3-iodopropynyl group, a 3,3-difluoropropionyl group or a 3,3,3-trifluoropropionyl group;

a compound of the formula (1) wherein $R^6$ represents a difluoromethoxy group, a trifluoromethoxy group, a 2,2-difluoroethoxy group, a 2,2,2-trifluoroethoxy group or a pentafluoroethoxy group;

a compound of the formula (1) wherein $R^6$ represents a methylthio group or an ethylthio group;

a compound of the formula (1) wherein $R^6$ represents a trifluoromethylthio group, a 2,2,2-trifluoroethylthio group, a 2,2,2-trichloromethylthio group or a pentafluoroethylthio group;

a compound of the formula (1) wherein $R^6$ represents a cyclopropyl group, a cyclobutyl group or a cyclopentyl group;

a compound of the formula (1) wherein $R^6$ represents a 1-fluorocyclopropyl group, a 1-chlorocyclopropyl group, a 1-bromocyclopropyl group, a 2-fluorocyclopropyl group, a 2-chlorocyclopropyl group, a 2-bromocyclopropyl group, a 2,2-difluorocyclopropyl group, a 2,2-dichlorocyclopropyl group, a 2,2-dibromocyclopropyl group, a 2,2,3,3-tetrafluorocyclopropyl group, a 2,2,3,3-tetrachlorocyclopropyl group or a 2,2,3,3-tetrabromocyclopropyl group;

a compound of the formula (1) wherein $R^6$ represents a methyl group, an ethyl group, a propyl group, a butyl group or an isobutyl group;

a compound of the formula (1) wherein $R^6$ represents a vinyl group, a 1-propenyl group or a 2-propenyl group;

a compound of the formula (1) wherein $R^6$ represents a methoxy group, an ethoxy group or a propyloxy group;

a compound of the formula (1) wherein $R^6$ represents a trifluoromethyl group, a difluoromethyl group, a pentafluoroethyl group, a 3,3,3-trifluoroethyl group or a 2,2-difluoroethyl group;

a compound of the formula (1) wherein $R^6$ represents a fluorine atom, a chlorine atom, a bromine atom or an iodine atom;

a compound of the formula (1) wherein $R^6$ represents a cyano group;

a compound of the formula (1) wherein $R^3$ represents a hydrogen atom;

a compound of the formula (1) wherein $R^3$ represents a methyl group, an ethyl group, a fluorine atom, a chlorine atom, a bromine atom or an iodine atom;

a compound of the formula (1) wherein $R^{10}$ represents a methyl group, an ethyl group, a difluoromethyl group, a trifluoromethyl group or a 2,2-difluoroethyl group;

a compound of the formula (1) wherein $R^{10}$ represents a methyl group;

a compound of the formula (1) wherein X represents an oxygen atom;

a compound of the formula (1) wherein X represents a sulfur atom;

a compound of the formula (1) wherein $A^1$ and $A^3$ may be same or different from each other, and represent independently of each other a hydrogen atom, a halogen atom or a cyano group;

a compound of the formula (1) wherein $A^1$ and $A^3$ may be same or different from each other, and represent independently of each other an C1-C6 alkyl group;

a compound of the formula (1) wherein $A^1$ and $A^3$ may be same or different from each other, and represent independently of each other a C1-C6 haloalkyl group;

a compound of the formula (1) wherein $A^2$ and $Z^4$ may be same or different from each other, and represent independently of each other an C1-C6 alkyl group;

a compound of the formula (1) wherein $A^2$ and $Z^4$ may be same or different from each other, and represent independently of each other a C1-C6 haloalkyl group;

a compound of the formula (1) wherein $A^2$ and $Z^4$ may be same or different from each other, and represent independently of each other an C1-C6 alkynyl group;

a compound of the formula (1) wherein $A^2$ and $Z^4$ may be same or different from each other, and represent independently of each other a C1-C6 haloalkynyl group;

a compound of the formula (1) wherein $Z^1$ represents an C1-C6 alkyl group which may be optionally substituted with a group selected from Group $P^1$;

a compound of the formula (1) wherein $Z^2$ represents an C1-C6 alkyl group which may be optionally substituted with a group selected from Group $P^1$;

a compound of the formula (1) wherein $R^2$, $R^4$, $R^5$, $R^7$, $R^8$, $R^9$ and $R^{11}$ represent a hydrogen atom;

a compound of the formula (1) wherein $R^2$, $R^4$, $R^5$, $R^7$, $R^8$, $R^9$ and $R^{11}$ represent a hydrogen atom and X represents an oxygen atom;

a compound of the formula (1) wherein $R^2$, $R^4$, $R^5$, $R^7$, $R^8$, $R^9$ and $R^{11}$ represent a hydrogen atom and $R^{10}$ represents a methyl group;

a compound of the formula (1) wherein $R^2$, $R^4$, $R^5$, $R^7$, $R^8$, $R^9$ and $R^{11}$ represent a hydrogen atom, $R^{10}$ represents a methyl group, and X represents an oxygen atom;

a compound of the formula (1) wherein $R^2$, $R^4$, $R^5$, $R^7$, $R^8$, $R^9$ and $R^{11}$ represent a hydrogen atom, $R^{10}$ represents a methyl group, X represents an oxygen atom and Q represents Q1 or Q2;

a compound of the formula (1) wherein $R^2$, $R^4$, $R^5$, $R^7$, $R^8$, $R^9$ and $R^{11}$ represent a hydrogen atom, $R^{10}$ represents a methyl group, X represents an oxygen atom and Q represents Q1, Q2 or Q4;

a compound of the formula (1) wherein $R^2$, $R^4$, $R^5$, $R^7$, $R^8$, $R^9$ and $R^{11}$ represent a hydrogen atom, $R^{10}$ represents a methyl group, X represents an oxygen atom and Q represents Q1;

a compound of the formula (1) wherein $R^2$, $R^4$, $R^5$, $R^7$, $R^8$, $R^9$ and $R^{11}$ represent a hydrogen atom, $R^{10}$ represents a methyl group, X represents an oxygen atom and Q represents Q2;

a compound of the formula (1) wherein $R^2$, $R^4$, $R^5$, $R^7$, $R^8$, $R^9$ and $R^{11}$ represent a hydrogen atom, $R^{10}$ represents a methyl group, X represents an oxygen atom and Q represents Q3;

a compound of the formula (1) wherein $R^2$, $R^4$, $R^5$, $R^7$, $R^8$, $R^9$ and $R^{11}$ represent a hydrogen atom, $R^{10}$ represents a methyl group, X represents an oxygen atom and Q represents Q4;

a compound of the formula (1) wherein $R^1$ represents a halogen atom;

a compound of the formula (1) wherein $R^1$ represents an C1-C3 alkyl group;

a compound of the formula (1) wherein $R^1$ represents a C1-C3 haloalkyl group;

a compound of the formula (1) wherein $R^1$ represents an C2-C3 alkynyl group;

a compound of the formula (1) wherein $R^1$ represents a C2-C3 haloalkynyl group;

a compound of the formula (1) wherein $R^1$ represents a C3-C5 cycloalkyl group;

a compound of the formula (1) wherein $R^1$ represents a C3-C5 halocycloalkyl group;

a compound of the formula (1) wherein $R^1$ represents an C1-C3 alkoxy group;

a compound of the formula (1) wherein $R^1$ represents a C1-C3 haloalkoxy group;

a compound of the formula (1) wherein $R^1$ represents a halogen atom, an C1-C3 alkyl group, a C1-C3 haloalkyl group or a C3-C5 cycloalkyl group;

a compound of the formula (1) wherein $R^1$ represents a halogen atom, an C1-C3 alkyl group or a C1-C3 haloalkyl group;

a compound of the formula (1) wherein $R^1$ represents a chlorine atom, a bromine atom, a methyl group, an ethyl group or a trifluoromethyl group;

a compound of the formula (1) wherein $R^3$ represents a hydrogen atom;

a compound of the formula (1) wherein $R^3$ represents a halogen atom;

a compound of the formula (1) wherein $R^3$ represents an C1-C3 alkyl group;

a compound of the formula (1) wherein $R^3$ represents a C1-C3 haloalkyl group;

a compound of the formula (1) wherein $R^3$ represents a hydrogen atom, a halogen atom or an C1-C3 alkyl group;

a compound of the formula (1) wherein $R^3$ represents a hydrogen atom, a chlorine atom or a methyl group;

a compound of the formula (1) wherein $R^3$ represents a hydrogen atom or a methyl group;

a compound of the formula (1) wherein $R^6$ represents an ethynyl group or a 1-propynyl group;

a compound of the formula (1) wherein $R^6$ represents an C2-C3 alkynyl group;

a compound of the formula (1) wherein $R^6$ represents a C2-C3 haloalkynyl group;

a compound of the formula (1) wherein $R^6$ represents a C1-C4 haloalkoxy group;

a compound of the formula (1) wherein $R^6$ represents an C1-C4 alkylthio group;

a compound of the formula (1) wherein $R^6$ represents an C1-C4 haloalkylthio group;

a compound of the formula (1) wherein $R^6$ represents a C3-C6 cycloalkyl group;

a compound of the formula (1) wherein $R^6$ represents a C3-C6 halocycloalkyl group;

a compound of the formula (1) wherein $R^6$ represents an ethynyl group, a 1-propynyl group, a C1-C4 haloalkoxy group, an C1-C4 alkylthio group or a C3-C6 cycloalkyl group;

a compound of the formula (1) wherein $R^6$ represents an ethynyl group, a 1-propynyl group, a C1-C2 haloalkoxy group, an C1-C2 alkylthio group or a C3-C4 cycloalkyl group;

a compound of the formula (1) wherein $R^6$ represents an ethynyl group, a 1-propynyl group, a difluoromethoxy group, a trifluoromethoxy group, a methylthio group or a cyclopropyl group;

a compound of the formula (1) wherein Q represents Q1, $R^1$ represents a halogen atom, an C1-C3 alkyl group, a C1-C3 haloalkyl group or a C3-C5 cycloalkyl group, $R^2$, $R^4$, $R^5$, $R^7$, $R^8$, $R^9$ and $R^{11}$ represent a hydrogen atom, $R^3$ represents a hydrogen atom, a halogen atom or an C1-C3 alkyl group, $R^6$ represents an ethynyl group, a 1-propynyl group, a C1-C4 haloalkoxy group, an C1-C4 alkylthio group or a C3-C6 cycloalkyl group, $R^{10}$ represents a methyl group, and X represents an oxygen atom;

a compound of the formula (1) wherein Q represents Q1, $R^1$ represents a halogen atom, an C1-C3 alkyl group, a C1-C3 haloalkyl group or a C3-C5 cycloalkyl group, $R^2$, $R^4$, $R^5$, $R^7$, $R^8$, $R^9$ and $R^{11}$ represent a hydrogen atom, $R^3$ represents a hydrogen atom, a halogen atom or an C1-C3 alkyl group, $R^6$ represents an ethynyl group, a 1-propynyl group, a C1-C2 haloalkoxy group, an C1-C2 alkylthio group or a C3-C4 cycloalkyl group, $R^{10}$ represents a methyl group, and X represents an oxygen atom;

a compound of the formula (1) wherein Q represents Q1, $R^1$ represents a halogen atom, an C1-C3 alkyl group, a C1-C3 haloalkyl group or a C3-C5 cycloalkyl group, $R^2$, $R^4$, $R^5$, $R^7$, $R^8$, $R^9$ and $R^{11}$ represent a hydrogen atom, $R^3$ represents a hydrogen atom, a halogen atom or an C1-C3 alkyl group, $R^6$ represents an ethynyl group, a 1-propynyl group, a difluoromethoxy group, a trifluoromethoxy group, a methylthio group or a cyclopropyl group, $R^{10}$ represents a methyl group, and X represents an oxygen atom;

a compound of the formula (1) wherein Q represents Q1, $R^1$ represents a halogen atom, an C1-C3 alkyl group, a C1-C3 haloalkyl group or a C3-C5 cycloalkyl group, $R^2$, $R^4$, $R^5$, $R^7$, $R^8$, $R^9$ and $R^{11}$ represent a hydrogen atom, $R^3$ represents a hydrogen atom, a chlorine atom or a methyl group, $R^6$ represents an ethynyl group, a 1-propynyl group, a C1-C4 haloalkoxy group, an C1-C4 alkylthio group or a C3-C6 cycloalkyl group, $R^{10}$ represents a methyl group, and X represents an oxygen atom;

a compound of the formula (1) wherein Q represents Q1, $R^1$ represents a halogen atom, an C1-C3 alkyl group, a C1-C3 haloalkyl group or a C3-C5 cycloalkyl group, $R^2$, $R^4$, $R^5$, $R^7$, $R^8$, $R^9$ and $R^{11}$ represent a hydrogen atom, $R^3$ represents a hydrogen atom, a chlorine atom or a methyl group, $R^6$ represents an ethynyl group, a 1-propynyl group, a C1-C2 haloalkoxy group, an C1-C2 alkylthio group or a C3-C4 cycloalkyl group, $R^{10}$ represents a methyl group, and X represents an oxygen atom;

a compound of the formula (1) wherein Q represents Q1, $R^1$ represents a halogen atom, an C1-C3 alkyl group, a C1-C3 haloalkyl group or a C3-C5 cycloalkyl group, $R^2$, $R^4$, $R^5$, $R^7$, $R^8$, $R^9$ and $R^{11}$ represent a hydrogen atom, $R^3$ represents a hydrogen atom, a chlorine atom or a methyl group, $R^6$ represents an ethynyl group, a 1-propynyl group, a difluoromethoxy group, a trifluoromethoxy group, a methylthio group or a cyclopropyl group, $R^{10}$ represents a methyl group, and X represents an oxygen atom;

a compound of the formula (1) wherein Q represents Q1, $R^1$ represents a halogen atom, an C1-C3 alkyl group, a C1-C3 haloalkyl group or a C3-C5 cycloalkyl group, $R^2$, $R^4$, $R^5$, $R^7$, $R^8$, $R^9$ and $R^{11}$ represent a hydrogen atom, $R^3$ represents a hydrogen atom or a methyl group, $R^6$ represents an ethynyl group, a 1-propynyl group, a C1-C4 haloalkoxy group, an C1-C4 alkylthio group or a C3-C6 cycloalkyl group, $R^{10}$ represents a methyl group, and X represents an oxygen atom;

a compound of the formula (1) wherein Q represents Q1, $R^1$ represents a halogen atom, an C1-C3 alkyl group, a C1-C3 haloalkyl group or a C3-C5 cycloalkyl group, $R^5$, $R^7$, $R^8$, $R^9$ and $R^{11}$ represent a hydrogen atom, $R^3$ represents a hydrogen atom or a methyl group, $R^6$ represents an ethynyl group, a 1-propynyl group, a C1-C2 haloalkoxy group, an C1-C2 alkylthio group or a C3-C4 cycloalkyl group, $R^{10}$ represents a methyl group, and X represents an oxygen atom;

a compound of the formula (1) wherein Q represents Q1, $R^1$ represents a halogen atom, an C1-C3 alkyl group, a C1-C3 haloalkyl group or a C3-C5 cycloalkyl group, $R^2$, $R^4$, $R^5$, $R^7$, $R^8$, $R^9$ and $R^{11}$ represent a hydrogen atom, $R^3$ represents a hydrogen atom or a methyl group, $R^6$ represents an ethynyl group, a 1-propynyl group, a difluoromethoxy group, a trifluoromethoxy group, a methylthio group or a cyclopropyl group, $R^{10}$ represents a methyl group, and X represents an oxygen atom;

a compound of the formula (1) wherein Q represents Q1, $R^1$ represents a halogen atom, an C1-C3 alkyl group or a C1-C3 haloalkyl group, $R^2$, $R^4$, $R^5$, $R^7$, $R^8$, $R^9$ and $R^{11}$ represent a hydrogen atom, $R^3$ represents a hydrogen atom, a halogen atom or an C1-C3 alkyl group, $R^6$ represents an ethynyl group, a 1-propynyl group, a C1-C4 haloalkoxy group, an C1-C4 alkylthio group or a C3-C6 cycloalkyl group, $R^{10}$ represents a methyl group, and X represents an oxygen atom;

a compound of the formula (1) wherein Q represents Q1, $R^1$ represents a halogen atom, an C1-C3 alkyl group or a C1-C3 haloalkyl group, $R^2$, $R^4$, $R^5$, $R^7$, $R^8$, $R^9$ and $R^{11}$ represent a hydrogen atom, $R^3$ represents a hydrogen atom, a halogen atom or an C1-C3 alkyl group, $R^6$ represents an ethynyl group, a 1-propynyl group, a C1-C2 haloalkoxy group, an C1-C2 alkylthio group or a C3-C4 cycloalkyl group, $R^{10}$ represents a methyl group, and X represents an oxygen atom;

a compound of the formula (1) wherein Q represents Q1, $R^1$ represents a halogen atom, an C1-C3 alkyl group or a C1-C3 haloalkyl group, $R^2$, $R^4$, $R^5$, $R^7$, $R^8$, $R^9$ and $R^{11}$ represent a hydrogen atom, $R^3$ represents a hydrogen atom, a halogen atom or an C1-C3 alkyl group, $R^6$ represents an ethynyl group, a 1-propynyl group, a difluoromethoxy group, a trifluoromethoxy group, a methylthio group or a cyclopropyl group, $R^{10}$ represents a methyl group, and X represents an oxygen atom;

a compound of the formula (1) wherein Q represents Q1, $R^1$ represents a halogen atom, an C1-C3 alkyl group or a C1-C3 haloalkyl group, $R^2$, $R^4$, $R^5$, $R^7$, $R^8$, $R^9$ and $R^{11}$ represent a hydrogen atom, $R^3$ represents a hydrogen atom, a chlorine atom or a methyl group, $R^6$ represents an ethynyl group, a 1-propynyl group, a C1-C4 haloalkoxy group, an C1-C4 alkylthio group or a C3-C6 cycloalkyl group, and X represents an oxygen atom;

a compound of the formula (1) wherein Q represents Q1, $R^1$ represents a halogen atom, an C1-C3 alkyl group or a C1-C3 haloalkyl group, $R^2$, $R^4$, $R^5$, $R^7$, $R^8$, $R^9$ and $R^{11}$ represent a hydrogen atom, $R^3$ represents a hydrogen atom, a chlorine atom or a methyl group, $R^6$ represents an ethynyl group, a 1-propynyl group, a C1-C2 haloalkoxy group, an C1-C alkylthio group or a C3-C4 cycloalkyl group, $R^{10}$ represents a methyl group, and X represents an oxygen atom;

a compound of the formula (1) wherein Q represents Q1, $R^1$ represents a halogen atom, an C1-C3 alkyl group or a C1-C3 haloalkyl group, $R^2$, $R^4$, $R^5$, $R^7$, $R^8$, $R^9$ and $R^{11}$ represent a hydrogen atom, $R^3$ represents a hydrogen atom, a chlorine atom or a methyl group, $R^6$ represents an ethynyl group, a 1-propynyl group, a difluoromethoxy group, a trifluoromethoxy group, a methylthio group or a cyclopropyl group, $R^{10}$ represents a methyl group, and X represents an oxygen atom;

a compound of the formula (1) wherein Q represents Q1, $R^1$ represents a halogen atom, an C1-C3 alkyl group or a C1-C3 haloalkyl group, $R^2$, $R^4$, $R^5$, $R^7$, $R^8$, $R^9$ and $R^{11}$ represent a hydrogen atom, $R^3$ represents a hydrogen atom or a methyl group, $R^6$ represents an ethynyl group, a 1-propynyl group, a C1-C4 haloalkoxy group, an C1-C4 alkylthio group or a C3-C6 cycloalkyl group, $R^{10}$ represents a methyl group, and X represents an oxygen atom;

a compound of the formula (1) wherein Q represents Q1, $R^1$ represents a halogen atom, an C1-C3 alkyl group or a C1-C3 haloalkyl group, $R^2$, $R^4$, $R^5$, $R^7$, $R^8$, $R^9$ and $R^{11}$ represent a hydrogen atom, $R^3$ represents a hydrogen atom or a methyl group, $R^6$ represents an ethynyl group, a 1-propynyl group, a C1-C2 haloalkoxy group, an C1-C2 alkylthio group or a C3-C4 cycloalkyl group, $R^{10}$ represents a methyl group, and X represents an oxygen atom;

a compound of the formula (1) wherein Q represents Q1, $R^1$ represents a halogen atom, an C1-C3 alkyl group or a C1-C3 haloalkyl group, $R^2$, $R^4$, $R^5$, $R^7$, $R^8$, $R^9$ and $R^{11}$ represent a hydrogen atom, $R^3$ represents a hydrogen atom or a methyl group, $R^6$ represents an ethynyl group, a 1-propynyl group, a difluoromethoxy group, a trifluoromethoxy group, a methylthio group or a cyclopropyl group, $R^{10}$ represents a methyl group, and X represents an oxygen atom;

a compound of the formula (1) wherein Q represents Q1, $R^1$ represents a chlorine atom, a bromine atom, a methyl group, an ethyl group or a trifluoromethyl group, $R^2$, $R^4$, $R^5$, $R^7$, $R^8$, $R^9$ and $R^{11}$ represent a hydrogen atom, $R^3$ represents a hydrogen atom, a halogen atom or an C1-C3 alkyl group, $R^6$ represents an ethynyl group, a 1-propynyl group, a C1-C4 haloalkoxy group, an C1-C4 alkylthio group or a C3-C6 cycloalkyl group, $R^{10}$ represents a methyl group, and X represents an oxygen atom;

a compound of the formula (1) wherein Q represents Q1, $R^1$ represents a chlorine atom, a bromine atom, a methyl group, an ethyl group or a trifluoromethyl group, $R^2$, $R^4$, $R^5$, $R^7$, $R^8$, $R^9$ and $R^{11}$ represent a hydrogen atom, $R^3$ represents a hydrogen atom, a halogen atom or an C1-C3 alkyl group, $R^6$ represents an ethynyl group, a 1-propynyl group, a C1-C2 haloalkoxy group, an C1-C2 alkylthio group or a C3-C4 cycloalkyl group, $R^{10}$ represents a methyl group, and X represents an oxygen atom;

a compound of the formula (1) wherein Q represents Q1, $R^1$ represents a chlorine atom, a bromine atom, a methyl group, an ethyl group or a trifluoromethyl group, $R^2$, $R^4$, $R^5$, $R^7$, $R^8$, $R^9$ and $R^{11}$ represent a hydrogen atom, $R^3$ represents a hydrogen atom, a halogen atom or an C1-C3 alkyl group, $R^6$ represents an ethynyl group, a 1-propynyl group, a difluoromethoxy group, a trifluoromethoxy group, a methylthio group or a cyclopropyl group, $R^{10}$ represents a methyl group, and X represents an oxygen atom;

a compound of the formula (1) wherein Q represents Q1, $R^1$ represents a chlorine atom, a bromine atom, a methyl group, an ethyl group or a trifluoromethyl group, $R^2$, $R^4$, $R^5$, $R^7$, $R^8$, $R^9$ and $R^{11}$ represent a hydrogen atom, $R^3$ represents a hydrogen atom, a chlorine atom or a methyl group, $R^6$ represents an ethynyl group, a 1-propynyl group, a C1-C4 haloalkoxy group, an C1-C4 alkylthio group or a C3-C6 cycloalkyl group, $R^{10}$ represents a methyl group, and X represents an oxygen atom;

a compound of the formula (1) wherein Q represents Q1, $R^1$ represents a chlorine atom, a bromine atom, a methyl group, an ethyl group or a trifluoromethyl group, $R^2$, $R^4$, $R^5$, $R^7$, $R^8$, $R^9$ and $R^{11}$ represent a hydrogen atom, $R^3$ represents a hydrogen atom, a chlorine atom or a methyl group, $R^6$ represents an ethynyl group, a 1-propynyl group, a C1-C2 haloalkoxy group, an C1-C2 alkylthio group or a C3-C4 cycloalkyl group, $R^{10}$ represents a methyl group, and X represents an oxygen atom;

a compound of the formula (1) wherein Q represents Q1, $R^1$ represents a chlorine atom, a bromine atom, a methyl group, an ethyl group or a trifluoromethyl group, $R^2, R^4, R^5, R^7, R^8, R^9$ and $R^{11}$ represent a hydrogen atom, $R^3$ represents a hydrogen atom, a chlorine atom or a methyl group, $R^6$ represents an ethynyl group, a 1-propynyl group, a difluoromethoxy group, a trifluoromethoxy group, a methylthio group or a cyclopropyl group, $R^{10}$ represents a methyl group, and X represents an oxygen atom;

a compound of the formula (1) wherein Q represents Q1, $R^1$ represents a chlorine atom, a bromine atom, a methyl group, an ethyl group or a trifluoromethyl group, $R^2, R^4, R^5, R^7, R^8, R^9$ and $R^{11}$ represent a hydrogen atom, $R^3$ represents a hydrogen atom or a methyl group, $R^6$ represents an ethynyl group, a 1-propynyl group, a C1-C4 haloalkoxy group, an C1-C4 alkylthio group or a C3-C6 cycloalkyl group, $R^{10}$ represents a methyl group, and X represents an oxygen atom;

a compound of the formula (1) wherein Q represents Q1, $R^1$ represents a chlorine atom, a bromine atom, a methyl group, an ethyl group or a trifluoromethyl group, $R^2, R^4, R^5, R^7, R^8, R^9$ and $R^{11}$ represent a hydrogen atom, $R^3$ represents a hydrogen atom or a methyl group, $R^6$ represents an ethynyl group, a 1-propynyl group, a C1-C2 haloalkoxy group, an C1-C2 alkylthio group or a C3-C4 cycloalkyl group, $R^{10}$ represents a methyl group, and X represents an oxygen atom;

a compound of the formula (1) wherein Q represents Q1, $R^1$ represents a chlorine atom, a bromine atom, a methyl group, an ethyl group or a trifluoromethyl group, $R^2, R^4, R^5, R^7, R^8, R^9$ and $R^{11}$ represent a hydrogen atom, $R^3$ represents a hydrogen atom or a methyl group, $R^6$ represents an ethynyl group, a 1-propynyl group, a difluoromethoxy group, a trifluoromethoxy group, a methylthio group or a cyclopropyl group, $R^{10}$ represents a methyl group, and X represents an oxygen atom;

a compound of the formula (1) wherein Q represents Q2, $R^1$ represents a halogen atom, an C1-C3 alkyl group, a C1-C3 haloalkyl group or a C3-C5 cycloalkyl group, $R^2, R^4, R^5, R^7, R^8, R^9$ and $R^{11}$ represent a hydrogen atom, $R^3$ represents a hydrogen atom, a halogen atom or an C1-C3 alkyl group, $R^6$ represents an ethynyl group, a 1-propynyl group, a C1-C4 haloalkoxy group, an C1-C4 alkylthio group or a C3-C6 cycloalkyl group, $R^{10}$ represents a methyl group, and X represents an oxygen atom;

a compound of the formula (1) wherein Q represents Q2, $R^1$ represents a halogen atom, an C1-C3 alkyl group, a C1-C3 haloalkyl group or a C3-C5 cycloalkyl group, $R^2, R^4, R^5, R^7, R^8, R^9$ and $R^{11}$ represent a hydrogen atom, $R^3$ represents a hydrogen atom, a halogen atom or an C1-C3 alkyl group, $R^6$ represents an ethynyl group, a 1-propynyl group, a C1-C2 haloalkoxy group, an C1-C2 alkylthio group or a C3-C4 cycloalkyl group, $R^{10}$ represents a methyl group, and X represents an oxygen atom;

a compound of the formula (1) wherein Q represents Q2, $R^1$ represents a halogen atom, an C1-C3 alkyl group, a C1-C3 haloalkyl group or a C3-C5 cycloalkyl group, $R^2, R^4, R^5, R^7, R^8, R^9$ and $R^{11}$ represent a hydrogen atom, $R^3$ represents a hydrogen atom, a halogen atom or an C1-C3 alkyl group, $R^6$ represents an ethynyl group, a 1-propynyl group, a difluoromethoxy group, a trifluoromethoxy group, a methylthio group or a cyclopropyl group, $R^{10}$ represents a methyl group, and X represents an oxygen atom;

a compound of the formula (1) wherein Q represents Q2, $R^1$ represents a halogen atom, an C1-C3 alkyl group, a C1-C3 haloalkyl group or a C3-C5 cycloalkyl group, $R^2, R^4, R^5, R^7, R^8, R^9$ and $R^{11}$ represent a hydrogen atom, $R^3$ represents a hydrogen atom, a chlorine atom or a methyl group, $R^6$ represents an ethynyl group, a 1-propynyl group, a C1-C4 haloalkoxy group, an C1-C4 alkylthio group or a C3-C6 cycloalkyl group, $R^{10}$ represents a methyl group, and X represents an oxygen atom;

a compound of the formula (1) wherein Q represents Q2, $R^1$ represents a halogen atom, an C1-C3 alkyl group, a C1-C3 haloalkyl group or a C3-C5 cycloalkyl group, $R^2, R^4, R^5, R^7, R^8, R^9$ and $R^{11}$ represent a hydrogen atom, $R^3$ represents a hydrogen atom, a chlorine atom or a methyl group, $R^6$ represents an ethynyl group, a 1-propynyl group, a C1-C2 haloalkoxy group, an C1-C2 alkylthio group or a C3-C4 cycloalkyl group, $R^{10}$ represents a methyl group, and X represents an oxygen atom;

a compound of the formula (1) wherein Q represents Q2, $R^1$ represents a halogen atom, an C1-C3 alkyl group, a C1-C3 haloalkyl group or a C3-C5 cycloalkyl group, $R^2, R^4, R^5, R^7, R^8, R^9$ and $R^{11}$ represent a hydrogen atom, $R^3$ represents a hydrogen atom, a chlorine atom or a methyl group, $R^6$ represents an ethynyl group, a 1-propynyl group, a difluoromethoxy group, a trifluoromethoxy group, a methylthio group or a cyclopropyl group, $R^{10}$ represents a methyl group, and X represents an oxygen atom;

a compound of the formula (1) wherein Q represents Q2, $R^1$ represents a halogen atom, an C1-C3 alkyl group, a C1-C3 haloalkyl group or a C3-C5 cycloalkyl group, $R^2, R^4, R^5, R^7, R^8, R^9$ and $R^{11}$ represent a hydrogen atom, $R^3$ represents a hydrogen atom or a methyl group, $R^6$ represents an ethynyl group, a 1-propynyl group, a C1-C4 haloalkoxy group, an C1-C4 alkylthio group or a C3-C6 cycloalkyl group, $R^{10}$ represents a methyl group, and X represents an oxygen atom;

a compound of the formula (1) wherein Q represents Q2, $R^1$ represents a halogen atom, an C1-C3 alkyl group, a C1-C3 haloalkyl group or a C3-C5 cycloalkyl group, $R^2, R^4, R^5, R^7, R^8, R^9$ and $R^{11}$ represent a hydrogen atom, $R^3$ represents a hydrogen atom or a methyl group, $R^6$ represents an ethynyl group, a 1-propynyl group, a C1-C2 haloalkoxy group, an C1-C2 alkylthio group or a C3-C4 cycloalkyl group, $R^{10}$ represents a methyl group, and X represents an oxygen atom;

a compound of the formula (1) wherein Q represents Q2, $R^1$ represents a halogen atom, an C1-C3 alkyl group, a C1-C3 haloalkyl group or a C3-C5 cycloalkyl group, $R^2, R^4, R^5, R^7, R^8, R^9$ and $R^{11}$ represent a hydrogen atom, $R^3$ represents a hydrogen atom or a methyl group, $R^6$ represents an ethynyl group, a 1-propynyl group, a difluoromethoxy group, a trifluoromethoxy group, a methylthio group or a cyclopropyl group, $R^{10}$ represents a methyl group, and X represents an oxygen atom;

a compound of the formula (1) wherein Q represents Q2, $R^1$ represents a halogen atom, an C1-C3 alkyl group or a C1-C3 haloalkyl group, $R^2, R^4, R^5, R^7, R^8, R^9$ and $R^{11}$ represent a hydrogen atom, $R^3$ represents a hydrogen atom, a halogen atom or an C1-C3 alkyl group, $R^6$ represents an ethynyl group, a 1-propynyl group, a C1-C4 haloalkoxy group, an C1-C4 alkylthio group or a C3-C6 cycloalkyl group, $R^{10}$ represents a methyl group, and X represents an oxygen atom;

a compound of the formula (1) wherein Q represents Q2, $R^1$ represents a halogen atom, an C1-C3 alkyl group or a C1-C3 haloalkyl group, $R^2, R^4, R^5, R^7, R^8, R^9$ and $R^{11}$ represent a hydrogen atom, $R^3$ represents a hydrogen atom, a halogen atom or an C1-C3 alkyl group, R⁶ represents an ethynyl group, a 1-propynyl group, a C1-C2 haloalkoxy group, an C1-C2 alkylthio group or a C3-C4 cycloalkyl group, R¹⁰ represents a methyl group, and X represents an oxygen atom;

a compound of the formula (1) wherein Q represents Q2, R¹ represents a halogen atom, an C1-C3 alkyl group or a C1-C3 haloalkyl group, R², R⁴, R⁵, R⁷, R⁸, R⁹ and R¹¹ represent a hydrogen atom, R³ represents a hydrogen atom, a halogen atom or an C1-C3 alkyl group, R⁶ represents an ethynyl group, a 1-propynyl group, a difluoromethoxy group, a trifluoromethoxy group, a methylthio group or a cyclopropyl group, R¹⁰ represents a methyl group, and X represents an oxygen atom;

a compound of the formula (1) wherein Q represents Q2, R¹ represents a halogen atom, an C1-C3 alkyl group or a C1-C3 haloalkyl group, R², R⁴, R⁵, R⁷, R⁸, R⁹ and R¹¹ represent a hydrogen atom, R³ represents a hydrogen atom, a chlorine atom or a methyl group, R⁶ represents an ethynyl group, a 1-propynyl group, a C1-C4 haloalkoxy group, an C1-C4 alkylthio group or a C3-C6 cycloalkyl group, and X represents an oxygen atom;

a compound of the formula (1) wherein Q represents Q2, R¹ represents a halogen atom, an C1-C3 alkyl group or a C1-C3 haloalkyl group, R², R⁴, R⁵, R⁷, R⁸, R⁹ and R¹¹ represent a hydrogen atom, R³ represents a hydrogen atom, a chlorine atom or a methyl group, R⁶ represents an ethynyl group, a 1-propynyl group, a C1-C2 haloalkoxy group, an C1-C alkylthio group or a C3-C4 cycloalkyl group, R¹⁰ represents a methyl group, and X represents an oxygen atom;

a compound of the formula (1) wherein Q represents Q2, R¹ represents a halogen atom, an C1-C3 alkyl group or a C1-C3 haloalkyl group, R², R⁴, R⁵, R⁷, R⁸, R⁹ and R¹¹ represent a hydrogen atom, R³ represents a hydrogen atom, a chlorine atom or a methyl group, R⁶ represents an ethynyl group, a 1-propynyl group, a difluoromethoxy group, a trifluoromethoxy group, a methylthio group or a cyclopropyl group, R¹⁰ represents a methyl group, and X represents an oxygen atom;

a compound of the formula (1) wherein Q represents Q2, R¹ represents a halogen atom, an C1-C3 alkyl group or a C1-C3 haloalkyl group, R², R⁴, R⁵, R⁷, R⁸, R⁹ and R¹¹ represent a hydrogen atom, R³ represents a hydrogen atom or a methyl group, R⁶ represents an ethynyl group, a 1-propynyl group, a C1-C4 haloalkoxy group, an C1-C4 alkylthio group or a C3-C6 cycloalkyl group, R¹⁰ represents a methyl group, and X represents an oxygen atom;

a compound of the formula (1) wherein Q represents Q2, R¹ represents a halogen atom, an C1-C3 alkyl group or a C1-C3 haloalkyl group, R², R⁴, R⁵, R⁷, R⁸, R⁹ and R¹¹ represent a hydrogen atom, R³ represents a hydrogen atom or a methyl group, R⁶ represents an ethynyl group, a 1-propynyl group, a C1-C2 haloalkoxy group, an C1-C2 alkylthio group or a C3-C4 cycloalkyl group, R¹⁰ represents a methyl group, and X represents an oxygen atom;

a compound of the formula (1) wherein Q represents Q2, R¹ represents a halogen atom, an C1-C3 alkyl group or a C1-C3 haloalkyl group, R², R⁴, R⁵, R⁷, R⁸, R⁹ and R¹¹ represent a hydrogen atom, R³ represents a hydrogen atom or a methyl group, R⁶ represents an ethynyl group, a 1-propynyl group, a difluoromethoxy group, a trifluoromethoxy group, a methylthio group or a cyclopropyl group, R¹⁰ represents a methyl group, and X represents an oxygen atom;

a compound of the formula (1) wherein Q represents Q2, R¹ represents a chlorine atom, a bromine atom, a methyl group, an ethyl group or a trifluoromethyl group, R², R⁴, R⁵, R⁷, R⁸, R⁹ and R¹¹ represent a hydrogen atom, R³ represents a hydrogen atom, a halogen atom or an C1-C3 alkyl group, R⁶ represents an ethynyl group, a 1-propynyl group, a C1-C4 haloalkoxy group, an C1-C4 alkylthio group or a C3-C6 cycloalkyl group, R¹⁰ represents a methyl group, and X represents an oxygen atom;

a compound of the formula (1) wherein Q represents Q2, R¹ represents a chlorine atom, a bromine atom, a methyl group, an ethyl group or a trifluoromethyl group, R², R⁴, R⁵, R⁷, R⁸, R⁹ and R¹¹ represent a hydrogen atom, R³ represents a hydrogen atom, a halogen atom or an C1-C3 alkyl group, R⁶ represents an ethynyl group, a 1-propynyl group, a C1-C2 haloalkoxy group, an C1-C2 alkylthio group or a C3-C4 cycloalkyl group, R¹⁰ represents a methyl group, and X represents an oxygen atom;

a compound of the formula (1) wherein Q represents Q2, R¹ represents a chlorine atom, a bromine atom, a methyl group, an ethyl group or a trifluoromethyl group, R², R⁴, R⁵, R⁷, R⁸, R⁹ and R¹¹ represent a hydrogen atom, R³ represents a hydrogen atom, a halogen atom or an C1-C3 alkyl group, R⁶ represents an ethynyl group, a 1-propynyl group, a difluoromethoxy group, a trifluoromethoxy group, a methylthio group or a cyclopropyl group, R¹⁰ represents a methyl group, and X represents an oxygen atom;

a compound of the formula (1) wherein Q represents Q2, R¹ represents a chlorine atom, a bromine atom, a methyl group, an ethyl group or a trifluoromethyl group, R², R⁴, R⁵, R⁷, R⁸, R⁹ and R¹¹ represent a hydrogen atom, R³ represents a hydrogen atom, a chlorine atom or a methyl group, R⁶ represents an ethynyl group, a 1-propynyl group, a C1-C4 haloalkoxy group, an C1-C4 alkylthio group or a C3-C6 cycloalkyl group, R¹⁰ represents a methyl group, and X represents an oxygen atom;

a compound of the formula (1) wherein Q represents Q2, R¹ represents a chlorine atom, a bromine atom, a methyl group, an ethyl group or a trifluoromethyl group, R², R⁴, R⁵, R⁷, R⁸, R⁹ and R¹¹ represent a hydrogen atom, R³ represents a hydrogen atom, a chlorine atom or a methyl group, R⁶ represents an ethynyl group, a 1-propynyl group, a C1-C2 haloalkoxy group, an C1-C2 alkylthio group or a C3-C4 cycloalkyl group, R¹⁰ represents a methyl group, and X represents an oxygen atom;

a compound of the formula (1) wherein Q represents Q2, R¹ represents a chlorine atom, a bromine atom, a methyl group, an ethyl group or a trifluoromethyl group, R², R⁴, R⁵, R⁷, R⁸, R⁹ and R¹¹ represent a hydrogen atom, R³ represents a hydrogen atom, a chlorine atom or a methyl group, R⁶ represents an ethynyl group, a 1-propynyl group, a difluoromethoxy group, a trifluoromethoxy group, a methylthio group or a cyclopropyl group, R¹⁰ represents a methyl group, and X represents an oxygen atom;

a compound of the formula (1) wherein Q represents Q2, R¹ represents a chlorine atom, a bromine atom, a methyl group, an ethyl group or a trifluoromethyl group, R², R⁴, R⁵, R⁷, R⁸, R⁹ and R¹¹ represent a hydrogen atom, R³ represents a hydrogen atom or a methyl group, R⁶ represents an ethynyl group, a 1-propynyl group, a C1-C4 haloalkoxy group, an C1-C4 alkylthio group or a C3-C6 cycloalkyl group, R¹⁰ represents a methyl group, and X represents an oxygen atom;

a compound of the formula (1) wherein Q represents Q2, R¹ represents a chlorine atom, a bromine atom, a methyl group, an ethyl group or a trifluoromethyl group, R², R⁴, R⁵, R⁷, R⁸, R⁹ and R¹¹ represent a hydrogen atom, R³ represents a hydrogen atom or a methyl group, R⁶ represents an ethynyl group, a 1-propynyl group, a C1-C2 haloalkoxy group, an C1-C2 alkylthio group or a C3-C4 cycloalkyl group, $R^{10}$ represents a methyl group, and X represents an oxygen atom;

a compound of the formula (1) wherein Q represents Q2, $R^1$ represents a chlorine atom, a bromine atom, a methyl group, an ethyl group or a trifluoromethyl group, $R^2$, $R^4$, $R^5$, $R^7$, $R^8$, $R^9$ and $R^{11}$ represent a hydrogen atom, $R^3$ represents a hydrogen atom or a methyl group, $R^6$ represents an ethynyl group, a 1-propynyl group, a difluoromethoxy group, a trifluoromethoxy group, a methylthio group or a cyclopropyl group, $R^{10}$ represents a methyl group, and X represents an oxygen atom;

a compound of the formula (1) wherein Q represents Q3, $R^1$ represents a halogen atom, an C1-C3 alkyl group, a C1-C3 haloalkyl group or a C3-C5 cycloalkyl group, $R^2$, $R^4$, $R^5$, $R^7$, $R^8$, $R^9$ and $R^{11}$ represent a hydrogen atom, $R^3$ represents a hydrogen atom, a halogen atom or an C1-C3 alkyl group, $R^6$ represents an ethynyl group, a 1-propynyl group, a C1-C4 haloalkoxy group, an C1-C4 alkylthio group or a C3-C6 cycloalkyl group, $R^{10}$ represents a methyl group, and X represents an oxygen atom;

a compound of the formula (1) wherein Q represents Q3, $R^1$ represents a halogen atom, an C1-C3 alkyl group, a C1-C3 haloalkyl group or a C3-C5 cycloalkyl group, $R^2$, $R^4$, $R^5$, $R^7$, $R^8$, $R^9$ and $R^{11}$ represent a hydrogen atom, $R^3$ represents a hydrogen atom, a halogen atom or an C1-C3 alkyl group, $R^6$ represents an ethynyl group, a 1-propynyl group, a C1-C2 haloalkoxy group, an C1-C2 alkylthio group or a C3-C4 cycloalkyl group, $R^{10}$ represents a methyl group, and X represents an oxygen atom;

a compound of the formula (1) wherein Q represents Q3, $R^1$ represents a halogen atom, an C1-C3 alkyl group, a C1-C3 haloalkyl group or a C3-C5 cycloalkyl group, $R^2$, $R^4$, $R^5$, $R^7$, $R^8$, $R^9$ and $R^{11}$ represent a hydrogen atom, $R^3$ represents a hydrogen atom, a halogen atom or an C1-C3 alkyl group, $R^6$ represents an ethynyl group, a 1-propynyl group, a difluoromethoxy group, a trifluoromethoxy group, a methylthio group or a cyclopropyl group, $R^{10}$ represents a methyl group, and X represents an oxygen atom;

a compound of the formula (1) wherein Q represents Q3, $R^1$ represents a halogen atom, an C1-C3 alkyl group, a C1-C3 haloalkyl group or a C3-C5 cycloalkyl group, $R^2$, $R^4$, $R^5$, $R^7$, $R^8$, $R^9$ and $R^{11}$ represent a hydrogen atom, $R^3$ represents a hydrogen atom, a chlorine atom or a methyl group, $R^6$ represents an ethynyl group, a 1-propynyl group, a C1-C4 haloalkoxy group, an C1-C4 alkylthio group or a C3-C6 cycloalkyl group, $R^{10}$ represents a methyl group, and X represents an oxygen atom;

a compound of the formula (1) wherein Q represents Q3, $R^1$ represents a halogen atom, an C1-C3 alkyl group, a C1-C3 haloalkyl group or a C3-C5 cycloalkyl group, $R^2$, $R^4$, $R^5$, $R^7$, $R^8$, $R^9$ and $R^{11}$ represent a hydrogen atom, $R^3$ represents a hydrogen atom, a chlorine atom or a methyl group, $R^6$ represents an ethynyl group, a 1-propynyl group, a C1-C2 haloalkoxy group, an C1-C2 alkylthio group or a C3-C4 cycloalkyl group, $R^{10}$ represents a methyl group, and X represents an oxygen atom;

a compound of the formula (1) wherein Q represents Q3, $R^1$ represents a halogen atom, an C1-C3 alkyl group, a C1-C3 haloalkyl group or a C3-C5 cycloalkyl group, $R^2$, $R^4$, $R^5$, $R^7$, $R^8$, $R^9$ and $R^{11}$ represent a hydrogen atom, $R^3$ represents a hydrogen atom, a chlorine atom or a methyl group, $R^6$ represents an ethynyl group, a 1-propynyl group, a difluoromethoxy group, a trifluoromethoxy group, a methylthio group or a cyclopropyl group, $R^{10}$ represents a methyl group, and X represents an oxygen atom;

a compound of the formula (1) wherein Q represents Q3, $R^1$ represents a halogen atom, an C1-C3 alkyl group, a C1-C3 haloalkyl group or a C3-C5 cycloalkyl group, $R^2$, $R^4$, $R^5$, $R^7$, $R^8$, $R^9$ and $R^{11}$ represent a hydrogen atom, $R^3$ represents a hydrogen atom or a methyl group, $R^6$ represents an ethynyl group, a 1-propynyl group, a C1-C4 haloalkoxy group, an C1-C4 alkylthio group or a C3-C6 cycloalkyl group, $R^{10}$ represents a methyl group, and X represents an oxygen atom;

a compound of the formula (1) wherein Q represents Q3, $R^1$ represents a halogen atom, an C1-C3 alkyl group, a C1-C3 haloalkyl group or a C3-C5 cycloalkyl group, $R^2$, $R^4$, $R^5$, $R^7$, $R^8$, $R^9$ and $R^{11}$ represent a hydrogen atom, $R^3$ represents a hydrogen atom or a methyl group, $R^6$ represents an ethynyl group, a 1-propynyl group, a C1-C2 haloalkoxy group, an C1-C2 alkylthio group or a C3-C4 cycloalkyl group, $R^{10}$ represents a methyl group, and X represents an oxygen atom;

a compound of the formula (1) wherein Q represents Q3, $R^1$ represents a halogen atom, an C1-C3 alkyl group, a C1-C3 haloalkyl group or a C3-C5 cycloalkyl group, $R^2$, $R^4$, $R^5$, $R^7$, $R^8$, $R^9$ and $R^{11}$ represent a hydrogen atom, $R^3$ represents a hydrogen atom or a methyl group, $R^6$ represents an ethynyl group, a 1-propynyl group, a difluoromethoxy group, a trifluoromethoxy group, a methylthio group or a cyclopropyl group, $R^{10}$ represents a methyl group, and X represents an oxygen atom;

a compound of the formula (1) wherein Q represents Q3, $R^1$ represents a halogen atom, an C1-C3 alkyl group or a C1-C3 haloalkyl group, $R^2$, $R^4$, $R^5$, $R^7$, $R^8$, $R^9$ and $R^{11}$ represent a hydrogen atom, $R^3$ represents a hydrogen atom, a halogen atom or an C1-C3 alkyl group, $R^6$ represents an ethynyl group, a 1-propynyl group, a C1-C4 haloalkoxy group, an C1-C4 alkylthio group or a C3-C6 cycloalkyl group, $R^{10}$ represents a methyl group, and X represents an oxygen atom;

a compound of the formula (1) wherein Q represents Q3, $R^1$ represents a halogen atom, an C1-C3 alkyl group or a C1-C3 haloalkyl group, $R^2$, $R^4$, $R^5$, $R^7$, $R^8$, $R^9$ and $R^{11}$ represent a hydrogen atom, $R^3$ represents a hydrogen atom, a halogen atom or an C1-C3 alkyl group, $R^6$ represents an ethynyl group, a 1-propynyl group, a C1-C2 haloalkoxy group, an C1-C2 alkylthio group or a C3-C4 cycloalkyl group, $R^{10}$ represents a methyl group, and X represents an oxygen atom; a compound of the formula (1) wherein Q represents Q3, $R^1$ represents a halogen atom, an C1-C3 alkyl group or a C1-C3 haloalkyl group, $R^2$, $R^4$, $R^5$, $R^7$, $R^8$, $R^9$ and $R^{11}$ represent a hydrogen atom, $R^3$ represents a hydrogen atom, a halogen atom or an C1-C3 alkyl group, $R^6$ represents an ethynyl group, a 1-propynyl group, a difluoromethoxy group, a trifluoromethoxy group, a methylthio group or a cyclopropyl group, $R^{10}$ represents a methyl group, and X represents an oxygen atom;

a compound of the formula (1) wherein Q represents Q3, $R^1$ represents a halogen atom, an C1-C3 alkyl group or a C1-C3 haloalkyl group, $R^2$, $R^4$, $R^5$, $R^7$, $R^8$, $R^9$ and $R^{11}$ represent a hydrogen atom, $R^3$ represents a hydrogen atom, a chlorine atom or a methyl group, $R^6$ represents an ethynyl group, a 1-propynyl group, a C1-C4 haloalkoxy group, an C1-C4 alkylthio group or a C3-C6 cycloalkyl group, and X represents an oxygen atom;

a compound of the formula (1) wherein Q represents Q3, $R^1$ represents a halogen atom, an C1-C3 alkyl group or a C1-C3 haloalkyl group, $R^2$, $R^4$, $R^5$, $R^7$, $R^8$, $R^9$ and $R^{11}$ represent a hydrogen atom, $R^3$ represents a hydrogen atom, a chlorine atom or a methyl group, $R^6$ represents an ethynyl group, a 1-propynyl group, a C1-C2 haloalkoxy group, an C1-C alkylthio group or a C3-C4 cycloalkyl group, $R^{10}$ represents a methyl group, and X represents an oxygen atom;

a compound of the formula (1) wherein Q represents Q3, $R^1$ represents a halogen atom, an C1-C3 alkyl group or a C1-C3 haloalkyl group, $R^2$, $R^4$, $R^5$, $R^7$, $R^8$, $R^9$ and $R^{11}$ represent a hydrogen atom, $R^3$ represents a hydrogen atom, a chlorine atom or a methyl group, $R^6$ represents an ethynyl group, a 1-propynyl group, a difluoromethoxy group, a trifluoromethoxy group, a methylthio group or a cyclopropyl group, $R^{10}$ represents a methyl group, and X represents an oxygen atom;

a compound of the formula (1) wherein Q represents Q3, $R^1$ represents a halogen atom, an C1-C3 alkyl group or a C1-C3 haloalkyl group, $R^2$, $R^4$, $R^5$, $R^7$, $R^8$, $R^9$ and $R^{11}$ represent a hydrogen atom, $R^3$ represents a hydrogen atom or a methyl group, $R^6$ represents an ethynyl group, a 1-propynyl group, a C1-C4 haloalkoxy group, an C1-C4 alkylthio group or a C3-C6 cycloalkyl group, $R^{10}$ represents a methyl group, and X represents an oxygen atom;

a compound of the formula (1) wherein Q represents Q3, $R^1$ represents a halogen atom, an C1-C3 alkyl group or a C1-C3 haloalkyl group, $R^2$, $R^4$, $R^5$, $R^7$, $R^8$, $R^9$ and $R^{11}$ represent a hydrogen atom, $R^3$ represents a hydrogen atom or a methyl group, $R^6$ represents an ethynyl group, a 1-propynyl group, a C1-C2 haloalkoxy group, an C1-C2 alkylthio group or a C3-C4 cycloalkyl group, $R^{10}$ represents a methyl group, and X represents an oxygen atom;

a compound of the formula (1) wherein Q represents Q3, $R^1$ represents a halogen atom, an C1-C3 alkyl group or a C1-C3 haloalkyl group, $R^2$, $R^4$, $R^5$, $R^7$, $R^8$, $R^9$ and $R^{11}$ represent a hydrogen atom, $R^3$ represents a hydrogen atom or a methyl group, $R^6$ represents an ethynyl group, a 1-propynyl group, a difluoromethoxy group, a trifluoromethoxy group, a methylthio group or a cyclopropyl group, $R^{10}$ represents a methyl group, and X represents an oxygen atom;

a compound of the formula (1) wherein Q represents Q3, $R^1$ represents a chlorine atom, a bromine atom, a methyl group, an ethyl group or a trifluoromethyl group, $R^2$, $R^4$, $R^5$, $R^7$, $R^8$, $R^9$ and $R^{11}$ represent a hydrogen atom, $R^3$ represents a hydrogen atom, a halogen atom or an C1-C3 alkyl group, $R^6$ represents an ethynyl group, a 1-propynyl group, a C1-C4 haloalkoxy group, an C1-C4 alkylthio group or a C3-C6 cycloalkyl group, $R^{10}$ represents a methyl group, and X represents an oxygen atom;

a compound of the formula (1) wherein Q represents Q3, $R^1$ represents a chlorine atom, a bromine atom, a methyl group, an ethyl group or a trifluoromethyl group, $R^2$, $R^4$, $R^5$, $R^7$, $R^8$, $R^9$ and $R^{11}$ represent a hydrogen atom, $R^3$ represents a hydrogen atom, a halogen atom or an C1-C3 alkyl group, $R^6$ represents an ethynyl group, a 1-propynyl group, a C1-C2 haloalkoxy group, an C1-C2 alkylthio group or a C3-C4 cycloalkyl group, $R^{10}$ represents a methyl group, and X represents an oxygen atom;

a compound of the formula (1) wherein Q represents Q3, $R^1$ represents a chlorine atom, a bromine atom, a methyl group, an ethyl group or a trifluoromethyl group, $R^2$, $R^4$, $R^5$, $R^7$, $R^8$, $R^9$ and $R^{11}$ represent a hydrogen atom, $R^3$ represents a hydrogen atom, a halogen atom or an C1-C3 alkyl group, $R^6$ represents an ethynyl group, a 1-propynyl group, a difluoromethoxy group, a trifluoromethoxy group, a methylthio group or a cyclopropyl group, $R^{10}$ represents a methyl group, and X represents an oxygen atom;

a compound of the formula (1) wherein Q represents Q3, $R^1$ represents a chlorine atom, a bromine atom, a methyl group, an ethyl group or a trifluoromethyl group, $R^2$, $R^4$, $R^5$, $R^7$, $R^8$, $R^9$ and $R^{11}$ represent a hydrogen atom, $R^3$ represents a hydrogen atom, a chlorine atom or a methyl group, $R^6$ represents an ethynyl group, a 1-propynyl group, a C1-C4 haloalkoxy group, an C1-C4 alkylthio group or a C3-C6 cycloalkyl group, $R^{10}$ represents a methyl group, and X represents an oxygen atom;

a compound of the formula (1) wherein Q represents Q3, $R^1$ represents a chlorine atom, a bromine atom, a methyl group, an ethyl group or a trifluoromethyl group, $R^2$, $R^4$, $R^5$, $R^7$, $R^8$, $R^9$ and $R^{11}$ represent a hydrogen atom, $R^3$ represents a hydrogen atom, a chlorine atom or a methyl group, $R^6$ represents an ethynyl group, a 1-propynyl group, a C1-C2 haloalkoxy group, an C1-C2 alkylthio group or a C3-C4 cycloalkyl group, $R^{10}$ represents a methyl group, and X represents an oxygen atom;

a compound of the formula (1) wherein Q represents Q3, $R^1$ represents a chlorine atom, a bromine atom, a methyl group, an ethyl group or a trifluoromethyl group, $R^2$, $R^4$, $R^5$, $R^7$, $R^8$, $R^9$ and $R^{11}$ represent a hydrogen atom, $R^3$ represents a hydrogen atom, a chlorine atom or a methyl group, $R^6$ represents an ethynyl group, a 1-propynyl group, a difluoromethoxy group, a trifluoromethoxy group, a methylthio group or a cyclopropyl group, $R^{10}$ represents a methyl group, and X represents an oxygen atom;

a compound of the formula (1) wherein Q represents Q3, $R^1$ represents a chlorine atom, a bromine atom, a methyl group, an ethyl group or a trifluoromethyl group, $R^2$, $R^4$, $R^5$, $R^7$, $R^8$, $R^9$ and $R^{11}$ represent a hydrogen atom, $R^3$ represents a hydrogen atom or a methyl group, $R^6$ represents an ethynyl group, a 1-propynyl group, a C1-C4 haloalkoxy group, an C1-C4 alkylthio group or a C3-C6 cycloalkyl group, $R^{10}$ represents a methyl group, and X represents an oxygen atom;

a compound of the formula (1) wherein Q represents Q3, $R^1$ represents a chlorine atom, a bromine atom, a methyl group, an ethyl group or a trifluoromethyl group, $R^2$, $R^4$, $R^5$, $R^7$, $R^8$, $R^9$ and $R^{11}$ represent a hydrogen atom, $R^3$ represents a hydrogen atom or a methyl group, $R^6$ represents an ethynyl group, a 1-propynyl group, a C1-C2 haloalkoxy group, an C1-C2 alkylthio group or a C3-C4 cycloalkyl group, $R^{10}$ represents a methyl group, and X represents an oxygen atom;

a compound of the formula (1) wherein Q represents Q3, $R^1$ represents a chlorine atom, a bromine atom, a methyl group, an ethyl group or a trifluoromethyl group, $R^2$, $R^4$, $R^5$, $R^7$, $R^8$, $R^9$ and $R^{11}$ represent a hydrogen atom, $R^3$ represents a hydrogen atom or a methyl group, $R^6$ represents an ethynyl group, a 1-propynyl group, a difluoromethoxy group, a trifluoromethoxy group, a methylthio group or a cyclopropyl group, $R^{10}$ represents a methyl group, and X represents an oxygen atom;

a compound of the formula (1) wherein Q represents Q4, $R^1$ represents a halogen atom, an C1-C3 alkyl group, a C1-C3 haloalkyl group or a C3-C5 cycloalkyl group, $R^2$, $R^4$, $R^5$, $R^7$, $R^8$, $R^9$ and $R^{11}$ represent a hydrogen atom, $R^3$ represents a hydrogen atom, a halogen atom or an C1-C3 alkyl group, $R^6$ represents an ethynyl group, a 1-propynyl group, a C1-C4 haloalkoxy group, an C1-C4 alkylthio group or a C3-C6 cycloalkyl group, $R^{10}$ represents a methyl group, and X represents an oxygen atom;

a compound of the formula (1) wherein Q represents Q4, $R^1$ represents a halogen atom, an C1-C3 alkyl group, a C1-C3 haloalkyl group or a C3-C5 cycloalkyl group, $R^2$, $R^4$, $R^5$, $R^7$, $R^8$, $R^9$ and $R^{11}$ represent a hydrogen atom, $R^3$ represents a hydrogen atom, a halogen atom or an C1-C3 alkyl group, $R^6$ represents an ethynyl group, a 1-propynyl group, a C1-C2 haloalkoxy group, an C1-C2 alkylthio group or a C3-C4 cycloalkyl group, $R^{10}$ represents a methyl group, and X represents an oxygen atom;

a compound of the formula (1) wherein Q represents Q4, $R^1$ represents a halogen atom, an C1-C3 alkyl group, a C1-C3 haloalkyl group or a C3-C5 cycloalkyl group, $R^2$, $R^4$, $R^5$, $R^7$, $R^8$, $R^9$ and $R^{11}$ represent a hydrogen atom, $R^3$ represents a hydrogen atom, a halogen atom or an C1-C3 alkyl group, $R^6$ represents an ethynyl group, a 1-propynyl group, a difluoromethoxy group, a trifluoromethoxy group, a methylthio group or a cyclopropyl group, $R^{10}$ represents a methyl group, and X represents an oxygen atom;

a compound of the formula (1) wherein Q represents Q4, $R^1$ represents a halogen atom, an C1-C3 alkyl group, a C1-C3 haloalkyl group or a C3-C5 cycloalkyl group, $R^2$, $R^4$, $R^5$, $R^7$, $R^8$, $R^9$ and $R^{11}$ represent a hydrogen atom, $R^3$ represents a hydrogen atom, a chlorine atom or a methyl group, $R^6$ represents an ethynyl group, a 1-propynyl group, a C1-C4 haloalkoxy group, an C1-C4 alkylthio group or a C3-C6 cycloalkyl group, $R^{10}$ represents a methyl group, and X represents an oxygen atom;

a compound of the formula (1) wherein Q represents Q4, $R^1$ represents a halogen atom, an C1-C3 alkyl group, a C1-C3 haloalkyl group or a C3-C5 cycloalkyl group, $R^2$, $R^4$, $R^5$, $R^7$, $R^8$, $R^9$ and $R^{11}$ represent a hydrogen atom, $R^3$ represents a hydrogen atom, a chlorine atom or a methyl group, $R^6$ represents an ethynyl group, a 1-propynyl group, a C1-C2 haloalkoxy group, an C1-C2 alkylthio group or a C3-C4 cycloalkyl group, $R^{10}$ represents a methyl group, and X represents an oxygen atom;

a compound of the formula (1) wherein Q represents Q4, $R^1$ represents a halogen atom, an C1-C3 alkyl group, a C1-C3 haloalkyl group or a C3-C5 cycloalkyl group, $R^2$, $R^4$, $R^5$, $R^7$, $R^8$, $R^9$ and $R^{11}$ represent a hydrogen atom, $R^3$ represents a hydrogen atom, a chlorine atom or a methyl group, $R^6$ represents an ethynyl group, a 1-propynyl group, a difluoromethoxy group, a trifluoromethoxy group, a methylthio group or a cyclopropyl group, $R^{10}$ represents a methyl group, and X represents an oxygen atom;

a compound of the formula (1) wherein Q represents Q4, $R^1$ represents a halogen atom, an C1-C3 alkyl group, a C1-C3 haloalkyl group or a C3-C5 cycloalkyl group, $R^2$, $R^4$, $R^5$, $R^7$, $R^8$, $R^9$ and $R^{11}$ represent a hydrogen atom, $R^3$ represents a hydrogen atom or a methyl group, $R^6$ represents an ethynyl group, a 1-propynyl group, a C1-C4 haloalkoxy group, an C1-C4 alkylthio group or a C3-C6 cycloalkyl group, $R^{10}$ represents a methyl group, and X represents an oxygen atom;

a compound of the formula (1) wherein Q represents Q4, $R^1$ represents a halogen atom, an C1-C3 alkyl group, a C1-C3 haloalkyl group or a C3-C5 cycloalkyl group, $R^2$, $R^4$, $R^5$, $R^7$, $R^8$, $R^9$ and $R^{11}$ represent a hydrogen atom, $R^3$ represents a hydrogen atom or a methyl group, $R^6$ represents an ethynyl group, a 1-propynyl group, a C1-C2 haloalkoxy group, an C1-C2 alkylthio group or a C3-C4 cycloalkyl group, $R^{10}$ represents a methyl group, and X represents an oxygen atom;

a compound of the formula (1) wherein Q represents Q4, $R^1$ represents a halogen atom, an C1-C3 alkyl group, a C1-C3 haloalkyl group or a C3-C5 cycloalkyl group, $R^2$, $R^4$, $R^5$, $R^7$, $R^8$, $R^9$ and $R^{11}$ represent a hydrogen atom, $R^3$ represents a hydrogen atom or a methyl group, $R^6$ represents an ethynyl group, a 1-propynyl group, a difluoromethoxy group, a trifluoromethoxy group, a methylthio group or a cyclopropyl group, $R^{10}$ represents a methyl group, and X represents an oxygen atom;

a compound of the formula (1) wherein Q represents Q4, $R^1$ represents a halogen atom, an C1-C3 alkyl group or a C1-C3 haloalkyl group, $R^2$, $R^4$, $R^5$, $R^7$, $R^8$, $R^9$ and $R^{11}$ represent a hydrogen atom, $R^3$ represents a hydrogen atom, a halogen atom or an C1-C3 alkyl group, $R^6$ represents an ethynyl group, a 1-propynyl group, a C1-C4 haloalkoxy group, an C1-C4 alkylthio group or a C3-C6 cycloalkyl group, $R^{10}$ represents a methyl group, and X represents an oxygen atom;

a compound of the formula (1) wherein Q represents Q4, $R^1$ represents a halogen atom, an C1-C3 alkyl group or a C1-C3 haloalkyl group, $R^2$, $R^4$, $R^5$, $R^7$, $R^8$, $R^9$ and $R^{11}$ represent a hydrogen atom, $R^3$ represents a hydrogen atom, a halogen atom or an C1-C3 alkyl group, $R^6$ represents an ethynyl group, a 1-propynyl group, a C1-C2 haloalkoxy group, an C1-C2 alkylthio group or a C3-C4 cycloalkyl group, $R^{10}$ represents a methyl group, and X represents an oxygen atom;

a compound of the formula (1) wherein Q represents Q4, $R^1$ represents a halogen atom, an C1-C3 alkyl group or a C1-C3 haloalkyl group, $R^2$, $R^4$, $R^5$, $R^7$, $R^8$, $R^9$ and $R^{11}$ represent a hydrogen atom, $R^3$ represents a hydrogen atom, a halogen atom or an C1-C3 alkyl group, $R^6$ represents an ethynyl group, a 1-propynyl group, a difluoromethoxy group, a trifluoromethoxy group, a methylthio group or a cyclopropyl group, $R^{10}$ represents a methyl group, and X represents an oxygen atom;

a compound of the formula (1) wherein Q represents Q4, $R^1$ represents a halogen atom, an C1-C3 alkyl group or a C1-C3 haloalkyl group, $R^2$, $R^4$, $R^5$, $R^7$, $R^8$, $R^9$ and $R^{11}$ represent a hydrogen atom, $R^3$ represents a hydrogen atom, a chlorine atom or a methyl group, $R^6$ represents an ethynyl group, a 1-propynyl group, a C1-C4 haloalkoxy group, an C1-C4 alkylthio group or a C3-C6 cycloalkyl group, and X represents an oxygen atom;

a compound of the formula (1) wherein Q represents Q4, $R^1$ represents a halogen atom, an C1-C3 alkyl group or a C1-C3 haloalkyl group, $R^2$, $R^4$, $R^5$, $R^7$, $R^8$, $R^9$ and $R^{11}$ represent a hydrogen atom, $R^3$ represents a hydrogen atom, a chlorine atom or a methyl group, $R^6$ represents an ethynyl group, a 1-propynyl group, a C1-C2 haloalkoxy group, an C1-C alkylthio group or a C3-C4 cycloalkyl group, $R^{10}$ represents a methyl group, and X represents an oxygen atom;

a compound of the formula (1) wherein Q represents Q4, $R^1$ represents a halogen atom, an C1-C3 alkyl group or a C1-C3 haloalkyl group, $R^2$, $R^4$, $R^5$, $R^7$, $R^8$, $R^9$ and $R^{11}$ represent a hydrogen atom, $R^3$ represents a hydrogen atom, a chlorine atom or a methyl group, $R^6$ represents an ethynyl group, a 1-propynyl group, a difluoromethoxy group, a trifluoromethoxy group, a methylthio group or a cyclopropyl group, $R^{10}$ represents a methyl group, and X represents an oxygen atom;

a compound of the formula (1) wherein Q represents Q4, $R^1$ represents a halogen atom, an C1-C3 alkyl group or a C1-C3 haloalkyl group, $R^2$, $R^4$, $R^5$, $R^7$, $R^8$, $R^9$ and $R^{11}$ represent a hydrogen atom, $R^3$ represents a hydrogen atom or a methyl group, $R^6$ represents an ethynyl group, a 1-propynyl group, a C1-C4 haloalkoxy group, an C1-C4 alkylthio group or a C3-C6 cycloalkyl group, $R^{10}$ represents a methyl group, and X represents an oxygen atom;

a compound of the formula (1) wherein Q represents Q4, $R^1$ represents a halogen atom, an C1-C3 alkyl group or a C1-C3 haloalkyl group, $R^2$, $R^4$, $R^5$, $R^7$, $R^8$, $R^9$ and $R^{11}$ represent a hydrogen atom, $R^3$ represents a hydrogen atom or a methyl group, $R^6$ represents an ethynyl group, a 1-propynyl group, a C1-C2 haloalkoxy group, an C1-C2 alkylthio group or a C3-C4 cycloalkyl group, $R^{10}$ represents a methyl group, and X represents an oxygen atom;

a compound of the formula (1) wherein Q represents Q4, $R^1$ represents a halogen atom, an C1-C3 alkyl group or a C1-C3 haloalkyl group, $R^2$, $R^4$, $R^5$, $R^7$, $R^8$, $R^9$ and $R^{11}$ represent a hydrogen atom, $R^3$ represents a hydrogen atom or a methyl group, $R^6$ represents an ethynyl group, a 1-propynyl group, a difluoromethoxy group, a trifluoromethoxy group, a methylthio group or a cyclopropyl group, $R^{10}$ represents a methyl group, and X represents an oxygen atom;

a compound of the formula (1) wherein Q represents Q4, $R^1$ represents a chlorine atom, a bromine atom, a methyl group, an ethyl group or a trifluoromethyl group, $R^2$, $R^4$, $R^5$, $R^7$, $R^8$, $R^9$ and $R^{11}$ represent a hydrogen atom, $R^3$ represents a hydrogen atom, a halogen atom or an C1-C3 alkyl group, $R^6$ represents an ethynyl group, a 1-propynyl group, a C1-C4 haloalkoxy group, an C1-C4 alkylthio group or a C3-C6 cycloalkyl group, $R^{10}$ represents a methyl group, and X represents an oxygen atom;

a compound of the formula (1) wherein Q represents Q4, $R^1$ represents a chlorine atom, a bromine atom, a methyl group, an ethyl group or a trifluoromethyl group, $R^2$, $R^4$, $R^5$, $R^7$, $R^8$, $R^9$ and $R^{11}$ represent a hydrogen atom, $R^3$ represents a hydrogen atom, a halogen atom or an C1-C3 alkyl group, $R^6$ represents an ethynyl group, a 1-propynyl group, a C1-C2 haloalkoxy group, an C1-C2 alkylthio group or a C3-C4 cycloalkyl group, $R^{10}$ represents a methyl group, and X represents an oxygen atom;

a compound of the formula (1) wherein Q represents Q4, $R^1$ represents a chlorine atom, a bromine atom, a methyl group, an ethyl group or a trifluoromethyl group, $R^2$, $R^4$, $R^5$, $R^7$, $R^8$, $R^9$ and $R^{11}$ represent a hydrogen atom, $R^3$ represents a hydrogen atom, a halogen atom or an C1-C3 alkyl group, $R^6$ represents an ethynyl group, a 1-propynyl group, a difluoromethoxy group, a trifluoromethoxy group, a methylthio group or a cyclopropyl group, $R^{10}$ represents a methyl group, and X represents an oxygen atom;

a compound of the formula (1) wherein Q represents Q4, $R^1$ represents a chlorine atom, a bromine atom, a methyl group, an ethyl group or a trifluoromethyl group, $R^2$, $R^4$, $R^5$, $R^7$, $R^8$, $R^9$ and $R^{11}$ represent a hydrogen atom, $R^3$ represents a hydrogen atom, a chlorine atom or a methyl group, $R^6$ represents an ethynyl group, a 1-propynyl group, a C1-C4 haloalkoxy group, an C1-C4 alkylthio group or a C3-C6 cycloalkyl group, $R^{10}$ represents a methyl group, and X represents an oxygen atom;

a compound of the formula (1) wherein Q represents Q4, $R^1$ represents a chlorine atom, a bromine atom, a methyl group, an ethyl group or a trifluoromethyl group, $R^2$, $R^4$, $R^5$, $R^7$, $R^8$, $R^9$ and $R^{11}$ represent a hydrogen atom, $R^3$ represents a hydrogen atom, a chlorine atom or a methyl group, $R^6$ represents an ethynyl group, a 1-propynyl group, a C1-C2 haloalkoxy group, an C1-C2 alkylthio group or a C3-C4 cycloalkyl group, $R^{10}$ represents a methyl group, and X represents an oxygen atom;

a compound of the formula (1) wherein Q represents Q4, $R^1$ represents a chlorine atom, a bromine atom, a methyl group, an ethyl group or a trifluoromethyl group, $R^2$, $R^4$, $R^5$, $R^7$, $R^8$, $R^9$ and $R^{11}$ represent a hydrogen atom, $R^3$ represents a hydrogen atom, a chlorine atom or a methyl group, $R^6$ represents an ethynyl group, a 1-propynyl group, a difluoromethoxy group, a trifluoromethoxy group, a methylthio group or a cyclopropyl group, $R^{10}$ represents a methyl group, and X represents an oxygen atom;

a compound of the formula (1) wherein Q represents Q4, $R^1$ represents a chlorine atom, a bromine atom, a methyl group, an ethyl group or a trifluoromethyl group, $R^2$, $R^4$, $R^5$, $R^7$, $R^8$, $R^9$ and $R^{11}$ represent a hydrogen atom, $R^3$ represents a hydrogen atom or a methyl group, $R^6$ represents an ethynyl group, a 1-propynyl group, a C1-C4 haloalkoxy group, an C1-C4 alkylthio group or a C3-C6 cycloalkyl group, $R^{10}$ represents a methyl group, and X represents an oxygen atom;

a compound of the formula (1) wherein Q represents Q4, $R^1$ represents a chlorine atom, a bromine atom, a methyl group, an ethyl group or a trifluoromethyl group, $R^2$, $R^4$, $R^5$, $R^7$, $R^8$, $R^9$ and $R^{11}$ represent a hydrogen atom, $R^3$ represents a hydrogen atom or a methyl group, $R^6$ represents an ethynyl group, a 1-propynyl group, a C1-C2 haloalkoxy group, an C1-C2 alkylthio group or a C3-C4 cycloalkyl group, $R^{10}$ represents a methyl group, and X represents an oxygen atom;

a compound of the formula (1) wherein Q represents Q4, $R^1$ represents a chlorine atom, a bromine atom, a methyl group, an ethyl group or a trifluoromethyl group, $R^2$, $R^4$, $R^5$, $R^7$, $R^8$, $R^9$ and $R^{11}$ represent a hydrogen atom, $R^3$ represents a hydrogen atom or a methyl group, $R^6$ represents an ethynyl group, a 1-propynyl group, a difluoromethoxy group, a trifluoromethoxy group, a methylthio group or a cyclopropyl group, $R^{10}$ represents a methyl group, and X represents an oxygen atom;

a compound of the formula (1) wherein $Y^1$ represents a hydrogen atom;

a compound of the formula (1) wherein $Y^1$ represents an C1-C6 alkyl group;

a compound of the formula (1) wherein $Y^1$ represents a C1-C6 haloalkyl group;

a compound of the formula (1) wherein $Y^1$ represents a C3-C6 cycloalkyl group;

a compound of the formula (1) wherein $Y^1$ represents a C3-C6 halocycloalkyl group;

a compound of the formula (1) wherein $Y^1$ represents a hydrogen atom, an C1-C6 alkyl group, a C1-C6 haloalkyl group or a C3-C6 cycloalkyl group;

a compound of the formula (1) wherein $Y^1$ represents a hydrogen atom, an C1-C6 alkyl group or a C1-C6 haloalkyl group;

a compound of the formula (1) wherein $Y^1$ represents a hydrogen atom, an C1-C3 alkyl group or a C1-C3 haloalkyl group;

a compound of the formula (1) wherein $Y^1$ represents a hydrogen atom, a methyl group, an ethyl group or a trifluoromethyl group;

a compound of the formula (1) wherein $Y^2$ represents a hydrogen atom;

a compound of the formula (1) wherein $Y^2$ represents a halogen atom;

a compound of the formula (1) wherein $Y^2$ represents an C1-C6 alkyl group;

a compound of the formula (1) wherein $Y^2$ represents a C1-C6 haloalkyl group;

a compound of the formula (1) wherein $Y^2$ represents an C1-C3 alkynyl group;

a compound of the formula (1) wherein $Y^2$ represents an C1-C6 alkoxy group;

a compound of the formula (1) wherein $Y^2$ represents a C1-C6 haloalkoxy group;

a compound of the formula (1) wherein $Y^2$ represents a C3-C6 cycloalkyl group;

a compound of the formula (1) wherein $Y^2$ represents a C3-C6 halocycloalkyl group;

a compound of the formula (1) wherein $Y^1$ and $Y^2$ connect via a divalent straight saturated carbon chain to form a five-membered or six-membered ring;

a compound of the formula (1) wherein $Y^1$ and $Y^2$ connect to each other to represent —$CH_2$—$CH_2$—$CH_2$— or —$CH_2$—$CH_2$—$CH_2$—$CH_2$—, which combines together with the carbon atoms to which $Y^1$ and $Y^2$ are attached to form a five-membered or six-membered ring;

a compound of the formula (1) wherein $Y^2$ represents a hydrogen atom, a halogen atom, an C1-C6 alkyl group, a C1-C6 haloalkyl group, an C1-C3 alkynyl group, an C1-C6 alkoxy group or a C3-C6 cycloalkyl group;

a compound of the formula (1) wherein $Y^2$ represents a hydrogen atom, a halogen atom, an C1-C3 alkyl group, a C1-C3 haloalkyl group, an C1-C3 alkynyl group, an C1-C3 alkoxy group or a C3-C4 cycloalkyl group;

a compound of the formula (1) wherein $Y^2$ represents a hydrogen atom, a fluorine atom, a chlorine atom, a bromine atom, a methyl group, an ethyl group, a propyl group, an isopropyl group, an ethynyl group, a 1-propynyl group, a trifluoromethyl group, a difluoromethyl group, a methoxy group, an ethoxy group or a cyclopropyl group;

a compound of the formula (1) wherein $Y^3$ represents a hydrogen atom;

a compound of the formula (1) wherein $Y^3$ represents an C1-C4 alkyl group;

a compound of the formula (1) wherein $Y^3$ represents a C1-C4 haloalkyl group;

a compound of the formula (1) wherein $Y^3$ represents a hydrogen atom, an C1-C3 alkyl group or a C1-C3 haloalkyl group;

a compound of the formula (1) wherein $Y^3$ represents a hydrogen atom, a methyl group or an ethyl group;

a compound of the formula (1) wherein $Y^2$ and $Y^3$ connect via a divalent straight saturated carbon chain to form a five-membered or six-membered ring;

a compound of the formula (1) wherein $Y^2$ and $Y^3$ connect to each other to represent —$CH_2$—$CH_2$—$CH_2$— or —$CH_2$—$CH_2$—$CH_2$—$CH_2$—, which combines together with the carbon atoms to which $Y^1$ and $Y^2$ are attached to form a five-membered or six-membered ring;

a compound of the formula (1) wherein Q represents Q1, $R^1$ represents a halogen atom, an C1-C3 alkyl group, a C1-C3 haloalkyl group or a C3-C5 cycloalkyl group, $R^2$, $R^4$, $R^5$, $R^7$, $R^8$, $R^9$ and $R^{11}$ represent a hydrogen atom, $R^3$ represents a hydrogen atom, a halogen atom or an C1-C3 alkyl group, $R^6$ represents an ethynyl group, a 1-propynyl group, a C1-C4 haloalkoxy group, an C1-C4 alkylthio group or a C3-C6 cycloalkyl group, $R^{10}$ represents a methyl group, X represents an oxygen atom, $Y^1$ represents a hydrogen atom, an C1-C6 alkyl group, a C1-C6 haloalkyl group or a C3-C6 cycloalkyl group, $Y^2$ represents a hydrogen atom, a halogen atom, an C1-C6 alkyl group, a C1-C6 haloalkyl group, an C2-C3 alkynyl group, an C1-C6 alkoxy group or a C3-C6 cycloalkyl group, $Y^3$ represents a hydrogen atom, an C1-C3 alkyl group or a C1-C3 haloalkyl group;

a compound of the formula (1) wherein Q represents Q1, $R^1$ represents a halogen atom, an C1-C3 alkyl group, a C1-C3 haloalkyl group or a C3-C5 cycloalkyl group, $R^2$, $R^4$, $R^5$, $R^7$, $R^8$, $R^9$ and $R^{11}$ represent a hydrogen atom, $R^3$ represents a hydrogen atom, a halogen atom or an C1-C3 alkyl group, $R^6$ represents an ethynyl group, a 1-propynyl group, a C1-C4 haloalkoxy group, an C1-C4 alkylthio group or a C3-C6 cycloalkyl group, $R^{10}$ represents a methyl group, X represents an oxygen atom, $Y^1$ represents a hydrogen atom, an C1-C6 alkyl group, a C1-C6 haloalkyl group or a C3-C6 cycloalkyl group, $Y^2$ represents a hydrogen atom, a halogen atom, an C1-C6 alkyl group, a C1-C6 haloalkyl group, an C2-C3 alkynyl group, an C1-C6 alkoxy group or a C3-C6 cycloalkyl group, alternatively $Y^1$ and $Y^2$ connect via a divalent straight saturated carbon chain to form a five-membered or six-membered ring, and $Y^3$ represents a hydrogen atom, an C1-C3 alkyl group or a C1-C3 haloalkyl group, alternatively $Y^2$ and $Y^3$ connect via a divalent straight saturated carbon chain to form a five-membered or six-membered ring;

a compound of the formula (1) wherein Q represents Q1, $R^1$ represents a halogen atom, an C1-C3 alkyl group, a C1-C3 haloalkyl group or a C3-C5 cycloalkyl group, $R^2$, $R^4$, $R^5$, $R^7$, $R^8$, $R^9$ and $R^{11}$ represent a hydrogen atom, $R^3$ represents a hydrogen atom, a halogen atom or an C1-C3 alkyl group, $R^6$ represents an ethynyl group, a 1-propynyl group, a C1-C4 haloalkoxy group, an C1-C4 alkylthio group or a C3-C6 cycloalkyl group, $R^{10}$ represents a methyl group, X represents an oxygen atom, $Y^1$ represents a hydrogen atom, an C1-C6 alkyl group, a C1-C6 haloalkyl group or a C3-C6 cycloalkyl group, $Y^2$ represents a hydrogen atom, a halogen atom, an C1-C3 alkyl group, a C1-C3 haloalkyl group, an C2-C3 alkynyl group, an C1-C3 alkoxy group or an C3-C4 cycloalkyl group, and $Y^3$ represents a hydrogen atom, an C1-C3 alkyl group or a C1-C3 haloalkyl group;

a compound of the formula (1) wherein Q represents Q1, $R^1$ represents a halogen atom, an C1-C3 alkyl group, a C1-C3 haloalkyl group or a C3-C5 cycloalkyl group, $R^2$, $R^4$, $R^5$, $R^7$, $R^8$, $R^9$ and $R^{11}$ represent a hydrogen atom, $R^3$ represents a hydrogen atom, a halogen atom or an C1-C3 alkyl group, $R^6$ represents an ethynyl group, a 1-propynyl group, a C1-C4 haloalkoxy group, an C1-C4 alkylthio group or a C3-C6 cycloalkyl group, $R^{10}$ represents a methyl group, X represents an oxygen atom, $Y^1$ represents a hydrogen atom, an C1-C6 alkyl group, a C1-C6 haloalkyl group or a C3-C6 cycloalkyl group, $Y^2$ represents a hydrogen atom, a halogen atom, an C1-C3 alkyl group, a C1-C3 haloalkyl group, an C2-C3 alkynyl group, an C1-C3 alkoxy group or an C3-C4 cycloalkyl group, and $Y^3$ represents a hydrogen atom, a methyl group or an ethyl group;

a compound of the formula (1) wherein Q represents Q1, $R^1$ represents a halogen atom, an C1-C3 alkyl group, a C1-C3 haloalkyl group or a C3-C5 cycloalkyl group, $R^2$, $R^4$, $R^5$, $R^7$, $R^8$, $R^9$ and $R^{11}$ represent a hydrogen atom, $R^3$ represents a hydrogen atom, a halogen atom or an C1-C3 alkyl group, $R^6$ represents an ethynyl group, a 1-propynyl group, a C1-C4 haloalkoxy group, an C1-C4 alkylthio group or a C3-C6 cycloalkyl group, $R^{10}$ represents a methyl group, X represents an oxygen atom, $Y^1$ represents a hydrogen atom, an C1-C6 alkyl group, a C1-C6 haloalkyl group or a C3-C6 cycloalkyl group, $Y^2$ represents a hydrogen atom, a fluorine atom, a chlorine atom, a bromine atom, a methyl group, an ethyl group, a propyl group, an isopropyl group, an ethynyl group, 1-propynyl group, a trifluoromethyl group, a difluoromethyl group, a methoxy group, an ethoxy group or a cyclopropyl group, and $Y^3$ represents a hydrogen atom, an C1-C3 alkyl group or a C1-C3 haloalkyl group;

a compound of the formula (1) wherein Q represents Q1, $R^1$ represents a halogen atom, an C1-C3 alkyl group, a C1-C3 haloalkyl group or a C3-C5 cycloalkyl group, $R^2$, $R^4$, $R^5$, $R^7$, $R^8$, $R^9$ and $R^{11}$ represent a hydrogen atom, $R^3$ represents a hydrogen atom, a halogen atom or an C1-C3 alkyl group, $R^6$ represents an ethynyl group, a 1-propynyl group, a C1-C4 haloalkoxy group, an C1-C4 alkylthio group or a C3-C6 cycloalkyl group, $R^{10}$ represents a methyl group, X represents an oxygen atom, $Y^1$ represents a hydrogen atom, an C1-C6 alkyl group, a C1-C6 haloalkyl group or a C3-C6 cycloalkyl group, $Y^2$ represents a hydrogen atom, a fluorine atom, a chlorine atom, a bromine atom, a methyl group, an ethyl group, a propyl group, an isopropyl group, an ethynyl group, 1-propynyl group, a trifluoromethyl group, a difluoromethyl group, a methoxy group, an ethoxy group or cyclopropyl group, and $Y^3$ represents a hydrogen atom, a methyl group or an ethyl group;

a compound of the formula (1) wherein Q represents Q1, $R^1$ represents a halogen atom, an C1-C3 alkyl group, a C1-C3 haloalkyl group or a C3-C5 cycloalkyl group, $R^2$, $R^4$, $R^5$, $R^7$, $R^8$, $R^9$ and $R^{11}$ represent a hydrogen atom, $R^3$ represents a hydrogen atom, a halogen atom or an C1-C3 alkyl group, $R^6$ represents an ethynyl group, a 1-propynyl group, a C1-C4 haloalkoxy group, an C1-C4 alkylthio group or a C3-C6 cycloalkyl group, $R^{10}$ represents a methyl group, X represents an oxygen atom, $Y^1$ represents a hydrogen atom, an C1-C6 alkyl group or a C1-C6 haloalkyl group, $Y^2$ represents a hydrogen atom, a halogen atom, an C1-C6 alkyl group, a C1-C6 haloalkyl group, an C2-C3 alkynyl group, an C1-C6 alkoxy group or a C3-C6 cycloalkyl group, and $Y^3$ represents a hydrogen atom, an C1-C3 alkyl group or a C1-C3 haloalkyl group;

a compound of the formula (1) wherein Q represents Q1, $R^1$ represents a halogen atom, an C1-C3 alkyl group, a C1-C3 haloalkyl group or a C3-C5 cycloalkyl group, $R^2$, $R^4$, $R^5$, $R^7$, $R^8$, $R^9$ and $R^{11}$ represent a hydrogen atom, $R^3$ represents a hydrogen atom, a halogen atom or an C1-C3 alkyl group, $R^6$ represents an ethynyl group, a 1-propynyl group, a C1-C4 haloalkoxy group, an C1-C4 alkylthio group or a C3-C6 cycloalkyl group, $R^{10}$ represents a methyl group, X represents an oxygen atom, $Y^1$ represents a hydrogen atom, an C1-C6 alkyl group or a C1-C6 haloalkyl group, $Y^2$ represents a hydrogen atom, a halogen atom, an C1-C6 alkyl group, a C1-C6 haloalkyl group, an C2-C3 alkynyl group, an C1-C6 alkoxy group or a C3-C6 cycloalkyl group, and $Y^3$ represents a hydrogen atom, a methyl group or an ethyl group;

a compound of the formula (1) wherein Q represents Q1, $R^1$ represents a halogen atom, an C1-C3 alkyl group, a C1-C3 haloalkyl group or a C3-C5 cycloalkyl group, $R^2$, $R^4$, $R^5$, $R^7$, $R^8$, $R^9$ and $R^{11}$ represent a hydrogen atom, $R^3$ represents a hydrogen atom, a halogen atom or an C1-C3 alkyl group, $R^6$ represents an ethynyl group, a 1-propynyl group, a C1-C4 haloalkoxy group, an C1-C4 alkylthio group or a C3-C6 cycloalkyl group, $R^{10}$ represents a methyl group, X represents an oxygen atom, $Y^1$ represents a hydrogen atom, an C1-C6 alkyl group or a C1-C6 haloalkyl group, $Y^2$ represents a hydrogen atom, a halogen atom, an C1-C3 alkyl group, a C1-C3 haloalkyl group, an C2-C3 alkynyl group, an C1-C3 alkoxy group or a C3-C4 cycloalkyl group, and $Y^3$ represents a hydrogen atom, a methyl group or an ethyl group;

a compound of the formula (1) wherein Q represents Q1, $R^1$ represents a halogen atom, an C1-C3 alkyl group, a C1-C3 haloalkyl group or a C3-C5 cycloalkyl group, $R^2$, $R^4$, $R^5$, $R^7$, $R^8$, $R^9$ and $R^{11}$ represent a hydrogen atom, $R^3$ represents a hydrogen atom, a halogen atom or an C1-C3 alkyl group, $R^6$ represents an ethynyl group, a 1-propynyl group, a C1-C4 haloalkoxy group, an C1-C4 alkylthio group or a C3-C6 cycloalkyl group, $R^{10}$ represents a methyl group, X represents an oxygen atom, $Y^1$ represents a hydrogen atom, an C1-C6 alkyl group or a C1-C6 haloalkyl group, $Y^2$ represents a hydrogen atom, a hydrogen atom, a fluorine atom, a chlorine atom, a bromine atom, a methyl group, an ethyl group, a propyl group, an isopropyl group, an ethynyl group, 1-propynyl group, a trifluoromethyl group, a difluoromethyl group, a methoxy group, an ethoxy group or a cyclopropyl group, and $Y^3$ represents a hydrogen atom, an C1-C3 alkyl group or a C1-C3 haloalkyl group;

a compound of the formula (1) wherein Q represents Q1, $R^1$ represents a halogen atom, an C1-C3 alkyl group, a C1-C3 haloalkyl group or a C3-C5 cycloalkyl group, $R^2$, $R^4$, $R^5$, $R^7$, $R^8$, $R^9$ and $R^{11}$ represent a hydrogen atom, $R^3$ represents a hydrogen atom, a halogen atom or an C1-C3 alkyl group, $R^6$ represents an ethynyl group, a 1-propynyl group, a C1-C4 haloalkoxy group, an C1-C4 alkylthio group or a C3-C6 cycloalkyl group, $R^{10}$ represents a methyl group, X represents an oxygen atom, $Y^1$ represents a hydrogen atom, an C1-C6 alkyl group or a C1-C6 haloalkyl group, $Y^2$ represents a hydrogen atom, a fluorine atom, a chlorine atom, a bromine atom, a methyl group, an ethyl group, a propyl group, an isopropyl group, an ethynyl group, 1-propynyl group, a trifluoromethyl group, a difluoromethyl group, a methoxy group, an ethoxy group or a cyclopropyl group, and $Y^3$ represents a hydrogen atom, a methyl group or an ethyl group;

a compound of the formula (1) wherein Q represents Q1, $R^1$ represents a halogen atom, an C1-C3 alkyl group, a C1-C3 haloalkyl group or a C3-C5 cycloalkyl group, $R^2$, $R^4$, $R^5$, $R^7$, $R^8$, $R^9$ and $R^{11}$ represent a hydrogen atom, $R^3$ represents a hydrogen atom, a halogen atom or an C1-C3 alkyl group, $R^6$ represents an ethynyl group, a 1-propynyl group, a C1-C4 haloalkoxy group, an C1-C4 alkylthio group or a C3-C6 cycloalkyl group, $R^{10}$ represents a methyl group, X represents an oxygen atom, $Y^1$ represents a hydrogen atom, an C1-C3 alkyl group or a C1-C3 haloalkyl group, $Y^2$ represents a hydrogen atom, a halogen atom, an C1-C6 alkyl group, a C1-C6 haloalkyl group, an C2-C3 alkynyl group, an C1-C6 alkoxy group or a C3-C6 cycloalkyl group, and $Y^3$ represents a hydrogen atom, an C1-C3 alkyl group or a C1-C3 haloalkyl group;

a compound of the formula (1) wherein Q represents Q1, $R^1$ represents a halogen atom, an C1-C3 alkyl group, a C1-C3 haloalkyl group or a C3-C5 cycloalkyl group, $R^2$, $R^4$, $R^5$, $R^7$, $R^8$, $R^9$ and $R^{11}$ represent a hydrogen atom, $R^3$ represents a hydrogen atom, a halogen atom or an C1-C3 alkyl group, $R^6$ represents an ethynyl group, a 1-propynyl group, a C1-C4 haloalkoxy group, an C1-C4 alkylthio group or a C3-C6 cycloalkyl group, $R^{10}$ represents a methyl group, X represents an oxygen atom, $Y^1$ represents a hydrogen atom, an C1-C3 alkyl group or a C1-C3 haloalkyl group, $Y^2$ represents a hydrogen atom, a halogen atom, an C1-C6 alkyl group, a C1-C6 haloalkyl group, an C2-C3 alkynyl group, an C1-C6 alkoxy group or a C3-C6 cycloalkyl group, and $Y^3$ represents a hydrogen atom, a methyl group or an ethyl group;

a compound of the formula (1) wherein Q represents Q1, $R^1$ represents a halogen atom, an C1-C3 alkyl group, a C1-C3 haloalkyl group or a C3-C5 cycloalkyl group, $R^2$, $R^4$, $R^5$, $R^7$, $R^8$, $R^9$ and $R^{11}$ represent a hydrogen atom, $R^3$ represents a hydrogen atom, a halogen atom or an C1-C3 alkyl group, $R^6$ represents an ethynyl group, a 1-propynyl group, a C1-C4 haloalkoxy group, an C1-C4 alkylthio group or a C3-C6 cycloalkyl group, $R^{10}$ represents a methyl group, X represents an oxygen atom, $Y^1$ represents a hydrogen atom, an C1-C3 alkyl group or a C1-C3 haloalkyl group, $Y^2$ represents a hydrogen atom, a halogen atom, an C1-C3 alkyl group, a C1-C3 haloalkyl group, an C2-C3 alkynyl group, an C1-C3 alkoxy group or a C3-C4 cycloalkyl group, and $Y^3$ represents a hydrogen atom, an C1-C3 alkyl group or a C1-C3 haloalkyl group;

a compound of the formula (1) wherein Q represents Q1, $R^1$ represents a halogen atom, an C1-C3 alkyl group, a C1-C3 haloalkyl group or a C3-C5 cycloalkyl group, $R^2$, $R^4$, $R^5$, $R^7$, $R^8$, $R^9$ and $R^{11}$ represent a hydrogen atom, $R^3$ represents a hydrogen atom, a halogen atom or an C1-C3 alkyl group, $R^6$ represents an ethynyl group, a 1-propynyl group, a C1-C4 haloalkoxy group, an C1-C4 alkylthio group or a C3-C6 cycloalkyl group, $R^{10}$ represents a methyl group, X represents an oxygen atom, $Y^1$ represents a hydrogen atom, an C1-C3 alkyl group or a C1-C3 haloalkyl group, $Y^2$ represents a hydrogen atom, a halogen atom, an C1-C3 alkyl group, a C1-C3 haloalkyl group, an C2-C3 alkynyl group, an C1-C3 alkoxy group or a C3-C4 cycloalkyl group, $Y^3$ represents a hydrogen atom, a methyl group or an ethyl group;

a compound of the formula (1) wherein Q represents Q1, $R^1$ represents a halogen atom, an C1-C3 alkyl group, a C1-C3 haloalkyl group or a C3-C5 cycloalkyl group, $R^2$, $R^4$, $R^5$, $R^7$, $R^8$, $R^9$ and $R^{11}$ represent a hydrogen atom, $R^3$ represents a hydrogen atom, a halogen atom or an C1-C3 alkyl group, $R^6$ represents an ethynyl group, a 1-propynyl group, a C1-C4 haloalkoxy group, an C1-C4 alkylthio group or a C3-C6 cycloalkyl group, $R^{10}$ represents a methyl group, X represents an oxygen atom, $Y^1$ represents a hydrogen atom, an C1-C3 alkyl group or a C1-C3 haloalkyl group, $Y^2$ represents a hydrogen atom, a fluorine atom, a chlorine atom, a bromine atom, a methyl group, an ethyl group, a propyl group, an isopropyl group, an ethynyl group, a 1-propynyl group, a trifluoromethyl group, a difluoromethyl group, a methoxy group, an ethoxy group or a cyclopropyl group, and $Y^3$ represents a hydrogen atom, an C1-C3 alkyl group or a C1-C3 haloalkyl group;

a compound of the formula (1) wherein Q represents Q1, $R^1$ represents a halogen atom, an C1-C3 alkyl group, a C1-C3 haloalkyl group or a C3-C5 cycloalkyl group, $R^2$, $R^4$, $R^5$, $R^7$, $R^8$, $R^9$ and $R^{11}$ represent a hydrogen atom, $R^3$ represents a hydrogen atom, a halogen atom or an C1-C3 alkyl group, $R^6$ represents an ethynyl group, a 1-propynyl group, a C1-C4 haloalkoxy group, an C1-C4 alkylthio group or a C3-C6 cycloalkyl group, $R^{10}$ represents a methyl group, X represents an oxygen atom, $Y^1$ represents a hydrogen atom, an C1-C3 alkyl group or a C1-C3 haloalkyl group, $Y^2$ represents a hydrogen atom, a fluorine atom, a chlorine atom, a bromine atom, a methyl group, an ethyl group, a propyl group, an isopropyl group, an ethynyl group, a 1-propynyl group, a trifluoromethyl group, a difluoromethyl group, a methoxy group, an ethoxy group or a cyclopropyl group, and $Y^3$ represents a hydrogen atom, a methyl group or an ethyl group;

a compound of the formula (1) wherein Q represents Q1, $R^1$ represents a halogen atom, an C1-C3 alkyl group, a C1-C3 haloalkyl group or a C3-C5 cycloalkyl group, $R^2$, $R^4$, $R^5$, $R^7$, $R^8$, $R^9$ and $R^{11}$ represent a hydrogen atom, $R^3$ represents a hydrogen atom, a halogen atom or an C1-C3 alkyl group, $R^6$ represents an ethynyl group, a 1-propynyl group, a C1-C4 haloalkoxy group, an C1-C4 alkylthio group or a C3-C6 cycloalkyl group, $R^{10}$ represents a methyl group, X represents an oxygen atom, $Y^1$ represents a hydrogen atom, a methyl group, an ethyl group or a trifluoromethyl group, $Y^2$ represents a hydrogen atom, a halogen atom, an C1-C6 alkyl group, a C1-C6 haloalkyl group, an C2-C3 alkynyl group, an C1-C6 alkoxy group or a C3-C6 cycloalkyl group, and $Y^3$ represents a hydrogen atom, an C1-C3 alkyl group or a C1-C3 haloalkyl group;

a compound of the formula (1) wherein Q represents Q1, $R^1$ represents a halogen atom, an C1-C3 alkyl group, a C1-C3 haloalkyl group or a C3-C5 cycloalkyl group, $R^2$, $R^4$, $R^5$, $R^7$, $R^8$, $R^9$ and $R^{11}$ represent a hydrogen atom, $R^3$ represents a hydrogen atom, a halogen atom or an C1-C3 alkyl group, $R^6$ represents an ethynyl group, a 1-propynyl group, a C1-C4 haloalkoxy group, an C1-C4 alkylthio group or a C3-C6 cycloalkyl group, $R^{10}$ represents a methyl group, X represents an oxygen atom, $Y^1$ represents a hydrogen atom, a methyl group, an ethyl group or a trifluoromethyl group, $Y^2$ represents a hydrogen atom, a halogen atom, an C1-C6 alkyl group, a C1-C6 haloalkyl group, an C2-C3 alkynyl group, an C1-C6 alkoxy group or a an C3-C6 cycloalkyl group, and $Y^3$ represents a hydrogen atom, a methyl group or an ethyl group;

a compound of the formula (1) wherein Q represents Q1, $R^1$ represents a halogen atom, an C1-C3 alkyl group, a C1-C3 haloalkyl group or a C3-C5 cycloalkyl group, $R^2$, $R^4$, $R^5$, $R^7$, $R^8$, $R^9$ and $R^{11}$ represent a hydrogen atom, $R^3$ represents a hydrogen atom, a halogen atom or an C1-C3 alkyl group, $R^6$ represents an ethynyl group, a 1-propynyl group, a C1-C4 haloalkoxy group, an C1-C4 alkylthio group or a C3-C6 cycloalkyl group, $R^{10}$ represents a methyl group, X represents an oxygen atom, $Y^1$ represents a hydrogen atom, a methyl group, an ethyl group or a trifluoromethyl group, $Y^2$ represents a hydrogen atom, a halogen atom, an C1-C3 alkyl group, a C1-C3 haloalkyl group, an C1-C3 alkynyl group, an C1-C3 alkoxy group or a C3-C4 cycloalkyl group, and $Y^3$ represents an C1-C3 alkyl group or a C1-C3 haloalkyl group;

a compound of the formula (1) wherein Q represents Q1, $R^1$ represents a halogen atom, an C1-C3 alkyl group, a C1-C3 haloalkyl group or a C3-C5 cycloalkyl group, $R^2$, $R^4$, $R^5$, $R^7$, $R^8$, $R^9$ and $R^{11}$ represent a hydrogen atom, $R^3$ represents a hydrogen atom, a halogen atom or an C1-C3 alkyl group, $R^6$ represents an ethynyl group, a 1-propynyl group, a C1-C4 haloalkoxy group, an C1-C4 alkylthio group or a C3-C6 cycloalkyl group, $R^{10}$ represents a methyl group, X represents an oxygen atom, $Y^1$ represents a hydrogen atom, a methyl group, an ethyl group or a trifluoromethyl group, $Y^2$ represents a hydrogen atom, a halogen atom, an C1-C3 alkyl group, a C1-C3 haloalkyl group, an C2-C3 alkynyl group, an C1-C3 alkoxy group or a C3-C4 cycloalkyl group, and $Y^3$ represents a hydrogen atom, a methyl group or an ethyl group;

a compound of the formula (1) wherein Q represents Q1, $R^1$ represents a halogen atom, an C1-C3 alkyl group, a C1-C3 haloalkyl group or a C3-C5 cycloalkyl group, $R^2$, $R^4$, $R^5$, $R^7$, $R^8$, $R^9$ and $R^{11}$ represent a hydrogen atom, $R^3$ represents a hydrogen atom, a halogen atom or an C1-C3 alkyl group, $R^6$ represents an ethynyl group, a 1-propynyl group, a C1-C4 haloalkoxy group, an C1-C4 alkylthio group or a C3-C6 cycloalkyl group, $R^{10}$ represents a methyl group, X represents an oxygen atom, $Y^1$ represents a hydrogen atom, a methyl group, an ethyl group or a trifluoromethyl group, $Y^2$ represents a hydrogen atom, a fluorine atom, a chlorine atom, a bromine atom, a methyl group, an ethyl group, a propyl group, an isopropyl group, an ethynyl group, a 1-propynyl group, a trifluoromethyl group, a difluoromethyl group, a methoxy group, an ethoxy group or a cyclopropyl group, and $Y^3$ represents a hydrogen atom, an C1-C3 alkyl group or a C1-C3 haloalkyl group;

a compound of the formula (1) wherein Q represents Q1, $R^1$ represents a halogen atom, an C1-C3 alkyl group, a C1-C3 haloalkyl group or a C3-C5 cycloalkyl group, $R^2$, $R^4$, $R^5$, $R^7$, $R^8$, $R^9$ and $R^{11}$ represent a hydrogen atom, $R^3$ represents a hydrogen atom, a halogen atom or an C1-C3 alkyl group, $R^6$ represents an ethynyl group, a 1-propynyl group, a C1-C4 haloalkoxy group, an C1-C4 alkylthio group or a C3-C6 cycloalkyl group, $R^{10}$ represents a methyl group, X represents an oxygen atom, $Y^2$ represents a hydrogen atom, a methyl group, an ethyl group or a trifluoromethyl group, $Y^2$ represents a hydrogen atom, a fluorine atom, a chlorine atom, a bromine atom, a methyl group, an ethyl group, a propyl group, an isopropyl group, an ethynyl group, a 1-propynyl group, a trifluoromethyl group, a difluoromethyl group, a methoxy group, an ethoxy group or a cyclopropyl group, and $Y^3$ represents a hydrogen atom, a methyl group or an ethyl group;

a compound of the formula (1) wherein Q represents Q1, $R^1$ represents a halogen atom, an C1-C3 alkyl group or a C1-C3 haloalkyl group, $R^2$, $R^4$, $R^5$, $R^7$, $R^8$, $R^9$ and $R^{11}$ represent a hydrogen atom, $R^3$ represents a hydrogen atom, a chlorine atom or a methyl group, $R^6$ represents an ethynyl group, a 1-propynyl group, a C1-C2 haloalkoxy group, an C1-C2 alkylthio group or a C3-C4 cycloalkyl group, $R^{10}$ represents a methyl group, X represents an oxygen atom, $Y^1$ represents a hydrogen atom, an C1-C6 alkyl group, a C1-C6 haloalkyl group or a C3-C6 cycloalkyl group, $Y^2$ represents a hydrogen atom, a halogen atom, an C1-C6 alkyl group, a C1-C6 haloalkyl group, an C2-C3 alkynyl group, an C1-C6 alkoxy group or a C3-C6 cycloalkyl group, and $Y^3$ represents a hydrogen atom, an C1-C3 alkyl group or a C1-C3 haloalkyl group;

a compound of the formula (1) wherein Q represents Q1, $R^1$ represents a halogen atom, an C1-C3 alkyl group or a C1-C3 haloalkyl group, $R^2$, $R^4$, $R^5$, $R^7$, $R^8$, $R^9$ and $R^{11}$ represent a hydrogen atom, $R^3$ represents a hydrogen atom, a chlorine atom or a methyl group, $R^6$ represents an ethynyl group, a 1-propynyl group, a C1-C2 haloalkoxy group, an C1-C2 alkylthio group or a C3-C4 cycloalkyl group, $R^{10}$ represents a methyl group, X represents an oxygen atom, $Y^1$ represents a hydrogen atom, an C1-C6 alkyl group, a C1-C6 haloalkyl group or a C3-C6 cycloalkyl group, $Y^2$ represents a hydrogen atom, a halogen atom, an C1-C6 alkyl group, a C1-C6 haloalkyl group, an C2-C3 alkynyl group, an C1-C6 alkoxy group or a C3-C6 cycloalkyl group, and $Y^3$ represents a hydrogen atom, a methyl group or an ethyl group;

a compound of the formula (1) wherein Q represents Q1, $R^1$ represents a halogen atom, an C1-C3 alkyl group or a C1-C3 haloalkyl group, $R^2$, $R^4$, $R^5$, $R^7$, $R^8$, $R^9$ and $R^{11}$ represent a hydrogen atom, $R^3$ represents a hydrogen atom, a chlorine atom or a methyl group, $R^6$ represents an ethynyl group, a 1-propynyl group, a C1-C2 haloalkoxy group, an C1-C2 alkylthio group or a C3-C4 cycloalkyl group, $R^{10}$ represents a methyl group, X represents an oxygen atom, $Y^1$ represents a hydrogen atom, an C1-C6 alkyl group, a C1-C6 haloalkyl group or a C3-C6 cycloalkyl group, $Y^2$ represents a hydrogen atom, a halogen atom, an C1-C3 alkyl group, a C1-C3 haloalkyl group, an C2-C3 alkynyl group, an C1-C3 alkoxy group or a C3-C4 cycloalkyl group, and $Y^3$ represents a hydrogen atom, an C1-C3 alkyl group or a C1-C3 haloalkyl group;

a compound of the formula (1) wherein Q represents Q1, $R^1$ represents a halogen atom, an C1-C3 alkyl group or a C1-C3 haloalkyl group, $R^2$, $R^4$, $R^5$, $R^7$, $R^8$, $R^9$ and $R^{11}$ represent a hydrogen atom, $R^3$ represents a hydrogen atom, a chlorine atom or a methyl group, $R^6$ represents an ethynyl group, a 1-propynyl group, a C1-C2 haloalkoxy group, an C1-C2 alkylthio group or a C3-C4 cycloalkyl group, $R^{10}$ represents a methyl group, X represents an oxygen atom, $Y^1$ represents a hydrogen atom, an C1-C6 alkyl group, a C1-C6 haloalkyl group or a C3-C6 cycloalkyl group, $Y^2$ represents a hydrogen atom, a halogen atom, an C1-C3 alkyl group, a C1-C3 haloalkyl group, an C2-C3 alkynyl group, an C1-C3 alkoxy group or a C3-C4 cycloalkyl group, and $Y^3$ represents a hydrogen atom, a methyl group or an ethyl group;

a compound of the formula (1) wherein Q represents Q1, $R^1$ represents a halogen atom, an C1-C3 alkyl group or a C1-C3 haloalkyl group, $R^2$, $R^4$, $R^5$, $R^7$, $R^8$, $R^9$ and $R^{11}$ represent a hydrogen atom, $R^3$ represents a hydrogen atom, a chlorine atom or a methyl group, $R^6$ represents an ethynyl group, a 1-propynyl group, a C1-C2 haloalkoxy group, an C1-C2 alkylthio group or a C3-C4 cycloalkyl group, $R^{10}$ represents a methyl group, X represents an oxygen atom, $Y^1$ represents a hydrogen atom, an C1-C6 alkyl group, a C1-C6 haloalkyl group or a C3-C6 cycloalkyl group, $Y^2$ represents a hydrogen atom, a fluorine atom, a chlorine atom, a bromine atom, a methyl group, an ethyl group, a propyl group, an isopropyl group, an ethynyl group, a 1-propynyl group, a trifluoromethyl group, a difluoromethyl group, a methoxy group, an ethoxy group or a cyclopropyl group, and $Y^3$ represents a hydrogen atom, an C1-C3 alkyl group or a C1-C3 haloalkyl group;

a compound of the formula (1) wherein Q represents Q1, $R^1$ represents a halogen atom, an C1-C3 alkyl group or a C1-C3 haloalkyl group, $R^2$, $R^4$, $R^5$, $R^7$, $R^8$, $R^9$ and $R^{11}$ represent a hydrogen atom, $R^3$ represents a hydrogen atom, a chlorine atom or a methyl group, $R^6$ represents an ethynyl group, a 1-propynyl group, a C1-C2 haloalkoxy group, an C1-C2 alkylthio group or a C3-C4 cycloalkyl group, $R^{10}$ represents a methyl group, X represents an oxygen atom, $Y^1$ represents a hydrogen atom, an C1-C6 alkyl group, a C1-C6 haloalkyl group or a C3-C6 cycloalkyl group, $Y^2$ represents a hydrogen atom, a fluorine atom, a chlorine atom, a bromine atom, a methyl group, an ethyl group, a propyl group, an isopropyl group, an ethynyl group, a 1-propynyl group, a trifluoromethyl group, a difluoromethyl group, a methoxy group, an ethoxy group or a cyclopropyl group, and $Y^3$ represents a hydrogen atom, a methyl group or an ethyl group;

a compound of the formula (1) wherein Q represents Q1, $R^1$ represents a halogen atom, an C1-C3 alkyl group or a C1-C3 haloalkyl group, $R^2$, $R^4$, $R^5$, $R^7$, $R^8$, $R^9$ and $R^{11}$ represent a hydrogen atom, $R^3$ represents a hydrogen atom, a chlorine atom or a methyl group, $R^6$ represents an ethynyl group, a 1-propynyl group, a C1-C2 haloalkoxy group, an C1-C2 alkylthio group or a C3-C4 cycloalkyl group, $R^{10}$ represents a methyl group, X represents an oxygen atom, $Y^1$ represents a hydrogen atom, an C1-C6 alkyl group or a C1-C6 haloalkyl group, $Y^2$ represents a hydrogen atom, a halogen atom, an C1-C6 alkyl group, a C1-C6 haloalkyl group, an C2-C3 alkynyl group, an C1-C6 alkoxy group or a C3-C6 cycloalkyl group, and $Y^3$ represents a hydrogen atom, an C1-C3 alkyl group or a C1-C3 haloalkyl group;

a compound of the formula (1) wherein Q represents Q1, $R^1$ represents a halogen atom, an C1-C3 alkyl group or a C1-C3 haloalkyl group, $R^2$, $R^4$, $R^5$, $R^7$, $R^8$, $R^9$ and $R^{11}$ represent a hydrogen atom, $R^3$ represents a hydrogen atom, a chlorine atom or a methyl group, $R^6$ represents an ethynyl group, a 1-propynyl group, a C1-C2 haloalkoxy group, an C1-C2 alkylthio group or a C3-C4 cycloalkyl group, $R^{10}$ represents a methyl group, X represents an oxygen atom, $Y^1$ represents a hydrogen atom, an C1-C6 alkyl group or a C1-C6 haloalkyl group, $Y^2$ represents a hydrogen atom, a halogen atom, an C1-C6 alkyl group, a C1-C6 haloalkyl group, an C2-C3 alkynyl group, an C1-C6 alkoxy group or a C3-C6 cycloalkyl group, and $Y^3$ represents a hydrogen atom, a methyl group or an ethyl group;

a compound of the formula (1) wherein Q represents Q1, $R^1$ represents a halogen atom, an C1-C3 alkyl group or a C1-C3 haloalkyl group, $R^2$, $R^4$, $R^5$, $R^7$, $R^8$, $R^9$ and $R^{11}$ represent a hydrogen atom, $R^3$ represents a hydrogen atom, a chlorine atom or a methyl group, $R^6$ represents an ethynyl group, a 1-propynyl group, a C1-C2 haloalkoxy group, an C1-C2 alkylthio group or a C3-C4 cycloalkyl group, $R^{10}$ represents a methyl group, X represents an oxygen atom, $Y^1$ represents a hydrogen atom, an C1-C6 alkyl group or a C1-C6 haloalkyl group, $Y^2$ represents a hydrogen atom, a halogen atom, an C1-C3 alkyl group, a C1-C3 haloalkyl group, an C2-C3 alkynyl group, an C1-C3 alkoxy group or a C3-C4 cycloalkyl group, and $Y^3$ represents a hydrogen atom, an C1-C3 alkyl group or a C1-C3 haloalkyl group;

a compound of the formula (1) wherein Q represents Q1, $R^1$ represents a halogen atom, an C1-C3 alkyl group or a C1-C3 haloalkyl group, $R^2$, $R^4$, $R^5$, $R^7$, $R^8$, $R^9$ and $R^{11}$ represent a hydrogen atom, $R^3$ represents a hydrogen atom, a chlorine atom or a methyl group, $R^6$ represents an ethynyl group, a 1-propynyl group, a C1-C2 haloalkoxy group, an C1-C2 alkylthio group or a C3-C4 cycloalkyl group, $R^{10}$ represents a methyl group, X represents an oxygen atom, $Y^1$ represents a hydrogen atom, an C1-C6 alkyl group or a C1-C6 haloalkyl group, $Y^2$ represents a hydrogen atom, a halogen atom, an C1-C3 alkyl group, a C1-C3 haloalkyl group, an C2-C3 alkynyl group, an C1-C3 alkoxy group or a C3-C4 cycloalkyl group, and $Y^3$ represents a hydrogen atom, a methyl group or an ethyl group;

a compound of the formula (1) wherein Q represents Q1, $R^1$ represents a halogen atom, an C1-C3 alkyl group or a C1-C3 haloalkyl group, $R^2$, $R^4$, $R^5$, $R^7$, $R^8$, $R^9$ and $R^{11}$ represent a hydrogen atom, $R^3$ represents a hydrogen atom, a chlorine atom or a methyl group, $R^6$ represents an ethynyl group, a 1-propynyl group, a C1-C2 haloalkoxy group, an C1-C2 alkylthio group or a C3-C4 cycloalkyl group, $R^{10}$ represents a methyl group, X represents an oxygen atom, $Y^1$ represents a hydrogen atom, an C1-C6 alkyl group or a C1-C6 haloalkyl group, $Y^2$ represents a hydrogen atom, a fluorine atom, a chlorine atom, a bromine atom, a methyl group, an ethyl group, a propyl group, an isopropyl group, an ethynyl group, a 1-propynyl group, a trifluoromethyl group, a difluoromethyl group, a methoxy group, an ethoxy group or a cyclopropyl group, and $Y^3$ represents a hydrogen atom, an C1-C3 alkyl group or a C1-C3 haloalkyl group;

a compound of the formula (1) wherein Q represents Q1, $R^1$ represents a halogen atom, an C1-C3 alkyl group or a C1-C3 haloalkyl group, $R^2$, $R^4$, $R^5$, $R^7$, $R^8$, $R^9$ and $R^{11}$ represent a hydrogen atom, $R^3$ represents a hydrogen atom, a chlorine atom or a methyl group, $R^6$ represents an ethynyl group, a 1-propynyl group, a C1-C2 haloalkoxy group, an C1-C2 alkylthio group or a C3-C4 cycloalkyl group, $R^{10}$ represents a methyl group, X represents an oxygen atom, $Y^1$ represents a hydrogen atom, an C1-C6 alkyl group or a C1-C6 haloalkyl group, $Y^2$ represents a hydrogen atom, a fluorine atom, a chlorine atom, a bromine atom, a methyl group, an ethyl group, a propyl group, an isopropyl group, an ethynyl group, a 1-propynyl group, a trifluoromethyl group, a difluoromethyl group, a methoxy group, an ethoxy group or a cyclopropyl group, $Y^3$ represents a hydrogen atom, a methyl group or an ethyl group;

a compound of the formula (1) wherein Q represents Q1, $R^1$ represents a halogen atom, an C1-C3 alkyl group or a C1-C3 haloalkyl group, $R^2$, $R^4$, $R^5$, $R^7$, $R^8$, $R^9$ and $R^{11}$ represent a hydrogen atom, $R^3$ represents a hydrogen atom, a chlorine atom or a methyl group, $R^6$ represents an ethynyl group, a 1-propynyl group, a C1-C2 haloalkoxy group, an C1-C2 alkylthio group or a C3-C4 cycloalkyl group, $R^{10}$ represents a methyl group, X represents an oxygen atom, $Y^1$ represents a hydrogen atom, an C1-C3 alkyl group or a C1-C3 haloalkyl group, $Y^2$ represents a hydrogen atom, a halogen atom, an C1-C6 alkyl group, a C1-C6 haloalkyl group, an C2-C3 alkynyl group, an C1-C6 alkoxy group or a C3-C6 cycloalkyl group, and $Y^3$ represents a hydrogen atom, an C1-C3 alkyl group or a C1-C3 haloalkyl group;

a compound of the formula (1) wherein Q represents Q1, $R^1$ represents a halogen atom, an C1-C3 alkyl group or a C1-C3 haloalkyl group, $R^2$, $R^4$, $R^5$, $R^7$, $R^8$, $R^9$ and $R^{11}$ represent a hydrogen atom, $R^3$ represents a hydrogen atom, a chlorine atom or a methyl group, $R^6$ represents an ethynyl group, a 1-propynyl group, a C1-C2 haloalkoxy group, an C1-C2 alkylthio group or a C3-C4 cycloalkyl group, $R^{10}$ represents a methyl group, X represents an oxygen atom, $Y^1$ represents a hydrogen atom, an C1-C3 alkyl group or a C1-C3 haloalkyl group, $Y^2$ represents a hydrogen atom, a halogen atom, an C1-C6 alkyl group, a C1-C6 haloalkyl group, an C2-C3 alkynyl group, an C1-C6 alkoxy group or a C3-C6 cycloalkyl group, and $Y^3$ represents a hydrogen atom, a methyl group or an ethyl group;

a compound of the formula (1) wherein Q represents Q1, $R^1$ represents a halogen atom, an C1-C3 alkyl group or a C1-C3 haloalkyl group, $R^2$, $R^4$, $R^5$, $R^7$, $R^8$, $R^9$ and $R^{11}$ represent a hydrogen atom, $R^3$ represents a hydrogen atom, a chlorine atom or a methyl group, $R^6$ represents an ethynyl group, a 1-propynyl group, a C1-C2 haloalkoxy group, an C1-C2 alkylthio group or a C3-C4 cycloalkyl group, $R^{10}$ represents a methyl group, X represents an oxygen atom, $Y^1$ represents a hydrogen atom, an C1-C3 alkyl group or a C1-C3 haloalkyl group, $Y^2$ represents a hydrogen atom, a halogen atom, an C1-C3 alkyl group, a C1-C3 haloalkyl group, an C2-C3 alkynyl group, an C1-C3 alkoxy group or a C3-C4 cycloalkyl group, and $Y^3$ represents a hydrogen atom, an C1-C3 alkyl group or a C1-C3 haloalkyl group;

a compound of the formula (1) wherein Q represents Q1, $R^1$ represents a halogen atom, an C1-C3 alkyl group or a C1-C3 haloalkyl group, $R^2$, $R^4$, $R^5$, $R^7$, $R^8$, $R^9$ and $R^{11}$ represent a hydrogen atom, $R^3$ represents a hydrogen atom, a chlorine atom or a methyl group, $R^6$ represents an ethynyl group, a 1-propynyl group, a C1-C2 haloalkoxy group, an C1-C2 alkylthio group or a C3-C4 cycloalkyl group, $R^{10}$ represents a methyl group, X represents an oxygen atom, $Y^1$ represents a hydrogen atom, an C1-C3 alkyl group or a C1-C3 haloalkyl group, $Y^2$ represents a hydrogen atom, a halogen atom, an C1-C3 alkyl group, a C1-C3 haloalkyl group, an C1-C3 alkynyl group, an C1-C3 alkoxy group or a C3-C4 cycloalkyl group, and $Y^3$ represents a hydrogen atom, a methyl group or an ethyl group;

a compound of the formula (1) wherein Q represents Q1, $R^1$ represents a halogen atom, an C1-C3 alkyl group or a C1-C3 haloalkyl group, $R^2$, $R^4$, $R^5$, $R^7$, $R^8$, $R^9$ and $R^{11}$ represent a hydrogen atom, $R^3$ represents a hydrogen atom, a chlorine atom or a methyl group, $R^6$ represents an ethynyl group, a 1-propynyl group, a C1-C2 haloalkoxy group, an C1-C2 alkylthio group or a C3-C4 cycloalkyl group, $R^{10}$ represents a methyl group, X represents an oxygen atom, $Y^1$ represents a hydrogen atom, an C1-C3 alkyl group or a C1-C3 haloalkyl group, $Y^2$ represents a hydrogen atom, a fluorine atom, a chlorine atom, a bromine atom, a methyl group, an ethyl group, a propyl group, an isopropyl group, an ethynyl group, a 1-propynyl group, a trifluoromethyl group, a difluoromethyl group, a methoxy group, an ethoxy group or a cyclopropyl group, and $Y^3$ represents a hydrogen atom, an C1-C3 alkyl group or a C1-C3 haloalkyl group;

a compound of the formula (1) wherein Q represents Q1, $R^1$ represents a halogen atom, an C1-C3 alkyl group or a C1-C3 haloalkyl group, $R^2$, $R^4$, $R^5$, $R^7$, $R^8$, $R^9$ and $R^{11}$ represent a hydrogen atom, $R^3$ represents a hydrogen atom, a chlorine atom or a methyl group, $R^6$ represents an ethynyl group, a 1-propynyl group, a C1-C2 haloalkoxy group, an C1-C2 alkylthio group or a C3-C4 cycloalkyl group, $R^{10}$ represents a methyl group, X represents an oxygen atom, $Y^1$ represents a hydrogen atom, an C1-C3 alkyl group or an C1-C3 haloalkyl group, $Y^2$ represents a hydrogen atom, a fluorine atom, a chlorine atom, a bromine atom, a methyl group, an ethyl group, a propyl group, an isopropyl group, an ethynyl group, a 1-propynyl group, a trifluoromethyl group, a difluoromethyl group, a methoxy group, an ethoxy group or a cyclopropyl group, and $Y^3$ represents a hydrogen atom, a methyl group or an ethyl group;

a compound of the formula (1) wherein Q represents Q1, $R^1$ represents a halogen atom, an C1-C3 alkyl group or a C1-C3 haloalkyl group, $R^2$, $R^4$, $R^5$, $R^7$, $R^8$, $R^9$ and $R^{11}$ represent a hydrogen atom, $R^3$ represents a hydrogen atom, a chlorine atom or a methyl group, $R^6$ represents an ethynyl group, a 1-propynyl group, a C1-C2 haloalkoxy group, an C1-C2 alkylthio group or a C3-C4 cycloalkyl group, $R^{10}$ represents a methyl group, X represents an oxygen atom, $Y^1$ represents a hydrogen atom, a methyl group, an ethyl group or a trifluoromethyl group, $Y^2$ represents a hydrogen atom, a halogen atom, an C1-C6 alkyl group, a C1-C6 haloalkyl group, an C2-C3 alkynyl group, an C1-C6 alkoxy group or a C3-C6 cycloalkyl group, and $Y^3$ represents a hydrogen atom, an C1-C3 alkyl group or an C1-C3 haloalkyl group;

a compound of the formula (1) wherein Q represents Q1, $R^1$ represents a halogen atom, an C1-C3 alkyl group or a C1-C3 haloalkyl group, $R^2$, $R^4$, $R^5$, $R^7$, $R^8$, $R^9$ and $R^{11}$ represent a hydrogen atom, $R^3$ represents a hydrogen atom, a chlorine atom or a methyl group, $R^6$ represents an ethynyl group, a 1-propynyl group, a C1-C2 haloalkoxy group, an C1-C2 alkylthio group or a C3-C4 cycloalkyl group, $R^{10}$ represents a methyl group, X represents an oxygen atom, $Y^1$ represents a hydrogen atom, a methyl group, an ethyl group or a trifluoromethyl group, $Y^2$ represents a hydrogen atom, a halogen atom, an C1-C6 alkyl group, a C1-C6 haloalkyl group, an C2-C3 alkynyl group, an C1-C6 alkoxy group or a C3-C6 cycloalkyl group, and $Y^3$ represents a hydrogen atom, a methyl group or an ethyl group;

a compound of the formula (1) wherein Q represents Q1, $R^1$ represents a halogen atom, an C1-C3 alkyl group or a C1-C3 haloalkyl group, $R^2$, $R^4$, $R^5$, $R^7$, $R^8$, $R^9$ and $R^{11}$ represent a hydrogen atom, $R^3$ represents a hydrogen atom, a chlorine atom or a methyl group, $R^6$ represents an ethynyl group, a 1-propynyl group, a C1-C2 haloalkoxy group, an C1-C2 alkylthio group or a C3-C4 cycloalkyl group, $R^{10}$ represents a methyl group, X represents an oxygen atom, $Y^1$ represents a hydrogen atom, a methyl group, an ethyl group or a trifluoromethyl group, $Y^2$ represents a hydrogen atom, a halogen atom, an C1-C3 alkyl group, a C1-C3 haloalkyl group, an C1-C3 alkynyl group, an C1-C3 alkoxy group or a C3-C4 cycloalkyl group, and $Y^3$ represents a hydrogen atom, a methyl group or an ethyl group;

a compound of the formula (1) wherein Q represents Q1, $R^1$ represents a halogen atom, an C1-C3 alkyl group or a C1-C3 haloalkyl group, $R^2$, $R^4$, $R^5$, $R^7$, $R^8$, $R^9$ and $R^{11}$ represent a hydrogen atom, $R^3$ represents a hydrogen atom, a chlorine atom or a methyl group, $R^6$ represents an ethynyl group, a 1-propynyl group, a C1-C2 haloalkoxy group, an C1-C2 alkylthio group or a C3-C4 cycloalkyl group, $R^{10}$ represents a methyl group, X represents an oxygen atom, $Y^1$ represents a hydrogen atom, a methyl group, an ethyl group or a trifluoromethyl group, $Y^2$ represents a hydrogen atom, a halogen atom, an C1-C3 alkyl group, a C1-C3 haloalkyl group, an C1-C3 alkynyl group, an C1-C3 alkoxy group or a C3-C4 cycloalkyl group, and $Y^3$ represents a hydrogen atom, a methyl group or an ethyl group;

a compound of the formula (1) wherein Q represents Q1, $R^1$ represents a halogen atom, an C1-C3 alkyl group or a C1-C3 haloalkyl group, $R^2$, $R^4$, $R^5$, $R^7$, $R^8$, $R^9$ and $R^{11}$ represent a hydrogen atom, $R^3$ represents a hydrogen atom, a chlorine atom or a methyl group, $R^6$ represents an ethynyl group, a 1-propynyl group, a C1-C2 haloalkoxy group, an C1-C2 alkylthio group or a C3-C4 cycloalkyl group, $R^{10}$ represents a methyl group, X represents an oxygen atom, $Y^1$ represents a hydrogen atom, a methyl group, an ethyl group or a trifluoromethyl group, $Y^2$ represents a hydrogen atom, a fluorine atom, a chlorine atom, a bromine atom, a methyl group, an ethyl group, a propyl group, an isopropyl group, an ethynyl group, a 1-propynyl group, a trifluoromethyl group, a difluoromethyl group, a methoxy group, an ethoxy group or cyclopropyl group, and $Y^3$ represents a hydrogen atom, an C1-C3 alkyl group or a C1-C3 haloalkyl group; a compound of the formula (1) wherein Q represents Q1, $R^1$ represents a halogen atom, an C1-C3 alkyl group or a C1-C3 haloalkyl group, $R^2$, $R^4$, $R^5$, $R^7$, $R^8$, $R^9$ and $R^{11}$ represent a hydrogen atom, $R^3$ represents a hydrogen atom, a chlorine atom or a methyl group, $R^6$ represents an ethynyl group, a 1-propynyl group, a C1-C2 haloalkoxy group, an C1-C2 alkylthio group or a C3-C4 cycloalkyl group, $R^{10}$ represents a methyl group, X represents an oxygen atom, $Y^1$ represents a hydrogen atom, a methyl group, an ethyl group or a trifluoromethyl group, $Y^2$ represents a hydrogen atom, a fluorine atom, a chlorine atom, a bromine atom, a methyl group, an ethyl group, a propyl group, an isopropyl group, an ethynyl group, a 1-propynyl group, a trifluoromethyl group, a difluoromethyl group, a methoxy group, an ethoxy group or cyclopropyl group, and $Y^3$ represents a hydrogen atom, a methyl group or an ethyl group;

a compound of the formula (1) wherein Q represents Q1, $R^1$ represents a chlorine atom, a bromine atom, a methyl group, an ethyl group or a trifluoromethyl group, $R^2$, $R^4$, $R^5$, $R^7$, $R^8$, $R^9$ and $R^{11}$ represent a hydrogen atom, $R^3$ represents a hydrogen atom or a methyl group, $R^6$ represents an ethynyl group, a 1-propynyl group, a difluoromethoxy group, a trifluoromethoxy group, a methylthio group or a cyclopropyl group, $R^{10}$ represents a methyl group, X represents an oxygen atom, $Y^1$ represents a hydrogen atom, an C1-C6 alkyl group, a C1-C6 haloalkyl group or a C3-C6 cycloalkyl group, $Y^2$ represents a hydrogen atom, a halogen atom, an C1-C6 alkyl group, a C1-C6 haloalkyl group, an C2-C3 alkynyl group, an C1-C6 alkoxy group or a C3-C6 cycloalkyl group, and $Y^3$ represents a hydrogen atom, an C1-C3 alkyl group or a C1-C3haloalkyl group;

a compound of the formula (1) wherein Q represents Q1, $R^1$ represents a chlorine atom, a bromine atom, a methyl group, an ethyl group or a trifluoromethyl group, $R^2$, $R^4$, $R^5$, $R^7$, $R^8$, $R^9$ and $R^{11}$ represent a hydrogen atom, $R^3$ represents a hydrogen atom or a methyl group, $R^6$ represents an ethynyl group, a 1-propynyl group, a difluoromethoxy group, a trifluoromethoxy group, a methylthio group or a cyclopropyl group, $R^{10}$ represents a methyl group, X represents an oxygen atom, $Y^1$ represents a hydrogen atom, an C1-C6 alkyl group, a C1-C6 haloalkyl group or a C3-C6 cycloalkyl group, $Y^2$ represents a hydrogen atom, a halogen atom, an C1-C6 alkyl group, a C1-C6 haloalkyl group, an C2-C3 alkynyl group, an C1-C6 alkoxy group or a C3-C6 cycloalkyl group, and $Y^3$ represents a hydrogen atom, a methyl group or an ethyl group;

a compound of the formula (1) wherein Q represents Q1, $R^1$ represents a chlorine atom, a bromine atom, a methyl group, an ethyl group or a trifluoromethyl group, $R^2$, $R^4$, $R^5$, $R^7$, $R^8$, $R^9$ and $R^{11}$ represent a hydrogen atom, $R^3$ represents a hydrogen atom or a methyl group, $R^6$ represents an ethynyl group, a 1-propynyl group, a difluoromethoxy group, a trifluoromethoxy group, a methylthio group or a cyclopropyl group, $R^{10}$ represents a methyl group, X represents an oxygen atom, $Y^1$ represents a hydrogen atom, an C1-C6 alkyl group, a C1-C6 haloalkyl group or a C3-C6 cycloalkyl group, $Y^2$ represents a hydrogen atom, a halogen atom, an C1-C3 alkyl group, a C1-C3 haloalkyl group, an C2-C3 alkynyl group, an C1-C3 alkoxy group or a C3-C4 cycloalkyl group, and $Y^3$ represents a hydrogen atom, an C1-C3 alkyl group or a C1-C3 haloalkyl group;

a compound of the formula (1) wherein Q represents Q1, $R^1$ represents a chlorine atom, a bromine atom, a methyl group, an ethyl group or a trifluoromethyl group, $R^2$, $R^4$, $R^5$, $R^7$, $R^8$, $R^9$ and $R^{11}$ represent a hydrogen atom, $R^3$ represents a hydrogen atom or a methyl group, $R^6$ represents an ethynyl group, a 1-propynyl group, a difluoromethoxy group, a trifluoromethoxy group, a methylthio group or a cyclopropyl group, $R^{10}$ represents a methyl group, X represents an oxygen atom, $Y^1$ represents a hydrogen atom, an C1-C6 alkyl group, a C1-C6 haloalkyl group or a C3-C6 cycloalkyl group, $Y^2$ represents a hydrogen atom, a halogen atom, an C1-C3 alkyl group, a C1-C3 haloalkyl group, an C2-C3 alkynyl group, an C1-C3 alkoxy group or a C3-C4 cycloalkyl group, and $Y^3$ represents a hydrogen atom, a methyl group or an ethyl group;

a compound of the formula (1) wherein Q represents Q1, $R^1$ represents a chlorine atom, a bromine atom, a methyl group, an ethyl group or a trifluoromethyl group, $R^2$, $R^4$, $R^5$, $R^7$, $R^8$, $R^9$ and $R^{11}$ represent a hydrogen atom, $R^3$ represents a hydrogen atom or a methyl group, $R^6$ represents an ethynyl group, a 1-propynyl group, a difluoromethoxy group, a trifluoromethoxy group, a methylthio group or a cyclopropyl group, $R^{10}$ represents a methyl group, X represents an oxygen atom, $Y^1$ represents a hydrogen atom, an C1-C6 alkyl group, a C1-C6 haloalkyl group or a C3-C6 cycloalkyl group, $Y^2$ represents a hydrogen atom, a fluorine atom, a chlorine atom, a bromine atom, a methyl group, an ethyl group, a propyl group, an isopropyl group, an ethynyl group, a 1-propynyl group, a trifluoromethyl group, a difluoromethyl group, a methoxy group, an ethoxy group or a cyclopropyl group, and $Y^3$ represents a hydrogen atom, an C1-C3 alkyl group or a C1-C3 haloalkyl group;

a compound of the formula (1) wherein Q represents Q1, $R^1$ represents a chlorine atom, a bromine atom, a methyl group, an ethyl group or a trifluoromethyl group, $R^2$, $R^4$, $R^5$, $R^7$, $R^8$, $R^9$ and $R^{11}$ represent a hydrogen atom, $R^3$ represents a hydrogen atom or a methyl group, $R^6$ represents an ethynyl group, a 1-propynyl group, a difluoromethoxy group, a trifluoromethoxy group, a methylthio group or a cyclopropyl group, $R^{10}$ represents a methyl group, X represents an oxygen atom, $Y^1$ represents a hydrogen atom, an C1-C6 alkyl group, a C1-C6 haloalkyl group or a C3-C6 cycloalkyl group, $Y^2$ represents a hydrogen atom, a fluorine atom, a chlorine atom, a bromine atom, a methyl group, an ethyl group, a propyl group, an isopropyl group, an ethynyl group, a 1-propynyl group, a trifluoromethyl group, a difluoromethyl group, a methoxy group, an ethoxy group or a cyclopropyl group, and $Y^3$ represents a hydrogen atom, a methyl group or an ethyl group;

a compound of the formula (1) wherein Q represents Q1, $R^1$ represents a chlorine atom, a bromine atom, a methyl group, an ethyl group or a trifluoromethyl group, $R^2$, $R^4$, $R^5$, $R^7$, $R^8$, $R^9$ and $R^{11}$ represent a hydrogen atom, $R^3$ represents a hydrogen atom or a methyl group, $R^6$ represents an ethynyl group, a 1-propynyl group, a difluoromethoxy group, a trifluoromethoxy group, a methylthio group or a cyclopropyl group, $R^{10}$ represents a methyl group, X represents an oxygen atom, $Y^1$ represents a hydrogen atom, an C1-C6 alkyl group or a C1-C6 haloalkyl group, $Y^2$ represents a hydrogen atom, a halogen atom, an C1-C6 alkyl group, a C1-C6 haloalkyl group, an C2-C3 alkynyl group, an C1-C6 alkoxy group or a C3-C6 cycloalkyl group, and $Y^3$ represents a hydrogen atom, an C1-C3 alkyl group or a C1-C3 haloalkyl group;

a compound of the formula (1) wherein Q represents Q1, $R^1$ represents a chlorine atom, a bromine atom, a methyl group, an ethyl group or a trifluoromethyl group, $R^2$, $R^4$, $R^5$, $R^7$, $R^8$, $R^9$ and $R^{11}$ represent a hydrogen atom, $R^3$ represents a hydrogen atom or a methyl group, $R^6$ represents an ethynyl group, a 1-propynyl group, a difluoromethoxy group, a trifluoromethoxy group, a methylthio group or a cyclopropyl group, $R^{10}$ represents a methyl group, X represents an oxygen atom, $Y^1$ represents a hydrogen atom, an C1-C6 alkyl group or a C1-C6 haloalkyl group, $Y^2$ represents a hydrogen atom, a halogen atom, an C1-C6 alkyl group, a C1-C6 haloalkyl group, an C2-C3 alkynyl group, an C1-C6 alkoxy group or a C3-C6 cycloalkyl group, and $Y^3$ represents a hydrogen atom, a methyl group or an ethyl group;

a compound of the formula (1) wherein Q represents Q1, $R^1$ represents a chlorine atom, a bromine atom, a methyl group, an ethyl group or a trifluoromethyl group, $R^2$, $R^4$, $R^5$, $R^7$, $R^8$, $R^9$ and $R^{11}$ represent a hydrogen atom, $R^3$ represents a hydrogen atom or a methyl group, $R^6$ represents an ethynyl group, a 1-propynyl group, a difluoromethoxy group, a trifluoromethoxy group, a methylthio group or a cyclopropyl group, $R^{10}$ represents a methyl group, X represents an oxygen atom, $Y^1$ represents a hydrogen atom, an C1-C6 alkyl group or a C1-C6 haloalkyl group, $Y^2$ represents a hydrogen atom, a halogen atom, an C1-C3 alkyl group, a C1-C3 haloalkyl group, an C1-C3 alkynyl group, an C1-C3 alkoxy group or a C3-C4 cycloalkyl group, and $Y^3$ represents a hydrogen atom, an C1-C3 alkyl group or a C1-C3 haloalkyl group;

a compound of the formula (1) wherein Q represents Q1, $R^1$ represents a chlorine atom, a bromine atom, a methyl group, an ethyl group or a trifluoromethyl group, $R^2$, $R^4$, $R^5$, $R^7$, $R^8$, $R^9$ and $R^{11}$ represent a hydrogen atom, $R^3$ represents a hydrogen atom or a methyl group, $R^6$ represents an ethynyl group, a 1-propynyl group, a difluoromethoxy group, a trifluoromethoxy group, a methylthio group or a cyclopropyl group, $R^{10}$ represents a methyl group, X represents an oxygen atom, $Y^1$ represents a hydrogen atom, an C1-C6 alkyl group or a C1-C6 haloalkyl group, $Y^2$ represents a hydrogen atom, a halogen atom, an C1-C3 alkyl group, a C1-C3 haloalkyl group, an C2-C3 alkynyl group, an C1-C3 alkoxy group or a C3-C4 cycloalkyl group, and $Y^3$ represents a hydrogen atom, a methyl group or an ethyl group;

a compound of the formula (1) wherein Q represents Q1, $R^1$ represents a chlorine atom, a bromine atom, a methyl group, an ethyl group or a trifluoromethyl group, $R^2$, $R^4$, $R^5$, $R^7$, $R^8$, $R^9$ and $R^{11}$ represent a hydrogen atom, $R^3$ represents a hydrogen atom or a methyl group, $R^6$ represents an ethynyl group, a 1-propynyl group, a difluoromethoxy group, a trifluoromethoxy group, a methylthio group or a cyclopropyl group, $R^{10}$ represents a methyl group, X represents an oxygen atom, $Y^1$ represents a hydrogen atom, an C1-C6 alkyl group or a C1-C6 haloalkyl group, $Y^2$ represents a hydrogen atom, a fluorine atom, a chlorine atom, a bromine atom, a methyl group, an ethyl group, a propyl group, an isopropyl group, an ethynyl group, a 1-propynyl group, a trifluoromethyl group, a difluoromethyl group, a methoxy group, an ethoxy group or a cyclopropyl group, and $Y^3$ represents a hydrogen atom, an C1-C3 alkyl group or a C1-C3 haloalkyl group;

a compound of the formula (1) wherein Q represents Q1, $R^1$ represents a chlorine atom, a bromine atom, a methyl group, an ethyl group or a trifluoromethyl group, $R^2$, $R^4$, $R^5$, $R^7$, $R^8$, $R^9$ and $R^{11}$ represent a hydrogen atom, $R^3$ represents a hydrogen atom or a methyl group, $R^6$ represents an ethynyl group, a 1-propynyl group, a difluoromethoxy group, a trifluoromethoxy group, a methylthio group or a cyclopropyl group, $R^{10}$ represents a methyl group, X represents an oxygen atom, $Y^1$ represents a hydrogen atom, an C1-C6 alkyl group or a C1-C6 haloalkyl group, $Y^2$ represents a hydrogen atom, a fluorine atom, a chlorine atom, a bromine atom, a methyl group, an ethyl group, a propyl group, an isopropyl group, an ethynyl group, a 1-propynyl group, a trifluoromethyl group, a difluoromethyl group, a methoxy group, an ethoxy group or a cyclopropyl group, and $Y^3$ represents a hydrogen atom, a methyl group or an ethyl group;

a compound of the formula (1) wherein Q represents Q1, $R^1$ represents a chlorine atom, a bromine atom, a methyl group, an ethyl group or a trifluoromethyl group, $R^2$, $R^4$, $R^5$, $R^7$, $R^8$, $R^9$ and $R^{11}$ represent a hydrogen atom, $R^3$ represents a hydrogen atom or a methyl group, $R^6$ represents an ethynyl group, a 1-propynyl group, a difluoromethoxy group, a trifluoromethoxy group, a methylthio group or a cyclopropyl group, $R^{10}$ represents a methyl group, X represents an oxygen atom, $Y^1$ represents a hydrogen atom, an C1-C3 alkyl group or a C1-C3 haloalkyl group, $Y^2$ represents a hydrogen atom, a halogen atom, an C1-C6 alkyl group, a C1-C6 haloalkyl group, an C2-C3 alkynyl group, an C1-C6 alkoxy group or a C3-C6 cycloalkyl group, and $Y^3$ represents a hydrogen atom, an C1-C3 alkyl group or a C1-C3 haloalkyl group;

a compound of the formula (1) wherein Q represents Q1, $R^1$ represents a chlorine atom, a bromine atom, a methyl group, an ethyl group or a trifluoromethyl group, $R^2$, $R^4$, $R^5$, $R^7$, $R^8$, $R^9$ and $R^{11}$ represent a hydrogen atom, $R^3$ represents a hydrogen atom or a methyl group, $R^6$ represents an ethynyl group, a 1-propynyl group, a difluoromethoxy group, a trifluoromethoxy group, a methylthio group or a cyclopropyl group, $R^{10}$ represents a methyl group, X represents an oxygen atom, $Y^1$ represents a hydrogen atom, an C1-C3 alkyl group or a C1-C3 haloalkyl group, $Y^2$ represents a hydrogen atom, a halogen atom, an C1-C6 alkyl group, a C1-C6 haloalkyl group, an C2-C3 alkynyl group, an C1-C6 alkoxy group or a C3-C6 cycloalkyl group, and $Y^3$ represents a hydrogen atom, a methyl group or an ethyl group;

a compound of the formula (1) wherein Q represents Q1, $R^1$ represents a chlorine atom, a bromine atom, a methyl group, an ethyl group or a trifluoromethyl group, $R^2$, $R^4$, $R^5$, $R^7$, $R^8$, $R^9$ and $R^{11}$ represent a hydrogen atom, $R^3$ represents a hydrogen atom or a methyl group, $R^6$ represents an ethynyl group, a 1-propynyl group, a difluoromethoxy group, a trifluoromethoxy group, a methylthio group or a cyclopropyl group, $R^{10}$ represents a methyl group, X represents an oxygen atom, $Y^1$ represents a hydrogen atom, an C1-C3 alkyl group or a C1-C3 haloalkyl group, $Y^2$ represents a hydrogen atom, a halogen atom, an C1-C3 alkyl group, a C1-C3 haloalkyl group, an C2-C3 alkynyl group, an C1-C3 alkoxy group or a C3-C4 cycloalkyl group, and $Y^3$ represents a hydrogen atom, an C1-C3 alkyl group or a C1-C3 haloalkyl group;

a compound of the formula (1) wherein Q represents Q1, $R^1$ represents a chlorine atom, a bromine atom, a methyl group, an ethyl group or a trifluoromethyl group, $R^2$, $R^4$, $R^5$, $R^7$, $R^8$, $R^9$ and $R^{11}$ represent a hydrogen atom, $R^3$ represents a hydrogen atom or a methyl group, $R^6$ represents an ethynyl group, a 1-propynyl group, a difluoromethoxy group, a trifluoromethoxy group, a methylthio group or a cyclopropyl group, $R^{10}$ represents a methyl group, X represents an oxygen atom, $Y^1$ represents a hydrogen atom, an C1-C3 alkyl group or a C1-C3 haloalkyl group, $Y^2$ represents a hydrogen atom, a halogen atom, an C1-C3 alkyl group, a C1-C3 haloalkyl group, an C2-C3 alkynyl group, an C1-C3 alkoxy group or a C3-C4 cycloalkyl group, and $Y^3$ represents a hydrogen atom, a methyl group or an ethyl group;

a compound of the formula (1) wherein Q represents Q1, $R^1$ represents a chlorine atom, a bromine atom, a methyl group, an ethyl group or a trifluoromethyl group, $R^2$, $R^4$, $R^5$, $R^7$, $R^8$, $R^9$ and $R^{11}$ represent a hydrogen atom, $R^3$ represents a hydrogen atom or a methyl group, $R^6$ represents an ethynyl group, a 1-propynyl group, a difluoromethoxy group, a trifluoromethoxy group, a methylthio group or a cyclopropyl group, $R^{10}$ represents a methyl group, X represents an oxygen atom, $Y^1$ represents a hydrogen atom, an C1-C3 alkyl group or a C1-C3 haloalkyl group, $Y^2$ represents a hydrogen atom, a fluorine atom, a chlorine atom, a bromine atom, a methyl group, an ethyl group, a propyl group, an isopropyl group, an ethynyl group, a 1-propynyl group, a trifluoromethyl group, a difluoromethyl group, a methoxy group, an ethoxy group or a cyclopropyl group, and $Y^3$ represents a hydrogen atom, an C1-C3 alkyl group or a C1-C3 haloalkyl group;

a compound of the formula (1) wherein Q represents Q1, $R^1$ represents a chlorine atom, a bromine atom, a methyl group, an ethyl group or a trifluoromethyl group, $R^2$, $R^4$, $R^5$, $R^7$, $R^8$, $R^9$ and $R^{11}$ represent a hydrogen atom, $R^3$ represents a hydrogen atom or a methyl group, $R^6$ represents an ethynyl group, a 1-propynyl group, a difluoromethoxy group, a trifluoromethoxy group, a methylthio group or a cyclopropyl group, $R^{10}$ represents a methyl group, X represents an oxygen atom, $Y^1$ represents a hydrogen atom, an C1-C3 alkyl group or a C1-C3 haloalkyl group, $Y^2$ represents a hydrogen atom, a fluorine atom, a chlorine atom, a bromine atom, a methyl group, an ethyl group, a propyl group, an isopropyl group, an ethynyl group, a 1-propynyl group, a trifluoromethyl group, a difluoromethyl group, a methoxy group, an ethoxy group or a cyclopropyl group, and $Y^3$ represents a hydrogen atom, a methyl group or an ethyl group;

a compound of the formula (1) wherein Q represents Q1, $R^1$ represents a chlorine atom, a bromine atom, a methyl group, an ethyl group or a trifluoromethyl group, $R^2$, $R^4$, $R^5$, $R^7$, $R^8$, $R^9$ and $R^{11}$ represent a hydrogen atom, $R^3$ represents a hydrogen atom or a methyl group, $R^6$ represents an ethynyl group, a 1-propynyl group, a difluoromethoxy group, a trifluoromethoxy group, a methylthio group or a cyclopropyl group, $R^{10}$ represents a methyl group, X represents an oxygen atom, $Y^1$ represents a hydrogen atom, a methyl group, an ethyl group or a trifluoromethyl group, $Y^2$ represents a hydrogen atom, a halogen atom, an C1-C6 alkyl group, a C1-C6 haloalkyl group, an C2-C3 alkynyl group, an C1-C6 alkoxy group or a C3-C6 cycloalkyl group, and $Y^3$ represents a hydrogen atom, an C1-C3 alkyl group or a C1-C3 haloalkyl group;

a compound of the formula (1) wherein Q represents Q1, $R^1$ represents a chlorine atom, a bromine atom, a methyl group, an ethyl group or a trifluoromethyl group, $R^2$, $R^4$, $R^5$, $R^7$, $R^8$, $R^9$ and $R^{11}$ represent a hydrogen atom, $R^3$ represents a hydrogen atom or a methyl group, $R^6$ represents an ethynyl group, a 1-propynyl group, a difluoromethoxy group, a trifluoromethoxy group, a methylthio group or a cyclopropyl group, $R^{10}$ represents a methyl group, X represents an oxygen atom, $Y^1$ represents a hydrogen atom, a methyl group, an ethyl group or a trifluoromethyl group, $Y^2$ represents a hydrogen atom, a halogen atom, an C1-C6 alkyl group, a C1-C6 haloalkyl group, an C2-C3 alkynyl group, an C1-C6 alkoxy group or a C3-C6 cycloalkyl group, and $Y^3$ represents a hydrogen atom, a methyl group or an ethyl group;

a compound of the formula (1) wherein Q represents Q1, $R^1$ represents a chlorine atom, a bromine atom, a methyl group, an ethyl group or a trifluoromethyl group, $R^2$, $R^4$, $R^5$, $R^7$, $R^8$, $R^9$ and $R^{11}$ represent a hydrogen atom, $R^3$ represents a hydrogen atom or a methyl group, $R^6$ represents an ethynyl group, a 1-propynyl group, a difluoromethoxy group, a trifluoromethoxy group, a methylthio group or a cyclopropyl group, $R^{10}$ represents a methyl group, X represents an oxygen atom, $Y^1$ represents a hydrogen atom, a methyl group, an ethyl group or a trifluoromethyl group, $Y^2$ represents a hydrogen atom, a halogen atom, an C1-C3 alkyl group, a C1-C3 haloalkyl group, an C2-C3 alkynyl group, an C1-C3 alkoxy group or a C3-C4 cycloalkyl group, and $Y^3$ represents a hydrogen atom, an C1-C3 alkyl group or a C1-C3 haloalkyl group;

a compound of the formula (1) wherein Q represents Q1, $R^1$ represents a chlorine atom, a bromine atom, a methyl group, an ethyl group or a trifluoromethyl group, $R^2$, $R^4$, $R^5$, $R^7$, $R^8$, $R^9$ and $R^{11}$ represent a hydrogen atom, $R^3$ represents a hydrogen atom or a methyl group, $R^6$ represents an ethynyl group, a 1-propynyl group, a difluoromethoxy group, a trifluoromethoxy group, a methylthio group or a cyclopropyl group, $R^{10}$ represents a methyl group, X represents an oxygen atom, $Y^1$ represents a hydrogen atom, a methyl group, an ethyl group or a trifluoromethyl group, $Y^2$ represents a hydrogen atom, a halogen atom, an C1-C3 alkyl group, a C1-C3 haloalkyl group, an C2-C3 alkynyl group, an C1-C3 alkoxy group or a C3-C4 cycloalkyl group, and $Y^3$ represents a hydrogen atom, a methyl group or an ethyl group;

a compound of the formula (1) wherein Q represents Q1, $R^1$ represents a chlorine atom, a bromine atom, a methyl group, an ethyl group or a trifluoromethyl group, $R^2$, $R^4$, $R^5$, $R^7$, $R^8$, $R^9$ and $R^{11}$ represent a hydrogen atom, $R^3$ represents a hydrogen atom or a methyl group, $R^6$ represents an ethynyl group, a 1-propynyl group, a difluoromethoxy group, a trifluoromethoxy group, a methylthio group or a cyclopropyl group, $R^{10}$ represents a methyl group, X represents an oxygen atom, $Y^1$ represents a hydrogen atom, a methyl group, an ethyl group or a trifluoromethyl group, $Y^2$ represents a hydrogen atom, a fluorine atom, a chlorine atom, a bromine atom, a methyl group, an ethyl group, a propyl group, an isopropyl group, an ethynyl group, a 1-propynyl group, a trifluoromethyl group, a difluoromethyl group, a methoxy group, an ethoxy group or a cyclopropyl group, and $Y^3$ represents a hydrogen atom, an C1-C3 alkyl group or a C1-C3 haloalkyl group;

a compound of the formula (1) wherein Q represents Q1, $R^1$ represents a chlorine atom, a bromine atom, a methyl group, an ethyl group or a trifluoromethyl group, $R^2$, $R^4$, $R^5$, $R^7$, $R^8$, $R^9$ and $R^{11}$ represent a hydrogen atom, $R^3$ represents a hydrogen atom or a methyl group, $R^6$ represents an ethynyl group, a 1-propynyl group, a difluoromethoxy group, a trifluoromethoxy group, a methylthio group or a cyclopropyl group, $R^{10}$ represents a methyl group, X represents an oxygen atom, $Y^1$ represents a hydrogen atom, a methyl group, an ethyl group or a trifluoromethyl group, $Y^2$ represents a hydrogen atom, a fluorine atom, a chlorine atom, a bromine atom, a methyl group, an ethyl group, a propyl group, an isopropyl group, an ethynyl group, a 1-propynyl group, a trifluoromethyl group, a difluoromethyl group, a methoxy group, an ethoxy group or a cyclopropyl group, and $Y^3$ represents a hydrogen atom, a methyl group or an ethyl group, alternatively $Y^1$ and $Y^2$ connect to each other to represent —$CH_2$—$CH_2$—$CH_2$— or —$CH_2$—$CH_2$—$CH_2$—$CH_2$—, which combines together with the carbon atoms to which $Y^1$ and $Y^2$ are attached to form a five-membered or six-membered ring, or $Y^2$ and $Y^3$ connect to each other to represent —$CH_2$—$CH_2$—$CH_2$— or —$CH_2$—$CH_2$—$CH_2$—$CH_2$—, which combines together with the carbon atoms to which $Y^2$ and $Y^3$ are attached to form a five-membered or six-membered ring;

a compound of the formula (1) wherein Q represents Q1, $R^1$ represents a chlorine atom, a bromine atom, a methyl group, an ethyl group or a trifluoromethyl group, $R^2$, $R^4$, $R^5$, $R^7$, $R^8$, $R^9$ and $R^{11}$ represent a hydrogen atom, $R^3$ represents a hydrogen atom or a methyl group, $R^6$ represents an ethynyl group, a 1-propynyl group, a difluoromethoxy group, a trifluoromethoxy group, a methylthio group or a cyclopropyl group, $R^{10}$ represents a methyl group, X represents an oxygen atom, $Y^1$ represents a hydrogen atom, a methyl group, an ethyl group or a trifluoromethyl group, $Y^2$ represents a hydrogen atom, a fluorine atom, a chlorine atom, a bromine atom, a methyl group, an ethyl group, a propyl group, an isopropyl group, an ethynyl group, a 1-propynyl group, a trifluoromethyl group, a difluoromethyl group, a methoxy group, an ethoxy group or a cyclopropyl group, and $Y^3$ represents a hydrogen atom, a methyl group or an ethyl group;

a compound of the formula (1) wherein $Z^1$ represents an C1-C6 alkyl group;

a compound of the formula (1) wherein $Z^1$ represents a C1-C6 haloalkyl group;

a compound of the formula (1) wherein $Z^1$ represents an C3-C6 alkynyl group;

a compound of the formula (1) wherein $Z^1$ represents a C3-C6 haloalkynyl group;

a compound of the formula (1) wherein $Z^1$ represents a C3-C6 cycloalkyl group;

a compound of the formula (1) wherein $Z^1$ represents a C4-C7 cycloalkylmethyl group;

a compound of the formula (1) wherein $Z^1$ represents an C1-C6 alkyl group, a C1-C6 haloalkyl group, an C3-C6 alkynyl group or a C4-C7 cycloalkylmethyl group;

a compound of the formula (1) wherein $Z^1$ represents an C1-C4 alkyl group, a C1-C3 haloalkyl group, an C3-C4 alkynyl group or a cyclopropylmethyl group;

a compound of the formula (1) wherein $Z^1$ represents a methyl group, an ethyl group, a propyl group, an isopropyl group, a difluoromethyl group, a trifluoromethyl group, a 2-propynyl group, a 2-butynyl group or a cyclopropylmethyl group;

a compound of the formula (1) wherein $Z^2$ represents a hydrogen atom;

a compound of the formula (1) wherein $Z^2$ represents a halogen atom;

a compound of the formula (1) wherein $Z^2$ represents an C1-C6 alkyl group;

a compound of the formula (1) wherein $Z^2$ represents a C1-C6 haloalkyl group;

a compound of the formula (1) wherein $Z^2$ represents a C3-C6 cycloalkyl group;

a compound of the formula (1) wherein $Z^2$ represents an C1-C6 alkoxy group;

a compound of the formula (1) wherein $Z^2$ represents a C1-C6 haloalkoxy group;

a compound of the formula (1) wherein $Z^2$ represents an C2-C6 alkynyl group;

a compound of the formula (1) wherein $Z^2$ represents a C2-C6 haloalkynyl group;

a compound of the formula (1) wherein $Z^2$ represents a hydrogen atom, an C1-C6 alkyl group, a C1-C6 haloalkyl group or a C3-C6 cycloalkyl group;

a compound of the formula (1) wherein $Z^2$ represents a hydrogen atom, an C1-C3 alkyl group, a C1-C3 haloalkyl group or a cyclopropyl group;

a compound of the formula (1) wherein $Z^2$ represents a hydrogen atom, a methyl group, an ethyl group, an isopropyl group or a cyclopropyl group;

a compound of the formula (1) wherein $Z^3$ represents a hydrogen atom;

a compound of the formula (1) wherein $Z^3$ represents a halogen atom;

a compound of the formula (1) wherein $Z^3$ represents an C1-C6 alkyl group;

a compound of the formula (1) wherein $Z^3$ represents a C1-C6 haloalkyl group;

a compound of the formula (1) wherein $Z^3$ represents a C3-C6 cycloalkyl group;

a compound of the formula (1) wherein $Z^3$ represents an C1-C6 alkoxy group;

a compound of the formula (1) wherein $Z^3$ represents a C1-C6 haloalkoxy group;

a compound of the formula (1) wherein $Z^3$ represents an C2-C6 alkynyl group;

a compound of the formula (1) wherein $Z^3$ represents a C2-C6 haloalkynyl group;

a compound of the formula (1) wherein $Z^3$ represents a hydrogen atom, a C1-C3 alkyl group, a C1-C3 haloalkyl group or a cyclopropyl group;

a compound of the formula (1) wherein $Z^3$ represents a hydrogen atom, a methyl group or an ethyl group;

a compound of the formula (1) wherein Q represents Q2, $R^1$ represents a halogen atom, an C1-C3 alkyl group, a C1-C3 haloalkyl group or a C3-C5 cycloalkyl group, $R^2$, $R^4$, $R^5$, $R^7$, $R^8$, $R^9$ and $R^{11}$ represent a hydrogen atom, $R^3$ represents a hydrogen atom, a halogen atom or an C1-C3 alkyl group, $R^6$ represents an ethynyl group, a 1-propynyl group, a C1-C4 haloalkoxy group, an C1-C4 alkylthio group or a C3-C6 cycloalkyl group, $R^{10}$ represents a methyl group, X represents an oxygen atom, $Z^1$ represents an C1-C6 alkyl group, a C1-C6 haloalkyl group, an C3-C6 alkynyl group or a C4-C7 cycloalkylmethyl group, $Z^2$ represents a hydrogen atom, an C1-C6 alkyl group, a C1-C6 haloalkyl group or a C3-C6 cycloalkyl group, and $Z^3$ represents a hydrogen atom, an C1-C3 alkyl group, a C1-C3 haloalkyl group or a cyclopropyl group;

a compound of the formula (1) wherein Q represents Q2, $R^1$ represents a halogen atom, an C1-C3 alkyl group, a C1-C3 haloalkyl group or a C3-C5 cycloalkyl group, $R^2$, $R^4$, $R^5$, $R^7$, $R^8$, $R^9$ and $R^{11}$ represent a hydrogen atom, $R^3$ represents a hydrogen atom, a halogen atom or an C1-C3 alkyl group, $R^6$ represents an ethynyl group, a 1-propynyl group, a C1-C4 haloalkoxy group, an C1-C4 alkylthio group or a C3-C6 cycloalkyl group, $R^{10}$ represents a methyl group, X represents an oxygen atom, $Z^1$ represents an C1-C6 alkyl group, a C1-C6 haloalkyl group, an C3-C6 alkynyl group or a C4-C7 cycloalkylmethyl group, $Z^2$ represents a hydrogen atom, an C1-C6 alkyl group, a C1-C6 haloalkyl group or a C3-C6 cycloalkyl group, and $Z^3$ represents a hydrogen atom, an C1-C3 alkyl group, a C1-C3 haloalkyl group or a cyclopropyl group, alternatively $Z^1$ and $Z^2$ connect via a divalent straight saturated carbon chain to form a five- or six-membered ring;

a compound of the formula (1) wherein Q represents Q2, $R^1$ represents a halogen atom, an C1-C3 alkyl group, a C1-C3 haloalkyl group or a C3-C5 cycloalkyl group, $R^2$, $R^4$, $R^5$, $R^7$, $R^8$, $R^9$ and $R^{11}$ represent a hydrogen atom, $R^3$ represents a hydrogen atom, a halogen atom or an C1-C3 alkyl group, $R^6$ represents an ethynyl group, a 1-propynyl group, a C1-C4 haloalkoxy group, an C1-C4 alkylthio group or a C3-C6 cycloalkyl group, $R^{10}$ represents a methyl group, X represents an oxygen atom, $Z^1$ represents an C1-C6 alkyl group, a C1-C6 haloalkyl group, an C3-C6 alkynyl group or a C4-C7 cycloalkylmethyl group, $Z^2$ represents a hydrogen atom, an C1-C6 alkyl group, a C1-C6 haloalkyl group or a C3-C6 cycloalkyl group, and $Z^3$ represents a hydrogen atom, an C1-C3 alkyl group, a C1-C3 haloalkyl group or a cyclopropyl group, alternatively $Z^1$ and $Z^2$ connect via a divalent straight saturated carbon chain to form a five- or six-membered ring;

a compound of the formula (1) wherein Q represents Q2, $R^1$ represents a halogen atom, an C1-C3 alkyl group, a C1-C3 haloalkyl group or a C3-C5 cycloalkyl group, $R^2$, $R^4$, $R^5$, $R^7$, $R^8$, $R^9$ and $R^{11}$ represent a hydrogen atom, $R^3$ represents a hydrogen atom, a halogen atom or an C1-C3 alkyl group, $R^6$ represents an ethynyl group, a 1-propynyl group, a C1-C4 haloalkoxy group, an C1-C4 alkylthio group or a C3-C6 cycloalkyl group, $R^{10}$ represents a methyl group, X represents an oxygen atom, $Z^1$ represents an C1-C6 alkyl group, a C1-C6 haloalkyl group, an C3-C6 alkynyl group or a C4-C7 cycloalkylmethyl group, $Z^2$ represents a hydrogen atom, an C1-C6 alkyl group, a C1-C6 haloalkyl group or a C3-C6 cycloalkyl group, and $Z^3$ represents a hydrogen atom, a methyl group or an ethyl group;

a compound of the formula (1) wherein Q represents Q2, $R^1$ represents a halogen atom, an C1-C3 alkyl group, a C1-C3 haloalkyl group or a C3-C5 cycloalkyl group, $R^2$, $R^4$, $R^5$, $R^7$, $R^8$, $R^9$ and $R^{11}$ represent a hydrogen atom, $R^3$ represents a hydrogen atom, a halogen atom or an C1-C3 alkyl group, $R^6$ represents an ethynyl group, a 1-propynyl group, a C1-C4 haloalkoxy group, an C1-C4 alkylthio group or a C3-C6 cycloalkyl group, $R^{10}$ represents a methyl group, X represents an oxygen atom, $Z^1$ represents an C1-C6 alkyl group, a C1-C6 haloalkyl group, an C3-C6 alkynyl group or a C4-C7 cycloalkylmethyl group, $Z^2$ represents a hydrogen atom, an C1-C3 alkyl group, a C1-C3 haloalkyl group or a cyclopropyl group, and $Z^3$ represents a hydrogen atom, an C1-C3 alkyl group, a C1-C3 haloalkyl group or a cyclopropyl group;

a compound of the formula (1) wherein Q represents Q2, $R^1$ represents a halogen atom, an C1-C3 alkyl group, a C1-C3 haloalkyl group or a C3-C5 cycloalkyl group, $R^2$, $R^4$, $R^5$, $R^7$, $R^8$, $R^9$ and $R^{11}$ represent a hydrogen atom, $R^3$ represents a hydrogen atom, a halogen atom or an C1-C3 alkyl group, $R^6$ represents an ethynyl group, a 1-propynyl group, a C1-C4 haloalkoxy group, an C1-C4 alkylthio group or a C3-C6 cycloalkyl group, $R^{10}$ represents a methyl group, X represents an oxygen atom, $Z^1$ represents an C1-C6 alkyl group, a C1-C6 haloalkyl group, an C3-C6 alkynyl group or a C4-C7 cycloalkylmethyl group, $Z^2$ represents a hydrogen atom, an C1-C3 alkyl group, a C1-C3 haloalkyl group or a cyclopropyl group, and $Z^3$ represents a hydrogen atom, an C1-C3 alkyl group, a C1-C3 haloalkyl group or a cyclopropyl group;

a compound of the formula (1) wherein Q represents Q2, $R^1$ represents a halogen atom, an C1-C3 alkyl group, a C1-C3 haloalkyl group or a C3-C5 cycloalkyl group, $R^2$, $R^4$, $R^5$, $R^7$, $R^8$, $R^9$ and $R^{11}$ represent a hydrogen atom, $R^3$ represents a hydrogen atom, a halogen atom or an C1-C3 alkyl group, $R^6$ represents an ethynyl group, a 1-propynyl group, a C1-C4 haloalkoxy group, an C1-C4 alkylthio group or a C3-C6 cycloalkyl group, $R^{10}$ represents a methyl group, X represents an oxygen atom, $Z^1$ represents an C1-C6 alkyl group, a C1-C6 haloalkyl group, an C3-C6 alkynyl group or a C4-C7 cycloalkylmethyl group, $Z^2$ represents a hydrogen atom, an C1-C3 alkyl group, a C1-C3 haloalkyl group or a cyclopropyl group, and $Z^3$ represents a hydrogen atom, a methyl group or an ethyl group;

a compound of the formula (1) wherein Q represents Q2, $R^1$ represents a halogen atom, an C1-C3 alkyl group, a C1-C3 haloalkyl group or a C3-C5 cycloalkyl group, $R^2$, $R^4$, $R^5$, $R^7$, $R^8$, $R^9$ and $R^{11}$ represent a hydrogen atom, $R^3$ represents a hydrogen atom, a halogen atom or an C1-C3 alkyl group, $R^6$ represents an ethynyl group, a 1-propynyl group, a C1-C4 haloalkoxy group, an C1-C4 alkylthio group or a C3-C6 cycloalkyl group, $R^{10}$ represents a methyl group, X represents an oxygen atom, $Z^1$ represents an C1-C6 alkyl group, a C1-C6 haloalkyl group, an C3-C6 alkynyl group or a C4-C7 cycloalkylmethyl group, $Z^2$ represents a hydrogen atom, a methyl group, an ethyl group, an isopropyl group or a cyclopropyl group, and $Z^3$ represents a hydrogen atom, an C1-C3 alkyl group, a C1-C3 haloalkyl group or a cyclopropyl group;

a compound of the formula (1) wherein Q represents Q2, $R^1$ represents a halogen atom, an C1-C3 alkyl group, a C1-C3 haloalkyl group or a C3-C5 cycloalkyl group, $R^2$, $R^4$, $R^5$, $R^7$, $R^8$, $R^9$ and $R^{11}$ represent a hydrogen atom, $R^3$ represents a hydrogen atom, a halogen atom or an C1-C3 alkyl group, $R^6$ represents an ethynyl group, a 1-propynyl group, a C1-C4 haloalkoxy group, an C1-C4 alkylthio group or a C3-C6 cycloalkyl group, $R^{10}$ represents a methyl group, X represents an oxygen atom, $Z^1$ represents an C1-C6 alkyl group, a C1-C6 haloalkyl group, an C3-C6 alkynyl group or a C4-C7 cycloalkylmethyl group, $Z^2$ represents a hydrogen atom, a methyl group, an ethyl group, an isopropyl group or a cyclopropyl group, and $Z^3$ represents a hydrogen atom, a methyl group or an ethyl group;

a compound of the formula (1) wherein Q represents Q2, $R^1$ represents a halogen atom, an C1-C3 alkyl group, a C1-C3 haloalkyl group or a C3-C5 cycloalkyl group, $R^2$, $R^4$, $R^5$, $R^7$, $R^8$, $R^9$ and $R^{11}$ represent a hydrogen atom, $R^3$ represents a hydrogen atom, a halogen atom or an C1-C3 alkyl group, $R^6$ represents an ethynyl group, a 1-propynyl group, a C1-C4 haloalkoxy group, an C1-C4 alkylthio group or a C3-C6 cycloalkyl group, $R^{10}$ represents a methyl group, X represents an oxygen atom, $Z^1$ represents an C1-C4 alkyl group, a C1-C3 haloalkyl group, an C3-C4 alkynyl group or a cyclopropylmethyl group, $Z^2$ represents a hydrogen atom, an C1-C6 alkyl group, a C1-C6 haloalkyl group or a C3-C6 cycloalkyl group, and $Z^3$ represents a hydrogen atom, an C1-C3 alkyl group, a C1-C3 haloalkyl group or a cyclopropyl group;

a compound of the formula (1) wherein Q represents Q2, $R^1$ represents a halogen atom, an C1-C3 alkyl group, a C1-C3 haloalkyl group or a C3-C5 cycloalkyl group, $R^2$, $R^4$, $R^5$, $R^7$, $R^8$, $R^9$ and $R^{11}$ represent a hydrogen atom, $R^3$ represents a hydrogen atom, a halogen atom or an C1-C3 alkyl group, $R^6$ represents an ethynyl group, a 1-propynyl group, a C1-C4 haloalkoxy group, an C1-C4 alkylthio group or a C3-C6 cycloalkyl group, $R^{10}$ represents a methyl group, X represents an oxygen atom, $Z^1$ represents an C1-C4 alkyl group, a C1-C3 haloalkyl group, an C3-C4 alkynyl group or a cyclopropylmethyl group, $Z^2$ represents a hydrogen atom, an C1-C6 alkyl group, a C1-C6 haloalkyl group or a C3-C6 cycloalkyl group, and $Z^3$ represents a hydrogen atom, a methyl group or an ethyl group;

a compound of the formula (1) wherein Q represents Q2, $R^1$ represents a halogen atom, an C1-C3 alkyl group, a C1-C3 haloalkyl group or a C3-C5 cycloalkyl group, $R^2$, $R^4$, $R^5$, $R^7$, $R^8$, $R^9$ and $R^{11}$ represent a hydrogen atom, $R^3$ represents a hydrogen atom, a halogen atom or an C1-C3 alkyl group, $R^6$ represents an ethynyl group, a 1-propynyl group, a C1-C4 haloalkoxy group, an C1-C4 alkylthio group or a C3-C6 cycloalkyl group, $R^{10}$ represents a methyl group, X represents an oxygen atom, $Z^1$ represents an C1-C4 alkyl group, a C1-C3 haloalkyl group, an C3-C4 alkynyl group or a cyclopropylmethyl group, $Z^2$ represents a hydrogen atom, an C1-C3 alkyl group, a C1-C3 haloalkyl group or a cyclopropyl group, and $Z^3$ represents a hydrogen atom, an C1-C3 alkyl group, a C1-C3 haloalkyl group or a cyclopropyl group;

a compound of the formula (1) wherein Q represents Q2, $R^1$ represents a halogen atom, an C1-C3 alkyl group, a C1-C3 haloalkyl group or a C3-C5 cycloalkyl group, $R^2$, $R^4$, $R^5$, $R^7$, $R^8$, $R^9$ and $R^{11}$ represent a hydrogen atom, $R^3$ represents a hydrogen atom, a halogen atom or an C1-C3 alkyl group, $R^6$ represents an ethynyl group, a 1-propynyl group, a C1-C4 haloalkoxy group, an C1-C4 alkylthio group or a C3-C6 cycloalkyl group, $R^{10}$ represents a methyl group, X represents an oxygen atom, $Z^1$ represents an C1-C4 alkyl group, a C1-C3 haloalkyl group, an C3-C4 alkynyl group or a cyclopropylmethyl group, $Z^2$ represents a hydrogen atom, an C1-C3 alkyl group, a C1-C3 haloalkyl group or a cyclopropyl group, and $Z^3$ represents a hydrogen atom, a methyl group or an ethyl group;

a compound of the formula (1) wherein Q represents Q2, $R^1$ represents a halogen atom, an C1-C3 alkyl group, a C1-C3 haloalkyl group or a C3-C5 cycloalkyl group, $R^2$, $R^4$, $R^5$, $R^7$, $R^8$, $R^9$ and $R^{11}$ represent a hydrogen atom, $R^3$ represents a hydrogen atom, a halogen atom or an C1-C3 alkyl group, $R^6$ represents an ethynyl group, a 1-propynyl group, a C1-C4 haloalkoxy group, an C1-C4 alkylthio group or a C3-C6 cycloalkyl group, $R^{10}$ represents a methyl group, X represents an oxygen atom, $Z^1$ represents an C1-C4 alkyl group, a C1-C3 haloalkyl group, an C3-C4 alkynyl group or a cyclopropylmethyl group, $Z^2$ represents a hydrogen atom, a methyl group, an ethyl group, a isopropyl group or a cyclopropyl group, and $Z^3$ represents a hydrogen atom, an C1-C3 alkyl group, a C1-C3 haloalkyl group or a cyclopropyl group;

a compound of the formula (1) wherein Q represents Q2, $R^1$ represents a halogen atom, an C1-C3 alkyl group, a C1-C3 haloalkyl group or a C3-C5 cycloalkyl group, $R^2$, $R^4$, $R^5$, $R^7$, $R^8$, $R^9$ and $R^{11}$ represent a hydrogen atom, $R^3$ represents a hydrogen atom, a halogen atom or an C1-C3 alkyl group, $R^6$ represents an ethynyl group, a 1-propynyl group, a C1-C4 haloalkoxy group, an C1-C4 alkylthio group or a C3-C6 cycloalkyl group, $R^{10}$ represents a methyl group, X represents an oxygen atom, $Z^1$ represents an C1-C4 alkyl group, a C1-C3 haloalkyl group, an C3-C4 alkynyl group or a cyclopropylmethyl group, $Z^2$ represents a hydrogen atom, a methyl group, an ethyl group, a isopropyl group or a cyclopropyl group, and $Z^3$ represents a hydrogen atom, a methyl group or an ethyl group;

a compound of the formula (1) wherein Q represents Q2, $R^1$ represents a halogen atom, an C1-C3 alkyl group, a C1-C3 haloalkyl group or a C3-C5 cycloalkyl group, $R^2$, $R^4$, $R^5$, $R^7$, $R^8$, $R^9$ and $R^{11}$ represent a hydrogen atom, $R^3$ represents a hydrogen atom, a halogen atom or an C1-C3 alkyl group, $R^6$ represents an ethynyl group, a 1-propynyl group, a C1-C4 haloalkoxy group, an C1-C4 alkylthio group or a C3-C6 cycloalkyl group, $R^{10}$ represents a methyl group, X represents an oxygen atom, $Z^1$ represents a methyl group, an ethyl group, a propyl group, an isopropyl group, a difluoromethyl group, a trifluoromethyl group, a 2-propenyl group, a 2-butynyl group or a cyclopropylmethyl group, $Z^2$ represents a hydrogen atom, an C1-C6 alkyl group, a C1-C3 haloalkyl group or a C3-C6 cycloalkyl group, and $Z^3$ represents a hydrogen atom, an C1-C3 alkyl group, a C1-C3 haloalkyl group or a cyclopropyl group;

a compound of the formula (1) wherein Q represents Q2, $R^1$ represents a halogen atom, an C1-C3 alkyl group, a C1-C3 haloalkyl group or a C3-C5 cycloalkyl group, $R^2$, $R^4$, $R^5$, $R^7$, $R^8$, $R^9$ and $R^{11}$ represent a hydrogen atom, $R^3$ represents a hydrogen atom, a halogen atom or an C1-C3 alkyl group, $R^6$ represents an ethynyl group, a 1-propynyl group, a C1-C4 haloalkoxy group, an C1-C4 alkylthio group or a C3-C6 cycloalkyl group, $R^{10}$ represents a methyl group, X represents an oxygen atom, $Z^1$ represents a methyl group, an ethyl group, a propyl group, an isopropyl group, a difluoromethyl group, a trifluoromethyl group, a 2-propenyl group, a 2-butynyl group or a cyclopropylmethyl group, $Z^2$ represents a hydrogen atom, an C1-C6 alkyl group, a C1-C6 haloalkyl group or a C3-C6 cycloalkyl group, and $Z^3$ represents a hydrogen atom, a methyl group or an ethyl group;

a compound of the formula (1) wherein Q represents Q2, $R^1$ represents a halogen atom, an C1-C3 alkyl group, a C1-C3 haloalkyl group or a C3-C5 cycloalkyl group, $R^2$, $R^4$, $R^5$, $R^7$, $R^8$, $R^9$ and $R^{11}$ represent a hydrogen atom, $R^3$ represents a hydrogen atom, a chlorine atom or an C1-C3 alkyl group, $R^6$ represents an ethynyl group, a 1-propynyl group, a C1-C4 haloalkoxy group, an C1-C4 alkylthio group or a C3-C6 cycloalkyl group, $R^{10}$ represents a methyl group, X represents an oxygen atom, $Z^1$ represents a methyl group, an ethyl group, a propyl group, an isopropyl group, a difluoromethyl group, a trifluoromethyl group, a 2-propenyl group, a 2-butynyl group or a cyclopropylmethyl group, $Z^2$ represents a hydrogen atom, an C1-C3 alkyl group, a C1-C3 haloalkyl group or a cyclopropyl group, and $Z^3$ represents a hydrogen atom, an C1-C3 alkyl group, a C1-C3 haloalkyl group or a cyclopropyl group;

a compound of the formula (1) wherein Q represents Q2, $R^1$ represents a halogen atom, an C1-C3 alkyl group, a C1-C3 haloalkyl group or a C3-C5 cycloalkyl group, $R^2$, $R^4$, $R^5$, $R^7$, $R^8$, $R^9$ and $R^{11}$ represent a hydrogen atom, $R^3$ represents a hydrogen atom, a halogen atom or an C1-C3 alkyl group, $R^6$ represents an ethynyl group, a 1-propynyl group, a C1-C4 haloalkoxy group, an C1-C4 alkylthio group or a C3-C6 cycloalkyl group, $R^{10}$ represents a methyl group, X represents an oxygen atom, $Z^1$ represents a methyl group, an ethyl group, a propyl group, an isopropyl group, a difluoromethyl group, a trifluoromethyl group, a 2-propenyl group, a 2-butynyl group or a cyclopropylmethyl group, $Z^2$ represents a hydrogen atom, an C1-C3 alkyl group, a C1-C3 haloalkyl group or a cyclopropyl group, and $Z^3$ represents a hydrogen atom, a methyl group or an ethyl group;

a compound of the formula (1) wherein Q represents Q2, $R^1$ represents a halogen atom, an C1-C3 alkyl group, a C1-C3 haloalkyl group or a C3-C5 cycloalkyl group, $R^2$, $R^4$, $R^5$, $R^7$, $R^8$, $R^9$ and $R^{11}$ represent a hydrogen atom, $R^3$ represents a hydrogen atom, a halogen atom or an C1-C3 alkyl group, $R^6$ represents an ethynyl group, a 1-propynyl group, a C1-C4 haloalkoxy group, an C1-C4 alkylthio group or a C3-C6 cycloalkyl group, $R^{10}$ represents a methyl group, X represents an oxygen atom, $Z^1$ represents a methyl group, an ethyl group, a propyl group, an isopropyl group, a difluoromethyl group, a trifluoromethyl group, a 2-propenyl group, a 2-butynyl group or a cyclopropylmethyl group, $Z^2$ represents a hydrogen atom, a methyl group, an ethyl group, an isopropyl group or a cyclopropyl group, and $Z^3$ represents a hydrogen atom, an C1-C3 alkyl group, a C1-C3 haloalkyl group or a cyclopropyl group;

a compound of the formula (1) wherein Q represents Q2, $R^1$ represents a halogen atom, an C1-C3 alkyl group, a C1-C3 haloalkyl group or a C3-C5 cycloalkyl group, $R^2$, $R^4$, $R^5$, $R^7$, $R^8$, $R^9$ and $R^{11}$ represent a hydrogen atom, $R^3$ represents a hydrogen atom, a halogen atom or an C1-C3 alkyl group, $R^6$ represents an ethynyl group, a 1-propynyl group, a C1-C4 haloalkoxy group, an C1-C4 alkylthio group or a C3-C6 cycloalkyl group, $R^{10}$ represents a methyl group, X represents an oxygen atom, $Z^1$ represents a methyl group, an ethyl group, a propyl group, an isopropyl group, a difluoromethyl group, a trifluoromethyl group, a 2-propenyl group, a 2-butynyl group or a cyclopropylmethyl group, $Z^2$ represents a hydrogen atom, a methyl group, an ethyl group, an isopropyl group or a cyclopropyl group, and $Z^3$ represents a hydrogen atom, a methyl group or an ethyl group;

a compound of the formula (1) wherein Q represents Q2, $R^1$ represents a halogen atom, an C1-C3 alkyl group or a C1-C3 haloalkyl group, $R^2$, $R^4$, $R^5$, $R^7$, $R^8$, $R^9$ and $R^{11}$ represent a hydrogen atom, $R^3$ represents a hydrogen atom, a chlorine atom or a methyl group, $R^6$ represents an ethynyl group, a 1-propynyl group, a C1-C2 haloalkoxy group, an C1-C2 alkylthio group or a C3-C4 cycloalkyl group, $R^{10}$ represents a methyl group, X represents an oxygen atom, $Z^1$ represents an C1-C6 alkyl group, a C1-C6 haloalkyl group, an C3-C6 alkynyl group or a C4-C7 cycloalkylmethyl group, $Z^2$ represents a hydrogen atom, an C1-C6 alkyl group, a C1-C6 haloalkyl group or a C3-C6 cycloalkyl group, and $Z^3$ represents a hydrogen atom, an C1-C3 alkyl group, a C1-C3 haloalkyl group or a cyclopropyl group;

a compound of the formula (1) wherein Q represents Q2, $R^1$ represents a halogen atom, an C1-C3 alkyl group or a C1-C3 haloalkyl group, $R^2$, $R^4$, $R^5$, $R^7$, $R^8$, $R^9$ and $R^{11}$ represent a hydrogen atom, $R^3$ represents a hydrogen atom, a chlorine atom or a methyl group, $R^6$ represents an ethynyl group, a 1-propynyl group, a C1-C2 haloalkoxy group, an C1-C2 alkylthio group or a C3-C4 cycloalkyl group, $R^{10}$ represents a methyl group, X represents an oxygen atom, $Z^1$ represents an C1-C6 alkyl group, a C1-C6 haloalkyl group, an C3-C6 alkynyl group or a C4-C7 cycloalkylmethyl group, $Z^2$ represents a hydrogen atom, an C1-C6 alkyl group, a C1-C6 haloalkyl group or a C3-C6 cycloalkyl group, and $Z^3$ represents a hydrogen atom, a methyl group or an ethyl group;

a compound of the formula (1) wherein Q represents Q2, $R^1$ represents a halogen atom, an C1-C3 alkyl group or a C1-C3 haloalkyl group, $R^2$, $R^4$, $R^5$, $R^7$, $R^8$, $R^9$ and $R^{11}$ represent a hydrogen atom, $R^3$ represents a hydrogen atom, a chlorine atom or a methyl group, $R^6$ represents an ethynyl group, a 1-propynyl group, a C1-C2 haloalkoxy group, an C1-C2 alkylthio group or a C3-C4 cycloalkyl group, $R^{10}$ represents a methyl group, X represents an oxygen atom, $Z^1$ represents an C1-C6 alkyl group, a C1-C6 haloalkyl group, an C3-C6 alkynyl group or a C4-C7 cycloalkylmethyl group, $Z^2$ represents a hydrogen atom, an C1-C3 alkyl group, a C1-C3 haloalkyl group or a cyclopropyl group, and $Z^3$ represents a hydrogen atom, an C1-C3 alkyl group, a C1-C3 haloalkyl group or a cyclopropyl group;

a compound of the formula (1) wherein Q represents Q2, $R^1$ represents a halogen atom, an C1-C3 alkyl group or a C1-C3 haloalkyl group, $R^2$, $R^4$, $R^5$, $R^7$, $R^8$, $R^9$ and $R^{11}$ represent a hydrogen atom, $R^3$ represents a hydrogen atom, a chlorine atom or a methyl group, $R^6$ represents an ethynyl group, a 1-propynyl group, a C1-C2 haloalkoxy group, an C1-C2 alkylthio group or a C3-C4 cycloalkyl group, $R^{10}$ represents a methyl group, X represents an oxygen atom, $Z^1$ represents an C1-C6 alkyl group, a C1-C6 haloalkyl group, an C3-C6 alkynyl group or a C4-C7 cycloalkylmethyl group, $Z^2$ represents a hydrogen atom, an C1-C3 alkyl group, a C1-C3 haloalkyl group or a cyclopropyl group, and $Z^3$ represents a hydrogen atom, a methyl group or an ethyl group;

a compound of the formula (1) wherein Q represents Q2, $R^1$ represents a halogen atom, an C1-C3 alkyl group or a C1-C3 haloalkyl group, $R^2$, $R^4$, $R^5$, $R^7$, $R^8$, $R^9$ and $R^{11}$ represent a hydrogen atom, $R^3$ represents a hydrogen atom, a chlorine atom or a methyl group, $R^6$ represents an ethynyl group, a 1-propynyl group, a C1-C2 haloalkoxy group, an C1-C2 alkylthio group or a C3-C4 cycloalkyl group, $R^{10}$ represents a methyl group, X represents an oxygen atom, $Z^1$ represents an C1-C6 alkyl group, a C1-C6 haloalkyl group, an C3-C6 alkynyl group or a C4-C7 cycloalkylmethyl group, $Z^2$ represents a hydrogen atom, a methyl group, an ethyl group, an isopropyl group or a cyclopropyl group, and $Z^3$ represents a hydrogen atom, an C1-C3 alkyl group, a C1-C3 haloalkyl group or a cyclopropyl group;

a compound of the formula (1) wherein Q represents Q2, $R^1$ represents a halogen atom, an C1-C3 alkyl group or a C1-C3 haloalkyl group, $R^2$, $R^4$, $R^5$, $R^7$, $R^8$, $R^9$ and $R^{11}$ represent a hydrogen atom, $R^3$ represents a hydrogen atom, a chlorine atom or a methyl group, $R^6$ represents an ethynyl group, a 1-propynyl group, a C1-C2 haloalkoxy group, an C1-C2 alkylthio group or a C3-C4 cycloalkyl group, $R^{10}$ represents a methyl group, X represents an oxygen atom, $Z^1$ represents an C1-C6 alkyl group, a C1-C6 haloalkyl group, an C3-C6 alkynyl group or a C4-C7 cycloalkylmethyl group, $Z^2$ represents a hydrogen atom, a methyl group, an ethyl group, an isopropyl group or a cyclopropyl group, and $Z^3$ represents a hydrogen atom, a methyl group or an ethyl group;

a compound of the formula (1) wherein Q represents Q2, $R^1$ represents a halogen atom, an C1-C3 alkyl group or a C1-C3 haloalkyl group, $R^2$, $R^4$, $R^5$, $R^7$, $R^8$, $R^9$ and $R^{11}$ represent a hydrogen atom, $R^3$ represents a hydrogen atom, a chlorine atom or a methyl group, $R^6$ represents an ethynyl group, a 1-propynyl group, a C1-C2 haloalkoxy group, an C1-C2 alkylthio group or a C3-C4 cycloalkyl group, $R^{10}$ represents a methyl group, X represents an oxygen atom, $Z^1$ represents an C1-C4 alkyl group, a C1-C3 haloalkyl group, an C3-C4 alkynyl group or a cyclopropylmethyl group, $Z^2$ represents a hydrogen atom, an C1-C6 alkyl group, a C1-C6 haloalkyl group or a C3-C6 cycloalkyl group, and $Z^3$ represents a hydrogen atom, an C1-C3 alkyl group, a C1-C3 haloalkyl group or a cyclopropyl group;

a compound of the formula (1) wherein Q represents Q2, $R^1$ represents a halogen atom, an C1-C3 alkyl group or a C1-C3 haloalkyl group, $R^2$, $R^4$, $R^5$, $R^7$, $R^8$, $R^9$ and $R^{11}$ represent a hydrogen atom, $R^3$ represents a hydrogen atom, a chlorine atom or a methyl group, $R^6$ represents an ethynyl group, a 1-propynyl group, a C1-C2 haloalkoxy group, an C1-C2 alkylthio group or a C3-C4 cycloalkyl group, $R^{10}$ represents a methyl group, X represents an oxygen atom, $Z^1$ represents an C1-C4 alkyl group, a C1-C3 haloalkyl group, an C3-C4 alkynyl group or a cyclopropylmethyl group, $Z^2$ represents a hydrogen atom, an C1-C6 alkyl group, a C1-C6 haloalkyl group or a C3-C6 cycloalkyl group, and $Z^3$ represents a hydrogen atom, a methyl group or an ethyl group;

a compound of the formula (1) wherein Q represents Q2, $R^1$ represents a halogen atom, an C1-C3 alkyl group or a C1-C3 haloalkyl group, $R^2$, $R^4$, $R^5$, $R^7$, $R^8$, $R^9$ and $R^{11}$ represent a hydrogen atom, $R^3$ represents a hydrogen atom, a chlorine atom or a methyl group, $R^6$ represents an ethynyl group, a 1-propynyl group, a C1-C2 haloalkoxy group, an C1-C2 alkylthio group or a C3-C4 cycloalkyl group, $R^{10}$ represents a methyl group, X represents an oxygen atom, $Z^1$ represents an C1-C4 alkyl group, a C1-C3 haloalkyl group, an C3-C4 alkynyl group or a cyclopropylmethyl group, $Z^2$ represents a hydrogen atom, an C1-C3 alkyl group, a C1-C3 haloalkyl group or a cyclopropyl group, and $Z^3$ represents a hydrogen atom, an C1-C3 alkyl group, a C1-C3 haloalkyl group or a cyclopropyl group;

a compound of the formula (1) wherein Q represents Q2, $R^1$ represents a halogen atom, an C1-C3 alkyl group or a C1-C3 haloalkyl group, $R^2$, $R^4$, $R^5$, $R^7$, $R^8$, $R^9$ and $R^{11}$ represent a hydrogen atom, $R^3$ represents a hydrogen atom, a chlorine atom or a methyl group, $R^6$ represents an ethynyl group, a 1-propynyl group, a C1-C2 haloalkoxy group, an C1-C2 alkylthio group or a C3-C4 cycloalkyl group, $R^{10}$ represents a methyl group, X represents an oxygen atom, $Z^1$ represents an C1-C4 alkyl group, a C1-C3 haloalkyl group, an C3-C4 alkynyl group or a cyclopropylmethyl group, $Z^2$ represents a hydrogen atom, an C1-C3 alkyl group, a C1-C3 haloalkyl group or a cyclopropyl group, and $Z^3$ represents a hydrogen atom, a methyl group or an ethyl group;

a compound of the formula (1) wherein Q represents Q2, $R^1$ represents a halogen atom, an C1-C3 alkyl group or a C1-C3 haloalkyl group, $R^2$, $R^4$, $R^5$, $R^7$, $R^8$, $R^9$ and $R^{11}$ represent a hydrogen atom, $R^3$ represents a hydrogen atom, a chlorine atom or a methyl group, $R^6$ represents an ethynyl group, a 1-propynyl group, a C1-C2 haloalkoxy group, an C1-C2 alkylthio group or a C3-C4 cycloalkyl group, $R^{10}$ represents a methyl group, X represents an oxygen atom, $Z^1$ represents an C1-C4 alkyl group, a C1-C3 haloalkyl group, an C3-C4 alkynyl group or a cyclopropylmethyl group, $Z^2$ represents a hydrogen atom, a methyl group, an ethyl group, an isopropyl group or a cyclopropyl group, and $Z^3$ represents a hydrogen atom, an C1-C3 alkyl group, a C1-C3 haloalkyl group or a cyclopropyl group;

a compound of the formula (1) wherein Q represents Q2, $R^1$ represents a halogen atom, an C1-C3 alkyl group or a C1-C3 haloalkyl group, $R^2$, $R^4$, $R^5$, $R^7$, $R^8$, $R^9$ and $R^{11}$ represent a hydrogen atom, $R^3$ represents a hydrogen atom, a chlorine atom or a methyl group, $R^6$ represents an ethynyl group, a 1-propynyl group, a C1-C2 haloalkoxy group, an C1-C2 alkylthio group or a C3-C4 cycloalkyl group, $R^{10}$ represents a methyl group, X represents an oxygen atom, $Z^1$ represents an C1-C4 alkyl group, a C1-C3 haloalkyl group, an C3-C4 alkynyl group or a cyclopropylmethyl group, $Z^2$ represents a hydrogen atom, a methyl group, an ethyl group, an isopropyl group or a cyclopropyl group, and $Z^3$ represents a hydrogen atom, a methyl group or an ethyl group;

a compound of the formula (1) wherein Q represents Q2, $R^1$ represents a halogen atom, an C1-C3 alkyl group or a C1-C3 haloalkyl group, $R^2$, $R^4$, $R^5$, $R^7$, $R^8$, $R^9$ and $R^{11}$ represent a hydrogen atom, $R^3$ represents a hydrogen atom, a chlorine atom or a methyl group, $R^6$ represents an ethynyl group, a 1-propynyl group, a C1-C2 haloalkoxy group, an C1-C2 alkylthio group or a C3-C4 cycloalkyl group, $R^{10}$ represents a methyl group, X represents an oxygen atom, $Z^1$ represents a methyl group, an ethyl group, a propyl group, an isopropyl group, a difluoromethyl group, a trifluoromethyl group, a 2-propynyl group, a 2-butynyl group or a cyclopropylmethyl group, $Z^2$ represents a hydrogen atom, an C1-C6 alkyl group, a C1-C6 haloalkyl group or a C3-C6 cycloalkyl group, and $Z^3$ represents a hydrogen atom, an C1-C3 alkyl group, a C1-C3 haloalkyl group or a cyclopropyl group;

a compound of the formula (1) wherein Q represents Q2, $R^1$ represents a halogen atom, an C1-C3 alkyl group or a C1-C3 haloalkyl group, $R^2$, $R^4$, $R^5$, $R^7$, $R^8$, $R^9$ and $R^{11}$ represent a hydrogen atom, $R^3$ represents a hydrogen atom, a chlorine atom or a methyl group, $R^6$ represents an ethynyl group, a 1-propynyl group, a C1-C2 haloalkoxy group, an C1-C2 alkylthio group or a C3-C4 cycloalkyl group, $R^{10}$ represents a methyl group, X represents an oxygen atom, $Z^1$ represents a methyl group, an ethyl group, a propyl group, an isopropyl group, a difluoromethyl group, a trifluoromethyl group, a 2-propynyl group, a 2-butynyl group or a cyclopropylmethyl group, $Z^2$ represents a hydrogen atom, an C1-C6 alkyl group, a C1-C6 haloalkyl group or a C3-C6 cycloalkyl group, and $Z^3$ represents a hydrogen atom, a methyl group or an ethyl group;

a compound of the formula (1) wherein Q represents Q2, $R^1$ represents a halogen atom, an C1-C3 alkyl group or a C1-C3 haloalkyl group, $R^2$, $R^4$, $R^5$, $R^7$, $R^8$, $R^9$ and $R^{11}$ represent a hydrogen atom, $R^3$ represents a hydrogen atom, a chlorine atom or a methyl group, $R^6$ represents an ethynyl group, a 1-propynyl group, a C1-C2 haloalkoxy group, an C1-C2 alkylthio group or a C3-C4 cycloalkyl group, $R^{10}$ represents a methyl group, X represents an oxygen atom, $Z^1$ represents a methyl group, an ethyl group, a propyl group, an isopropyl group, a difluoromethyl group, a trifluoromethyl group, a 2-propynyl group, a 2-butynyl group or a cyclopropylmethyl group, $Z^2$ represents a hydrogen atom, an C1-C3 alkyl group, a C1-C3 haloalkyl group or a cyclopropyl group, and $Z^3$ represents a hydrogen atom, an C1-C3 alkyl group, a C1-C3 haloalkyl group or a cyclopropyl group;

a compound of the formula (1) wherein Q represents Q2, $R^1$ represents a halogen atom, an C1-C3 alkyl group or a C1-C3 haloalkyl group, $R^2$, $R^4$, $R^5$, $R^7$, $R^8$, $R^9$ and $R^{11}$ represent a hydrogen atom, $R^3$ represents a hydrogen atom, a chlorine atom or a methyl group, $R^6$ represents an ethynyl group, a 1-propynyl group, a C1-C2 haloalkoxy group, an C1-C2 alkylthio group or a C3-C4 cycloalkyl group, $R^{10}$ represents a methyl group, X represents an oxygen atom, $Z^1$ represents a methyl group, an ethyl group, a propyl group, an isopropyl group, a difluoromethyl group, a trifluoromethyl group, a 2-propynyl group, a 2-butynyl group or a cyclopropylmethyl group, $Z^2$ represents a hydrogen atom, an C1-C3 alkyl group, a C1-C3 haloalkyl group or a cyclopropyl group, and $Z^3$ represents a hydrogen atom, a methyl group or an ethyl group;

a compound of the formula (1) wherein Q represents Q2, $R^1$ represents a halogen atom, an C1-C3 alkyl group or a C1-C3 haloalkyl group, $R^2$, $R^4$, $R^5$, $R^7$, $R^8$, $R^9$ and $R^{11}$ represent a hydrogen atom, $R^3$ represents a hydrogen atom, a chlorine atom or a methyl group, $R^6$ represents an ethynyl group, a 1-propynyl group, a C1-C2 haloalkoxy group, an C1-C2 alkylthio group or a C3-C4 cycloalkyl group, $R^{10}$ represents a methyl group, X represents an oxygen atom, $Z^1$ represents a methyl group, an ethyl group, a propyl group, an isopropyl group, a difluoromethyl group, a trifluoromethyl group, a 2-propynyl group, a 2-butynyl group or a cyclopropylmethyl group, $Z^2$ represents a hydrogen atom, a methyl group, an ethyl group, an isopropyl group or a cyclopropyl group, and $Z^3$ represents a hydrogen atom, an C1-C3 alkoxy group, a C1-C3 haloalkoxy group or a cyclopropyl group;

a compound of the formula (1) wherein Q represents Q2, $R^1$ represents a halogen atom, an C1-C3 alkyl group or a C1-C3 haloalkyl group, $R^2$, $R^4$, $R^5$, $R^7$, $R^8$, $R^9$ and $R^{11}$ represent a hydrogen atom, $R^3$ represents a hydrogen atom, a chlorine atom or a methyl group, $R^6$ represents an ethynyl group, a 1-propynyl group, a C1-C2 haloalkoxy group, an C1-C2 alkylthio group or a C3-C4 cycloalkyl group, $R^{10}$ represents a methyl group, X represents an oxygen atom, $Z^1$ represents a methyl group, an ethyl group, a propyl group, an isopropyl group, a difluoromethyl group, a trifluoromethyl group, a 2-propynyl group, a 2-butynyl group or a cyclopropylmethyl group, $Z^2$ represents a hydrogen atom, a methyl group, an ethyl group, an isopropyl group or a cyclopropyl group, and $Z^3$ represents a hydrogen atom, a methyl group or an ethyl group;

a compound of the formula (1) wherein Q represents Q2, $R^1$ represents a chlorine atom, a bromine atom, a methyl group, an ethyl group or a trifluoromethyl group, $R^2$, $R^4$, $R^5$, $R^7$, $R^8$, $R^9$ and $R^{11}$ represent a hydrogen atom, $R^3$ represents a hydrogen atom or a methyl group, $R^6$ represents an ethynyl group, a 1-propynyl group, a difluoromethoxy group, a trifluoromethoxy group, a methylthio group or a cyclopropyl group, $R^{10}$ represents a methyl group, X represents an oxygen atom, $Z^1$ represents an C1-C6 alkyl group, a C1-C6 haloalkyl group, an C3-C6 alkynyl group or a C4-C7 cycloalkylmethyl group, $Z^2$ represents a hydrogen atom, an C1-C6 alkyl group, a C1-C6 haloalkyl group or a C3-C6 cycloalkyl group, and $Z^3$ represents a hydrogen atom, an C1-C3 alkyl group, a C1-C3 haloalkyl group or a cyclopropyl group;

a compound of the formula (1) wherein Q represents Q2, $R^1$ represents a chlorine atom, a bromine atom, a methyl group, an ethyl group or a trifluoromethyl group, $R^2$, $R^4$, $R^5$, $R^7$, $R^8$, $R^9$ and $R^{11}$ represent a hydrogen atom, $R^3$ represents a hydrogen atom or a methyl group, $R^6$ represents an ethynyl group, a 1-propynyl group, a difluoromethoxy group, a trifluoromethoxy group, a methylthio group or a cyclopropyl group, $R^{10}$ represents a methyl group, X represents an oxygen atom, $Z^1$ represents an C1-C6 alkyl group, a C1-C6 haloalkyl group, an C3-C6 alkynyl group or a C4-C7 cycloalkylmethyl group, $Z^2$ represents a hydrogen atom, an C1-C6 alkyl group, a C1-C6 haloalkyl group or a C3-C6 cycloalkyl group, and $Z^3$ represents a hydrogen atom, a methyl group or an ethyl group;

a compound of the formula (1) wherein Q represents Q2, $R^1$ represents a chlorine atom, a bromine atom, a methyl group, an ethyl group or a trifluoromethyl group, $R^2$, $R^4$, $R^5$, $R^7$, $R^8$, $R^9$ and $R^{11}$ represent a hydrogen atom, $R^3$ represents a hydrogen atom or a methyl group, $R^6$ represents an ethynyl group, a 1-propynyl group, a difluoromethoxy group, a trifluoromethoxy group, a methylthio group or a cyclopropyl group, $R^{10}$ represents a methyl group, X represents an oxygen atom, $Z^1$ represents an C1-C6 alkyl group, a C1-C6 haloalkyl group, an C3-C6 alkynyl group or a C4-C7 cycloalkylmethyl group, $Z^2$ represents a hydrogen atom, an C1-C3 alkyl group, a C1-C3 haloalkyl group or a cyclopropyl group, and $Z^3$ represents a hydrogen atom, an C1-C3 alkyl group, a C1-C3 haloalkyl group or a cyclopropyl group;

a compound of the formula (1) wherein Q represents Q2, $R^1$ represents a chlorine atom, a bromine atom, a methyl group, an ethyl group or a trifluoromethyl group, $R^2$, $R^4$, $R^5$, $R^7$, $R^8$, $R^9$ and $R^{11}$ represent a hydrogen atom, $R^3$ represents a hydrogen atom or a methyl group, $R^6$ represents an ethynyl group, a 1-propynyl group, a difluoromethoxy group, a trifluoromethoxy group, a methylthio group or a cyclopropyl group, $R^{10}$ represents a methyl group, X represents an oxygen atom, $Z^1$ represents an C1-C6 alkyl group, a C1-C6 haloalkyl group, an C3-C6 alkynyl group or a C4-C7 cycloalkylmethyl group, $Z^2$ represents a hydrogen atom, an C1-C3 alkyl group, a C1-C3 haloalkyl group or a cyclopropyl group, and $Z^3$ represents a hydrogen atom, a methyl group or an ethyl group;

a compound of the formula (1) wherein Q represents Q2, $R^1$ represents a chlorine atom, a bromine atom, a methyl group, an ethyl group or a trifluoromethyl group, $R^2$, $R^4$, $R^5$, $R^7$, $R^8$, $R^9$ and $R^{11}$ represent a hydrogen atom, $R^3$ represents a hydrogen atom or a methyl group, $R^6$ represents an ethynyl group, a 1-propynyl group, a difluoromethoxy group, a trifluoromethoxy group, a methylthio group or a cyclopropyl group, $R^{10}$ represents a methyl group, X represents an oxygen atom, $Z^1$ represents an C1-C6 alkyl group, a C1-C6 haloalkyl group, an C3-C6 alkynyl group or a C4-C7 cycloalkylmethyl group, $Z^2$ represents a hydrogen atom, a methyl group, an ethyl group, an isopropyl group or a cyclopropyl group, and $Z^3$ represents a hydrogen atom, an C1-C3 alkyl group, a C1-C3 haloalkyl group or a cyclopropyl group;

a compound of the formula (1) wherein Q represents Q2, $R^1$ represents a chlorine atom, a bromine atom, a methyl group, an ethyl group or a trifluoromethyl group, $R^2$, $R^4$, $R^5$, $R^7$, $R^8$, $R^9$ and $R^{11}$ represent a hydrogen atom, $R^3$ represents a hydrogen atom or a methyl group, $R^6$ represents an ethynyl group, a 1-propynyl group, a difluoromethoxy group, a trifluoromethoxy group, a methylthio group or a cyclopropyl group, $R^{10}$ represents a methyl group, X represents an oxygen atom, $Z^1$ represents an C1-C6 alkyl group, a C1-C6 haloalkyl group, an C3-C6 alkynyl group or a C4-C7 cycloalkylmethyl group, $Z^2$ represents a hydrogen atom, a methyl group, an ethyl group, an isopropyl group or a cyclopropyl group, and $Z^3$ represents a hydrogen atom, a methyl group or an ethyl group;

a compound of the formula (1) wherein Q represents Q2, $R^1$ represents a chlorine atom, a bromine atom, a methyl group, an ethyl group or a trifluoromethyl group, $R^2$, $R^4$, $R^5$, $R^7$, $R^8$, $R^9$ and $R^{11}$ represent a hydrogen atom, $R^3$ represents a hydrogen atom or a methyl group, $R^6$ represents an ethynyl group, a 1-propynyl group, a difluoromethoxy group, a trifluoromethoxy group, a methylthio group or a cyclopropyl group, $R^{10}$ represents a methyl group, X represents an oxygen atom, $Z^1$ represents an C1-C4 alkyl group, a C1-C4 haloalkyl group, an C3-C4 alkynyl group or a cyclopropylmethyl group, $Z^2$ represents a hydrogen atom, an C1-C6 alkyl group, a C1-C6 haloalkyl group or a C3-C6 cycloalkyl group, and $Z^3$ represents a hydrogen atom, an C1-C3 alkyl group, a C1-C3 haloalkyl group or a cyclopropyl group;

a compound of the formula (1) wherein Q represents Q2, $R^1$ represents a chlorine atom, a bromine atom, a methyl group, an ethyl group or a trifluoromethyl group, $R^2$, $R^4$, $R^5$, $R^7$, $R^8$, $R^9$ and $R^{11}$ represent a hydrogen atom, $R^3$ represents a hydrogen atom or a methyl group, $R^6$ represents an ethynyl group, a 1-propynyl group, a difluoromethoxy group, a trifluoromethoxy group, a methylthio group or a cyclopropyl group, $R^{10}$ represents a methyl group, X represents an oxygen atom, $Z^1$ represents an C1-C4 alkyl group, a C1-C4 haloalkyl group, an C3-C4 alkynyl group or a cyclopropylmethyl group, $Z^2$ represents a hydrogen atom, an C1-C6 alkyl group, a C1-C6 haloalkyl group or a C3-C6 cycloalkyl group, and $Z^3$ represents a hydrogen atom, a methyl group or an ethyl group;

a compound of the formula (1) wherein Q represents Q2, $R^1$ represents a chlorine atom, a bromine atom, a methyl group, an ethyl group or a trifluoromethyl group, $R^2$, $R^4$, $R^5$, $R^7$, $R^8$, $R^9$ and $R^{11}$ represent a hydrogen atom, $R^3$ represents a hydrogen atom or a methyl group, $R^6$ represents an ethynyl group, a 1-propynyl group, a difluoromethoxy group, a trifluoromethoxy group, a methylthio group or a cyclopropyl group, $R^{10}$ represents a methyl group, X represents an oxygen atom, $Z^1$ represents an C1-C4 alkyl group, a C1-C4 haloalkyl group, an C3-C4 alkynyl group or a cyclopropylmethyl group, $Z^2$ represents a hydrogen atom, an C1-C3 alkyl group, a C1-C3 haloalkyl group or a cyclopropyl group, and $Z^3$ represents a hydrogen atom, an C1-C3 alkyl group, a C1-C3 haloalkyl group or a cyclopropyl group;

a compound of the formula (1) wherein Q represents Q2, $R^1$ represents a chlorine atom, a bromine atom, a methyl group, an ethyl group or a trifluoromethyl group, $R^2$, $R^4$, $R^5$, $R^7$, $R^8$, $R^9$ and $R^{11}$ represent a hydrogen atom, $R^3$ represents a hydrogen atom or a methyl group, $R^6$ represents an ethynyl group, a 1-propynyl group, a difluoromethoxy group, a trifluoromethoxy group, a methylthio group or a cyclopropyl group, $R^{10}$ represents a methyl group, X represents an oxygen atom, $Z^1$ represents an C1-C4 alkyl group, a C1-C4 haloalkyl group, an C3-C4 alkynyl group or a cyclopropylmethyl group, $Z^2$ represents a hydrogen atom, an C1-C3 alkyl group, a C1-C3 haloalkyl group or a cyclopropyl group, and $Z^3$ represents a hydrogen atom, a methyl group or an ethyl group;

a compound of the formula (1) wherein Q represents Q2, $R^1$ represents a chlorine atom, a bromine atom, a methyl group, an ethyl group or a trifluoromethyl group, $R^2$, $R^4$, $R^5$, $R^7$, $R^8$, $R^9$ and $R^{11}$ represent a hydrogen atom, $R^3$ represents a hydrogen atom or a methyl group, $R^6$ represents an ethynyl group, a 1-propynyl group, a difluoromethoxy group, a trifluoromethoxy group, a methylthio group or a cyclopropyl group, $R^{10}$ represents a methyl group, X represents an oxygen atom, $Z^1$ represents an C1-C4 alkyl group, a C1-C4 haloalkyl group, an C3-C4 alkynyl group or a cyclopropylmethyl group, $Z^2$ represents a hydrogen atom, a methyl group, an ethyl group, an isopropyl group or a cyclopropyl group, and $Z^3$ represents a hydrogen atom, an C1-C3 alkyl group, a C1-C3 haloalkyl group or a cyclopropyl group;

a compound of the formula (1) wherein Q represents Q2, $R^1$ represents a chlorine atom, a bromine atom, a methyl group, an ethyl group or a trifluoromethyl group, $R^2$, $R^4$, $R^5$, $R^7$, $R^8$, $R^9$ and $R^{11}$ represent a hydrogen atom, $R^3$ represents a hydrogen atom or a methyl group, $R^6$ represents an ethynyl group, a 1-propynyl group, a difluoromethoxy group, a trifluoromethoxy group, a methylthio group or a cyclopropyl group, $R^{10}$ represents a methyl group, X represents an oxygen atom, $Z^1$ represents an C1-C4 alkyl group, a C1-C4 haloalkyl group, an C3-C4 alkynyl group or a cyclopropylmethyl group, $Z^2$ represents a hydrogen atom, a methyl group, an ethyl group, an isopropyl group or a cyclopropyl group, and $Z^3$ represents a hydrogen atom, a methyl group or an ethyl group;

a compound of the formula (1) wherein Q represents Q2, $R^1$ represents a chlorine atom, a bromine atom, a methyl group, an ethyl group or a trifluoromethyl group, $R^2$, $R^4$, $R^5$, $R^7$, $R^8$, $R^9$ and $R^{11}$ represent a hydrogen atom, $R^3$ represents a hydrogen atom or a methyl group, $R^6$ represents an ethynyl group, a 1-propynyl group, a difluoromethoxy group, a trifluoromethoxy group, a methylthio group or a cyclopropyl group, $R^{10}$ represents a methyl group, X represents an oxygen atom, $Z^1$ represents a methyl group, an ethyl group, a propyl group, an isopropyl group, a difluoromethyl group, a trifluoromethyl group, a 2-propynyl group, a 2-butynyl group or a cyclopropylmethyl group, $Z^2$ represents a hydrogen atom, an C1-C6 alkyl group, a C1-C6 haloalkyl group or a C3-C6 cycloalkyl group, and $Z^3$ represents a hydrogen atom, an C1-C3 alkyl group, a C1-C3 haloalkyl group or a cyclopropyl group;

a compound of the formula (1) wherein Q represents Q2, $R^1$ represents a chlorine atom, a bromine atom, a methyl group, an ethyl group or a trifluoromethyl group, $R^2$, $R^4$, $R^5$, $R^7$, $R^8$, $R^9$ and $R^{11}$ represent a hydrogen atom, $R^3$ represents a hydrogen atom or a methyl group, $R^6$ represents an ethynyl group, a 1-propynyl group, a difluoromethoxy group, a trifluoromethoxy group, a methylthio group or a cyclopropyl group, $R^{10}$ represents a methyl group, X represents an oxygen atom, $Z^1$ represents a methyl group, an ethyl group, a propyl group, an isopropyl group, a difluoromethyl group, a trifluoromethyl group, a 2-propynyl group, a 2-butynyl group or a cyclopropylmethyl group, $Z^2$ represents a hydrogen atom, an C1-C6 alkyl group, a C1-C6 haloalkyl group or a C3-C6 cycloalkyl group, and $Z^3$ represents a hydrogen atom, a methyl group or an ethyl group;

a compound of the formula (1) wherein Q represents Q2, $R^1$ represents a chlorine atom, a bromine atom, a methyl group, an ethyl group or a trifluoromethyl group, $R^2$, $R^4$, $R^5$, $R^7$, $R^8$, $R^9$ and $R^{11}$ represent a hydrogen atom, $R^3$ represents a hydrogen atom or a methyl group, $R^6$ represents an ethynyl group, a 1-propynyl group, a difluoromethoxy group, a trifluoromethoxy group, a methylthio group or a cyclopropyl group, $R^{10}$ represents a methyl group, X represents an oxygen atom, $Z^1$ represents a methyl group, an ethyl group, a propyl group, an isopropyl group, a difluoromethyl group, a trifluoromethyl group, a 2-propynyl group, a 2-butynyl group or a cyclopropylmethyl group, $Z^2$ represents a hydrogen atom, an C1-C3 alkyl group, a C1-C3 haloalkyl group or a cyclopropyl group, and $Z^3$ represents a hydrogen atom, an C1-C3 alkyl group, a C1-C3 haloalkyl group or a cyclopropyl group;

a compound of the formula (1) wherein Q represents Q2, $R^1$ represents a chlorine atom, a bromine atom, a methyl group, an ethyl group or a trifluoromethyl group, $R^2$, $R^4$, $R^5$, $R^7$, $R^8$, $R^9$ and $R^{11}$ represent a hydrogen atom, $R^3$ represents a hydrogen atom or a methyl group, $R^6$ represents an ethynyl group, a 1-propynyl group, a difluoromethoxy group, a trifluoromethoxy group, a methylthio group or a cyclopropyl group, $R^{10}$ represents a methyl group, X represents an oxygen atom, $Z^1$ represents a methyl group, an ethyl group, a propyl group, an isopropyl group, a difluoromethyl group, a trifluoromethyl group, a 2-propynyl group, a 2-butynyl group or a cyclopropylmethyl group, $Z^2$ represents a hydrogen atom, an C1-C3 alkyl group, a C1-C3 haloalkyl group or a cyclopropyl group, and $Z^3$ represents a hydrogen atom, a methyl group or an ethyl group;

a compound of the formula (1) wherein Q represents Q2, $R^1$ represents a chlorine atom, a bromine atom, a methyl group, an ethyl group or a trifluoromethyl group, $R^2$, $R^4$, $R^5$, $R^7$, $R^8$, $R^9$ and $R^{11}$ represent a hydrogen atom, $R^3$ represents a hydrogen atom or a methyl group, $R^6$ represents an ethynyl group, a 1-propynyl group, a difluoromethoxy group, a trifluoromethoxy group, a methylthio group or a cyclopropyl group, $R^{10}$ represents a methyl group, X represents an oxygen atom, $Z^1$ represents a methyl group, an ethyl group, a propyl group, an isopropyl group, a difluoromethyl group, a trifluoromethyl group, a 2-propynyl group, a 2-butynyl group or a cyclopropylmethyl group, $Z^2$ represents a hydrogen atom, a methyl group, an ethyl group, an isopropyl group or a cyclopropyl group, and $Z^3$ represents a hydrogen atom, an C1-C3 alkyl group, a C1-C3 haloalkyl group or a cyclopropyl group;

a compound of the formula (1) wherein Q represents Q2, $R^1$ represents a chlorine atom, a bromine atom, a methyl group, an ethyl group or a trifluoromethyl group, $R^2$, $R^4$, $R^5$, $R^7$, $R^8$, $R^9$ and $R^{11}$ represent a hydrogen atom, $R^3$ represents a hydrogen atom or a methyl group, $R^6$ represents an ethynyl group, a 1-propynyl group, a difluoromethoxy group, a trifluoromethoxy group, a methylthio group or a cyclopropyl group, $R^{10}$ represents a methyl group, X represents an oxygen atom, $Z^1$ represents a methyl group, an ethyl group, a propyl group, an isopropyl group, a difluoromethyl group, a trifluoromethyl group, a 2-propynyl group, a 2-butynyl group or a cyclopropylmethyl group, $Z^2$ represents a hydrogen atom, a methyl group, an ethyl group, an isopropyl group or a cyclopropyl group, and $Z^3$ represents a hydrogen atom, a methyl group or an ethyl group;

a compound of the formula (1) wherein Q represents Q1, $R^1$ represents a halogen atom or an C1-C6 alkyl group, $R^2$, $R^3$, $R^4$, $R^5$, $R^7$, $R^8$, $R^9$ and $R^{11}$ represent a hydrogen atom, $R^{10}$ represents a methyl group, $R^6$ represents a C3-C6 cycloalkyl group or a C1-C4 haloalkoxy group, X represents an oxygen atom, $Y^1$ represents a hydrogen atom or an C1-C6 alkyl group, $Y^2$ represents a hydrogen atom, an C1-C6 alkyl group or an C1-C6 alkoxy group, $Y^3$ represents a hydrogen atom or an C1-C6 alkoxy group, alternatively $Y^1$ and $Y^2$ connect via a divalent saturated carbon chain to form a six-membered ring, or $Y^2$ and $Y^3$ connect via a divalent saturated carbon chain to form a six-membered ring;

a compound of the formula (1) wherein Q represents Q1, $R^1$ represents a halogen atom or an C1-C6 alkyl group, $R^2$, $R^4$, $R^5$, $R^7$, $R^8$, $R^9$ and $R^{11}$ represent a hydrogen atom, $R^3$ represents a hydrogen atom or an C1-C6 alkyl group, $R^{10}$ represents a methyl group, $R^6$ represents a C3-C6 cycloalkyl group, a C1-C4 haloalkoxy group or an C2-6 alkynyl group, X represents an oxygen atom, $Y^1$ represents a hydrogen atom, an C1-C6 alkyl group or a C3-C6 cycloalkyl group, $Y^2$ represents a hydrogen atom, an C1-C6 alkyl group or a C1-C6 haloalkyl group, and $Y^3$ represents a hydrogen atom or an C1-C6 alkoxy group, alternatively $Y^1$ and $Y^2$ connect via a divalent saturated carbon chain to form a six-membered ring, or $Y^2$ and $Y^3$ connect via a divalent saturated carbon chain to form a six-membered ring;

a compound of the formula (1) wherein Q represents Q2, $R^1$ represents an C1-C6 alkyl group, $R^2$, $R^3$, $R^4$, $R^5$, $R^7$, $R^8$, $R^9$ and $R^{11}$ represent a hydrogen atom, $R^{10}$ represents a methyl group, $R^6$ represents a C3-C6 cycloalkyl group or a C1-C4 haloalkoxy group, X represents an oxygen atom, $Z^1$ represents an C1-C6 alkyl group, $Z^2$ represents a hydrogen atom or an C1-C6 alkyl group, and $Z^3$ represents a hydrogen atom;

a compound of the formula (1) wherein Q represents Q2, $R^1$ represents a halogen atom or an C1-C6 alkyl group, $R^2$, $R^4$, $R^5$, $R^7$, $R^8$, $R^9$ and $R^{11}$ represent a hydrogen atom, $R^3$ represents a hydrogen atom or an C1-C6 alkyl group, $R^{10}$ represents a methyl group, $R^6$ represents a C3-C6 cycloalkyl group or a C1-C4 haloalkoxy group, X represents an oxygen atom, $Z^1$ represents an C1-C6 alkyl group, $Z^2$ represents an C1-C6 alkyl group optionally having halogen atom or a halogen atom, and $Z^3$ represents a hydrogen atom or an C1-C6 alkyl group;

a compound of the formula (1) wherein Q represents Q2, $R^1$ represents an C1-C6 alkyl group, $R^2$, $R^3$, $R^4$, $R^5$, $R^7$, $R^8$, $R^9$ and $R^{11}$ represent a hydrogen atom, $R^{10}$ represents a methyl group, $R^6$ represents a C3-C6 cycloalkyl group or a C1-C4 haloalkoxy group, X represents an oxygen atom, $Z^1$ represents an C1-C6 alkyl group, $Z^2$ represents a hydrogen atom, an C1-C6 alkyl group or a C1-C3 haloalkyl group, and $Z^3$ represents a hydrogen atom or an C1-C3 alkyl group;

a compound of the formula (1) wherein Q represents Q3, $R^1$ represents a halogen atom or an C1-C6 alkyl group, $R^2$, $R^3$, $R^4$, $R^5$, $R^7$, $R^8$, $R^9$ and $R^{11}$ represent a hydrogen atom, $R^{10}$ represents a methyl group, $R^6$ represents an C3-C6 cycloalkyl group, X represents an oxygen atom, $A^1$ represents a hydrogen atom, $A^2$ represents an C1-C6 alkyl group, and $A^3$ represents a hydrogen atom;

a compound of the formula (1) wherein Q represents Q4, $R^1$ represents an C1-C6 alkyl group, $R^2$, $R^3$, $R^4$, $R^5$, $R^7$, $R^8$, $R^9$ and $R^{11}$ represent a hydrogen atom, $R^{10}$ represents a methyl group, $R^6$ represents a C3-C6 cycloalkyl group, X represents an oxygen atom, $Z^2$ represents an C1-C6 alkyl group, $Z^3$ represents a hydrogen atom, and $Z^4$ represents an C1-C6 alkyl group;

a compound of the formula (1) wherein Q represents Q1, $R^1$ represents a hydrogen atom, a chlorine atom, a bromine atom, a methyl group, an ethyl group or a cyclopropyl group, $R^3$ represents a hydrogen atom or a methyl group, $R^2$, $R^4$, $R^5$, $R^7$, $R^8$, $R^9$ and $R^{11}$ represent a hydrogen atom, $R^{10}$ represents a methyl group, $R^6$ represents a cyclopropyl group, a difluoromethoxy group, a methylthio group or an ethynyl group, X represents an oxygen atom or a sulfur atom, $Y^1$ represents a hydrogen atom or a methyl group, $Y^2$ represents a hydrogen atom, a chlorine atom, a bromine atom, a methyl group, an ethyl group or a methoxy group, $Y^3$ represents a hydrogen atom or a methyl group, alternatively $Y^1$ and $Y^2$ connect via a divalent saturated carbon chain to form a six-membered ring, or $Y^2$ and $Y^3$ connect via a divalent saturated carbon chain to form a six-membered ring;

a compound of the formula (1) wherein Q represents Q2, $R^1$ represents a chlorine atom, a bromine atom, a methyl group, an ethyl group or a cyclopropyl group, $R^3$ represents a hydrogen atom or a methyl group, $R^2$, $R^4$, $R^5$, $R^7$, $R^8$, $R^9$ and $R^{11}$ represent a hydrogen atom, $R^{10}$ represents a methyl group, $R^6$ represents a cyclopropyl group, a difluoromethoxy group, a methylthio group or an ethynyl group, X represents an oxygen atom or a sulfur atom, $Z^1$ represents a methyl group, an ethyl group or an isopropyl group, $Z^2$ represents a hydrogen atom, a methyl group or a trifluoromethyl group, and $Z^3$ represents a hydrogen atom, a chlorine atom, a bromine atom or a methyl group;

a compound of the formula (1) wherein Q represents Q1, $R^1$ represents a chlorine atom or a methyl group, $R^2$, $R^3$, $R^4$, $R^5$, $R^7$, $R^8$, $R^9$ and $R^{11}$ represent a hydrogen atom, $R^{10}$ represents a methyl group, $R^6$ represents a cyclopropyl group or a difluoromethoxy group, X represents an oxygen atom, $Y^1$ represents a hydrogen atom or a methyl group, $Y^2$ represents a hydrogen atom, a methyl group or a methoxy group, and $Y^3$ represents a hydrogen atom or a methyl group, alternatively $Y^1$ and $Y^2$ connect via a divalent saturated carbon chain to form a six-membered ring, or $Y^2$ and $Y^3$ connect via a divalent saturated carbon chain to form a six-membered ring;

a compound of the formula (1) wherein Q represents Q2, $R^1$ represents a methyl group, $R^2$, $R^3$, $R^4$, $R^5$, $R^7$, $R^8$, $R^9$ and $R^{11}$ represent a hydrogen atom, $R^{10}$ represents a methyl group, $R^6$ represents a cyclopropyl group or a difluoromethoxy group, X represents an oxygen atom, $Z^1$ represents a methyl group, an ethyl group or an isopropyl group, $Z^2$ represents a hydrogen atom, a methyl group or a trifluoromethyl group, and $Z^3$ represents a hydrogen atom or a methyl group;

a compound of the formula (1) wherein Q represents Q3, $R^1$ represents a methyl group, $R^2$, $R^3$, $R^4$, $R^5$, $R^7$, $R^8$, $R^9$ and $R^{11}$ represent a hydrogen atom, $R^{10}$ represents a methyl group, $R^6$ represents a cyclopropyl group, X represents an oxygen atom, $A^1$ represents a hydrogen atom, $A^2$ represents a methyl group, and $A^3$ represents a hydrogen atom;

a compound of the formula (1) wherein Q represents Q1, $R^1$ represents a halogen atom or an C1-C6 alkyl group, $R^2$, $R^3$, $R^4$, $R^5$, $R^7$, $R^8$, $R^9$ and $R^{11}$ represent a hydrogen atom, $R^{10}$ represents a methyl group, $R^6$ represents a C3-C6 cycloalkyl group, X represents an oxygen atom, $Y^1$ represents a hydrogen atom or an C1-C6 alkyl group, $Y^2$ represents a hydrogen atom, an C1-C6 alkyl group or an C1-C6 alkoxy group, and $Y^3$ represents a hydrogen atom or an C1-C6 alkyl group, alternatively $Y^1$ and $Y^2$ connect via a divalent saturated carbon chain to form a six-membered ring, or $Y^2$ and $Y^3$ connect via a divalent saturated carbon chain to form a six-membered ring;

a compound of the formula (1) wherein Q represents Q2, $R^1$ represents an C1-C6 alkyl group, $R^2$, $R^3$, $R^4$, $R^5$, $R^7$, $R^8$, $R^9$ and $R^{11}$ represent a hydrogen atom, $R^{10}$ represents a methyl group, $R^6$ represents a C3-C6 cycloalkyl group, X represents an oxygen atom, $Z^1$ represents an C1-C6 alkyl group, $Z^2$ represents a hydrogen atom, an C1-C6 alkyl group or a C1-C3 haloalkyl group, and $Z^3$ represents a hydrogen atom or an C1-C4 alkyl group;

a compound of the formula (1) wherein Q represents Q1, $R^1$ represents a chlorine atom, a bromine atom, a methyl group, an ethyl group or a cyclopropyl group, $R^3$ represents a hydrogen atom or a methyl group, $R^2$, $R^4$, $R^5$, $R^7$, $R^8$, $R^9$ and $R^{11}$ represent a hydrogen atom, $R^{10}$ represents a methyl group, $R^6$ represents an C3-C6 cycloalkyl group, X represents an oxygen atom or a sulfur atom, $Y^1$ represents a hydrogen atom or a methyl group, $Y^2$ represents a hydrogen atom, a chlorine atom, a bromine atom, a methyl group, an ethyl group or a methoxy group, $Y^3$ represents a hydrogen atom or a methyl group, alternatively $Y^1$ and $Y^2$ connect via a divalent saturated carbon chain to form a six-membered ring, or $Y^2$ and $Y^3$ connect via a divalent saturated carbon chain to form a six-membered ring;

a compound of the formula (1) wherein Q represents Q2, $R^1$ represents a chlorine atom, a bromine atom, a methyl group, an ethyl group or a cyclopropyl group, $R^3$ represents a hydrogen atom or a methyl group, $R^2$, $R^4$, $R^5$, $R^7$, $R^8$, $R^9$ and $R^{11}$ represent a hydrogen atom, $R^{10}$ represents a methyl group, $R^6$ represents an C3-C6 cycloalkyl group, X represents an oxygen atom or a sulfur atom, $Z^1$ represents a methyl group, an ethyl group or an isopropyl group, $Z^2$ represents a hydrogen atom, a methyl group or a trifluoromethyl group, and $Z^3$ represents a hydrogen atom, a chlorine atom, a bromine atom or a methyl group;

a compound of the formula (1) wherein Q represents Q1, $R^1$ represents a chlorine atom or a methyl group, $R^2$, $R^3$, $R^4$, $R^5$, $R^7$, $R^8$, $R^9$ and $R^{11}$ represent a hydrogen atom, $R^{10}$ represents a methyl group, $R^6$ represents a C3-C6 cycloalkyl group, X represents an oxygen atom, $Y^1$ represents a hydrogen atom or a methyl group, $Y^2$ represents a hydrogen atom, a methyl group, an ethyl group or a methoxy group, $Y^3$ represents a hydrogen atom or a methyl group, alternatively $Y^1$ and $Y^2$ connect via a divalent saturated carbon chain to form a six-membered ring, or $Y^2$ and $Y^3$ connect via a divalent saturated carbon chain to form a six-membered ring;

a compound of the formula (1) wherein Q represents Q2, $R^1$ represents a methyl group, $R^2$, $R^3$, $R^4$, $R^5$, $R^7$, $R^8$, $R^9$ and $R^{11}$ represent a hydrogen atom, $R^{10}$ represents a methyl group, $R^6$ represents a C3-C6 cycloalkyl group, X represents an oxygen atom, $Z^1$ represents a methyl group, an ethyl group or an isopropyl group, $Z^2$ represents a hydrogen atom, a methyl group or a trifluoromethyl group, and $Z^3$ represents a hydrogen atom or a methyl group;

a compound of the formula (1) wherein Q represents Q1, $R^1$ represents a hydrogen atom or an C1-C6 alkyl group, $R^2$, $R^3$, $R^4$, $R^5$, $R^7$, $R^8$, $R^9$ and $R^{11}$ represent a hydrogen atom, $R^{10}$ represents a methyl group, $R^6$ represents a cyclopropyl group, X represents an oxygen atom, $Y^1$ represents a hydrogen atom or an C1-C6 alkyl group, $Y^2$ represents a hydrogen atom, an C1-C6 alkyl group or an C1-C6 alkoxy group, and $Y^3$ represents a hydrogen atom or an C1-C6 alkyl group, alternatively $Y^1$ and $Y^2$ connect via a divalent saturated carbon chain to form a six-membered ring, or $Y^2$ and $Y^3$ connect via a divalent saturated carbon chain to form a six-membered ring;

a compound of the formula (1) wherein Q represents Q2, $R^1$ represents an C1-C6 alkyl group, $R^2$, $R^3$, $R^4$, $R^5$, $R^7$, $R^8$, $R^9$ and $R^{11}$ represent a hydrogen atom, $R^{10}$ represents a methyl group, $R^6$ represents a cyclopropyl group, X represents an oxygen atom, $Z^1$ represents an C1-C6 alkyl group, $Z^2$ represents a hydrogen atom, an C1-C6 alkyl group or a C1-C3 haloalkyl group, and $Z^3$ represents a hydrogen atom or an C1-C4 alkyl group;

a compound of the formula (1) wherein Q represents Q1, $R^1$ represents a chlorine atom, a bromine atom, a methyl group, an ethyl group or a cyclopropyl group, $R^3$ represents a hydrogen atom or a methyl group, $R^2$, $R^4$, $R^5$, $R^7$, $R^8$, $R^9$ and $R^{11}$ represent a hydrogen atom, $R^{10}$ represents a methyl group, $R^6$ represents a cyclopropyl group, X represents an oxygen atom or a sulfur atom, $Y^1$ represents a hydrogen atom or a methyl group, $Y^2$ represents a hydrogen atom, a chlorine atom, a bromine atom, a methyl group, an ethyl group or a methoxy group, $Y^3$ represents a hydrogen atom or a methyl group, alternatively $Y^1$ and $Y^2$ connect via a divalent saturated carbon chain to form a six-membered ring, or $Y^2$ and $Y^3$ connect via a divalent saturated carbon chain to form a six-membered ring;

a compound of the formula (1) wherein Q represents Q2, $R^1$ represents a chlorine atom, a bromine atom, a methyl group, an ethyl group or a cyclopropyl group, $R^3$ represents a hydrogen atom or a methyl group, $R^2$, $R^4$, $R^5$, $R^7$, $R^8$, $R^9$ and $R^{11}$ represent a hydrogen atom, $R^{10}$ represents a methyl group, $R^6$ represents a cyclopropyl group, X represents an oxygen atom or a sulfur atom, $Z^1$ represents a methyl group, an ethyl group or an isopropyl group, $Z^2$ represents a hydrogen atom, a methyl group or a trifluoromethyl group, and $Z^3$ represents a hydrogen atom, a chlorine atom, a bromine atom or a methyl group;

a compound of the formula (1) wherein Q represents Q1, $R^1$ represents a chlorine atom or a methyl group, $R^2$, $R^3$, $R^4$, $R^5$, $R^7$, $R^8$, $R^9$ and $R^{11}$ represent a hydrogen atom, $R^{10}$ represents a methyl group, $R^6$ represents a cyclopropyl group, X represents an oxygen atom, $Y^1$ represents a hydrogen atom or a methyl group, $Y^2$ represents a hydrogen atom, a methyl group, an ethyl group or a methoxy group, and $Y^3$ represents a hydrogen atom or a methyl group, alternatively $Y^1$ and $Y^2$ connect via a divalent saturated carbon chain to form a six-membered ring, or $Y^2$ and $Y^3$ connect via a divalent saturated carbon chain to form a six-membered ring;

a compound of the formula (1) wherein Q represents Q2, $R^1$ represents a methyl group, $R^2$, $R^3$, $R^4$, $R^5$, $R^7$, $R^8$, $R^9$ and $R^{11}$ represent a hydrogen atom, $R^{10}$ represents a methyl group, $R^6$ represents a C1-C4 haloalkoxy group, X represents an oxygen atom, $Y^1$ represents a hydrogen atom or an C1-C6 alkyl group, $Y^2$ represents a hydrogen atom, an C1-C6 alkyl group or an C1-C6 alkoxy group, $Y^3$ represents a hydrogen atom or an C1-C6 alkyl group, alternatively $Y^1$ and $Y^2$ connect via a divalent saturated carbon chain to form a six-membered ring, or $Y^2$ and $Y^3$ connect via a divalent saturated carbon chain to form a six-membered ring;

a compound of the formula (1) wherein Q represents Q2, $R^1$ represents an C1-C6 alkyl group, $R^2$, $R^3$, $R^4$, $R^5$, $R^7$, $R^8$, $R^9$ and $R^{11}$ represent a hydrogen atom, $R^{10}$ represents a methyl group, $R^6$ represents an C1-C4 haloalkoxy group, X represents an oxygen atom, $Z^1$ represents an C1-C6 alkyl group, $Z^2$ represents a hydrogen atom, an C1-C6 alkyl group or a C1-C3 haloalkyl group, and $Z^3$ represents a hydrogen atom or an C1-C4 alkyl group;

a compound of the formula (1) wherein Q represents Q1, $R^1$ represents a chlorine atom, a bromine atom, a methyl group, an ethyl group or a cyclopropyl group, $R^3$ represents a hydrogen atom or a methyl group, $R^2$, $R^4$, $R^5$, $R^7$, $R^8$, $R^9$ and $R^{11}$ represent a hydrogen atom, $R^{10}$ represents a methyl group, $R^6$ represents a C1-C4 haloalkoxy group, X represents an oxygen atom or a sulfur atom, $Y^1$ represents a hydrogen atom or a methyl group, $Y^2$ represents a hydrogen atom, a chlorine atom, a bromine atom, a methyl group, an ethyl group or a methoxy group, $Y^3$ represents a hydrogen atom or a methyl group, alternatively $Y^1$ and $Y^2$ connect via a divalent saturated carbon chain to form a six-membered ring, or $Y^2$ and $Y^3$ connect via a divalent saturated carbon chain to form a six-membered ring;

a compound of the formula (1) wherein Q represents Q2, $R^1$ represents a chlorine atom, a bromine atom, a methyl group, an ethyl group or a cyclopropyl group, $R^3$ represents a hydrogen atom or a methyl group, $R^2$, $R^4$, $R^5$, $R^7$, $R^8$, $R^9$ and $R^{11}$ represent a hydrogen atom, $R^{10}$ represents a methyl group, $R^6$ represents a C1-C4 haloalkoxy group, X represents an oxygen atom or a sulfur atom, $Z^1$ represents a methyl group, an ethyl group or an isopropyl group, $Z^2$ represents a hydrogen atom, a methyl group or a trifluoromethyl group, and $Z^3$ represents a hydrogen atom, a chlorine atom, a bromine atom or a methyl group;

a compound of the formula (1) wherein Q represents Q1, $R^1$ represents a chlorine atom or a methyl group, $R^2$, $R^3$, $R^4$, $R^5$, $R^7$, $R^8$, $R^9$ and $R^{11}$ represent a hydrogen atom, $R^{10}$ represents a methyl group, $R^6$ represents a C1-C4 haloalkoxy group, X represents an oxygen atom, $Y^1$ represents a hydrogen atom or a methyl group, $Y^2$ represents a hydrogen atom, a methyl group, an ethyl group or a methoxy group, and $Y^3$ represents a hydrogen atom or a methyl group, alternatively $Y^1$ and $Y^2$ connect via a divalent saturated carbon chain to form a six-membered ring, or $Y^2$ and $Y^3$ connect via a divalent saturated carbon chain to form a six-membered ring;

a compound of the formula (1) wherein Q represents Q2, $R^1$ represents a methyl group, $R^2$, $R^3$, $R^4$, $R^5$, $R^7$, $R^8$, $R^9$ and $R^{11}$ represent a hydrogen atom, $R^{10}$ represents a methyl group, $R^6$ represents a C1-C4 haloalkoxy group, X represents an oxygen atom, $Z^1$ represents a methyl group, an ethyl group or an isopropyl group, $Z^2$ represents a hydrogen atom, a methyl group or a trifluoromethyl group, and $Z^3$ represents a hydrogen atom or a methyl group;

a compound of the formula (1) wherein Q represents Q1, $R^1$ represents a halogen atom or an C1-C6 alkyl group, $R^2$, $R^3$, $R^4$, $R^5$, $R^7$, $R^8$, $R^9$ and $R^{11}$ represent a hydrogen atom, $R^{10}$ represents a methyl group, $R^6$ represents a difluoromethoxy group, X represents an oxygen atom, $Y^1$ represents a hydrogen atom or an C1-C6 alkyl group, $Y^2$ represents a hydrogen atom, an C1-C6 alkyl group or an C1-C6 alkoxy group, and $Y^3$ represents a hydrogen atom or an C1-C6 alkyl group, alternatively $Y^1$ and $Y^2$ connect via a divalent saturated carbon chain to form a six-membered ring, or $Y^2$ and $Y^3$ connect via a divalent saturated carbon chain to form a six-membered ring;

a compound of the formula (1) wherein Q represents Q2, $R^1$ represents an C1-C6 alkyl group, $R^2$, $R^3$, $R^4$, $R^5$, $R^7$, $R^8$, $R^9$ and $R^{11}$ represent a hydrogen atom, $R^{10}$ represents a methyl group, $R^6$ represents a difluoromethoxy group, X represents an oxygen atom, $Z^1$ represents an C1-C6 alkyl group, $Z^2$ represents a hydrogen atom, an C1-C6 alkyl group or a C1-C3 haloalkyl group, and $Z^3$ represents a hydrogen atom or an C1-C4 alkyl group;

a compound of the formula (1) wherein Q represents Q1, $R^1$ represents a chlorine atom, a bromine atom, a methyl group, an ethyl group or a cyclopropyl group, $R^3$ represents a hydrogen atom or a methyl group, $R^2$, $R^4$, $R^5$, $R^7$, $R^8$, $R^9$ and $R^{11}$ represent a hydrogen atom, $R^{10}$ represents a methyl group, $R^6$ represents a difluoromethoxy group, X represents an oxygen atom or a sulfur atom, $Y^1$ represents a hydrogen atom or a methyl group, $Y^2$ represents a hydrogen atom, a chlorine atom, a bromine atom, a methyl group, an ethyl group or a methoxy group, and $Y^3$ represents a hydrogen atom or a methyl group, alternatively $Y^1$ and $Y^2$ connect via a divalent saturated carbon chain to form a six-membered ring, or $Y^2$ and $Y^3$ connect via a divalent saturated carbon chain to form a six-membered ring;

a compound of the formula (1) wherein Q represents Q2, $R^1$ represents a chlorine atom, a bromine atom, a methyl group, an ethyl group or a cyclopropyl group, $R^3$ represents a hydrogen atom or a methyl group, $R^2$, $R^4$, $R^5$, $R^7$, $R^8$, $R^9$ and $R^{11}$ represent a hydrogen atom, $R^{10}$ represents a methyl group, $R^6$ represents a difluoromethoxy group, X represents an oxygen atom or a sulfur atom, $Z^1$ represents a methyl group, an ethyl group or an isopropyl group, $Z^2$ represents a hydrogen atom, a methyl group or a trifluoromethyl group, and $Z^3$ represents a hydrogen atom, a chlorine atom, a bromine atom or a methyl group;

a compound of the formula (1) wherein Q represents Q1, $R^1$ represents a chlorine atom or a methyl group, $R^2$, $R^3$, $R^4$, $R^5$, $R^7$, $R^8$, $R^9$ and $R^{11}$ represent a hydrogen atom, $R^{10}$ represents a methyl group, $R^6$ represents a difluoromethoxy group, X represents an oxygen atom, $Y^1$ represents a hydrogen atom or a methyl group, $Y^2$ represents a hydrogen atom, a methyl group, an ethyl group or a methoxy group, and $Y^3$ represents a hydrogen atom or a methyl group, alternatively $Y^1$ and $Y^2$ connect via a divalent saturated carbon chain to form a six-membered ring, or $Y^2$ and $Y^3$ connect via a divalent saturated carbon chain to form a six-membered ring;

a compound of the formula (1) wherein Q represents Q2, $R^1$ represents a methyl group, $R^2$, $R^3$, $R^4$, $R^5$, $R^7$, $R^8$, $R^9$ and $R^{11}$ represent a hydrogen atom, $R^{10}$ represents a methyl group, $R^6$ represents a difluoromethoxy group, X represents an oxygen atom, $Z^1$ represents a hydrogen atom or a methyl group, $Z^2$ represents a hydrogen atom, a methyl group, an ethyl group or a methoxy group, and $Z^3$ represents a hydrogen atom or a methyl group;

a compound of the formula (1) wherein Q represents Q2, $R^1$ represents a halogen atom or an C1-C3 alkyl group, $R^3$ represents a hydrogen atom or a methyl group, $R^2$, $R^4$, $R^5$, $R^7$, $R^8$, $R^9$ and $R^{11}$ represent a hydrogen atom, $R^{10}$ represents a methyl group, $R^6$ represents a difluoromethoxy group, a cyclopropyl group or a methylthio group, X represents an oxygen atom, $Z^1$ represents an C1-C3 alkyl group, $Z^2$ represents a hydrogen atom, an C1-C6 alkyl group, a C1-C3 haloalkyl group, an C1-C6 alkoxy group, a halogen atom or an C1-C6 alkylthio group, and $Z^3$ represents a hydrogen atom, a halogen atom or an C1-C3 alkyl group;

a compound of the formula (1) wherein Q represents Q2, $R^1$ represents a halogen atom or an C1-C3 alkyl group, $R^3$ represents a hydrogen atom or a methyl group, $R^2$, $R^4$, $R^5$, $R^7$, $R^8$, $R^9$ and $R^{11}$ represent a hydrogen atom, $R^{10}$ represents a methyl group, $R^6$ represents a difluoromethoxy group, a cyclopropyl group or a methylthio group, X represents an oxygen atom, $Z^1$ represents an C1-C3 alkyl group, $Z^2$ represents a hydrogen atom, an C1-C6 alkyl group, a C1-C6 haloalkyl group, an C1-C6 alkoxy group, an C1-C6 alkylthio group, a halogen atom or a cyano group, and $Z^3$ represents a hydrogen atom, a halogen atom or an C1-C3 alkyl group;

a compound of the formula (1) wherein Q represents Q2, $R^1$ represents a chlorine atom or a methyl group, $R^3$ represents a hydrogen atom or a methyl group, $R^2$, $R^4$, $R^5$, $R^7$, $R^8$, $R^9$ and $R^{11}$ represent a hydrogen atom, $R^{10}$ represents a methyl group, $R^6$ represents a difluoromethoxy group, a cyclopropyl group or a methylthio group, X represents an oxygen atom, $Z^1$ represents a methyl group, an ethyl group or an isopropyl group, $Z^2$ represents a hydrogen atom, a methyl group, a trifluoromethyl group, a methylthio group, a methoxy group, an ethoxy group, a chlorine atom or a cyano group, and Z3 represents a hydrogen atom, a chlorine atom or a methyl group;

a compound of the formula (1) wherein Q represents Q2, $R^1$ represents a chlorine atom or an C1-C3 alkyl group, $R^3$ represents a hydrogen atom or a methyl group, $R^2$, $R^4$, $R^5$, $R^7$, $R^8$, $R^9$ and $R^{11}$ represent a hydrogen atom, $R^{10}$ represents a methyl group, $R^6$ represents a cyclopropyl group, X represents an oxygen atom, $Z^1$ represents an C1-C3 alkyl group, $Z^2$ represents a hydrogen atom, an C1-C6 alkyl group, a C1-C6 haloalkyl group, an C1-C6 alkoxy group, a halogen atom or an C1-C6 alkylthio group, and $Z^3$ represents a hydrogen atom, a halogen atom or an C1-C3 alkyl group;

a compound of the formula (1) wherein Q represents Q2, $R^1$ represents a halogen atom or an C1-C3 alkyl group, $R^3$ represents a hydrogen atom or a methyl group, $R^2$, $R^4$, $R^5$, $R^7$, $R^8$, $R^9$ and $R^{11}$ represent a hydrogen atom, $R^{10}$ represents a methyl group, $R^6$ represents a cyclopropyl group, X represents an oxygen atom, $Z^1$ represents an C1-C3 alkyl group, $Z^2$ represents a hydrogen atom, an C1-C6 alkyl group, a C1-C6 haloalkyl group, an C1-C6 alkoxy group, an C1-C6 alkylthio group, a halogen atom or a cyano group and $Z^3$ represents a hydrogen atom, a halogen atom or an C1-C3 alkyl group;

a compound of the formula (1) wherein Q represents Q2, $R^1$ represents a chlorine atom or a methyl group, $R^3$ represents a hydrogen atom or a methyl group, $R^2$, $R^4$, $R^5$, $R^7$, $R^8$, $R^9$ and $R^{11}$ represent a hydrogen atom, $R^{10}$ represents a methyl group, $R^6$ represents a cyclopropyl group, X represents an oxygen atom, $Z^1$ represents a methyl group, an ethyl group or an isopropyl group, $Z^2$ represents a hydrogen atom, a methyl group, a trifluoromethyl group, a methylthio group, a methoxy group, an ethoxy group or a chlorine atom, and $Z^3$ represents a hydrogen atom, a chlorine atom or a methyl group;

a compound of the formula (1) wherein Q represents Q2, $R^1$ represents a chlorine atom or a methyl group, $R^3$ represents a hydrogen atom or a methyl group, $R^2$, $R^4$, $R^5$, $R^7$, $R^8$, $R^9$ and $R^{11}$ represent a hydrogen atom, $R^{10}$ represents a methyl group, $R^6$ represents a cyclopropyl group, X represents an oxygen atom, $Z^1$ represents a methyl group, an ethyl group or an isopropyl group, $Z^2$ represents a hydrogen atom, a methyl group, a trifluoromethyl group, a methylthio group, a methoxy group, an ethoxy group, a chlorine atom or a cyano group, and $Z^3$ represents a hydrogen atom, a chlorine atom or a methyl group;

a compound of the formula (1) wherein Q represents Q2, $R^1$ represents a chlorine atom or a methyl group, $R^2$, $R^3$, $R^4$, $R^5$, $R^7$, $R^8$, $R^9$ and $R^{11}$ represent a hydrogen atom, $R^{10}$ represents a methyl group, $R^6$ represents a cyclopropyl group, X represents an oxygen atom, $Z^1$ represents an C1-C3 alkyl group, $Z^2$ represents a hydrogen atom, a methyl group, a trifluoromethyl group, a methylthio group, a methoxy group, an ethoxy group, a chlorine atom or a cyano group, and $Z^3$ represents a hydrogen atom, a chlorine atom or a methyl group;

a compound of the formula (1) wherein Q represents Q2, $R^1$ represents an C1-C3 alkyl group, $R^2$, $R^3$, $R^4$, $R^5$, $R^7$, $R^8$, $R^9$ and $R^{11}$ represent a hydrogen atom, $R^{10}$ represents a methyl group, $R^6$ represents a difluoromethoxy group, X represents an oxygen atom, $Z^1$ represents an C1-C3 alkyl group, $Z^2$ represents a hydrogen atom, an C1-C6 alkyl group, an C1-C6 alkoxy group or a halogen atom, and $Z^3$ represents a hydrogen atom or an C1-C3 alkoxy group;

a compound of the formula (1) wherein Q represents Q2, $R^1$ represents an C1-C3 alkyl group, $R^2$, $R^3$, $R^4$, $R^5$, $R^7$, $R^8$, $R^9$ and $R^{11}$ represent a hydrogen atom, $R^{10}$ represents a methyl group, $R^6$ represents a difluoromethoxy group, X represents an oxygen atom, $Z^1$ represents an C1-C3 alkyl group, $Z^2$ represents a hydrogen atom, an C1-C6 alkyl group, an C1-C6 alkoxy group, a halogen atom or a cyano group, and $Z^3$ represents a hydrogen atom or an C1-C3 alkyl group;

a compound of the formula (1) wherein Q represents Q2, $R^1$ represents a methyl group, $R^3$ represents a hydrogen atom or a methyl group, $R^2$, $R^4$, $R^5$, $R^7$, $R^8$, $R^9$ and $R^{11}$ represent a hydrogen atom, $R^{10}$ represents a methyl group, $R^6$ represents a difluoromethoxy group, X represents an oxygen atom, $Z^1$ represents a methyl group, $Z^2$ represents a hydrogen atom, a methyl group, a methoxy group, an ethoxy group or a chlorine atom, and $Z^3$ represents a hydrogen atom or a methyl group;

a compound of the formula (1) wherein Q represents Q2, $R^1$ represents a methyl group, $R^3$ represents a hydrogen atom or a methyl group, $R^2$, $R^4$, $R^5$, $R^7$, $R^8$, $R^9$ and $R^{11}$ represent a hydrogen atom, $R^{10}$ represents a methyl group, $R^6$ represents a difluoromethoxy group, X represents an oxygen atom, $Z^1$ represents a methyl group, $Z^2$ represents a hydrogen atom, a methyl group, a methoxy group, an ethoxy group, a chlorine atom or a cyano group, and $Z^3$ represents a hydrogen atom or a methyl group;

a compound of the formula (1) wherein Q represents Q2, $R^1$ represents an C1-C3 alkyl group, $R^2$, $R^3$, $R^4$, $R^5$, $R^7$, $R^8$, $R^9$ and $R^{11}$ represent a hydrogen atom, $R^{10}$ represents a methyl group, $R^6$ represents a methylthio group, X represents an oxygen atom, $Z^1$ represents an C1-C3 alkyl group, $Z^2$ represents an C1-C6 alkoxy group or a halogen atom, and $Z^3$ represents an C1-C3 alkyl group;

a compound of the formula (1) wherein Q represents Q2, $R^1$ represents a methyl group, $R^2$, $R^3$, $R^4$, $R^5$, $R^7$, $R^8$, $R^9$ and $R^{11}$ represent a hydrogen atom, $R^{10}$ represents a methyl group, $R^6$ represents a methylthio group, X represents an oxygen atom, $Z^1$ represents a methyl group, $Z^2$ represents an ethoxy group or a chlorine atom, and $Z^3$ represents a methyl group.

a compound of the formula (1) wherein Q represents Q1, $R^1$ represents an C1-C3 alkyl group, a halogen atom, a C1-C3 haloalkyl group, an C2-C3 alkynyl group, a C2-C3 haloalkynyl group, a C3-C5 cycloalkyl group, a C3-C5 halocycloalkyl group, an C1-C3 alkoxy group or a C1-C3 haloalkoxy group, $R^2$, $R^4$, $R^5$, $R^7$, $R^8$, $R^9$ and $R^{11}$ represent a hydrogen atom, $R^3$ represents a hydrogen atom, a halogen atom, an C1-C3 alkyl group or a C1-C3 haloalkyl group, $R^6$ represents a C3-C6 cycloalkyl group, an C2-C4 alkynyl group, a C2-C4 haloalkynyl group, a C1-C4 haloalkoxy group, an C1-C4 alkythio group, a C1-C4 haloalkylthio group or a C3-C6 halocycloalkyl group, $R^{10}$ represents a methyl group, X represents an oxygen atom, $Y^1$ and $Y^2$ connect to each other to represent —CH$_2$—CH$_2$—CH$_2$— or —CH$_2$—CH$_2$—CH$_2$—CH$_2$—, which combines together with the carbon atoms to which $Y^1$ and $Y^2$ are attached to form a five-membered or six-membered ring, $Y^2$ and $Y^3$ connect to each other to represent —CH$_2$—CH$_2$—CH$_2$— or —CH$_2$—CH$_2$—CH$_2$—CH$_2$—, which combines together with the carbon atoms to which $Y^2$ and $Y^3$ are attached to form a five-membered or six-membered ring, when each of $Y^1$, $Y^2$ and $Y^3$ does not form the five- or six-membered saturated ring, $Y^1$ represents a hydrogen atom, an C1-C3 alkyl group, a C1-C3 haloalkyl group or a cyclopropyl group, $Y^2$ represents a hydrogen atom, an C1-C3 alkyl group, a C1-C3 haloalkyl group or an C1-C3 alkoxy group, $Y^3$ represents a hydrogen atom or a methyl group.

a compound of the formula (1) wherein Q represents Q2, $R^1$ represents an C1-C3 alkyl group, a halogen atom, a C1-C3 haloalkyl group, an C2-C3 alkynyl group, a C2-C3 haloalkynyl group, a C3-C5 cycloalkyl group, a C3-C5 halocycloalkyl group, an C1-C3 alkoxy group or a C1-C3 haloalkoxy group, $R^2$, $R^4$, $R^5$, $R^7$, $R^8$, $R^9$ and $R^{11}$ represent a hydrogen atom, $R^3$ represents a hydrogen atom, a halogen atom, an C1-C3 alkyl group or a C1-C3 haloalkyl group, $R^6$ represents a C3-C6 cycloalkyl group, an C2-C4 alkynyl group, a C2-C4 haloalkynyl group, a C1-C4 haloalkoxy group, an C1-C4 alkythio group, a C1-C4 haloalkylthio group or a C3-C6 halocycloalkyl group, $R^{10}$ represents a methyl group, X represents an oxygen atom, $Z^1$ represents an C1-C6 alkyl group, $Z^2$ represents a hydrogen atom, a halogen atom, an C1-C6 alkyl group, a C1-C6 haloalkyl group, an C1-C6 alkoxy group or a C1-C6 alkylthio group, $Z^3$ represents a hydrogen atom, a halogen atom or an C1-C4 alkyl group.

a compound of the formula (1) wherein Q represents Q2, $R^1$ represents an C1-C3 alkyl group, a halogen atom, a C1-C3 haloalkyl group, an C2-C3 alkynyl group, a C2-C3 haloalkynyl group, a C3-C5 cycloalkyl group, a C3-C5 halocycloalkyl group, an C1-C3 alkoxy group or a C1-C3 haloalkoxy group, $R^2$, $R^4$, $R^5$, $R^7$, $R^8$, $R^9$ and $R^{11}$ represent a hydrogen atom, $R^3$ represents a hydrogen atom, a halogen atom, an C1-C3 alkyl group or a C1-C3 haloalkyl group, $R^6$ represents a C3-C6 cycloalkyl group, an C2-C4 alkynyl group, a C2-C4 haloalkynyl group, a C1-C4 haloalkoxy group, an C1-C4 alkythio group, a C1-C4 haloalkylthio group or a C3-C6 halocycloalkyl group, $R^{10}$ represents a methyl group, X represents an oxygen atom, $Z^1$ represents an C1-C3 alkyl group, $Z^2$ represents a hydrogen atom, a chloro atom, a methoxy group, an ethoxy group, a methylthio group, a trifluoromethyl group or an C1-C3 alkyl group, $Z^3$ represents a hydrogen atom, a halogen atom or a methyl group.

a compound of the formula (1) wherein Q represents Q2, $R^1$ represents an C1-C3 alkyl group, a halogen atom, a C1-C3 haloalkyl group, an C2-C3 alkynyl group, a C2-C3 haloalkynyl group, a C3-C5 cycloalkyl group, a C3-C5 halocycloalkyl group, an C1-C3 alkoxy group or a C1-C3 haloalkoxy group, $R^2$, $R^4$, $R^5$, $R^7$, $R^8$, $R^9$ and $R^{11}$ represent a hydrogen atom, $R^3$ represents a hydrogen atom, a halogen atom, an C1-C3 alkyl group or a C1-C3 haloalkyl group, $R^6$ represents a C3-C6 cycloalkyl group, an C2-C4 alkynyl group, a C2-C4 haloalkynyl group, a C1-C4 haloalkoxy group, an C1-C4 alkythio group, a C1-C4 haloalkylthio group or a C3-C6 halocycloalkyl group, $R^{10}$ represents a methyl group, X represents an oxygen atom, $Z^1$ represents an C1-C6 alkyl group or a C1-C6 haloalkyl group, $Z^2$ represents a hydrogen atom or an C1-C3 alkyl group, $Z^3$ represents a hydrogen atom or a methyl group.

a compound of the formula (1) wherein Q represents Q1, $R^1$ represents a methyl group, an ethyl group, a chlorine atom, a bromine atom or a trifluoromethyl group, $R^2$, $R^4$, $R^5$, $R^7$, $R^8$, $R^9$ and $R^{11}$ represent a hydrogen atom, $R^3$ represents a hydrogen atom or a methyl group, $R^6$ represents a cyclopropyl group, an ethynyl group, an difluoromethoxy group or a methylthio group, $R^{10}$ represents a methyl group, X represents an oxygen atom, $Y^1$ and $Y^2$ connect to each other to represent —CH$_2$—CH$_2$—CH$_2$— or —CH$_2$—CH$_2$—CH$_2$—CH$_2$—, which combines together with the carbon atoms to which $Y^1$ and $Y^2$ are attached to form a five-membered or six-membered ring, $Y^2$ and $Y^3$ connect to each other to represent —CH$_2$—CH$_2$—CH$_2$— or —CH$_2$—CH$_2$—CH$_2$—CH$_2$—, which combines together with the carbon atoms to which $Y^2$ and $Y^3$ are attached to form a five-membered or six-membered ring, when each of $Y^1$, $Y^2$ and $Y^3$ does not form the five- or six-membered saturated ring, $Y^1$ represents a hydrogen atom, an C1-C3 alkyl group, a C1-C3 haloalkyl group or a cyclopropyl group, $Y^2$ represents a hydrogen atom, an C1-C3 alkyl group, a C1-C3 haloalkyl group or an C1-C3 alkoxy group, $Y^3$ represents a hydrogen atom or a methyl group.

a compound of the formula (1) wherein Q represents Q2, $R^1$ represents a methyl group, an ethyl group, a chlorine atom, a bromine atom or a trifluoromethyl group, $R^2$, $R^4$, $R^5$, $R^7$, $R^8$, $R^9$ and $R^{11}$ represent a hydrogen atom, $R^3$ represents a hydrogen atom or a methyl group, $R^6$ represents a cyclopropyl group, an ethynyl group, an difluoromethoxy group or a methylthio group, group, $R^{10}$ represents a methyl group, X represents an oxygen atom, $Z^1$ represents an C1-C6 alkyl group, $Z^2$ represents a hydrogen atom, a halogen atom, an C1-C6 alkyl group, a C1-C6 haloalkyl group, an C1-C6 alkoxy group or a C1-C6 alkylthio group, $Z^3$ represents a hydrogen atom, a halogen atom or an C1-C4 alkyl group.

a compound of the formula (1) wherein Q represents Q2, $R^1$ represents a methyl group, an ethyl group, a chlorine atom, a bromine atom or a trifluoromethyl group, $R^2$, $R^4$, $R^5$, $R^7$, $R^8$, $R^9$ and $R^{11}$ represent a hydrogen atom, $R^3$ represents a hydrogen atom or a methyl group, $R^6$ represents a cyclopropyl group, an ethynyl group, an difluoromethoxy group or a methylthio group, group, $R^{10}$ represents a methyl group, X represents an oxygen atom, $Z^1$ represents an C1-C3 alkyl group, $Z^2$ represents a hydrogen atom, a chloro atom, a methoxy group, an ethoxy group, a methylthio group, a trifluoromethyl group or an C1-C3 alkyl group, $Z^3$ represents a hydrogen atom, a halogen atom or a methyl group.

a compound of the formula (1) wherein Q represents Q2, $R^1$ represents a methyl group, an ethyl group, a chlorine atom, a bromine atom or a trifluoromethyl group, $R^2$, $R^4$, $R^5$, $R^7$, $R^8$, $R^9$ and $R^{11}$ represent a hydrogen atom, $R^3$ represents a hydrogen atom or a methyl group, $R^6$ represents a cyclopropyl group, an ethynyl group, an difluoromethoxy group or a methylthio group, group, $R^{10}$ represents a methyl group, X represents an oxygen atom, $Z^1$ represents an C1-C6 alkyl group or a C1-C6 haloalkyl group, $Z^2$ represents a hydrogen atom or an C1-C3 alkyl group, $Z^3$ represents a hydrogen atom or a methyl group.

a compound of the formula (1) wherein Q represents Q2, $R^1$ represents a methyl group, an ethyl group, a chlorine atom, a bromine atom or a trifluoromethyl group, $R^2$, $R^4$, $R^5$, $R^7$, $R^8$, $R^9$ and $R^{11}$ represent a hydrogen atom, $R^3$ represents a hydrogen atom or a methyl group, $R^6$ represents a cyclopropyl group $R^{10}$ represents a methyl group, X represents an oxygen atom, $Z^1$ represents an C1-C6 alkyl group group, $Z^2$ represents a hydrogen atom, a halogen atom, an C1-C6 alkyl group, a C1-C6 haloalkyl group, a cyano group, an C1-C6 alkoxy group or a C1-C6 alkylthio group, $Z^3$ represents a hydrogen atom, a halogen atom or an C1-C4 alkyl group.

a compound of the formula (1) wherein Q represents Q2, $R^1$ represents a methyl group, an ethyl group, a chlorine atom, a bromine atom or a trifluoromethyl group, $R^2$, $R^4$, $R^5$, $R^7$, $R^8$, $R^9$ and $R^{11}$ represent a hydrogen atom, $R^3$ represents a hydrogen atom or a methyl group, $R^6$ represents a cyclopropyl group $R^{10}$ represents a methyl group, X represents an oxygen atom, $Z^1$ represents an C1-C6 alkyl group group, $Z^2$ represents a hydrogen atom, a halogen atom, an C1-C6 alkyl group, a C1-C6 haloalkyl group, a cyano group, an C1-C6 alkoxy group or a C1-C6 alkylthio group, $Z^3$ represents a hydrogen atom, a halogen atom or an C1-C4 alkyl group, an C1-C6 alkoxy group and a cyano group.

Examples of an embodiment of the present compound include the compounds of the formula (2) wherein the substituents represent the following ones.

a compound of the formula (2) wherein $R^1$ represents a methyl group, an ethyl group, a chlorine atom or a bromine atom, $R^3$ represents a hydrogen atom or a methyl group, $R^6$ represents a cyclopropyl group, and $R^{12}$ represents an C1-C6 alkyl group;

a compound of the formula (2) wherein $R^1$ represents a methyl group, an ethyl group, a chlorine atom or a bromine atom, $R^3$ represents a hydrogen atom or a methyl group, $R^6$ represents a cyclopropyl group, and $R^{12}$ represents a methyl group or an ethyl group;

a compound of the formula (2) wherein $R^1$ represents a methyl group, an ethyl group, a chlorine atom or a bromine atom, $R^3$ represents a hydrogen atom or a methyl group, $R^6$ represents a difluoromethoxy group, and $R^{12}$ represents an C1-C6 alkyl group;

a compound of the formula (2) wherein $R^1$ represents a methyl group, an ethyl group, a chlorine atom or a bromine atom, $R^3$ represents a hydrogen atom or a methyl group, $R^6$ represents a difluoromethoxy group, and $R^{12}$ represents a methyl group or an ethyl group.

Herein, when in a formula (I), $R^4$ and $R^5$ are different from each other, the present compound of the formula (1) may have an asymmetric carbon atom therein, and may thus include optically active substances and racemates, without being limited thereto.

Next, a process for preparing the present compound is explained.

The present compound can be prepared, for example, according to the below-mentioned process.

(Process A)

The present compound of the formula (1) can be prepared by reacting a compound of a formula (A-1) (hereinafter, described as Compound (A-1)) with a compound of a formula (A-2) (hereinafter, described as Compound (A-2)) in the presence of a base.

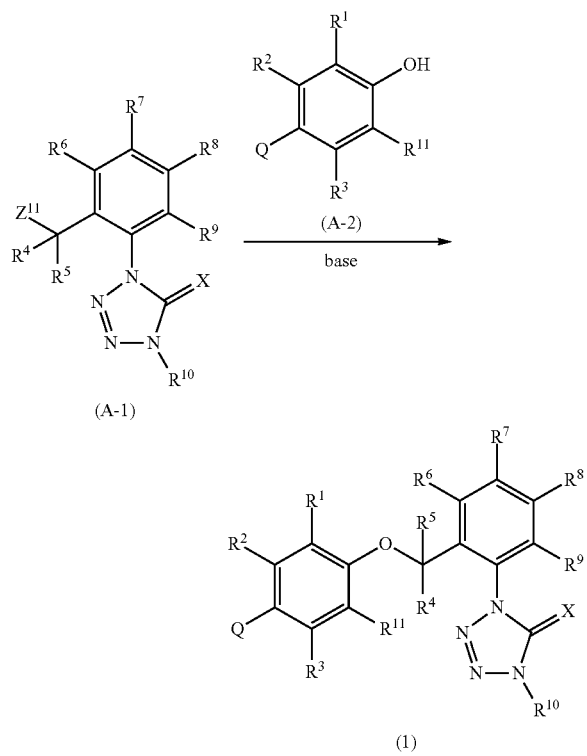

[wherein $R^1$, $R^2$, $R^3$, $R^4$, $R^5$, $R^6$, $R^7$, $R^8$, $R^9$, $R^{10}$, $R^{11}$, X and Q are the same as defined above, $Z^{11}$ represents a leaving group such as a chlorine atom, a bromine atom, an iodine atom, a methanesulfonyloxy group, a trifluoromethanesulfonyloxy group, or a p-toluenesulfonyloxy group]

This reaction is usually carried out in a solvent.

Examples of the solvent to be used in the reaction include hydrocarbons such as heptane, hexane, cyclohexane, pentane, toluene, xylene; ethers such as diethyl ether, tetrahydrofuran, 1,4-dioxane, ethyleneglycol dimethyl ether, anisole, methyl tert-butyl ether, diisopropyl ether; halogenated hydrocarbons such as carbon tetrachloride, chloroform, dichloromethane, 1,2-dichloroethane, tetrachloroethane, chlorobenzene; acid amides such as N,N-dimethylformamide, 1,3-dimethyl-2-imidazolidinone, N-methylpyrrolidone; esters such as ethyl acetate, methyl acetate; sulfoxides such as dimethyl sulfoxide; ketones such as acetone, methyl ethyl ketone, methyl isobutyl ketone; nitriles such as acetonitrile, propionitrile; water; and mixed solvents thereof.

Examples of the base to be used in the reaction include organic bases such as triethylamine, pyridine, N-methylmorpholine, N-methylpiperidine, 4-dimethylaminopyridine, diisopropylethylamine, lutidine, collidine, diazabicycloundecene, diazabicyclononene; alkali metal carbonates such as lithium carbonate, sodium carbonate, potassium carbonate, cesium carbonate; alkali metal bicarbonates such as lithium bicarbonate, sodium bicarbonate, potassium bicarbonate, cesium bicarbonate; alkali metal hydroxides such as lithium hydroxide, sodium hydroxide, potassium hydroxide, cesium hydroxide; alkali metal halides such as sodium fluoride, potassium fluoride, cesium fluoride; alkali metal hydrides such as lithium hydride, sodium hydride, potassium hydride; and alkali metal alkoxides such as sodium tert-butoxide, potassium tert-butoxide.

In the reaction, Compound (A-2) is used usually within a range of 1 to 10 molar ratio(s), and the base is used usually within a range of 1 to 10 molar ratio(s), as opposed to 1 mole of Compound (A-1).

The reaction temperature is usually within a range of −20 to 150° C. The reaction period of the reaction is usually within a range of 0.1 to 24 hours.

If necessary, sodium iodide, tetrabutylammonium iodide and the others may be added to the reaction and these compounds are used usually within a range of 0.001 to 1.2 molar ratios as opposed to 1 mole of Compound (A-1).

When the reaction is completed, the reaction mixtures are extracted with organic solvent(s), and the resulting organic layers are worked up (for example, drying and concentration) to isolate the present compound of the formula (1). The isolated present compound may be further purified, for example, by chromatography and recrystallization.

(Process B)

The present compound of the formula (1) can be prepared by reacting a compound of a formula (B-1) (hereinafter, described as Compound (B-1)) with a compound of a formula (B-2) (hereinafter, described as Compound (B-2)) in the presence of a base.

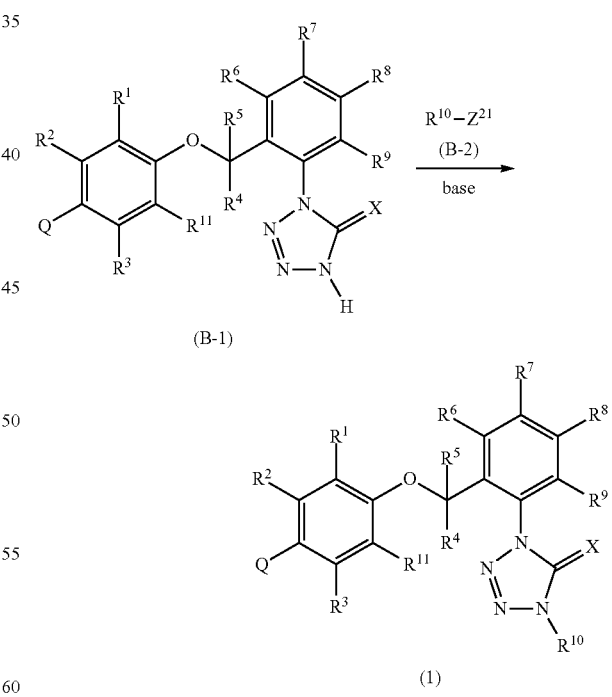

[wherein $R^1$, $R^2$, $R^3$, $R^4$, $R^5$, $R^6$, $R^7$, $R^8$, $R^9$, $R^{10}$, $R^{11}$, X and Q are the same as defined above, $Z^{21}$ represents a leaving group such as a chlorine atom, a bromine atom, an iodine atom, a methanesulfonyloxy group, a methoxysulfonyloxy group, a trifluoromethanesulfonyloxy group, or a p-toluenesulfonyloxy group]

This reaction is usually carried out in a solvent.

Examples of the solvent to be used in the reaction include hydrocarbons such as heptane, hexane, cyclohexane, pentane, toluene, xylene; ethers such as diethyl ether, tetrahydrofuran, 1,4-dioxane, ethyleneglycol dimethyl ether, anisole, methyl tert-butyl ether, diisopropyl ether; halogenated hydrocarbons such as carbon tetrachloride, chloroform, dichloromethane, 1,2-dichloroethane, tetrachloroethane, chlorobenzene; acid amides such as N,N-dimethylformamide, 1,3-dimethyl-2-imidazolidinone, N-methylpyrrolidone; esters such as ethyl acetate, methyl acetate; sulfoxides such as dimethyl sulfoxide; ketones such as acetone, methyl ethyl ketone, methyl isobutyl ketone; nitriles such as acetonitrile, propionitrile; water; and mixed solvents thereof.

Compound (B-2) to be used in the reaction can be usually used as a commercially available product. Specific examples include alkyl halides such as chlorodifluoromethane, methyl bromide, ethyl bromide, propyl bromide, methyl iodide, ethyl iodide, propyl bromide, aryl bromide, cyclopropyl bromide, 1,1-difluoro-2-iodoethane; alkyl or aryl sulfates such as dimethyl sulfate, methyl p-toluenesulfonate, ethyl p-toluenesulfonate, propyl p-toluenesulfonate, methyl methanesulfonate, ethyl methanesulfonate and propyl methanesulfonate.

Examples of the base to be used in the reaction include organic bases such as triethylamine, pyridine, N-methylmorpholine, N-methylpiperidine, 4-dimethylaminopyridine, diisopropylethylamine, lutidine, collidine, diazabicycloundecene, diazabicyclononene; alkali metal carbonates such as lithium carbonate, sodium carbonate, potassium carbonate, cesium carbonate; alkali metal bicarbonates such as lithium bicarbonate, sodium bicarbonate, potassium bicarbonate, cesium bicarbonate; alkali metal hydroxides such as lithium hydroxide, sodium hydroxide, potassium hydroxide, cesium hydroxide; alkali metal halides such as sodium fluoride, potassium fluoride, cesium fluoride; alkali metal hydrides such as lithium hydride, sodium hydride, potassium hydride; and alkali metal alkoxides such as sodium tert-butoxide, potassium tert-butoxide.

In the reaction, Compound (B-2) is used usually within a range of 1 to 10 molar ratio(s), and the base is used usually within a range of 1 to 10 molar ratios, as opposed to 1 mole of Compound (B-1).

The reaction temperature is usually within a range of −20 to 150° C. The reaction period of the reaction is usually within a range of 0.1 to 24 hours.

When the reaction is completed, the reaction mixtures are extracted with organic solvent(s), and the resulting organic layers are worked up (for example, drying and concentration) to isolate the present compound of the formula (1). The isolated present compound may be further purified, for example, by chromatography and recrystallization.

(Process C)

The present compound of the formula (1) wherein X represents a sulfur atom, i.e., the compound of a formula (1-S) (hereinafter, described as Compound (1-S)) can be prepared by reacting the present compound of the formula (1) wherein X represents an oxygen atom (hereinafter, described as Compound (1-O)) by well-known sulfurization.

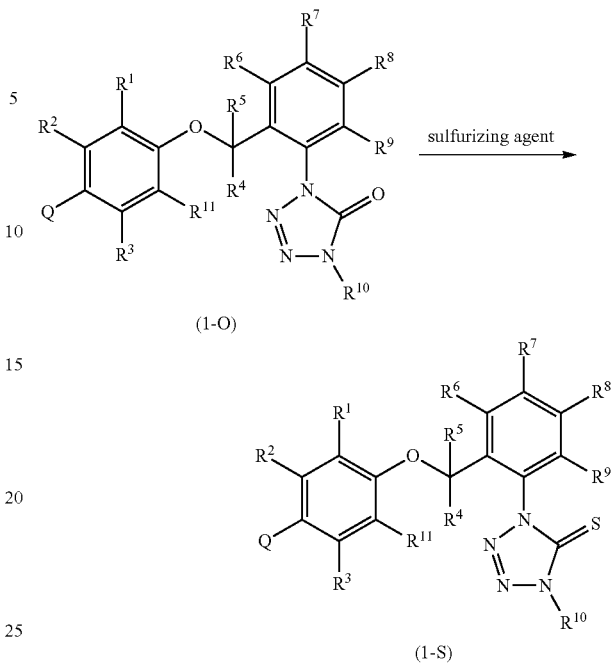

[wherein
$R^1$, $R^2$, $R^3$, $R^4$, $R^5$, $R^6$, $R^7$, $R^8$, $R^9$, $R^{10}$, $R^{11}$ and Q are the same as defined above.]

This reaction is usually carried out in a solvent.

Examples of the solvent to be used in the reaction include hydrocarbons such as heptane, hexane, cyclohexane, pentane, toluene, xylene; ethers such as diethyl ether, tetrahydrofuran, 1,4-dioxane, ethyleneglycol dimethyl ether, anisole, methyl tert-butyl ether, diisopropyl ether; halogenated hydrocarbons such as carbon tetrachloride, chloroform, dichloromethane, 1,2-dichloroethane, tetrachloroethane, chlorobenzene; nitriles such as acetonitrile, propionitrile; and mixed solvents thereof.

Examples of the sulfurating agent to be used in the reaction include phosphorus pentasulfide, Lawesson's reagent (2,4-bis(4-methoxyphenyl)-1,3,2,4-dithiadiphosphetane 2,4-disulfide).

In the reaction, the sulfurating agent is used within a range of 0.5 to 10 molar ratios as opposed to 1 mole of Compound (1-O).

The reaction temperature is usually within a range of −20 to 150° C. The reaction period of the reaction is usually within a range of 0.1 to 24 hours.

If necessary, organic bases such as pyridine and triethylamine and inorganic bases such as alkali metal hydroxides and alkali metal carbonates and the others may be added to the reaction and these compounds are used usually within a range of 0.5 to 10 molar ratios as opposed to 1 mole of Compound (1-O).

When the reaction is completed, the reaction mixtures are extracted with organic solvent(s), and the resulting organic layers are worked up (for example, drying and concentration) to isolate the present compound of the formula (1-S). The isolated present compound may be further purified, for example, by chromatography and recrystallization.

(Process D)

The present compound of the formula (1) wherein $R^6$ represents $R^{41}$, i.e., the compound of a formula (1-1) (hereinafter, described as Compound (1-1)), can be prepared by coupling Compound (D-1) (hereinafter, described as Compound (D-1)) with a compound of a formula (D-2) (hereinafter, described as Compound (D-2)) in the presence of a base and a catalyst.

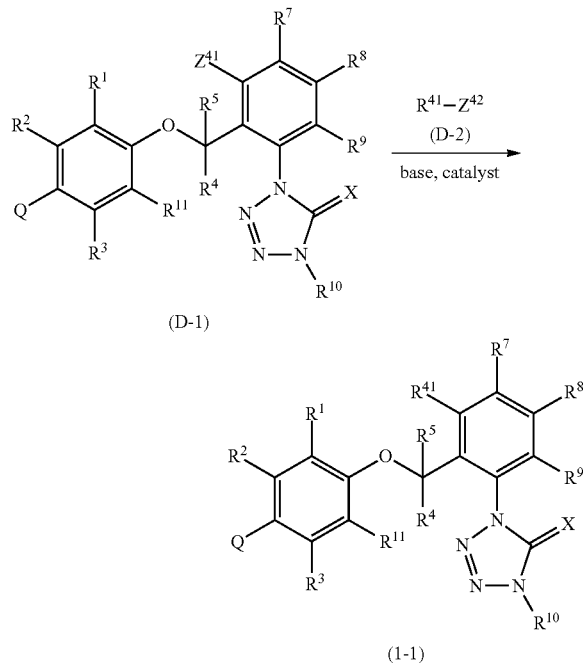

[wherein $R^1$, $R^2$, $R^3$, $R^4$, $R^5$, $R^6$, $R^7$, $R^8$, $R^9$, $R^{10}$, $R^{11}$, X and Q are the same as defined above, $Z^{41}$ represents a chlorine atom, a bromine atom, an iodine atom or a trifluoromethanesulfonyloxy group, $R^{41}$ represents a C3-C6 cycloalkyl group or a C3-C6 halocycloalkyl group, and $Z^{42}$ represents a $B(OH)_2$, an alkoxyboryl group or a trifluoroborate salts ($BF_3^-K^+$).]

This reaction is usually carried out in a solvent.

Examples of the solvent to be used in the reaction include hydrocarbons such as heptane, hexane, cyclohexane, pentane, toluene, xylene; ethers such as diethyl ether, tetrahydrofuran, 1,4-dioxane, ethyleneglycol dimethyl ether, anisole, methyl tert-butyl ether, diisopropyl ether; halogenated hydrocarbons such as carbon tetrachloride, chloroform, dichloromethane, 1,2-dichloroethane, tetrachloroethane, chlorobenzene; acid amides such as N,N-dimethylformamide, 1,3-dimethyl-2-imidazolidinone, N-methylpyrrolidone; esters such as ethyl acetate, methyl acetate; sulfoxides such as dimethyl sulfoxide; ketones such as acetone, methyl ethyl ketone, methyl isobutyl ketone; nitriles such as acetonitrile, propionitrile; alcohols such as methanol, ethanol, propanol, butanol; water; and mixed solvents thereof.

Compound (D-2) to be used in the reaction may be usually used as a commercially available product, or may be prepared according to a method described in a review article of N. Miyaura and A. Suzuki, Chem. Rev. 1995, 95, 2457 and the others. Compound (D-2) to be used in the reaction can be also prepared, for example, by reacting an iodo compound ($R^{41}$—I) or a bromo compound ($R^{41}$—Br) with an alkyl lithium (such as butyl lithium), followed by reacting the resulting mixtures with borate esters to obtain boronate ester derivatives. Also, the obtained boronate ester derivatives can be hydrolyzed to the corresponding boronate esters derivatives as needed. Further, according to a method described in a review article of Molander et al. Acc. Chem. Res. 2007, 40, 275 and the others, the above-mentioned boronate ester derivatives can be fluorinated with potassium bifluoride and the like to obtain the trifluoroborate salts ($BF_3^-K^+$).

Examples of the catalyst to be used in the reaction include palladium(II) acetate, dichlorobis(triphenylphosphine)palladium, tetrakistriphenylphosphinepalladium(0), palladium (II) acetate/triscyclohexylphosphine, bis(diphenylphoshine ferrocenyl)palladium(II) dichloride, 1,3-bis(2,6-diisopropylphenyl)imidazole-2-ylidene (1,4-naphthoquinone)palladium dimer, aryl(chloro) (1,3-dimethyl-1,3-dihydro-2H-imidazole-2-ylidene)palladium or palladium(II) acetate/ dicyclohexyl(2',4',6'-triisopropylbiphenyl-2-yl)phosphine, and tris(dibenzylideneacetone)dipalladium and the others.

Examples of the base to be used in the reaction include organic bases such as triethylamine, pyridine, N-methylmorpholine, N-methylpiperidine, 4-dimethylaminopyridine, diisopropylethylamine, lutidine, collidine, diazabicycloundecene, diazabicyclononene; alkali metal carbonates such as lithium carbonate, sodium carbonate, potassium carbonate, cesium carbonate; alkali metal bicarbonates such as lithium bicarbonate, sodium bicarbonate, potassium bicarbonate, cesium bicarbonate; alkali metal hydroxides such as lithium hydroxide, sodium hydroxide, potassium hydroxide, cesium hydroxide; alkali metal halides such as sodium fluoride, potassium fluoride, cesium fluoride, cesium chloride; alkali metal hydrides such as lithium hydride, sodium hydride, potassium hydride; alkali metal phosphates such as tripotassium phosphate; and alkali metal alkoxides such as sodium methoxide, sodium ethoxide, sodium tert-butoxide, potassium tert-butoxide.

In the reaction, Compound (D-2) is used usually within a range of 1 to 10 molar ratio(s), and the base is used usually within a range of 1 to 10 molar ratio(s), and the catalyst is used usually within a range of 0.0001 to 1 molar ratio(s), as opposed to 1 mole of Compound (D-1).

The reaction temperature is usually within a range of 0 to 150° C. The reaction period of the reaction is usually within a range of 0.1 to 24 hours.

When the reaction is completed, the reaction mixtures are extracted with organic solvent(s), and the resulting organic layers are worked up (for example, drying and concentration) to isolate the present compound of the formula (1-1). The isolated present compound may be further purified, for example, by chromatography and recrystallization.

According to the process for preparing the above-mentioned Compound (1-1), the present compound of the formula (1) wherein $R^7$ represents $R^{42}$, i.e., compound of a below-mentioned formula (1-1-2) (hereinafter, described as Compound (1-1-2)), can be prepared by coupling compound of a formula (D-3) (hereinafter, describes as Compound (D-3)) with compound of a formula (D-2-2) (hereinafter, describes as Compound (D-2-2)) in the presence of a base and the catalyst.

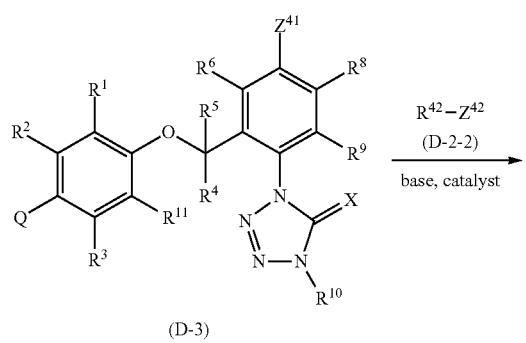

(D-3)

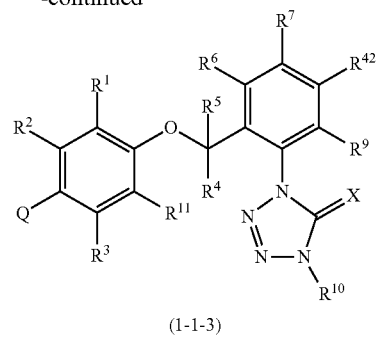

(1-1-3)

[wherein
$R^1, R^2, R^3, R^4, R^5, R^6, R^7, R^9, R^{10}, R^{11}, X, Q, Z^{41}$ and $Z^{42}$ are the same as defined above]

According to the process for preparing the above-mentioned Compound (1-1), the present compound of the formula (1) wherein $R^9$ represents $R^{42}$, i.e., a compound of a below-mentioned formula (1-1-4) (hereinafter, described as Compound (1-1-4)), can be prepared by coupling a compound of a below-mentioned formula (D-5) (hereinafter, described as Compound (D-5)) with Compound (D-2-2) (hereinafter, described as Compound (D-2-2)) in the presence of a base and a catalyst.

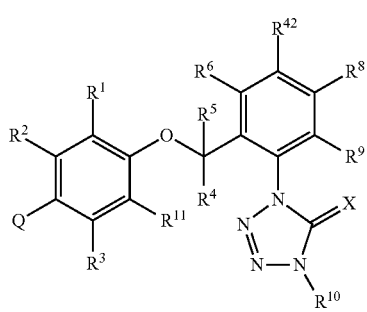

(1-1-2)

[wherein
$R^1, R^2, R^3, R^4, R^5, R^6, R^8, R^9, R^{10}, R^{11}, X, Q, Z^{41}$ and $Z^{42}$ are the same as defined above, $R^{42}$ represents an C1-C3 alkyl group, a C1-C3 haloalkyl group, an C2-C3 alkenyl group or a C2-C3 haloalkenyl group]

According to the process for preparing the above-mentioned Compound (1-1), the present compound of the formula (1) wherein $R^8$ represents $R^{42}$, i.e., a compound of a below-mentioned formula (1-1-3) (hereinafter, described as Compound (1-1-3)), can be prepared by coupling a compound of a below-mentioned formula (D-4) (hereinafter, described as Compound (D-4)) with Compound (D-2-2) (hereinafter, described as Compound (D-2-2)) in the presence of a base and a catalyst.

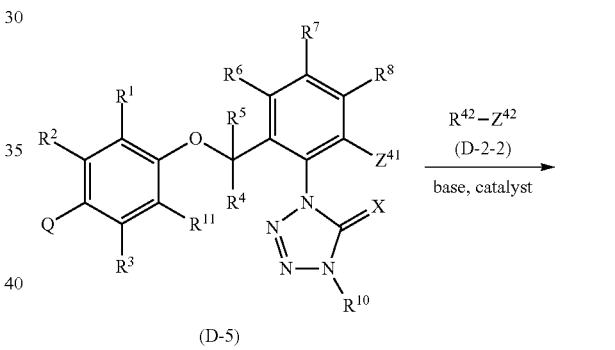

(D-5)

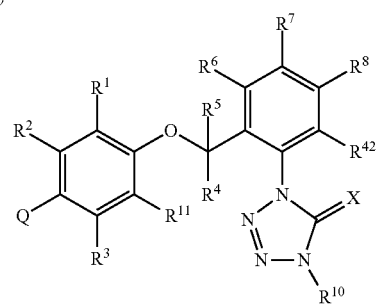

(1-1-4)

[wherein
$R^1, R^2, R^3, R^4, R^5, R^6, R^7, R^8, R^{10}, R^{11}, R^{42}, X, Q, Z^{41}$ and $Z^{42}$ are the same as defined above]

The present compound of the formula (1) wherein $R^6$ represents $R^{41}$, and one or more substituents selected from the group consisting of $R^7$, $R^8$ and $R^9$ is $R^{42}$ can be prepared according to the above-mentioned Process D.

Compound (1-1), Compound (1-1-2), Compound (1-1-3) and Compound (1-1-4) can be prepared by using other known coupling reaction in place of the above-mentioned coupling reaction of Process D.

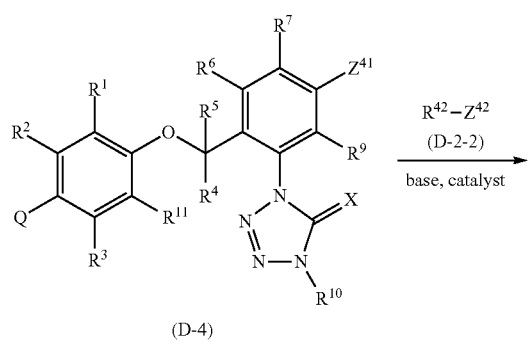

(D-4)

(Process E)

The present compound of the formula (1) wherein $R^1$ represents $R^{51}$, i.e., the compound of a formula (1-2) (hereinafter, described as Compound (1-2)), can be prepared by coupling Compound (E-1) (hereinafter, described as Compound (E-1)) with a compound of a formula (E-2) (hereinafter, described as Compound (E-2)) in the presence of a base and a catalyst.

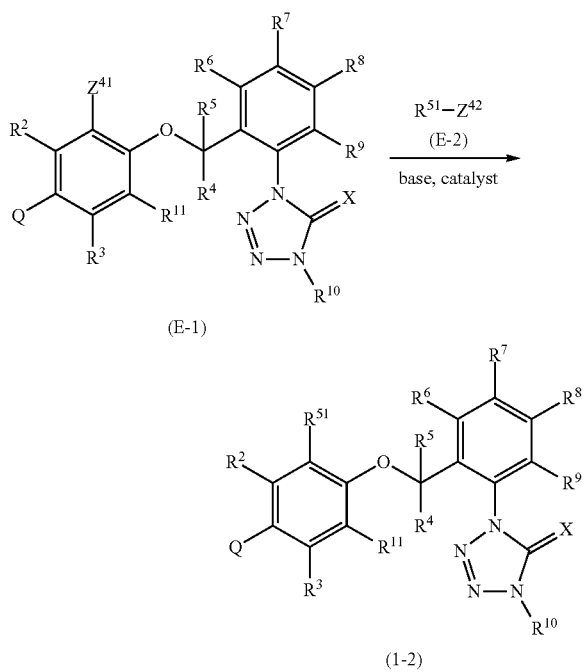

[wherein
$R^2$, $R^3$, $R^4$, $R^5$, $R^6$, $R^7$, $R^8$, $R^9$, $R^{10}$, $R^{11}$, $Z^{41}$, $Z^{42}$, X and Q are the same as defined above, $R^{51}$ represents an C1-C6 alkyl group, a C1-C6 haloalkyl group, an C2-C6 alkenyl group, a C2-C6 haloalkenyl group, an C2-C6 alkynyl group, a C2-C6 haloalkynyl group, a C3-C6 cycloalkyl group or a C3-C6 halocycloalkyl group]

This reaction is usually carried out in a solvent.

Examples of the solvent to be used in the reaction include hydrocarbons such as heptane, hexane, cyclohexane, pentane, toluene, xylene; ethers such as diethyl ether, tetrahydrofuran, 1,4-dioxane, ethyleneglycol dimethyl ether, anisole, methyl tert-butyl ether, diisopropyl ether; halogenated hydrocarbons such as carbon tetrachloride, chloroform, dichloromethane, 1,2-dichloroethane, tetrachloroethane, chlorobenzene; acid amides such as N,N-dimethylformamide, 1,3-dimethyl-2-imidazolidinone, N-methylpyrrolidone; esters such as ethyl acetate, methyl acetate; sulfoxides such as dimethyl sulfoxide; ketones such as acetone, methyl ethyl ketone, methyl isobutyl ketone; nitriles such as acetonitrile, propionitrile; alcohols such as methanol, ethanol, propanol, butanol; water; and mixed solvents thereof.

Compound (E-2) to be used in the reaction may be usually used as a commercially available product, or may be prepared according to a method described in a review article of N. Miyaura and A. Suzuki, Chem. Rev. 1995, 95, 2457 and the others. Compound (E-2) to be used in the reaction can be also prepared, for example, by reacting an iodo compound ($R^{51}$—I) or a bromo compound ($R^{51}$—Br) with an alkyl lithium (such as butyl lithium), followed by reacting the resulting mixtures with borate esters to obtain boronate ester derivatives. Also, the obtained boronate ester derivatives can be hydrolyzed to the corresponding boronate esters derivatives as needed. Further, according to a method described in a review article of Molander et al. Acc. Chem. Res. 2007, 40, 275 and the others, the above-mentioned boronate ester derivatives can be fluorinated with potassium bifluoride and the like to obtain the trifluoroborate salts ($BF_3^-K^+$).

Examples of the catalyst to be used in the reaction include palladium(II) acetate, dichlorobis(triphenylphosphine)palladium, tetrakistriphenylphosphinepalladium(0), palladium (II) acetate/triscyclohexylphosphine, bis(diphenylphoshine ferrocenyl)palladium(II) dichloride, 1,3-bis(2,6-diisopropylphenyl)imidazole-2-ylidene (1,4-naphthoquinone)palladium dimer, aryl(chloro) (1,3-dimethyl-1,3-dihydro-2H-imidazole-2-ylidene)palladium or palladium(II) acetate/dicyclohexyl(2',4',6'-triisopropylbiphenyl-2-yl)phosphine, and tris(dibenzylideneacetone)dipalladium and the others.

Examples of the base to be used in the reaction include organic bases such as triethylamine, pyridine, N-methylmorpholine, N-methylpiperidine, 4-dimethylaminopyridine, diisopropylethylamine, lutidine, collidine, diazabicycloundecene, diazabicyclononene; alkali metal carbonates such as lithium carbonate, sodium carbonate, potassium carbonate, cesium carbonate; alkali metal bicarbonates such as lithium bicarbonate, sodium bicarbonate, potassium bicarbonate, cesium bicarbonate; alkali metal hydroxides such as lithium hydroxide, sodium hydroxide, potassium hydroxide, cesium hydroxide; alkali metal halides such as sodium fluoride, potassium fluoride, cesium fluoride, cesium chloride; alkali metal hydrides such as lithium hydride, sodium hydride, potassium hydride; alkali metal phosphates such as tripotassium phosphate; and alkali metal alkoxides such as sodium methoxide, sodium ethoxide, sodium tert-butoxide, potassium tert-butoxide.

In the reaction, Compound (E-2) is used usually within a range of 1 to 10 molar ratio(s), and the base is used usually within a range of 1 to 10 molar ratio(s), and the catalyst is used usually within a range of 0.0001 to 1 molar ratio(s), as opposed to 1 mole of Compound (E-1).

The reaction temperature is usually within a range of 0 to 150° C. The reaction period of the reaction is usually within a range of 0.1 to 24 hours.

When the reaction is completed, the reaction mixtures are extracted with organic solvent(s), and the resulting organic layers are worked up (for example, drying and concentration) to isolate the present compound of the formula (1-2). The isolated present compound may be further purified, for example, by chromatography and recrystallization.

According to the process for preparing the above-mentioned Compound (1-2), the present compound of the formula (1) wherein $R^2$ represents $R^{51}$, i.e., a compound of a below-mentioned formula (1-2-2) (hereinafter, described as Compound (1-2-2)), can be prepared by coupling a compound of a below-mentioned formula (E-3) (hereinafter, described as Compound (E-3)) with Compound (E-2) (hereinafter, described as Compound (E-2)) in the presence of a base and a catalyst.

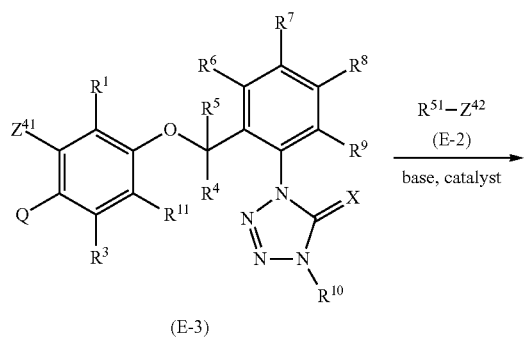

(E-3)

[wherein
$R^1$, $R^3$, $R^4$, $R^5$, $R^6$, $R^7$, $R^8$, $R^9$, $R^{10}$, $R^{11}$, $R^{51}$, X, Q, $Z^{41}$ and $Z^{42}$ are the same as defined above]

According to the process for preparing the above-mentioned Compound (1-2), the present compound of the formula (1) wherein $R^3$ represents $R^{51}$, i.e., a compound of a below-mentioned formula (1-2-3) (hereinafter, described as Compound (1-2-3)), can be prepared by coupling a compound of a below-mentioned formula (E-4) (hereinafter, described as Compound (E-4)) with Compound (E-2) (hereinafter, described as Compound (E-2)) in the presence of a base and a catalyst.

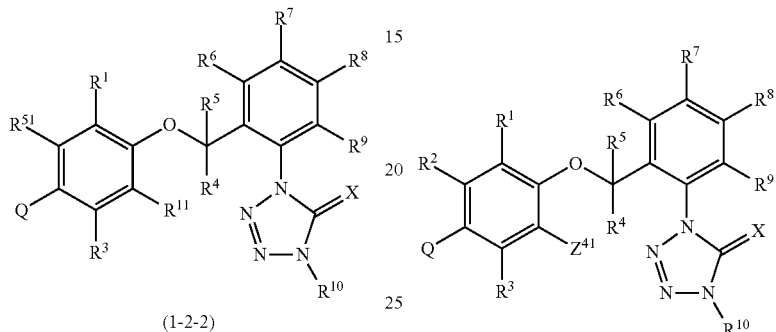

[wherein
$R^1$, $R^2$, $R^4$, $R^5$, $R^6$, $R^7$, $R^8$, $R^9$, $R^{10}$, $R^{11}$, $R^{51}$, X, Q, $Z^{41}$ and $Z^{42}$ are the same as defined above]

According to the process for preparing the above-mentioned Compound (1-2), the present compound of the formula (1) wherein $R^{11}$ represents $R^{51}$, i.e., a compound of a below-mentioned formula (1-2-4) (hereinafter, described as Compound (1-2-4)), can be prepared by coupling a compound of a below-mentioned formula (E-5) (hereinafter, described as Compound (E-5)) with Compound (E-2) (hereinafter, described as Compound (E-2)) in the presence of a base and a catalyst.

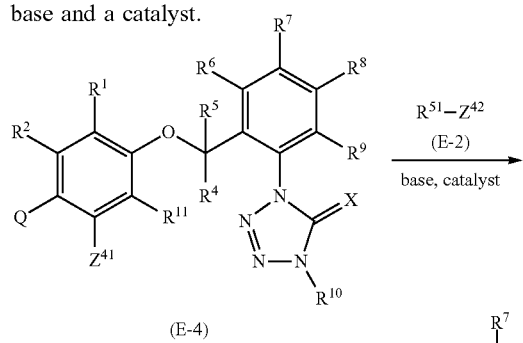

(E-5)

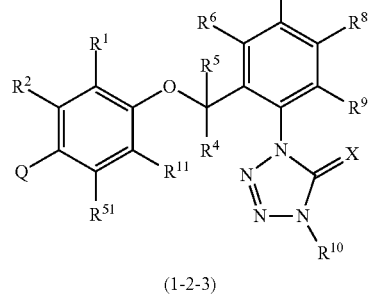

(1-2-4)

[wherein
$R^1$, $R^2$, $R^3$, $R^4$, $R^5$, $R^6$, $R^7$, $R^8$, $R^9$, $R^{10}$, $R^{51}$, X, Q, $Z^{41}$ and $Z^{42}$ are the same as defined above]

The present compound of the formula (1) wherein two or more substituents selected from the group consisting of $R^1$, $R^2$, $R^3$ and $R^{11}$ is $R^{51}$ can be prepared according to the above-mentioned Process E.

Compound (1-2), Compound (1-2-2), Compound (1-2-3) and Compound (1-2-4) can be prepared by using other known coupling reaction in place of the above-mentioned coupling reaction of Process E.

(Process F)

The present compound of the formula (1) wherein Q represents Q2, and $Z^1$ and $Z^2$ represent a hydrogen atom, i.e., a compound of a below-mentioned formula (1-3) (hereinafter, described as Compound (1-3)), can be prepared by reacting a compound of a below-mentioned formula (F-1) (hereinafter, described as Compound (F-1)) with hydrazines.

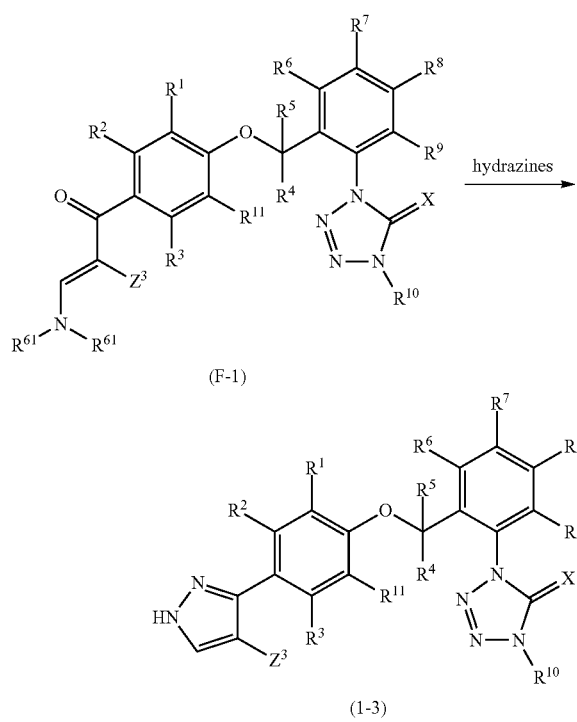

(F-1)

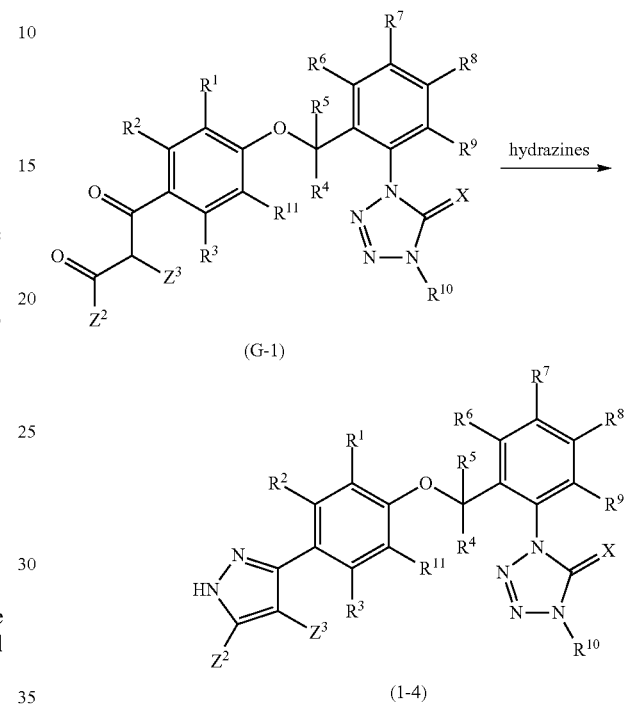

(G-1)

(1-3)

(1-4)

[wherein

R¹, R², R³, R⁴, R⁵, R⁶, R⁷, R⁸, R⁹, R¹⁰, R¹¹, X and Z³ are the same as defined above, and R⁶¹ represents a methyl group or an ethyl group]

This reaction is usually carried out in a solvent.

Examples of the solvent to be used in the reaction include ethers such as diethyl ether, tetrahydrofuran, 1,4-dioxane, ethyleneglycol dimethyl ether, anisole, methyl tert-butyl ether, diisopropyl ether; hydrocarbons such as heptane, hexane, cyclohexane, pentane, toluene, xylene; halogenated hydrocarbons such as carbon tetrachloride, chloroform, dichloromethane, 1,2-dichloroethane, tetrachloroethane, chlorobenzene; nitriles such as acetonitrile, propionitrile; acid amides such as N,N-dimethylformamide, 1,3-dimethyl-2-imidazolidinone, N-methylpyrrolidone; sulfoxides such as dimethyl sulfoxide; alcohols such as methanol, ethanol, propanol, butanol; water; and mixed solvents thereof.

Examples of the hydrazines to be used in the reaction include hydrazine monohydrate, hydrazine hydrochloride, hydroazine sulfate, anhydrous hydrazine and the others.

In the reaction, hydrazines is used usually within a range of 1 to 100 molar ratio(s) as opposed to 1 mole of Compound (F-1).

The reaction temperature is usually within a range of −20 to 150° C. The reaction period of the reaction is usually within a range of 0.1 to 24 hours.

When the reaction is completed, the reaction mixtures are extracted with organic solvent(s), and the resulting organic layers are worked up (for example, drying and concentration) to isolate the present compound of the formula (1-3). Alternatively, the reaction is completed, the reaction mixtures are worked up (for example, concentration) to isolate the present compound of the formula (1-3). These isolated present compound may be further purified, for example, by distillation, chromatography and recrystallization.

(Process G)

The present compound of the formula (1) wherein Q represents Q2, and Z¹ represents a hydrogen atom, i.e., a compound of a below-mentioned formula (1-4) (hereinafter, described as Compound (1-4)), can be prepared by reacting a compound of a below-mentioned formula (G-1) (hereinafter, described as Compound (G-1)) with hydrazines.

[wherein

R¹, R², R³, R⁴, R⁵, R⁶, R⁷, R⁸, R⁹, R¹⁰, R¹¹, X, Z² and Z³ are the same as defined above]

This reaction is usually carried out in a solvent.

Examples of the solvent to be used in the reaction include ethers such as diethyl ether, tetrahydrofuran, 1,4-dioxane, ethyleneglycol dimethyl ether, anisole, methyl tert-butyl ether, diisopropyl ether; hydrocarbons such as heptane, hexane, cyclohexane, pentane, toluene, xylene; halogenated hydrocarbons such as carbon tetrachloride, chloroform, dichloromethane, 1,2-dichloroethane, tetrachloroethane, chlorobenzene; nitriles such as acetonitrile, propionitrile; acid amides such as N,N-dimethylformamide, 1,3-dimethyl-2-imidazolidinone, N-methylpyrrolidone; sulfoxides such as dimethyl sulfoxide; alcohols such as methanol, ethanol, propanol, butanol; water; and mixed solvents thereof.

Examples of the hydrazines to be used in the reaction include hydrazine monohydrate, hydrazine hydrochloride, hydroazine sulfate, anhydrous hydrazine and the others.

In the reaction, hydrazines is used usually within a range of 1 to 100 molar ratio(s) as opposed to 1 mole of Compound (G-1).

The reaction temperature is usually within a range of −20 to 150° C. The reaction period of the reaction is usually within a range of 0.1 to 24 hours.

When the reaction is completed, the reaction mixtures are extracted with organic solvent(s), and the resulting organic layers are worked up (for example, drying and concentration) to isolate the present compound of the formula (1-4). The isolated present compound may be further purified, for example, by chromatography and recrystallization.

(Process H)

The present compound of the formula (1) wherein Q represents Q2, i.e., the compound of a formula (1-5) (hereinafter, described as Compound (1-5)), can be prepared by reacting Compound (1-4) (hereinafter, described as Compound (1-4)) with a compound of a formula (H-1) (hereinafter, described as Compound (H-1)) in the presence of a base.

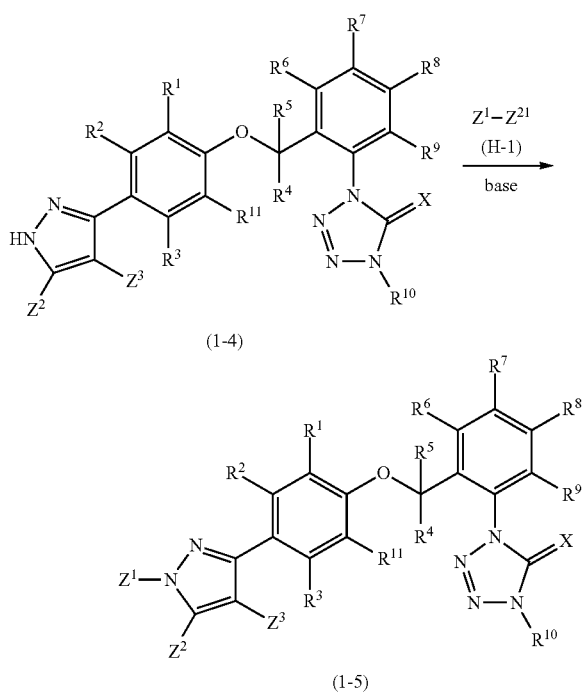

(1-4)

(1-5)

[wherein
$R^1$, $R^2$, $R^3$, $R^4$, $R^5$, $R^6$, $R^7$, $R^8$, $R^9$, $R^{10}$, $R^{11}$, $Z^1$, $Z^2$, $Z^3$, $Z^{21}$ and X are the same as defined above]

This reaction is usually carried out in a solvent.

Examples of the solvent to be used in the reaction include hydrocarbons such as heptane, hexane, cyclohexane, pentane, toluene, xylene; ethers such as diethyl ether, tetrahydrofuran, 1,4-dioxane, ethyleneglycol dimethyl ether, anisole, methyl tert-butyl ether, diisopropyl ether; halogenated hydrocarbons such as carbon tetrachloride, chloroform, dichloromethane, 1,2-dichloroethane, tetrachloroethane, chlorobenzene; acid amides such as N,N-dimethylformamide, 1,3-dimethyl-2-imidazolidinone, N-methylpyrrolidone; esters such as ethyl acetate, methyl acetate; sulfoxides such as dimethyl sulfoxide; ketones such as acetone, methyl ethyl ketone, methyl isobutyl ketone; nitriles such as acetonitrile, propionitrile; water; and mixed solvents thereof.

Compound (H-1) to be used in the reaction may be usually used as a commercially available product. Specific examples include halogenated alkyls such as chlorodifluoromethane, methyl bromide, ethyl bromide, propyl bromide, butyl bromide, pentyl bromide, hexyl bromide, methyl iodide, ethyl iodide, propyl iodide, isopropyl iodide, isobutyl iodide, isoamyl iodide, 2-propinyl iodide, 2-butynyl iodide, allyl bromide, cyclopropyl bromide, 2-propynyl bromide, 2-butynyl bromide, cyclopropylmethyl bromide, 1,1-difluoro-2-iodoethane and 1,1,1-trifluoro-2-iodoethane; alkyl or aryl sulfonates such as dimethyl sulfates, methyl p-toluenesulfonate, ethyl p-toluenesulfonate, propyl p-toluenesulfonate, methyl methanesulfonate, ethyl methanesulfonate, propyl methanesulfonate; carboxylic halides such as acetyl chloride; and sulfonic halides such as methanesulfonyl chloride, ethanesulfonyl chloride, isopropynyl sulfonyl chloride, cyclopropynyl sulfonyl chloride and N,N-dimethylsulfonyl chloride.

Examples of the base to be used in the reaction include organic bases such as triethylamine, pyridine, N-methylmorpholine, N-methylpiperidine, 4-dimethylaminopyridine, diisopropylethylamine, lutidine, collidine, diazabicycloundecene, diazabicyclononene; alkali metal carbonates such as lithium carbonate, sodium carbonate, potassium carbonate, cesium carbonate; alkali metal bicarbonates such as lithium bicarbonate, sodium bicarbonate, potassium bicarbonate, cesium bicarbonate; alkali metal hydroxides such as lithium hydroxide, sodium hydroxide, potassium hydroxide, cesium hydroxide; alkali metal halides such as sodium fluoride, potassium fluoride, cesium fluoride, cesium chloride; alkali metal hydrides such as lithium hydride, sodium hydride, potassium hydride; and alkali metal alkoxides such as sodium tert-butoxide and potassium tert-butoxide.

In the reaction, Compound (H-1) is used usually within a range of 1 to 10 molar ratio(s), and the base is used usually within a range of 1 to 10 molar ratio(s), as opposed to 1 mole of Compound (1-4).

The reaction temperature is usually within a range of −20 to 150° C. The reaction period of the reaction is usually within a range of 0.1 to 24 hours.

When the reaction is completed, the reaction mixtures are extracted with organic solvent(s), and the resulting organic layers are worked up (for example, drying and concentration) to isolate the present compound of the formula (1-5). The isolated present compound may be further purified, for example, by chromatography and recrystallization.

(Process I)

The present compound of the formula (1) wherein Q represents Q4, i.e., the compound of a formula (1-6) (hereinafter, described as Compound (1-6)), can be prepared by reacting Compound (1-4) (hereinafter, described as Compound (1-4)) with a compound of a formula (I-1) (hereinafter, described as Compound (I-1)) in the presence of a base.

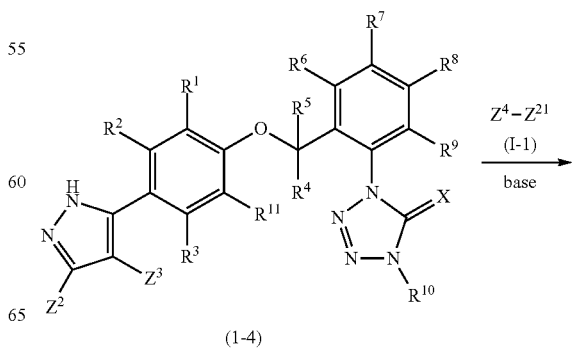

(1-4)

-continued

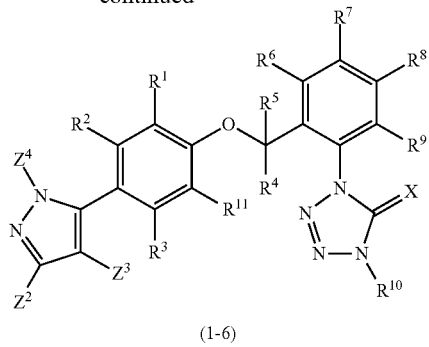

(1-6)

[wherein
$R^1$, $R^2$, $R^3$, $R^4$, $R^5$, $R^6$, $R^7$, $R^8$, $R^9$, $R^{10}$, $R^{11}$, $Z^2$, $Z^3$, $Z^4$, $Z^{21}$ and X are the same as defined above]

This reaction is usually carried out in a solvent.

Examples of the solvent to be used in the reaction include hydrocarbons such as heptane, hexane, cyclohexane, pentane, toluene, xylene; ethers such as diethyl ether, tetrahydrofuran, 1,4-dioxane, ethyleneglycol dimethyl ether, anisole, methyl tert-butyl ether, diisopropyl ether; halogenated hydrocarbons such as carbon tetrachloride, chloroform, dichloromethane, 1,2-dichloroethane, tetrachloroethane, chlorobenzene; acid amides such as N,N-dimethylformamide, 1,3-dimethyl-2-imidazolidinone, N-methylpyrrolidone; esters such as ethyl acetate, methyl acetate; sulfoxides such as dimethyl sulfoxide; ketones such as acetone, methyl ethyl ketone, methyl isobutyl ketone; nitriles such as acetonitrile, propionitrile; water; and mixed solvents thereof.

Compound (I-1) to be used in the reaction may be usually used as a commercially available product. Specific examples include halogenated alkyls such as chlorodifluoromethane, methyl bromide, ethyl bromide, propyl bromide, butyl bromide, pentyl bromide, hexyl bromide, methyl iodide, ethyl iodide, propyl iodide, isopropyl iodide, isobutyl iodide, isoamyl iodide, allyl bromide, cyclopropyl bromide and 1,1-difluoro-2-iodoethane; alkyl or aryl sulfonates such as dimethyl sulfates, methyl p-toluenesulfonate, ethyl p-toluenesulfonate, propyl p-toluenesulfonate, methyl methanesulfonate, ethyl methanesulfonate, propyl methanesulfonate; carboxylic halides such as acetyl chloride; and sulfonic halides such as methanesulfonyl chloride, ethanesulfonyl chloride, isopropynyl sulfonyl chloride, cyclopropynyl sulfonyl chloride and N,N-dimethylsulfonyl chloride.

Examples of the base to be used in the reaction include organic bases such as triethylamine, pyridine, N-methylmorpholine, N-methylpiperidine, 4-dimethylaminopyridine, diisopropylethylamine, lutidine, collidine, diazabicycloundecene, diazabicyclononene; alkali metal carbonates such as lithium carbonate, sodium carbonate, potassium carbonate, cesium carbonate; alkali metal bicarbonates such as lithium bicarbonate, sodium bicarbonate, potassium bicarbonate, cesium bicarbonate; alkali metal hydroxides such as lithium hydroxide, sodium hydroxide, potassium hydroxide, cesium hydroxide; alkali metal halides such as sodium fluoride, potassium fluoride, cesium fluoride, cesium chloride; alkali metal hydrides such as lithium hydride, sodium hydride, potassium hydride; and alkali metal alkoxides such as sodium tert-butoxide and potassium tert-butoxide.

In the reaction, Compound (I-1) is used usually within a range of 1 to 10 molar ratio(s), and the base is used usually within a range of 1 to 10 molar ratio(s), as opposed to 1 mole of Compound (1-4).

The reaction temperature is usually within a range of −20 to 150° C. The reaction period of the reaction is usually within a range of 0.1 to 24 hours.

When the reaction is completed, the reaction mixtures are extracted with organic solvent(s), and the resulting organic layers are worked up (for example, drying and concentration) to isolate the present compound of the formula (1-6). The isolated present compound may be further purified, for example, by chromatography and recrystallization.

(Process J)

The present compound of the formula (1) wherein Q represents Q1 and $Y^2$ represents $R^{100}$, i.e., the compound of a formula (1-8) (hereinafter, described as Compound (1-8)), can be prepared by reacting Compound (1-7) (hereinafter, described as Compound (1-7)) with a halogenating agent.

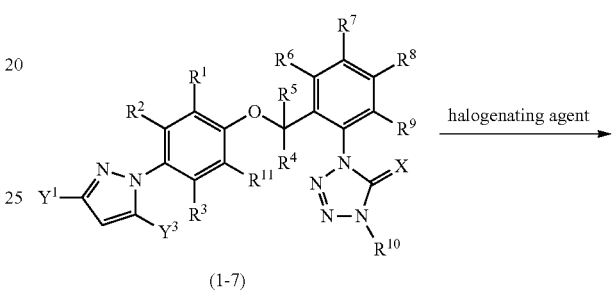

(1-7)

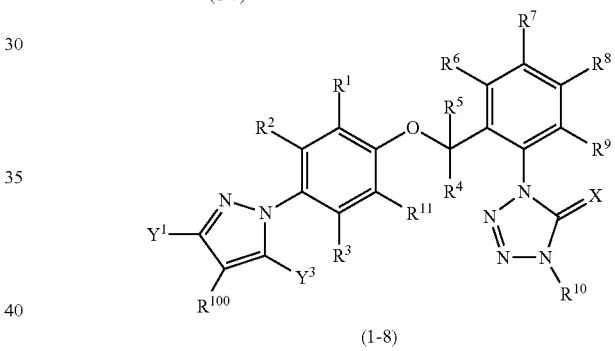

(1-8)

[wherein
$R^1$, $R^2$, $R^3$, $R^4$, $R^5$, $R^6$, $R^7$, $R^8$, $R^9$, $R^{10}$, $R^{11}$, $Y^1$, $Y^3$ and X are the same as defined above, and $R^{100}$ represents a chlorine atom, a bromine atom, or an iodine atom.]

This reaction is usually carried out in a solvent.

Examples of the solvent to be used in the reaction include hydrocarbons such as heptane, hexane, cyclohexane, pentane, toluene, xylene; ethers such as diethyl ether, tetrahydrofuran, 1,4-dioxane, ethyleneglycol dimethyl ether, anisole, methyl tert-butyl ether, diisopropyl ether; halogenated hydrocarbons such as carbon tetrachloride, chloroform, dichloromethane, 1,2-dichloroethane, tetrachloroethane and chlorobenzene; acid amides such as N,N-dimethylformamide, 1,3-dimethyl-2-imidazolidinone, N-methylpyrrolidone; esters such as ethyl acetate, methyl acetate; sulfoxides such as dimethyl sulfoxide; nitriles such as acetonitrile, propionitrile; water; and mixed solvents thereof.

Examples of the halogenating agent to be used in the reaction include N-chlorosuccinimide, N-bromosuccinimide, N-iodosuccinimide, chlorine, bromine, iodine and sulfuryl chloride.

In the reaction, the halogenating agent is used usually within a range of 1 to 10 molar ratio(s) as opposed to 1 mole of Compound (1-7).

The reaction temperature is usually within a range of −20 to 150° C. The reaction period of the reaction is usually within a range of 0.1 to 24 hours.

When the reaction is completed, the reaction mixtures are extracted with organic solvent(s), and the resulting organic layers are worked up (for example, drying and concentration) to isolate the present compound of the formula (1-8). The isolated present compound may be further purified, for example, by chromatography and recrystallization.

According to the process for preparing the above-mentioned Compound (1-8), the present compound of the formula (1) wherein Q represents Q2 and $Z^3$ represents $R^{100}$, i.e., the compound of a formula (1-10) (hereinafter, described as Compound (1-10)), can be prepared by reacting Compound (1-9) (hereinafter, described as Compound (1-9)) with a halogenating agent.

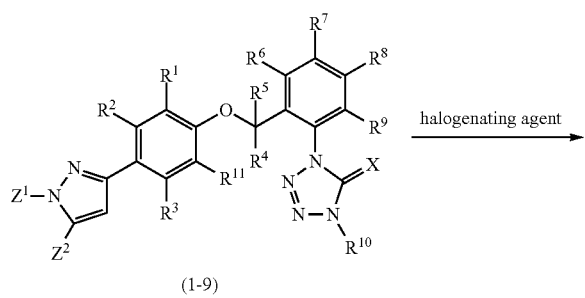

(1-9)

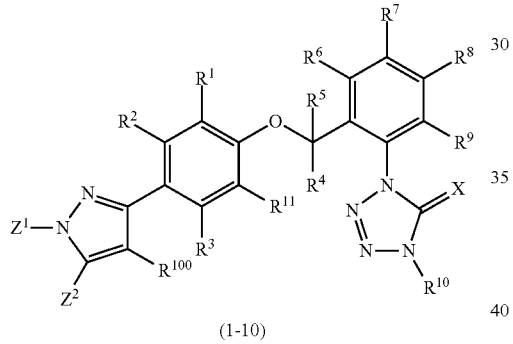

(1-10)

[wherein
$R^1$, $R^2$, $R^3$, $R^4$, $R^5$, $R^6$, $R^7$, $R^8$, $R^9$, $R^{10}$, $R^{11}$, $Z^1$, $Z^2$, $R^{100}$ and X are the same as defined above]

According to the process for preparing the above-mentioned Compound (1-8), the present compound of the formula (1) wherein Q represents Q4 and $Z^3$ represents $R^{100}$, i.e., the compound of a formula (1-12) (hereinafter, described as Compound (1-12)), can be prepared by reacting Compound (1-11) (hereinafter, described as Compound (1-11)) with a halogenating agent.

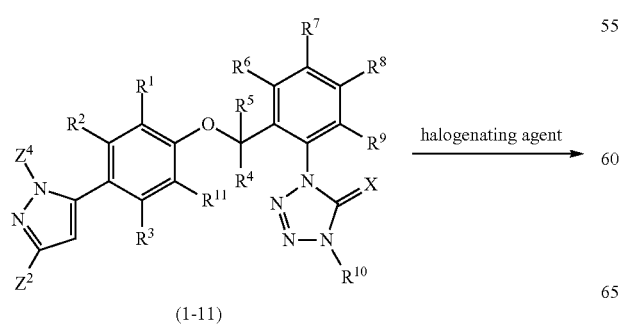

(1-11)

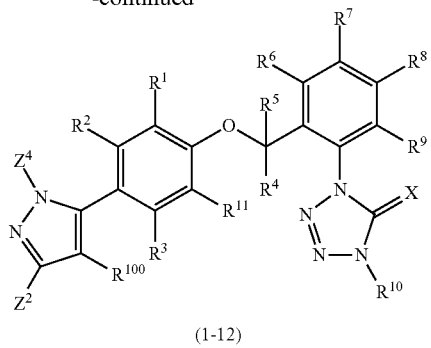

(1-12)

[wherein
$R^1$, $R^2$, $R^3$, $R^4$, $R^5$, $R^6$, $R^7$, $R^8$, $R^9$, $R^{10}$, $R^{11}$, $Z^2$, $Z^4$, $R^{100}$ and X are the same as defined above]

(Process K)

The present compound of the formula (1) wherein Q represents Q1 and $Y^2$ represents an aldehyde group, i.e., the compound of a formula (1-13) (hereinafter, described as Compound (1-13)), can be prepared by reacting Compound (1-7) (hereinafter, described as Compound (1-7)) with a formylating agent, which is prepared from N,N-dimethylformamide and phosphorus oxychloride, followed by reacting the resulting mixtures with water.

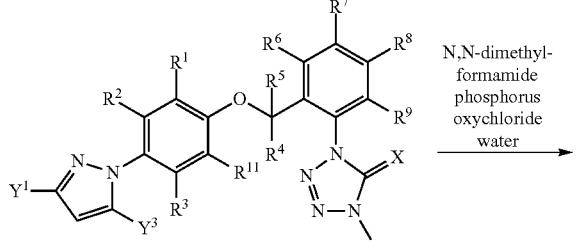

(1-7)

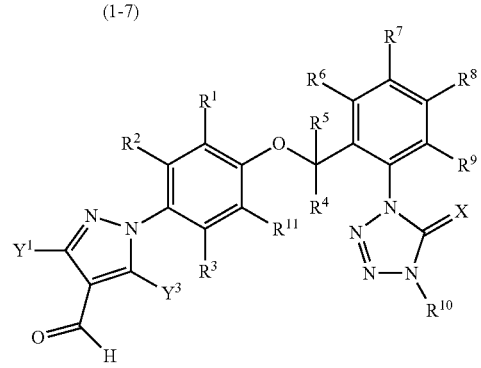

(1-13)

[wherein
$R^1$, $R^2$, $R^3$, $R^4$, $R^5$, $R^6$, $R^7$, $R^8$, $R^9$, $R^{10}$, $R^{11}$, $Y^1$, $Y^3$ and X are the same as defined above]

This reaction is usually carried out in a solvent.

Examples of the solvent to be used in the reaction include hydrocarbons such as heptane, hexane, cyclohexane, pentane; ethers such as diethyl ether, tetrahydrofuran, 1,4-dioxane, ethyleneglycol dimethyl ether, methyl tert-butyl ether, diisopropyl ether; halogenated hydrocarbons such as carbon tetrachloride, chloroform, dichloromethane, 1,2-dichloroethane, tetrachloroethane and chlorobenzene; acid amides such as N,N-dimethylformamide, 1,3-dimethyl-2-imidazolidinone, N-methylpyrrolidone; esters such as ethyl acetate, methyl acetate; sulfoxides such as dimethyl sulfoxide; ketones such as acetone, methyl ethyl ketone, methyl isobutyl ketone; nitriles such as acetonitrile, propionitrile; and mixed solvents thereof.

In the reaction, the formylating agent is used as a mixture of 1 to 10 molar ratio(s) of N,N-dimethylformamide and 1 to 10 molar ratio(s) of phosphorus oxychloride, as opposed to 1 mole of Compound (1-7), and water is used within a range of 1 to 10 molar ratio(s) as opposed to 1 mole of Compound (1-7).

The reaction temperature is usually within a range of −20 to 150° C. The reaction period of the reaction is usually within a range of 0.1 to 24 hours.

When the reaction is completed, thereto is usually added 1 mole or more of water, and the reaction mixtures are extracted with organic solvent(s), and the resulting organic layers are worked up (for example, drying and concentration) to isolate the present compound of the formula (1-13). The isolated present compound may be further purified, for example, by chromatography and recrystallization.

According to the process for preparing the above-mentioned Compound (1-13), the present compound of the formula (1) wherein Q represents Q2 and $Z^3$ represents an aldehyde group, i.e., the compound of a formula (1-14) (hereinafter, described as Compound (1-14)), can be prepared by reacting Compound (1-9) (hereinafter, described as Compound (1-9)) with formylating agent, which is prepared from N,N-dimethylformamide and phosphorus oxychloride, followed by reacting the resulting mixtures with water.

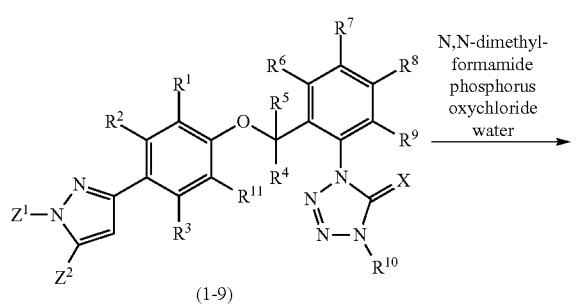

(1-9)

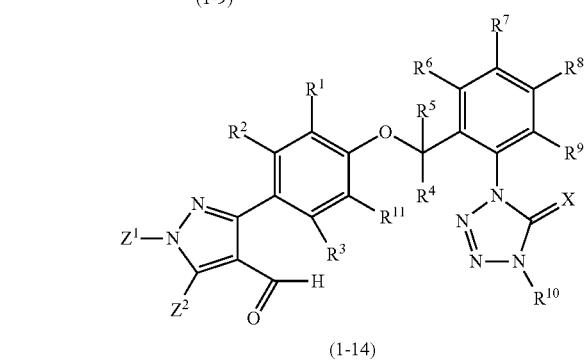

(1-14)

[wherein
$R^1$, $R^2$, $R^3$, $R^4$, $R^5$, $R^6$, $R^7$, $R^8$, $R^9$, $R^{10}$, $R^{11}$, $Z^1$, $Z^2$ and X are the same as defined above]

According to the process for preparing the above-mentioned Compound (1-13), the present compound of the formula (1) wherein Q represents Q4 and $Z^3$ represents an aldehyde group, i.e., the compound of a formula (1-15) (hereinafter, described as Compound (1-15)), can be prepared by reacting Compound (1-11) (hereinafter, described as Compound (1-11)) with formylating agent, which is prepared from N,N-dimethylformamide and phosphorus oxychloride, followed by reacting the resulting mixtures with water.

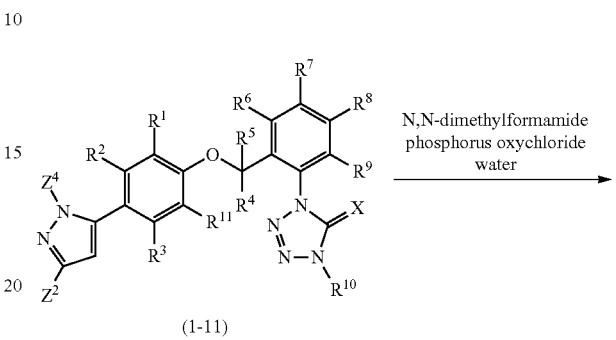

(1-11)

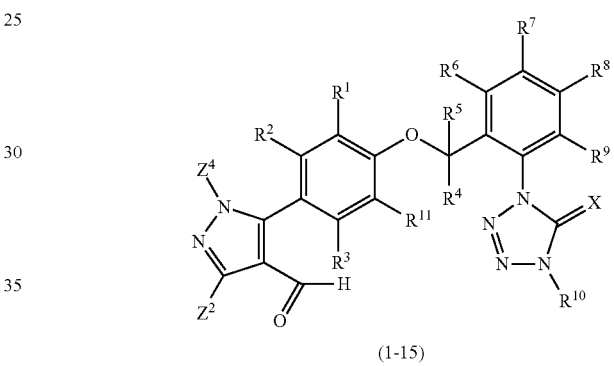

(1-15)

[wherein
$R^1$, $R^2$, $R^3$, $R^4$, $R^5$, $R^6$, $R^7$, $R^8$, $R^9$, $R^{10}$, $R^{11}$, $Z^2$, $Z^4$ and X are the same as defined above]

(Process L)

The present compound of the formula (1) wherein Q represents Q1 and $Y^2$ represents $R^{51}$, i.e., the compound of a formula (1-16) (hereinafter, described as Compound (1-16)), can be prepared by coupling Compound (1-8) (hereinafter, described as Compound (1-8)) with a compound of a formula (E-2) (hereinafter, described as Compound (E-2)) in the presence of a base and a catalyst.

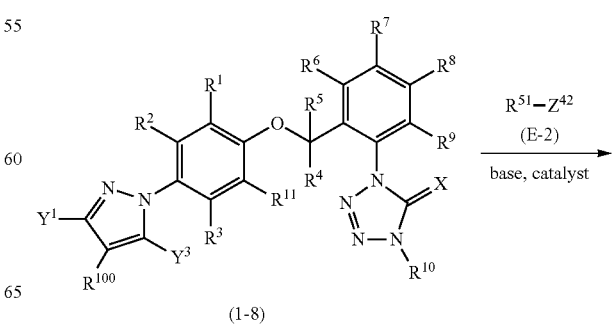

(1-8)

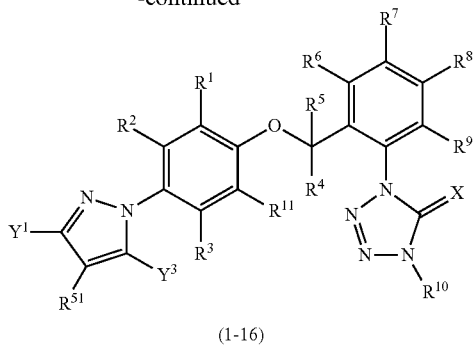

(1-16)

[wherein
$R^1, R^2, R^3, R^4, R^5, R^6, R^7, R^8, R^9, R^{10}, R^{11}, R^{51}, R^{100}, Y^1, Y^3, X$ and $Z^{42}$ are the same as defined above]

This reaction is usually carried out in a solvent.

Examples of the solvent to be used in the reaction include hydrocarbons such as heptane, hexane, cyclohexane, pentane, toluene, xylene; ethers such as diethyl ether, tetrahydrofuran, 1,4-dioxane, ethyleneglycol dimethyl ether, anisole, methyl tert-butyl ether, diisopropyl ether; halogenated hydrocarbons such as carbon tetrachloride, chloroform, dichloromethane, 1,2-dichloroethane, tetrachloroethane, chlorobenzene; acid amides such as N,N-dimethylformamide, 1,3-dimethyl-2-imidazolidinone, N-methylpyrrolidone; esters such as ethyl acetate, methyl acetate; sulfoxides such as dimethyl sulfoxide; ketones such as acetone, methyl ethyl ketone, methyl isobutyl ketone; nitriles such as acetonitrile, propionitrile; alcohols such as methanol, ethanol, propanol, butanol; water; and mixed solvents thereof.

Compound (E-2) to be used in the reaction may be usually used as a commercially available product, or may be prepared according to a method described in a review article of N. Miyaura and A. Suzuki, Chem. Rev. 1995, 95, 2457 and the others. Compound (E-2) to be used in the reaction can be also prepared, for example, by reacting an iodo compound ($R^{51}$—I) or a bromo compound ($R^{51}$—Br) with an alkyl lithium (such as butyl lithium), followed by reacting the resulting mixtures with borate esters to obtain boronate esters and further, as needed, hydrolyzing the obtained boronate esters. Further, according to a method described in a review article of Molander et al. Acc. Chem. Res. 2007, 40, 275 and the others, the above-mentioned boronate ester can be fluorinated with potassium bifluoride and the like to obtain the trifluoroborate salts ($BF_3^-K^+$).

Examples of the catalyst to be used in the reaction include palladium(II) acetate, dichlorobis(triphenylphosphine)palladium, tetrakistriphenylphosphinepalladium(0), palladium (II) acetate/tricyclohexylphosphine, bis(diphenylphoshine ferrocenyl)palladium(II) dichloride, 1,3-bis(2,6-diisopropylphenyl)imidazole-2-ylidene (1,4-naphthoquinone)palladium dimer, aryl(chloro) (1,3-dimethyl-1,3-dihydro-2H-imidazole-2-ylidene)palladium or palladium(II) acetate/dicyclohexyl(2',4',6'-triisopropylbiphenyl-2-yl)phosphine, and tris(dibenzylideneacetone)dipalladium and the others.

Examples of the base to be used in the reaction include organic bases such as triethylamine, pyridine, N-methylmorpholine, N-methylpiperidine, 4-dimethylaminopyridine, diisopropylethylamine, lutidine, collidine, diazabicycloundecene, diazabicyclononene; alkali metal carbonates such as lithium carbonate, sodium carbonate, potassium carbonate, cesium carbonate; alkali metal bicarbonates such as lithium bicarbonate, sodium bicarbonate, potassium bicarbonate, cesium bicarbonate; alkali metal hydroxides such as lithium hydroxide, sodium hydroxide, potassium hydroxide, cesium hydroxide; alkali metal halides such as sodium fluoride, potassium fluoride, cesium fluoride, cesium chloride; alkali metal hydrides such as lithium hydride, sodium hydride, potassium hydride; alkali metal phosphates such as tripotassium phosphate; and alkali metal alkoxides such as sodium methoxide, sodium ethoxide, sodium tert-butoxide, potassium tert-butoxide.

In the reaction, Compound (E-2) is used usually within a range of 1 to 10 molar ratio(s), and the base is used usually within a range of 1 to 10 molar ratio(s), and the catalyst is used usually within a range of 0.0001 to 1 molar ratio(s), as opposed to 1 mole of Compound (1-8).

The reaction temperature is usually within a range of 0 to 150° C. The reaction period of the reaction is usually within a range of 0.1 to 24 hours.

When the reaction is completed, the reaction mixtures are extracted with organic solvent(s), and the resulting organic layers are worked up (for example, drying and concentration) to isolate the present compound of the formula (1-16). The isolated present compound may be further purified, for example, by chromatography and recrystallization.

According to the process for preparing the above-mentioned Compound (1-16), the present compound of the formula (1) wherein Q represents Q2 and $Z^3$ represents $R^{51}$, i.e., the compound of a formula (1-17) (hereinafter, described as Compound (1-17)), can be prepared by reacting Compound (1-10) (hereinafter, described as Compound (1-10)) with a compound of a formula (E-2) (hereinafter, described as Compound (E-2)) in the presence of a base and a catalyst.

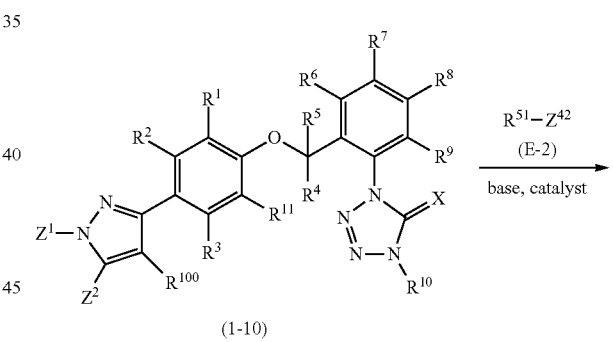

(1-10)

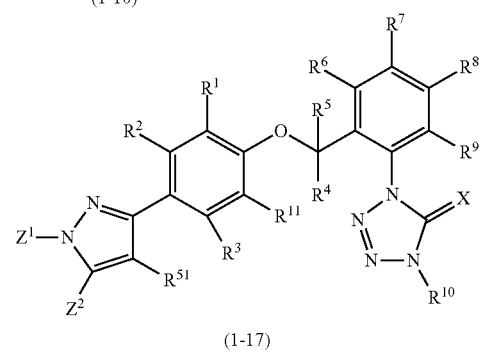

(1-17)

[wherein
$R^1, R^2, R^3, R^4, R^5, R^6, R^7, R^8, R^9, R^{10}, R^{11}, R^{51}, R^{100}, X, Z^1, Z^2$ and $Z^{42}$ are the same as defined above]

According to the process for preparing the above-mentioned Compound (1-16), the present compound of the formula (1) wherein Q represents Q4 and $Z^3$ represents $R^{51}$, i.e., the compound of a formula (1-18) (hereinafter, described as Compound (1-18)), can be prepared by reacting Compound (1-12) (hereinafter, described as Compound (1-12)) with a compound of a formula (E-2) (hereinafter, described as Compound (E-2)) in the presence of a base and a catalyst.

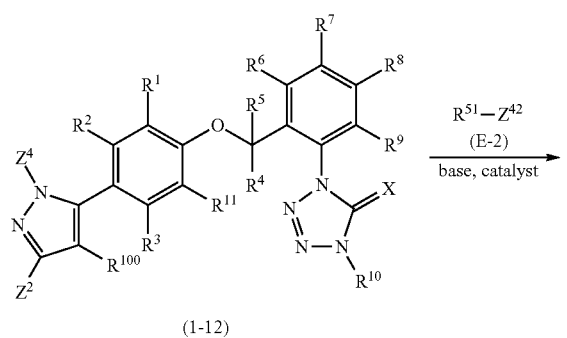

(1-12)

$R^{51}-Z^{42}$
(E-2)
base, catalyst

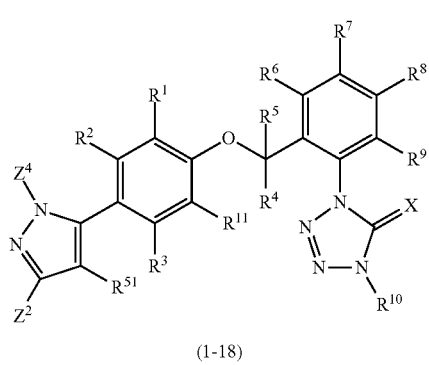

(1-18)

[wherein
$R^1, R^2, R^3, R^4, R^5, R^6, R^7, R^8, R^9, R^{10}, R^{11}, R^{51}, R^{100}, X, Z^2, Z^4$ and $Z^{42}$ are the same as defined above]

(Process M)

The present compound of the formula (1) wherein Q represents Q1 and $Y^2$ represents a difluoromethyl group, i.e., the compound of a formula (1-19) (hereinafter, described as Compound (1-19)), can be prepared by reacting Compound (1-13) with a fluorinating agent.

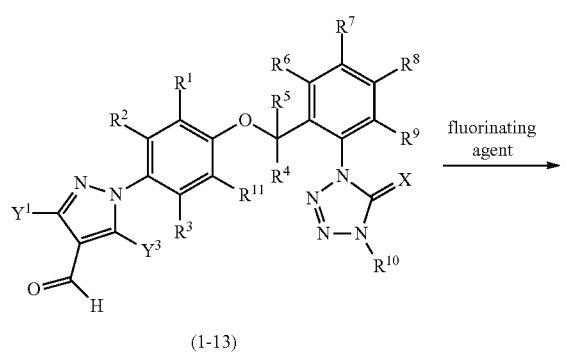

(1-13)

fluorinating agent

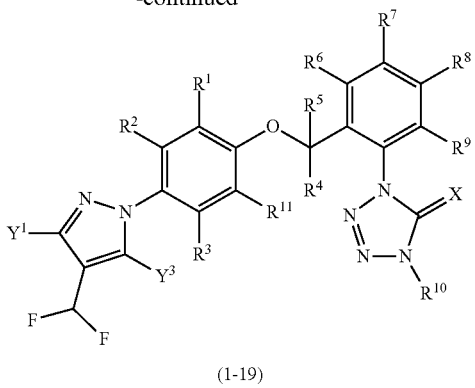

(1-19)

[wherein
$R^1, R^2, R^3, R^4, R^5, R^6, R^7, R^8, R^9, R^{10}, R^{11}, Y^1, Y^3$ and X are the same as defined above]

This reaction is usually carried out in a solvent.

Examples of the solvent to be used in the reaction include hydrocarbons such as heptane, hexane, cyclohexane, pentane, toluene, xylene; ethers such as diethyl ether, tetrahydrofuran, 1,4-dioxane, ethyleneglycol dimethyl ether, anisole, methyl tert-butyl ether, diisopropyl ether; halogenated hydrocarbons such as carbon tetrachloride, chloroform, dichloromethane, 1,2-dichloroethane, tetrachloroethane, chlorobenzene; acid amides such as N,N-dimethylformamide, 1,3-dimethyl-2-imidazolidinone, N-methylpyrrolidone; esters such as ethyl acetate, methyl acetate; sulfoxides such as dimethyl sulfoxide; ketones such as acetone, methyl ethyl ketone, methyl isobutyl ketone; nitriles such as acetonitrile, propionitrile; and mixed solvents thereof.

A fluorinating agent to be used in the reaction may be usually used as a commercially available product, and includes, for example, (diethylamino)-sulfur trifluoride, bis(methoxyethyl)-aminosulfur trifluoride, 4-tert-butyl-2,6-dimethylphenylsulfur trifluoride, (diethylamino)-difluorosulfonium tetrahydroborate, and difluoro(morphrino)sulfonium tetrahydroborate. In the reaction, a reaction accelerator may be also added, and includes, for example, (1.8-diazabicyclo[5.4.0]undec-7-ene and triethylamine trihydroborate.

In the reaction, the fluorinating agent is used usually within a range of 1 to 20 molar ratios, and the reaction accelerator is used usually within a range of 0 to 10 molar ratios, as opposed to 1 mole of Compound (1-13).

The reaction temperature is usually within a range of 0 to 150° C. The reaction period of the reaction is usually within a range of 0.1 to 24 hours.

When the reaction is completed, the reaction mixtures are extracted with organic solvent(s), and the resulting organic layers are worked up (for example, drying and concentration) to isolate the present compound of the formula (1-19). The isolated present compound may be further purified, for example, by chromatography and recrystallization.

According to the process for preparing the above-mentioned Compound (1-19), the present compound of the formula (1) wherein Q represents Q2 and $Z^3$ represents a difluoromethyl group, i.e., the compound of a formula (1-20) (hereinafter, described as Compound (1-20)), can be prepared by reacting Compound (1-14) (hereinafter, described as Compound (1-14)) with a fluorinating agent.

(1-14) → fluorinating agent → (1-20)

[wherein
R¹, R², R³, R⁴, R⁵, R⁶, R⁷, R⁸, R⁹, R¹⁰, R¹¹, Z¹, Z² and X are the same as defined above]

According to the process for preparing the above-mentioned Compound (1-19), the present compound of the formula (1) wherein Q represents Q4 and Z³ represents a difluoromethyl group, i.e., the compound of a formula (1-21) (hereinafter, described as Compound (1-21)), can be prepared by reacting Compound (1-15) (hereinafter, described as Compound (1-15)) with a fluorinating agent.

(1-15) → fluorinating agent → (1-21)

[wherein
R¹, R², R³, R⁴, R⁵, R⁶, R⁷, R⁸, R⁹, R¹⁰, R¹¹, Z², Z⁴ and X are the same as defined above]

(Process N)

The present compound of the formula (2) (hereinafter, described as Compound (2)) can be prepared by reacting a compound of a formula (A-1-2) (hereinafter, described as Compound (A-1-2)) with a compound of a formula (XV1-2) (hereinafter, described as Compound (XV1-2)) in the presence of a base.

(A-1-2) + (XV1-2) → base → (2)

[wherein
R¹, R³, R⁶, R¹² and Z¹¹ are the same as defined above]

This reaction is usually carried out in a solvent.

Examples of the solvent to be used in the reaction include hydrocarbons such as heptane, hexane, cyclohexane, pentane, toluene, xylene; ethers such as diethyl ether, tetrahydrofuran, 1,4-dioxane, ethyleneglycol dimethyl ether, anisole, methyl tert-butyl ether, diisopropyl ether; halogenated hydrocarbons such as carbon tetrachloride, chloroform, dichloromethane, 1,2-dichloroethane, tetrachloroethane, chlorobenzene; acid amides such as N,N-dimethylformamide, 1,3-dimethyl-2-imidazolidinone, N-methylpyrrolidone; esters such as ethyl acetate, methyl acetate; sulfoxides such as dimethyl sulfoxide; ketones such as acetone, methyl ethyl ketone, methyl isobutyl ketone; nitriles such as acetonitrile, propionitrile; water; and mixed solvents thereof.

Examples of the base to be used in the reaction include organic bases such as triethylamine, pyridine, N-methylmorpholine, N-methylpiperidine, 4-dimethylaminopyridine, diisopropylethylamine, lutidine, collidine, diazabicycloundecene, diazabicyclononene; alkali metal carbonates such as lithium carbonate, sodium carbonate, potassium carbonate, cesium carbonate; alkali metal bicarbonates such as lithium bicarbonate, sodium bicarbonate, potassium bicarbonate, cesium bicarbonate; alkali metal hydroxides such as lithium hydroxide, sodium hydroxide, potassium hydroxide, cesium hydroxide; alkali metal halides such as sodium fluoride, potassium fluoride, cesium fluoride; alkali metal hydrides such as lithium hydride, sodium hydride, potassium hydride; and alkali metal alkoxides such as sodium tert-butoxide, potassium tert-butoxide.

In the reaction, Compound (XV1-2) is used usually within a range of 1 to 10 molar ratio(s), and the base is used usually within a range of 1 to 10 molar ratio(s), as opposed to 1 mole of Compound (A-1-2).

The reaction temperature is usually within a range of −20 to 150° C. The reaction period of the reaction is usually within a range of 0.1 to 24 hours.

If necessary, sodium iodide, tetrabutylammonium iodide and the others may be added to the reaction and these compounds are used usually within a range of 0.001 to 1.2 molar ratios as opposed to 1 mole of Compound (A-1-2).

When the reaction is completed, the reaction mixtures are extracted with organic solvent(s), and the resulting organic layers are worked up (for example, drying and concentration) to isolate the present compound of the formula (2). Alternatively, the reaction mixtures are worked up (for example, drying and concentration) to isolate the present compound of the formula (2). These isolated present compound may be further purified, for example, by chromatography and recrystallization.

(Process O)

According to the process for preparing the above-mentioned Compound (1-13), the present compound of the formula (1) wherein Q represents Q2, $Z^2$ represents a chlorine atom, and $Z^3$ represents an aldehyde group, i.e., the compound of a formula (1-14-1) (hereinafter, described as Compound (1-14-1)), can be prepared by reacting Compound (1-9) wherein $Z^2$ represents a hydroxy group, i.e., the compound of a formula (1-9-1) (hereinafter, described as Compound (1-9-1)) with a formylating agent, which is prepared from N,N-dimethylformamide and phosphorus oxychloride, followed by reacting the resulting mixtures with water.

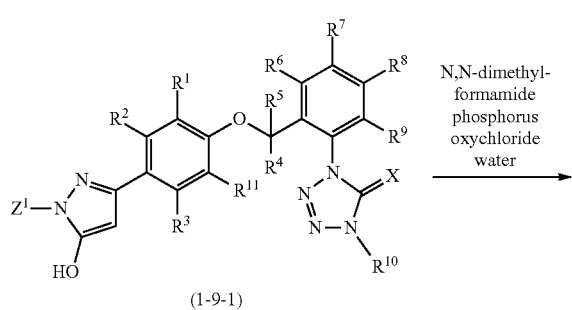

(1-14-1)

[wherein
$R^1$, $R^2$, $R^3$, $R^4$, $R^5$, $R^6$, $R^7$, $R^8$, $R^9$, $R^{10}$, $R^{11}$, $Z^1$, $Z^2$ and X are the same as defined above]

(Process P)

The present compound of the formula (1) wherein Q represents Q2, $Z^2$ represents $Z^{2H}$ and $Z^3$ represents an aldehyde group, i.e., a compound of a formula (1-14-2) (hereinafter, described as Compound (1-14-2)) can be prepared by reacting a compound of a formula (1-14-1) with a compound of a formula (O-1) (hereinafter, described as Compound (O-1)) in the presence of a base.

(1-14-1)

(1-14-2)

[wherein
$R^1$, $R^2$, $R^3$, $R^4$, $R^5$, $R^6$, $R^7$, $R^8$, $R^9$, $R^{10}$, $R^{11}$, $R^{51}$, $Z^1$ and X are the same as defined above, $R^{52}$ represents an C1-C6 alkyl group, a C1-C6 haloalkyl group and $Z^{2H}$ represents $R^{51}$—O—, $R^{51}$—S or $(R^{51})_2$—N]

This reaction is usually carried out in a solvent.

Examples of the solvent to be used in the reaction include hydrocarbons such as heptane, hexane, cyclohexane, pentane, toluene, xylene; ethers such as diethyl ether, tetrahydrofuran, 1,4-dioxane, ethyleneglycol dimethyl ether, anisole, methyl tert-butyl ether, diisopropyl ether; halogenated hydrocarbons such as carbon tetrachloride, chloroform, dichloromethane, 1,2-dichloroethane, tetrachloroethane, chlorobenzene; acid amides such as N,N-dimethylformamide, 1,3-dimethyl-2-imidazolidinone, N-methylpyrrolidone; esters such as ethyl acetate, methyl acetate; sulfoxides such as dimethyl sulfoxide; ketones such as acetone, methyl ethyl ketone, methyl isobutyl ketone; nitriles such as acetonitrile, propionitrile; water; and mixed solvents thereof.

Examples of the base to be used in the reaction include organic bases such as triethylamine, pyridine, N-methylmorpholine, N-methylpiperidine, 4-dimethylaminopyridine, diisopropylethylamine, lutidine, collidine, diazabicycloundecene, diazabicyclononene; alkali metal carbonates such as lithium carbonate, sodium carbonate, potassium carbonate, cesium carbonate; alkali metal bicarbonates such as lithium bicarbonate, sodium bicarbonate, potassium bicarbonate, cesium bicarbonate; alkali metal hydroxides such as lithium hydroxide, sodium hydroxide, potassium hydroxide, cesium hydroxide; alkali metal halides such as sodium fluoride, potassium fluoride, cesium fluoride; alkali metal hydrides such as lithium hydride, sodium hydride, potassium hydride; and alkali metal alkoxides such as sodium tert-butoxide, potassium tert-butoxide.

In the reaction, Compound (O-1) is used usually within a range of 1 to 10 molar ratio(s), and the base is used usually within a range of 1 to 10 molar ratio(s), as opposed to 1 mole of Compound (1-14-1).

The reaction temperature is usually within a range of −20 to 150° C. The reaction period of the reaction is usually within a range of 0.1 to 24 hours.

In the reaction, metal salts of Compound (O-1) can be also used, which is previously prepared by reacting Compound (O-1) with a base. Examples of the salts to be used include sodium methoxide, sodium ethoxide, sodium propoxide, sodium isopropoxide, potassium methoxide, potassium ethoxide, sodium thiomethoxide and sodium thioethoxide.

In the reaction, the metal salts of Compound (O-1) is used usually within a range of 1 to 10 molar ratio(s) as opposed to 1 mole of Compound (1-14-1).

When the reaction is completed, the reaction mixtures are extracted with organic solvent(s), and the resulting organic layers are worked up (for example, drying and concentration) to isolate the present compound of the formula (1-14-2). Alternatively, the reaction mixtures are worked up (for example, drying and concentration) to isolate the present compound of the formula (1-14-2). These isolated present compound may be further purified, for example, by chromatography and recrystallization.

(Process Q)

The present compound of the formula (1) wherein Q represents Q2, $Z^2$ represents $Z^{2H}$ and $Z^3$ represents a methyl group, i.e., a compound of a formula (1-14-3) (hereinafter, described as Compound (1-14-3)) can be prepared by reacting a compound of a formula (1-14-2) with a reducing agent in the presence of an acid.

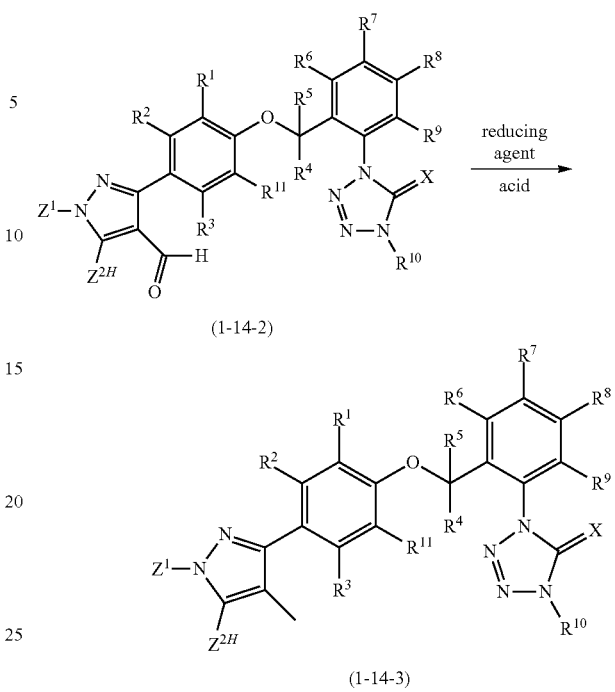

[wherein
$R^1$, $R^2$, $R^3$, $R^4$, $R^5$, $R^6$, $R^7$, $R^8$, $R^9$, $R^{10}$, $R^{11}$, $Z^1$, $Z^{2H}$ and X are the same as defined above]

This reaction is usually carried out in a solvent.

Examples of the solvent to be used in the reaction include hydrocarbons such as heptane, hexane, cyclohexane, pentane, toluene, xylene; ethers such as diethyl ether, tetrahydrofuran, 1,4-dioxane, ethyleneglycol dimethyl ether, anisole, methyl tert-butyl ether, diisopropyl ether; halogenated hydrocarbons such as carbon tetrachloride, chloroform, dichloromethane, 1,2-dichloroethane, tetrachloroethane, chlorobenzene; acid amides such as N,N-dimethylformamide, 1,3-dimethyl-2-imidazolidinone, N-methylpyrrolidone; esters such as ethyl acetate, methyl acetate; sulfoxides such as dimethyl sulfoxide; ketones such as acetone, methyl ethyl ketone, methyl isobutyl ketone; nitriles such as acetonitrile, propionitrile; water; and mixed solvents thereof.

Examples of the reducing agent to be used in the reaction include metal boronate compounds such as lithium borohydride, sodium borohydride, potassium borohydride; and trialkylsilane compounds such as triethylsilane.

Examples of the acids to be used in the reaction include boron trifluoride and trifluoroacetic acid.

In the reaction, the reducing agent is used usually within a range of 1 to 10 molar ratio(s), and the acid is used usually within a range of 1 to 10 molar ratio(s) or a large excess molar ratio(s), as opposed to 1 mole of Compound (1-14-2).

The reaction temperature is usually within a range of −20 to 150° C. The reaction period of the reaction is usually within a range of 0.1 to 24 hours.

When the reaction is completed, the reaction mixtures are extracted with organic solvent(s), and the resulting organic layers are worked up (for example, drying and concentration) to isolate the present compound of the formula (1-14-3). Alternatively, the reaction mixtures are worked up (for example, drying and concentration) to isolate the present compound of the formula (1-14-3). These isolated present compound may be further purified, for example, by chromatography and recrystallization.

(Process R)

The present compound of the formula (1) wherein Q represents Q2, $Z^1$ represents a hydrogen atom and $Z^2$ represents an C2-C6 alkoxycarbonyl group, i.e., a compound of a formula (1-4-R) (hereinafter, described as Compound (1-4-R)), can be prepared by reacting a compound of a formula (G-1-1) (hereinafter, described as Compound (G-1-1)) with hydrazines.

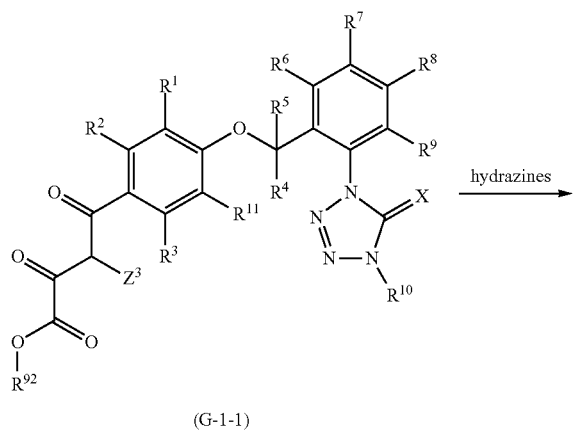

(G-1-1)

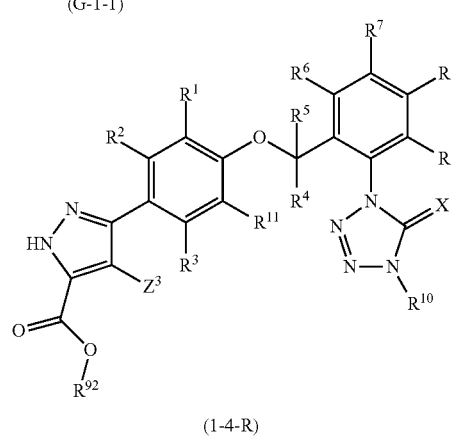

(1-4-R)

[wherein
$R^1$, $R^2$, $R^3$, $R^4$, $R^5$, $R^6$, $R^7$, $R^8$, $R^9$, $R^{10}$, $R^{11}$, X and $Z^3$ are the same as defined above, and $R^{92}$ represents an C1-C5 alkyl group]

This reaction is usually carried out in a solvent.

Examples of the solvent to be used in the reaction include ethers such as diethyl ether, tetrahydrofuran, 1,4-dioxane, ethyleneglycol dimethyl ether, anisole, methyl tert-butyl ether, diisopropyl ether; hydrocarbons such as heptane, hexane, cyclohexane, pentane, toluene, xylene; halogenated hydrocarbons such as carbon tetrachloride, chloroform, dichloromethane, 1,2-dichloroethane, tetrachloroethane, chlorobenzene; nitriles such as acetonitrile, propionitrile; acid amides such as N,N-dimethylformamide, 1,3-dimethyl-2-imidazolidinone, N-methylpyrrolidone; sulfoxides such as dimethyl sulfoxide; alcohols such as methanol, ethanol, propanol, butanol; water; and mixed solvents thereof.

Examples of the hydrazines to be used in the reaction include hydrazine monohydrate, hydrazine hydrochloride, hydrazine sulfate, anhydrous hydrazine and the others.

In the reaction, hydrazines is used usually within a range of 1 to 100 molar ratio(s) as opposed to 1 mole of Compound (G-1-1).

The reaction temperature is usually within a range of −20 to 150° C. The reaction period of the reaction is usually within a range of 0.1 to 24 hours.

When the reaction is completed, the reaction mixtures are extracted with organic solvent(s), and the resulting organic layers are worked up (for example, drying and concentration) to isolate the present compound of the formula (1-4-R). The isolated present compound may be further purified, for example, by chromatography and recrystallization.

(Process S)

The present compound of the formula (1) wherein Q represents Q2 and $Z^2$ represents an C2-C6 alkoxycarbonyl group, i.e., a compound of a formula (1-5-S) (hereinafter, described as Compound (1-5-S)) can be prepared by reacting Compound (1-4-R) with Compound (H-1) optionally in the presence of a base.

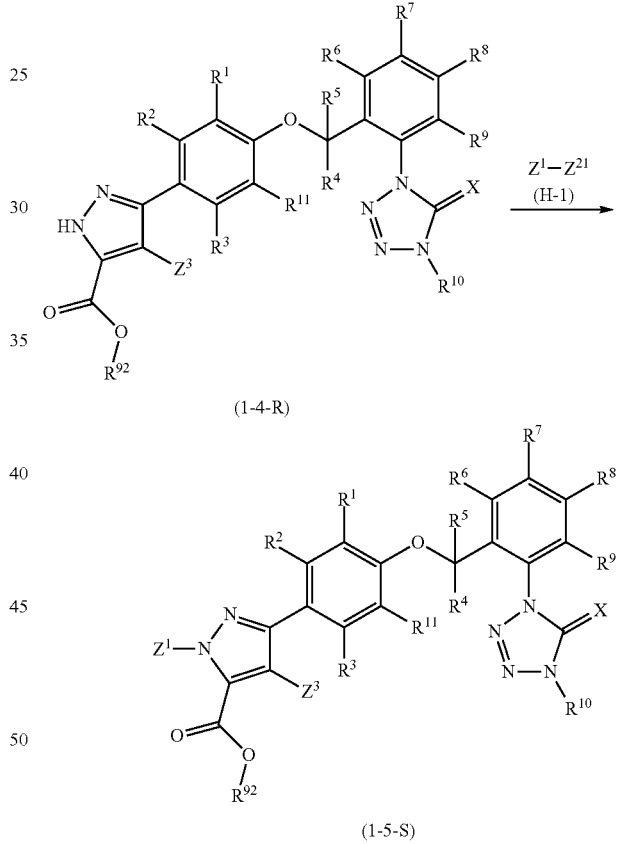

[wherein
$R^1$, $R^2$, $R^3$, $R^4$, $R^5$, $R^6$, $R^7$, $R^8$, $R^9$, $R^{10}$, $R^{11}$, $R^{92}$, X, $Z^1$, $Z^3$ and $Z^{21}$ are the same as defined above]

This reaction is usually carried out in a solvent.

Examples of the solvent to be used in the reaction include hydrocarbons such as heptane, hexane, cyclohexane, pentane, toluene, xylene; ethers such as diethyl ether, tetrahydrofuran, 1,4-dioxane, ethyleneglycol dimethyl ether, anisole, methyl tert-butyl ether, diisopropyl ether; halogenated hydrocarbons such as carbon tetrachloride, chloroform, dichloromethane, 1,2-dichloroethane, tetrachloroethane, chlorobenzene; acid amides such as N,N-dimethylformamide, 1,3-dimethyl-2-imidazolidinone, N-methylpyrrolidone; esters such as ethyl acetate, methyl acetate; sulfoxides such as dimethyl sulfoxide; ketones such as acetone, methyl ethyl ketone, methyl isobutyl ketone; nitriles such as acetonitrile, propionitrile; water; and mixed solvents thereof.

Compound (H-1) to be used in the reaction can be usually used as a commercially available product. Specific examples include alkyl halides such as chlorodifluoromethane, methyl bromide, ethyl bromide, propyl bromide, butyl bromide, propyl bromide, hexyl bromide, methyl iodide, ethyl iodide, propyl iodide, isopropyl iodide, isobutyl iodide, isoamyl iodide, 2-propinyl iodide, 2-butynyl iodide, allyl bromide, cyclopropyl bromide, 2-propynyl bromide, 2-butynyl bromide, cyclopropylmethyl bromide, 1,1-difluoro-2-iodoethane and 1,1,1-trifluoro-2-iodoethane; alkyl or aryl sulfonates such as dimethyl sulfates, methyl p-toluenesulfonate, ethyl p-toluenesulfonate, propyl p-toluenesulfonate, methyl methanesulfonate, ethyl methanesulfonate, propyl methanesulfonate; carboxylic halides such as acetyl chloride; and sulfonic halides such as methanesulfonyl chloride, ethanesulfonyl chloride, isopropynyl sulfonyl chloride, cyclopropynyl sulfonyl chloride and N,N-dimethylsulfonyl chloride.

In the reaction, a base may be used, and includes, for example, organic bases such as triethylamine, pyridine, N-methylmorpholine, N-methylpiperidine, 4-dimethylaminopyridine, diisopropylethylamine, lutidine, collidine, diazabicycloundecene, diazabicyclononene; alkali metal carbonates such as lithium carbonate, sodium carbonate, potassium carbonate, cesium carbonate; alkali metal bicarbonates such as lithium bicarbonate, sodium bicarbonate, potassium bicarbonate, cesium bicarbonate; alkali metal hydroxides such as lithium hydroxide, sodium hydroxide, potassium hydroxide, cesium hydroxide; alkali metal halides such as sodium fluoride, potassium fluoride, cesium fluoride; alkali metal hydrides such as lithium hydride, sodium hydride, potassium hydride; and alkali metal alkoxides such as sodium tert-butoxide, potassium tert-butoxide.

In the reaction, Compound (H-1) is used usually within a range of 1 to 10 molar ratio(s), and the base is used usually within a range of 1 to 10 molar ratios, as opposed to 1 mole of Compound (1-4-R).

The reaction temperature is usually within a range of −20 to 150° C. The reaction period of the reaction is usually within a range of 0.1 to 24 hours.

When the reaction is completed, the reaction mixtures are extracted with organic solvent(s), and the resulting organic layers are worked up (for example, drying and concentration) to isolate the present compound of the formula (1-5-S). The isolated present compound may be further purified, for example, by chromatography and recrystallization.

(Process T)

The present compound of the formula (1) wherein Q represents Q4 and $Z^2$ represents an C2-C6 alkoxycarbonyl group, i.e., a compound of a formula (1-6-T) (hereinafter, described as Compound (1-6-T)) can be prepared by reacting a compound of a formula (1-4-T) (hereinafter, described as Compound (1-4-T)) with Compound (I-1) optionally in the presence of a base.

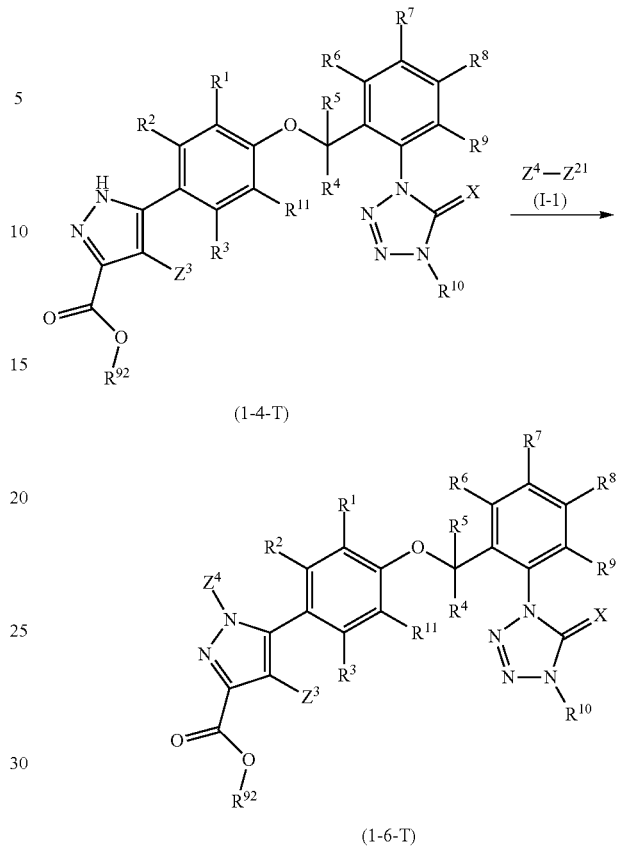

[wherein
$R^1$, $R^2$, $R^3$, $R^4$, $R^5$, $R^6$, $R^7$, $R^8$, $R^9$, $R^{10}$, $R^{11}$, $R^{92}$, X, $Z^3$, $Z^4$ and $Z^{21}$ are the same as defined above]

This reaction is usually carried out in a solvent.

Examples of the solvent to be used in the reaction include hydrocarbons such as heptane, hexane, cyclohexane, pentane, toluene, xylene; ethers such as diethyl ether, tetrahydrofuran, 1,4-dioxane, ethyleneglycol dimethyl ether, anisole, methyl tert-butyl ether, diisopropyl ether; halogenated hydrocarbons such as carbon tetrachloride, chloroform, dichloromethane, 1,2-dichloroethane, tetrachloroethane, chlorobenzene; acid amides such as N,N-dimethylformamide, 1,3-dimethyl-2-imidazolidinone, N-methylpyrrolidone; esters such as ethyl acetate, methyl acetate; sulfoxides such as dimethyl sulfoxide; ketones such as acetone, methyl ethyl ketone, methyl isobutyl ketone; nitriles such as acetonitrile, propionitrile; water; and mixed solvents thereof.

Compound (I-1) to be used in the reaction can be usually used as a commercially available product. Specific examples include alkyl halides such as chlorodifluoromethane, methyl bromide, ethyl bromide, propyl bromide, butyl bromide, propyl bromide, hexyl bromide, methyl iodide, ethyl iodide, propyl iodide, isopropyl iodide, isobutyl iodide, isoamyl iodide, allyl bromide, cyclopropyl bromide and 1,1-difluoro-2-iodoethane; alkyl or aryl sulfonates such as dimethyl sulfates, methyl p-toluenesulfonate, ethyl p-toluenesulfonate, propyl p-toluenesulfonate, methyl methanesulfonate, ethyl methanesulfonate, propyl methanesulfonate; carboxylic halides such as acetyl chloride; and sulfonic halides such as methanesulfonyl chloride, ethanesulfonyl chloride, isopropynyl sulfonyl chloride, cyclopropyl sulfonyl chloride and N,N-dimethylsulfonyl chloride.

In the reaction, a base may be used, and includes, for example, organic bases such as triethylamine, pyridine, N-methylmorpholine, N-methylpiperidine, 4-dimethylaminopyridine, diisopropylethylamine, lutidine, collidine, diazabicycloundecene, diazabicyclononene; alkali metal carbonates such as lithium carbonate, sodium carbonate, potassium carbonate, cesium carbonate; alkali metal bicarbonates such as lithium bicarbonate, sodium bicarbonate, potassium bicarbonate, cesium bicarbonate; alkali metal hydroxides such as lithium hydroxide, sodium hydroxide, potassium hydroxide, cesium hydroxide; alkali metal halides such as sodium fluoride, potassium fluoride, cesium fluoride; alkali metal hydrides such as lithium hydride, sodium hydride, potassium hydride; and alkali metal alkoxides such as sodium tert-butoxide, potassium tert-butoxide.

In the reaction, Compound (I-1) is used usually within a range of 1 to 10 molar ratio(s), and the base is used usually within a range of 1 to 10 molar ratios, as opposed to 1 mole of Compound (1-4-T).

The reaction temperature is usually within a range of −20 to 150° C. The reaction period of the reaction is usually within a range of 0.1 to 24 hours.

When the reaction is completed, the reaction mixtures are extracted with organic solvent(s), and the resulting organic layers are worked up (for example, drying and concentration) to isolate the present compound of the formula (1-6-T). The isolated present compound may be further purified, for example, by chromatography and recrystallization.

(Process U)

The present compound of the formula (1) wherein Q represents Q2 and $Z^2$ represents an aminocarbonyl group, i.e., a compound of a formula (1-5-U) (hereinafter, described as Compound (1-5-U)) can be prepared by reacting Compound (1-5-S) with an amidating agent.

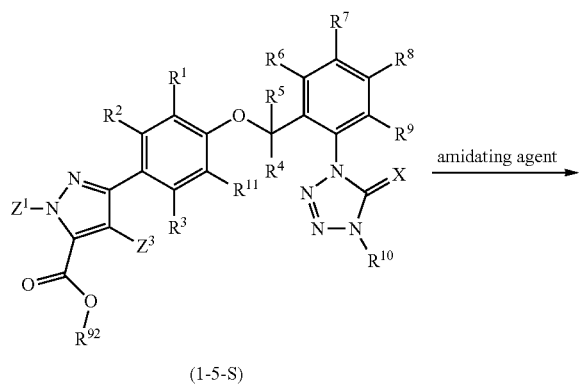

(1-5-S)

[wherein
$R^1$, $R^2$, $R^3$, $R^4$, $R^5$, $R^6$, $R^7$, $R^8$, $R^9$, $R^{10}$, $R^{11}$, $R^{92}$, X, $Z^1$ and $Z^3$ are the same as defined above]

This reaction is usually carried out in a solvent.

Examples of the solvent to be used in the reaction include ethers such as diethyl ether, tetrahydrofuran, 1,4-dioxane, ethyleneglycol dimethyl ether, anisole, methyl tert-butyl ether, diisopropyl ether; hydrocarbons such as heptane, hexane, cyclohexane, pentane, toluene, xylene; halogenated hydrocarbons such as carbon tetrachloride, chloroform, dichloromethane, 1,2-dichloroethane, tetrachloroethane, chlorobenzene; nitriles such as acetonitrile, propionitrile; acid amides such as N,N-dimethylformamide, 1,3-dimethyl-2-imidazolidinone, N-methylpyrrolidone; sulfoxides such as dimethyl sulfoxide; alcohols such as methanol, ethanol, propanol, butanol; water; and mixed solvents thereof.

Examples of the amidating agent to be used in the reaction include aqueous ammonia, ammonia hydrochloride salt, ammonia hydrosulfate salt and ammonia gas. Also the amidating agent can be used as solvent.

In the reaction, the amidating agent is used usually within a range of 1 to a large excess molar ratio(s) as opposed to 1 mole of Compound (1-5-S).

The reaction temperature is usually within a range of −20 to 150° C. The reaction period of the reaction is usually within a range of 0.1 to 72 hours.

When the reaction is completed, the reaction mixtures are extracted with organic solvent(s), and the resulting organic layers are worked up (for example, drying and concentration) to isolate the present compound of the formula (1-5-U). Also, when any precipitates are formed, the precipitates are filtered off to isolate the present compound of the formula (1-5-U). These isolated present compounds may be further purified, for example, by chromatography and recrystallization.

(Process V)

The present compound of the formula (1) wherein Q represents Q2 and $Z^2$ represents a cyano group, i.e., a compound of a formula (1-5-V) (hereinafter, described as Compound (1-5-V)) can be prepared by reacting Compound (1-5-U) with a cyanating agent.

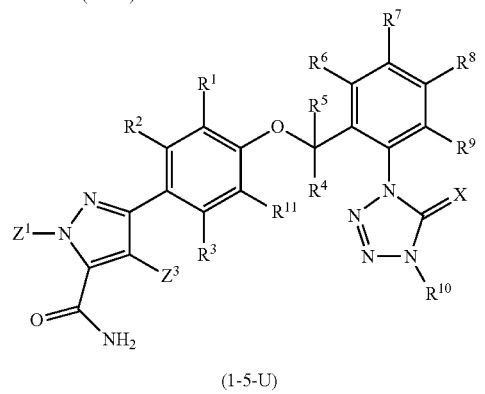

(1-5-U)

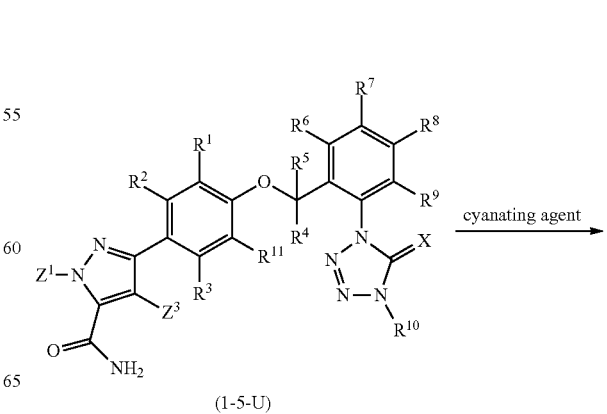

(1-5-U)

127
-continued

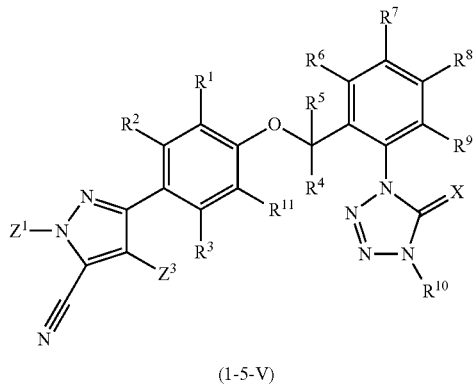

(1-5-V)

[wherein $R^1$, $R^2$, $R^3$, $R^4$, $R^5$, $R^6$, $R^7$, $R^8$, $R^9$, $R^{10}$, $R^{11}$, X, $Z^1$ and $Z^3$ are the same as defined above]

This reaction is usually carried out in a solvent.

Examples of the solvent to be used in the reaction include ethers such as diethyl ether, tetrahydrofuran, 1,4-dioxane, ethyleneglycol dimethyl ether, anisole, methyl tert-butyl ether, diisopropyl ether; hydrocarbons such as heptane, hexane, cyclohexane, pentane, toluene, xylene; halogenated hydrocarbons such as carbon tetrachloride, chloroform, dichloromethane, 1,2-dichloroethane, tetrachloroethane, chlorobenzene; nitriles such as acetonitrile, propionitrile; acid amides such as N,N-dimethylformamide, 1,3-dimethyl-2-imidazolidinone, N-methylpyrrolidone; sulfoxides such as dimethyl sulfoxide; alcohols such as methanol, ethanol, propanol, butanol; and mixed solvents thereof.

Examples of the cyanating agent to be used in the reaction include phosphorous oxychloride, phosphorous pentachloride and phosphorous oxybromide.

In the reaction, a base may be used, which include, for example, organic bases such as triethylamine, pyridine, N-methylmorpholine, N-methylpiperidine, 4-dimethylaminopyridine, diisopropylethylamine, lutidine, collidine, diazabicycloundecene and diazabicyclononene. The base may be used also as a solvent.

In the reaction, the cyanating agent is used usually within a range of 1 to 20 molar ratio(s), and the base is used usually within a range of 1 to a large amount of molar ratio(s), as opposed to 1 mole of Compound (1-5-U).

The reaction temperature is usually within a range of −20 to 150° C. The reaction period of the reaction is usually within a range of 0.1 to 72 hours.

When the reaction is completed, the reaction mixtures are extracted with organic solvent(s), and the resulting organic layers are worked up (for example, drying and concentration) to isolate the present compound of the formula (1-5-V). Also, when any precipitates are formed, the precipitates are filtered off to isolate the present compound of the formula (1-5-V). These isolated present compounds may be further purified, for example, by chromatography and recrystallization.

128

(Process W)

Compound (1-5-U) can be prepared by reacting a compound of a formula (1-5-W) (hereinafter, described as Compound (1-5-W)) with an amidating agent.

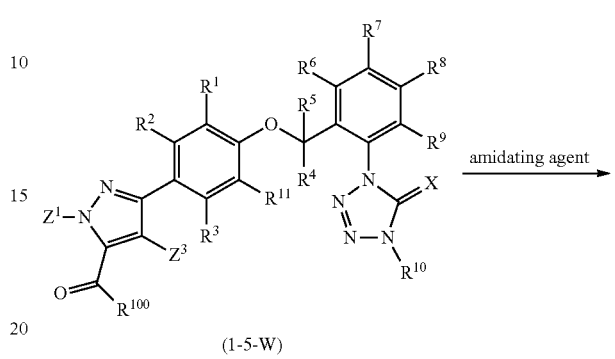

(1-5-W)

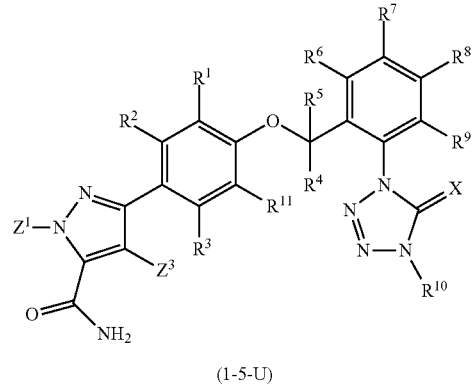

(1-5-U)

[wherein $R^1$, $R^2$, $R^3$, $R^4$, $R^5$, $R^6$, $R^7$, $R^8$, $R^9$, $R^{10}$, $R^{11}$, $R^{100}$, X, $Z^1$ and $Z^3$ are the same as defined above]

The reaction can be carried out according to Process U.

Next, methods for preparing intermediate compounds are described below in detail.

(Reference Process A)

A compound of a formula (XA3) (hereinafter, described as Compound (XA3)) can be prepared by reacting a compound of a formula (XA1) (hereinafter, described as Compound (XA1)) or a compound of a formula (XA2) (hereinafter, described as Compound (XA2)) with an azidation agent.

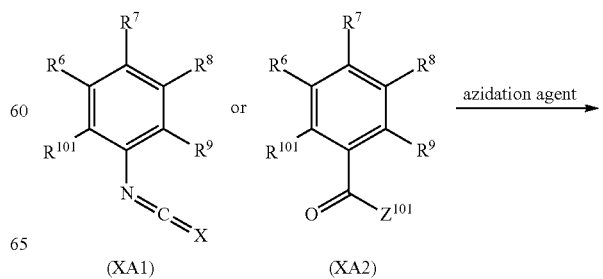

(XA1)　　(XA2)

-continued

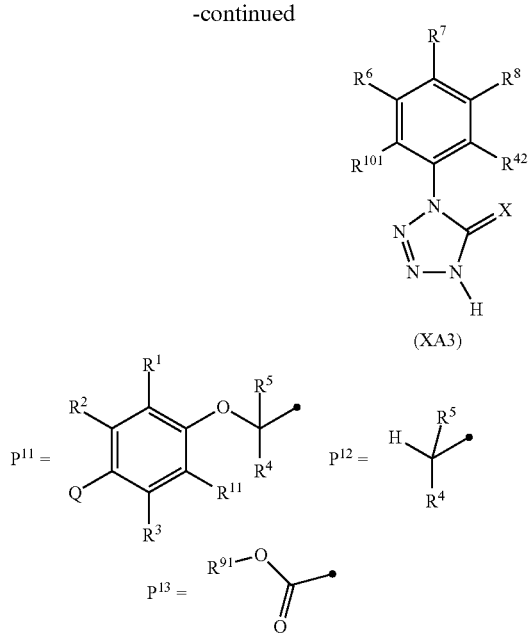

[wherein
R$^1$, R$^2$, R$^3$, R$^4$, R$^5$, R$^6$, R$^7$, R$^8$, R$^9$, R$^{11}$, X and Q are the same as defined above; R$^{101}$ represents P$^{11}$, P$^{12}$ or P$^{13}$; R$^{91}$ represents an C1-C12 alkyl group; Z$^{101}$ represents a chlorine atom or a bromine atom; and a dot represents a binding site]

This reaction is usually carried out in a solvent.

Examples of the solvent to be used in the reaction include hydrocarbons such as heptane, hexane, cyclohexane, pentane, toluene, xylene; ethers such as diethyl ether, tetrahydrofuran, 1,4-dioxane, ethyleneglycol dimethyl ether, anisole, methyl tert-butyl ether, diisopropyl ether; halogenated hydrocarbons such as carbon tetrachloride, chloroform, dichloromethane, 1,2-dichloroethane, tetrachloroethane, chlorobenzene; acid amides such as N,N-dimethylformamide, 1,3-dimethyl-2-imidazolidinone, N-methylpyrrolidone; esters such as ethyl acetate, methyl acetate; sulfoxides such as dimethyl sulfoxide; ketones such as acetone, methyl ethyl ketone, methyl isobutyl ketone; nitriles such as acetonitrile, propionitrile; and mixed solvents thereof.

Examples of the azidation agent to be used in the reaction include inorganic azides such as sodium azide, barium azide and lithium azide; and organic azides such as trimethylsilyl azide and diphenylphosphoryl azide.

In the reaction, the azidation agent is used usually within a range of 1 to 10 molar ratio(s) as opposed to 1 mole of Compound (XA1) or Compound (XA2).

The reaction temperature is usually within a range of −20 to 150° C. The reaction period of the reaction is usually within a range of 0.1 to 24 hours.

If necessary, a Lewis acid such as aluminium chloride and zinc chloride may be added to the reaction, and these compounds are used usually within a range of 0.05 to 5 molar ratio(s) as opposed to 1 mole of Compound (XA1) or Compound (XA2).

When the reaction is completed, the reaction mixtures are extracted with organic solvent(s), and the resulting organic layers are worked up (for example, drying and concentration) to isolate Compound (XA3). The isolated Compound (XA3) may be further purified, for example, by chromatography and recrystallization.

(Reference Process B)

Compound (XA1) can be prepared by reacting a compound of a formula (XB1) (hereinafter, described as Compound (XB1)) with an isocyanation agent.

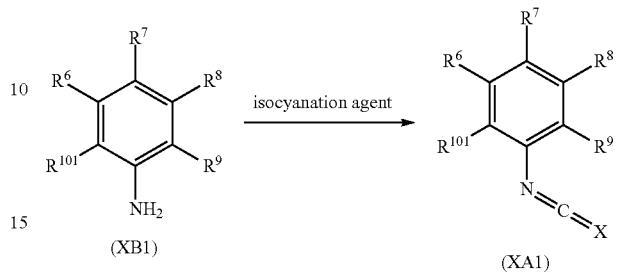

[wherein
R$^6$, R$^7$, R$^8$, R$^9$, R$^{101}$ and X are the same as defined above]

This reaction is usually carried out in a solvent.

Examples of the solvent to be used in the reaction include hydrocarbons such as heptane, hexane, cyclohexane, pentane, toluene, xylene; ethers such as diethyl ether, tetrahydrofuran, 1,4-dioxane, ethyleneglycol dimethyl ether, anisole, methyl tert-butyl ether, diisopropyl ether; halogenated hydrocarbons such as carbon tetrachloride, chloroform, dichloromethane, 1,2-dichloroethane, tetrachloroethane, chlorobenzene; esters such as ethyl acetate, methyl acetate; ketones such as acetone, methyl ethyl ketone, methyl isobutyl ketone; nitriles such as acetonitrile, propionitrile; and mixed solvents thereof.

Examples of the isocyanation agent to be used in the reaction include phosgene, diphosgene, triphosgene, thiophosgenes, N,N-carbodiimidazole and N,N-thio carbodiimidazole.

In the reaction, the isocyanation agent is used usually within a range of 1 to 10 molar ratio(s) as opposed to 1 mole of Compound (XB1).

The reaction temperature is usually within a range of −20 to 150° C. The reaction period of the reaction is usually within a range of 0.1 to 24 hours.

If necessary, organic bases such as triethylamine, pyridine, N-methylmorpholine, N-methylpiperidine, 4-dimethylaminopyridine, diisopropylethylamine, lutidine, collidine, diazabicycloundecene and diazabicyclononene, alkali metal carbonates such as lithium carbonate, sodium carbonate, potassium carbonate and cesium carbonate, alkali metal bicarbonates such as lithium bicarbonate, sodium bicarbonate, potassium bicarbonate and cesium bicarbonates and the others may be added to the reaction, and these compounds are used usually within a range of 0.05 to 5 molar ratios as opposed to 1 mole of Compound (XB1).

When the reaction is completed, the reaction mixtures are extracted with organic solvent(s), and the resulting organic layers are worked up (for example, drying and concentration) to isolate Compound (XA1). The isolated Compound (XA1) may be further purified, for example, by distillation, chromatography and recrystallization.

(Reference Process C)

Compound (XA2) can be prepared by reacting a compound of a formula (XC1) (hereinafter, described as Compound (XC1)) with a halogenating agent.

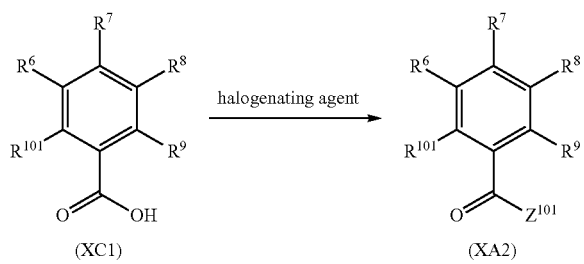

[wherein
$R^6$, $R^7$, $R^8$, $R^9$, $R^{101}$ and $Z^{101}$ are the same as defined above]

This reaction is usually carried out in a solvent.

Examples of the solvent to be used in the reaction include hydrocarbons such as heptane, hexane, cyclohexane, pentane, toluene, xylene; ethers such as diethyl ether, tetrahydrofuran, 1,4-dioxane, ethyleneglycol dimethyl ether, anisole, methyl tert-butyl ether, diisopropyl ether; halogenated hydrocarbons such as carbon tetrachloride, chloroform, dichloromethane, 1,2-dichloroethane, tetrachloroethane and chlorobenzene; esters such as ethyl acetate, methyl acetate; ketones such as acetone, methyl ethyl ketone, methyl isobutyl ketone; nitriles such as acetonitrile, propionitrile; and mixed solvents thereof.

Examples of the halogenating agent to be used in the reaction include phosphorous oxychloride, phosphorous trichloride, phosphorous pentachloride, thionyl chloride, phosphorous oxybromide, phosphorous tribromide, phosphorous pentabromide, phosphorus triiodide, oxalyl dichloride, oxalyl dibromide, triphosgene, diphosgene, phosgene and sulfuryl chloride.

In the reaction, the halogenating agent is used usually within a range of 1 to 10 molar ratio(s) as opposed to 1 mole of Compound (XC1).

The reaction temperature is usually within a range of −20 to 150° C. The reaction period of the reaction is usually within a range of 0.1 to 24 hours.

A catalyst may be added to the reaction, and includes, for example, N,N-dimethylformide. The catalyst is used usually within a range of 0.001 to 1 molar ratio(s) as opposed to 1 mole of Compound (XC1).

If necessary, organic bases such as triethylamine, pyridine, N-methylmorpholine, N-methylpiperidine, 4-dimethylaminopyridine, diisopropylethylamine, lutidine, collidine, diazabicycloundecene and diazabicyclononene, alkali metal carbonates such as lithium carbonate, sodium carbonate, potassium carbonate and cesium carbonate, alkali metal bicarbonates such as lithium bicarbonate, sodium bicarbonate, potassium bicarbonate and cesium bicarbonates and the others may be added to the reaction, and these compounds are used usually within a range of 0.05 to 5 molar ratios as opposed to 1 mole of Compound (XC1).

When the reaction is completed, the reaction mixtures are extracted with organic solvent(s), and the resulting organic layers are worked up (for example, drying and concentration) to isolate Compound (XA2). The isolated Compound (XA2) may be further purified, for example, by distillation, chromatography and recrystallization.

(Reference Process D)

Compound (XA1) can be prepared by reacting Compound (XB1) with a carbamating agent to form a compound of a formula (XD1) (hereinafter, described as Compound (XD1)), followed by reacting the resulting Compound (XD1) with an isocyanation agent.

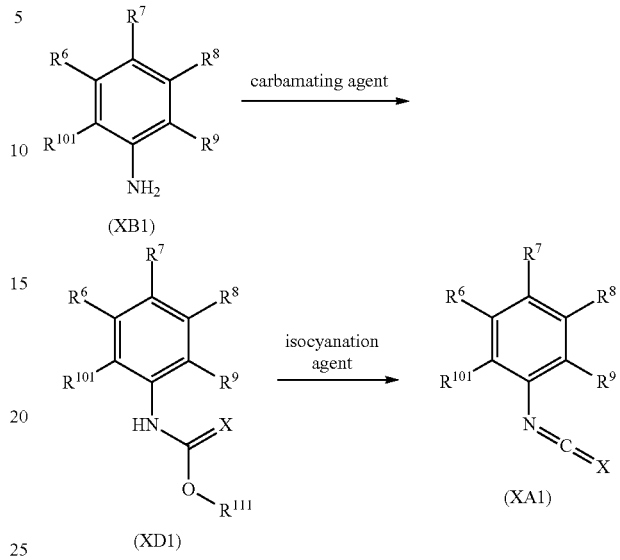

[wherein
$R^6$, $R^7$, $R^8$, $R^9$ and $R^{101}$ are the same as described above; $R^{111}$ represents an C1-C12 alkyl group or a phenyl group]

Hereinafter, the process for preparing Compound (XD1) from Compound (XB1) is explained.

This reaction is usually carried out in a solvent.

Examples of the solvent that can be used in the reaction include hydrocarbons such as heptane, hexane, cyclohexane, pentane, toluene, xylene; ethers such as diethyl ether, tetrahydrofuran, 1,4-dioxane, ethyleneglycol dimethyl ether, anisole, methyl tert-butyl ether, diisopropyl ether; halogenated hydrocarbons such as carbon tetrachloride, chloroform, dichloromethane, 1,2-dichloroethane, tetrachloroethane, chlorobenzene; acid amides such as N,N-dimethylformamide, 1,3-dimethyl-2-imidazolidinone, N-methylpyrrolidone; esters such as ethyl acetate, methyl acetate; sulfoxides such as dimethyl sulfoxide; ketones such as acetone, methyl ethyl ketone, methyl isobutyl ketone; nitriles such as acetonitrile, propionitrile; water; and mixed solvents thereof.

Examples of the carbamating agent to be used in the reaction include phenyl chlorocarbonate, methyl chlorocarbonate, ethyl chlorocarbonate, propyl chlorocarbonate, isopropyl chlorocarbonate, butyl chlorocarbonate, tert-butyl chlorocarbonate, di-tert-butyl dicarbonate, dimethyl dicarbonate, diethyl dicarbonate, phenyl chlorothioformate, methyl chlorothioformate and ethyl chlorothioformate.

In the reaction, the carbamating agent is used usually within a range of 1 to 10 molar ratio(s) as opposed to 1 mole of Compound (XB1).

The reaction temperature is usually within a range of −20 to 150° C. The reaction period of the reaction is usually within a range of 0.1 to 24 hours.

If necessary, organic bases such as triethylamine, pyridine, N-methylmorpholine, N-methylpiperidine, 4-dimethylaminopyridine, diisopropylethylamine, lutidine, collidine, diazabicycloundecene and diazabicyclononene, alkali-metal carbonates such as lithium carbonate, sodium carbonate, potassium carbonate and cesium carbonate, alkali-metal bicarbonates such as lithium bicarbonate, sodium bicarbonate, potassium bicarbonate and cesium bicarbonate may be added to the reaction, and these compounds are used usually within a range of 0.05 to 5 molar ratios as opposed to 1 mole of Compound (XB1).

When the reaction is completed, the reaction mixtures are extracted with organic solvent(s), and the resulting organic layers are worked up (for example, drying and concentration) to isolate Compound (XD1). The isolated Compound (XD1) may be further purified, for example, by distillation, chromatography and recrystallization.

Hereinafter, the process for preparing Compound (XA1) from Compound (XD1) is explained.

This reaction is usually carried out in a solvent.

Examples of the solvent that can be used in the reaction include ethers such as tetrahydrofuran, dioxane, ethyleneglycol dimethyl ether, methyl tert-butyl ether; hydrocarbons such as toluene, xylene; halogenated hydrocarbons such as carbon tetrachloride, chloroform, 1,2-dichloroethane, chlorobenzene; nitriles such as acetonitrile; acid amides such as N,N-dimethylformamide, 1,3-dimethyl-2-imidazolidinone, N-methylpyrrolidone; sulfoxides such as dimethyl sulfoxide; ketones such as acetone, methyl ethyl ketone, methyl isobutyl ketone; and mixed solvents thereof.

Examples of the isocyanation agent to be used in the reaction include phosphorous pentachloride, phosphorous oxychloride, diphosphorus pentoxide, trichlorosilane, dichlorosilane, monochlorosilane, boron trichloride, 2-chloro-1,3,2-benzodioxaborole, diiodosilane, methyl trichlorosilane, dimethyl dichlorosilane and chlorotrimethylsilane.

In the reaction, the isocyanation agent is used usually within a range of 1 to 10 molar ratio(s) as opposed to 1 mole of Compound (XD1).

The reaction temperature is usually within a range of −20 to 250° C. The reaction period of the reaction is usually within a range of 0.1 to 24 hours.

If necessary, organic bases such as triethylamine, pyridine, N-methylmorpholine, N-methylpiperidine, 4-dimethylaminopyridine, diisopropylethylamine, lutidine, collidine, diazabicycloundecene and diazabicyclononene, alkali-metal carbonates such as lithium carbonate, sodium carbonate, potassium carbonate and cesium carbonate, alkali-metal bicarbonates such as lithium bicarbonate, sodium bicarbonate, potassium bicarbonate and cesium bicarbonate may be added to the reaction, and these bases are used usually within a range of 0.05 to 5 molar ratios as opposed to 1 mole of Compound (XD1).

When the reaction is completed, the reaction mixtures are extracted with organic solvent(s), and the resulting organic layers are worked up (for example, drying and concentration) to isolate Compound (XA1). The isolated Compound (XA1) may be further purified, for example, by distillation, chromatography and recrystallization.

(Reference Process E)

A compound of a formula (XE2) (hereinafter, described as Compound (XE2)) can be prepared by reacting a compound of a formula (XE1) (hereinafter, described as Compound (XE1)) with hydrogen gas in the presence of a catalyst.

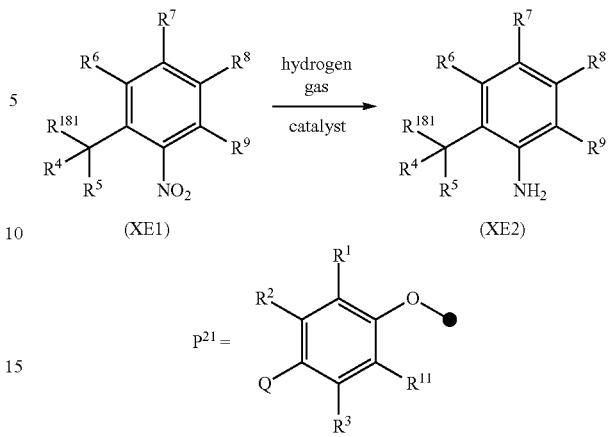

[wherein
$R^1$, $R^2$, $R^3$, $R^4$, $R^5$, $R^6$, $R^7$, $R^8$, $R^9$, $R^{11}$ and Q are the same as described above; $R^{181}$ represents a hydrogen atom or $P^{21}$; and a dot represents a binding site]

This reaction is usually carried out in a solvent.

Examples of the solvent that can be used in the reaction include alcohols such as methanol, ethanol, propanol, butanol: esters such as ethyl acetate, butyl acetate; halogenated hydrocarbons such as carbon tetrachloride, chloroform, dichloromethane, 1,2-dichloroethane, tetrachloroethane, chlorobenzene; ethers such as diethyl ether, tetrahydrofuran, 1,4-dioxane, ethyleneglycol dimethyl ether, anisole, methyl tert-butyl ether, diisopropyl ether; hydrocarbons such as heptane, hexane, cyclohexane, pentane, toluene, xylene; acetic acid; water; and mixed solvents thereof.

Examples of the catalyst to be used in the reaction includes palladium on carbon (Pd/C), platinum on carbon (Pt/C), osmium on carbon (Os/C), ruthenium on carbon (Ru/C), rhodium on carbon (Rh/C) and Raney nickel.

In the reaction, the catalyst is used usually within in a range of 0.1 to 1 molar ratio(s), and hydrogen gas is used usually in an excess amount, as opposed to 1 mole of Compound (XE1).

The reaction temperature is usually within a range of −20 to 150° C. The reaction period of the reaction is usually within a range of 0.1 to 24 hours.

When the reaction is completed, the catalyst is filtered off, and the resulting organic layers are worked up (for example, concentration) to isolate Compound (XE2). The isolated Compound (XE2) may be further purified, for example, by distillation, chromatography and recrystallization.

(Reference Process F)

Compound (XE2) can be prepared by reacting the above-mentioned Compound (XE1) with a reducing agent in the presence of an acid.

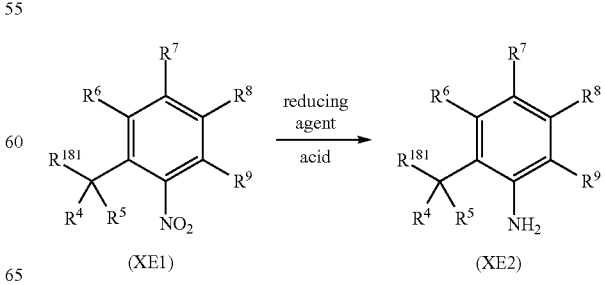

[wherein $R^4$, $R^5$, $R^6$, $R^7$, $R^8$, $R^9$ and $R^{181}$ are the same as described above]

This reaction is usually carried out in a solvent.

Examples of the solvent to be used in the reaction include aliphatic carboxylic acids such as acetic acid; alcohols such as methanol, ethanol; water; and mixed solvents thereof.

Examples of the reducing agent to be used in the reaction include iron; tin compounds such as tin; and zinc compounds such as zinc.

Examples of the acid to be used in the reaction include hydrochloric acid, sulfuric acid, acetic acid, aqueous ammonium chloride solution.

In the reaction, the reducing agent is used usually within a range of 1 to 30 molar ratio(s), and the acid is used usually within a range of 1 to 100 molar ratio(s), as opposed to 1 mole of Compound (XE1).

The reaction temperature is usually within a range of −20 to 150° C. The reaction period of the reaction is usually within a range of 0.1 to 24 hours.

When the reaction is completed, the reaction mixtures are extracted with organic solvent(s), and the resulting organic layers are worked up (for example, drying and concentration) to isolate Compound (XE2). The isolated Compound (XE2) may be further purified, for example, by distillation, chromatography and recrystallization.

(Reference Process G)

A compound of a formula (XG2) (hereinafter, described as Compound (XG2)) can be prepared by reacting a compound of a formula (XG1) (hereinafter, described as Compound (XG1)) and Compound (B-2) in the presence of a base.

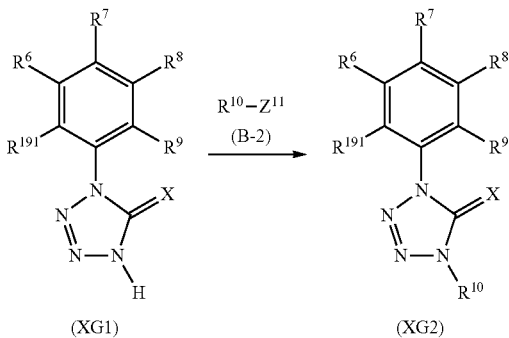

[wherein $R^6$, $R^7$, $R^8$, $R^9$, $R^{10}$, X and $Z^{11}$ are the same as described above; and $R^{191}$ represents $P^{12}$ or $P^{13}$]

The reaction can be carried out according to the above-mentioned process B.

(Reference Process H)

A compound of a formula (XH2) (hereinafter, described as Compound (XH2)) can be prepared by reacting a compound of a formula (XH1) (hereinafter, described as Compound (XH1)) with a halogenating agent in the presence of a radical initiator.

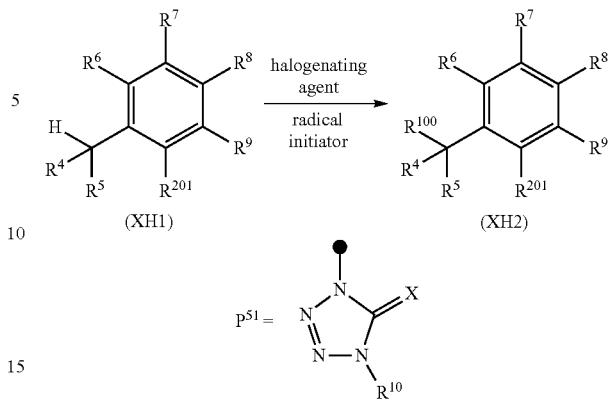

[wherein $R^4$, $R^5$, $R^6$, $R^7$, $R^8$, $R^9$, $R^{10}$, $R^{100}$ and X are the same as described above; and $R^{201}$ represents $P^{51}$ or a nitro group]

This reaction is usually carried out in a solvent.

Examples of the solvent that can be used in the reaction include hydrocarbons such as heptane, hexane, cyclohexane, pentane, toluene, xylene; ethers such as diethyl ether, tetrahydrofuran, 1,4-dioxane, ethyleneglycol dimethyl ether, anisole, methyl tert-butyl ether, diisopropyl ether; halogenated hydrocarbons such as carbon tetrachloride, chloroform, dichloromethane, 1,2-dichloroethane, tetrachloroethane, fluorobenzene, difluorobenzene, trifluorobenzene, chlorobenzene, dichlorobenzene, trichlorobenzene, α,α,α-trifluorotoluene, α,α,α-trichlorotoluene; esters such as ethyl acetate, methyl acetate; ketones such as acetone, methyl ethyl ketone, methyl isobutyl ketone; nitriles such as acetonitrile, propionitrile; and mixed solvents thereof.

Examples of the halogenating agent to be used in the reaction include a chlorinating agent, a brominating agent or iodinating agent such as chlorine, bromine, iodine, sulfuryl chloride, N-chlorosuccinimide, N-bromosuccinimide, 1,3-dibromo-5,5-dimethylhydantoin, iodosuccinimide, tert-butyl hypochlorite, N-chloroglutarimide, N-bromoglutarimide, N-chloro-N-cyclohexyl-benzenesulfonamide and N-bromophthalimide.

Examples of the radical initiator to be used in the reaction include benzoyl peroxide, azobisisobutyronitrile (AIBN), 1,1-azobis(cyan cyclohexane), diacylperoxide, dialkyl peroxydicarbonate, tert-alkyl peroxyester, monoperoxy carbonate, di(tert-alkylperoxy)ketal, ketone peroxide and triethylborane.

In the reaction, the halogenating agent is used usually within a range of 1 to 10 molar ratio(s), and the radical initiator is used usually within a range of 0.01 to 5 molar ratios, as opposed to 1 mole of Compound (XH1).

The reaction temperature is usually within a range of −20 to 150° C. The reaction period of the reaction is usually within a range of 0.1 to 24 hours.

When the reaction is completed, the reaction mixtures are extracted with organic solvent(s), and the resulting organic layers are worked up (for example, drying and concentration) to isolate Compound (XH2). The isolated Compound (XH2) may be further purified, for example, by distillation, chromatography and recrystallization.

(Reference Process I)

A compound of a formula (XI2) (hereinafter, described as Compound (XI2)) can be prepared by reacting Compound (XH2) with a compound of a formula (XI1) (hereinafter, described as Compound (XI1)).

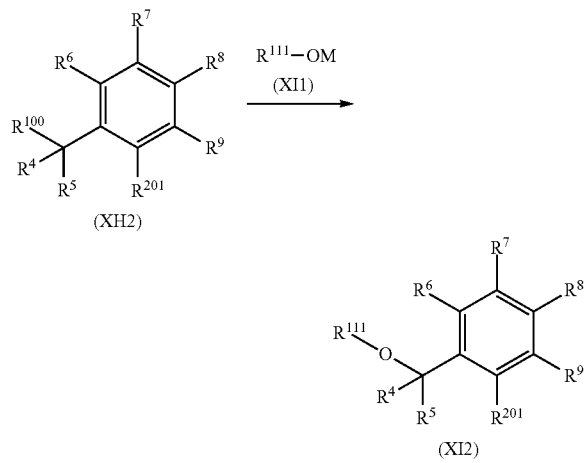

[wherein $R^4$, $R^5$, $R^6$, $R^7$, $R^8$, $R^9$, $R^{100}$, $R^{201}$ and $R^{111}$ are the same as described above; and M represents sodium, potassium or lithium]

This reaction is usually carried out in a solvent.

Examples of the solvent that can be used in the reaction include ethers such as diethyl ether, tetrahydrofuran, 1,4-dioxane, ethyleneglycol dimethyl ether, anisole, methyl tert-butyl ether, diisopropyl ether; hydrocarbons such as heptane, hexane, cyclohexane, pentane, toluene, xylene; halogenated hydrocarbons such as carbon tetrachloride, chloroform, dichloromethane, 1,2-dichloroethane, tetrachloroethane, chlorobenzene; nitriles such as acetonitrile, propionitrile; acid amides such as N,N-dimethylformamide, 1,3-dimethyl-2-imidazolidinone, N-methylpyrrolidone; sulfoxides such as dimethyl sulfoxide; ketones such as acetone, methyl ethyl ketone, methyl isobutyl ketone; alcohols such as methanol, ethanol, propanol, butanol; and mixed solvents thereof.

Examples of Compound (XI1) include sodium methoxide, sodium ethoxide, sodium propoxide, sodium butoxide, sodium isopropoxide, sodium sec-butoxide, sodium tert-butoxide, potassium methoxide, potassium ethoxide, potassium propoxide, potassium butoxide, potassium isopropoxide, potassium sec-butoxide, potassium tert-butoxide and sodium phenoxide.

In the reaction, Compound (XI1) is used usually within a range of 1 to 10 molar ratio(s) as opposed to 1 mole of Compound (XH2).

The reaction temperature is usually within a range of −20 to 150° C. The reaction period of the reaction is usually within a range of 0.1 to 24 hours.

When the reaction is completed, the reaction mixtures are extracted with organic solvent(s), and the resulting organic layers are worked up (for example, drying and concentration) to isolate Compound (XI2). The isolated Compound (XI2) may be further purified, for example, by distillation, chromatography and recrystallization.

(Reference Process J)

A compound of a formula (XJ1) (hereinafter, described as Compound (XJ1)) can be prepared by reacting Compound (XH2) and water in the presence of a base.

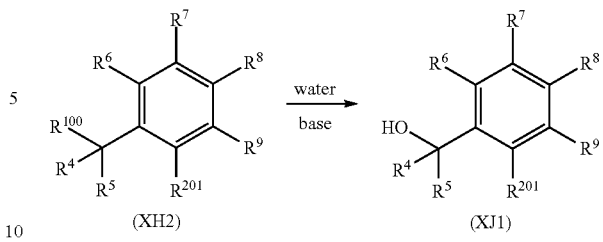

[wherein $R^4$, $R^5$, $R^6$, $R^7$, $R^8$, $R^9$, $R^{100}$ and $R^{201}$ are the same as described above]

This reaction is usually carried out in water or a solvent containing water.

Examples of the solvent that can be used in the reaction include ethers such as diethyl ether, tetrahydrofuran, 1,4-dioxane, ethyleneglycol dimethyl ether, anisole, methyl tert-butyl ether, diisopropyl ether; hydrocarbons such as heptane, hexane, cyclohexane, pentane, toluene, xylene; halogenated hydrocarbons such as carbon tetrachloride, chloroform, dichloromethane, 1,2-dichloroethane, tetrachloroethane, chlorobenzene; nitriles such as acetonitrile, propionitrile; acid amides such as N,N-dimethylformamide, 1,3-dimethyl-2-imidazolidinone, N-methylpyrrolidone; sulfoxides such as dimethyl sulfoxide; ketones such as acetone, methyl ethyl ketone, methyl isobutyl ketone; alcohols such as methanol, ethanol, propanol, butanol; and mixed solvents thereof.

Examples of the base to be used in the reaction include organic bases such as triethylamine, pyridine, N-methylmorpholine, N-methylpiperidine, 4-dimethylaminopyridine, diisopropylethylamine, lutidine, collidine, diazabicycloundecene, diazabicyclononene; metallic organic acid salts such as lithium formate, lithium acetate, sodium formate, sodium acetate, potassium formate, potassium acetate; metal nitrates such as silver nitrate, sodium nitrate; alkali-metal carbonates such as lithium carbonate, sodium carbonate, potassium carbonate, cesium carbonate; alkali-metal bicarbonates such as lithium bicarbonate, sodium bicarbonate, potassium bicarbonate, cesium bicarbonate; alkali-metal hydroxides such as lithium hydroxide, sodium hydroxide, potassium hydroxide, cesium hydroxide; and alkali metal alkoxides such as sodium methoxide, sodium ethoxide, sodium tert-butoxide, potassium tert-butoxide.

In the reaction, the base is used usually within a range of 1 to 100 molar ratio(s) as opposed to 1 mole of Compound (XH2).

In the reaction, water is used usually within a range of 1 to a large excess molar ratio(s) as opposed to 1 mole of Compound (XH2).

The reaction temperature is usually within a range of −20 to 150° C. The reaction period of the reaction is usually within a range of 0.1 to 24 hours.

When the reaction is completed, the reaction mixtures are extracted with organic solvent(s), and the resulting organic layers are worked up (for example, drying and concentration) to isolate Compound (XJ1). The isolated Compound (XJ1) may be further purified, for example, by distillation, chromatography and recrystallization.

(Reference Process K)

Compound (XH2) can be prepared by reacting Compound (XI2) and a halogenating agent.

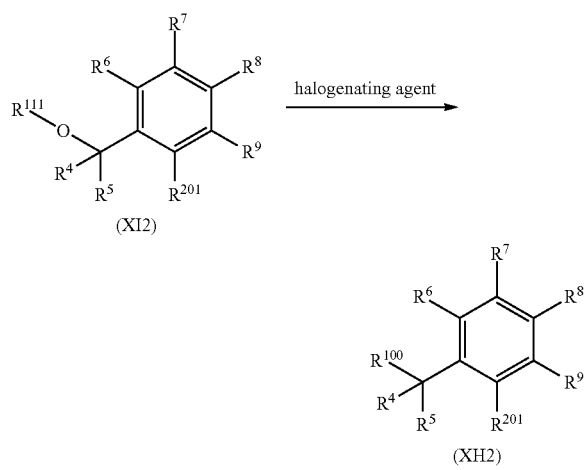

(XI2) → halogenating agent → (XH2)

[wherein
$R^4$, $R^5$, $R^6$, $R^7$, $R^8$, $R^9$, $R^{100}$, $R^{111}$ and $R^{201}$ are the same as described above]

This reaction is usually carried out in a solvent.

Examples of the solvent to be used in the reaction include hydrocarbons such as heptane, hexane, cyclohexane, pentane, toluene, xylene; ethers such as diethyl ether, tetrahydrofuran, 1,4-dioxane, ethyleneglycol dimethyl ether, anisole, methyl tert-butyl ether, diisopropyl ether; halogenated hydrocarbons such as carbon tetrachloride, chloroform, dichloromethane, 1,2-dichloroethane, tetrachloroethane, chlorobenzene; esters such as ethyl acetate, methyl acetate; ketones such as acetone, methyl ethyl ketone, methyl isobutyl ketone; nitriles such as acetonitrile, propionitrile; organic acids such as formic acid, acetic acid, trifluoroacetic acid; water; and mixed solvents thereof.

Examples of the halogenating agent include hydrochloric acid, hydrobromic acid and hydroiodic acid.

In the reaction, the halogenating agent is used usually in 1 or more molar ratio(s) as opposed to 1 mole of Compound (XI2).

The reaction temperature is usually within a range of −20 to 150° C. The reaction period of the reaction is usually within a range of 0.1 to 24 hours.

When the reaction is completed, the reaction mixtures are extracted with organic solvent(s), and the resulting organic layers are worked up (for example, drying and concentration) to isolate Compound (XH2). The isolated Compound (XH2) may be further purified, for example, by distillation, chromatography and recrystallization.

(Reference Process L)

Compound (XH2) can be prepared by reacting a compound of a formula (XJ1) (hereinafter, described as Compound (XJ1)) and a halogenating agent.

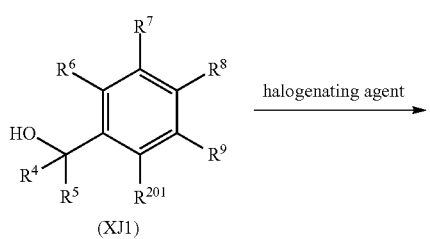

(XJ1) → halogenating agent →

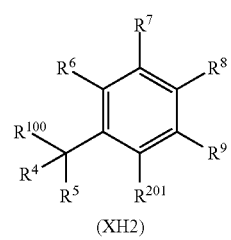

(XH2)

[wherein
$R^4$, $R^5$, $R^6$, $R^7$, $R^8$, $R^9$, $R^{100}$ and $R^{201}$ are the same as described above]

This reaction is usually carried out in a solvent.

Examples of the solvent to be used in the reaction include hydrocarbons such as heptane, hexane, cyclohexane, pentane, toluene, xylene; ethers such as diethyl ether, tetrahydrofuran, 1,4-dioxane, ethyleneglycol dimethyl ether, anisole, methyl tert-butyl ether, diisopropyl ether; halogenated hydrocarbons such as carbon tetrachloride, chloroform, dichloromethane, 1,2-dichloroethane, tetrachloroethane, chlorobenzene; esters such as ethyl acetate, methyl acetate; ketones such as acetone, methyl ethyl ketone, methyl isobutyl ketone; nitriles such as acetonitrile, propionitrile; organic acids such as formic acid, acetic acid, trifluoroacetic acid; water; and mixed solvents thereof.

Examples of the halogenating agent to be used in the reaction include bromine, chlorine, sulfuryl chloride, hydrochloric acid, hydrobromic acid, hydroiodic acid, boron tribromide, phosphorus tribromide, trimethylsilyl chloride, trimethylsilyl bromide, trimethylsilyl iodide, thionyl chloride, thionyl bromide, phosphorous oxychloride, phosphorous trichloride, phosphorous pentachloride, thionyl chloride, phosphorous oxybromide, phosphorous pentabromide, phosphorus triiodide, oxalyl dichloride, oxalyl dibromide, acetyl chloride, carbon tetrabromide, N-bromosuccinimide, lithium chloride, sodium iodide and acetyl bromide.

In the reaction, the halogenating agent is used usually within a range of 1 to 10 molar ratio(s) as opposed to 1 mole of Compound (XJ1).

To promote the reaction, an additive agent may be added depending on the halogenating agent used, and specifically includes zinc chloride for acetyl chloride; triphenylphosphine for carbon tetrabromide; dimethyl sulfide for N-bromosuccinimide; boron trifluoride diethyl etherate complex for sodium iodide; boron trifluoride diethyl etherate complex for acetyl bromide; triethylamine and methanesulfonyl chloride for lithium chloride; aluminium chloride for sodium iodide; and trimethylsilyl chloride for sodium iodide. The amount of the additive agent is used usually within a range of 0.01 to 5 molar ratios as opposed to 1 mole of Compound (XJ1).

The reaction temperature is usually within a range of −20 to 150° C. The reaction period of the reaction is usually within a range of 0.1 to 24 hours.

When the reaction is completed, the reaction mixtures are extracted with organic solvent(s), and the resulting organic layers are worked up (for example, drying and concentration) to isolate Compound (XH2). The isolated Compound (XH2) may be further purified, for example, by distillation, chromatography and recrystallization.

(Reference Process M)

A compound of a formula (XM2) (hereinafter, described as Compound (XM2)) can be prepared by reacting Compound (XJ1) with a compound of a formula (XM1) (hereinafter, described as Compound (XM1)) in the presence of a base.

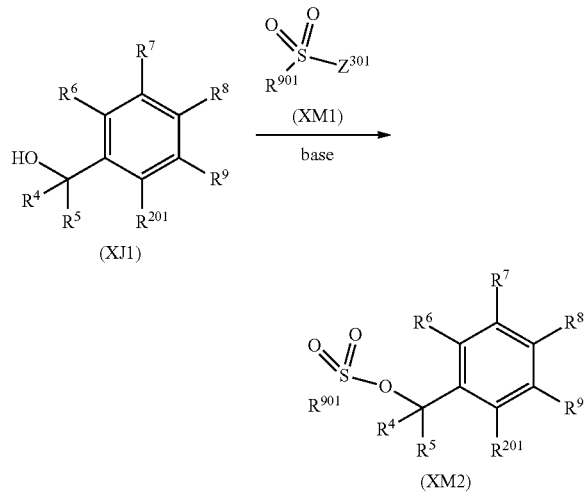

[wherein $R^4$, $R^5$, $R^6$, $R^7$, $R^8$, $R^9$ and $R^{201}$ are the same as described above; $R^{901}$ represents a p-methylphenyl group, a methyl group or a trifluoromethyl group; $Z^{301}$ represents a fluorine atom, a chlorine atom, a bromine atom, an iodine atom, a methanesulfonyloxy group or a trifluoromethanesulfonyloxy group]

This reaction is usually carried out in a solvent.

Examples of the solvent to be used in the reaction include hydrocarbons such as heptane, hexane, cyclohexane, pentane, toluene, xylene; ethers such as diethyl ether, tetrahydrofuran, 1,4-dioxane, ethyleneglycol dimethyl ether, anisole, methyl tert-butyl ether, diisopropyl ether; halogenated hydrocarbons such as carbon tetrachloride, chloroform, dichloromethane, 1,2-dichloroethane, tetrachloroethane, chlorobenzene; nitriles such as acetonitrile, propionitrile; acid amides such as N,N-dimethylformamide, 1,3-dimethyl-2-imidazolidinone, N-methylpyrrolidone; sulfoxides such as dimethyl sulfoxide; ketones such as acetone, methyl ethyl ketone, methyl isobutyl ketone; water; and mixed solvents thereof.

Examples of the base to be used in the reaction include organic bases such as triethylamine, pyridine, N-methylmorpholine, N-methylpiperidine, 4-dimethylaminopyridine, diisopropylethylamine, lutidine, collidine, diazabicycloundecene, diazabicyclononene; alkali metal carbonates such as lithium carbonate, sodium carbonate, potassium carbonate, cesium carbonate; alkali metal bicarbonates such as lithium bicarbonate, sodium bicarbonate, potassium bicarbonate, cesium bicarbonate; alkali metal hydroxides such as lithium hydroxide, sodium hydroxide, potassium hydroxide, cesium hydroxide; alkali metal hydrides such as lithium hydride, sodium hydride, potassium hydride; alkali metal alkoxides such as sodium methoxide, sodium ethoxide, sodium tert-butoxide, potassium tert-butoxide.

In the reaction, Compound (XM1) is used usually within a range of 1 to 10 molar ratio(s), and the base is used usually within a range of 1 to 5 molar ratio(s), as opposed to 1 mole of Compound (XJ1).

The reaction temperature is usually within a range of −20 to 150° C. The reaction period of the reaction is usually within a range of 0.1 to 24 hours.

If necessary, an additive agent may be added to the reaction, and specifically, includes sodium iodide and tetrabutylammonium iodide and the others. These additive agents are used usually within a range of 0.001 to 1.2 molar ratios as opposed to 1 mole of Compound (XJ1).

When the reaction is completed, the reaction mixtures are extracted with organic solvent(s), and the resulting organic layers are worked up (for example, drying and concentration) to isolate Compound (XM2). The isolated Compound (XM2) may be further purified, for example, by chromatography and recrystallization.

(Reference Process N)

A compound of a formula (XN12) (hereinafter, described as Compound (XN12)) can be prepared by coupling a compound of a formula (XN11) (hereinafter, described as Compound (XN11)) with Compound (D-2) in the presence of a base and a catalyst.

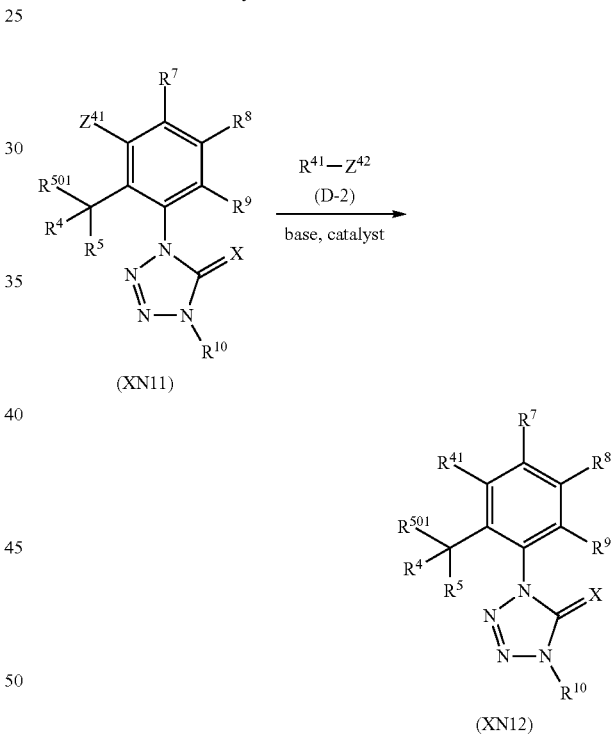

[wherein $R^{501}$ represents a hydrogen atom or an $OR^{111}$ group; $R^4$, $R^5$, $R^7$, $R^8$, $R^9$, $R^{10}$, $R^{41}$, X, $Z^{41}$ and $Z^{42}$ are the same as described above]

The reaction can be carried out according to the above-mentioned Process D.

A compound of a formula (XN22) (hereinafter, described as Compound (XN22)) can be prepared by coupling a compound of a formula (XN21) (hereinafter, described as Compound (XN21)) with Compound (D-2-2) in the presence of a base and a catalyst.

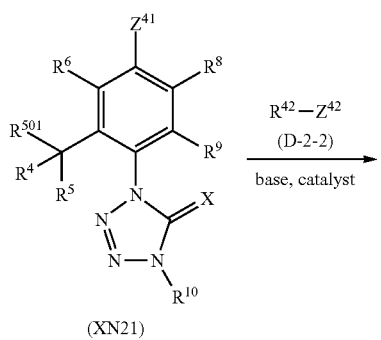

(XN21)

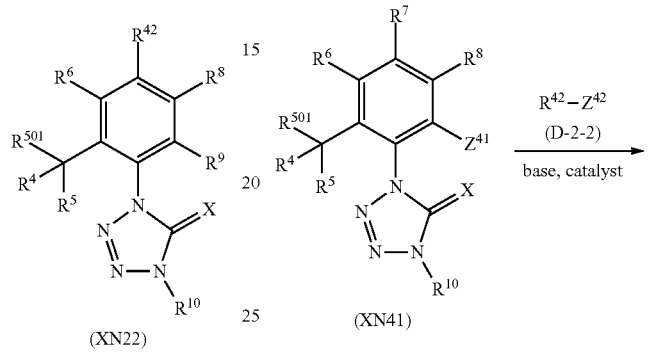

(XN22)

[wherein

R⁴, R⁵, R⁶, R⁸, R⁹, R¹⁰, R⁴², R⁵⁰¹, X, Z⁴¹ and Z⁴² are the same as described above]

The reaction can be carried out according to the above-mentioned Process D.

A compound of a formula (XN32) (hereinafter, described as Compound (XN32)) can be prepared by coupling a compound of a formula (XN31) (hereinafter, described as Compound (XN31)) with Compound (D-2-2) in the presence of a base and a catalyst.

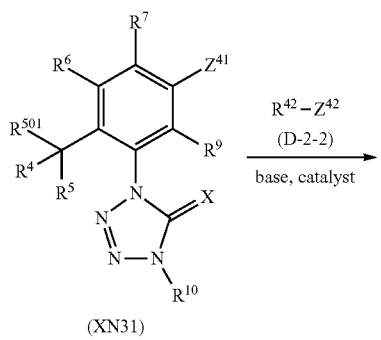

(XN31)

[wherein

R⁴, R⁵, R⁶, R⁷, R⁹, R¹⁰, R⁴², R⁵⁰¹, X, Z⁴¹ and Z⁴² are the same as described above]

The reaction can be carried out according to the above-mentioned Process D.

A compound of a formula (XN42) (hereinafter, described as Compound (XN42)) can be prepared by coupling a compound of a formula (XN41) (hereinafter, described as Compound (XN41)) with Compound (D-2-2) in the presence of a base and a catalyst.

(XN41)

(XN42)

[wherein

R⁴, R⁵, R⁶, R⁷, R⁸, R⁹, R¹⁰, R⁴², R⁵⁰¹, X, Z⁴¹ and Z⁴² are the same as described above]

The reaction can be carried out according to the above-mentioned Process D.

(Reference Process O)

A compound of a formula (XO12) (hereinafter, described as Compound (XO12)) can be prepared by reacting a compound of a formula (XO11) (hereinafter, described as Compound (XO11)) with Compound (D-2) in the presence of a base and a catalyst.

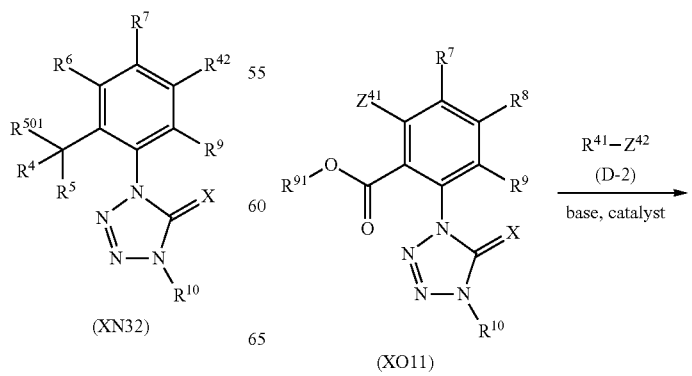

(XN32)

(XO11)

-continued

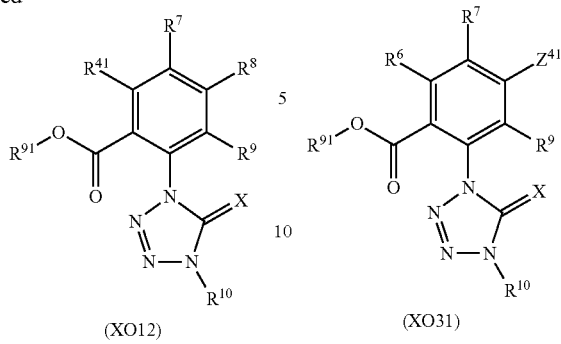

(XO12)

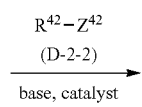

(XO31)

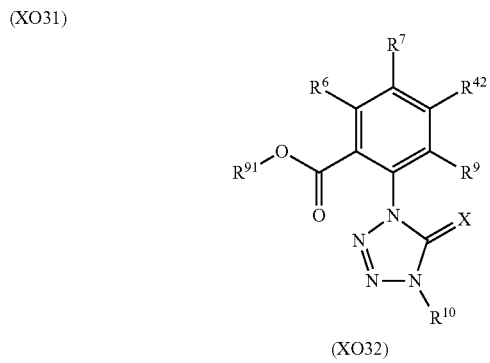

(XO32)

[wherein
R⁷, R⁸, R⁹, R¹⁰, R⁴¹, R⁹¹, X, Z⁴¹ and Z⁴² are the same as described above]

The reaction can be carried out according to the above-mentioned Process D.

A compound of a formula (XO22) (hereinafter, described as Compound (XO22)) can be prepared by reacting a compound of a formula (XO21) (hereinafter, described as Compound (XO21)) with Compound (D-2-2) in the presence of a base and a catalyst.

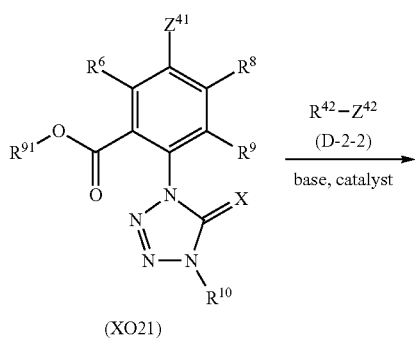

(XO21)

[wherein
R⁶, R⁷, R⁹, R¹⁰, R⁴², R⁹¹, X, Z⁴¹ and Z⁴² are the same as described above]

The reaction can be carried out according to the above-mentioned Process D.

A compound of a formula (XO42) (hereinafter, described as Compound (XO42)) can be prepared by reacting a compound of a formula (XO41) (hereinafter, described as Compound (XO41)) with Compound (D-2-2) in the presence of a base and a catalyst.

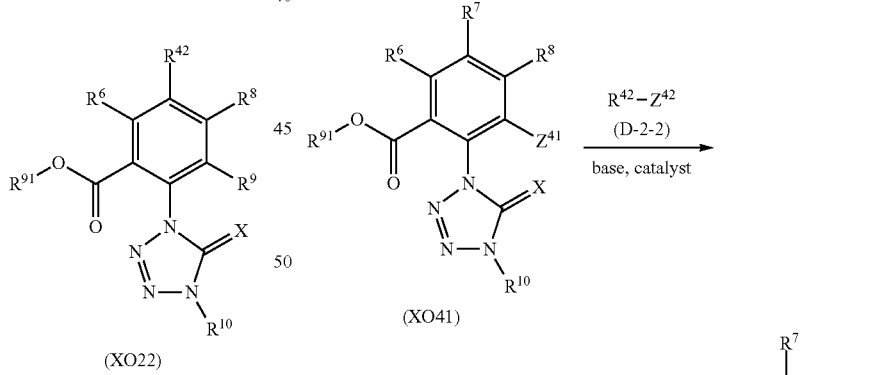

(XO22)                                    (XO41)

[wherein
R⁶, R⁸, R⁹, R¹⁰, R⁴², R⁹¹, X, Z⁴¹ and Z⁴² are the same as described above]

The reaction can be carried out according to the above-mentioned Process D.

A compound of a formula (XO32) (hereinafter, described as Compound (XO32)) can be prepared by reacting a compound of a formula (XO31) (hereinafter, described as Compound (XO31)) with Compound (D-2-2) in the presence of a base and a catalyst.

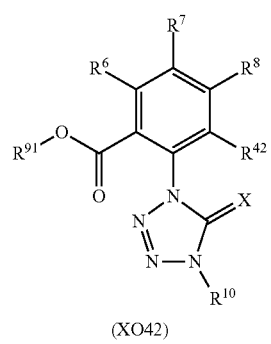

(XO42)

[wherein

R$^6$, R$^7$, R$^8$, R$^{10}$, R$^{42}$, R$^{91}$, X, Z$^{41}$ and Z$^{42}$ are the same as described above]

The reaction can be carried out according to the above-mentioned Process D.

(Reference Process P)

A compound of a formula (XP3) (hereinafter, described as Compound (XP3)) can be prepared by reacting a compound of a formula (XP1) (hereinafter, described as Compound (X P1)) with a compound of a formula (XP2) (hereinafter, described as Compound (XP2)) in the presence of a reaction accelerator.

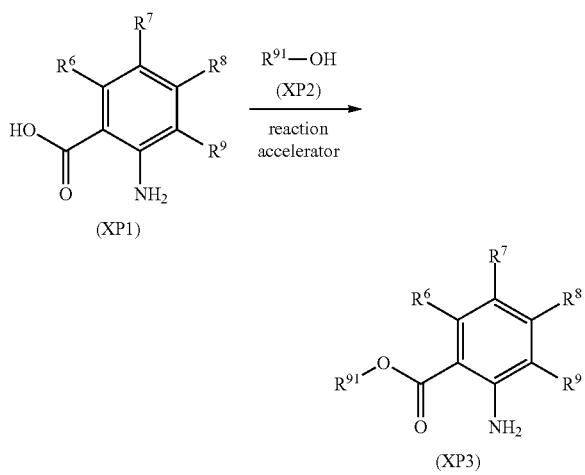

[wherein

R$^6$, R$^7$, R$^8$, R$^9$ and R$^{91}$ are the same as described above]

This reaction is usually carried out in a solvent.

Examples of the solvent to be used in the reaction include hydrocarbons such as heptane, hexane, cyclohexane, pentane, toluene, xylene; ethers such as diethyl ether, tetrahydrofuran, 1,4-dioxane, ethyleneglycol dimethyl ether, anisole, methyl tert-butyl ether, diisopropyl ether; halogenated hydrocarbons such as carbon tetrachloride, chloroform, dichloromethane, 1,2-dichloroethane, tetrachloroethane, chlorobenzene; acid amides such as N,N-dimethylformamide, 1,3-dimethyl-2-imidazolidinone, N-methylpyrrolidone; esters such as ethyl acetate, methyl acetate; sulfoxides such as dimethyl sulfoxide; ketones such as acetone, methyl ethyl ketone, methyl isobutyl ketone; nitriles such as acetonitrile, propionitrile; and mixed solvents thereof, and Compound (XP2) may be used as solvent.

Examples of Compound (XP2) to be used in the reaction include alcohols such as methanol, ethanol, propanol, isopropanol, butanol, sec-butanol, t-butanol, and pentanol.

Examples of the reaction accelerator to be used in the reaction include mineral acids such as hydrochloric acid, sulfuric acid; carbodiimides such as dicyclohexylcarbodiimide, diisopropylcarbodiimide, N'-(3-dimethylaminopropyl)-N-ethylcarbodiimide; organic acids such as methanesulfonic acid, toluenesulfonic acid; Mitsunobu reagents such as triphenylphosphine/diethyl azodicarboxylate; thionyl chloride; boron trifluoride-ethyl ether complex. In the reaction, the reaction accelerator is used usually within a range of 0.01 to 10 molar ratios as opposed to 1 mole of Compound (XP1).

If necessary, organic bases such as triethylamine, pyridine, N-methylmorpholine, N-methylpiperidine, 4-dimethylaminopyridine, diisopropylethylamine, lutidine, collidine, diazabicycloundecene and diazabicyclononene, alkali metal carbonates such as lithium carbonate, sodium carbonate, potassium carbonate and cesium carbonate, alkali metal bicarbonates such as lithium bicarbonate, sodium bicarbonate, potassium bicarbonate and cesium bicarbonate may be added to the reaction, and these compounds are used usually within a range of 0.001 to 5 molar ratios as opposed to 1 mole of Compound (XP1).

In the reaction, Compound (XP2) is used usually in an excess molar ratios as opposed to 1 mole of Compound (XP1).

The reaction temperature is usually within a range of −78 to 100° C. The reaction period of the reaction is usually within a range of 0.1 to 24 hours.

When the reaction is completed, the reaction mixtures are extracted with organic solvent(s), and the resulting organic layers are worked up (for example, drying and concentration) to isolate Compound (XP3). The isolated Compound (XP3) may be further purified, for example, by distillation, chromatography and recrystallization.

(Reference Process Q)

Compound (XP3) can be prepared by reacting Compound (XP1) with a halogenating agent to form a below-mentioned compound of a formula (XQ1) (hereinafter, described as Compound (XQ1)), followed by reacting the resulting Compound (XQ1) with Compound (XP2).

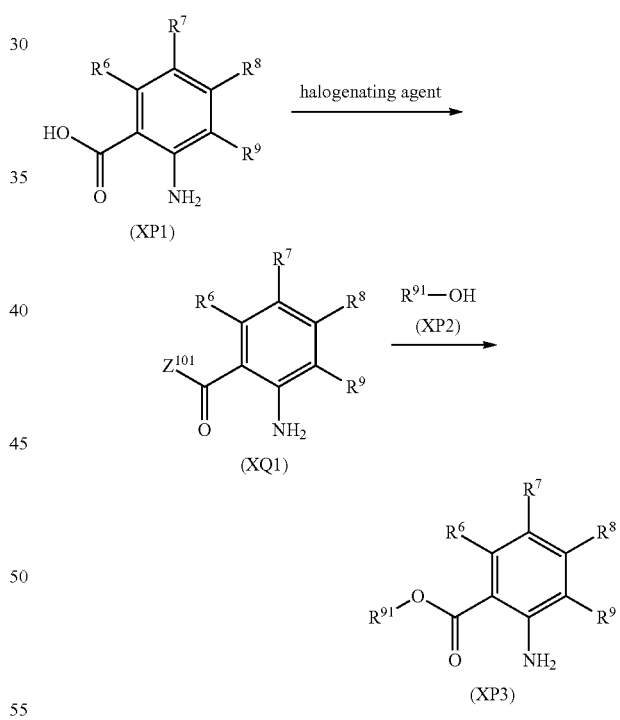

[wherein

R$^6$, R$^7$, R$^8$, R$^9$, R$^{91}$ and Z$^{101}$ are the same as described above]

The process for preparing Compound (XQ1) by reacting Compound (XP1) and a halogenating agent can be carried out according to Reference Process C.

Hereinafter, a process for preparing Compound (XP3) from Compound (XQ1) is explained.

This reaction is usually carried out in a solvent.

Examples of the solvent to be used in the reaction include hydrocarbons such as heptane, hexane, cyclohexane, pentane, toluene, xylene; ethers such as diethyl ether, tetrahydrofuran, 1,4-dioxane, ethyleneglycol dimethyl ether, anisole, methyl tert-butyl ether, diisopropyl ether; halogenated hydrocarbons such as carbon tetrachloride, chloroform, dichloromethane, 1,2-dichloroethane, tetrachloroethane, chlorobenzene; acid amides such as N,N-dimethylformamide, 1,3-dimethyl-2-imidazolidinone, N-methylpyrrolidone; esters such as ethyl acetate, methyl acetate; sulfoxides such as dimethyl sulfoxide; ketones such as acetone, methyl ethyl ketone, methyl isobutyl ketone; nitriles such as acetonitrile, propionitrile; and mixed solvents thereof, and Compound (XP2) may be used as solvent.

Examples of Compound (XP2) to be used in the reaction include alcohols such as methanol, ethanol, propanol, isopropanol, butanol, sec-butanol, t-butanol, and pentanol. In the reaction, Compound (XP2) is used usually within a range of 1 to 50 molar ratio(s) as opposed to 1 mole of Compound (XQ1).

The reaction temperature is usually within a range of −78 to 100° C. The reaction period of the reaction is usually within a range of 0.1 to 24 hours.

When the reaction is completed, the reaction mixtures are extracted with organic solvent(s), and the resulting organic layers are worked up (for example, drying and concentration) to isolate Compound (XP3). The isolated Compound (XP3) may be further purified, for example, by distillation, chromatography and recrystallization.

(Reference Process R)

Compound (XP3) can be prepared by reacting Compound (XP1) with an alkylating agent.

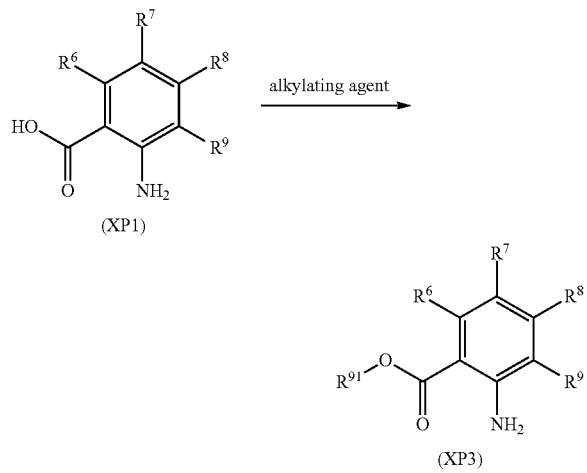

[wherein
$R^6$, $R^7$, $R^8$, $R^9$ and $R^{91}$ are the same as described above]

This reaction is usually carried out in a solvent.

Examples of the solvent that can be used in the reaction include hydrocarbons such as heptane, hexane, cyclohexane, pentane, toluene, xylene; ethers such as diethyl ether, tetrahydrofuran, 1,4-dioxane, ethyleneglycol dimethyl ether, anisole, methyl tert-butyl ether, diisopropyl ether; halogenated hydrocarbons such as carbon tetrachloride, chloroform, dichloromethane, 1,2-dichloroethane, tetrachloroethane, chlorobenzene; acid amides such as N,N-dimethylformamide, 1,3-dimethyl-2-imidazolidinone, N-methylpyrrolidone; esters such as ethyl acetate, methyl acetate; sulfoxides such as dimethyl sulfoxide; ketones such as acetone, methyl ethyl ketone, methyl isobutyl ketone; nitriles such as acetonitrile, propionitrile; water; and mixed solvents thereof.

Examples of the alkylating agent to be used in the reaction include Diaz compounds such as diazomethane, trimethylsilyldiazomethane; halogenated alkyls such as chlorodifluoromethane, methyl bromide, ethyl bromide, propyl bromide, methyl iodide, ethyl iodide, propyl bromide, aryl bromide, cyclopropyl bromide, benzyl bromide, 1,1-difluoro-2-iodomethane; dialkyl sulfates such as dimethyl sulfates, diethyl sulfates, di-propyl sulfates; and alkyl or aryl sulfonates such as methyl p-toluenesulfonate, ethyl p-toluenesulfonate, propyl p-toluenesulfonate, methyl methanesulfonate, ethyl methanesulfonate, propyl methanesulfonate.

In the reaction, the alkylating agent is used usually within a range of 1 to 10 molar ratios as opposed to 1 mole of Compound (XP1).

If necessary, an additive agent may be added to the reaction, and specifically, includes organic bases such as triethylamine, pyridine, N-methylmorpholine, N-methylpiperidine, 4-dimethylaminopyridine, diisopropylethylamine, lutidine, collidine, diazabicycloundecene and diazabicyclononene; alkali metal carbonates such as lithium carbonate, sodium carbonate, potassium carbonate and cesium carbonate; alkali metal bicarbonates such as lithium bicarbonate, sodium bicarbonate, potassium bicarbonate and cesium bicarbonate; and quaternary ammonium salts such as tetra(butyl)ammonium hydroxide. These additive agent is used usually within a range of 0.001 to 5 molar ratios as opposed to 1 mole of Compound (XP1).

The reaction temperature is usually within a range of −78 to 100° C. The reaction period of the reaction is usually within a range of 0.1 to 24 hours.

When the reaction is completed, the reaction mixtures are extracted with organic solvent(s), and the resulting organic layers are worked up (for example, drying and concentration) to isolate Compound (XP3). The isolated Compound (XP3) may be further purified, for example, by distillation, chromatography and recrystallization.

(Reference Process S)

A compound of a formula (XS2) (hereinafter, described as Compound (XS2)) can be prepared by reacting a compound of a formula (XS1) (hereinafter, described as Compound (XS1)) with a reducing agent.

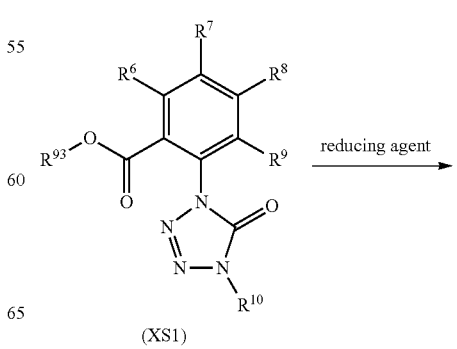

-continued

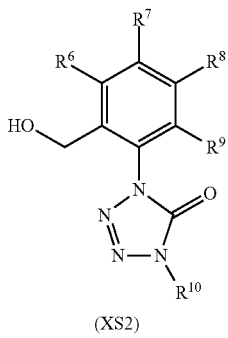

(XS2)

[wherein

R⁶, R⁷, R⁸, R⁹ and R¹⁰ are the same as described above; R⁹³ represents a hydrogen atom or an C1-C3 alkyl group]

This reaction is usually carried out in a solvent.

Examples of the solvent to be used in the reaction include hydrocarbons such as heptane, hexane, cyclohexane, pentane, toluene, xylene; ethers such as diethyl ether, tetrahydrofuran, 1,4-dioxane, ethyleneglycol dimethyl ether, anisole, methyl tert-butyl ether, diisopropyl ether; halogenated hydrocarbons such as carbon tetrachloride, chloroform, dichloromethane, 1,2-dichloroethane, tetrachloroethane, chlorobenzene; alcohols such as methanol, ethanol, propanol, butanol; water; and mixed solvents thereof.

Examples of the reducing agent to be used in the reaction include lithium triethylborohydride, diisobutylaluminium hydride, lithium aminoborohydride, lithium borohydride, sodium borohydride, borane, borane-dimethyl sulfide complex and borane-tetrahydrofuran complex.

In the reaction, the reducing agent is used usually within a range of 1 to 10 molar ratio(s) as opposed to 1 mole of Compound (XS1).

The reaction temperature is usually within a range of −78 to 100° C. The reaction period of the reaction is usually within a range of 0.1 to 24 hours.

When the reaction is completed, the reaction mixtures are extracted with organic solvent(s), and the resulting organic layers are worked up (for example, drying and concentration) to isolate Compound (XS2). Compound (XS2) may be further purified, for example, by distillation, chromatography and recrystallization.

(Reference Process T)

A compound of a formula (XT2) (hereinafter, described as Compound (XT2)) can be prepared by reacting a compound of a formula (XT1) (hereinafter, described as Compound (XT1)) with a reducing agent.

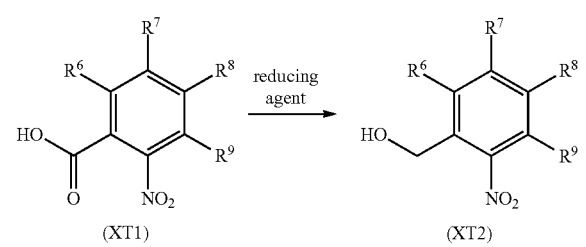

[wherein

R⁶, R⁷, R⁸ and R⁹ are the same as described above]

This reaction is usually carried out in a solvent.

Examples of the solvent to be used in the reaction include hydrocarbons such as heptane, hexane, cyclohexane, pentane, toluene, xylene; ethers such as diethyl ether, tetrahydrofuran, 1,4-dioxane, ethyleneglycol dimethyl ether, anisole, methyl tert-butyl ether, diisopropyl ether; halogenated hydrocarbons such as carbon tetrachloride, chloroform, dichloromethane, 1,2-dichloroethane, tetrachloroethane, chlorobenzene; acid amides such as N,N-dimethylformamide, 1,3-dimethyl-2-imidazolidinone, N-methylpyrrolidone; sulfoxides such as dimethyl sulfoxide; nitriles such as acetonitrile, propionitrile; alcohols such as methanol, ethanol, propanol, butanol; water; and mixed solvents thereof.

Examples of the reducing agent to be used in the reaction include, borane, borane-tetrahydrofuran complex, borane-dimethyl sulfide complex. Also, borohydrides such as sodium borohydride and potassium borohydride are mixed with acids such as sulfuric acid, hydrochloric acid, methanesulfonic acid and boron trifluoride diethyl etherate complex to develop a borane, which also can be used.

In the reaction, the reducing agent is used usually within a range of 1 to 10 molar ratio(s) as opposed as 1 mole of Compound (XT1).

The reaction temperature is usually within a range of −20 to 100° C. The reaction period of the reaction is usually within a range of 0.1 to 72 hours.

When the reaction is completed, the reaction mixtures are extracted with organic solvent(s), and the resulting organic layers are worked up (for example, drying and concentration) to isolate Compound (XT2). The isolated Compound (XT2) may be further purified, for example, by distillation, chromatography and recrystallization.

(Reference Process U)

Compound (F-1) can be prepared by reacting a compound of a formula (XU1) (hereinafter, described as Compound (XU1)) with a compound of a formula (XU2) (hereinafter, described as Compound (XU2)).

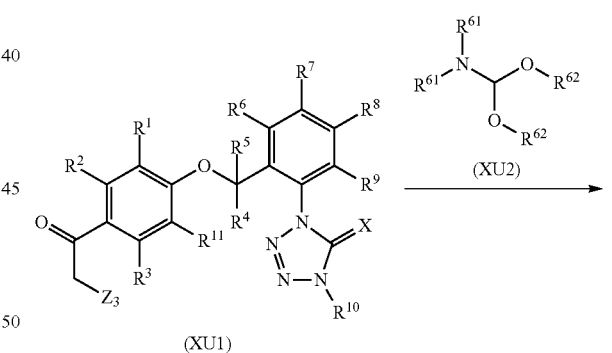

(XU1)

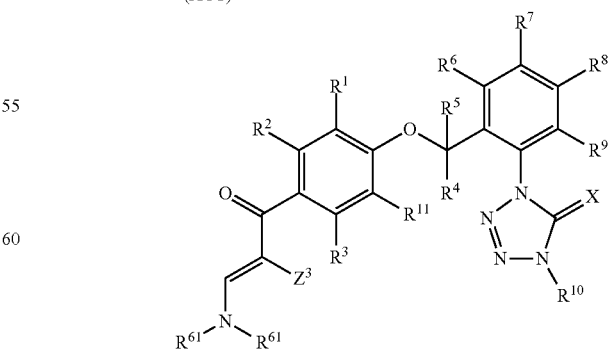

(F-1)

[wherein

R$^1$, R$^2$, R$^3$, R$^4$, R$^5$, R$^6$, R$^7$, R$^8$, R$^9$, R$^{10}$, R$^{11}$, R$^{61}$, X and Z$^3$ are the same as described above; R$^{62}$ represents a methyl group, an ethyl group, a propyl group, a butyl group or a benzyl group]

This reaction is usually carried out in a solvent or in a solvent-free system.

Examples of the solvent to be used in the reaction include hydrocarbons such as heptane, hexane, cyclohexane, pentane, toluene, xylene; ethers such as diethyl ether, tetrahydrofuran, 1,4-dioxane, ethyleneglycol dimethyl ether, anisole, methyl tert-butyl ether, diisopropyl ether; halogenated hydrocarbons such as carbon tetrachloride, chloroform, dichloromethane, 1,2-dichloroethane, tetrachloroethane, chlorobenzene; acid amides such as N,N-dimethylformamide, 1,3-dimethyl-2-imidazolidinone, N-methylpyrrolidone; sulfoxides such as dimethyl sulfoxide; nitriles such as acetonitrile, propionitrile; alcohols such as methanol, ethanol, propanol, butanol; water; and mixed solvents thereof.

In the reaction, Compound (XU2) is used usually within a range of 1 to 10 molar ratio(s) as opposed as 1 mole of Compound (XU1).

The reaction temperature is usually within a range of −20 to 150° C. The reaction period of the reaction is usually within a range of 0.1 to 72 hours.

When the reaction is completed, the reaction mixtures are extracted with organic solvent(s), and the resulting organic layers are worked up (for example, drying and concentration) to isolate Compound (F-1). Alternatively, the reaction mixtures are worked up (for example, concentration) to isolate Compound (F-1). The isolated Compound (F-1) may be further purified, for example, by distillation, chromatography and recrystallization.

(Reference Process V)

Compound (XU1) can be prepared by reacting Compound (A-1) with a compound of a formula (XV1) (hereinafter, described as Compound (XV1)) in the presence of a base.

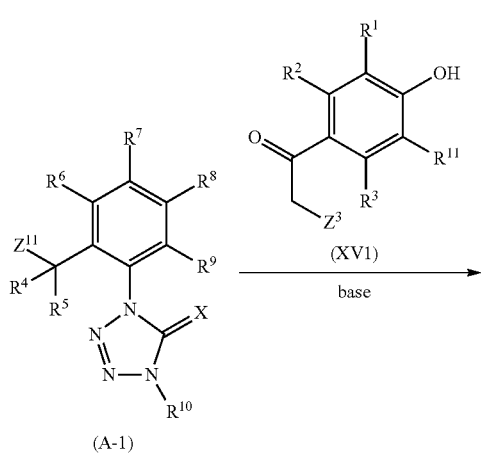

(A-1)

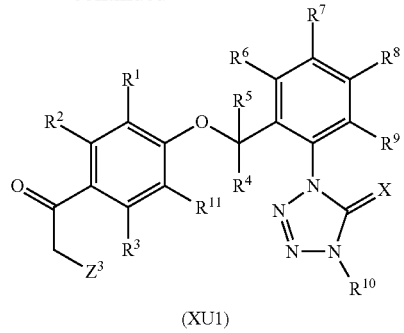

(XU1)

[wherein

R$^1$, R$^2$, R$^3$, R$^4$, R$^5$, R$^6$, R$^7$, R$^8$, R$^9$, R$^{10}$, R$^{11}$, X, Z$^3$ and Z$^{11}$ are the same as described above]

This reaction is usually carried out in a solvent.

Examples of the solvent to be used in the reaction include hydrocarbons such as heptane, hexane, cyclohexane, pentane, toluene, xylene; ethers such as diethyl ether, tetrahydrofuran, 1,4-dioxane, ethyleneglycol dimethyl ether, anisole, methyl tert-butyl ether, diisopropyl ether; halogenated hydrocarbons such as carbon tetrachloride, chloroform, dichloromethane, 1,2-dichloroethane, tetrachloroethane, chlorobenzene; acid amides such as N,N-dimethylformamide, 1,3-dimethyl-2-imidazolidinone, N-methylpyrrolidone; esters such as ethyl acetate, methyl acetate; sulfoxides such as dimethyl sulfoxide; ketones such as acetone, methyl ethyl ketone, methyl isobutyl ketone; nitriles such as acetonitrile, propionitrile; water; and mixed solvents thereof.

Examples of the base to be used in the reaction include organic bases such as triethylamine, pyridine, N-methylmorpholine, N-methylpiperidine, 4-dimethylaminopyridine, diisopropylethylamine, lutidine, collidine, diazabicycloundecene, diazabicyclononene; alkali metal carbonates such as lithium carbonate, sodium carbonate, potassium carbonate, cesium carbonate; alkali metal bicarbonates such as lithium bicarbonate, sodium bicarbonate, potassium bicarbonate, cesium bicarbonate; alkali metal hydroxides such as lithium hydroxide, sodium hydroxide, potassium hydroxide, cesium hydroxide; alkali metal halides such as sodium fluoride, potassium fluoride, cesium fluoride; alkali metal hydrides such as lithium hydride, sodium hydride, potassium hydride; and alkali metal alkoxides such as sodium tert-butoxide, potassium tert-butoxide.

In the reaction, Compound (XV1) is used usually within a range of 1 to 10 molar ratio(s), and the base is used usually within a range of 1 to 10 molar ratio(s), as opposed as 1 mole of Compound (A-1).

The reaction temperature is usually within a range of −20 to 150° C. The reaction period of the reaction is usually within a range of 0.1 to 24 hours.

If necessary, sodium iodide, tetrabutylammonium iodide and the others may be added to the reaction and these compounds are used usually within a range of 0.001 to 1.2 molar ratios as opposed to 1 mole of Compound (A-1).

When the reaction is completed, the reaction mixtures are extracted with organic solvent(s), and the resulting organic layers are worked up (for example, drying and concentration) to isolate Compound (XU1). Alternatively, the reaction mixtures are worked up (for example, concentration) to isolate Compound (XU1). The isolated Compound (XU1) may be further purified, for example, by chromatography and recrystallization.

(Reference Process W)

Compound (G-1) can be prepared by reacting Compound (XU1) with a compound of a formula (XW1) (hereinafter, described as Compound (XW1)) in the presence of a base.

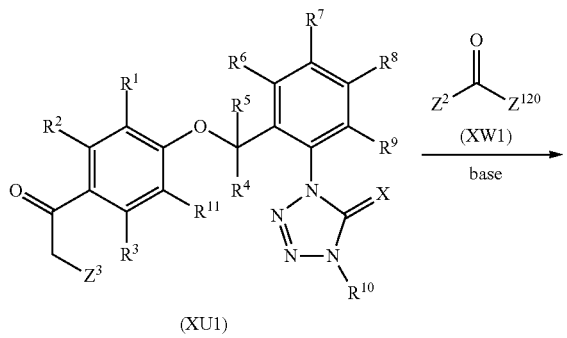

(XU1)

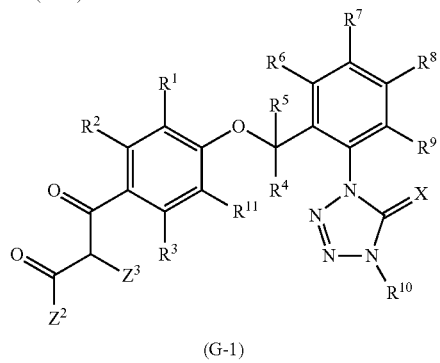

(G-1)

[wherein $R^1$, $R^2$, $R^3$, $R^4$, $R^5$, $R^6$, $R^7$, $R^8$, $R^9$, $R^{10}$, $R^{11}$, X, $Z^2$ and $Z^3$ are the same as described above; and $Z^{120}$ represents a fluorine atom, a chlorine atom, a bromine atom, an iodine atom, an C1-C6 alkoxy group, an acetyloxy group or a phenoxy group]

This reaction is usually carried out in a solvent.

Examples of the solvent to be used in the reaction include hydrocarbons such as heptane, hexane, cyclohexane, pentane, toluene, xylene; ethers such as diethyl ether, tetrahydrofuran, 1,4-dioxane, ethyleneglycol dimethyl ether, anisole, methyl tert-butyl ether, diisopropyl ether; halogenated hydrocarbons such as carbon tetrachloride, chloroform, dichloromethane, 1,2-dichloroethane, tetrachloroethane, chlorobenzene; acid amides such as N,N-dimethylformamide, 1,3-dimethyl-2-imidazolidinone, N-methylpyrrolidone; esters such as ethyl acetate, methyl acetate; sulfoxides such as dimethyl sulfoxide; ketones such as acetone, methyl ethyl ketone, methyl isobutyl ketone; nitriles such as acetonitrile, propionitrile; water; and mixed solvents thereof.

Examples of the base to be used in the reaction include organic bases such as triethylamine, pyridine, N-methylmorpholine, N-methylpiperidine, 4-dimethylaminopyridine, diisopropylethylamine, lutidine, collidine, diazabicycloundecene, diazabicyclononene; alkali metal carbonates such as lithium carbonate, sodium carbonate, potassium carbonate, cesium carbonate; alkali metal bicarbonates such as lithium bicarbonate, sodium bicarbonate, potassium bicarbonate, cesium bicarbonate; alkali metal hydroxides such as lithium hydroxide, sodium hydroxide, potassium hydroxide, cesium hydroxide; alkali metal halides such as sodium fluoride, potassium fluoride, cesium fluoride; alkali metal hydrides such as lithium hydride, sodium hydride, potassium hydride; and alkali metal alkoxides such as sodium methoxide, sodium ethoxide, sodium tert-butoxide, potassium tert-butoxide.

In the reaction, Compound (XW1) is used usually within a range of 1 to 10 molar ratio(s), and the base is used usually within a range of 1 to 10 molar ratio(s), as opposed as 1 mole of Compound (XU1).

The reaction temperature is usually within a range of −20 to 150° C. The reaction period of the reaction is usually within a range of 0.1 to 24 hours.

If necessary, an additive agent may be added to the reaction, and specifically includes, for example, 18-crown-6, dibenzo-18-crown-6 and the others. The additive agent is used usually within a range of 0.001 to 1.2 molar ratios as opposed to 1 mole of Compound (XU1).

When the reaction is completed, the reaction mixtures are extracted with organic solvent(s), and the resulting organic layers are worked up (for example, drying and concentration) to isolate Compound (G-1). The isolated Compound (G-1) may be further purified, for example, by chromatography and recrystallization.

(Reference Process X)

Compound (G-1-1) can be prepared by reacting Compound (XU1) with a compound of a formula (XX1) (hereinafter, described as Compound (XX1)) in the presence of a base.

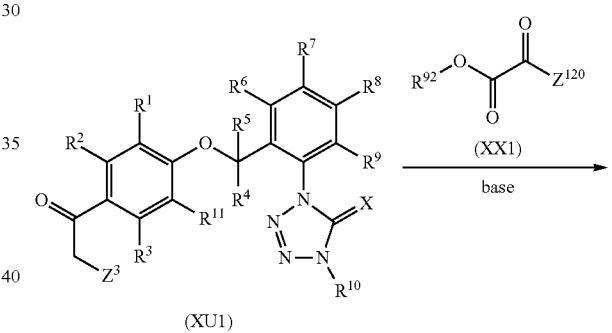

(XU1)

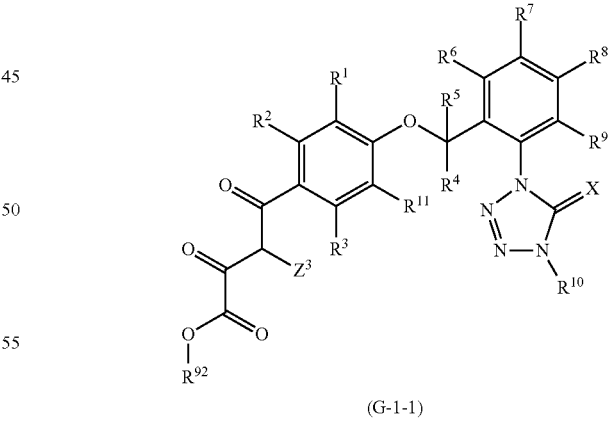

(G-1-1)

[wherein $R^1$, $R^2$, $R^3$, $R^4$, $R^5$, $R^6$, $R^7$, $R^8$, $R^9$, $R^{10}$, $R^{11}$, $R^{92}$, X, $Z^3$ and $Z^{120}$ are the same as described above]

This reaction is usually carried out in a solvent.

Examples of the solvent to be used in the reaction include hydrocarbons such as heptane, hexane, cyclohexane, pentane, toluene, xylene; ethers such as diethyl ether, tetrahydrofuran, 1,4-dioxane, ethyleneglycol dimethyl ether, anisole, methyl tert-butyl ether, diisopropyl ether; halogenated hydrocarbons such as carbon tetrachloride, chloroform, dichloromethane, 1,2-dichloroethane, tetrachloroethane, chlorobenzene; acid amides such as N,N-dimethylformamide, 1,3-dimethyl-2-imidazolidinone, N-methylpyrrolidone; esters such as ethyl acetate, methyl acetate; sulfoxides such as dimethyl sulfoxide; ketones such as acetone, methyl ethyl ketone, methyl isobutyl ketone; nitriles such as acetonitrile, propionitrile; water; and mixed solvents thereof.

Examples of the base to be used in the reaction include organic bases such as triethylamine, pyridine, N-methylmorpholine, N-methylpiperidine, 4-dimethylaminopyridine, diisopropylethylamine, lutidine, collidine, diazabicycloundecene, diazabicyclononene; alkali metal carbonates such as lithium carbonate, sodium carbonate, potassium carbonate, cesium carbonate; alkali metal bicarbonates such as lithium bicarbonate, sodium bicarbonate, potassium bicarbonate, cesium bicarbonate; alkali metal hydroxides such as lithium hydroxide, sodium hydroxide, potassium hydroxide, cesium hydroxide; alkali metal halides such as sodium fluoride, potassium fluoride, cesium fluoride; alkali metal hydrides such as lithium hydride, sodium hydride, potassium hydride; and alkali metal alkoxides such as sodium methoxide, sodium ethoxide, sodium tert-butoxide, potassium tert-butoxide.

In the reaction, Compound (XX1) is used usually within a range of 1 to 10 molar ratio(s), and the base is used usually within a range of 1 to 10 molar ratio(s), as opposed as 1 mole of Compound (XU1).

The reaction temperature is usually within a range of −20 to 150° C. The reaction period of the reaction is usually within a range of 0.1 to 24 hours.

If necessary, an additive agent may be added to the reaction, and specifically includes, for example, 18-crown-6, dibenzo-18-crown-6 and the others. The additive agent is used usually within a range of 0.001 to 1.2 molar ratios as opposed to 1 mole of Compound (XU1).

When the reaction is completed, the reaction mixtures are extracted with organic solvent(s), and the resulting organic layers are worked up (for example, drying and concentration) to isolate Compound (G-1-1). The isolated Compound (G-1-1) may be further purified, for example, by chromatography and recrystallization.

(Reference Process Y)

Compound (1-5-W) can be prepared by reacting a compound of a formula (1-5-Y) (hereinafter, described as Compound (1-5-Y)) with a halogenating agent.

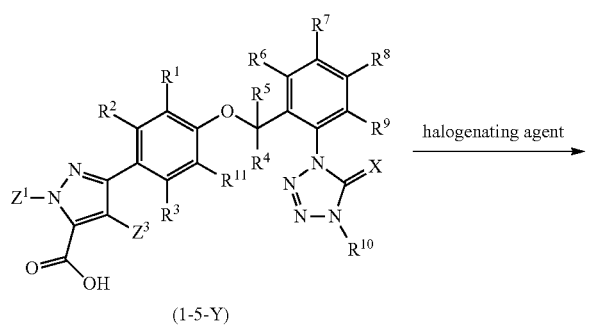

(1-5-Y)

halogenating agent

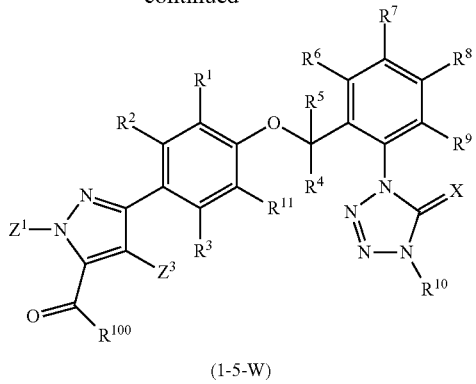

(1-5-W)

[wherein
$R^1$, $R^2$, $R^3$, $R^4$, $R^5$, $R^6$, $R^7$, $R^8$, $R^9$, $R^{10}$, $R^{11}$, $R^{100}$, X, $Z^1$ and $Z^3$ are the same as described above]

This reaction is usually carried out in a solvent.

Examples of the solvent to be used in the reaction include hydrocarbons such as heptane, hexane, cyclohexane, pentane, toluene, xylene; ethers such as diethyl ether, tetrahydrofuran, 1,4-dioxane, ethyleneglycol dimethyl ether, anisole, methyl tert-butyl ether, diisopropyl ether; halogenated hydrocarbons such as carbon tetrachloride, chloroform, dichloromethane, 1,2-dichloroethane, tetrachloroethane, chlorobenzene; esters such as ethyl acetate, methyl acetate; ketones such as acetone, methyl ethyl ketone, methyl isobutyl ketone; nitriles such as acetonitrile, propionitrile; and mixed solvents thereof.

Examples of the halogenating agent to be used in the reaction include phosphorous oxychloride, phosphorous trichloride, phosphorous pentachloride, thionyl chloride, phosphorous oxybromide, phosphorous tribromide, phosphorous pentabromide, phosphorus triiodide, oxalyl dichloride, oxalyl dibromide, triphosgene, diphosgene, phosgene and sulfuryl chloride.

In the reaction, the halogenating agent is used usually within a range of 1 to 10 molar ratio(s) as opposed to 1 mole of Compound (1-5-Y).

The reaction temperature is usually within a range of −20 to 150° C. The reaction period of the reaction is usually within a range of 0.1 to 24 hours.

A catalyst may be added to the reaction, and includes, for example, N,N-dimethylformide, triethylamine and diisopropylethylamine. The catalyst is used usually within a range of 0.001 to 1 molar ratio(s) as opposed to 1 mole of Compound (1-5-Y).

If necessary, organic bases such as triethylamine, pyridine, N-methylmorpholine, N-methylpiperidine, 4-dimethylaminopyridine, diisopropylethylamine, lutidine, collidine, diazabicycloundecene and diazabicyclononene, alkali metal carbonates such as lithium carbonate, sodium carbonate, potassium carbonate and cesium carbonate, alkali metal bicarbonates such as lithium bicarbonate, sodium bicarbonate, potassium bicarbonate and cesium bicarbonates and the others may be added to the reaction, and these compounds are used usually within a range of 0.05 to 5 molar ratio(s) as opposed to 1 mole of Compound (1-5-Y).

When the reaction is completed, the reaction mixtures are extracted with organic solvent(s), and the resulting organic layers are worked up (for example, drying and concentration) to isolate Compound (1-5-W). The isolated Compound (1-5-W) may be further purified, for example, by chromatography and recrystallization.

(Reference Process Z)

Compound (1-5-Y) can be prepared by reacting a Compound (1-5-S) with a hydrolytic agent.

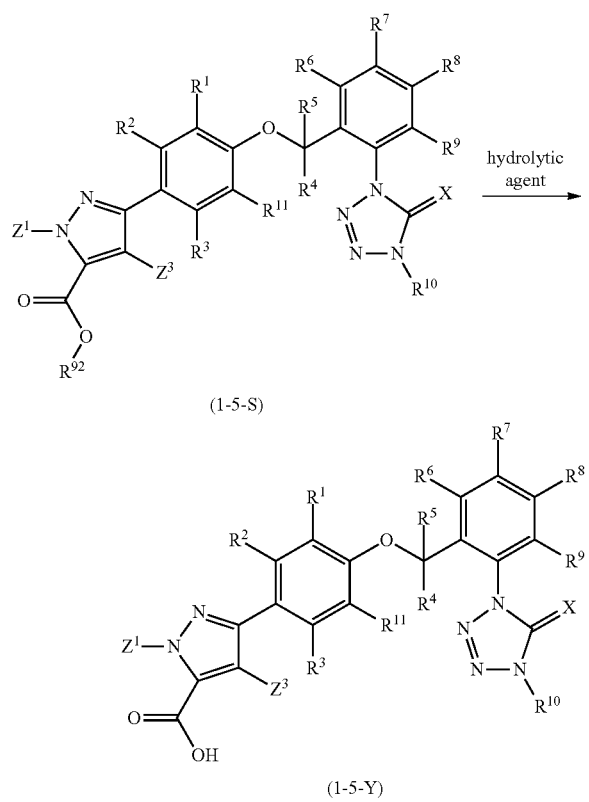

(1-5-S)

(1-5-Y)

[wherein
$R^1$, $R^2$, $R^3$, $R^4$, $R^5$, $R^6$, $R^7$, $R^8$, $R^9$, $R^{10}$, $R^{11}$, $R^{92}$, X, $Z^1$ and $Z^3$ are the same as described above]

This reaction is usually carried out in a solvent.

Examples of the solvent to be used in the reaction include water; alcohols such as methanol, ethanol, propanol, butanol; hydrocarbons such as heptane, hexane, cyclohexane, pentane, toluene, xylene; ethers such as diethyl ether, tetrahydrofuran, 1,4-dioxane, ethyleneglycol dimethyl ether, anisole, methyl tert-butyl ether, diisopropyl ether; halogenated hydrocarbons such as carbon tetrachloride, chloroform, dichloromethane, 1,2-dichloroethane, tetrachloroethane, chlorobenzene; ketones such as acetone, methyl ethyl ketone, methyl isobutyl ketone; and mixed solvents thereof.

Examples of the hydrolytic agent to be used in the reaction include bases such as aqueous potassium hydroxide solution and aqueous sodium hydroxide solution; and acids such as hydrochloric acid and sulfuric acid.

In the reaction, the hydrolytic agent is used usually within a range of 0.5 to 20 molar ratio(s) as opposed to 1 mole of Compound (1-5-S).

The reaction temperature is usually within a range of −20 to 150° C. The reaction period of the reaction is usually within a range of 0.1 to 72 hours.

When the reaction is completed, the reaction mixtures are extracted with organic solvent(s), and the resulting organic layers are worked up (for example, drying and concentration) to isolate Compound (1-5-Y). The isolated Compound (1-5-Y) may be further purified, for example, by chromatography and recrystallization.

(Reference Process AA)

A compound of a formula (YA3) (hereinafter, described as Compound (YA3)) can be prepared by reacting a compound of a formula (YA1) (hereinafter, described as Compound (YA1)) with a compound of a formula (YA2) (hereinafter, described as Compound (YA2)).

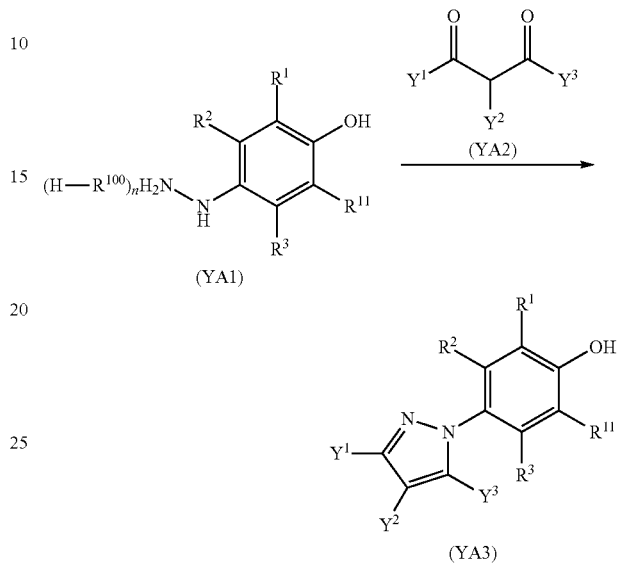

(YA1)

(YA3)

[wherein
$R^1$, $R^2$, $R^3$, $R^{11}$, $R^{100}$, $Y^1$, $Y^2$ and $Y^3$ are the same as described above; and n represents 0 or 1]

This reaction is usually carried out in a solvent.

Examples of the solvent to be used in the reaction include hydrocarbons such as heptane, hexane, cyclohexane, pentane, toluene, xylene; ethers such as diethyl ether, tetrahydrofuran, 1,4-dioxane, ethyleneglycol dimethyl ether, anisole, methyl tert-butyl ether, diisopropyl ether; halogenated hydrocarbons such as carbon tetrachloride, chloroform, dichloromethane, 1,2-dichloroethane, tetrachloroethane, chlorobenzene; acid amides such as N,N-dimethylformamide, 1,3-dimethyl-2-imidazolidinone, N-methylpyrrolidone; esters such as ethyl acetate, methyl acetate; sulfoxides such as dimethyl sulfoxide; nitriles such as acetonitrile, propionitrile; alcohols such as methanol, ethanol, propanol, butanol; water; and mixed solvents thereof.

In the reaction, Compound (YA2) is used usually within a range of 1 to 10 molar ratio(s) as opposed as 1 mole of Compound (YA1).

The reaction temperature is usually within a range of −20 to 150° C. The reaction period of the reaction is usually within a range of 0.1 to 24 hours.

When the reaction is completed, the reaction mixtures are extracted with organic solvent(s), and the resulting organic layers are worked up (for example, drying and concentration) to isolate Compound (YA3). Alternatively, the reaction mixtures are worked up (for example, concentration) to isolate Compound (YA3). The isolated Compound (YA3) may be further purified, for example, by chromatography and recrystallization.

(Reference Process AB)

Compound (YA1) can be prepared by reacting a compound of a formula (YB1) (hereinafter, described as Compound (YB1)) with a nitrosating agent, followed by reacting the resulting mixtures with a reducing agent.

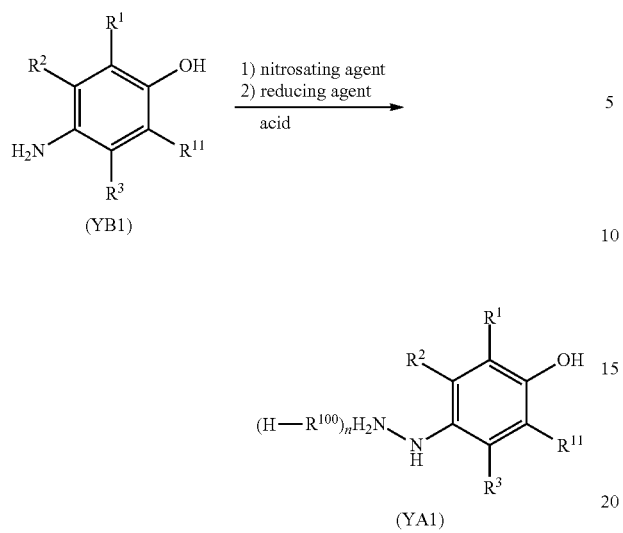

(YB1)

(YA1)

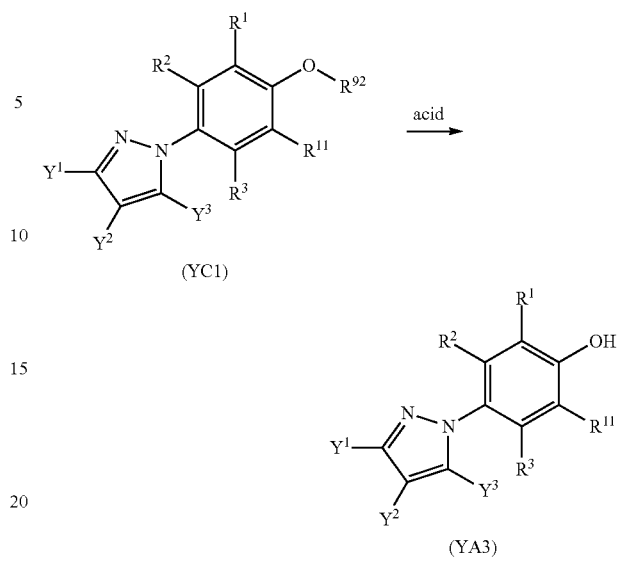

(YC1)

(YA3)

[wherein $R^1$, $R^2$, $R^3$, $R^{11}$, $R^{100}$ and n are the same as described above]

This reaction is usually carried out in a solvent.

Examples of the solvent to be used in the reaction include alcohols such as methanol, ethanol, propanol, butanol; water; and mixed solvents thereof.

Examples of the nitrosating agent to be used in the reaction include sodium nitrite, potassium nitrite, tert-butyl nitrite and isoamyl nitrite.

Examples of the acid to be used in the reaction include acetic acid, hydrochloric acid and hydrobromic acid, and these aqueous solutions may be used as solvent.

Examples of the reducing agent to be used in the reaction include iron, zinc and tin, and specifically, include tin(II) chloride.

In the reaction, the nitrosating agent is used usually within a range of 1 to 10 molar ratio(s), the reducing agent is used usually within a range of 1 to 10 molar ratio(s) and the acid is used usually within a range of 1 to an excess molar ratio(s), as opposed as 1 mole of Compound (YB1).

The reaction temperature is usually within a range of −20 to 150° C. The reaction period of the reaction is usually within a range of 0.1 to 24 hours.

When the reaction is completed, the reaction mixtures are extracted with organic solvent(s), and the resulting organic layers are worked up (for example, drying and concentration) to isolate Compound (YA1). Alternatively, the reaction mixtures are worked up (for example, concentration) to isolate Compound (YA1). The isolated Compound (YA1) may be further purified, for example, by chromatography and recrystallization.

(Reference Process AC)

Compound (YA3) can be prepared by reacting a compound of a formula (YC1) (hereinafter, described as Compound (YC1)) with an acid.

[wherein $R^1$, $R^2$, $R^3$, $R^{11}$, $R^{92}$, $Y^1$, $Y^2$ and $Y^3$ are the same as described above]

This reaction is usually carried out in a solvent.

Examples of the solvent to be used in the reaction include alcohols such as methanol, ethanol, propanol, butanol; water; acetic acid; and mixed solvents thereof.

Examples of the acid to be used in the reaction include acetic acid, hydrochloric acid and hydrobromic acid, and these aqueous solutions may be used as solvent.

In the reaction, the acid is used usually in a range of a large excess molar ratios as opposed as 1 mole of Compound (YC1).

The reaction temperature is usually within a range of −20 to 150° C. The reaction period of the reaction is usually within a range of 0.1 to 100 hours.

When the reaction is completed, the reaction mixtures are extracted with organic solvent(s), and the resulting organic layers are worked up (for example, drying and concentration) to isolate Compound (YA3). Alternatively, the reaction mixtures are worked up (for example, concentration) to isolate Compound (YA3). The isolated Compound (YA3) may be further purified, for example, by chromatography and recrystallization.

(Reference Process AD)

Compound (YC1) can be prepared by reacting a compound of a formula (YD1) (hereinafter, described as Compound (YD1)) with a compound of a formula (YD2) (hereinafter, described as Compound (YD2)) in the presence of a copper reagent and a base.

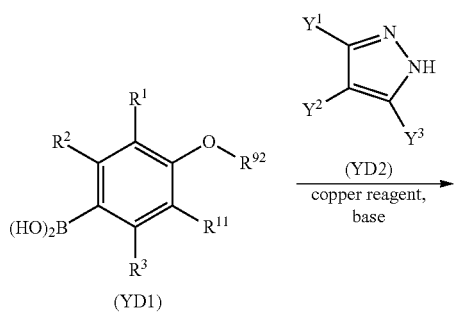

(YD1)

-continued

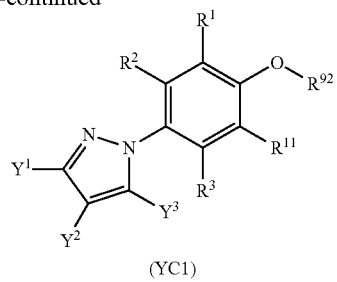

(YC1)

[wherein
$R^1$, $R^2$, $R^3$, $R^{11}$, $R^{92}$, $Y^1$, $Y^2$ and $Y^3$ are the same as described above]

This reaction is usually carried out in a solvent.

Examples of the solvent to be used in the reaction include hydrocarbons such as heptane, hexane, cyclohexane, pentane, toluene, xylene; ethers such as diethyl ether, tetrahydrofuran, 1,4-dioxane, ethyleneglycol dimethyl ether, anisole, methyl tert-butyl ether, diisopropyl ether; halogenated hydrocarbons such as carbon tetrachloride, chloroform, dichloromethane, 1,2-dichloroethane, tetrachloroethane, chlorobenzene; acid amides such as N,N-dimethylformamide, 1,3-dimethyl-2-imidazolidinone, N-methylpyrrolidone; esters such as ethyl acetate, methyl acetate; sulfoxides such as dimethyl sulfoxide; nitriles such as acetonitrile, propionitrile; alcohols such as methanol, ethanol, propanol, butanol; water; and mixed solvents thereof.

Examples of the copper reagent to be used in the reaction include copper(II) acetate.

Examples of the base to be used in the reaction include organic bases such as triethylamine, pyridine, N-methylmorpholine, N-methylpiperidine, 4-dimethylaminopyridine, diisopropylethylamine, lutidine, collidine, diazabicycloundecene, diazabicyclononene; alkali metal carbonates such as lithium carbonate, sodium carbonate, potassium carbonate, cesium carbonate; alkali metal bicarbonates such as lithium bicarbonate, sodium bicarbonate, potassium bicarbonate, cesium bicarbonate; alkali metal hydroxides such as lithium hydroxide, sodium hydroxide, potassium hydroxide, cesium hydroxide; alkali metal halides such as sodium fluoride, potassium fluoride, cesium fluoride; alkali metal hydrides such as lithium hydride, sodium hydride, potassium hydride; and alkali metal alkoxides such as sodium tert-butoxide, potassium tert-butoxide.

In the reaction, Compound (YD2) is used usually within a range of 1 to 10 molar ratio(s), the copper reagent is used usually within a range of 1 to 10 molar ratio(s), and the base is used usually within a range of 1 to 10 molar ratio(s), as opposed as 1 mole of Compound (YD1).

If necessary, dehydration agent such as molecular sieve may be used in the reaction, and the dehydration agent is used usually within a range of 100 to 500 percent by mass as opposed as 1 mole of Compound (YD1).

The reaction temperature is usually within a range of −20 to 150° C. The reaction period of the reaction is usually within a range of 0.1 to 120 hours.

When the reaction is completed, the reaction mixtures are extracted with organic solvent(s), and the resulting organic layers are worked up (for example, drying and concentration) to isolate Compound (YC1). The isolated Compound (YC1) may be further purified, for example, by chromatography and recrystallization.

(Reference Process AE)

A compound of a formula (YE2) (hereinafter, described as Compound (YE2)) can be prepared by reacting a compound of a formula (YE1) (hereinafter, described as Compound (YE1)) with an acid.

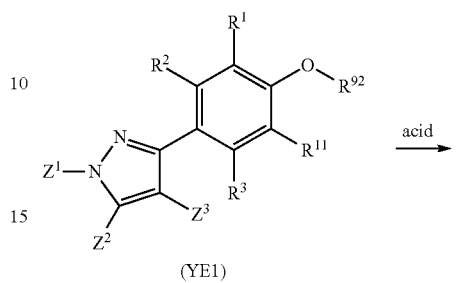

(YE1)

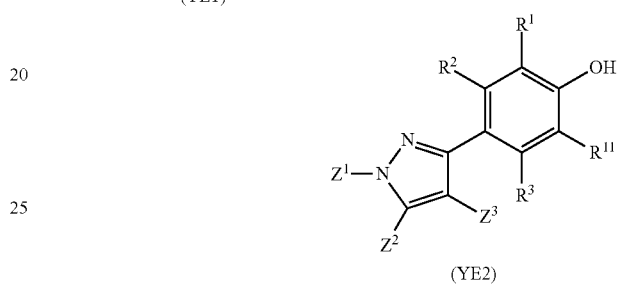

(YE2)

[wherein
$R^1$, $R^2$, $R^3$, $R^{11}$, $R^{92}$, $Z^1$, $Z^2$ and $Z^3$ are the same as described above]

The reaction can be carried out according to Reference Process AC.

(Reference Process AF)

A compound of a formula (YF2) (hereinafter, described as Compound (YF2)) can be prepared by reacting a compound of a formula (YF1) (hereinafter, described as Compound (YF1)) with an acid.

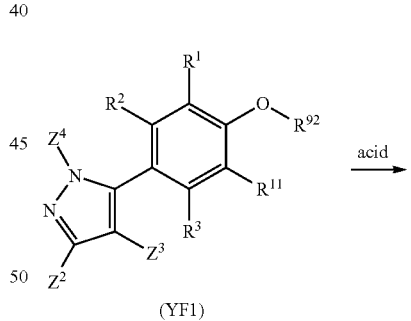

(YF1)

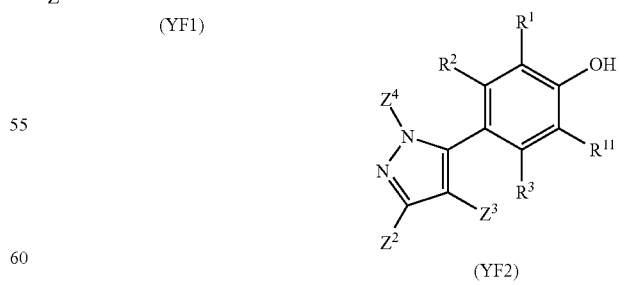

(YF2)

[wherein
$R^1$, $R^2$, $R^3$, $R^{11}$, $R^{92}$, $Z^2$, $Z^3$ and $Z^4$ are the same as described above]

The reaction can be carried out according to Reference Process AC.

(Reference Process AG)

Compound (YE1) can be prepared by reacting a compound of a formula (YG1) (hereinafter, described as Compound (YG1)) with Compound (H-1) in the presence of a base.

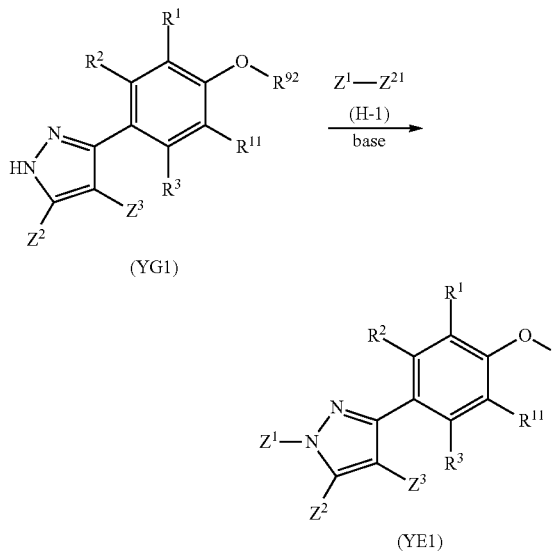

[wherein $R^1$, $R^2$, $R^3$, $R^{11}$, $R^{92}$, $Z^1$, $Z^2$, $Z^3$ and $Z^{21}$ are the same as described above]

The reaction can be carried out according to Process H.

(Reference Process AH)

Compound (YF2) can be prepared by reacting Compound (YG1) with Compound (I-1) in the presence of a base.

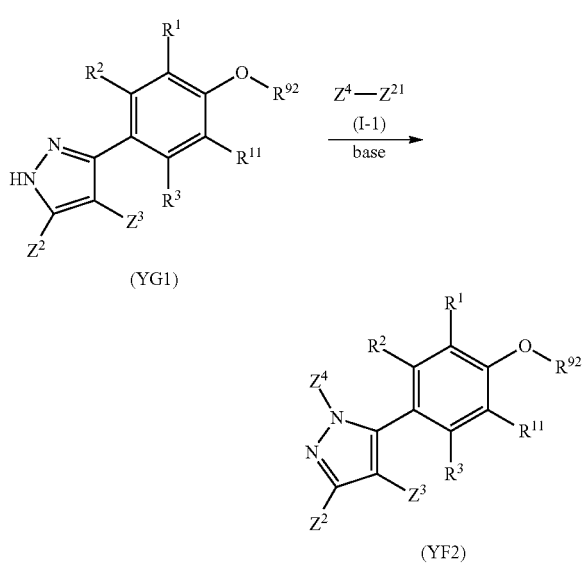

[wherein $R^1$, $R^2$, $R^3$, $R^{11}$, $R^{92}$, $Z^2$, $Z^3$, $Z^4$ and $Z^{21}$ are the same as described above]

The reaction can be carried out according to Process I.

(Reference Process AI)

A compound of a formula (YI2) (hereinafter, described as Compound (YI2)) can be prepared by reacting a compound of a formula (YI1) (hereinafter, described as Compound (YI1)) with hydrazines.

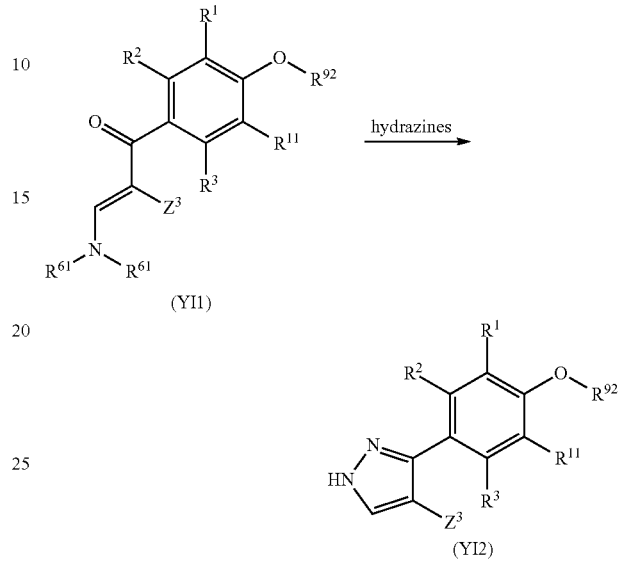

[wherein $R^1$, $R^2$, $R^3$, $R^{11}$, $R^{61}$, $R^{92}$ and $Z^3$ are the same as described above]

The reaction can be carried out according to Process F.

(Reference Process AJ)

Compound (YG1) can be prepared by reacting a compound of a formula (YJ1) (hereinafter, described as Compound (YJ1)) with hydrazines.

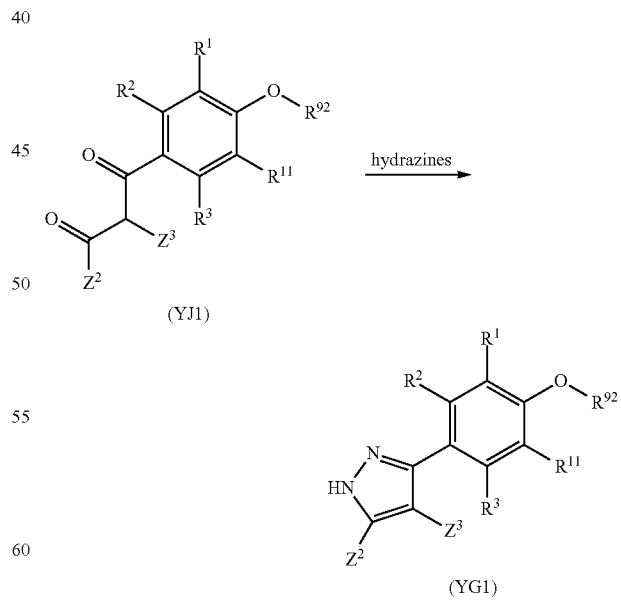

[wherein $R^1$, $R^2$, $R^3$, $R^{11}$, $R^{92}$, $Z^2$ and $Z^3$ are the same as described above]

The reaction can be carried out according to Process G.

(Reference Process AK)

Compound (YI1) can be prepared by reacting a compound of a formula (YK1) (hereinafter, described as Compound (YK1)) with Compound (XU2).

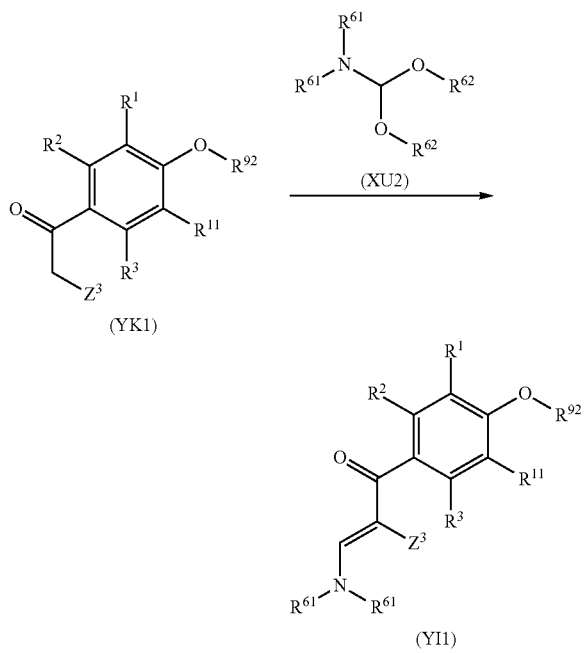

[wherein
$R^1$, $R^2$, $R^3$, $R^{11}$, $R^{61}$, $R^{62}$, $R^{92}$ and $Z^3$ are the same as described above]

The reaction can be carried out according to Reference Process U.

(Reference Process AL)

Compound (YJ1) can be prepared by reacting a compound of a formula (YL1) (hereinafter, described as Compound (YL1)) with Compound (XW1) in the presence of a base.

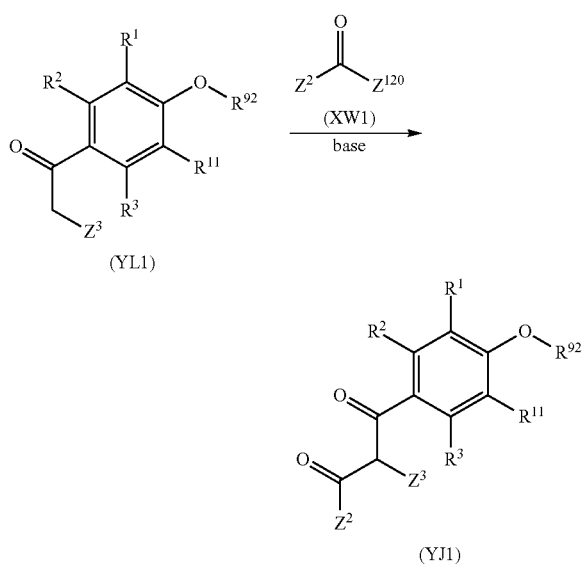

[wherein
$R^1$, $R^2$, $R^3$, $R^{11}$, $R^{92}$, $Z^2$, $Z^3$ and $Z^{120}$ are the same as described above]

The reaction can be carried out according to Reference Process W.

(Reference Process AM)

Compound (YJ1) can be prepared also by reacting a compound of a formula (YM1) (hereinafter, described as Compound (YM1)) with a compound of a formula (YM2) (hereinafter, described as Compound (YM2)) in the presence of a base.

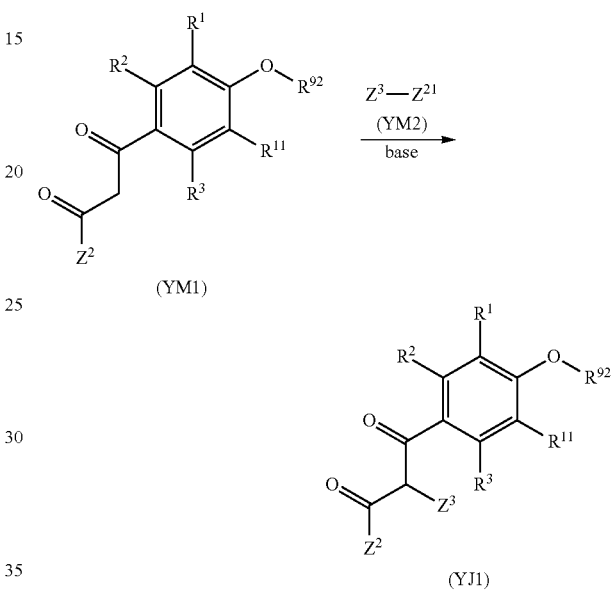

[wherein
$R^1$, $R^2$, $R^3$, $R^{11}$, $R^{92}$, $Z^2$, $Z^3$ and $Z^{21}$ are the same as described above]

This reaction is usually carried out in a solvent.

Examples of the solvent to be used in the reaction include hydrocarbons such as heptane, hexane, cyclohexane, pentane, toluene, xylene; ethers such as diethyl ether, tetrahydrofuran, 1,4-dioxane, ethyleneglycol dimethyl ether, anisole, methyl tert-butyl ether, diisopropyl ether; halogenated hydrocarbons such as carbon tetrachloride, chloroform, dichloromethane, 1,2-dichloroethane, tetrachloroethane, chlorobenzene; acid amides such as N,N-dimethylformamide, 1,3-dimethyl-2-imidazolidinone, N-methylpyrrolidone; esters such as ethyl acetate, methyl acetate; sulfoxides such as dimethyl sulfoxide; ketones such as acetone, methyl ethyl ketone, methyl isobutyl ketone; nitriles such as acetonitrile, propionitrile; water; and mixed solvents thereof.

Compound (YM2) to be used in the reaction can be usually used as a commercially available product. Specific examples include alkyl halides such as chlorodifluoromethane, methyl bromide, ethyl bromide, propyl bromide, methyl iodide, ethyl iodide, propyl bromide, aryl bromide, cyclopropyl bromide, 1,1-difluoro-2-iodoethane; alkyl or aryl sulfates such as dimethyl sulfate, methyl p-toluenesulfonate, ethyl p-toluenesulfonate, propyl p-toluenesulfonate, methyl methanesulfonate, ethyl methanesulfonate and propyl methanesulfonate.

Examples of the base to be used in the reaction include organic bases such as triethylamine, pyridine, N-methylmorpholine, N-methylpiperidine, 4-dimethylaminopyridine, diisopropylethylamine, lutidine, collidine, diazabicycloundecene, diazabicyclononene; alkali metal carbonates such as lithium carbonate, sodium carbonate, potassium carbonate, cesium carbonate; alkali metal bicarbonates such as lithium bicarbonate, sodium bicarbonate, potassium bicarbonate, cesium bicarbonate; alkali metal hydroxides such as lithium hydroxide, sodium hydroxide, potassium hydroxide, cesium hydroxide; alkali metal halides such as sodium fluoride, potassium fluoride, cesium fluoride; alkali metal hydrides such as lithium hydride, sodium hydride, potassium hydride; and alkali metal alkoxides such as sodium tert-butoxide, potassium tert-butoxide.

If necessary, an additive agent may be added to the reaction, and specifically, includes tetrabutylammonium bromide and tetrabutylammonium fluoride and the others.

In the reaction, Compound (YM2) is used usually within a range of 1 to 10 molar ratio(s), the base is used usually within a range of 1 to 10 molar ratio(s), and the additive agent is used usually within a range of 0.01 to 1 molar ratio(s), as opposed to 1 mole of Compound (YM1).

The reaction temperature is usually within a range of −20 to 150° C. The reaction period of the reaction is usually within a range of 0.1 to 24 hours.

When the reaction is completed, the reaction mixtures are extracted with organic solvent(s), and the resulting organic layers are worked up (for example, drying and concentration) to isolate Compound (YJ1). The isolated present Compound (YJ1) may be further purified, for example, by chromatography and recrystallization.

(Reference Process AN)

A compound of a formula (YN2) (hereinafter, described as Compound (YN2)) can be prepared by reacting a compound of a formula (YN1) (hereinafter, described as Compound (YN1)) with an acid.

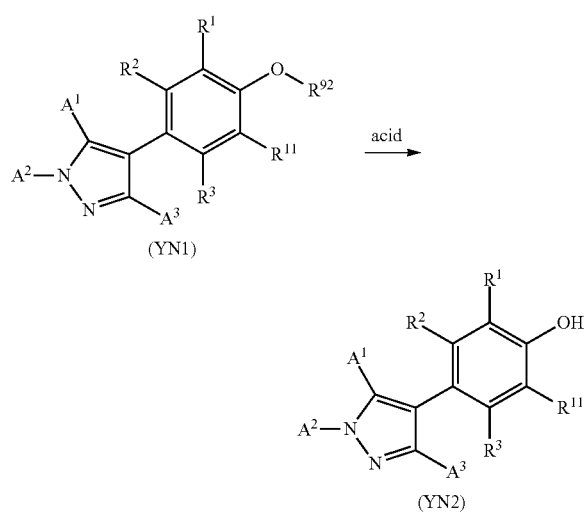

[wherein $R^1$, $R^2$, $R^3$, $R^{11}$, $R^{92}$, $A^1$, $A^2$ and $A^3$ are the same as described above]

The reaction can be carried out according to Reference Process AC.

(Reference Process AO)

Compound (YN1) can be prepared by coupling a compound of a formula (YO1) (hereinafter, described as Compound (YO1)) with a compound of a formula (YO2) (hereinafter, described as Compound (YO2)) in the presence of a base and a catalyst.

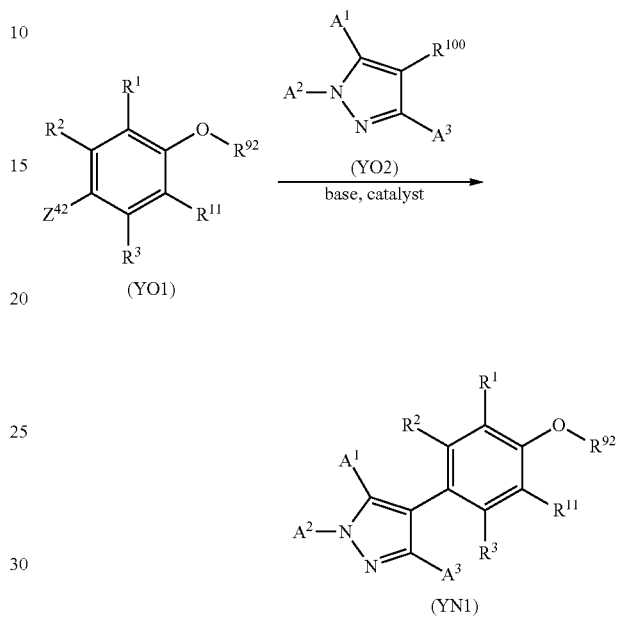

[wherein $R^1$, $R^2$, $R^3$, $R^{11}$, $R^{92}$, $R^{100}$, $A^1$, $A^2$, $A^3$ and $Z^{42}$ are the same as described above]

The reaction can be carried out according to Process D.

(Reference Process AP)

Compound (YO2) can be prepared by coupling a compound of a formula (YP1) (hereinafter, described as Compound (YP1)) with a compound of a formula (YP2) (hereinafter, described as Compound (YP2)) in the presence of a base.

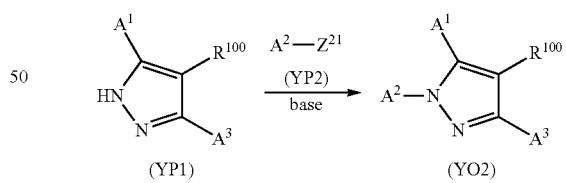

[wherein $R^{100}$, $A^1$, $A^2$, $A^3$ and $Z^{21}$ are the same as described above]

The reaction can be carried out according to Process H.

(Reference Process AQ)

Compound (YE1) wherein $Z^3$ represents $R^{51}$, i.e., a compound of a formula (YE1-1) (hereinafter, described as Compound (YE1-1)) can be prepared by coupling a compound of a formula (YE1-2) (hereinafter, described as Compound (YE1-2)) with Compound (E-2) in the presence of a base and a catalyst.

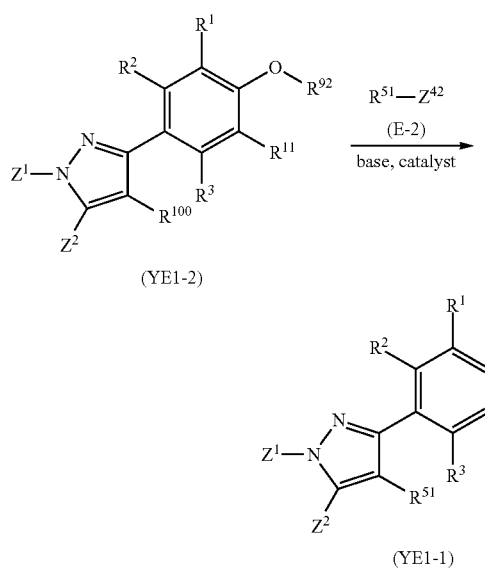

(YE1-2)

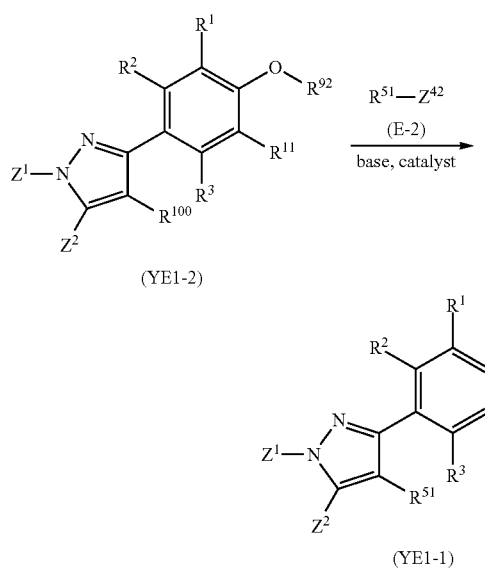

(YE1-1)

[wherein
$R^1$, $R^2$, $R^3$, $R^{11}$, $R^{51}$, $R^{92}$, $R^{100}$, $Z^1$, $Z^2$ and $Z^{42}$ are the same as described above]

The reaction can be carried out according to Process L.

(Reference Process AR)

Compound (YE1-2) can be prepared by reacting a compound of a formula (YE1) wherein $Z^3$ represents a hydrogen atom, i.e., a compound of a formula (YE1-3) (hereinafter, described as Compound (YE1-3)) with a halogenating agent.

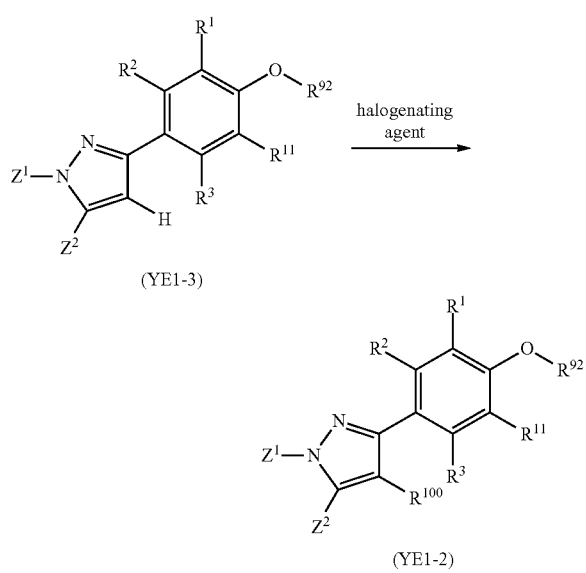

(YE1-3)

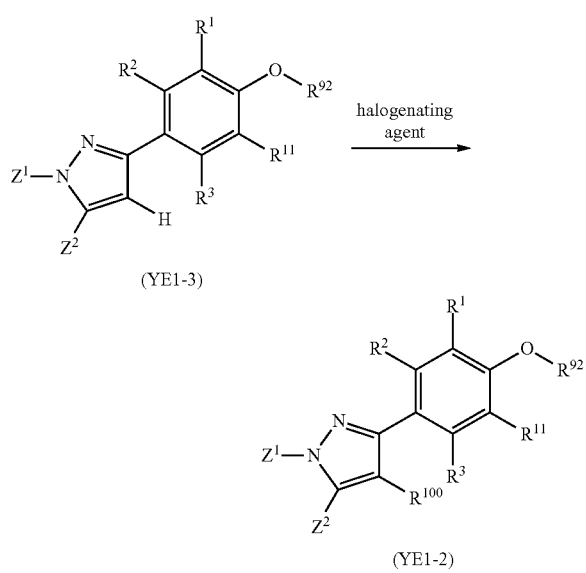

(YE1-2)

[wherein
$R^1$, $R^2$, $R^3$, $R^{11}$, $R^{92}$, $R^{100}$, $Z^1$ and $Z^2$ are the same as described above]

The reaction can be carried out according to Process J.

(Reference Process AS)

A compound of a formula (XE1) wherein $Z^1$ represents $R^{92}$ and $Z^2$ represents a chloro atom, i.e., a compound of a formula (YE1-11) (hereinafter, described as Compound (XE1-11)) can be prepared by reacting a compound of a formula (YE1) wherein $Z^1$ represents $R^{92}$ and $Z^2$ represents a hydroxy group, i.e., a compound of a formula (YE1-12) (hereinafter, described as Compound (XE1-12)) with a chlorinating agent.

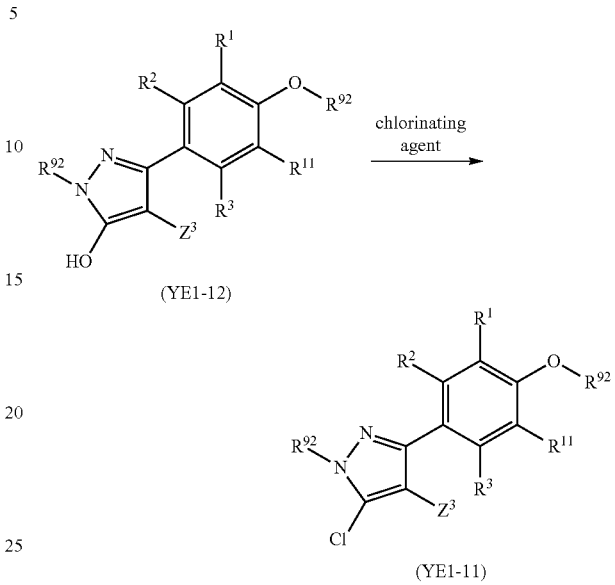

(YE1-12)

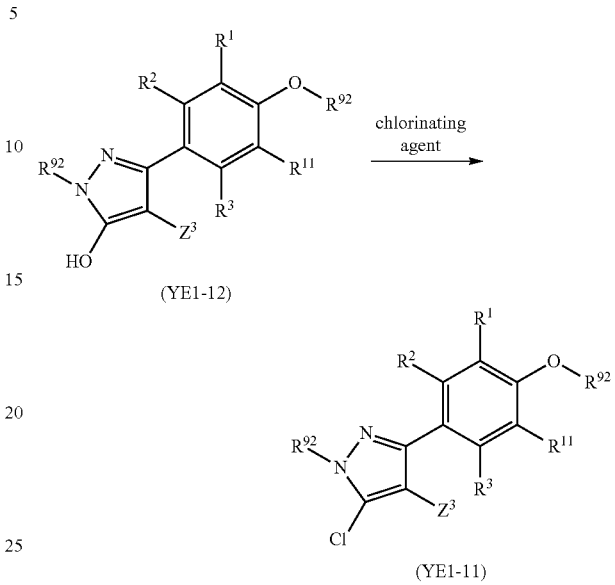

(YE1-11)

[wherein
$R^1$, $R^2$, $R^3$, $R^{11}$, $R^{92}$ and $Z^3$ are the same as described above]

This reaction is usually carried out in a solvent or in a solvent-free system.

Examples of the solvent that can be used in the reaction include hydrocarbons such as heptane, hexane, cyclohexane, pentane, toluene, xylene; ethers such as diethyl ether, tetrahydrofuran, 1,4-dioxane, ethyleneglycol dimethyl ether, anisole, methyl tert-butyl ether, diisopropyl ether; halogenated hydrocarbons such as carbon tetrachloride, chloroform, dichloromethane, 1,2-dichloroethane, tetrachloroethane, chlorobenzene; esters such as ethyl acetate, methyl acetate; sulfoxides such as dimethyl sulfoxide; ketones such as acetone, methyl ethyl ketone, methyl isobutyl ketone; nitriles such as acetonitrile, propionitrile; and mixed solvents thereof.

The chlorinating agent to be used in the reaction may be usually used as a commercially available product. Specific examples include thionyl chloride, phosphorous oxychloride, phosphorous pentachloride and mixtures thereof. If necessary, a base may be added to the reaction, and specifically, includes organic bases such as triethylamine, pyridine, N-methylmorpholine, N-methylpiperidine, 4-dimethylaminopyridine, diisopropylethylamine, lutidine, collidine, diazabicycloundecene and diazabicyclononene.

In the reaction, the chlorinating agent is used usually within a range of 1 to a large excess molar ratio(s), and the base is used usually within a range of 1 to 10 molar ratio(s), as opposed to 1 mole of Compound (YE1-12).

The reaction temperature is usually within a range of −20 to 150° C. The reaction period of the reaction is usually within a range of 0.1 to 72 hours.

When the reaction is completed, the reaction mixtures are extracted with organic solvent(s), and the resulting organic layers are worked up (for example, drying and concentration) to isolate Compound (YE1-11). The isolated present Compound (YE1-11) may be further purified, for example, by chromatography and recrystallization.

(Reference Process AT)

Compound (YE1-12) can be prepared by reacting a compound of a formula (YE1-13) (hereinafter, described as Compound (XE1-13)) with Compound (AT1).

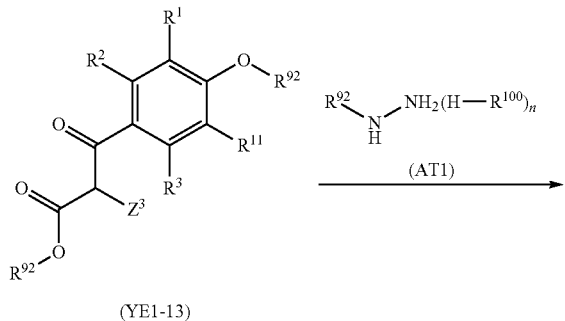

(YE1-13)

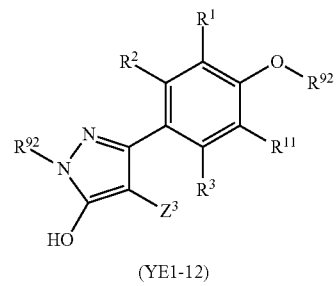

(YE1-12)

[wherein $R^1$, $R^2$, $R^3$, $R^{11}$, $R^{92}$ and $Z^3$ are the same as described above; and n is 0 or 1]

This reaction is usually carried out in a solvent or in a solvent-free system.

Examples of the solvent that can be used in the reaction include hydrocarbons such as heptane, hexane, cyclohexane, pentane, toluene, xylene; ethers such as diethyl ether, tetrahydrofuran, 1,4-dioxane, ethyleneglycol dimethyl ether, anisole, methyl tert-butyl ether, diisopropyl ether; halogenated hydrocarbons such as carbon tetrachloride, chloroform, dichloromethane, 1,2-dichloroethane, tetrachloroethane, chlorobenzene; acid amides such as N,N-dimethylformamide, 1,3-dimethyl-2-imidazolidinone, N-methylpyrrolidone; esters such as ethyl acetate, methyl acetate; sulfoxides such as dimethyl sulfoxide; nitriles such as acetonitrile, propionitrile; water; and mixed solvents thereof. If necessary, an acid may be added to the reaction, and examples of the acid to be used in the reaction include hydrochloric acid, sulfuric acid, acetic acid, hydrobromic acid and p-toluenesulfonic acid.

In the reaction, Compound (AI1) is used usually within a range of 1 to 100 molar ratio(s), and the acid is used usually within a range of 1 to 100 molar ratio(s), as opposed to 1 mole of Compound (YE1-13).

The reaction temperature is usually within a range of −20 to 150° C. The reaction period of the reaction is usually within a range of 0.1 to 24 hours.

When the reaction is completed, the reaction mixtures are extracted with organic solvent(s), and the resulting organic layers are worked up (for example, drying, concentration and filtration) to isolate Compound (YE1-12). The isolated present Compound (YE1-12) may be further purified, for example, by chromatography and recrystallization.

(Reference Process AU)

Compound (YE1-13) can be prepared by reacting Compound (YL1) with a compound of a formula (AU1) (hereinafter, described as Compound (AU1)) in the presence of a base.

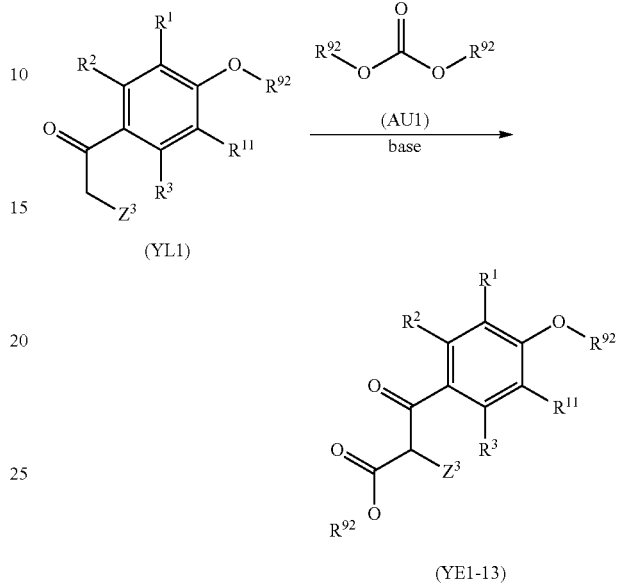

[wherein $R^1$, $R^2$, $R^3$, $R^{11}$, $R^{92}$ and $Z^3$ are the same as described above]

This reaction is usually carried out in a solvent.

Examples of the solvent that can be used in the reaction include hydrocarbons such as heptane, hexane, cyclohexane, pentane, toluene, xylene; ethers such as diethyl ether, tetrahydrofuran, 1,4-dioxane, ethyleneglycol dimethyl ether, anisole, methyl tert-butyl ether, diisopropyl ether; halogenated hydrocarbons such as carbon tetrachloride, chloroform, dichloromethane, 1,2-dichloroethane, tetrachloroethane, chlorobenzene; acid amides such as N,N-dimethylformamide, 1,3-dimethyl-2-imidazolidinone, N-methylpyrrolidone; esters such as ethyl acetate, methyl acetate; sulfoxides such as dimethyl sulfoxide; ketones such as acetone, methyl ethyl ketone, methyl isobutyl ketone; nitriles such as acetonitrile, propionitrile; water; and mixed solvents thereof.

Examples of the base to be used in the reaction include organic bases such as triethylamine, pyridine, N-methylmorpholine, N-methylpiperidine, 4-dimethylaminopyridine, diisopropylethylamine, lutidine, collidine, diazabicycloundecene, diazabicyclononene; alkali metal carbonates such as lithium carbonate, sodium carbonate, potassium carbonate, cesium carbonate; alkali metal bicarbonates such as lithium bicarbonate, sodium bicarbonate, potassium bicarbonate, cesium bicarbonate; alkali metal hydroxides such as lithium hydroxide, sodium hydroxide, potassium hydroxide, cesium hydroxide; alkali metal halides such as sodium fluoride, potassium fluoride, cesium fluoride; alkali metal hydrides such as lithium hydride, sodium hydride, potassium hydride; and alkali metal alkoxides such as sodium tert-butoxide, potassium tert-butoxide.

In the reaction, Compound (AU1) is used usually within a range of 1 to 10 molar ratio(s), and the base is used usually within a range of 1 to 10 molar ratio(s), as opposed to 1 mole of Compound (YL1).

The reaction temperature is usually within a range of −20 to 150° C. The reaction period of the reaction is usually within a range of 0.1 to 24 hours.

If necessary, an additive agent may be added to the reaction, and specifically includes, for example, 18-crown-6, dibenzo-18-crown-6 and the others. The additive agent is used usually within a range of 0.001 to 1.2 molar ratios as opposed to 1 mole of Compound (XL1).

When the reaction is completed, the reaction mixtures are extracted with organic solvent(s), and the resulting organic layers are worked up (for example, drying and concentration) to isolate Compound (YE1-13). The isolated present Compound (YE1-13) may be further purified, for example, by chromatography and recrystallization.

(Reference Process AV)

Compound (XV1-2) can be prepared by reacting a compound of a formula (XV1-3) (hereinafter, described as Compound (XV1-3)) in the presence of an acid.

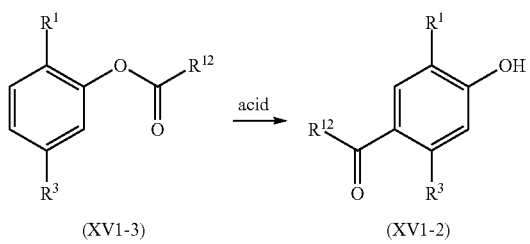

[wherein $R^1$, $R^3$ and $R^{12}$ are the same as described above]

This reaction is usually carried out in a solvent.

Examples of the solvent that can be used in the reaction include hydrocarbons such as heptane, hexane, cyclohexane, pentane, toluene, xylene; ethers such as diethyl ether, tetrahydrofuran, 1,4-dioxane, ethyleneglycol dimethyl ether, anisole, methyl tert-butyl ether, diisopropyl ether; halogenated hydrocarbons such as carbon tetrachloride, chloroform, dichloromethane, 1,2-dichloroethane, tetrachloroethane, chlorobenzene; nitriles such as nitromethane, acetonitrile, propionitrile; and mixed solvents thereof.

Examples of the acid to be used in the reaction include aluminum trichloride, titanium chloride, iron trichloride, hydrogen fluoride, hypochlorous acid and polyphosphoric acid.

In the reaction, the acid is used usually within a range of 1 to 10 molar ratio(s) as opposed to 1 mole of Compound (XV1-3).

The reaction temperature is usually within a range of −20 to 150° C. The reaction period of the reaction is usually within a range of 0.1 to 72 hours.

When the reaction is completed, the reaction mixtures are extracted with organic solvent(s), and the resulting organic layers are worked up (for example, drying and concentration) to isolate Compound (YV1-2). The isolated present Compound (YV1-2) may be further purified, for example, by chromatography and recrystallization.

(Reference Process AW)

Compound (XV1-3) can be prepared by reacting a compound of a formula (XV1-4) (hereinafter, described as Compound (XV1-4)) with a compound of a formula (AW1) (hereinafter, described as Compound (AW1)) in the presence of a base.

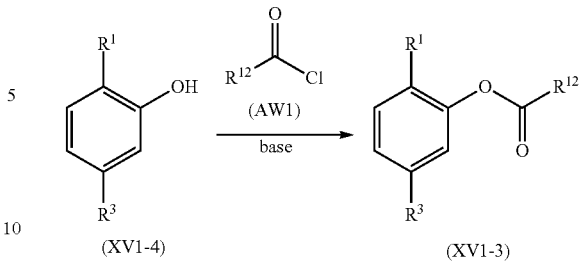

[wherein $R^1$, $R^3$ and $R^{12}$ are the same as described above]

This reaction is usually carried out in a solvent.

Examples of the solvent that can be used in the reaction include hydrocarbons such as heptane, hexane, cyclohexane, pentane, toluene, xylene; ethers such as diethyl ether, tetrahydrofuran, 1,4-dioxane, ethyleneglycol dimethyl ether, anisole, methyl tert-butyl ether, diisopropyl ether; halogenated hydrocarbons such as carbon tetrachloride, chloroform, dichloromethane, 1,2-dichloroethane, tetrachloroethane, chlorobenzene; acid amides such as N,N-dimethylformamide, 1,3-dimethyl-2-imidazolidinone, N-methylpyrrolidone; esters such as ethyl acetate, methyl acetate; sulfoxides such as dimethyl sulfoxide; nitriles such as acetonitrile, propionitrile; and mixed solvents thereof.

Examples of the base to be used in the reaction include organic bases such as triethylamine, pyridine, N-methylmorpholine, N-methylpiperidine, 4-dimethylaminopyridine, diisopropylethylamine, lutidine, collidine, diazabicycloundecene, diazabicyclononene; alkali metal carbonates such as lithium carbonate, sodium carbonate, potassium carbonate, cesium carbonate; alkali metal bicarbonates such as lithium bicarbonate, sodium bicarbonate, potassium bicarbonate, cesium bicarbonate; alkali metal hydroxides such as lithium hydroxide, sodium hydroxide, potassium hydroxide, cesium hydroxide; alkali metal halides such as sodium fluoride, potassium fluoride, cesium fluoride; alkali metal hydrides such as lithium hydride, sodium hydride, potassium hydride; and alkali metal alkoxides such as sodium tert-butoxide, potassium tert-butoxide.

In the reaction, Compound (AW1) is used usually within a range of 1 to 10 molar ratio(s), and the base is used usually within a range of 1 to 10 molar ratio(s), as opposed to 1 mole of Compound (XV1-4).

The reaction temperature is usually within a range of −78 to 150° C. The reaction period of the reaction is usually within a range of 0.1 to 72 hours.

When the reaction is completed, the reaction mixtures are extracted with organic solvent(s), and the resulting organic layers are worked up (for example, drying and concentration) to isolate Compound (YV1-3). The isolated present Compound (YV1-3) may be further purified, for example, by chromatography and recrystallization.

(Reference Process AX)

Compound (YE1) wherein $Z^1$ represents $R^{92}$, and $Z^2$ represents Rf., i.e., a compound of a formula (YE1-Rf) (hereinafter, described as Compound (YE1-Rf), can be prepared by reacting a compound of a formula (YE1-Rf1) (hereinafter, described as Compound (YE1-Rf1)) in the presence of an acid.

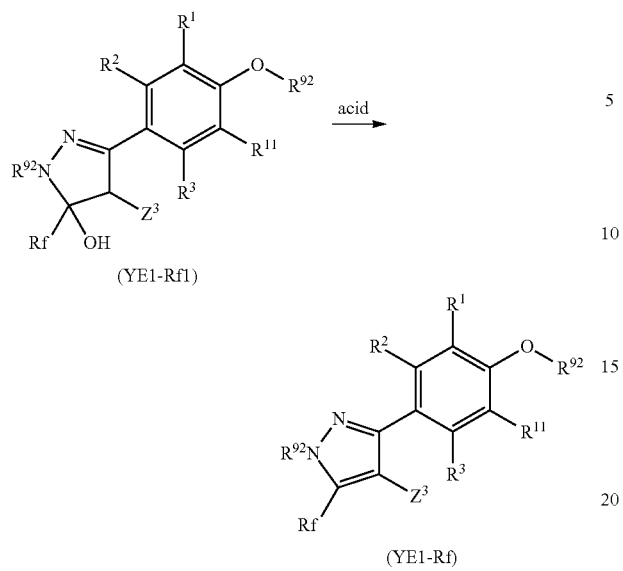

(YE1-Rf1)

(YE1-Rf)

[wherein $R^1$, $R^2$, $R^3$, $R^{11}$, $R^{92}$ and $Z^3$ are the same as described above; and Rf represents a C1-C6 perfluoroalkyl group, a 1,1-difluoroethyl group, a 1,1-difluropropyl group or a 2,2-difluropropyl group]

This reaction is usually carried out in a solvent.

Examples of the solvent that can be used in the reaction include hydrocarbons such as heptane, hexane, cyclohexane, pentane, toluene, xylene; ethers such as diethyl ether, tetrahydrofuran, 1,4-dioxane, ethyleneglycol dimethyl ether, anisole, methyl tert-butyl ether, diisopropyl ether; halogenated hydrocarbons such as carbon tetrachloride, chloroform, dichloromethane, 1,2-dichloroethane, tetrachloroethane, chlorobenzene; acid amides such as N,N-dimethylformamide, 1,3-dimethyl-2-imidazolidinone, N-methylpyrrolidone; esters such as ethyl acetate, methyl acetate; sulfoxides such as dimethyl sulfoxide; nitriles such as acetonitrile, propionitrile; alcohols such as methanol, ethanol, isopropanol; water; and mixed solvents thereof.

Examples of the acid to be used in the reaction include acetic acid, hydrochloric acid and hydrobromic acid, and these aqueous solutions may be used as solvent.

In the reaction, the acid is used usually within a range of 1 to 10 molar ratio(s) as opposed to 1 mole of Compound (YE1-Rf1).

The reaction temperature is usually within a range of −78 to 150° C. The reaction period of the reaction is usually within a range of 0.1 to 72 hours.

When the reaction is completed, the reaction mixtures are extracted with organic solvent(s), and the resulting organic layers are worked up (for example, drying and concentration) to isolate Compound (YE1-Rf). The isolated present Compound (YE1-Rf) may be further purified, for example, by chromatography and recrystallization.

(Reference Process AY)

Compound (YE1-Rf1) and a compound of a formula (YF2) wherein $Z^2$ represents Rf and $Z^4$ represents $R^{92}$, i.e., a compound of a formula (YF2-Rf) (hereinafter, described as Compound (YF2-Rf)), can be prepared by reacting a compound of a formula (YJ1) wherein $Z^2$ represents Rf, i.e., a compound of a formula (YJ1-Rf) (hereinafter, described as Compound (YJ1-Rf)) with Compound (AT1).

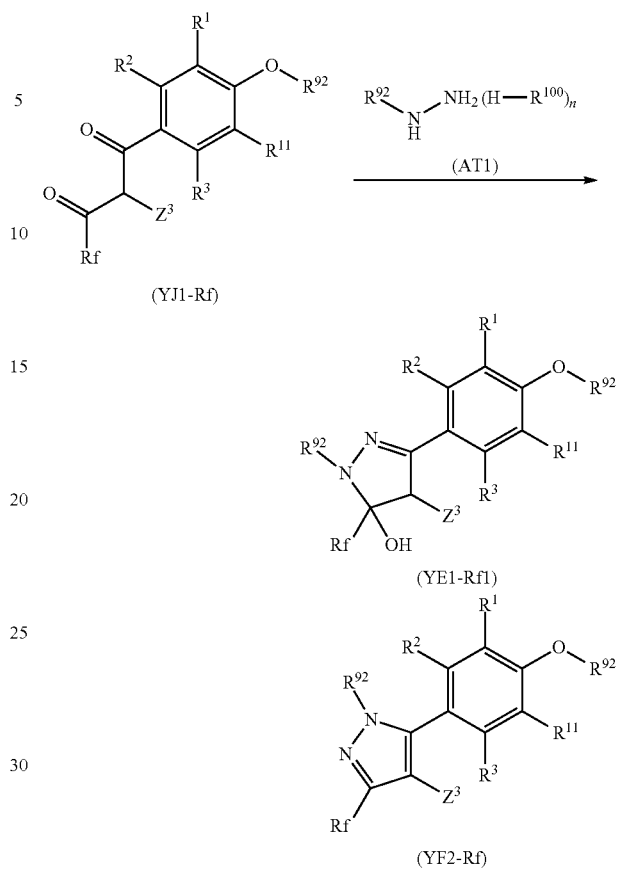

(YJ1-Rf)

(YE1-Rf1)

(YF2-Rf)

[wherein $R^1$, $R^2$, $R^3$, $R^{11}$, $R^{92}$, $Z^3$ and Rf are the same as described above; and n is 0 or 1]

This reaction is usually carried out in a solvent.

Examples of the solvent that can be used in the reaction include hydrocarbons such as heptane, hexane, cyclohexane, pentane, toluene, xylene; ethers such as diethyl ether, tetrahydrofuran, 1,4-dioxane, ethyleneglycol dimethyl ether, anisole, methyl tert-butyl ether, diisopropyl ether; halogenated hydrocarbons such as carbon tetrachloride, chloroform, dichloromethane, 1,2-dichloroethane, tetrachloroethane, chlorobenzene; acid amides such as N,N-dimethylformamide, 1,3-dimethyl-2-imidazolidinone, N-methylpyrrolidone; esters such as ethyl acetate, methyl acetate; sulfoxides such as dimethyl sulfoxide; nitriles such as acetonitrile, propionitrile; alcohols such as methanol, ethanol, isopropanol; water; and mixed solvents thereof.

In the reaction, Compound (AT1) is used usually within a range of 1 to 10 molar ratio(s) as opposed to 1 mole of Compound (YJ1-Rf1).

The reaction temperature is usually within a range of −78 to 150° C. The reaction period of the reaction is usually within a range of 0.1 to 72 hours.

When the reaction is completed, the reaction mixtures are extracted with organic solvent(s), and the resulting organic layers are worked up (for example, drying and concentration) to isolate Compound (YE1-Rf1) and Compound (YF2-Rf). The isolated present Compound (YE1-Rf1) and the isolated present Compound (YF2-Rf) may be further purified, for example, by chromatography and recrystallization.

(Reference Process AZ)

The present compound of the formula (YE1-11) wherein $Z^3$ represents an aldehyde group, i.e., the compound of a formula (YE1-11-1) (hereinafter, described as Compound (YE1-11-1)), can be prepared by reacting a compound of a formula (YE1-12) wherein $Z^3$ represents a hydrogen atom (hereinafter, described as Compound (YE1-12)) with a formylating agent, which is prepared from N,N-dimethylformamide and phosphorus oxychloride, followed by reacting the resulting mixtures with water.

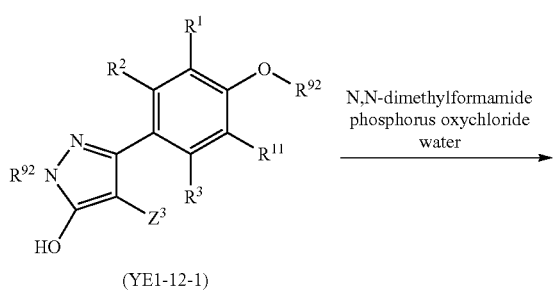

(YE1-12-1)

N,N-dimethylformamide
phosphorus oxychloride
water
→

(YE1-11-1)

[wherein $R^1$, $R^2$, $R^3$, $R^{11}$, $R^{92}$ and $Z^3$ are the same as described above]

The reaction can be carried out according to Process K.

(Reference Process BA)

Compound (YE1) wherein $Z^2$ represents $Z^{2H}$ and $Z^3$ represents an aldehyde group, i.e., a compound of a formula (YE1-11-2) (hereinafter, described as Compound (YE1-11-2)) can be prepared by reacting a compound of a formula (YE1-11-1) with Compound (O-1) in the presence of a base.

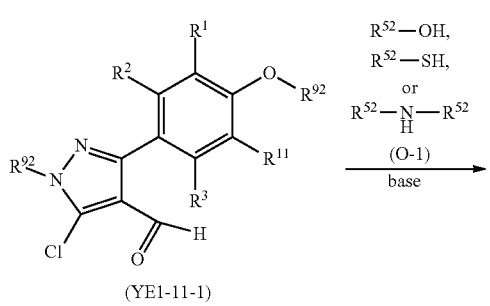

(YE1-11-1)

$R^{52}$—OH,
$R^{52}$—SH,
or
$R^{52}$—N—$R^{52}$
    H
(O-1)
base
→

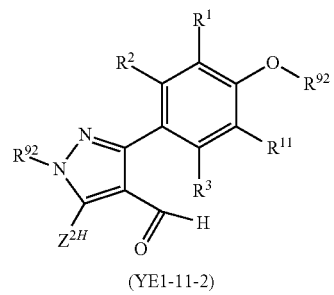

(YE1-11-2)

[wherein $R^1$, $R^2$, $R^3$, $R^{11}$, $R^{92}$ and $Z^{2H}$ are the same as defined above]

The reaction can be carried out according to Process P.

(Reference Process BB)

Compound (YE1) wherein $Z^2$ represents $Z^{2H}$ and $Z^3$ represents a methyl group, i.e., a compound of a formula (YE1-11-3) (hereinafter, described as Compound (YE1-11-3)) can be prepared by reacting a compound of a formula (YE1-11-2) with a reducing agent in the presence of a base.

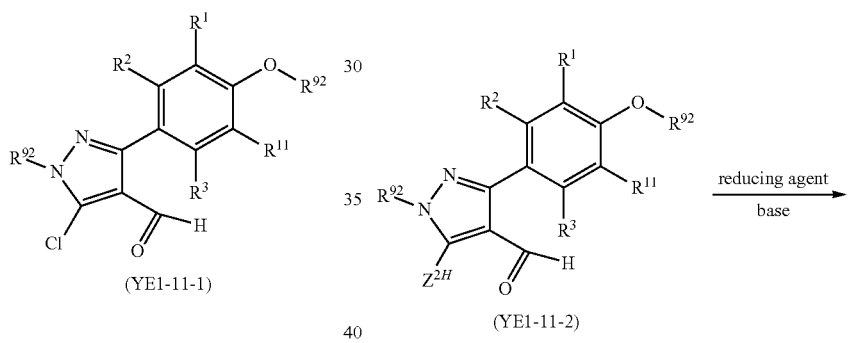

[wherein $R^1$, $R^2$, $R^3$, $R^{11}$, $R^{92}$ and $Z^{2H}$ are the same as defined above]

The reaction can be carried out according to Process Q.

(Reference Process BC)

Compound (YE1) wherein $Z^2$ represents a chloro atom and $Z^3$ represents a methyl group, i.e., a compound of a formula (YE1-11-4) (hereinafter, described as Compound (YE1-11-4)) can be prepared by reacting a compound of a formula (YE1-11-1) with a reducing agent in the presence of an acid.

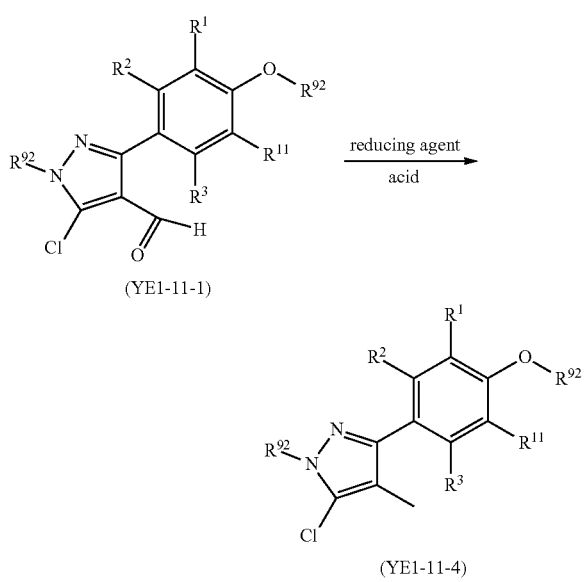

[wherein

R$^1$, R$^2$, R$^3$, R$^{11}$, R$^{92}$ and Z$^{2H}$ are the same as defined above]

The reaction can be carried out according to Process Q.

Although a form used for the present compound may be the present compound as itself, the present compound is usually prepared by mixing the present compound with solid carriers, liquid carriers, gas carriers, surfactants and the others, and if necessary, adding stickers, dispersers and stabilizers, to formulate into wettable powders, water dispersible granules, flowables, granules, dry flowables, emulsifiable concentrates, aqueous solutions, oil solutions, smoking agents, aerosols, microcapsules and the others, In these formulations, the present compound is contained in a range of usually 0.1 to 99%, preferably 0.2 to 90% by weight.

Examples of the solid carrier include clays (for example, kaolin, diatomaceous earth, synthetic hydrated silicon dioxide, Fubasami clay, bentonite and acid clay), talcs or the other inorganic minerals (for example, sericite, quartz powder, sulfur powder, activated charcoal, calcium carbonate and hydrated silica) in the form of fine powders or particulates, and examples of the liquid carries include water, alcohols (for example, methanol and ethanol), ketones (for example, acetone and methyl ethyl ketone), aromatic hydrocarbons (for example, benzene, toluene, xylene, ethylbenzene and methyl naphthalene), aliphatic hydrocarbons (for example, hexane, cyclohexane and kerosene), esters (for example, ethyl acetate and butyl acetate), nitriles (for example, acetonitrile and isobutyronitrile), ethers (for example, dioxane and diisopropylether), acid amides (for example, N,N-dimethyl formamide (DMF) and dimethylacetamide), halogenated hydrocarbons (for example, dichloroethane, trichloro ethylene and carbon tetrachloride) and the others.

Examples of the surfactants include alkyl sulfates, alkyl sulfonates, alkyl aryl sulfonates, alkyl aryl ethers and polyoxyethylenated compounds thereof, polyethylene glycol ethers, polyol esters and sugar alcohol derivatives Examples of other auxiliary agents for formulation include stickers, dispersers and stabilizers, specifically casein, gelatin, polysaccharides (for example, starch, gum arabic, cellulose derivatives and alginic acid), lignin derivatives, bentonite, sugars, water-soluble synthetic polymers (for example, polyvinyl alcohol, polyvinyl pyrrolidone and polyacrylic acids), PAP (acidic isopropyl phosphate), BHT (2,6-di-tert-butyl-4-methylphenol), BHA (a mixture of 2-tert-butyl-4-methoxyphenol and 3-tert-butyl-4-methoxyphenol), vegetable oils, mineral oils, fatty acids or fatty acid esters thereof and the others.

The method for applying the present compound is not particularly limited, as far as the applying form is a form by which the present compound may be applied substantially, and includes, for example, an application to plants such as a foliage application; an application to area for cultivating plants such as a submerged treatment; and an application to soil such as seed disinfection.

The application dose varies depending on weather conditions, dosage forms, timing of application, methods of application, areas to be applied, target diseases and target crops etc., but is in the range of usually from 1 to 500 g, and preferably from 2 to 200 g per 1,000 m$^2$ of the area to be applied. The emulsifiable concentrate, the wettable powder or the suspension concentrate, etc., is usually applied by diluting it with water. In this case, the concentration of the present compound after dilution is in the range of usually 0.0005 to 2% by weight, and preferably 0.005 to 1% by weight. The dust formulation or the granular formulation etc., is usually applied as itself without diluting it. In the application to seeds, the amount of the present compound is in the range of usually from 0.001 to 100 g, and preferably from 0.01 to 50 g per 1 kg of the seeds.

Herein, examples of the place where the pests live include paddy fields, fields, tea gardens, orchards, non-agricultural lands, houses, nursery trays, nursery boxes, nursery soils and nursery bed.

Also, in another embodiment, for example, the present compound can be administered to the inside (inside of the body) or the outside (body surface) of the below-mentioned vertebrate to exterminate systemically or unsystemically the living things or parasites which are parasitic on the vertebrate. Examples of a method of the internal medication include an oral administration, an anal administration, a transplanation, an administration via injection subcutaneously, intramuscularly or intravenously. Examples of a method of outside medication include a transdermal administration. Also, the present compound can be ingested to a livestock animal so as to exterminate sanitary insects which occur in the excrement of the animal.

When the present compound is applied to the animals such as the livestock animal and pets on which pests are parasitic, the dose varies depending on the administration method etc., but it is desirable in general to administer the present compound so that a dose of the active ingredient (the present compound or salts thereof) is in the range of generally from 0.1 mg to 2,000 mg and preferably 0.5 mg to 1,000 mg per 1 kg of body weight of the animal.

The present compound can be used as agent for controlling plant disease in agricultural lands such as fields, paddy fields, lawns, orchards. The compound of the present invention can control diseases occurred in the agricultural lands or the others for cultivating the following "plant".

Crops:
corn, rice, wheat, barley, rye, oat, sorghum, cotton, soybean, peanut, buckwheat, beet, rapeseed, sunflower, sugar cane, tobacco, and the others;

Vegetables:
solanaceous vegetables (for example, eggplant, tomato, pimento, pepper and potato),
cucurbitaceous vegetables (for example, cucumber, pumpkin, zucchini, water melon and melon), cruciferous vegetables (for example, Japanese radish, white turnip, horseradish, kohlrabi, Chinese cabbage, cabbage, leaf mustard, broccoli, cauliflower), asteraceous vegetables (for example, burdock, crown daisy, artichoke and lettuce), liliaceous vegetables (for example, green onion, onion, garlic and asparagus), ammiaceous vegetables (for example, carrot, parsley, celery and parsnip), chenopodiaceous vegetables (for example, spinach and Swiss chard), lamiaceous vegetables (for example, *Perilla frutescens*, mint and basil), strawberry, sweet potato, *Dioscorea japonica, colocasia* and the others;

Flowers:
Ornamental Foliage Plants:
Fruits:

pomaceous fruits (for example, apple, pear, Japanese pear, Chinese quince and quince), stone fruits (for example, peach, plum, nectarine, *Prunus mume*, cherry fruit, apricot and prune), citrus fruits (for example, Citrus unshiu, orange, lemon, lime and grapefruit), nuts (for example, chestnut, walnuts, hazelnuts, almond, pistachio, cashew nuts and macadamia nuts), berry fruits (for example, blueberry, cranberry, blackberry and raspberry), grape, kaki persimmon, olive, Japanese plum, banana, coffee, date palm, coconuts, and the others;

Trees Other than Fruit Trees:
tea, mulberry, flowering plant, roadside trees (for example, ash, birch, dogwood, *Eucalyptus, Ginkgo biloba*, lilac, maple, *Quercus*, poplar, Judas tree, *Liquidambar formosana*, plane tree, zelkova, Japanese arborvitae, fir wood, hemlock, juniper, *Pinus, Picea*, and *Taxus* cuspidate);

and the others.

The above-mentioned "plant" includes genetically modified crops.

The pests on which the present compound has a control efficacy include plant pathogens such as filamentous fungus, as well as harmful arthropods such as harmful insects and harmful mites, and nemathelminth such as nematodes, and specifically include the following examples, but are not limited thereto.

Rice diseases: blast (*Magnaporthe grisea*), brown spot (*Cochliobolus miyabeanus*), sheath blight (*Rhizoctonia solani*), bakanae disease (*Gibberella fujikuroi*), and downy mildew (Sclerophthora *macrospora*);

Wheat diseases: powdery mildew (*Erysiphe graminis*), fusarium blight (*Fusarium gaminearum, F. avenaceum, F. culmorum, Microdochium nivale*), rust (*Puccinia striiformis, P. graminis, P. recondita*), snow mould (*Micronectriella nivale*), typhula snow blight (*Typhula* sp.), loose smut (*Ustilago tritici*), stinking smut (*Tilletia caries, T. controversa*), eyespot (*Pseudocercosporella herpotrichoides*), leaf blotch (*Septoria tritici*), glume blotch (*Stagonospora nodorum*), tan spot (*Pyrenophora tritici-repentis*), rhizoctonia seeding blight (*Rhizoctonia solani*), and take all disease (*Gaeumannomyces graminis*);

Barly diseases: powdery mildew (*Erysiphe graminis*), fusarium blight (*Fusarium gaminearum, F. avenaceum, F. culmorum, Microdochium nivale*), rust (*Puccinia striiformis, P. graminis, P. hordei*), loose smut (*Ustilago nuda*), scald (*Rhynchosporium secalis*), net blotch (*Pyrenophora teres*), spot blotch (*Cochliobolus sativus*), leaf stripe (*Pyrenophora graminea*), Ramularia disease (*Ramularia collo-cygni*), and rhizoctonia seeding blight (*Rhizoctonia solani*);

Corn diseases: rust (*Puccinia sorghi*), southern rust (*Puccinia polysora*), northern leaf blight (*Setosphaeria turcica*), southern leaf blight (*Cochliobolus heterostrophus*), anthracnose (*Colletotrichum gfaminicola*), gray leaf spot (*Cercospora zeae-maydis*), eyespot (*Kabatiella zeae*), and phaeosphaeria leaf spot (*Phaeosphaeria maydis*);

Cotton diseases: anthracnose (*Colletotrichum gossypii*), grey mildew (*Ramuraria areola*), alternaria leaf spot (*Alternaria macrospora, A. gossypii*);

Coffee diseases: rust (*Hemileia vastatrix*);

Rape seed diseases: sclerotinia rot (*Sclerotinia sclerotiorum*), black spot (*Alternaria brassicae*), and black leg (*Phoma lingam*);

Citrus diseases: melanose (*Diaporthe citri*), scab (*Elsinoe fawcetti*), and fruit rot (*Penicillium digitatum, P. italicum*);

Apple diseases: blossom blight (*Monilinia mali*), canker (*Valsa ceratosperma*), powdery mildew (*Podosphaera leucotricha*), alternaria leaf spot (*Alternaria alternata* apple pathotype), scab (*Venturia inaequalis*), and bitter rot (*Colletotrichum acutatum*);

Pear diseases: scab (*Venturia nashicola, V. pirina*), black spot (*Alternaria alternata* Japanese pear pathotype) and rust (*Gymnosporangium haraeanum*);

Peach diseases: brown rot (*Monilinia fructicola*), scab (*Cladosporium carpophilum*) and Phomopsis rot (*Phomopsis* sp.);

Grapes diseases: anthracnose (*Elsinoe ampelina*), ripe rot (*Glomerella cingulata*), powdery mildew (*Uncinula necator*), rust (*Phakopsora ampelopsidis*), black rot (*Guignardia bidwellii*), and downy mildew (*Plasmopara viticola*);

Diseases of Japanese persimmon: anthracnose (*Gloeosporium kaki*) and leaf spot (*Cercospora kaki, Mycosphaerella nawae*);

Diseases of gourd family: anthracnose (*Colletotrichum lagenarium*), powdery mildew (*Sphaerotheca fuliginea*), gummy stem blight (*Didymella bryoniae*), target spot (*Corynespora cassiicola*), fusarium wilt (*Fusarium oxysporum*), downy mildew (*Pseudoperonospora cubensis*), phytophthora rot (*Phytophthora* sp.) and damping-off (*Pythium* sp.);

Tomato diseases: early blight (*Alternaria solani*), leaf mold (*Cladosporium fulvum*), leaf mold (*Pseudocercospora fuligena*), and late blight (*Phytophthora infestans*);

Eggplant disease: brown spot (*Phomopsis vexans*) and powdery mildew (*Erysiphe cichoracearum*);

Diseases of Cruciferous Vegetables: alternaria leaf spot (*Alternaria japonica*), white spot (*Cercosporella brassicae*), clubroot (*Plasmodiophora parasitica*), downy mildew (*Peronospora parasitica*);

Welsh onion diseases: rust (*Puccinia allii*);

Soybean diseases: purple stain (*Cercospora kikuchii*), sphaceloma scad (*Elsinoe glycines*), pod and stem blight (*Diaporthe phaseolorum* var. *sojae*), rust (*phakopsora pachyrhizi*), target spot (*Corynespora cassiicola*), anthracnose (*Colletotrithum glycines, C. truncatum*), Rhizoctonia aerial blight (*Rhizoctonia solani*), septoria brown spot (*Septoria glycines*), and frog eye leaf spot (*Cercospora sojina*);

Kindney bean diseases: anthracnose (*Colletotrichum lindemthianum*);

Peanut diseases: early leaf spot (*Cercospora personata*), late leaf spot (*Cercospora arachidicola*) and southern blight (*Sclerotium rolfsii*);

Garden pea diseases: powdery mildew (*Erysiphe pisi*);

Potato diseases: early blight (*Alternaria solani*), late blight (*Phytophthora infestans*), and verticillium wilt (*verticillium albo-atrum, V. dahliae, V. nigrescens*);

Strawberry diseases: powdery mildew (*Sphaerotheca humuli*);

Tea diseases: net blister blight (*Exobasidium reticulatum*), white scab (*Elsinoe leucospila*), gray blight (*Pestalotiopsis* sp.) and anthracnose (*Colletotrichum theae-sinensis*);

Tabacco diseases: brown spot (*Alternaria longipes*), powdery mildew (*Erysiphe cichoracearum*), anthracnose (*Colletotrichum tabacum*), downy mildew (*Peronospora tabacina*), and black shank (*Phytophthora nicotianae*);

Sugar beet diseases: cercospora leaf spot (*Cercospora beticola*), leaf blight (*Thanatephorus cucumeris*), root rot (*Thanatephorus cucumeris*) and aphanomyces root rot (*Aphanomyces sochlioides*);

Rose diseases: black spot (*Diplocarpon rosae*) and powdery mildew (*Sphaerotheca pannosa*);

Diseases of *Chrysanthemum*: leaf blight (*Septoria chrysanthemi-indici*) and white rust (*Puccinia horiana*);

Onion diseases: botrytis leaf blight (*Botrytis cinerea, B. byssoidea, B. squamosa*), gray-mold neck rot (*Botrytis slli*), and small sclerotial rot (*Botrytis squamosa*);

Various crops diseases: gray mold (*Botrytis cinerea*), and sclerotinia rot (*Sclerotinia sclerotiorum*);

Diseases of Japanese radish: alternaria leaf spot (*Alternaria brassicicola*);

Turfgrass diseases: dollar spot (*Sclerotinia homeocarpa*), brown patch and large patch (*Rhizoctonia solani*); and Banana diseases: Sigatoka disease (*Mycosphaerella fijiensis, Mycosphaerella musicola*).

Hemiptera:
Delphacidae (for example, *Laodelphax striatellus, Nilaparvata lugens*, or *Sogatella furcifera*);
Deltocephalidae (for example, *Nephotettix cincticeps*, or *Nephotettix virescens*);
Aphididae (for example, *Aphis gossypii, Myzus persicae, Brevicoryne brassicae, Macrosiphum euphorbiae, Aulacorthum solani, Rhopalosiphum padi, Toxoptera citricidus*);
Pentatomidae (for example, *Nezara antennata, Riptortus clavetus, Leptocorisa chinensis, Eysarcoris parvus, Halyomorpha mista*, or *Lygus lineolaris*);
Aleyrodidae (for example, *Trialeurodes vaporariorum*, or *Bemisia argentifolii*);
Coccoidea (for example, *Aonidiella aurantii, Comstockaspis perniciosa, Unaspis citri, Ceroplastes rubens*, or *Icerya purchasi*);
Tingidae;
Psyllidae;
Bed bugs (*Cimex lectularius*) and the others;
Lepidoptera:
Pyralidae (for example, *Chilo suppressalis, Tryporyza incertulas, Cnaphalocrocis medinalis, Notarcha derogata, Plodia interpunctella, Ostrinia furnacalis, Hellula undalis, Pediasia teterrellus*);
Noctuidae (for example, *Spodoptera litura, Spodoptera exigua, Pseudaletia separata, Mamestra brassicae, Agrotis ipsilon, Plusia nigrisigna, Trichoplusia* spp., *Heliothis* spp. or *Helicoverpa* spp.;
Pieridae (for example, *Pieris rapae*);
Tortricidae (for example, *Adoxophyes* spp., *Grapholita molesta, Cydia pomonella, Leguminivora glycinivorella, Matsumuraeses azukivora, Adophyes orana fasciata, Adoxophyes* sp., *Homona magnanima, Archips fuscocupreanus, Cydia pomonella*);
Gracillariidae (for example, *Caloptilia theivora, Phyllonorycter ringoneella*);
Carposinidae (for example, *Carposina niponensis*);
Lyonetiidae (for example, *Lyonetia* spp.);
Lymantriidae (for example, *Lymantria* spp., or *Euproctis* spp.);
Yponomeutidae (for example, *Plutella xylostella*);
Gelechiidae (for example, *Pectinophora gossypiella* or *Phthorimaea operculella*);
Arctiidae (for example, *Hyphantria cunea*);
Tineidae (for example, *Tinea translucens*, or *Tineola bisselliella*); and the others;
Thysanoptera:
Thysanoptera (for example, *Frankliniella occidentalis, Thrips palmi, Scirtothrips dorsalis, Thrips tabaci, Frankliniella intonsa, Frankliniella fusca*);
Diptera:
*Musca domestica, Culex popiens pallens, Tabanus trigonus, Hylemya antiqua, Hylemya platura, Anopheles sinensis, Agromyza oryzae, Hydrellia griseola, Chlorops oryzae, Dacus cucurbitae, Ceratitis capitata, Liriomyza trifolii*, and the others;
Coleoptera:
*Epilachna vigintioctopunctata, Aulacophora femoralis, Phyllotreta striolata, Oulema oryzae, Echinocnemus squameus, Lissorhoptrus oryzophilus, Anthonomus grandis, Callosobruchus chinensis, Sphenophorus venatus, Popillia japonica, Anomala cuprea, Diabrotica* spp., *Leptinotarsa decemlineata, Agriotes* spp., *Lasioderma serricorne, Anthrenus verbasci, Tribolium castaneum, Lyctus brunneus, Anoplophora malasiaca, Tomicus piniperda*), and the others;
Orthoptera:
*Locusta migratoria, Gryllotalpa africana, Oxya yezoensis, Oxya japonica*, and the others;
Hymenoptera:
*Athalia rosae, Acromyrmex* spp., *Solenopsis* spp., and the others;
Nematodes:
*Aphelenchoides besseyi, Nothotylenchus acris, Heterodera glycines, Meloidogyne incognita, Pratylenchus, Nacobbus aberrans*, and the others;
Blattariae:
*Blattella germanica, Periplaneta fuliginosa, Periplaneta americana, Periplaneta brunnea, Blatta orientalis*, and the others;
Acarina:
Tetranychidae (for example, *Tetranychus urticae, Panonychus citri*, or *Oligonychus* spp.);
Eriophyidae (for example, *Aculops pelekassi*);
Tarsonemidae (for example, *Polyphagotarsonemus latus*);
Tenuipalpidae;
Tuckerellidae;
Acaridae (for example, *Tyrophagus putrescentiae*);
Pyroglyphidae (for example, *Dermatophagoides farinae*, or *Dermatophagoides ptrenyssnus*);
Cheyletidae (for example, *Cheyletus eruditus, Cheyletus malaccensis*, or *Cheyletus moorei*);
Dermanyssidae;
and the others.

Also the formulation comprising the present compound or salts thereof can be used in the field relating to a treatment of livestock diseases or livestock industry, and for example, can exterminate the living things or parasites which are parasitic on the inside and/or the outside of a vertebrate such as human being, cow, sheep, pig, poultry, dog, cat and fish, so as to maintain public health. Examples of the pests include *Isodes* spp. (for example, *Isodes scapularis*), *Boophilus* spp. (for example, *Boophilus microplus*), *Amblyomma* spp., *Hyalomma* spp., *Rhipicephalus* spp. (for example, *Rhipicephalus sanguineus*), *Haemaphysalis* spp. (for example, *Haemaphysalis longicornis*), *dermacentor* spp., *Ornithodoros* spp. (for example, *Ornithodoros moubata*), *Dermahyssus gallinae, Ornithonyssus sylviarum, Sarcoptes* spp. (for example, *Sarcoptes scabiei*), *Psoroptes* spp., *Chorioptes* spp., *Demodex* spp., *Eutrombicula* spp., *Ades* spp. (for example, *Aedes albopictus*), *Anopheles* spp., *Culex* spp., *Culicodes* spp., *Musca* spp., *Hypoderma* spp., *Gasterophilus* spp., *Haematobia* spp., *Tabanus* spp., *Simulium* spp., *Triatoma* spp., *Phthiraptera* (for example, *Damalinia* spp.), *Linognathus* spp., *Haematopinus* spp., *Ctenocephalides* spp. (for example, *Ctenocephalides felis*) *Xenosylla* spp., *monomorium* pharaonic and nematodes [for example, hairworm (for example, *Nippostrongylus brasiliensis, Trichostrongylus axei, Trichostrongylus colubriformis*), *Trichinella* spp. (for example, *Trichinella spiriralis*), *Haemonchus contortus, Nematodirus* spp. (for example, *Nematodirus battus*), *Ostertagia circumcincta, Cooperia* spp., *Hymenolepis nana*, and the others.

EXAMPLES

The following Examples including Preparation examples, Formulation examples and Test examples, serve to illustrate the present invention in more detail, which should not intend to limit the present invention.

The Preparation examples are shown below. $^1$H NMR means a proton nuclear magnetic resonance, spectrum and Tetramethyl silane is used as an internal standard and chemical shift (δ) is expressed in ppm.

Preparation Example 1

A mixture of 1-(2-bromomethyl-3-difluoromethoxyphenyl)-4-methyl-1,4-dihydrotetrazole-5-one (described in Reference Preparation example 1) 0.30 g, 2-methyl-4-(3,4,5-trimethyl-pyrazol-1-yl)-phenol (described in Reference Preparation example 20) 0.26 g, potassium carbonate 0.21 g and acetonitrile 10 ml was stirred with heating under reflux for six hours. After cooling to room temperature, the reaction mixture was filtered, and the filtrate was then concentrated. The resulting residue was subjected to a silica gel column chromatography to give 1-{3-difluoromethoxy-2-[2-methyl-4-(3,4,5-trimethyl-pyrazol-1-yl)-phenoxymethyl]-phenyl}-4-methyl-1,4-dihydrotetrazole-5-one (hereinafter, referred to as "Present compound 1") 0.31 g.

Present compound 1

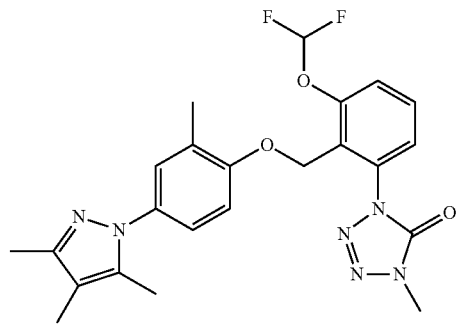

$^1$H-NMR (CDCl$_3$) δ: 7.56 (1H, t, J=8.2 Hz), 7.39 (2H, t, J=8.2 Hz), 7.14 (1H, d, J=2.4 Hz), 7.11-7.06 (1H, m), 6.91-6.87 (1H, m), 6.59 (1H, t, J=72.8 Hz), 5.27 (2H, s), 3.62 (3H, d, J=0.5 Hz), 2.22 (3H, s), 2.16 (3H, s), 2.02 (3H, s), 1.96 (3H, s).

Preparation Example 2

A mixture of 1-(2-bromomethyl-3-cyclopropylphenyl)-4-methyl-1,4-dihydrotetrazole-5-one (described in Reference Preparation example 2) 0.50 g, 2-methyl-4-(3,4,5-trimethyl-pyrazol-1-yl)-phenol (described in Reference Preparation example 20) 0.36 g, potassium carbonate 0.29 g and acetonitrile 15 ml was stirred with heating under reflux for seven hours. After cooling to room temperature, the reaction mixture was filtered, and the filtrate was then concentrated. The resulting residue was subjected to a silica gel column chromatography to give 1-{3-cyclopropyl-2-[2-methyl-4-(3,4,5-trimethyl-pyrazol-1-yl)-phenoxymethyl]-phenyl}-4-methyl-1,4-dihydrotetrazole-5-one (hereinafter, referred to as "Present compound 2") 0.51 g.

Present compound 2

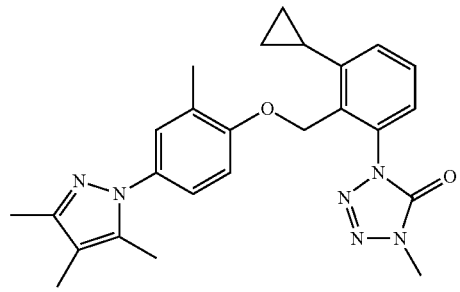

$^1$H-NMR (CDCl$_3$) δ: 7.44 (1H, t, J=7.9 Hz), 7.28 (2H, d, J=8.3 Hz), 7.15 (1H, d, J=2.2 Hz), 7.11 (1H, dd, J=8.5, 2.4 Hz), 6.90 (1H, d, J=8.5 Hz), 5.28 (2H, s), 3.63 (3H, s), 2.23 (3H, s), 2.17 (3H, s), 2.13-2.09 (4H, m), 1.97 (3H, s), 1.02-0.97 (2H, m), 0.76 (2H, q, J=5.4 Hz).

Preparation Example 3

A similar reaction to Preparation example 2 using 2-methyl-4-(3,5-dimethyl-pyrazol-1-yl)-phenol (described in Reference Preparation example 21) instead of 2-methyl-4-(3,4,5-trimethyl-pyrazol-1-yl)-phenol gave 1-{3-cyclopropyl-2-[2-methyl-4-(3,5-dimethyl-pyrazol-1-yl)-phenoxymethyl]-phenyl}-4-methyl-1,4-dihydrotetrazole-5-one (hereinafter, referred to as "Present compound 3").

Present compound 3

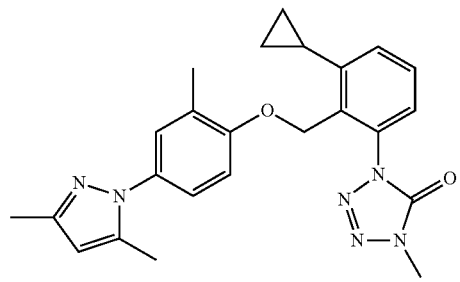

$^1$H-NMR (CDCl$_3$) δ: 7.44 (1H, t, J=7.8 Hz), 7.28 (2H, d, J=8.0 Hz), 7.17 (1H, d, J=2.4 Hz), 7.14 (1H, dd, J=8.5, 2.7

Hz), 6.91 (1H, d, J=8.5 Hz), 5.95 (1H, s), 5.28 (2H, s), 3.63 (3H, s), 2.28 (3H, s), 2.24 (3H, s), 2.14-2.08 (4H, m), 1.02-0.97 (2H, m), 0.79-0.75 (2H, m).

Preparation Example 4

A similar reaction to Preparation example 2 using 2-chloro-4-(3,5-dimethyl-pyrazol-1-yl)-phenol (described in Reference Preparation example 17) instead of 2-methyl-4-(3,4,5-trimethyl-pyrazol-1-yl)-phenol gave 1-{3-cyclopropyl-2-[2-chloro-4-(3,5-dimethyl-pyrazol-1-yl)-phenoxymethyl]-phenyl}-4-methyl-1,4-dihydrotetrazole-5-one (hereinafter, referred to as "Present compound 4").

Present compound 4

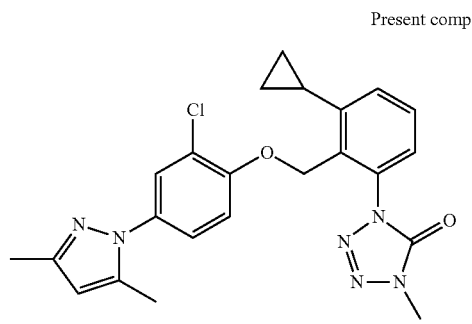

$^1$H-NMR (CDCl$_3$) δ: 7.46-7.41 (2H, m), 7.30 (2H, t, J=6.8 Hz), 7.23 (1H, dd, J=8.7, 2.6 Hz), 6.98 (1H, d, J=8.8 Hz), 5.96 (1H, s), 5.44 (2H, s), 3.66 (3H, s), 2.27 (3H, s), 2.26 (3H, s), 2.20-2.12 (1H, m), 1.04-0.99 (2H, m), 0.79-0.74 (2H, m).

Preparation Example 5

A similar reaction to Preparation example 2 using 2-methyl-4-(3-methyl-pyrazol-1-yl)-phenol (described in Reference Preparation example 22) instead of 2-methyl-4-(3,4,5-trimethyl-pyrazol-1-yl)-phenol gave 1-{3-cyclopropyl-2-[2-methyl-4-(3-methyl-pyrazol-1-yl)-phenoxymethyl]-phenyl}-4-methyl-1,4-dihydrotetrazole-5-one (hereinafter, referred to as "Present compound 5").

Present compound 5

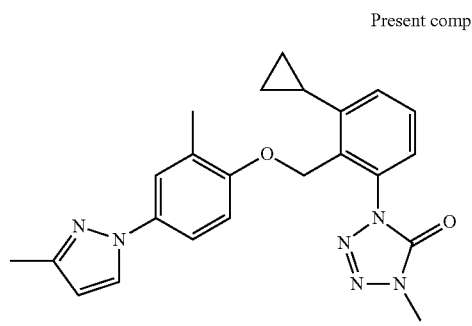

$^1$H-NMR (CDCl$_3$) δ: 7.69 (1H, d, J=2.2 Hz), 7.46-7.40 (2H, m), 7.34 (1H, dd, J=8.5, 2.7 Hz), 7.28 (1H, s), 7.26 (1H, s), 6.89 (1H, d, J=8.8 Hz), 6.20 (1H, d, J=2.4 Hz), 5.28 (2H, s), 3.61 (3H, s), 2.36 (3H, s), 2.15-2.09 (4H, m), 1.02-0.97 (2H, m), 0.79-0.74 (2H, m).

Preparation Example 6

A similar reaction to Preparation example 2 using 2-methyl-4-(3,4-dimethyl-pyrazol-1-yl)-phenol (described in Reference Preparation example 23) instead of 2-methyl-4-(3,4,5-trimethyl-pyrazol-1-yl)-phenol gave 1-{3-cyclopropyl-2-[2-methyl-4-(3,4-dimethyl-pyrazol-1-yl)-phenoxymethyl]-phenyl}-4-methyl-1,4-dihydrotetrazole-5-one (hereinafter, referred to as "Present compound 6").

Present compound 6

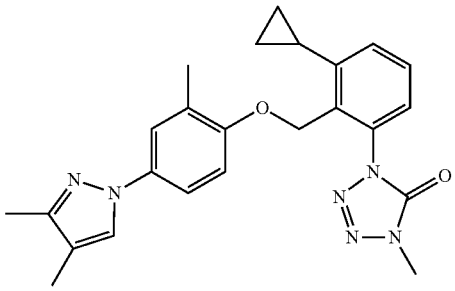

$^1$H-NMR (CDCl$_3$) δ: 7.52 (1H, s), 7.43 (1H, t, J=7.8 Hz), 7.38 (1H, d, J=2.7 Hz), 7.31-7.25 (3H, m), 6.88 (1H, d, J=8.5 Hz), 5.27 (2H, s), 3.60 (3H, s), 2.27 (3H, s), 2.15-2.10 (4H, m), 2.06 (3H, s), 1.02-0.97 (2H, m), 0.78-0.74 (2H, m).

Preparation Example 7

A similar reaction to Preparation example 2 using 2-chloro-4-(3,4,5-trimethyl-pyrazol-1-yl)-phenol (described in Reference Preparation example 16) instead of 2-methyl-4-(3,4,5-trimethyl-pyrazol-1-yl)-phenol gave 1-{3-cyclopropyl-2-[2-chloro-4-(3,4,5-trimethyl-pyrazol-1-yl)-phenoxymethyl]-phenyl}-4-methyl-1,4-dihydrotetrazole-5-one (hereinafter, referred to as "Present compound 7").

Present compound 7

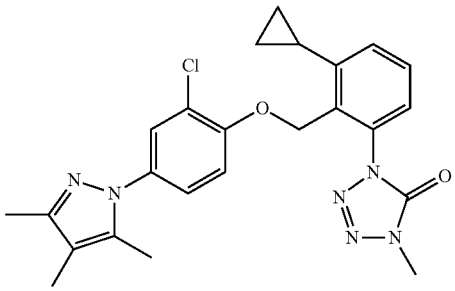

$^1$H-NMR (CDCl$_3$) δ: 7.43 (1H, t, J=7.8 Hz), 7.40 (1H, d, J=2.7 Hz), 7.32-7.28 (2H, m), 7.21 (1H, dd, J=8.8, 2.5 Hz), 6.97 (1H, d, J=8.9 Hz), 5.43 (2H, s), 3.66 (3H, s), 2.24 (3H, d, J=20.3 Hz), 2.19-2.14 (4H, m), 1.96 (3H, s), 1.04-0.99 (2H, m), 0.79-0.74 (2H, m).

Preparation Example 8

A similar reaction to Preparation example 2 using 2-methyl-4-(4,5,6,7-tetrahydro-indazol-1-yl)-phenol (described in Reference Preparation example 27) instead of 2-methyl-4-(3,4,5-trimethyl-pyrazol-1-yl)-phenol gave 1-{3-cyclopropyl-2-[2-methyl-4-(4,5,6,7-tetrahydro-indazol-1-yl)-phenoxymethyl]-phenyl}-4-methyl-1,4-dihydrotetrazole-5-one (hereinafter, referred to as "Present compound 8").

Present compound 8

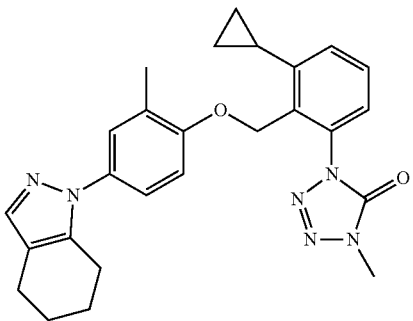

¹H-NMR (CDCl₃) δ: 7.46-7.41 (2H, m), 7.29-7.24 (3H, m), 7.20 (1H, dd, J=8.7, 2.6 Hz), 6.91 (1H, d, J=8.5 Hz), 5.29 (2H, s), 3.62 (3H, s), 2.66 (2H, t, J=5.4 Hz), 2.58 (2H, t, J=5.4 Hz), 2.17-2.09 (4H, m), 1.82-1.75 (4H, m), 1.02-0.98 (2H, m), 0.79-0.74 (2H, m).

Preparation Example 9

A similar reaction to Preparation example 2 using 2-methyl-4-(4,5,6,7-tetrahydro-indazol-2-yl)-phenol (described in Reference Preparation example 26) instead of 2-methyl-4-(3,4,5-trimethyl-pyrazol-1-yl)-phenol gave 1-{3-cyclopropyl-2-[2-methyl-4-(4,5,6,7-tetrahydro-indazol-2-yl)-phenoxymethyl]-phenyl}-4-methyl-1,4-dihydro-tetrazole-5-one (hereinafter, referred to as "Present compound 9").

Present compound 9

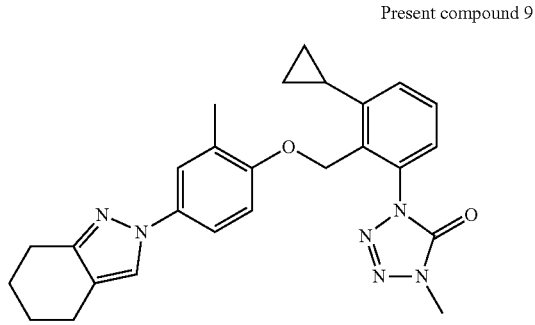 [SMILES: Cc1cc(-n2cc3c(n2)CCCC3)ccc1OCc1c(C2CC2)cccc1-n1nnn(C)c1=O]

¹H-NMR (CDCl₃) δ: 7.50 (1H, s), 7.43 (1H, t, J=7.9 Hz), 7.40 (1H, d, J=2.2 Hz), 7.31 (1H, dd, J=8.7, 2.6 Hz), 7.29-7.25 (2H, m), 6.88 (1H, d, J=8.8 Hz), 5.27 (2H, s), 3.60 (3H, s), 2.76 (2H, t, J=6.2 Hz), 2.60 (2H, t, J=6.1 Hz), 2.15-2.09 (4H, m), 1.89-1.82 (2H, m), 1.81-1.74 (2H, m), 1.02-0.97 (2H, m), 0.79-0.74 (2H, m).

Preparation Example 10

A similar reaction to Preparation example 2 using 2-methyl-4-(4,5-dimethyl-pyrazol-1-yl)-phenol (described in Reference Preparation example 24) instead of 2-methyl-4-(3,4,5-trimethyl-pyrazol-1-yl)-phenol gave 1-{3-cyclopropyl-2-[2-methyl-4-(4,5-dimethyl-pyrazol-1-yl)-phenoxymethyl]-phenyl}-4-methyl-1,4-dihydrotetrazole-5-one (hereinafter, referred to as "Present compound 10").

Present compound 10

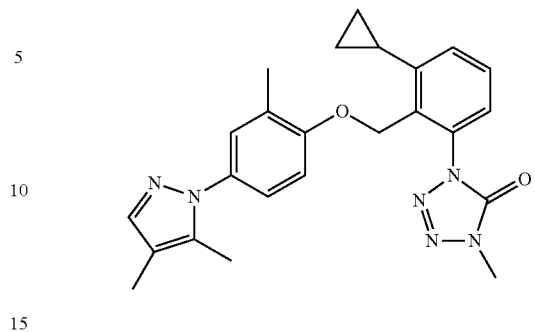

¹H-NMR (CDCl₃) δ: 7.44 (1H, t, J=7.8 Hz), 7.40 (1H, s), 7.29 (1H, s), 7.27-7.26 (1H, m), 7.18-7.13 (2H, m), 6.92 (1H, d, J=8.5 Hz), 5.29 (2H, s), 3.63 (3H, s), 2.20 (3H, s), 2.15-2.10 (4H, m), 2.05 (3H, s), 1.03-0.98 (2H, m), 0.80-0.75 (2H, m).

Preparation Example 11

A similar reaction to Preparation example 2 using 2-chloro-4-(3,5-dimethyl-4-methoxy-pyrazol-1-yl)-phenol (described in Reference Preparation example 18) instead of 2-methyl-4-(3,4,5-trimethyl-pyrazol-1-yl)-phenol gave 1-{3-cyclopropyl-2-[2-chloro-4-(3,5-dimethyl-4-methoxy-pyrazol-1-yl)-phenoxymethyl]-phenyl}-4-methyl-1,4-dihydrotetrazole-5-one (hereinafter, referred to as "Present compound 11").

Present compound 11

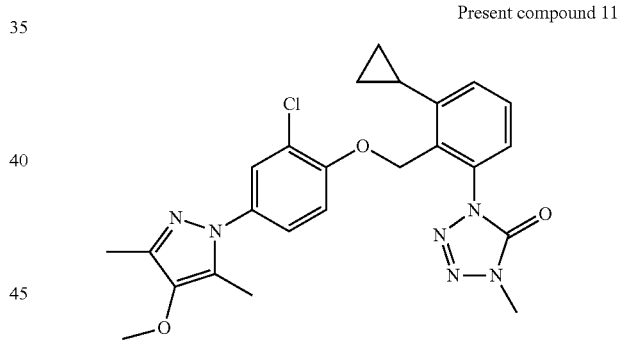

¹H-NMR (CDCl₃) δ: 7.50-7.44 (2H, m), 7.36-7.31 (2H, m), 7.27-7.23 (1H, m), 7.01 (1H, d, J=8.9 Hz), 5.47 (2H, s), 3.80 (3H, s), 3.70 (3H, s), 2.31 (3H, s), 2.26 (3H, s), 2.22-2.17 (1H, m), 1.08-1.03 (2H, m), 0.82-0.78 (2H, m).

Preparation Example 12

A mixture of 1-(2-bromomethyl-3-cyclopropylphenyl)-4-methyl-1,4-dihydrotetrazole-5-one 0.30 g, 2-methyl-4-(1-methyl-1H-pyrazol-3-yl)-phenol (described in Reference Preparation example 29) 0.18 g, potassium carbonate 0.18 g and acetonitrile 10 ml was stirred with heating under reflux for four hours. After cooling to room temperature, the reaction mixture was filtered, and the filtrate was then concentrated. The resulting residue was subjected to a silica gel column chromatography to give 1-{3-cyclopropyl-2-[2-methyl-4-(1-methyl-1H-pyrazol-3-yl)-phenoxymethyl]-phenyl}-4-methyl-1,4-dihydrotetrazole-5-one (hereinafter, referred to as "Present compound 12") 0.22 g.

Present compound 12

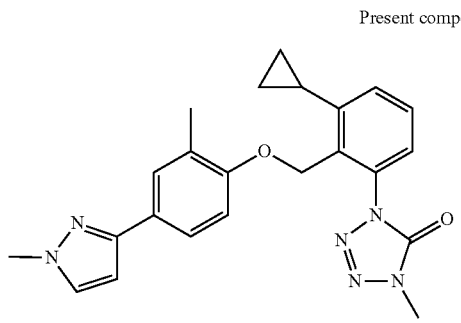

¹H-NMR (CDCl₃) δ: 7.57-7.56 (1H, m), 7.53 (1H, dd, J=8.3, 2.2 Hz), 7.43 (1H, t, J=7.9 Hz), 7.34 (1H, d, J=2.2 Hz), 7.29-7.25 (2H, m), 6.90 (1H, d, J=8.5 Hz), 6.45 (1H, d, J=2.2 Hz), 5.28 (2H, s), 3.93 (3H, s), 3.59 (3H, s), 2.15-2.11 (4H, m), 1.01-0.96 (2H, m), 0.78-0.74 (2H, m).

Preparation Example 13

A similar reaction to Preparation example 2 using 2-methyl-4-(1-ethyl-1H-pyrazol-3-yl)-phenol (described in Reference Preparation example 30) instead of 2-methyl-4-(3,4,5-trimethyl-pyrazol-1-yl)-phenol gave 1-{3-cyclopropyl-2-[2-methyl-4-(1-ethyl-1H-pyrazol-3-yl)-phenoxymethyl]-phenyl}-4-methyl-1,4-dihydrotetrazole-5-one (hereinafter, referred to as "Present compound 13").

Present compound 13

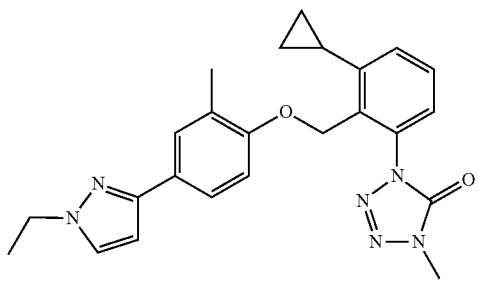

¹H-NMR (CDCl₃) δ: 7.58-7.56 (1H, m), 7.55-7.51 (1H, m), 7.43 (1H, t, J=7.8 Hz), 7.38 (1H, d, J=2.2 Hz), 7.30-7.25 (2H, m), 6.90 (1H, d, J=8.2 Hz), 6.45 (1H, d, J=2.2 Hz), 5.28 (2H, s), 4.20 (2H, q, J=7.3 Hz), 3.60 (3H, s), 2.16-2.10 (4H, m), 1.52 (3H, t, J=7.2 Hz), 1.02-0.96 (2H, m), 0.81-0.74 (2H, m).

Preparation Example 14

A similar reaction to Preparation example 2 using 2-methyl-4-(1-isopropyl-1H-pyrazol-3-yl)-phenol (described in Reference Preparation example 31) instead of 2-methyl-4-(3,4,5-trimethyl-pyrazol-1-yl)-phenol gave 1-{3-cyclopropyl-2-[2-methyl-4-(1-isopropyl-1H-pyrazol-3-yl)-phenoxymethyl]-phenyl}-4-methyl-1,4-dihydrotetrazole-5-one (hereinafter, referred to as "Present compound 14").

Present compound 14

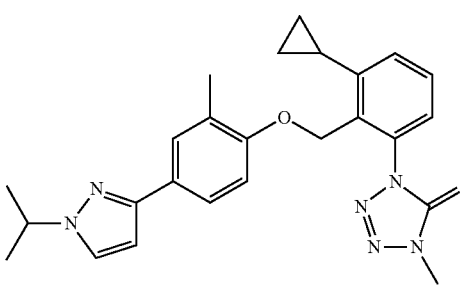

¹H-NMR (CDCl₃) δ: 7.58-7.56 (1H, m), 7.54 (1H, dd, J=8.7, 1.9 Hz), 7.43-7.40 (2H, m), 7.30-7.25 (2H, m), 6.89 (1H, d, J=8.5 Hz), 6.44 (1H, d, J=2.4 Hz), 5.28 (2H, s), 4.57-4.51 (1H, m), 3.60 (3H, s), 2.16-2.10 (4H, m), 1.53 (6H, d, J=6.8 Hz), 1.03-0.96 (2H, m), 0.81-0.73 (2H, m).

Preparation Example 15

A similar reaction to Preparation example 2 using 2-methyl-4-(1,5-dimethyl-1H-pyrazol-3-yl)-phenol (described in Reference Preparation example 32) instead of 2-methyl-4-(3,4,5-trimethyl-pyrazol-1-yl)-phenol gave 1-{3-cyclopropyl-2-[2-methyl-4-(1,5-dimethyl-1H-pyrazol-3-yl)-phenoxymethyl]-phenyl}-4-methyl-1,4-dihydrotetrazole-5-one (hereinafter, referred to as "Present compound 15").

Present compound 15

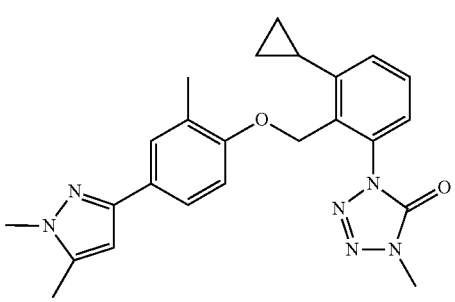

¹H-NMR (CDCl₃) δ: 7.53 (1H, d, J=1.5 Hz), 7.49 (1H, dd, J=8.3, 2.0 Hz), 7.42 (1H, t, J=7.9 Hz), 7.27 (2H, dd, J=8.8, 4.9 Hz), 6.88 (1H, d, J=8.5 Hz), 6.23 (1H, s), 5.28 (2H, s), 3.80 (3H, s), 3.59 (3H, s), 2.29 (3H, s), 2.15-2.10 (4H, m), 1.02-0.96 (2H, m), 0.79-0.73 (2H, m).

Preparation Example 16

A similar reaction to Preparation example 1 using 2-methyl-4-(1-methyl-1H-pyrazol-4-yl)-phenol (described in Reference Preparation example 28) instead of 2-methyl-4-(3,4,5-trimethyl-pyrazol-1-yl)-phenol gave 1-{3-cyclopropyl-2-[2-methyl-4-(1-methyl-1H-pyrazol-4-yl)-phenoxymethyl]-phenyl}-4-methyl-1,4-dihydrotetrazole-5-one (hereinafter, referred to as "Present compound 16").

Present compound 16

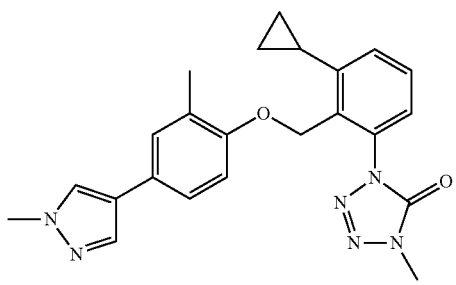

¹H-NMR (CDCl₃) δ: 7.67 (1H, s), 7.51 (1H, s), 7.43 (1H, t, J=7.9 Hz), 7.28-7.21 (4H, m), 6.87 (1H, d, J=8.0 Hz), 5.26 (2H, s), 3.92 (3H, s), 3.60 (3H, s), 2.16-2.10 (4H, m), 1.02-0.97 (2H, m), 0.79-0.74 (2H, m).

Preparation Example 17

A similar reaction to Preparation example 1 using 2-chloro-4-(3,4,5-trimethyl-pyrazol-1-yl)-phenol (described in Reference Preparation example 16) instead of 2-methyl-4-(3,4,5-trimethyl-pyrazol-1-yl)-phenol gave 1-{3-difluoromethoxy-2-[2-chloro-4-(3,4,5-trimethyl-pyrazol-1-yl)-phenoxymethyl]-phenyl}-4-methyl-1,4-dihydrotetrazole-5-one (hereinafter, referred to as "Present compound 17").

Present compound 17

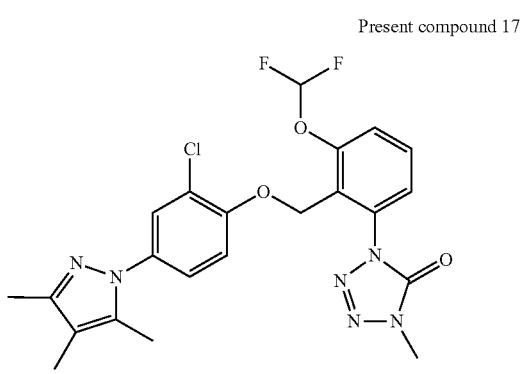 [SMILES: Cc1nn(-c2ccc(OCc3c(OC(F)F)cccc3-n3nnn(C)c3=O)c(Cl)c2)c(C)c1C]

¹H-NMR (CDCl₃) δ: 7.56 (1H, t, J=8.1 Hz), 7.44 (1H, dd, J=8.1, 0.8 Hz), 7.40 (1H, d, J=2.7 Hz), 7.36 (1H, d, J=8.2 Hz), 7.21 (1H, dd, J=8.7, 2.7 Hz), 7.00-6.96 (1H, m), 6.63 (1H, t, J=73.0 Hz), 5.41 (2H, s), 3.65 (3H, s), 2.22 (3H, s), 2.18 (3H, s), 1.96 (3H, s).

Preparation Example 18

A similar reaction to Preparation example 1 using 2-methyl-4-(1-methyl-1H-pyrazol-3-yl)-phenol (described in Reference Preparation example 29) instead of 2-methyl-4-(3,4,5-trimethyl-pyrazol-1-yl)-phenol gave 1-{3-difluoromethoxy-2-[2-methyl-4-(1-methyl-1H-pyrazol-3-yl)-phenoxymethyl]-phenyl}-4-methyl-1,4-dihydrotetrazole-5-one (hereinafter, referred to as "Present compound 18").

Present compound 18

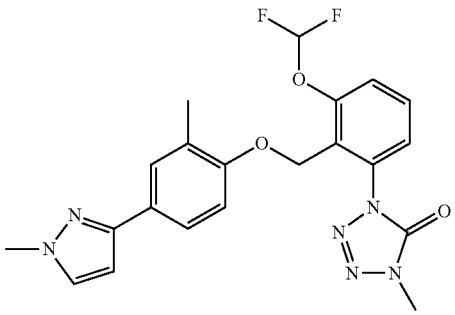

¹H-NMR (CDCl₃) δ: 7.57-7.50 (3H, m), 7.41-7.33 (3H, m), 6.87 (1H, d, J=8.5 Hz), 6.58 (1H, t, J=73.2 Hz), 6.44 (1H, d, J=2.4 Hz), 5.28 (2H, d, J=3.9 Hz), 3.93 (3H, s), 3.57 (3H, s), 2.03 (3H, s).

Preparation Example 19

A similar reaction to Preparation example 2 using 2-chloro-4-(3,5-dimethyl-4-ethyl-pyrazol-1-yl)-phenol (described in Reference Preparation example 19) instead of 2-methyl-4-(3,4,5-trimethyl-pyrazol-1-yl)-phenol gave 1-{3-cyclopropyl-2-[2-chloro-4-(4-ethyl-3,5-dimethyl-pyrazol-1-yl)-phenoxymethyl]-phenyl}-4-methyl-1,4-dihydrotetrazole-5-one (hereinafter, referred to as "Present compound 19").

Present compound 19

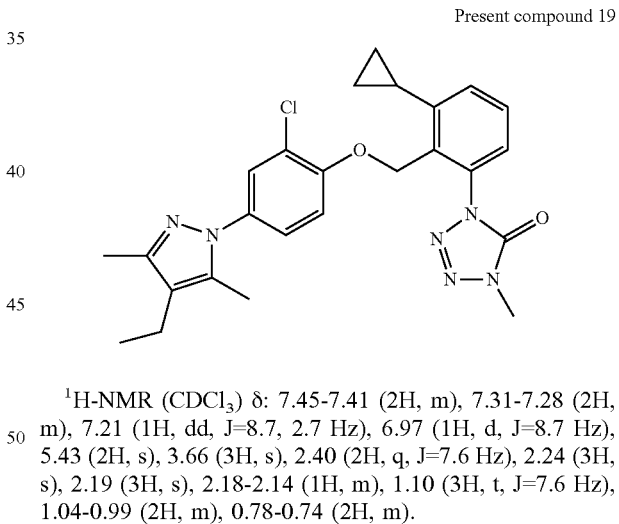

¹H-NMR (CDCl₃) δ: 7.45-7.41 (2H, m), 7.31-7.28 (2H, m), 7.21 (1H, dd, J=8.7, 2.7 Hz), 6.97 (1H, d, J=8.7 Hz), 5.43 (2H, s), 3.66 (3H, s), 2.40 (2H, q, J=7.6 Hz), 2.24 (3H, s), 2.19 (3H, s), 2.18-2.14 (1H, m), 1.10 (3H, t, J=7.6 Hz), 1.04-0.99 (2H, m), 0.78-0.74 (2H, m).

Preparation Example 20

A mixture of 1-{2-(2-methyl-4-(3,4,5-trimethyl-pyrazol-1-yl)-phenoxymethyl)-3-trimethylsilylethynyl-phenyl}-4-methyl-1,4-dihydrotetrazole-5-one (described in Reference Preparation example 71) 0.2 g, potassium carbonate 0.7 g, chloroform 5 ml and methanol 5 ml was stirred at room temperature for three hours, and then the resulting mixture was heated to 60° C. and was stirred for three hours. The reaction mixture was filtered, and the filtrate was then concentrated under reduced pressure. The resulting residue was subjected to a silica gel column chromatography to give 1-{3-ethynyl-2-[2-methyl-4-(3,4,5-trimethyl-pyrazol-1-yl)- phenoxymethyl]-phenyl}-4-methyl-1,4-dihydrotetrazole-5-one (hereinafter, referred to as "Present compound 20") 0.07 g.

Present compound 20

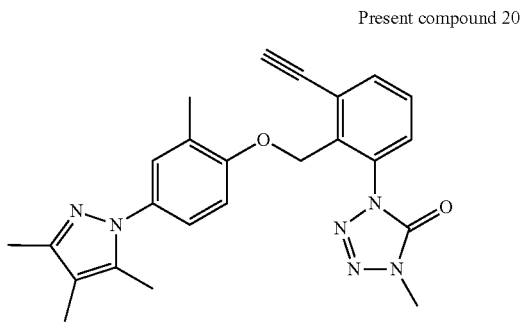 [SMILES: C#Cc1cccc(-n2nnn(C)c2=O)c1COc1ccc(-n2nc(C)c(C)c2C)cc1C]

¹H-NMR (CDCl₃) δ: 7.72 (1H, dd, J=5.8, 3.4 Hz), 7.49 (1H, d, J=2.2 Hz), 7.48 (1H, s), 7.13 (1H, d, J=2.4 Hz), 7.09 (1H, dd, J=8.6, 2.5 Hz), 6.90 (1H, d, J=8.7 Hz), 5.45 (2H, s), 3.61 (3H, s), 3.38 (1H, s), 2.22 (3H, s), 2.15 (3H, s), 2.02 (3H, s), 1.96 (3H, s).

Preparation Example 21

A similar reaction to Preparation example 2 using 2,5-dimethyl-4-(3-methyl-pyrazol-1-yl)-phenol (described in Reference Preparation example 73) instead of 2-methyl-4-(3,4,5-trimethyl-pyrazol-1-yl)-phenol gave 1-{3-cyclopropyl-2-[2,5-dimethyl-4-(3-methyl-pyrazol-1-yl)-phenoxymethyl]-phenyl}-4-methyl-1,4-dihydrotetrazole-5-one (hereinafter, referred to as "Present compound 21").

Present compound 21

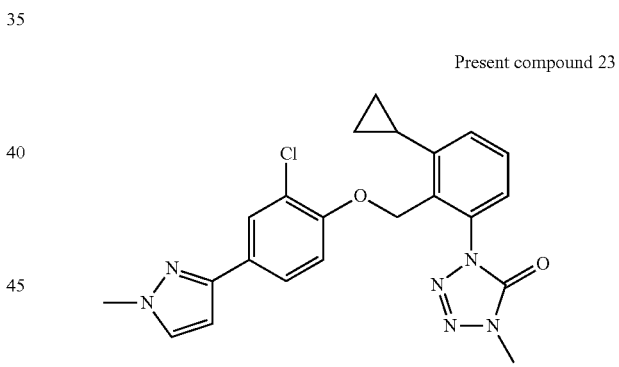

¹H-NMR (CDCl₃) δ: 7.44 (1H, t, J=7.9 Hz), 7.40 (1H, d, J=2.1 Hz), 7.28 (1H, s), 7.26 (1H, s), 7.06 (1H, s), 6.74 (1H, s), 6.17 (1H, d, J=2.3 Hz), 5.27 (2H, s), 3.65 (3H, s), 2.35 (3H, s), 2.17 (3H, s), 2.14-2.10 (1H, m), 2.04 (3H, s), 1.02-0.98 (2H, m), 0.79-0.75 (2H, m).

Preparation Example 22

A similar reaction to Preparation example 2 using 2-chloro-4-(1,4-dimethyl-1H-pyrazol-3-yl)-phenol (described in Reference Preparation example 60) instead of 2-methyl-4-(3,4,5-trimethyl-pyrazol-1-yl)-phenol gave 1-{3-cyclopropyl-2-[2-chloro-4-(1,4-dimethyl-1H-pyrazol-3-yl)-phenoxymethyl]-phenyl}-4-methyl-1,4-dihydrotetrazole-5-one (hereinafter, referred to as "Present compound 22").

Present compound 22

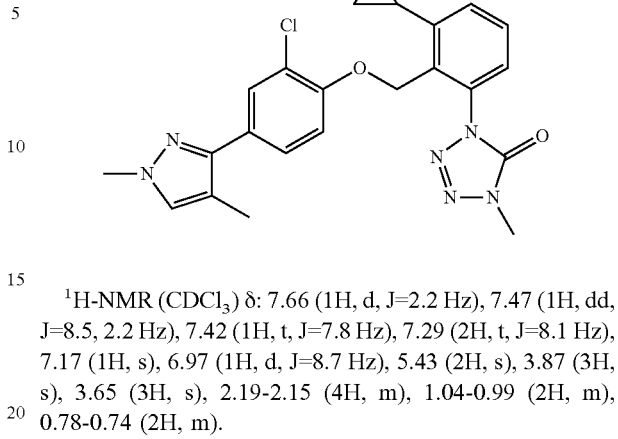

¹H-NMR (CDCl₃) δ: 7.66 (1H, d, J=2.2 Hz), 7.47 (1H, dd, J=8.5, 2.2 Hz), 7.42 (1H, t, J=7.8 Hz), 7.29 (2H, t, J=8.1 Hz), 7.17 (1H, s), 6.97 (1H, d, J=8.7 Hz), 5.43 (2H, s), 3.87 (3H, s), 3.65 (3H, s), 2.19-2.15 (4H, m), 1.04-0.99 (2H, m), 0.78-0.74 (2H, m).

Preparation Example 23

A similar reaction to Preparation example 2 using 2-chloro-4-(1-methyl-1H-pyrazol-3-yl)-phenol (described in Reference Preparation example 54) instead of 2-methyl-4-(3,4,5-trimethyl-pyrazol-1-yl)-phenol gave 1-{3-cyclopropyl-2-[2-chloro-4-(1-methyl-1H-pyrazol-3-yl)-phenoxymethyl]-phenyl}-4-methyl-1,4-dihydrotetrazole-5-one (hereinafter, referred to as "Present compound 23").

Present compound 23

¹H-NMR (CDCl₃) δ: 7.76 (1H, d, J=2.2 Hz), 7.58 (1H, dd, J=8.5, 2.2 Hz), 7.42 (1H, t, J=7.8 Hz), 7.35 (1H, d, J=2.2 Hz), 7.29 (2H, t, J=7.8 Hz), 6.94 (1H, d, J=8.5 Hz), 6.43 (1H, d, J=2.4 Hz), 5.43 (2H, s), 3.93 (3H, s), 3.64 (3H, s), 2.21-2.14 (1H, m), 1.04-0.99 (2H, m), 0.78-0.74 (2H, m).

Preparation Example 24

A similar reaction to Preparation example 2 using 4-(1,4-dimethyl-1H-pyrazol-3-yl)-2-methyl-phenol (described in Reference Preparation example 59) instead of 2-methyl-4-(3,4,5-trimethyl-pyrazol-1-yl)-phenol gave 1-{3-cyclopropyl-2-[4-(1,4-dimethyl-1H-pyrazol-3-yl)-2-methyl-phenoxymethyl]-phenyl}-4-methyl-1,4-dihydrotetrazole-5-one (hereinafter, referred to as "Present compound 24").

Present compound 24

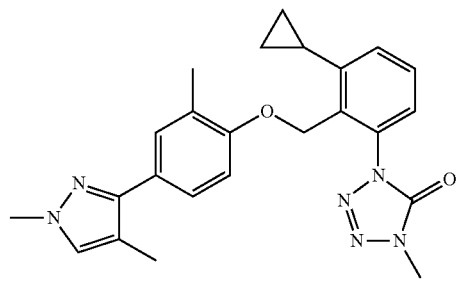

Present compound 26

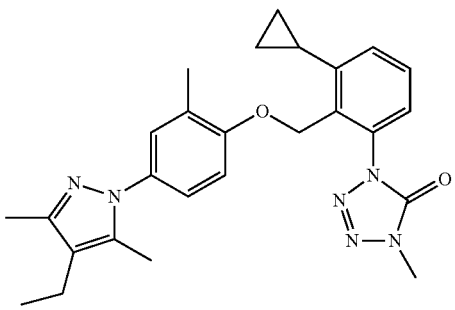

$^1$H-NMR (CDCl$_3$) δ: 7.45-7.40 (3H, m), 7.28-7.26 (2H, m), 7.17 (1H, s), 6.92 (1H, d, J=8.5 Hz), 5.29 (2H, s), 3.87 (3H, s), 3.61 (3H, s), 2.20 (3H, s), 2.16-2.10 (4H, m), 1.02-0.97 (2H, m), 0.79-0.74 (2H, m).

Preparation Example 25

A similar reaction to Preparation example 2 using 2-methyl-4-(1,4,5-trimethyl-1H-pyrazol-3-yl)-2-methyl-phenol (described in Reference Preparation example 66) instead of 2-methyl-4-(3,4,5-trimethyl-pyrazol-1-yl)-phenol gave 1-{3-cyclopropyl-2-[2-methyl-4-(1,4,5-trimethyl-1H-pyrazol-3-yl)-2-methyl-phenoxymethyl]-phenyl}-4-methyl-1,4-dihydrotetrazole-5-one (hereinafter, referred to as "Present compound 25").

$^1$H-NMR (CDCl$_3$) δ: 7.44 (1H, t, J=7.9 Hz), 7.28-7.26 (2H, m), 7.16 (1H, d, J=2.5 Hz), 7.12 (1H, dd, J=8.5, 2.5 Hz), 6.90 (1H, d, J=8.5 Hz), 5.28 (2H, s), 3.62 (3H, s), 2.41 (2H, q, J=7.6 Hz), 2.25 (3H, s), 2.17 (3H, s), 2.13-2.10 (4H, m), 1.11 (3H, t, J=7.6 Hz), 1.02-0.97 (2H, m), 0.78-0.74 (2H, m).

Preparation Example 27

A similar reaction to Preparation example 2 using 2-methyl-4-(3-trifluoromethyl-pyrazol-1-yl)-phenol (described in Reference Preparation example 75) instead of 2-methyl-4-(3,4,5-trimethyl-pyrazol-1-yl)-phenol gave 1-{3-cyclopropyl-2-[2-methyl-4-(3-trifluoromethyl-pyrazol-1-yl)-phenoxymethyl]-phenyl}-4-methyl-1,4-dihydrotetrazole-5-one (hereinafter, referred to as "Present compound 27").

Present compound 25

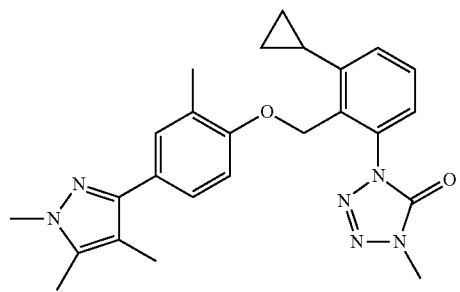

Present compound 27

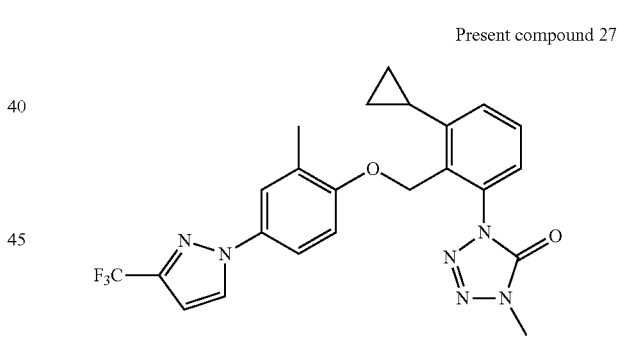

$^1$H-NMR (CDCl$_3$) δ: 7.45-7.40 (2H, m), 7.37 (1H, dd, J=8.4, 1.7 Hz), 7.28-7.26 (2H, m), 6.92 (1H, d, J=8.5 Hz), 5.28 (2H, s), 3.80 (3H, s), 3.60 (3H, s), 2.21 (3H, s), 2.16-2.11 (4H, m), 2.10 (3H, s), 1.01-0.96 (2H, m), 0.78-0.74 (2H, m).

Preparation Example 26

A similar reaction to Preparation example 2 using 4-(3,5-dimethyl-4-ethyl-pyrazol-1-yl)-2-methyl-phenol (described in Reference Preparation example 63) instead of 2-methyl-4-(3,4,5-trimethyl-pyrazol-1-yl)-phenol gave 1-{3-cyclopropyl-2-[4-(3,5-dimethyl-4-ethyl-pyrazol-1-yl)-2-methyl-phenoxymethyl]-phenyl}-4-methyl-1,4-dihydrotetrazole-5-one (hereinafter, referred to as "Present compound 26").

$^1$H-NMR (CDCl$_3$) δ: 7.83 (1H, dd, J=2.5, 0.9 Hz), 7.47-7.43 (2H, m), 7.41 (1H, dd, J=8.7, 2.7 Hz), 7.29 (1H, s), 7.27 (1H, s), 6.93 (1H, d, J=8.7 Hz), 6.68 (1H, d, J=2.5 Hz), 5.31 (2H, s), 3.62 (3H, s), 2.15-2.09 (4H, m), 1.03-0.98 (2H, m), 0.79-0.75 (2H, m).

Preparation Example 28

A similar reaction to Preparation example 2 using 2-methyl-4-(3-trifluoromethyl-pyrazol-1-yl)-phenol (described in Reference Preparation example 86) instead of 2-methyl-4-(3,4,5-trimethyl-pyrazol-1-yl)-phenol gave 1-{3-cyclopropyl-2-[2,5-dimethyl-4-(3-trifluoromethyl-pyrazol-1-yl)-phenoxymethyl]-phenyl}-4-methyl-1,4-dihydrotetrazole-5-one (hereinafter, referred to as "Present compound 28").

Present compound 28

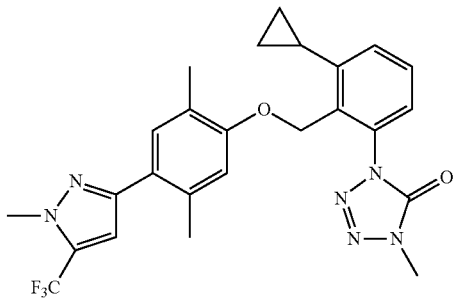

¹H-NMR (CDCl₃) δ: 7.43 (1H, t, J=7.9 Hz), 7.28-7.26 (3H, m), 6.75 (1H, s), 6.68 (1H, s), 5.27 (2H, s), 4.02 (3H, s), 3.63 (3H, s), 2.42 (3H, s), 2.17-2.10 (1H, m), 2.06 (3H, s), 1.02-0.97 (2H, m), 0.79-0.75 (2H, m).

Preparation Example 29

A similar reaction to Preparation example 2 using 2-methyl-4-(1,3-dimethyl-1H-pyrazol-5-yl)-phenol (described in Reference Preparation example 69) instead of 2-methyl-4-(3,4,5-trimethyl-pyrazol-1-yl)-phenol gave 1-{2-[3-cyclopropyl-2-methyl-4-(1,3-dimethyl-1H-pyrazol-5-yl)-phenoxymethyl]-phenyl}-4-methyl-1,4-dihydrotetrazole-5-one (hereinafter, referred to as "Present compound 29").

Present compound 29

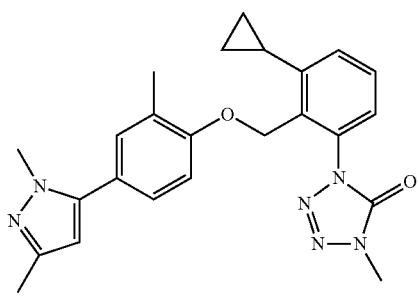

¹H-NMR (CDCl₃) δ: 7.45 (1H, t, J=7.9 Hz), 7.29 (1H, s), 7.27 (1H, s), 7.17 (1H, dd, J=8.2, 2.3 Hz), 7.14-7.13 (1H, m), 6.94 (1H, d, J=8.5 Hz), 6.01 (1H, s), 5.29 (2H, s), 3.80 (3H, s), 3.63 (3H, s), 2.29 (3H, s), 2.18-2.10 (4H, m), 1.03-0.98 (2H, m), 0.80-0.76 (2H, m).

Preparation Example 30

A similar reaction to Preparation example 2 using cyclopropyl-(4-hydroxy-3-methyl-phenyl)-methanone (described in Reference Preparation example 88) instead of 2-methyl-4-(3,4,5-trimethyl-pyrazol-1-yl)-phenol gave 1-[3-cyclopropyl-2-(4-cyclopropanecarbonyl-2-methyl-phenoxymethyl)-phenyl]-4-methyl-1,4-dihydrotetrazole-5-one (hereinafter, referred to as "Present compound 30").

Present compound 30

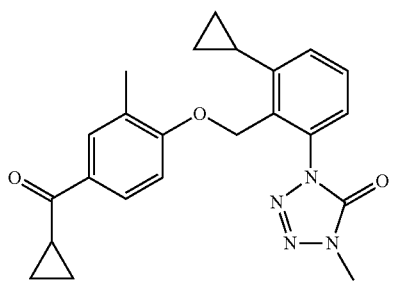

1H-NMR (CDCl3) δ: 7.88 (1H, dd, J=8.70, 2.18 Hz), 7.82-7.80 (1H, m), 7.45 (1H, t, J=7.90 Hz), 7.31-7.27 (2H, m), 6.94 (1H, d, J=8.70 Hz), 5.34 (2H, s), 3.61 (3H, s), 2.65-2.61 (1H, m), 2.13-2.07 (4H, m), 1.22-1.16 (2H, m), 1.02-0.97 (4H, m), 0.80-0.74 (2H, m).

Preparation Example 31

A similar reaction to Preparation example 2 using 2-methyl-4-(3-cyclopropyl-pyrazol-1-yl)-phenol (described in Reference Preparation example 68) instead of 2-methyl-4-(3,4,5-trimethyl-pyrazol-1-yl)-phenol gave 1-{3-cyclopropyl-2-[2-methyl-4-(3-cyclopropyl-pyrazol-1-yl)-phenoxymethyl]-phenyl}-4-methyl-1,4-dihydrotetrazole-5-one (hereinafter, referred to as "Present compound 31").

Present compound 31

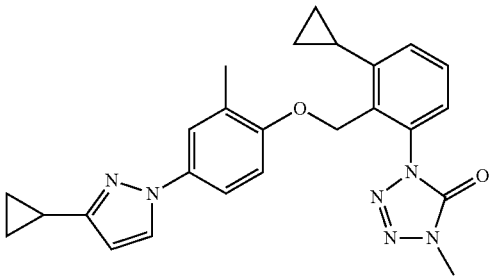

¹H-NMR (CDCl₃) δ: 7.67-7.66 (1H, m), 7.46-7.40 (2H, m), 7.34 (1H, dd, J=8.8, 2.9 Hz), 7.28 (1H, s), 6.89 (1H, d, J=8.4 Hz), 6.05 (1H, d, J=2.3 Hz), 5.28 (2H, s), 3.61 (3H, s), 2.14-2.10 (4H, m), 2.06-2.01 (2H, m), 1.02-0.93 (4H, m), 0.80-0.74 (4H, m).

Preparation Example 32

A similar reaction to Preparation example 2 using 2-methyl-4-(1-methyl-5-trifluoromethyl-1H-pyrazol-3-yl)-phenol (described in Reference Preparation example 79) instead of 2-methyl-4-(3,4,5-trimethyl-pyrazol-1-yl)-phenol gave 1-{3-cyclopropyl-2-[2-methyl-4-(3-trifluoromethyl-pyrazol-1-yl)-phenoxymethyl]-phenyl}-4-methyl-1,4-dihydrotetrazole-5-one (hereinafter, referred to as "Present compound 32").

Present compound 32

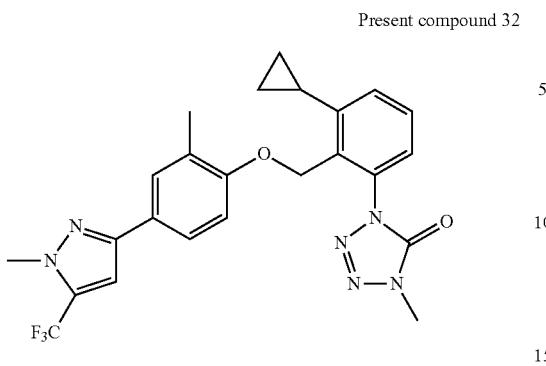

¹H-NMR (CDCl₃) δ: 7.53-7.50 (2H, m), 7.43 (1H, t, J=7.8 Hz), 7.27 (2H, d, J=8.0 Hz), 6.91 (1H, d, J=8.2 Hz), 6.80 (1H, s), 5.29 (2H, s), 4.01 (3H, s), 3.60 (3H, s), 2.15-2.09 (4H, m), 1.02-0.97 (2H, m), 0.79-0.75 (2H, m).

Preparation Example 33

A similar reaction to Preparation example 2 using 4-(5-chloro-1,4-dimethyl-1H-pyrazol-3-yl)-2-methyl-phenol (described in Reference Preparation example 109) instead of 2-methyl-4-(3,4,5-trimethyl-pyrazol-1-yl)-phenol gave 1-{3-cyclopropyl-2-[2-methyl-4-(5-chloro-1,4-dimethyl-1H-pyrazol-3-yl)-phenoxymethyl]-phenyl}-4-methyl-1,4-dihydrotetrazole-5-one (hereinafter, referred to as "Present compound 33").

Present compound 33

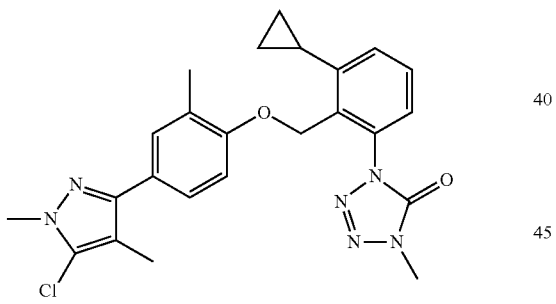

¹H-NMR (CDCl₃) δ: 7.43 (1H, t, J=7.9 Hz), 7.40 (1H, d, J=1.8 Hz), 7.38 (1H, dd, J=8.4, 2.2 Hz), 7.28 (2H, s), 6.93 (1H, d, J=8.2 Hz), 5.29 (2H, s), 3.85 (3H, s), 3.61 (3H, s), 2.15 (3H, s), 2.14-2.12 (4H, m), 1.01-0.97 (2H, m), 0.78-0.74 (2H, m).

Preparation Example 34

A similar reaction to Preparation example 2 using 4-(1,4-dimethyl-5-methoxy-1H-pyrazol-3-yl)-2-methyl-phenol (described in Reference Preparation example 99) instead of 2-methyl-4-(3,4,5-trimethyl-pyrazol-1-yl)-phenol gave 1-{3-cyclopropyl-2-[2-methyl-4-(5-methoxy-1,4-dimethyl-1H-pyrazol-3-yl)-phenoxymethyl]-phenyl}-4-methyl-1,4-dihydrotetrazole-5-one (hereinafter, referred to as "Present compound 34").

Present compound 34

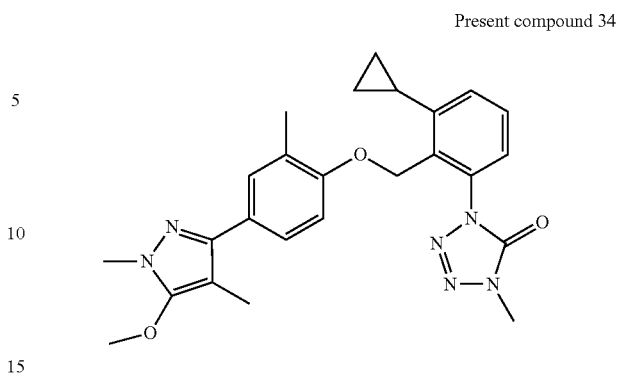

¹H-NMR (CDCl₃) δ: 7.44 (1H, t, J=7.9 Hz), 7.41 (1H, d, J=1.4 Hz), 7.37 (1H, dd, J=8.2, 2.1 Hz), 7.28 (2H, d, J=8.0 Hz), 6.93 (1H, d, J=8.5 Hz), 5.30 (2H, s), 3.95 (3H, s), 3.72 (3H, s), 3.62 (3H, s), 2.16-2.13 (4H, m), 2.12 (3H, s), 1.03-0.98 (2H, m), 0.79-0.75 (2H, m).

Preparation Example 35

A similar reaction to Preparation example 2 using 4-(4-butyl-3,5-dimethyl-pyrazol-1-yl)-2-methyl-phenol (described in Reference Preparation example 108) instead of 2-methyl-4-(3,4,5-trimethyl-pyrazol-1-yl)-phenol gave 1-{3-cyclopropyl-2-[2-methyl-4-(4-butyl-3,5-dimethyl-pyrazol-1-yl)-phenoxymethyl]-phenyl}-4-methyl-1,4-dihydrotetrazole-5-one (hereinafter, referred to as "Present compound 35").

Present compound 35

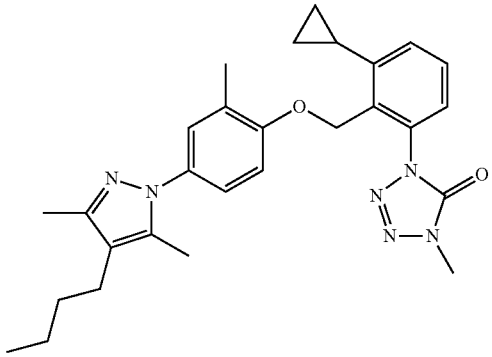

¹H-NMR (CDCl₃) δ: 7.44 (1H, t, J=8.0 Hz), 7.28 (2H, d, J=8.0 Hz), 7.16 (1H, d, J=2.4 Hz), 7.12 (1H, dd, J=8.6, 2.5 Hz), 6.90 (1H, d, J=8.7 Hz), 5.28 (2H, s), 3.63 (3H, s), 2.38 (2H, t, J=7.5 Hz), 2.24 (3H, s), 2.17 (3H, s), 2.14-2.08 (4H, m), 1.48-1.44 (2H, m), 1.39-1.33 (2H, m), 1.02-0.97 (2H, m), 0.94 (3H, t, J=7.2 Hz), 0.79-0.74 (2H, m).

Preparation Example 36

A mixture of 1-{3-cyclopropyl-2-(2-methyl-4-(1,5-dimethyl-1H-pyrazol-3-yl)-phenoxymethyl]-phenyl}-4-methyl-1,4-dihydrotetrazole-5-one (described in Preparation example 15) (Present compound 15) 0.37 g, N-chlorosuccinimide 0.12 g and chloroform 5 ml was stirred at room temperature for twelve hours. The resulting mixture was extracted with chloroform and was washed with saturated saline. The organic layer was dried over anhydrous magnesium sulfate and was then concentrated under reduced pressure. The resulting residue was subjected to a silica gel column chromatography to give 1-{3-cyclopropyl-2-(2-methyl-4-(4-chloro-1,5-dimethyl-1H-pyrazol-3-yl)-phenoxymethyl]-phenyl}-4-methyl-1,4-dihydrotetrazole-5-one (hereinafter, referred to as "Present compound 36") 0.13 g.

Present compound 36

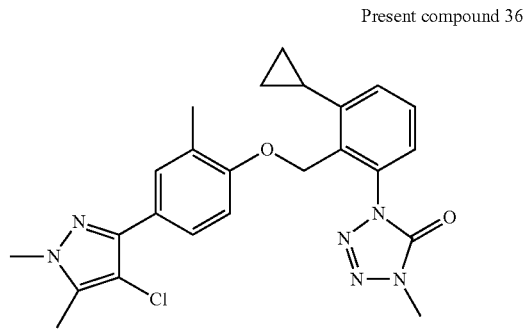 [SMILES: Cc1cc(-c2nn(C)c(C)c2Cl)ccc1OCc1c(C2CC2)cccc1-n1nnn(C)c1=O]

$^1$H-NMR (CDCl$_3$) δ: 7.66 (1H, dd, J=8.5, 2.2 Hz), 7.60 (1H, d, J=1.9 Hz), 7.43 (1H, t, J=7.8 Hz), 7.28-7.26 (2H, m), 6.93 (1H, d, J=8.5 Hz), 5.29 (2H, s), 3.82 (3H, s), 3.60 (3H, s), 2.28 (3H, s), 2.16-2.09 (4H, m), 1.01-0.97 (2H, m), 0.78-0.74 (2H, m).

Preparation Example 37

A similar reaction to Preparation example 2 using 4-(1,4-dimethyl-5-ethoxy-1H-pyrazol-3-yl)-2-methyl-phenol (described in Reference Preparation example 102) instead of 2-methyl-4-(3,4,5-trimethyl-pyrazol-1-yl)-phenol gave 1-{3-cyclopropyl-2-[2-methyl-4-(5-ethoxy-1,4-dimethyl-1H-pyrazol-3-yl)-phenoxymethyl]-phenyl}-4-methyl-1,4-dihydrotetrazole-5-one (hereinafter, referred to as "Present compound 37").

Present compound 37

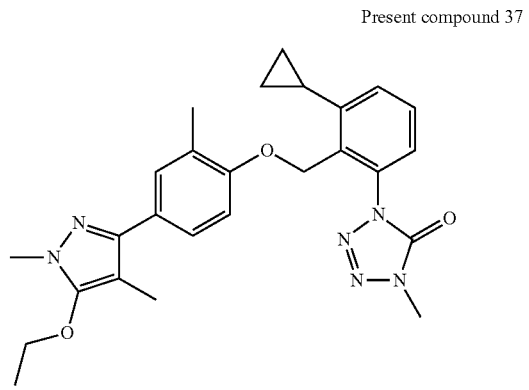 [SMILES: CCOc1c(C)c(-c2ccc(OCc3c(C4CC4)cccc3-n3nnn(C)c3=O)c(C)c2)nn1C]

$^1$H-NMR (CDCl$_3$) δ: 7.45-7.41 (2H, m), 7.37 (1H, dd, J=8.5, 2.3 Hz), 7.27-7.26 (2H, m), 6.91 (1H, d, J=8.5 Hz), 5.28 (2H, s), 4.17-4.12 (2H, m), 3.70 (3H, s), 3.60 (3H, s), 2.14-2.10 (7H, m), 1.41 (3H, t, J=7.1 Hz), 1.00-0.96 (2H, m), 0.78-0.75 (2H, m).

Preparation Example 38

A mixture of 1-(2-bromomethyl-3-methylthiophenyl)-4-methyl-1,4-dihydrotetrazole-5-one (described in Preparation example 13) 1.5 g, 4-(5-chloro-1,4-dimethyl-1H-pyra-zol-3-yl)-2-methyl-phenol 1 g, potassium carbonate 0.9 g and acetonitrile 20 ml was stirred with heating under reflux for five hours. The reaction mixture was concentrated and the resulting residue was subjected to a silica gel column chromatography to give 1-{3-methylthio-2-[2-methyl-4-(5-chloro-1,4-dimethyl-1H-pyrazol-3-yl)-phenoxymethyl]-phenyl}-4-methyl-1,4-dihydrotetrazole-5-one (hereinafter, referred to as "Present compound 38") 2.1 g.

Present compound 38

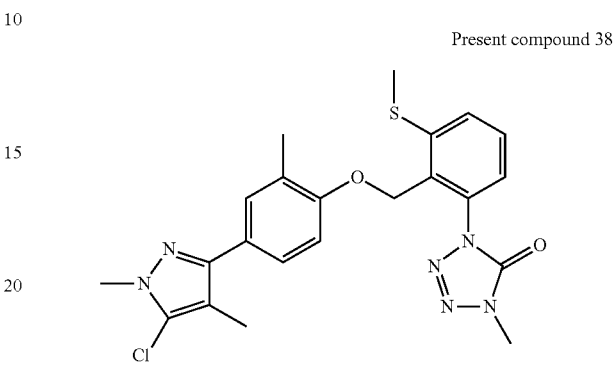

$^1$H-NMR (CDCl$_3$) δ: 7.52-7.50 (2H, m), 7.40 (1H, d, J=1.6 Hz), 7.39-7.36 (1H, m), 7.29-7.27 (1H, m), 6.93 (1H, d, J=8.2 Hz), 5.27 (2H, s), 3.86 (3H, s), 3.63 (3H, s), 2.54 (3H, s), 2.16 (3H, s), 2.11 (3H, s).

Preparation Example 39

A similar reaction to Preparation example 38 using 4-(1,4-dimethyl-5-ethoxy-1H-pyrazol-3-yl)-2-methyl-phenol (described in Reference Preparation example 102) instead of 4-(5-chloro-1,4-dimethyl-1H-pyrazol-3-yl)-2-methyl-phenol gave 1-{3-methylthio-2-[2-methyl-4-(5-ethoxy-1,4-dimethyl-1H-pyrazol-3-yl)-phenoxymethyl]-phenyl}-4-methyl-1,4-dihydrotetrazole-5-one (hereinafter, referred to as "Present compound 39").

Present compound 39

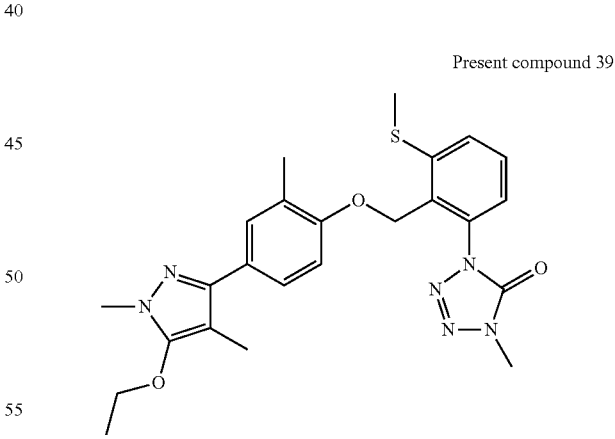

$^1$H-NMR (CDCl$_3$) δ: 7.50-7.46 (2H, m), 7.40 (1H, d, J=1.6 Hz), 7.35 (1H, dd, J=8.4, 2.2 Hz), 7.27-7.25 (1H, m), 6.90 (1H, d, J=8.5 Hz), 5.25 (2H, s), 4.14 (2H, q, J=7.1 Hz), 3.70 (3H, s), 3.61 (3H, s), 2.52 (3H, s), 2.10 (3H, s), 2.09 (3H, s), 1.41 (3H, t, J=7.0 Hz).

Preparation Examples 40 and 41

At room temperature, a mixture of 1-{3-methylthio-2-[2-methyl-4-(5-ethoxy-1,4-dimethyl-1H-pyrazol-3-yl)-phenoxymethyl]-phenyl}-4-methyl-1,4-dihydrotetrazole-5-one (described in Preparation example 39) (Present compound 40) 1 g, m-chloroperoxybenzoic acid 0.55 g and chloroform 15 ml was stirred for four hours. The reaction mixture was extracted with chloroform. The organic layer was washed with water and aqueous sodium thiosulfate solution, and was dried over anhydrous magnesium sulfate. The resulting mixture was concentrated. The resulting residue was subjected to a silica gel column chromatography to give 1-{2-[4-(5-chloro-1,4-dimethyl-1H-pyrazol-3-yl)-2-methyl-phenoxymethyl]-3-methanesulfonyl-phenyl}-4-methyl-1,4-dihydrotetrazole-5-one (hereinafter, referred to as "Present compound 40") 0.12 g and 1-{2-[4-(5-chloro-1,4-dimethyl-1H-pyrazol-3-yl)-2-methyl-phenoxymethyl]-3-methanesulfinyl-phenyl}-4-methyl-1,4-dihydrotetrazole-5-one (hereinafter, referred to as "Present compound 41") 0.95 g.

1-{2-[4-(5-chloro-1,4-dimethyl-1H-pyrazol-3-yl)-2-methyl-phenoxymethyl]-3-methanesulfonyl-phenyl}-4-methyl-1,4-dihydrotetrazole-5-one Present compound 40

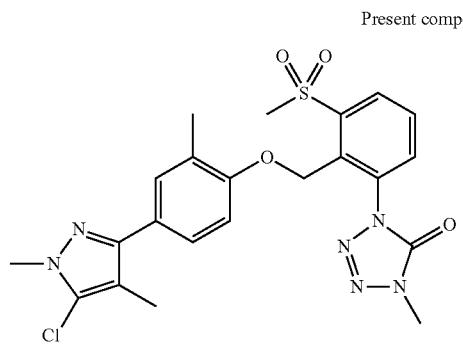

$^1$H-NMR (CDCl$_3$) δ: 8.39 (1H, dd, J=7.0, 2.4 Hz), 7.81-7.75 (2H, m), 7.41-7.38 (2H, m), 6.99 (1H, d, J=8.2 Hz), 5.63 (2H, s), 3.86 (3H, s), 3.56 (3H, s), 3.19 (3H, s), 2.15 (3H, s), 2.07 (3H, s).

1-{2-[4-(5-chloro-1,4-dimethyl-1H-pyrazol-3-yl)-2-methyl-phenoxymethyl]-3-methanesulfinyl-phenyl}-4-methyl-1,4-dihydrotetrazole-5-one (hereinafter, referred to as Present compound 41

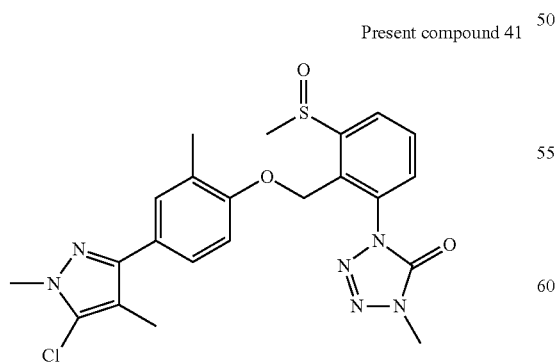

$^1$H-NMR (CDCl$_3$) δ: 8.33 (1H, dd, J=8.0, 1.1 Hz), 7.82 (1H, t, J=8.0 Hz), 7.63 (1H, dd, J=7.9, 1.3 Hz), 7.42 (1H, dd, J=2.1, 0.7 Hz), 7.39-7.36 (1H, m), 6.87 (1H, d, J=8.5 Hz), 5.27 (1H, d, J=11.9 Hz), 5.08 (1H, d, J=11.9 Hz), 3.85 (3H, s), 3.63 (3H, s), 2.81 (3H, s), 2.14 (3H, s), 2.12 (3H, s).

Preparation Example 42

A similar reaction to Preparation example 1 using 4-(1,4-dimethyl-5-methoxy-1H-pyrazol-3-yl)-2-methyl-phenol (described in Reference Preparation example 99) instead of 2-methyl-4-(3,4,5-trimethyl-pyrazol-1-yl)-phenol gave 1-{3-difluoromethoxy-2-[2-methyl-4-(5-methoxy-1,4-dimethyl-1H-pyrazol-3-yl)-phenoxymethyl]-phenyl}-4-methyl-1,4-dihydrotetrazole-5-one (hereinafter, referred to as "Present compound 42").

Present compound 42

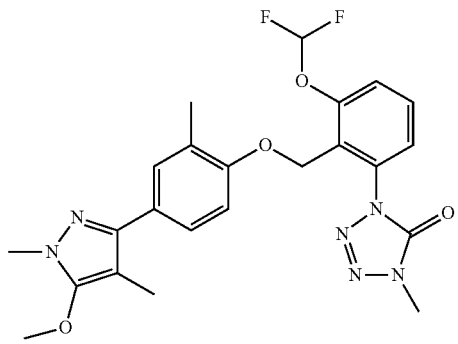

$^1$H-NMR (CDCl$_3$) δ: 7.54 (1H, t, J=8.3 Hz), 7.40-7.36 (3H, m), 7.34 (1H, dd, J=8.4, 2.3 Hz), 6.88 (1H, d, J=8.4 Hz), 6.57 (1H, t, J=73.2 Hz), 5.27 (2H, s), 3.93 (3H, s), 3.70 (3H, s), 3.58 (3H, s), 2.12 (3H, s), 2.02 (3H, s).

Preparation Example 43

A similar reaction to Preparation example 1 using 4-(1,4-dimethyl-5-ethoxy-1H-pyrazol-3-yl)-2-methyl-phenol (described in Reference Preparation example 102) instead of 2-methyl-4-(3,4,5-trimethyl-pyrazol-1-yl)-phenol gave 1-{3-difluoromethoxy-2-[2-methyl-4-(5-ethoxy-1,4-dimethyl-1H-pyrazol-3-yl)-phenoxymethyl]-phenyl}-4-methyl-1,4-dihydrotetrazole-5-one (hereinafter, referred to as "Present compound 43").

Present compound 43

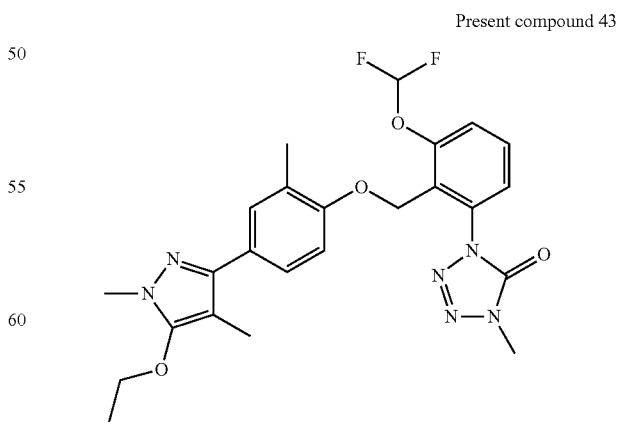

$^1$H-NMR (CDCl$_3$) δ: 7.54 (1H, t, J=8.2 Hz), 7.40-7.34 (4H, m), 6.88 (1H, d, J=8.5 Hz), 6.57 (1H, t, J=73.2 Hz), 5.27 (2H, s), 4.14 (2H, q, J=7.1 Hz), 3.70 (3H, s), 3.58 (3H, s), 2.10 (3H, s), 2.03 (3H, s), 1.41 (3H, t, J=7.1 Hz).

Preparation Example 44

A similar reaction to Preparation example 1 using 4-(5-chloro-1,4-dimethyl-1H-pyrazol-3-yl)-2-methyl-phenol (described in Reference Preparation example 109) instead of 2-methyl-4-(3,4,5-trimethyl-pyrazol-1-yl)-phenol gave 1-{3-difluoromethoxy-2-[2-methyl-4-(5-chloro-1,4-dimethyl-1H-pyrazol-3-yl)-phenoxymethyl]-phenyl}-4-methyl-1,4-dihydrotetrazole-5-one (hereinafter, referred to as "Present compound 44").

Present compound 44

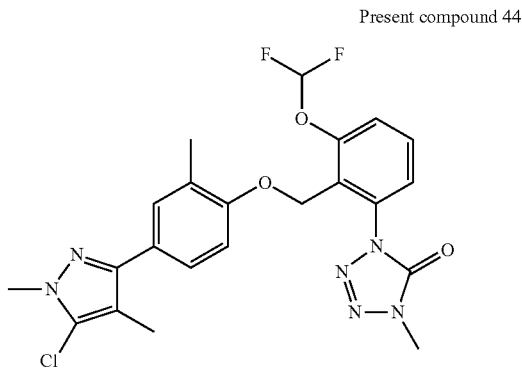 [SMILES: Cc1cc(-c2nn(C)c(Cl)c2C)ccc1OCc1c(OC(F)F)cccc1-n1nnn(C)c1=O]

¹H-NMR (CDCl₃) δ: 7.55 (1H, t, J=8.2 Hz), 7.40-7.34 (4H, m), 6.89 (1H, d, J=8.4 Hz), 6.58 (1H, t, J=73.1 Hz), 5.27 (2H, s), 3.84 (3H, s), 3.59 (3H, s), 2.14 (3H, s), 2.03 (3H, s)

Preparation Example 45

A similar reaction to Preparation example 2 using 4-(1,4-dimethyl-5-methylthio-1H-pyrazol-3-yl)-2-methyl-phenol (described in Reference Preparation example 105) instead of 2-methyl-4-(3,4,5-trimethyl-pyrazol-1-yl)-phenol gave 1-{3-cyclopropyl-2-[2-methyl-4-(1,4-dimethyl-5-methylthio-1H-pyrazol-3-yl)-phenoxymethyl]-phenyl}-4-methyl-1,4-dihydrotetrazole-5-one (hereinafter, referred to as "Present compound 45").

Present compound 45

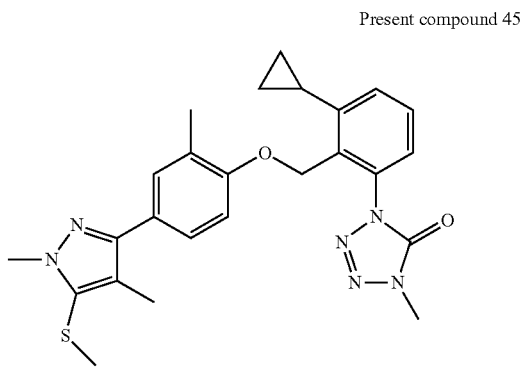 [SMILES: CSc1c(C)c(-c2ccc(OCc3c(C4CC4)cccc3-n3nnn(C)c3=O)c(C)c2)nn1C]

¹H-NMR (CDCl₃) δ: 7.45-7.39 (3H, m), 7.28-7.26 (2H, m), 6.93 (1H, d, J=8.5 Hz), 5.29 (2H, s), 3.99 (3H, s), 3.61 (3H, s), 2.27 (6H, s), 2.16-2.10 (4H, m), 1.00-0.97 (2H, m), 0.78-0.76 (2H, m).

Preparation Example 46

A similar reaction to Preparation example 1 using 4-(1,4-dimethyl-5-methylthio-1H-pyrazol-3-yl)-2-methyl-phenol (described in Reference Preparation example 105) instead of 2-methyl-4-(3,4,5-trimethyl-pyrazol-1-yl)-phenol gave 1-{3-difluoromethoxy-2-[2-methyl-4-(1,4-dimethyl-5-methylthio-1H-pyrazol-3-yl)-phenoxymethyl]-phenyl}-4-methyl-1,4-dihydrotetrazole-5-one (hereinafter, referred to as "Present compound 46").

Present compound 46

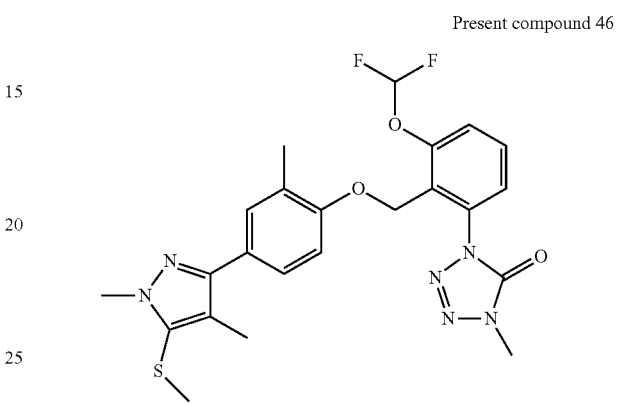

¹H-NMR (CDCl₃) δ: 7.55 (1H, t, J=8.2 Hz), 7.41-7.37 (4H, m), 6.89 (1H, d, J=8.4 Hz), 6.58 (1H, t, J=73.2 Hz), 5.27 (2H, s), 3.98 (3H, s), 3.59 (3H, s), 2.26 (3H, s), 2.25 (3H, s), 2.03 (3H, s).

Preparation Example 47

A similar reaction to Preparation example 2 using 1-(4-hydroxy-3-methyl-phenyl)-propane-1-one (described in Reference Preparation example 114) instead of 2-methyl-4-(3,4,5-trimethyl-pyrazol-1-yl)-phenol gave 1-[3-Cyclopropyl-2-(2-methyl-4-propionyl-phenoxymethyl)-phenyl]-4-methyl-1,4-dihydro-tetrazol-5-one (hereinafter, referred to as "Present compound 47").

Present compound 47

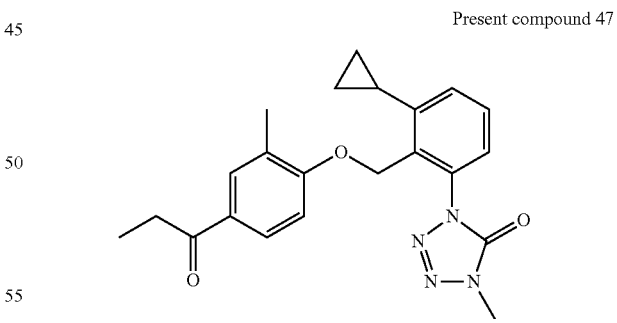

¹H-NMR (CDCl₃) δ: 7.81 (1H, dd, J=8.5, 2.2 Hz), 7.76 (1H, dd, J=2.2, 0.8 Hz), 7.45 (1H, t, J=7.9 Hz), 7.29 (2H, d, J=7.9 Hz), 6.91 (1H, d, J=8.6 Hz), 5.33 (2H, s), 3.61 (3H, s), 2.95 (2H, q, J=7.3 Hz), 2.13-2.07 (4H, m), 1.21 (3H, t, J=7.2 Hz), 1.02-0.97 (2H, m), 0.79-0.75 (2H, m).

Preparation Example 48

At room temperature, to a mixture of 4-{4-[2-cyclopropyl-6-(4-methyl-5-oxo-4,5-dihydro-tetrazol-1-yl)-benzyloxy]-3-methyl-phenyl}-3-methyl-2,4-dioxo-butyric acid ethyl ester (described in Reference Preparation example 115) 5.5 g, tetrahydrofuran 100 ml was added hydrazine one hydrate 0.56 g and the resulting mixture was stirred for twelve hours. The reaction mixture was concentrated under reduced pressure to give 5-{4-[2-cyclopropyl-6-(4-methyl-5-oxo-4,5-dihydro-tetrazol-1-yl)-benzyloxy]-3-methyl-phenyl}-4-methyl-2H-pyrazole-3-carboxylic acid ethyl ester crude product 5 g. Next, the mixture of the above-mentioned 5-{4-[2-cyclopropyl-6-(4-methyl-5-oxo-4,5-dihydro-tetrazol-1-yl)-benzyloxy]-3-methyl-phenyl}-4-methyl-2H-pyrazole-3-carboxylic acid ethyl ester crude product 5 g, toluene 70 ml and dimethyl sulfate 3.8 g was stirred at 100° C. for three hours. To the reaction mixture was added water and was extracted with ethyl acetate. The organic layer was washed with water and was dried over anhydrous magnesium sulfate, and was then concentrated under reduced pressure. The resulting residue was subjected to a silica gel column chromatography to give 5-{4-[2-cyclopropyl-6-(4-methyl-5-oxo-4,5-dihydro-tetrazol-1-yl)-benzyloxy]-3-methyl-phenyl}-2,4-dimethyl-2H-pyrazole-3-carboxylic acid ethyl ester 1.4 g (hereinafter, referred to as "Present compound 48").

Present compound 48

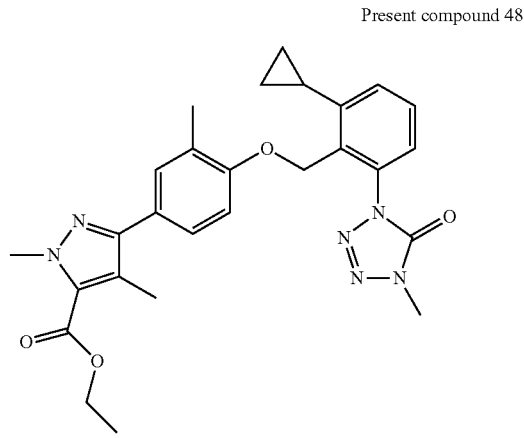 [SMILES: CCOC(=O)c1c(C)c(-c2ccc(OCc3c(C4CC4)cccc3-n3nnn(C)c3=O)c(C)c2)nn1C]

$^1$H-NMR (CDCl$_3$) δ: 7.44 (1H, t, J=7.9 Hz), 7.38-7.31 (2H, m), 7.28 (1H, s), 7.20 (1H, d, J=7.8 Hz), 6.94 (1H, d, J=8.0 Hz), 5.29 (2H, s), 4.40 (2H, q, J=7.2 Hz), 4.17 (3H, s), 3.62 (3H, s), 2.36 (3H, s), 2.17-2.10 (4H, m), 1.42 (3H, t, J=7.2 Hz), 1.05-0.97 (2H, m), 0.79-0.72 (2H, m).

Preparation Example 49

At room temperature, to 28%-Ammonia solution 50 ml was added 5-{4-[2-Cyclopropyl-6-(4-methyl-5-oxo-4,5-dihydro-tetrazol-1-yl)-benzyloxy]-3-methyl-phenyl}-2,4-dimethyl-2H-pyrazole-3-carbonyl chloride (described in Reference Preparation example 117) 1.3 g. The mixture was stirred for twelve hours and concentrated under reduced pressure and added 10%-hydrochloric acid solution 10 ml. The precipitates were filtrated and were washed with water and were dried under reduced pressure to give 1-{3-cyclopropyl-2-[2-methyl-4-(5-aminocarbonyl-1,4-dimethyl-1H-pyrazol-3-yl)-phenoxymethyl]-phenyl}-4-methyl-1,4-dihydrotetrazole-5-one (hereinafter, referred to as "Present compound 49") 0.8 g.

Present compound 49

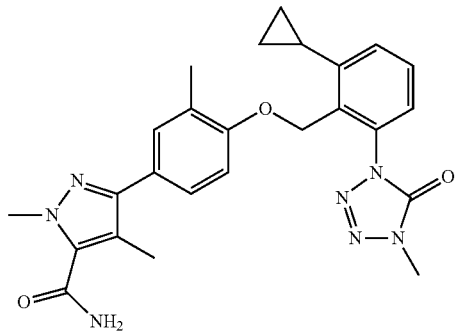

$^1$H-NMR (CDCl$_3$) δ: 7.44 (1H, t, J=7.9 Hz), 7.33-7.27 (4H, m), 6.94 (1H, d, J=8.2 Hz), 5.76 (2H, br s), 5.29 (2H, s), 4.13 (3H, s), 3.62 (3H, s), 2.36 (3H, s), 2.17-2.10 (4H, m), 1.03-0.97 (2H, m), 0.79-0.73 (2H, m).

Preparation Example 50

At room temperature, to the mixture of 1-{3-cyclopropyl-2-[2-methyl-4-(5-aminocarbonyl-1,4-dimethyl-1H-pyrazol-3-yl)-phenoxymethyl]-phenyl}-4-methyl-1,4-dihydrotetrazole-5-one (Present compound 49) 0.8 g and pyridine 10 ml was added phosphorus oxychloride 0.58 g and was stirred for two hours. To the resulting mixture was added water 40 ml and precipitates were filtrated. The precipitates were washed with water and dried under reduced pressure to give 1-{3-cyclopropyl-2-[2-methyl-4-(5-cyano-1,4-dimethyl-1H-pyrazol-3-yl)-phenoxymethyl]-phenyl}-4-methyl-1,4-dihydrotetrazole-5-one (hereinafter, referred to as "Present compound 50") 0.6 g.

Present compound 50

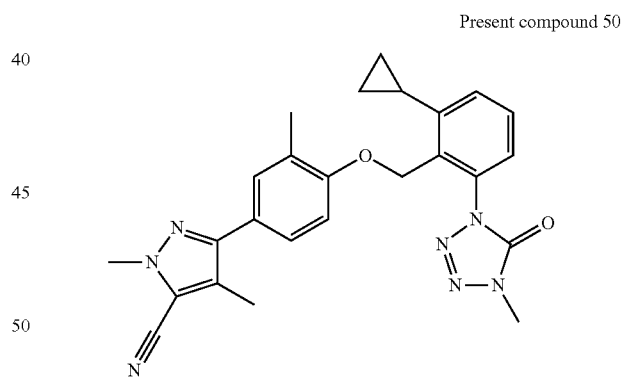

$^1$H-NMR (CDCl$_3$) δ: 7.44 (1H, t, J=7.8 Hz), 7.40-7.36 (2H, m), 7.28 (2H, d, J=7.9 Hz), 6.94 (1H, d, J=8.4 Hz), 5.29 (2H, s), 4.03 (3H, s), 3.62 (3H, s), 2.34 (3H, s), 2.16-2.09 (4H, m), 1.02-0.97 (2H, m), 0.79-0.75 (2H, m).

Preparation Example 51

At room temperature, a mixture of N,N-dimethylformamide 20 ml and phosphorus oxychloride 0.85 ml was stirred for one hour. To the above-mentioned mixture was added 1-{3-cyclopropyl-2-[2-methyl-4-(3,5-dimethyl-pyrazol-1-yl)-phenoxymethyl]-phenyl}-4-methyl-1,4-dihydrotetrazole-5-one (Present compound 3) 2.0 g and was stirred at 100° C. for three hours. At room temperature, to the resulting mixture was added water 10 ml. The mixture was extracted with ethyl acetate. The organic layer was washed with water and was dried over anhydrous magnesium sulfate, and was then concentrated under reduced pressure. The resulting residue was subjected to a silica gel column chromatography to give 1-{3-cyclopropyl-2-[2-methyl-4-(3,5-dimethyl-4-formyl-pyrazol-1-yl)-phenoxymethyl]-phenyl}-4-methyl-1,4-dihydrotetrazole-5-one (hereinafter, referred to as "Present compound 51") 1.7 g.

Present compound 51

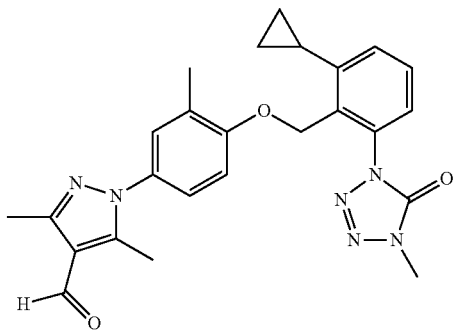

$^1$H-NMR (CDCl$_3$) δ: 9.98 (1H, s), 7.44 (1H, t, J=7.8 Hz), 7.28 (2H, d, J=7.8 Hz), 7.15-7.12 (2H, m), 6.94 (1H, d, J=8.2 Hz), 5.29 (2H, s), 3.63 (3H, s), 2.49 (6H, s), 2.12-2.09 (4H, m), 1.02-0.97 (2H, m), 0.78-0.74 (2H, m).

Preparation Example 52

At room temperature, to the mixture of 1-{4-[2-Cyclopropyl-6-(4-methyl-5-oxo-4,5-dihydro-tetrazol-1-yl)-benzyloxy]-3-methyl-phenyl}-3,5-dimethyl-1H-pyrazole-4-carbaldehyde oxime (described in Reference Preparation example 118) 1.5 g and N,N-dimethylformamide was added 2,4,6-trichloro-[1,3,5]triazine 0.6 g and the resulting mixture was stirred at room temperature for three hours. To the resulting mixture was added water 100 ml and the precipitates were filtrated. The precipitates were washed with water and dried under reduced pressure to give 1-{3-cyclopropyl-2-[2-methyl-4-(4-cyano-3,5-dimethyl-pyrazol-1-yl)-phenoxymethyl]-phenyl}-4-methyl-1,4-dihydrotetrazole-5-one (hereinafter, referred to as "Present compound 52") 1.0 g.

Present compound 52

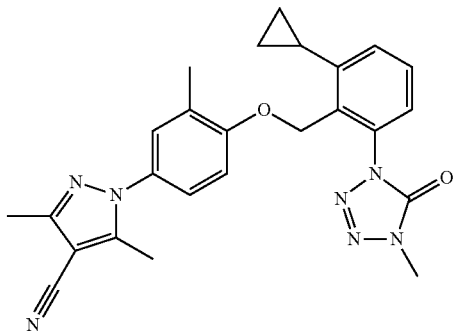

$^1$H-NMR (CDCl$_3$) δ: 7.45 (1H, t, J=7.9 Hz), 7.28 (2H, d, J=7.9 Hz), 7.13-7.11 (2H, m), 6.93 (1H, d, J=8.2 Hz), 5.30 (2H, s), 3.64 (3H, s), 2.39 (3H, s), 2.39 (3H, s), 2.12-2.08 (4H, m), 1.02-0.97 (2H, m), 0.79-0.75 (2H, m).

Preparation Example 53

A similar reaction to Preparation example 2 using 4-(4-Chloro-5-methoxy-1-methyl-1H-pyrazol-3-yl)-2-methyl-phenol (described in Reference Preparation example 112) instead of 2-methyl-4-(3,4,5-trimethyl-pyrazol-1-yl)-phenol gave 1-{2-[4-(4-Chloro-5-methoxy-1-methyl-1H-pyrazol-3-yl)-2-methyl-phenoxymethyl]-3-cyclopropyl-phenyl}-4-methyl-1,4-dihydro-tetrazol-5-one (hereinafter, referred to as "Present compound 53").

Present compound 53

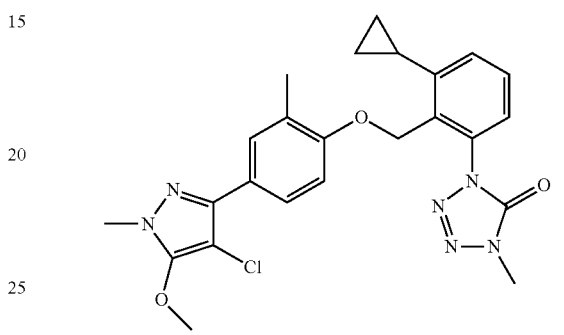

$^1$H-NMR (CDCl$_3$) δ: 7.64-7.61 (1H, m), 7.58-7.57 (1H, m), 7.44 (1H, t, J=7.8 Hz), 7.30-7.27 (2H, m), 6.94 (1H, d, J=8.5 Hz), 5.30 (2H, s), 4.12 (3H, s), 3.71 (3H, s), 3.61 (3H, s), 2.14-2.11 (4H, m), 1.01-0.97 (2H, m), 0.79-0.76 (2H, m).

Next, regarding an intermediate for preparing the above-mentioned Present compounds, Reference Preparation examples are shown below.

Reference Preparation Example 1

To a mixture of 1-(2-methyl-3-difluoromethoxyphenyl)-4-methyl-1,4-dihydrotetrazole-5-one (described in Reference Preparation example 2) 1.0 g, 1,1'-azobis(cyclohexane-1-carbonitrile) 0.19 g, N-bromosuccinimide 0.80 g and chlorobenzene 50 ml was stirred with heating under reflux for eight hours. After cooling the mixture, to the reaction solutions was added water and the resulting mixture was extracted with ethyl acetate. The organic layer was washed with water and saturated saline, and was dried over anhydrous magnesium sulfate and was then concentrated under reduced pressure. The resulting residue was subjected to a silica gel column chromatography to give 1-(2-bromomethyl-3-difluoromethoxyphenyl)-4-methyl-1,4-dihydrotetrazole-5-one 1.1 g.

1-(2-bromomethyl-3-difluoromethoxyphenyl)-4-methyl-1,4-dihydrotetrazole-5-one

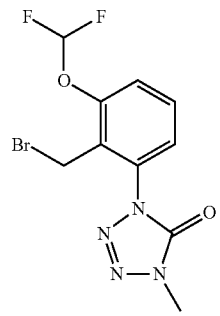

$^1$H-NMR (CDCl$_3$) δ(ppm): 7.50 (1H, t, J=8.2 Hz), 7.34 (2H, d, J=8.2 Hz), 6.62 (1H, t, J=72.8 Hz), 4.65 (2H, s), 3.76 (3H, d, J=0.5 Hz).

Reference Preparation Example 2

Under ice-cooling, to a mixture of N,N-dimethylformamide 200 ml and aluminium trichloride 5.91 g was added sodium azide 2.64 g, and the resulting mixture was stirred for one hour. Thereto was then added 1-difluoromethoxy-3-isocyanato-2-methylbenzene 7.36 g and the reaction mixture was heated to 75° C. and was stirred for nine hours. The reaction mixture was cooled and under ice-cooling to the reaction mixture was added ice water 50 ml, followed by an addition of a mixture of sodium nitrite 4.1 g and water 100 ml. The resulting mixture was acidified with concentrated hydrochloric acid to make it pH about 4. The resulting mixture was extracted with ethyl acetate. The organic layer was washed with water and saturated saline and then was dried over anhydrous magnesium sulfate and was then concentrated under reduced pressure. To the resulting residues containing 1-(2-methyl-3-difluoromethoxyphenyl)-1,4-dihydrotetrazole-5-one was added N,N-dimethylformamide 100 ml, potassium carbonate 7.66 g, dimethyl sulfate 9.32 g, and the resulting mixture was stirred at room temperature for four hours. Thereto was added water 100 ml, and the resulting mixture was extracted with ethyl acetate, and the organic layer was washed with water and saturated saline, and dried over anhydrous magnesium sulfate and was then concentrated under reduced pressure. The resulting residue was subjected to a silica gel column chromatography to give 1-(2-methyl-3-difluoromethoxyphenyl)-4-methyl-1,4-dihydrotetrazole-5-one 1.0 g.

Reference Preparation Example 3

A mixture of 2-methyl-3-nitrophenol 7.17 g, potassium hydroxide 27 g, bromodifluoromethyl-dimethyl phosphonate 25 g, water 100 ml and acetonitrile 100 ml was mixed at room temperature for twenty four hours. The reaction mixture was extracted with ethyl acetate. The organic layer was washed with water and saturated saline, and was dried over anhydrous magnesium sulfate, and was then concentrated under reduced pressure. The resulting residue was subjected to a silica gel column chromatography to give 1-difluoromethoxy-2-methyl-3-nitrobenzene 7.50 g.

1-difluoromethoxy-2-methyl-3-nitrobenzene

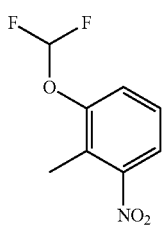

$^1$H-NMR (CDCl$_3$) δ(ppm): 7.74 (1H, dd, J=7.6, 1.8 Hz), 7.40-7.32 (2H, m), 6.56 (1H, t, J=72.4 Hz), 2.46 (3H, s).

Reference Preparation Example 4

A mixture of the above-prepared 1-difluoromethoxy-2-methyl-3-nitrobenzene (described in Reference Preparation example 3) 7.50 g, palladium-carbon (palladium 5%) 0.8 g and ethanol 80 ml was stirred at room temperature under hydrogen atmosphere for eight hours. The reaction mixture was filtered and the filtrate was concentrated to give 3-difluoromethoxy-2-methylaniline 6.4 g.

3-difluoromethoxy-2-methylaniline

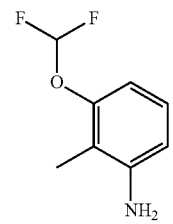

$^1$H-NMR (CDCl$_3$) δ(ppm): 6.99 (1H, t, J=8.1 Hz), 6.55 (1H, d, J=8.0 Hz), 6.51 (1H, d, J=8.2 Hz), 6.46 (1H, td, J=74.4, 0.4 Hz), 3.72 (2H, br s), 2.09 (3H, s).

Reference Preparation Example 5

At room temperature, to a mixture of 3-difluoromethoxy-2-methylaniline 6.4 g and toluene 100 ml was added triphosgene 5.48 g, and the resulting mixture was stirred with heating under reflux for one hour. The reaction mixture was concentrated under reduced pressure to give 1-difluoromethoxy-3-isocyanato-2-methylbenzene 7.36 g.

1-difluoromethoxy-3-isocyanato-2-methylbenzene

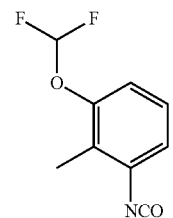

$^1$H-NMR (CDCl$_3$) δ(ppm): 7.14 (1H, t, J=8.1 Hz), 6.97 (2H, t, J=8.5 Hz), 6.50 (1H, td, J=73.6, 0.4 Hz), 2.27 (3H, s).

Reference Preparation Example 6

A mixture of 1-(2-methoxymethyl-3-cyclopropylphenyl)-4-methyl-1,4-dihydrotetrazole-5-one (described in Reference Preparation example 7) 26.0 g, acetic acid 40 ml and 25% hydrogen bromide-acetic acid solution 40 ml was stirred at 65° C. for two hours. To the reaction mixture was added saturated saline, and the reaction mixture was extracted with ethyl acetate. The organic layer was washed with aqueous saturated sodium bicarbonate solution and was dried over anhydrous sodium sulfate. The mixture was concentrated under reduced pressure to give 1-(2-bromomethyl-3-cyclopropylphenyl)-4-methyl-1,4-dihydrotetrazole-5-one 30.8 g.

1-(2-bromomethyl-3-cyclopropylphenyl)-4-methyl-1,4-dihydrotetrazole-5-one

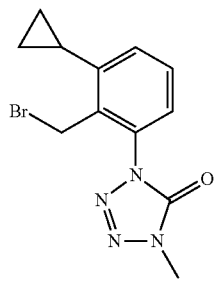 [SMILES: Cn1nnn(-c2cccc(C3CC3)c2CBr)c1=O]

$^1$H-NMR (CDCl$_3$) δ(ppm): 7.38 (1H, t, J=7.8 Hz), 7.26-7.22 (2H, m), 4.77 (2H, s), 3.75 (3H, s), 2.16-2.09 (1H, m), 1.10-1.06 (2H, m), 0.82-0.78 (2H, m).

Reference Preparation Example 7

A mixture of 1-(2-methoxymethyl-3-bromophenyl)-4-methyl-1,4-dihydrotetrazole-5-one (described in Reference Preparation example 8) 30.1 g, cyclopropylboronic acid 12.9 g, cesium fluoride 46.2 g, [1,1'-bis(diphenylphosphino)ferrocene]palladium(II) dichloride dichloromethane adduct 8.2 g and dioxane 680 ml was stirred at 90° C. for four hours. After cooling the reaction mixture, the reaction mixture was filtered and the filtrate was concentrated under reduced pressure. The resulting residue was subjected to a silica gel column chromatography to give 1-(2-methoxymethyl-3-cyclopropylphenyl)-4-methyl-1,4-dihydrotetrazole-5-one 26.0 g.

1-(2-methoxymethyl-3-cyclopropylphenyl)-4-methyl-1,4-dihydrotetrazole-5-one

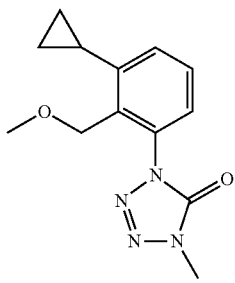 [SMILES: COCc1c(C2CC2)cccc1-n1nnn(C)c1=O]

$^1$H-NMR (CDCl$_3$) δ(ppm): 7.36 (1H, t, J=8.0 Hz), 7.20 (2H, d, J=8.0 Hz), 4.64 (2H, s), 3.72 (3H, s), 3.24 (3H, s), 2.20-2.13 (1H, m), 1.04-1.00 (2H, m), 0.76-0.72 (2H, m).

Reference Preparation Example 8

A mixture of 1-(2-bromomethyl-3-bromophenyl)-4-methyl-1,4-dihydrotetrazole-5-one 45.0 g, sodium methoxide 37.4 g and tetrahydrofuran 600 ml was stirred at room temperature for three hours. To the reaction mixture was added aqueous saturated sodium bicarbonate solution and the resulting mixture was extracted with ethyl acetate. The organic layer was washed with aqueous saturated sodium bicarbonate solution and was dried over anhydrous magnesium sulfate. The resulting mixture was concentrated under reduced pressure to give 1-(2-methoxymethyl-3-bromophenyl)-4-methyl-1,4-dihydrotetrazole-5-one 36.2 g.

1-(2-methoxymethyl-3-bromophenyl)-4-methyl-1,4-dihydrotetrazole-5-one

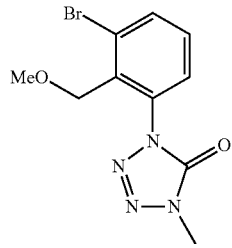 [SMILES: COCc1c(Br)cccc1-n1nnn(C)c1=O]

$^1$H-NMR (CDCl$_3$) δ(ppm): 3.23 (3H, s), 3.72 (3H, s), 4.67 (2H, s), 7.33 (1H, t, J=7.8 Hz), 7.38 (1H, dd, J=1.2, 8.1 Hz), 7.76 (1H, dd, J=1.5, 7.8 Hz).

Reference Preparation Example 9

Anhydrous aluminium chloride 19.7 g was added to N,N-dimethylformamide 220 ml under ice-cooling, and the resulting mixture was stirred for fifteen minutes. Thereto was added sodium azide 9.6 g and the resulting mixture was stirred for fifteen minutes. Thereto was then added 1-bromo-3-isocyanato-2-methylbenzene 30.3 g and the resulting mixture was heated at 80° C. for five hours. After cooling, the reaction solutions was added to a mixture of sodium nitrite 33 g, water 2 L and ice 500 g with stirring. The reaction mixture was acidified with 10% hydrochloric acid and was extracted with ethyl acetate. The organic layer was washed with water and saturated saline and then was dried over anhydrous magnesium sulfate and was then concentrated under reduced pressure to give 1-(2-methyl-3-bromophenyl)-1,4-dihydrotetrazole-5-one 31.4 g. 1-(2-methyl-3-bromophenyl)-1,4-dihydrotetrazole-5-one

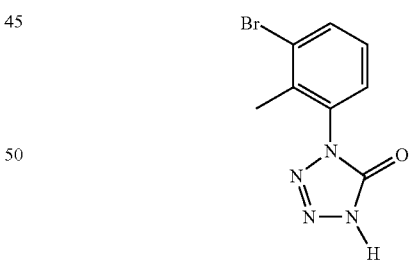

$^1$H-NMR (DMSO-d$_6$) δ(ppm): 2.22 (3H, s), 7.34 (1H, t, J=7.2 Hz), 7.49 (1H, dd, J=8.2, 1.1 Hz), 7.82 (1H, dd, J=8.0, 1.0 Hz), 14.72 (1H, s).

Reference Preparation Example 10

To a mixture of 1-(2-methyl-3-bromophenyl)-1,4-dihydrotetrazole-5-one (described in Reference Preparation example 9) 31.40 g and N,N-dimethylformamide 250 ml was added 60% sodium hydride 5.90 g under ice-cooling. The reaction mixture was raised to room temperature and was stirred for one hour. To the reaction mixture was added methyl iodide 8.4 ml under ice-cooling. The resulting mixture was raised to room temperature and was stirred for fourteen hours. To the reaction mixture was added water and the reaction mixture was extracted with ethyl acetate. The organic layer was washed with 10% hydrochloric acid, water and saturated saline, and was dried over anhydrous magnesium sulfate and was then concentrated under reduced pressure. The resulting residue was subjected to a silica gel column chromatography to give 1-(2-methyl-3-bromophenyl)-4-methyl-1,4-dihydrotetrazole-5-one 8.47 g.

1-(2-methyl-3-bromophenyl)-4-methyl-1,4-dihydrotetrazole-5-one

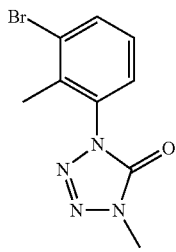

$^1$H-NMR (CDCl$_3$) δ(ppm): 2.33 (3H, s), 3.73 (3H, s), 7.21 (1H, dt, J=0.5, 7.8 Hz), 7.30 (1H, dd, J=1.0, 8.0 Hz), 7.71 (1H, dd, J=1.2, 8.3 Hz).

Reference Preparation Example 11

A mixture of 1-(2-methyl-3-bromophenyl)-4-methyl-1,4-dihydrotetrazole-5-one (described in Reference Preparation example 10) 8.47 g, 1,1'-azobis(cyclohexane-1-carbonitrile) 1.54 g, N-bromosuccinimide 6.44 g and chlorobenzene 125 ml was stirred with heating under reflux for five hours. After cooling the mixture, to the reaction solutions was added water and the resulting mixture was extracted with ethyl acetate. The organic layer was washed with water and saturated saline, and was dried over anhydrous magnesium sulfate and was then concentrated under reduced pressure. The resulting residue was subjected to a silica gel column chromatography to give 1-(2-bromomethyl-3-bromophenyl)-4-methyl-1,4-dihydrotetrazole-5-one 7.52 g.

1-(2-bromomethyl-3-bromophenyl)-4-methyl-1,4-dihydrotetrazole-5-one

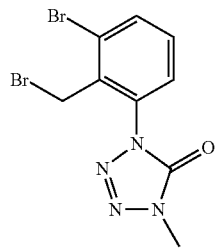 [SMILES: Cn1nnn(-c2cccc(Br)c2CBr)c1=O]

$^1$H-NMR (CDCl$_3$) δ(ppm): 3.76 (3H, s), 4.71 (2H, s), 7.34 (1H, t, J=7.8 Hz), 7.38 (1H, dd, J=8.0, 1.7 Hz), 7.77 (1H, dd, J=7.8, 1.7 Hz).

Reference Preparation Example 12

A mixture of 1-bromo-2-methyl-3-aminobenzene 25.0 g, triphosgene 60.0 g and toluene 400 ml was stirred with heating under reflux for three hours. The reaction mixture after standing to cool was concentrated under reduced pressure to give 1-bromo-3-isocyanato-2-methylbenzene 30.3 g.

1-bromo-3-isocyanato-2-methylbenzene

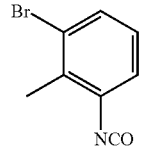

$^1$H-NMR (CDCl$_3$) δ(ppm): 2.42 (3H, s), 7.00 (1H, dt, J=0.5, 8.0 Hz), 7.05 (1H, dd, J=1.7, 8.0 Hz), 7.39 (1H, dd, 1.5, 7.7 Hz).

Reference Preparation Example 13

To a mixture of 1-(2-methyl-3-methylsulfanylphenyl)-4-methyl-1,4-dihydrotetrazole-5-one (described in Reference Preparation example 15) 1.50 g, 1,1'-azobis(cyclohexane-1-carbonitrile) 0.620 g, N-bromosuccinimide 1.30 g and chlorobenzene 15 ml was stirred with heating under reflux for four hours. After cooling the mixture, to the reaction solutions was added water and the resulting mixture was extracted with ethyl acetate. The organic layer was washed with water and saturated saline, and was dried over anhydrous magnesium sulfate and was then concentrated under reduced pressure. The resulting residue was subjected to a silica gel column chromatography to give 1-(2-bromomethyl-3-methylthiophenyl)-4-methyl-1,4-dihydrotetrazole-5-one 0.400 g.

1-(2-bromomethyl-3-methylthiophenyl)-4-methyl-1,4-dihydrotetrazole-5-one

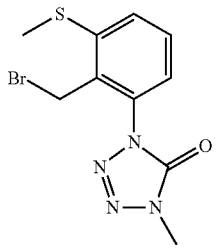 [SMILES: CSc1cccc(-n2nnn(C)c2=O)c1CBr]

$^1$H-NMR (CDCl$_3$) δ(ppm): 2.57 (3H, s), 3.75 (3H, s), 4.69 (2H, s), 7.20 (1H, t, J=4.5 Hz), 7.44 (2H, d, J=4.5 Hz).

Reference Preparation Example 14

Under ice-cooling, to a mixture of triisopropylsilanethiol 4.99 g and toluene 30 ml was added 60% sodium hydride 0.63 g, and the resulting mixture was stirred for thirty minutes. To the reaction mixture was added 1-(2-methyl-3-bromophenyl)-4-methyl-1,4-dihydrotetrazole-5-one (described in Reference Preparation example 10) 2.82 g and [1,1'-bis(diphenylphosphino)ferrocene]palladium(II) dichloride dichloromethane adduct 0.856 g. The reaction mixture was heated to 90° C. and was stirred for four hours. After cooling the reaction mixture, thereto was added water and the resulting mixture was extracted with ethyl acetate. The organic layer was washed with water and saturated saline, and was dried over anhydrous magnesium sulfate and was then concentrated under reduced pressure. The resulting residue was subjected to a silica gel column chromatography to give 1-(2-methyl-3-triisopropylsilanylsulfanylphenyl)-4-methyl-1,4-dihydrotetrazole-5-one 3.64 g.

1-(2-methyl-3-triisopropylsilanylsulfanylphenyl)-4-methyl-1,4-dihydrotetrazole-5-one

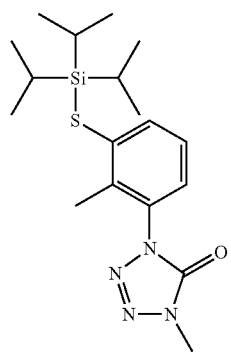 [SMILES: Cc1c(S[Si](C(C)C)(C(C)C)C(C)C)cccc1-n1nnn(C)c1=O]

$^1$H-NMR (CDCl$_3$) δ(ppm): 1.09 (18H, d, J=6.6 Hz), 1.31 (3H, q, J=6.6 Hz), 2.45 (3H, s), 3.71 (3H, s), 7.16-7.21 (2H, m), 7.64 (1H, dd, J=6.6, 2.7 Hz).

Reference Preparation Example 15

A mixture of 1-(2-methyl-3-triisopropylsilanylsulfanyl-phenyl)-4-methyl-1,4-dihydrotetrazole-5-one 3.63 g, cesium fluoride 2.91 g and N,N-dimethylformamide 10 ml was stirred at room temperature for thirty minutes. To the resulting mixture was added methyl iodide 2.72 g and the resulting mixture was stirred at room temperature for three hours. To the reaction mixture was added water and the resulting mixture was extracted with ethyl acetate. The organic layer was washed with water and saturated saline, and was dried over anhydrous magnesium sulfate and was then concentrated under reduced pressure. The resulting residue was subjected to a silica gel column chromatography to give 1-(2-methyl-3-methylthiophenyl)-4-methyl-1,4-dihydrotetrazole-5-one 1.65 g.

1-(2-methyl-3-methylthiophenyl)-4-methyl-1,4-dihydrotetrazole-5-one

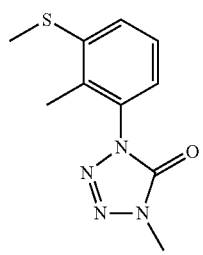 [SMILES: CSc1cccc(-n2nnn(C)c2=O)c1C]

$^1$H-NMR (CDCl$_3$) δ(ppm): 2.22 (3H, s), 2.51 (3H, s), 3.72 (3H, s), 7.10-7.16 (1H, m), 7.36-7.29 (2H, m).

Reference Preparation Example 16

A mixture of 2-chloro-4-hydrazinophenol hydrochloride salt 3.0 g, 3-methyl-2,4-pentanedione, ethanol 100 ml was stirred with heating under reflux for twelve hours. The solvent was distilled off and thereto was added ethyl acetate 200 ml, and the resulting mixture was stirred for one hour. The precipitates was filtered and was washed with hexane, and was then dried under reduced pressure to give 2-chloro-4-(3,4,5-trimethyl-pyrazol-1-yl)-phenol 3.3 g.

2-chloro-4-(3,4,5-trimethyl-pyrazol-1-yl)-phenol

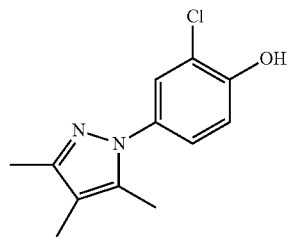 [SMILES: Cc1nn(-c2ccc(O)c(Cl)c2)c(C)c1C]

$^1$H-NMR (DMSO-D$_6$) δ: 7.43 (1H, d, J=2.7 Hz), 7.24 (1H, dd, J=8.7, 2.6 Hz), 7.07 (1H, d, J=8.8 Hz), 2.15 (3H, s), 2.13 (3H, s), 1.92 (3H, s).

Reference Preparation Example 17

A similar reaction to Reference Preparation example 16 using acetylacetone instead of 3-methyl-2,4-pentanedione gave 2-chloro-4-(3,5-dimethyl-pyrazol-1-yl)-phenol.

2-chloro-4-(3,5-dimethyl-pyrazol-1-yl)-phenol

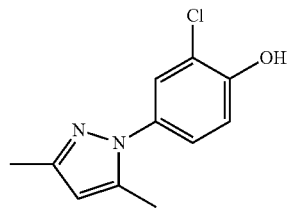

$^1$H-NMR (DMSO-D$_6$) δ: 8.66 (1H, br s), 7.46 (1H, d, J=2.6 Hz), 7.26 (1H, dd, J=8.7, 2.6 Hz), 7.10 (1H, d, J=8.8 Hz), 6.07 (1H, s), 2.23 (3H, s), 2.14 (3H, s)

Reference Preparation Example 18

A mixture of iodosobenzene 2.5 g, boron trifluoride-ethyl ether 1.6 g, methanol 20 ml and 2,4-pentanedione 1.14 g was stirred at room temperature for five hours. The resulting mixture was concentrated under reduced pressure and was extracted with tert-butyl methyl ether. The organic layer was washed with aqueous sodium bicarbonate solution and water, and was dried over anhydrous sodium sulfate. The resulting mixture was concentrated under reduced pressure and thereto was added ethanol 30 ml and 2-chloro-4-hydrazinophenol hydrochloride salt (described in Reference Preparation example 112) 2 g, and the resulting mixture was then stirred with heating under reflux for sixteen hours. The reaction mixture was concentrated under reduced pressure and thereto was added ethyl acetate 100 ml, and the resulting mixture was stirred at room temperature for two hours. The precipitates were filtered and were dried under reduced pressure to give 2-chloro-4-(3,5-dimethyl-4-methoxy-pyrazol-1-yl)-phenol 0.75 g.

2-chloro-4-(3,5-dimethyl-4-methoxy-pyrazol-1-yl)-phenol

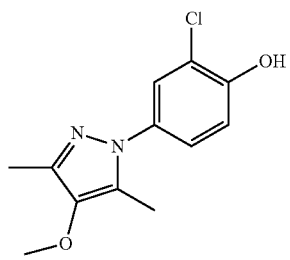

MS+; 253

Reference Preparation Example 19

A similar reaction to Reference Preparation example 19 using 3-ethyl-2,4-pentanedione instead of 3-methyl-2,4-pentanedione gave 2-chloro-4-(3,5-dimethyl-4-ethyl-pyrazol-1-yl)-phenol.

2-chloro-4-(3,5-dimethyl-4-ethyl-pyrazol-1-yl)-phenol

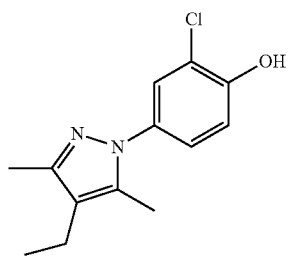 [SMILES: CCc1c(C)nn(-c2ccc(O)c(Cl)c2)c1C]

$^1$H-NMR (DMSO-D$_6$) δ: 7.45 (1H, s), 7.27-7.23 (1H, m), 7.11-7.07 (1H, m), 2.37 (2H, q, J=7.5 Hz), 2.17 (3H, s), 2.16 (3H, s), 1.05 (3H, t, J=7.6 Hz).

Reference Preparation Example 20

A mixture of 1-(4-methoxy-3-methyl-phenyl)-3,4,5-trimethyl-1H-pyrazole (described in Reference Preparation example 33) 7.3 g, 47% hydrobromic acid 50 ml and acetic acid 50 ml was stirred with heating under reflux for thirty hours. The solvent was distilled off and to the resulting residues was added ethyl acetate 400 ml, and the resulting mixture was stirred at room temperature for one hour. The precipitates were filtered and were washed with hexane, and were concentrated under reduced pressure to give 2-methyl-4-(3,4,5-trimethyl-pyrazol-1-yl)-phenol 6.1 g.

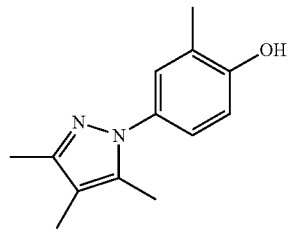 [SMILES: Cc1cc(-n2nc(C)c(C)c2C)ccc1O]

$^1$H-NMR (DMSO-D$_6$) δ: 7.22 (1H, d, J=2.2 Hz), 7.14 (1H, dd, J=8.4, 2.3 Hz), 6.91 (1H, d, J=8.3 Hz), 2.22 (3H, s), 2.17 (3H, s), 2.16 (3H, s), 1.97 (3H, s).

Reference Preparation Example 21

A similar reaction to Reference Preparation example 20 using 1-(4-methoxy-3-methyl-phenyl)-3,5-dimethyl-1H-pyrazole instead of 1-(4-methoxy-3-methyl-phenyl)-3,4,5-trimethyl-1H-pyrazole gave 2-methyl-4-(3,5-dimethyl-pyrazol-1-yl)-phenol.

2-methyl-4-(3,5-dimethyl-pyrazol-1-yl)-phenol

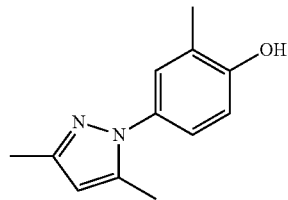

$^1$H-NMR (DMSO-D$_6$) δ: 9.68 (1H, br s), 7.19 (1H, s), 7.10 (1H, dd, J=8.8, 2.3 Hz), 6.87 (1H, d, J=8.8 Hz), 6.13 (1H, s), 2.20 (6H, s), 2.16 (3H, s).

Reference Preparation Example 22

A similar reaction to Reference Preparation example 20 using 1-(4-methoxy-3-methyl-phenyl)-3-methyl-1H-pyrazole (described in Reference Preparation example 35) instead of 1-(4-methoxy-3-methyl-phenyl)-3,4,5-trimethyl-1H-pyrazole gave 2-methyl-4-(3-methyl-pyrazol-1-yl)-phenol.

2-methyl-4-(3-methyl-pyrazol-1-yl)-phenol

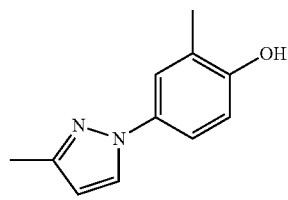

$^1$H-NMR (DMSO-D$_6$) δ: 8.13 (1H, d, J=2.4 Hz), 7.46 (1H, d, J=2.7 Hz), 7.35 (1H, dd, J=8.5, 2.7 Hz), 6.81 (1H, d, J=8.5 Hz), 6.23 (1H, d, J=2.4 Hz), 2.23 (3H, s), 2.17 (3H, s).

Reference Preparation Example 23

A similar reaction to Reference Preparation example 20 using 1-(4-methoxy-phenyl-3-methyl-phenyl)-3,4-dimethyl-1H-pyrazole (described in Reference Preparation example 36) instead of 1-(4-methoxy-3-methyl-phenyl)-3,4,5-trimethyl-1H-pyrazole gave 2-methyl-4-(3,4-dimethyl-pyrazol-1-yl)-phenol.

2-methyl-4-(3,4-dimethyl-pyrazol-1-yl)-phenol

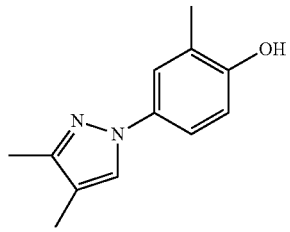

$^1$H-NMR (DMSO-D$_6$) δ: 7.94 (1H, s), 7.41 (1H, d, J=2.2 Hz), 7.29 (1H, dd, J=8.5, 2.7 Hz), 6.80 (1H, d, J=8.5 Hz), 2.15 (6H, s), 1.99 (3H, s).

Reference Preparation Example 24

A similar reaction to Reference Preparation example 20 using 1-(4-methoxy-3-methyl-phenyl)-4,5-dimethyl-1H-pyrazole (described in Reference Preparation example 36) instead of 1-(4-methoxy-3-methyl-phenyl)-3,4,5-trimethyl-1H-pyrazole gave 2-methyl-4-(4,5-dimethyl-pyrazol-1-yl)-phenol.

2-methyl-4-(4,5-dimethyl-pyrazol-1-yl)-phenol

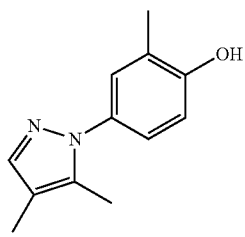

$^1$H-NMR (DMSO-D$_6$) δ: 7.51 (1H, s), 7.17 (1H, d, J=2.2 Hz), 7.08 (1H, dd, J=8.5, 2.4 Hz), 6.88 (1H, d, J=8.5 Hz), 2.16 (3H, s), 2.15 (3H, s), 2.01 (3H, s).

Reference Preparation Example 25

A similar reaction to Reference Preparation example 20 using 1-(4-methoxy-3-trifluoromethyl-phenyl)-3,4,5-trimethyl-1H-pyrazole (described in Reference Preparation example 38) instead of 1-(4-methoxy-3-methyl-phenyl)-3,4,5-trimethyl-1H-pyrazole gave 2-trifluoromethyl-4-(3,4,5-trimethyl-pyrazol-1-yl)-phenol.

2-trifluoromethyl-4-(3,4,5-trimethyl-pyrazol-1-yl)-phenol

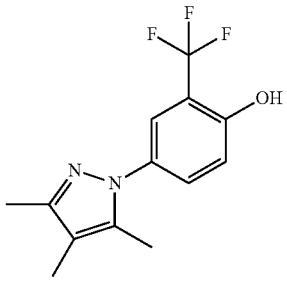 [SMILES: Cc1nn(-c2ccc(O)c(C(F)(F)F)c2)c(C)c1C]

$^1$H-NMR (DMSO-D$_6$) δ: 10.96 (1H, s), 7.59-7.55 (2H, m), 7.16-7.12 (1H, m), 2.16 (3H, s), 2.15 (3H, s), 1.94 (3H, s).

Reference Preparation Example 26

A similar reaction to Reference Preparation example 20 using 2-(4-methoxy-3-methyl-phenyl)-4,5,6,7-tetrahydro-2H-indazole (described in Reference Preparation example 37) instead of 1-(4-methoxy-3-methyl-phenyl)-3,4,5-trimethyl-1H-pyrazole gave 2-methyl-4-(4,5,6,7-tetrahydro-indazol-2-yl)-phenol.

2-methyl-4-(4,5,6,7-tetrahydro-indazol-2-yl)-phenol

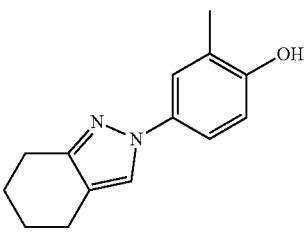 [SMILES: Cc1cc(-n2cc3c(n2)CCCC3)ccc1O]

$^1$H-NMR (DMSO-D$_6$) δ: 7.92 (1H, s), 7.43 (1H, d, J=2.7 Hz), 7.31 (1H, dd, J=8.7, 2.7 Hz), 6.79 (1H, d, J=8.7 Hz), 2.61 (2H, t, J=6.2 Hz), 2.55-2.51 (2H, m), 2.16-2.13 (3H, m), 1.79-1.72 (2H, m), 1.72-1.65 (2H, m).

Reference Preparation Example 27

A similar reaction to Reference Preparation example 20 using 1-(4-methoxy-3-methyl-phenyl)-4,5,6,7-tetrahydro-1H-indazole (described in Reference Preparation example 37) instead of 1-(4-methoxy-3-methyl-phenyl)-3,4,5-trimethyl-1H-pyrazole gave 2-methyl-4-(4,5,6,7-tetrahydro-indazol-1-yl)-phenol.

2-methyl-4-(4,5,6,7-tetrahydro-indazol-1-yl)-phenol

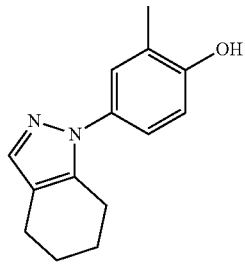 [SMILES: Cc1cc(-n2ncc3c2CCCC3)ccc1O]

¹H-NMR (DMSO-D₆) δ: 7.39 (1H, s), 7.20 (1H, s), 7.12-7.09 (1H, m), 6.84 (1H, d, J=8.5 Hz), 2.64-2.59 (2H, m), 2.52-2.48 (2H, m), 2.16 (3H, s), 1.75-1.65 (4H, m).

Reference Preparation Example 28

A similar reaction to Reference Preparation example 20 using 4-(4-methoxy-3-methyl-phenyl)-1-methyl-1H-pyrazole (described in Reference Preparation example 39) instead of 1-(4-methoxy-3-methyl-phenyl)-3,4,5-trimethyl-1H-pyrazole gave 2-methyl-4-(1-methyl-1H-pyrazol-4-yl)-phenol.

2-methyl-4-(1-methyl-1H-pyrazol-4-yl)-phenol

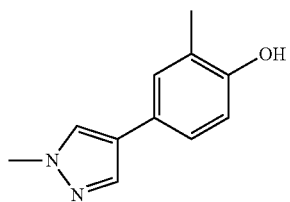

¹H-NMR (DMSO-D₆) δ: 7.92 (1H, s), 7.68 (1H, s), 7.24 (1H, s), 7.15 (1H, d, J=8.2 Hz), 6.73 (1H, d, J=8.5 Hz), 3.82 (3H, d, J=0.7 Hz), 2.12 (3H, s).

Reference Preparation Example 29

A mixture of 3-(4-methoxy-3-methyl-phenyl)-1-methyl-1H-pyrazole 2.9 g, 47% hydrobromic acid 21 ml and acetic acid 21 ml was stirred with heating under reflux for twenty hours. The solvent was distilled off and to the resulting residues was added ethyl acetate 100 ml, and the resulting mixture was stirred at room temperature for one hour. The precipitates were filtered and were washed with hexane, and were concentrated under reduced pressure to give 2-methyl-4-(1-methyl-1H-pyrazol-3-yl)-phenol 2.45 g.

2-methyl-4-(1-methyl-1H-pyrazol-3-yl)-phenol

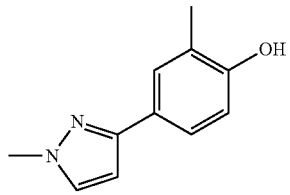

¹H-NMR (DMSO-D₆) δ: 9.30 (1H, br s), 7.64 (1H, s), 7.48 (1H, s), 7.38 (1H, d, J=8.3 Hz), 6.76 (1H, d, J=8.0 Hz), 6.50-6.49 (1H, m), 3.83 (3H, s), 2.14 (3H, s).

Reference Preparation Example 30

A similar reaction to Reference Preparation example 29 using 3-(4-methoxy-3-methyl-phenyl)-1-ethyl-1H-pyrazole (described in Reference Preparation example 41) instead of 3-(4-methoxy-3-methyl-phenyl)-1-methyl-1H-pyrazole gave 2-methyl-4-(1-ethyl-1H-pyrazol-3-yl)-phenol.

2-methyl-4-(1-ethyl-1H-pyrazol-3-yl)-phenol

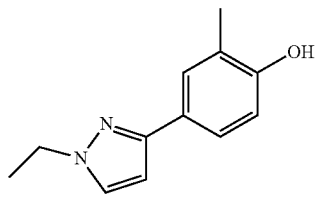

¹H-NMR (DMSO-D₆) δ: 9.30 (1H, br s), 7.68 (1H, d, J=2.2 Hz), 7.48 (1H, d, J=2.2 Hz), 7.39 (1H, dd, J=8.3, 2.2 Hz), 6.76 (1H, d, J=8.3 Hz), 6.49 (1H, d, J=2.2 Hz), 4.12 (2H, q, J=6.2 Hz), 2.14 (3H, s), 1.38 (3H, t, J=7.2 Hz).

Reference Preparation Example 31

A similar reaction to Reference Preparation example 29 using 3-(4-methoxy-3-methyl-phenyl)-1-isopropyl-1H-pyrazole (described in Reference Preparation example 42) instead of 3-(4-methoxy-3-methyl-phenyl)-1-methyl-1H-pyrazole gave 2-methyl-4-(1-isopropyl-1H-pyrazol-3-yl)-phenol.

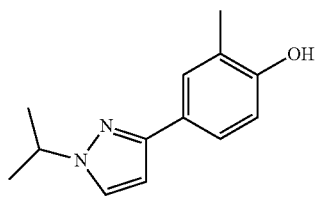 [SMILES: Cc1cc(-c2ccn(C(C)C)n2)ccc1O]

¹H-NMR (DMSO-D₆) δ: 9.30 (1H, br s), 7.71 (1H, d, J=2.2 Hz), 7.49-7.48 (1H, m), 7.39 (1H, dd, J=8.2, 2.2 Hz), 6.76 (1H, d, J=8.2 Hz), 6.49 (1H, d, J=2.2 Hz), 4.53-4.42 (1H, m), 2.15 (3H, s), 1.43 (6H, d, J=6.5 Hz).

Reference Preparation Example 32

A similar reaction to Reference Preparation example 29 using 3-(4-methoxy-3-methyl-phenyl)-1,5-dimethyl-1H-pyrazole (described in Reference Preparation example 43) instead of 3-(4-methoxy-3-methyl-phenyl)-1-methyl-1H-pyrazole gave 2-methyl-4-(1,5-dimethyl-1H-pyrazol-3-yl)-phenol.

2-methyl-4-(1,5-dimethyl-1H-pyrazol-3-yl)-phenol

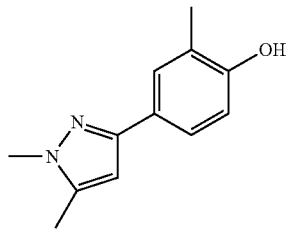

¹H-NMR (DMSO-D₆) δ: 9.31 (1H, br s), 7.43 (1H, d, J=1.7 Hz), 7.33 (1H, dd, J=8.2, 2.2 Hz), 6.75 (1H, d, J=8.2 Hz), 6.29 (1H, s), 3.71 (3H, s), 2.24 (3H, s), 2.13 (3H, s).

Reference Preparation Example 33

A mixture of 4-methoxy-3-methyl-phenylboronic acid 10 g, 3,4,5-trimethyl-1H-pyrazole (described in Reference Preparation example 49) 7.3 g, copper(II) acetate 18.4 g, pyridine 10.0 g, molecular sieves 4A 20.0 g and acetonitrile 300 ml was stirred with heating under reflux for thirty hours. The reaction mixture was filtered through Celite and was concentrated under reduced pressure. The resulting residue was subjected to a silica gel column chromatography to give 1-(4-methoxy-3-methyl-phenyl)-3,4,5-trimethyl-1H-pyrazole 7.3 g.

1-(4-methoxy-3-methyl-phenyl)-3,4,5-trimethyl-1H-pyrazole

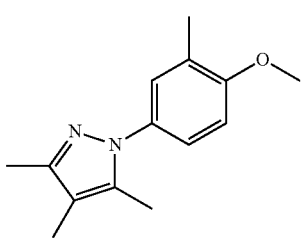

¹H-NMR (CDCl₃) δ: 7.19-7.17 (1H, m), 7.14 (1H, dd, J=8.5, 2.7 Hz), 6.84 (1H, d, J=8.5 Hz), 3.86 (3H, s), 2.24 (6H, s), 2.16 (3H, s), 1.97 (3H, s).

Reference Preparation Example 34

A similar reaction to Reference Preparation example 33 using 3,5-dimethyl-1H-pyrazole instead of 3,4,5-trimethyl-1H-pyrazole gave 1-(4-methoxy-3-methyl-phenyl)-3,5-dimethyl-1H-pyrazole.

1-(4-methoxy-3-methyl-phenyl)-3,5-dimethyl-1H-pyrazole

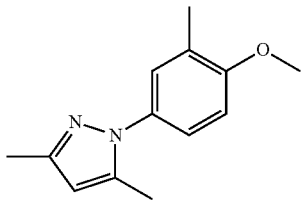

¹H-NMR (CDCl₃) δ: 7.20 (1H, d, J=2.0 Hz), 7.16 (1H, dd, J=8.5, 2.7 Hz), 6.84 (1H, d, J=8.5 Hz), 5.95 (1H, s), 3.86 (3H, s), 2.29 (3H, s), 2.24 (3H, s), 2.24 (3H, s).

Reference Preparation Example 35

A similar reaction to Reference Preparation example 33 using 3-methyl-1H-pyrazole instead of 3,4,5-trimethyl-1H-pyrazole gave 1-(4-methoxy-3-methyl-phenyl)-3-methyl-1H-pyrazole and 1-(4-methoxy-3-methyl-phenyl)-5-methyl-1H-pyrazole.

1-(4-methoxy-3-methyl-phenyl)-3-methyl-1H-pyrazole

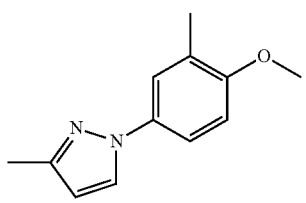

¹H-NMR (CDCl₃) δ: 7.70 (1H, d, J=2.2 Hz), 7.44 (1H, d, J=2.7 Hz), 7.37 (1H, dd, J=8.6, 2.7 Hz), 6.84 (1H, d, J=8.6 Hz), 6.20 (1H, d, J=2.2 Hz), 3.85 (3H, s), 2.37 (3H, s), 2.26 (3H, s).

1-(4-methoxy-3-methyl-phenyl)-5-methyl-1H-pyrazole

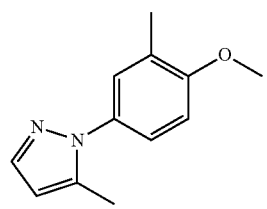

¹H-NMR (CDCl₃) δ: 7.54 (1H, d, J=1.7 Hz), 7.23-7.17 (2H, m), 6.87 (1H, d, J=8.5 Hz), 6.17-6.15 (1H, m), 3.88 (3H, s), 2.29 (3H, s), 2.26 (3H, s).

Reference Preparation Example 36

A similar reaction to Reference Preparation example 33 using 3,4-dimethyl-1H-pyrazole instead of 3,4,5-trimethyl- 1H-pyrazole gave 1-(4-methoxy-3-methyl-phenyl)-3,4-dimethyl-1H-pyrazole and 1-(4-methoxy-3-methyl-phenyl)-4,5-dimethyl-1H-pyrazole.

1-(4-methoxy-3-methyl-phenyl)-3,4-dimethyl-1H-pyrazole

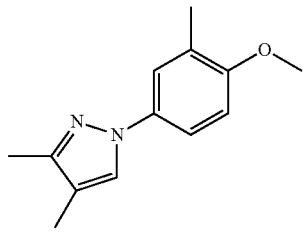

¹H-NMR (CDCl₃) δ: 7.52 (1H, s), 7.41 (1H, d, J=2.7 Hz), 7.32 (1H, dd, J=8.7, 2.9 Hz), 6.82 (1H, d, J=8.7 Hz), 3.84 (3H, s), 2.27 (3H, s), 2.25 (3H, s), 2.06 (3H, s).

1-(4-methoxy-3-methyl-phenyl)-4,5-dimethyl-1H-pyrazole

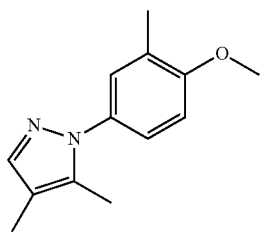 [SMILES: COc1ccc(-n2ncc(C)c2C)cc1C]

¹H-NMR (CDCl₃) δ: 7.41 (1H, s), 7.20-7.15 (2H, m), 6.86 (1H, d, J=8.5 Hz), 3.87 (3H, s), 2.25 (3H, s), 2.19 (3H, s), 2.05 (3H, s).

Reference Preparation Example 37

A similar reaction to Reference Preparation example 33 using 4,5,6,7-tetrahydroindazole instead of 3,4,5-trimethyl-1H-pyrazole gave 2-(4-methoxy-3-methyl-phenyl)-4,5,6,7-tetrahydro-2H-indazole and 1-(4-methoxy-3-methyl-phenyl)-4,5,6,7-tetrahydro-2H-indazole.

2-(4-methoxy-3-methyl-phenyl)-4,5,6,7-tetrahydro-2H-indazole

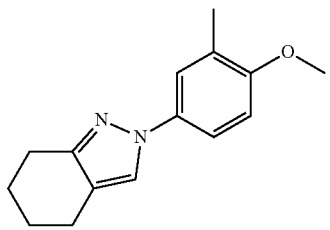 [SMILES: COc1ccc(-n2cc3c(n2)CCCC3)cc1C]

¹H-NMR (CDCl₃) δ: 7.51 (1H, s), 7.43 (1H, d, J=2.7 Hz), 7.34 (1H, dd, J=8.7, 2.8 Hz), 6.83 (1H, d, J=8.8 Hz), 3.85 (3H, s), 2.77 (2H, t, J=6.2 Hz), 2.61 (2H, t, J=6.1 Hz), 2.25 (3H, s), 1.89-1.82 (2H, m), 1.81-1.74 (2H, m).

1-(4-methoxy-3-methyl-phenyl)-4,5,6,7-tetrahydro-2H-indazole

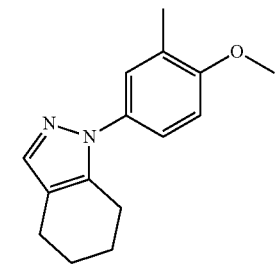 [SMILES: COc1ccc(-n2ncc3c2CCCC3)cc1C]

¹H-NMR (CDCl₃) δ: 7.42 (1H, s), 7.29-7.25 (1H, m), 7.22 (1H, dd, J=8.5, 2.7 Hz), 6.85 (1H, d, J=8.5 Hz), 3.86 (3H, s), 2.66 (2H, t, J=5.2 Hz), 2.58 (2H, t, J=5.2 Hz), 2.25 (3H, s), 1.83-1.74 (4H, m).

Reference Preparation Example 38

A similar reaction to Reference Preparation example 33 using 4-methoxy-3-trifluoromethyl-phenylboronic acid instead of 4-methoxy-3-methyl-phenylboronic acid gave 1-(4-methoxy-3-trifluoromethyl-phenyl)-3,4,5-trimethyl-1H-pyrazole.

1-(4-methoxy-3-trifluoromethyl-phenyl)-3,4,5-trimethyl-1H-pyrazole

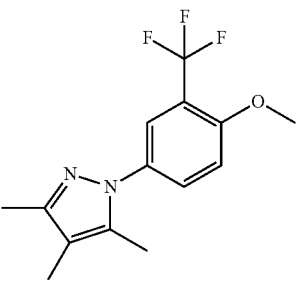

¹H-NMR (CDCl₃) δ: 7.62 (1H, d, J=2.7 Hz), 7.52 (1H, dd, J=8.9, 2.7 Hz), 7.06 (1H, d, J=8.7 Hz), 3.95 (3H, s), 2.23 (3H, s), 2.18 (3H, s), 1.97 (3H, s).

Reference Preparation Example 39

Under nitrogen atmosphere, a mixture of 4-methoxy-3-methyl-phenylboronic acid 1.62 g, 4-bromo-1-methyl-1H-pyrazole 1.57 g, 1,1'-bis(diphenylphosphino)ferrocene-palladium(II) dichloride dichloromethane complex 0.79 g, sodium carbonate 3.51 g, dioxane 100 ml and water 30 ml was stirred with heating under reflux for four hours. The resulting mixture was extracted with ethyl acetate. The organic layer was washed with water, and was dried over anhydrous magnesium sulfate and was then concentrated under reduced pressure. The resulting residue was subjected to a silica gel column chromatography to give 4-(4-methoxy-3-methyl-phenyl)-1-methyl-1H-pyrazole 1.3 g.

4-(4-methoxy-3-methyl-phenyl)-1-methyl-1H-pyrazole

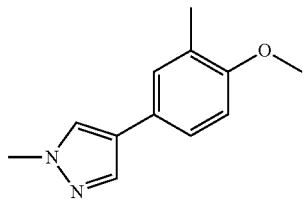

¹H-NMR (CDCl₃) δ: 7.68 (1H, s), 7.52 (1H, s), 7.28-7.24 (2H, m), 6.82 (1H, d, J=8.3 Hz), 3.93 (3H, s), 3.84 (3H, s), 2.24 (3H, s).

Reference Preparation Example 40

At room temperature, to a mixture of 3-(4-methoxy-3-methyl-phenyl)-1H-pyrazole (described in Reference Preparation example 44) 5.38 g and N,N-dimethylformamide 100 ml was added 55% sodium hydride 1.5 g and the resulting mixture was stirred for a half hour and thereto was added methyl iodide 7.9 g. The resulting mixture was stirred for twelve hours and thereto was added water, and then the resulting mixture was extracted with ethyl acetate. The organic layer was washed with water, and was dried over anhydrous magnesium sulfate and was then concentrated under reduced pressure. The resulting residue was subjected to a silica gel column chromatography to give 3-(4-methoxy-3-methyl-phenyl)-1-methyl-1H-pyrazole 2.9 g and 5-(4-methoxy-3-methyl-phenyl)-1-methyl-1H-pyrazole 1.0 g.

3-(4-methoxy-3-methyl-phenyl)-1-methyl-1H-pyrazole

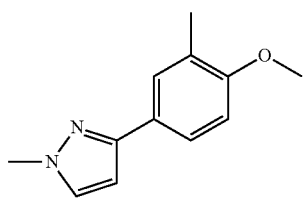

¹H-NMR (CDCl₃) δ: 7.61-7.58 (1H, m), 7.56 (1H, dd, J=8.3, 2.2 Hz), 7.34 (1H, d, J=2.2 Hz), 6.84 (1H, d, J=8.3 Hz), 6.45 (1H, d, J=2.2 Hz), 3.93 (3H, s), 3.85 (3H, s), 2.26 (3H, s).

5-(4-methoxy-3-methyl-phenyl)-1-methyl-1H-pyrazole

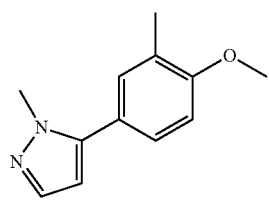

¹H-NMR (CDCl₃) δ: 7.49 (1H, d, J=1.7 Hz), 7.22-7.19 (2H, m), 6.89 (1H, d, J=8.5 Hz), 6.24 (1H, d, J=1.7 Hz), 3.88 (3H, s), 3.87 (3H, s), 2.26 (3H, s).

Reference Preparation Example 41

A similar reaction to Reference Preparation example 40 using ethyl iodide instead of methyl iodide gave 3-(4-methoxy-3-methyl-phenyl)-1-ethyl-1H-pyrazole.

3-(4-methoxy-3-methyl-phenyl)-1-ethyl-1H-pyrazole

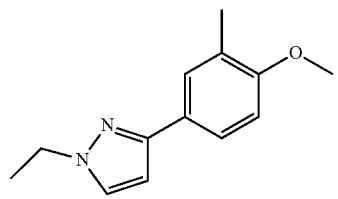 [SMILES: CCn1ccc(-c2ccc(OC)c(C)c2)n1]

¹H-NMR (CDCl₃) δ: 7.60 (1H, s), 7.57 (1H, dd, J=8.5, 2.2 Hz), 7.38 (1H, d, J=2.4 Hz), 6.84 (1H, d, J=8.2 Hz), 6.45 (1H, d, J=2.2 Hz), 4.20 (2H, q, J=7.3 Hz), 3.85 (3H, s), 2.26 (3H, s), 1.52 (3H, t, J=7.4 Hz).

Reference Preparation Example 42

A similar reaction to Reference Preparation example 40 using isopropyl iodide instead of methyl iodide gave 3-(4-methoxy-3-methyl-phenyl)-1-isopropyl-1H-pyrazole.

3-(4-methoxy-3-methyl-phenyl)-1-isopropyl-1H-pyrazole

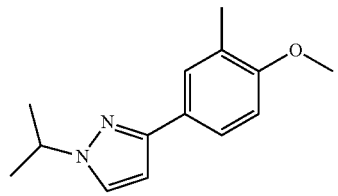 [SMILES: COc1ccc(-c2ccn(C(C)C)n2)cc1C]

¹H-NMR (CDCl₃) δ: 7.60 (1H, s), 7.58-7.54 (1H, m), 7.42 (1H, d, J=2.4 Hz), 6.84 (1H, d, J=8.2 Hz), 6.45 (1H, d, J=2.4 Hz), 4.60-4.50 (1H, m), 3.85 (3H, s), 2.26 (3H, s), 1.54 (6H, d, J=6.8 Hz).

Reference Preparation Example 43

A similar reaction to Reference Preparation example 40 using 3-(4-methoxy-3-methyl-phenyl)-5-methyl-1H-pyrazole (described in Reference Preparation example 45) instead of 3-(4-methoxy-3-methyl-phenyl)-1H-pyrazole gave 3-(4-methoxy-3-methyl-phenyl)-1,5-dimethyl-1H-pyrazole and 5-(4-methoxy-3-methyl-phenyl)-1,3-dimethyl-1H-pyrazole.

3-(4-methoxy-3-methyl-phenyl)-1,5-dimethyl-1H-pyrazole

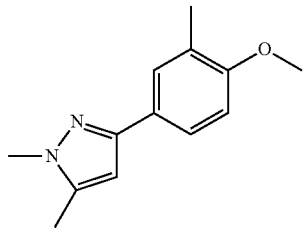

¹H-NMR (CDCl₃) δ: 7.56-7.55 (1H, m), 7.53-7.50 (1H, m), 6.82 (1H, d, J=8.5 Hz), 6.24 (1H, d, J=0.7 Hz), 3.84 (3H, s), 3.80 (3H, s), 2.29 (3H, s), 2.25 (3H, s).

5-(4-methoxy-3-methyl-phenyl)-1,3-dimethyl-1H-pyrazole

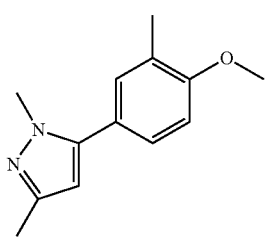 [SMILES: COc1ccc(-c2cc(C)nn2C)cc1C]

¹H-NMR (CDCl₃) δ: 7.20-7.17 (2H, m), 6.88 (1H, d, J=8.2 Hz), 6.02 (1H, s), 3.87 (3H, s), 3.79 (3H, s), 2.29 (3H, s), 2.26 (3H, s).

Reference Preparation Example 44

At room temperature, to a mixture of 3-dimethylamino-1-(4-methoxy-3-methyl-phenyl)-propenone (described in Reference Preparation example 46) 7.69 g and ethanol 100 ml was added hydrazine one hydrate 9.8 ml and the resulting mixture was stirred for twenty four hours. The reaction mixture was concentrated under reduced pressure so as to make ethanol in the reaction mixture about 10 ml. The resulting residue was subjected to a silica gel column chromatography to give 3-(4-methoxy-3-methyl-phenyl)-1H-pyrazole 5.4 g.

3-(4-methoxy-3-methyl-phenyl)-1,3-dimethyl-1H-pyrazole

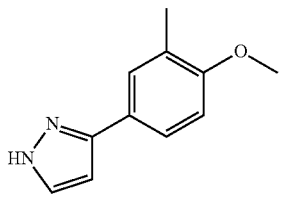

¹H-NMR (CDCl₃) δ: 11.91 (1H, br s), 7.58 (1H, d, J=2.2 Hz), 7.54-7.50 (2H, m), 6.84-6.80 (1H, m), 6.51 (1H, d, J=2.0 Hz), 3.85 (3H, s), 2.24 (3H, s).

Reference Preparation Example 45

A similar reaction to Reference Preparation example 44 using 1-(4-methoxy-3-methylphenyl)-butane-1,3-dione (described in Reference Preparation example 47) instead of 3-dimethylamino-1-(4-methoxy-3-methyl-phenyl)-propenone gave 3-(4-methoxy-3-methyl-phenyl)-5-methyl-1H-pyrazole.

3-(4-methoxy-3-methyl-phenyl)-5-methyl-1H-pyrazole

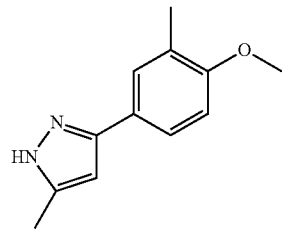

¹H-NMR (CDCl₃) δ: 7.49-7.46 (2H, m), 6.83-6.80 (1H, m), 6.26 (1H, s), 3.84 (3H, s), 2.31 (3H, 2.23 (3H,

Reference Preparation Example 46

A mixture of 1-(4-methoxy-3-methylphenyl)-ethanone (described in Reference Preparation example 48) 5.76 g and N,N-dimethylformamide diethylacetal 7.46 ml was stirred with heating under reflux for twenty four hours. The resulting mixture was concentrated under reduce pressure to give 3-dimethylamino-1-(4-methoxy-3-methyl-phenyl)-propenone 4.78 g.

3-dimethylamino-1-(4-methoxy-3-methyl-phenyl)-propenone

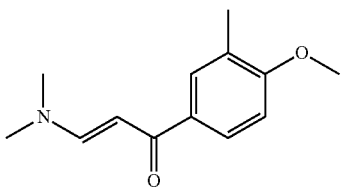

¹H-NMR (DMSO-D₆) δ: 7.76 (1H, dd, J=8.5, 2.2 Hz), 7.72 (1H, s), 7.64 (1H, d, J=12.4 Hz), 6.95 (1H, d, J=8.5 Hz), 5.80 (1H, d, J=12.4 Hz), 3.83 (3H, s), 3.11 (3H, br s), 2.90 (3H, br s), 2.18 (3H, s).

Reference Preparation Example 47

At room temperature, to tetrahydrofuran 50 ml was added 55% sodium hydride 3.07 g and ethyl acetate 5.90 g and the resulting mixture was stirred for a half hour. Then, thereto was added 1-(4-methoxy-3-methylphenyl)-ethanone (described in Reference Preparation example 48) 5.50 g, dibenzo-18-crown-6 0.024 g and ethanol 1 ml and the resulting mixture was stirred with heating under reflux for six hours. To the reaction mixture was added water and the resulting mixture was acidified with aqueous 10% hydrochloric acid solution and was extracted with ethyl acetate. The organic layer was washed with water and was dried over anhydrous magnesium sulfate, and was then concentrated under reduced pressure. The resulting residue was subjected to a silica gel column chromatography to give 1-(4-methoxy-3-methyl-phenyl)-butane-1,3-dione 6.50 g.

1-(4-methoxy-3-methyl-phenyl)-butane-1,3-dione

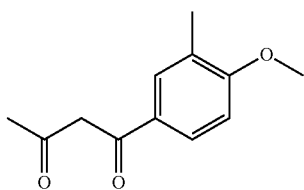

$^1$H-NMR (CDCl$_3$: 23° C.) δ: 7.76 (1H, dd, J=8.6, 2.3 Hz), 7.69 (1H, d, J=1.4 Hz), 6.85 (1H, d, J=8.5 Hz), 6.12 (1H, s), 3.89 (3H, s), 2.25 (3H, s), 2.17 (3H, s).

Reference Preparation Example 48

A mixture of 1-(4-hydroxy-3-methylphenyl)-ethanone 5.0 g, methyl iodide 5.70 g, potassium carbonate 20.0 g and acetone 200 ml was stirred with heating under reflux for six hours. The reaction mixture was filtered and was extracted with ethyl acetate. The organic layer was washed with water and was dried over anhydrous magnesium sulfate, and was then concentrated under reduced pressure to give 1-(4-methoxy-3-methylphenyl)-ethanone 5.3 g.

1-(4-methoxy-3-methylphenyl)-ethanone

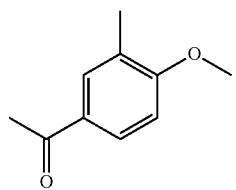

$^1$H-NMR (CDCl$_3$) δ: 7.82 (1H, dd, J=8.5, 1.7 Hz), 7.79-7.76 (1H, m), 6.85 (1H, d, J=8.5 Hz), 3.90 (3H, s), 2.55 (3H, s), 2.25 (3H, s).

Reference Preparation Example 49

At 0° C., to a mixture of water 5 ml and acetic acid 5 ml was added 3-methyl-2,4-pentanedione 5.88 g and hydrazine one hydrate 2.41 g, and the resulting mixture was stirred for five hours. The precipitates were filtered and were washed with water and hexane, and were concentrated under reduced pressure to give 3,4,5-toriemthyl-1H-pyrazole 3.68 g.

3,4,5-toriemthyl-1H-pyrazole

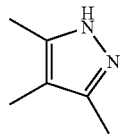

$^1$H-NMR (CDCl$_3$) δ: 2.19 (6H, s), 1.90 (3H, s).

Reference Preparation Example 50

At 0° C., to a mixture of 3-amino-2-chlorophenol 100 g and concentrated hydrochloric acid 250 ml was added slowly aqueous solution 300 ml containing sodium nitrite 67.0 g and followed by addition of water 400 ml. The resulting mixture was stirred for two hours and thereto was added slowly anhydrous tin(II) chloride 292 g and concentrated hydrochloric acid 250 ml and the resulting mixture was stirred for one hour. At room temperature, the resulting mixture was stirred for additional twelve hours, and then the reaction mixture was filtered and was washed with aqueous 10% hydrochloric acid and hexane to give 2-chloro-4-hydrazinophenol hydrochloride salt 105 g.

2-chloro-4-hydrazinophenol hydrochloride salt

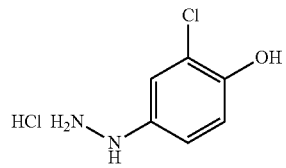

$^1$H-NMR (DMSO-D$_6$) δ: 10.00 (3H, s), 9.90 (1H, s), 7.92 (1H, br s), 7.07 (1H, d, J=2.7 Hz), 6.93 (1H, d, J=8.8 Hz), 6.85 (1H, dd, J=8.8, 2.7 Hz).

Reference Preparation Example 51

A similar reaction to Reference Preparation example 46 using 1-(3-chloro-4-methoxy)-ethanone instead of 1-(4-methoxy-3-methyl)-ethanone gave 3-dimethylamino-1-(3-chloro-4-methoxy-phenyl)-propenone.

3-dimethylamino-1-(3-chloro-4-methoxy-phenyl)-propenone

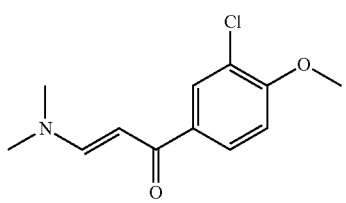

¹H-NMR (CDCl₃) δ: 7.95 (1H, d, J=2.2 Hz), 7.84 (1H, dd, J=8.7, 2.2 Hz), 7.80 (1H, d, J=12.3 Hz), 6.94 (1H, d, J=8.7 Hz), 5.65 (1H, d, J=12.3 Hz), 3.95 (3H, s), 3.14 (3H, s), 2.95 (3H, s).

Reference Preparation Example 52

A similar reaction to Reference Preparation example 44 using 3-dimethylamino-1-(3-chloro-4-methoxy-phenyl)-propenone (described in Reference Preparation example 51) instead of 3-dimethylamino-1-(4-methoxy-3-methyl-phenyl)-propenone gave 3-(3-chloro-4-methoxy-phenyl)-1H-pyrazole.

3-(3-chloro-4-methoxy-phenyl)-1H-pyrazole

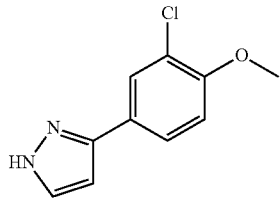

¹H-NMR (CDCl₃) δ: 7.78 (1H, d, J=1.9 Hz), 7.61-7.59 (2H, m), 6.92 (1H, d, J=8.7 Hz), 6.54 (1H, dd, J=2.2, 0.7 Hz), 3.92 (3H, s).

Reference Preparation Example 53

A similar reaction to Reference Preparation example 40 using 3-(3-chloro-4-methoxy-phenyl)-1H-pyrazole (described in Reference Preparation example 52) instead of 3-(4-methoxy-3-methyl-phenyl)-1H-pyrazole gave 3-(3-chloro-4-methoxy-phenyl)-1-methyl-1H-pyrazole and 5-(3-chloro-4-methoxy-phenyl)-1-methyl-1H-pyrazole.

3-(3-chloro-4-methoxy-phenyl)-1-methyl-1H-pyrazole

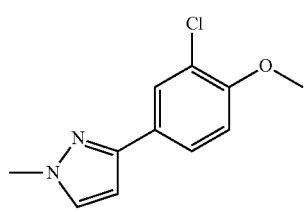

¹H-NMR (CDCl₃) δ: 7.81 (1H, d, J=2.2 Hz), 7.64 (1H, dd, J=8.6, 2.1 Hz), 7.36 (1H, d, J=2.2 Hz), 6.95 (1H, d, J=8.5 Hz), 6.45 (1H, d, J=2.2 Hz), 3.94 (3H, s), 3.93 (3H, s)

5-(3-chloro-4-methoxy-phenyl)-1-methyl-1H-pyrazole

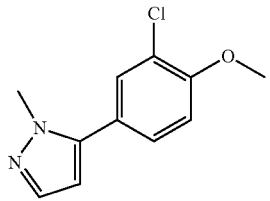

¹H-NMR (CDCl₃) δ: 7.50 (1H, d, J=1.9 Hz), 7.44 (1H, d, J=2.2 Hz), 7.29-7.26 (1H, m), 7.01 (1H, d, J=8.5 Hz), 6.26 (1H, d, J=1.9 Hz), 3.96 (3H, s), 3.87 (3H, s).

Reference Preparation Example 54

A similar reaction to Reference Preparation example 29 using 3-(3-chloro-4-methoxy-phenyl)-1-methyl-1H-pyrazole (described in Reference Preparation example 53) instead of 3-(4-methoxy-3-methyl-phenyl)-1H-pyrazole gave 2-chloro-4-(1-methyl-1H-pyrazol-3-yl)-phenol.

2-chloro-4-(1-methyl-1H-pyrazol-3-yl)-phenol

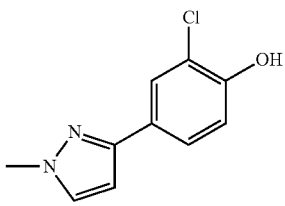

¹H-NMR (DMSO-D₆) δ: 7.70 (2H, dd, J=7.2, 1.7 Hz), 7.55 (1H, dd, J=8.5, 1.4 Hz), 6.98 (1H, d, J=8.5 Hz), 6.61-6.60 (1H, m), 3.85 (3H, s).

Reference Preparation Example 55

At room temperature, a mixture of 3-(4-methoxy-3-methyl-phenyl)-1-methyl-1H-pyrazole (described in Reference Preparation example 29) 3 g, N-bromosuccinimide 2.9 g and chloroform 50 ml was stirred for sixteen hours. To the reaction mixture was added water and the resulting mixture was extracted with chloroform. The organic layer was washed with water and was dried over anhydrous magnesium sulfate, and was then concentrated under reduced pressure. The resulting residue was subjected to a silica gel column chromatography to give 3-(4-methoxy-3-methyl-phenyl)-4-bromo-1-methyl-1H-pyrazole 3.9 g.

3-(4-methoxy-3-methyl-phenyl)-4-bromo-1-methyl-1H-pyrazole

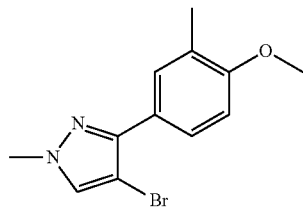

$^1$H-NMR (CDCl$_3$) δ: 7.69 (1H, dd, J=8.5, 2.4 Hz), 7.63 (1H, d, J=2.2 Hz), 7.43 (1H, s), 6.87 (1H, d, J=8.5 Hz), 3.91 (3H, s), 3.86 (3H, s), 2.26 (3H, s).

Reference Preparation Example 56

A similar reaction to Reference Preparation example 120 using 3-(3-chloro-4-methoxy-phenyl)-1-methyl-1H-pyrazole (described in Reference Preparation example 53) instead of 3-(4-methoxy-3-methyl-phenyl)-1-methyl-1H-pyrazole gave 3-(4-methoxy-3-chloro-phenyl)-4-bromo-1-methyl-1H-pyrazole.

3-(4-methoxy-3-chloro-phenyl)-4-bromo-1-methyl-1H-pyrazole

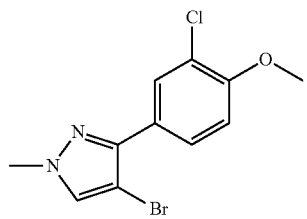

$^1$H-NMR (CDCl$_3$) δ: 7.92-7.91 (1H, m), 7.79-7.76 (1H, m), 7.44 (1H, s), 6.98 (1H, d, J=8.5 Hz), 3.94 (3H, s), 3.92 (3H, s).

Reference Preparation Example 57

A mixture of 3-(4-methoxy-3-methyl-phenyl)-4-bromo-1-methyl-1H-pyrazole (described in Reference Preparation example 55) 3.9 g, 1,4-dioxane 80 ml, water 20 ml, methylboronic acid 3.3 g, 1,1'-bis(diphenylphosphino)ferrocene-palladium(II) dichloride dichloromethane adducts 1.4 g and potassium phosphate 11.8 g was stirred with heating under reflux for six hours. The reaction mixture was extracted with ethyl acetate. The organic layer was washed with water, and was dried over anhydrous magnesium sulfate and was then concentrated under reduced pressure. The resulting residue was subjected to a silica gel column chromatography to give 3-(4-methoxy-3-methyl-phenyl)-1,4-dimethyl-1H-pyrazole 2.4 g.

3-(4-methoxy-3-methyl-phenyl)-1,4-dimethyl-1H-pyrazole

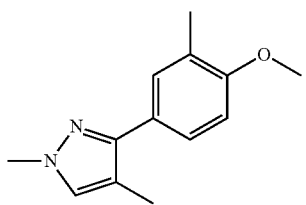

$^1$H-NMR (CDCl$_3$) δ: 7.47 (1H, s), 7.43 (1H, dd, J=8.2, 2.2 Hz), 7.16 (1H, s), 6.86 (1H, d, J=8.2 Hz), 3.87 (3H, s), 3.85 (3H, s), 2.26 (3H, s), 2.20 (3H, s).

Reference Preparation Example 58

A similar reaction to Reference Preparation example 57 using 3-(4-methoxy-3-chloro-phenyl)-4-bromo-1-methyl-1H-pyrazole (described in Reference Preparation example 56) instead of 3-(4-methoxy-3-methyl-phenyl)-4-bromo-1-methyl-1H-pyrazole gave 3-(4-methoxy-3-chloro-phenyl)-1,4-dimethyl-1H-pyrazole.

3-(4-methoxy-3-chloro-phenyl)-1,4-dimethyl-1H-pyrazole

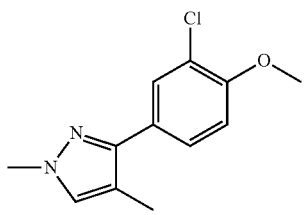

$^1$H-NMR (CDCl$_3$) δ: 7.70 (1H, d, J=2.2 Hz), 7.53 (1H, dd, J=8.5, 2.2 Hz), 7.18 (1H, s), 6.97 (1H, d, J=8.5 Hz), 3.93 (3H, s), 3.88 (3H, s), 2.20 (3H, s).

Reference Preparation Example 59

A mixture of 3-(4-methoxy-3-methyl-phenyl)-1,4-dimethyl-1H-pyrazole (described in Reference Preparation example 57) 2.4 g, 47% hydrobromic acid 18 ml and acetic acid 18 ml was stirred with heating under reflux for sixteen hours. The solvent was distilled off and to the resulting residues was added ethyl acetate 50 ml, and the resulting mixture was stirred at room temperature for one hour. The precipitates were filtered and were washed with hexane, and were concentrated under reduced pressure to give 4-(1,4-dimethyl-1H-pyrazol-3-yl)-2-methyl-phenol 2.1 g.

4-(1,4-dimethyl-1H-pyrazol-3-yl)-2-methyl-phenol

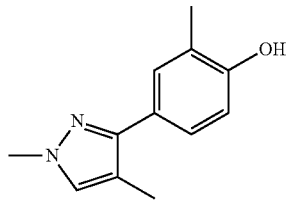

¹H-NMR (DMSO-D₆) δ: 7.58 (1H, s), 7.34 (1H, s), 7.25 (1H, dd, J=8.2, 2.2 Hz), 6.83 (1H, d, J=8.5 Hz), 3.81 (3H, s), 2.16 (3H, s), 2.13 (3H, s)

Reference Preparation Example 60

A similar reaction to Reference Preparation example 59 using 3-(4-methoxy-3-chloro-phenyl)-1,4-dimethyl-1H-pyrazole (described in Reference Preparation example 58) instead of 3-(4-methoxy-3-methyl-phenyl)-1,4-dimethyl-1H-pyrazole gave 4-(1,4-dimethyl-1H-pyrazol-3-yl)-2-chloro-phenol.

4-(1,4-dimethyl-1H-pyrazol-3-yl)-2-chloro-phenol

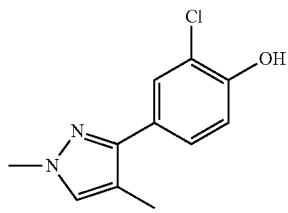

¹H-NMR (DMSO-D₆) δ: 7.54 (1H, d, J=2.2 Hz), 7.52 (1H, s), 7.41 (1H, dd, J=8.5, 1.9 Hz), 7.01 (1H, d, J=8.5 Hz), 3.79 (3H, s), 2.13 (3H, s).

Reference Preparation Example 61

At room temperature, to a mixture of 3-ethyl-2,4-pentanedione 5 g and ethanol 50 ml was added hydrazine one hydrate 2.9 g and the resulting mixture was stirred for five hours. The ethanol was distilled off and the resulting residue was subjected to a silica gel column chromatography to give 3,5-dimethyl-4-ethyl-1H-pyrazole 6.0 g.

3,5-dimethyl-4-ethyl-1H-pyrazole

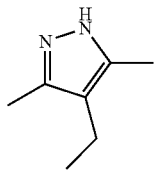

¹H-NMR (CDCl₃) δ: 2.36 (2H, q, J=7.6 Hz), 2.20 (6H, s), 1.07 (3H, t, J=7.6 Hz).

Reference Preparation Example 62

A similar reaction to Reference Preparation example 33 using 3,5-dimethyl-4-ethyl-1H-pyrazole (described in Reference Preparation example 61) instead of 3,4,5-trimethyl-1H-pyrazole gave 1-(4-methoxy-3-methyl-phenyl)-3,5-dimethyl-4-ethyl-1H-pyrazole.

1-(4-methoxy-3-methyl-phenyl)-3,5-dimethyl-4-ethyl-1H-pyrazole

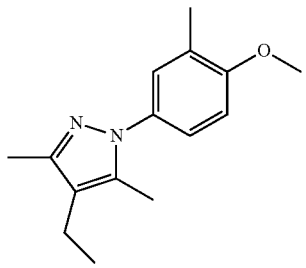

¹H-NMR (CDCl₃) δ: 7.19 (1H, d, J=2.7 Hz), 7.14 (1H, dd, J=8.5, 2.7 Hz), 6.84 (1H, d, J=8.7 Hz), 3.86 (3H, s), 2.41 (2H, q, J=7.6 Hz), 2.26 (3H, s), 2.24 (3H, s), 2.17 (3H, s), 1.11 (3H, t, J=7.5 Hz).

Reference Preparation Example 63

A similar reaction to Reference Preparation example 20 using 1-(4-methoxy-3-methyl-phenyl)-3,5-dimethyl-4-ethyl-1H-pyrazole (described in Reference Preparation example 62) instead of 1-(4-methoxy-3-methyl-phenyl)-3,4,5-trimethyl-1H-pyrazole gave 2-methyl-4-(3,5-dimethyl-4-ethyl-pyrazol-1-yl)-phenol.

2-methyl-4-(3,5-dimethyl-4-ethyl-pyrazol-1-yl)-phenol

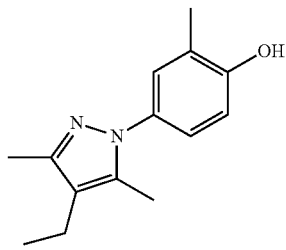 [SMILES: CCc1c(C)nn(-c2ccc(O)c(C)c2)c1C]

¹H-NMR (DMSO-D₆) δ: 7.24 (1H, d, J=2.5 Hz), 7.15 (1H, dd, J=8.5, 2.7 Hz), 6.93-6.91 (1H, m), 2.43 (2H, q, J=7.6 Hz), 2.25 (3H, s), 2.17 (3H, s), 2.17 (3H, s), 1.07 (3H, t, J=7.6 Hz)

Reference Preparation Example 64

At room temperature, a mixture of 3-(4-methoxy-3-methyl-phenyl)-1,5-dimethyl-1H-pyrazole (described in Reference Preparation example 43) 5.9 g, N-bromosuccinimide 5.8 g and chloroform 100 ml was stirred for seventeen hours. To the reaction mixture was added water and the resulting mixture was extracted with chloroform. The organic layer was washed with water and was dried over anhydrous magnesium sulfate, and was then concentrated under reduced pressure. The resulting residue was subjected to a silica gel column chromatography to give 3-(4-methoxy-3-methyl-phenyl)-4-bromo-1,5-dimethyl-1H-pyrazole 4.0 g.

3-(4-methoxy-3-methyl-phenyl)-4-bromo-1,5-dimethyl-1H-pyrazole

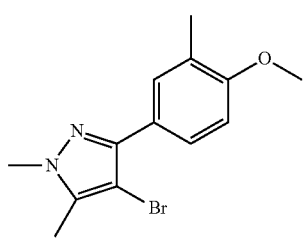

$^1$H-NMR (CDCl$_3$) δ: 7.67 (1H, dd, J=8.5, 2.2 Hz), 7.62 (1H, d, J=1.9 Hz), 6.87 (1H, d, J=8.5 Hz), 3.86 (3H, s), 3.84 (3H, s), 2.31 (3H, s), 2.26 (3H, s).

Reference Preparation Example 65

A mixture of 3-(4-methoxy-3-methyl-phenyl)-4-bromo-1,5-dimethyl-1H-pyrazole (described in Reference Preparation example 64) 1.3 g, 1,4-dioxane 30 ml, water 5 ml, methylboronic acid 1.0 g, 1,1'-bis(diphenylphosphino)ferrocene-palladium(II) dichloride dichloromethane adducts 0.4 g and potassium phosphate 3.7 g was stirred with heating under reflux for nine hours. The reaction mixture was extracted with ethyl acetate. The organic layer was washed with water, and was dried over anhydrous magnesium sulfate and was then concentrated under reduced pressure. The resulting residue was subjected to a silica gel column chromatography to give 3-(4-methoxy-3-methyl-phenyl)-1,4,5-trimethyl-1H-pyrazole 0.6 g.

3-(4-methoxy-3-methyl-phenyl)-1,4,5-trimethyl-1H-pyrazole

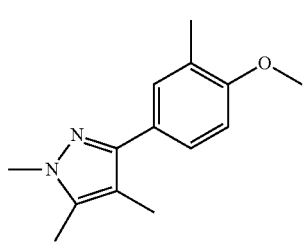

$^1$H-NMR (CDCl$_3$) δ: 7.43 (1H, s), 7.40 (1H, dd, J=8.2, 2.2 Hz), 6.86 (1H, d, J=8.5 Hz), 3.85 (3H, s), 3.80 (3H, s), 2.25 (3H, s), 2.21 (3H, s), 2.11 (3H, s).

Reference Preparation Example 66

A mixture of 3-(4-methoxy-3-methyl-phenyl)-1,4,5-trimethyl-1H-pyrazole (described in Reference Preparation example 65) 0.6 g, 47% hydrobromic acid 5 ml and acetic acid 5 ml was stirred with heating under reflux for thirteen hours. The solvent was distilled off and to the resulting residues was added ethyl acetate 30 ml, and the resulting mixture was stirred at room temperature for one hour. The precipitates were filtered and were washed with hexane, and were concentrated under reduced pressure to give 4-(1,4,5-trimethyl-1H-pyrazol-3-yl)-2-methyl-phenol 0.5 g.

4-(1,4,5-trimethyl-1H-pyrazol-3-yl)-2-methyl-phenol

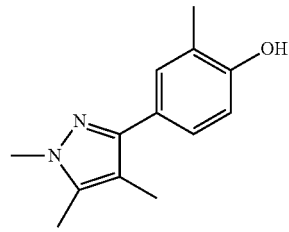 [SMILES: Cc1cc(-c2nn(C)c(C)c2C)ccc1O]

$^1$H-NMR (DMSO-D$_6$) δ: 7.33 (1H, d, J=2.2 Hz), 7.26 (1H, dd, J=8.2, 2.2 Hz), 6.88 (1H, d, J=8.2 Hz), 3.82 (3H, s), 2.26 (3H, s), 2.17 (3H, s), 2.08 (3H, s).

Reference Preparation Example 67

A similar reaction to Reference Preparation example 33 using 3-cyclopropyl-1H-pyrazole instead of 3,4,5-trimethyl-1H-pyrazole gave 1-(4-methoxy-3-methyl-phenyl)-3-cyclopropyl-1H-pyrazole and 1-(4-methoxy-3-methyl-phenyl)-5-cyclopropyl-1H-pyrazole.

1-(4-methoxy-3-methyl-phenyl)-3-cyclopropyl-1H-pyrazole

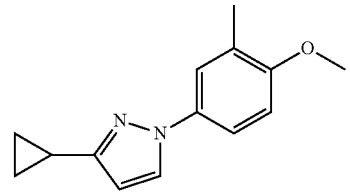 [SMILES: COc1ccc(-n2ccc(C3CC3)n2)cc1C]

$^1$H-NMR (CDCl$_3$) δ: 7.67 (1H, d, J=2.4 Hz), 7.43 (1H, d, J=2.9 Hz), 7.37 (1H, dd, J=8.7, 2.7 Hz), 6.83 (1H, d, J=8.7 Hz), 6.05 (1H, d, J=2.4 Hz), 3.85 (3H, s), 2.26 (3H, s), 2.07-2.00 (1H, m), 0.98-0.93 (2H, m), 0.80-0.76 (2H, m).

1-(4-methoxy-3-methyl-phenyl)-5-cyclopropyl-1H-pyrazole

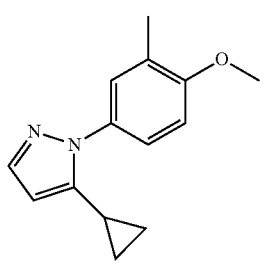 [SMILES: COc1ccc(-n2nccc2C2CC2)cc1C]

¹H-NMR (CDCl₃) δ: 7.51 (1H, d, J=1.9 Hz), 7.37-7.35 (2H, m), 6.89-6.87 (1H, m), 5.91 (1H, d, J=1.9 Hz), 3.88 (3H, s), 2.27 (3H, s), 1.81-1.74 (1H, m), 0.97-0.93 (2H, m), 0.76-0.72 (2H, m).

Reference Preparation Example 68

A similar reaction to Reference Preparation example 20 using 1-(4-methoxy-3-methyl-phenyl)-5-cyclopropyl-1H-pyrazole (described in Reference Preparation example 67) instead of 3,4,5-trimethyl-1H-pyrazole gave 2-methyl-(4-methoxy-3-cyclopropyl-1H-pyrazol-3-yl)-phenol.

2-methyl-(4-methoxy-3-cyclopropyl-1H-pyrazol-3-yl)-phenol

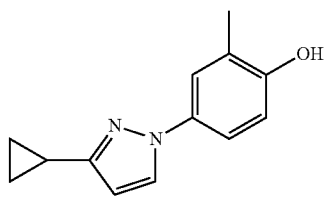 [SMILES: Cc1cc(-n2ccc(C3CC3)n2)ccc1O]

¹H-NMR (DMSO-D₆) δ: 8.10 (1H, d, J=1.4 Hz), 7.45 (1H, d, J=2.2 Hz), 7.35-7.32 (1H, m), 6.81 (1H, d, J=8.2 Hz), 6.15-6.14 (1H, m), 2.16 (3H, s), 1.97-1.90 (1H, m), 0.91-0.87 (2H, m), 0.71-0.67 (2H, m).

Reference Preparation Example 69

A similar reaction to Reference Preparation example 29 using 5-(4-methoxy-3-methyl-phenyl)-1-methyl-1H-pyrazole (described in Reference Preparation example 43) instead of 3-(4-methoxy-3-methyl-phenyl)-1-methyl-1H-pyrazole gave 2-methyl-(1,3-dimethyl-1H-pyrazol-5-yl)-phenol.

2-methyl-(1,3-dimethyl-1H-pyrazol-5-yl)-phenol

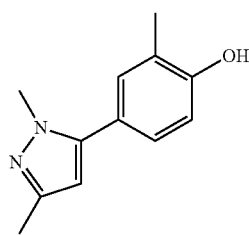

¹H-NMR (DMSO-D₆) δ: 7.22 (1H, s), 7.15 (1H, dd, J=8.2, 1.9 Hz), 6.89 (1H, d, J=8.2 Hz), 6.20 (1H, s), 3.77 (3H, s), 2.21 (3H, s), 2.16 (3H, s).

Reference Preparation Example 70

A mixture of 1-(2-bromomethyl-3-bromophenyl)-4-methyl-1,4-dihydrotetrazole-5-one (described in Reference Preparation example 11) 3.1 g, 2-methyl-4-(3,4,5-trimethyl-pyrazol-1-yl)-phenol (described in Reference Preparation example 20) 1.6 g, potassium carbonate 1.3 g and acetonitrile 70 ml was stirred with heating under reflux for six hours, and the reaction mixture was then filtered and was concentrated under reduced pressure. The resulting residue was subjected to a silica gel column chromatography to give 1-{3-bromo-2-[2-methyl-4-(3,4,5-trimethyl-pyrazol-1-yl)-phenoxymethyl]-phenyl}-4-methyl-1,4-dihydrotetrazole-5-one 3.1 g.

1-{3-bromo-2-[2-methyl-4-(3,4,5-trimethyl-pyrazol-1-yl)-phenoxymethyl]-phenyl}-4-methyl-1,4-dihydrotetrazole-5-one

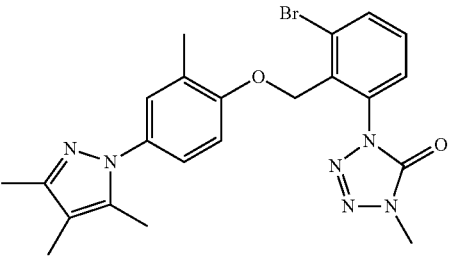 [SMILES: Cc1cc(-n2nc(C)c(C)c2C)ccc1OCc1c(Br)cccc1-n1nnn(C)c1=O]

¹H-NMR (CDCl₃) δ: 7.81 (1H, dd, J=7.7, 1.4 Hz), 7.46-7.38 (2H, m), 7.15 (1H, d, J=2.4 Hz), 7.10 (1H, dd, J=8.6, 2.5 Hz), 6.86 (1H, d, J=8.5 Hz), 5.32 (2H, s), 3.62 (3H, s), 2.23 (3H, s), 2.16 (3H, s), 2.06 (3H, s), 1.96 (3H, s).

Reference Preparation Example 71

A mixture of 1-{3-bromo-2-[2-methyl-4-(3,4,5-trimethyl-pyrazol-1-yl)-phenoxymethyl]-phenyl}-4-methyl-1,4-dihydrotetrazole-5-one (described in Reference Preparation example 70) 0.3 g, trimethylsilylacetylene 0.2 g, tetrakis triphenylphosphine palladium 0.05 g, tri-tert-butylphosphine 0.07 g, potassium phosphate 0.6 g, 1,4-dioxane 5 ml and water 0.5 ml was stirred at 100° C. for five hours. After cooling, the reaction mixture was extracted with ethyl acetate. The organic layer was washed with water and saturated saline, and was dried over anhydrous magnesium sulfate and was then concentrated under reduced pressure. The resulting residue was subjected to a silica gel column chromatography to give 1-{2-[2-methyl-4-(3,4,5-trimethyl-pyrazol-1-yl)-phenoxymethyl]-3-trimethylsilylethynyl-phenyl}-4-methyl-1,4-dihydrotetrazole-5-one 0.1 g.

1-{2-[2-methyl-4-(3,4,5-trimethyl-pyrazol-1-yl)-phenoxymethyl]-3-trimethylsilylethynyl-phenyl}-4-methyl-1,4-dihydrotetrazole-5-one

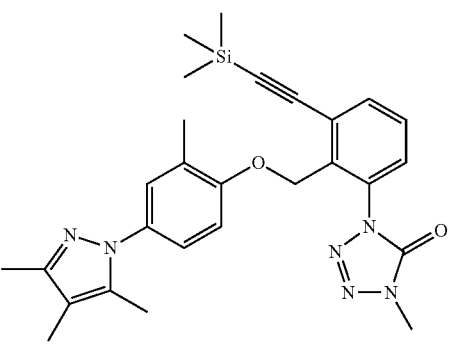 [SMILES: Cc1cc(-n2nc(C)c(C)c2C)ccc1OCc1c(C#C[Si](C)(C)C)cccc1-n1nnn(C)c1=O]

$^1$H-NMR (CDCl$_3$) δ: 7.67 (1H, dd, J=7.2, 1.9 Hz), 7.48-7.44 (2H, m), 7.13 (1H, d, J=2.5 Hz), 7.11-7.08 (1H, m), 6.92 (1H, d, J=8.5 Hz), 5.42 (2H, s), 3.64 (3H, s), 2.22 (3H, s), 2.15 (3H, s), 2.03 (3H, s), 1.96 (3H, s), 0.19 (9H, s).

Reference Preparation Example 72

A similar reaction to Reference Preparation example 33 using 2,5-dimethyl-4-methoxy-phenylboronic acid instead of 4-methoxy-3-methyl-phenylboronic acid, and using 3-methyl-1H-pyrazole instead of 3,4,5-trimethyl-1H-pyrazole gave 1-(2,5-dimethyl-4-methoxy-phenyl)-3-methyl-1H-pyrazole.

1-(2,5-dimethyl-4-methoxy-phenyl)-3-methyl-1H-pyrazole

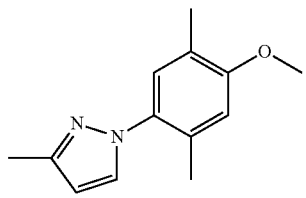

$^1$H-NMR (CDCl$_3$) δ: 7.40 (1H, d, J=2.2 Hz), 7.09 (1H, s), 6.69 (1H, s), 6.17 (1H, d, J=2.2 Hz), 3.86 (3H, s), 2.36 (3H, s), 2.18 (3H, s), 2.18 (3H, s).

Reference Preparation Example 73

A similar reaction to Reference Preparation example 20 using 1-(2,5-dimethyl-4-methoxy-phenyl)-3-methyl-1H-pyrazole (described in Reference Preparation example 72) instead of 1-(4-methoxy-3-methyl-phenyl)-3,4,5-trimethyl-1H-pyrazole gave 2,5-dimethyl-4-(3-methyl-pyrazol-1-yl)-phenol.

2,5-dimethyl-4-(3-methyl-pyrazol-1-yl)-phenol

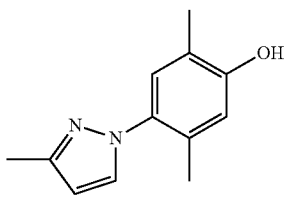

$^1$H-NMR (DMSO-D$_6$) δ: 7.74 (1H, d, J=2.2 Hz), 7.00 (1H, s), 6.70 (1H, s), 6.22 (1H, d, J=2.2 Hz), 2.23 (3H, s), 2.10 (3H, s), 2.02 (3H, s).

Reference Preparation Example 74

A similar reaction to Reference Preparation example 33 using 1-(4-methoxy-3-methyl-phenyl)-3-trifluoromethyl-1H-pyrazole instead of 3,4,5-trimethyl-1H-pyrazole gave 1-(4-methoxy-3-methyl-phenyl)-3-trifluoromethyl-1H-pyrazole.

1-(4-methoxy-3-methyl-phenyl)-3-trifluoromethyl-1H-pyrazole

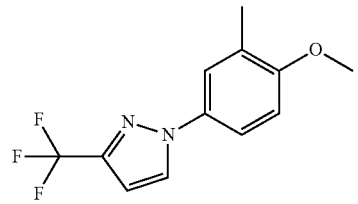 [SMILES: COc1ccc(-n2ccc(C(F)(F)F)n2)cc1C]

$^1$H-NMR (CDCl$_3$) δ: 7.83 (1H, dd, J=2.3, 0.9 Hz), 7.48 (1H, d, J=2.4 Hz), 7.43 (1H, dd, J=8.8, 2.7 Hz), 6.87 (1H, d, J=8.8 Hz), 6.68 (1H, d, J=2.4 Hz), 3.87 (3H, s), 2.28 (3H, s).

Reference Preparation Example 75

A similar reaction to Reference Preparation example 20 using 1-(4-methoxy-3-methyl-phenyl)-3-trifluoromethyl-1H-pyrazole (described in Reference Preparation example 74) instead of 1-(4-methoxy-3-methyl-phenyl)-3,4,5-trimethyl-1H-pyrazole gave 2-methyl-4-(3-trifluoromethyl-pyrazol-1-yl)-phenol.

2-methyl-4-(3-trifluoromethyl-pyrazol-1-yl)-phenol

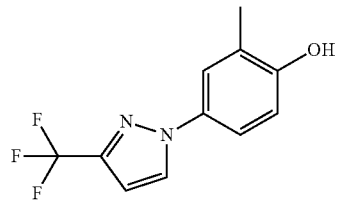

$^1$H-NMR (CDCl$_3$) δ: 7.83-7.80 (1H, m), 7.45 (1H, d, J=2.2 Hz), 7.32 (1H, dd, J=8.5, 2.4 Hz), 6.82 (1H, d, J=8.5 Hz), 6.68 (1H, d, J=2.2 Hz), 5.46 (1H, s), 2.29 (3H, s).

Reference Preparation Example 76

At room temperature, to a mixture of 1-(4-methoxy-3-methylphenyl)-ethanone (described in Reference Preparation example 48) 6.9 g and tetrahydrofuran 200 ml was added trifluoroacetic acid ethyl ester 11.9 g and 20% solution of sodium ethoxide in ethanol 28.5 g. The resulting mixture was stirred with heating under reflux for six hours. To the reaction mixture was added water, and the resulting mixture was acidified with 6N aqueous hydrochloric acid solution. The resulting mixture was extracted with ethyl acetate. The organic layer was washed with water and was dried over anhydrous magnesium sulfate, and was then concentrated under reduced pressure. The resulting residue was subjected to a silica gel column chromatography to give 4,4,4-trifluoro-1-(4-methoxy-3-methyl-phenyl)-butane-1,3-dione 10 g.

4,4,4-trifluoro-1-(4-methoxy-3-methyl-phenyl)-butane-1,3-dione

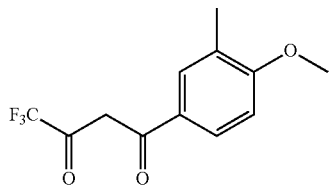 [SMILES: COc1ccc(C(=O)CC(=O)C(F)(F)F)cc1C]

¹H-NMR (CDCl₃: 23° C.) δ: 7.84 (1H, dd, J=8.7, 2.4 Hz), 7.75 (1H, dd, J=1.7, 0.7 Hz), 6.90 (1H, d, J=8.7 Hz), 6.51 (1H, s), 3.93 (3H, s), 2.27 (3H, s).

Reference Preparation Example 77

At 0° C., to a mixture of 4,4,4-trifluoro-1-(4-methoxy-3-methyl-phenyl)-butane-1,3-dione (described in Reference Preparation example 76) 6.8 g and ethanol 100 ml was added methyl hydrazine 1.7 g. The resulting mixture was raised to room temperature and was stirred for one hour. The reaction mixture was concentrated under reduced pressure and the resulting residue was subjected to a silica gel column chromatography to give 5-(4-methoxy-3-methyl-phenyl)-2-methyl-3-trifluoromethyl-3,4-dihydro-2H-pyrazol-3-ol 3.2 g and 5-(4-methoxy-3-methyl-phenyl)-1-methyl-3-trifluoromethyl-1H-pyrazole 2 g.

5-(4-methoxy-3-methyl-phenyl)-2-methyl-3-trifluoromethyl-3,4-dihydro-2H-pyrazol-3-ol

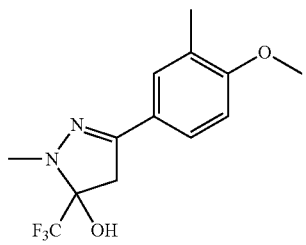

¹H-NMR (CDCl₃) δ: 7.44-7.44 (1H, m), 7.33 (1H, dd, J=8.5, 2.4 Hz), 6.79 (1H, d, J=8.5 Hz), 3.85 (3H, s), 3.50 (1H, d, J=17.6 Hz), 3.24 (1H, d, J=17.6 Hz), 3.06 (3H, s), 2.87 (1H, s), 2.22 (3H, s).

5-(4-methoxy-3-methyl-phenyl)-1-methyl-3-trifluoromethyl-1H-pyrazole

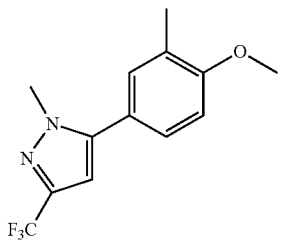 [SMILES: COc1ccc(-c2cc(C(F)(F)F)nn2C)cc1C]

¹H-NMR (CDCl₃) δ: 7.22-7.17 (2H, m), 6.91 (1H, d, J=8.5 Hz), 6.48 (1H, s), 3.90 (3H, s), 3.89 (3H, s), 2.27 (3H, s).

Reference Preparation Example 78

A mixture of 5-(4-methoxy-3-methyl-phenyl)-2-methyl-3-trifluoromethyl-3,4-dihydro-2H-pyrazol-3-ol (described in Reference preparation example 77) 2.3 g, 6N aqueous hydrochloric acid solution 4 ml and tetrahydrofuran 30 ml was stirred with heating under reflux for two hours. The reaction mixture was extracted with ethyl acetate. The organic layer was washed with saturated aqueous sodium carbonate solution and saturated saline. The organic layer was dried over anhydrous magnesium sulfate, and was then concentrated under reduced pressure. The resulting residue was subjected to a silica gel column chromatography to give 3-(4-methoxy-3-methyl-phenyl)-1-methyl-5-trifluoromethyl-1H-pyrazole 2.2 g.

3-(4-methoxy-3-methyl-phenyl)-1-methyl-5-trifluoromethyl-1H-pyrazole

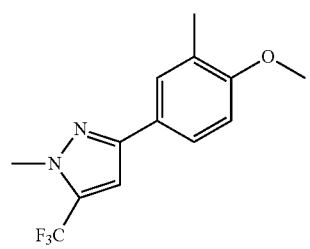

¹H-NMR (CDCl₃) δ: 7.56-7.53 (2H, m), 6.85 (1H, d, J=8.2 Hz), 6.81 (1H, s), 4.01 (3H, s), 3.86 (3H, s), 2.26 (3H, s).

Reference Preparation Example 79

A mixture of 3-(4-methoxy-3-methyl-phenyl)-1-methyl-5-trifluoromethyl-1H-pyrazole (described in Reference Preparation example 78) 0.4 g, 47% hydrobromic acid 24 ml and acetic acid 24 ml was stirred with heating under reflux for twelve hours. The solvent was distilled off and to the resulting residues was added ice water 70 ml. The precipitates were filtered and were washed with ice water 70 ml, and then were concentrated under reduced pressure to give 2-methyl-4-(1-methyl-5-trifluoromethyl-1H-pyrazol-3-yl)-phenol 2 g.

2-methyl-4-(1-methyl-5-trifluoromethyl-1H-pyrazol-3-yl)-phenol

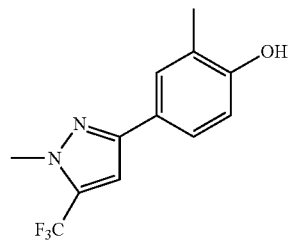 [SMILES: Cc1cc(-c2cc(C(F)(F)F)n(C)n2)ccc1O]

$^1$H-NMR (DMSO-D$_6$) δ: 9.52 (1H, s), 7.57 (1H, s), 7.47 (1H, d, J=8.2 Hz), 7.22 (1H, s), 6.80 (1H, d, J=8.5 Hz), 3.96 (3H, s), 2.15 (3H, s).

Reference Preparation Example 80

At 0° C., to a mixture of 2,5-dimethylphenol 20 g and chloroform 150 ml was added acetyl chloride 15 g and triethylamine 49 g. The resulting mixture was raised to room temperature and was stirred for four hours. Then, the reaction mixture was extracted with chloroform. The organic layer was washed with water and was dried over anhydrous magnesium sulfate, and was then concentrated under reduced pressure. The resulting residue was subjected to a silica gel column chromatography to give acetic acid 2,5-dimethylphenyl ester 24 g.

Acetic acid 2,5-dimethylphenyl ester

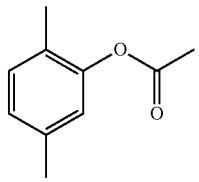

$^1$H-NMR (CDCl$_3$) δ: 7.10 (1H, d, J=7.7 Hz), 6.95 (1H, d, J=7.2 Hz), 6.82 (1H, s), 2.31 (6H, s), 2.13 (3H, s).

Reference Preparation Example 81

At room temperature, to a mixture of acetic acid 2,5-dimethylphenyl ester (described in Reference Preparation example 80) 24 g and nitromethane 200 ml was added aluminium trichloride 49 g, and the resulting mixture was heated to 50° C. The resulting mixture was stirred for eight and a half hours and thereto was added ice water 300 ml. The resulting mixture was extracted with chloroform. The organic layer was washed with water and was dried over anhydrous magnesium sulfate, and was then concentrated under reduced pressure. The resulting residue was subjected to a silica gel column chromatography to give 1-(2,5-dimetyl-4-hydroxy-phenyl)-ethanone 21 g.

1-(2,5-dimetyl-4-hydroxy-phenyl)-ethanone

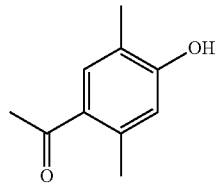

$^1$H-NMR (CDCl$_3$) δ: 7.59 (1H, s), 6.64 (1H, s), 5.56 (1H, s), 2.55 (3H, s), 2.50 (3H, s), 2.26 (3H,

Reference Preparation Example 82

A mixture of 1-(2,5-dimethyl-4-hydroxy-phenyl)-ethanone 14.6 g, methyl iodide 16.6 g, potassium carbonate 26.8 g and acetone 200 ml was stirred with heating under reflux for eight hours. The reaction mixture was cooled to room temperature and was filtered, and was then concentrated under reduced pressure. The resulting residue was subjected to a silica gel column chromatography to give 1-(4-methoxy-2,5-dimethyl-phenyl)-ethanone 15.1 g.

1-(4-methoxy-2,5-dimethyl-phenyl)-ethanone

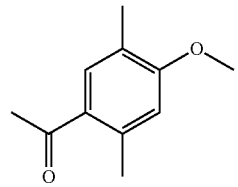

$^1$H-NMR (CDCl$_3$) δ: 7.56 (1H, s), 6.65 (1H, s), 3.87 (3H, s), 2.56 (3H, s), 2.54 (3H, s), 2.21 (3H, s).

Reference Preparation Example 83

At room temperature, to a mixture of 1-(4-methoxy-2,5-dimethylphenyl)-ethanone (described in Reference Preparation example 82) 5 g and tetrahydrofuran 200 ml was added trifluoroacetic acid ethyl ester 7.9 g and 20% sodium ethoxide solution in ethanol 19 g. The resulting mixture was stirred with heating under reflux for seven hours, and then to the reaction mixture was added water 70 ml, and the resulting mixture was acidified with 6N aqueous hydrochloric acid solution. The resulting mixture was extracted with ethyl acetate. The organic layer was washed with water and was dried over anhydrous magnesium sulfate, and was then concentrated under reduced pressure. The resulting residue was subjected to a silica gel column chromatography to give 4,4,4-trifluoro-1-(4-methoxy-2,5-dimethyl-phenyl)-butane-1,3-dione 6.8 g.

4,4,4-trifluoro-1-(4-methoxy-2,5-dimethyl-phenyl)-butane-1,3-dione

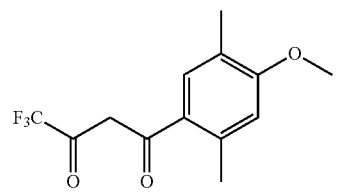 [SMILES: COc1cc(C)c(C(=O)CC(=O)C(F)(F)F)cc1C]

$^1$H-NMR (CDCl$_3$: 23° C.)) δ: 7.44 (1H, s), 6.69 (1H, s), 6.35 (1H, s), 3.89 (3H, s), 2.57 (3H, s), 2.21 (3H, s).

Reference Preparation Example 84

At 0° C., to a mixture of 4,4,4-trifluoro-1-(4-methoxy-2,5-dimethyl-phenyl)-butane-1,3-dione (described in Reference Preparation example 83) 6.8 g and ethanol 100 ml was added methyl hydrazine 1.7 g. The resulting mixture was raised to room temperature and was stirred for one hour. The reaction mixture was concentrated under reduced pressure and the resulting residue was subjected to a silica gel column chromatography to give 5-(4-methoxy-2,5-dimethyl-phenyl)-2-methyl-3-trifluoromethyl-3,4-dihydro-2H-pyrazole- 3-ol 3.2 g and 5-(4-methoxy-2,5-dimethyl-phenyl)-1-methyl-3-trifluoromethyl-1H-pyrazole 3 g.

5-(4-methoxy-2,5-dimethyl-phenyl)-2-methyl-3-trifluoromethyl-3,4-dihydro-2H-pyrazole-3-ol

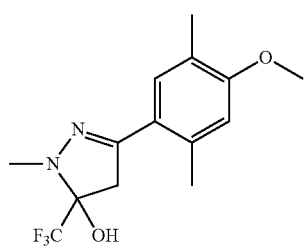

$^1$H-NMR (CDCl$_3$) δ: 7.06 (1H, s), 6.67 (1H, s), 3.84 (3H, s), 3.59 (1H, d, J=17.4 Hz), 3.27 (1H, d, J=17.4 Hz), 3.06 (3H, s), 2.78 (1H, s), 2.53 (3H, s), 2.18 (3H, s).

5-(4-methoxy-2,5-dimethyl-phenyl)-1-methyl-3-trifluoromethyl-1H-pyrazole

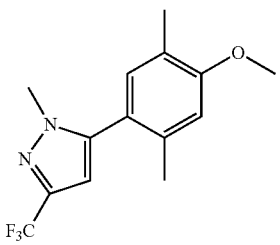 [SMILES: COc1cc(C)c(-c2cc(C(F)(F)F)nn2C)cc1C]

$^1$H-NMR (CDCl$_3$) δ: 6.96 (1H, s), 6.75 (1H, s), 6.41 (1H, s), 3.87 (3H, s), 3.69 (3H, s), 2.20 (3H, s), 2.14 (3H, s).

Reference Preparation Example 85

A mixture of 5-(4-methoxy-2,5-dimethyl-phenyl)-1-methyl-3-trifluoromethyl-1H-pyrazole (described in Reference preparation example 84) 3.2 g, 6N aqueous hydrochloric acid solution 5.3 ml and tetrahydrofuran 50 ml was stirred with heating under reflux for one hour. The reaction mixture was extracted with ethyl acetate. The organic layer was washed with saturated aqueous sodium carbonate solution and saturated saline. The organic layer was dried over anhydrous magnesium sulfate, and was then concentrated under reduced pressure. The resulting residue was subjected to a silica gel column chromatography to give 3-(4-methoxy-2,5-dimethyl-phenyl)-1-methyl-5-trifluoromethyl-1H-pyrazole 3 g.

3-(4-methoxy-2,5-dimethyl-phenyl)-1-methyl-5-trifluoromethyl-1H-pyrazole

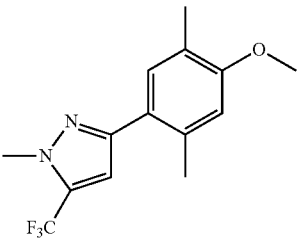

$^1$H-NMR (CDCl$_3$) δ: 7.30 (1H, s), 6.70 (1H, s), 6.69 (1H, s), 4.03 (3H, s), 3.85 (3H, s), 2.43 (3H, s), 2.21 (3H, s).

Reference Preparation Example 86

A mixture of 3-(4-methoxy-2,5-dimethyl-phenyl)-1-methyl-5-trifluoromethyl-1H-pyrazole (described in Reference Preparation example 85) 3 g, 47% hydrobromic acid 29 ml and acetic acid 29 ml was stirred with heating under reflux for twenty one hours. The solvent was distilled off and to the resulting residues was added ice water 90 ml. The precipitates were filtered and were washed with ice water 90 ml and hexane 100 ml, and then were concentrated under reduced pressure to give 2,5-dimethyl-4-(1-methyl-5-trifluoromethyl-1H-pyrazol-3-yl)-phenol 2.9 g.

2,5-dimethyl-4-(1-methyl-5-trifluoromethyl-1H-pyrazol-3-yl)-phenol

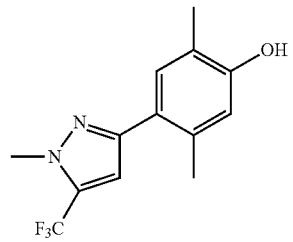 [SMILES: Cc1cc(-c2cc(C(F)(F)F)n(C)n2)c(C)cc1O]

$^1$H-NMR (DMSO-D$_6$) δ: 9.37 (1H, s), 7.26 (1H, s), 7.02 (1H, s), 6.66 (1H, s), 3.98 (3H, s), 2.32 (3H, s), 2.10 (3H, s).

Reference Preparation Example 87

At 0° C., to a mixture of 0-cresol 5.9 g and chloroform 50 ml was added cyclopropanecarbonyl chloride 6.8 g and triethylamine 16.6 g. The resulting mixture was raised to room temperature and was stirred for two hours. Then the reaction mixture was extracted with chloroform and the organic layer was washed with water and was dried over anhydrous magnesium sulfate, and was then concentrated under reduced pressure. The resulting residue was subjected to a silica gel column chromatography to give cyclopropanecarboxylic acid 2-methylphenyl ester 9.8 g.

Cyclopropanecarboxylic acid 2-methylphenyl ester

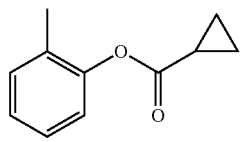

$^1$H-NMR (CDCl$_3$) δ: 7.24-7.17 (2H, m), 7.13 (1H, td, J=7.38, 1.26 Hz), 7.01 (1H, dd, J=7.67, 1.26 Hz), 2.19 (3H, s), 1.88 (1H, tt, J=8.01, 3.78 Hz), 1.21-1.16 (2H, m), 1.06-1.00 (2H, m).

Reference Preparation Example 88

At 0° C., to a mixture of nitromethane 100 ml and cyclopropanecarboxylic acid 2-methylphenyl ester (described in Reference Preparation example 87) 9.5 g was added aluminium trichloride 18 g, and the resulting mixture was then heated to 50° C. and was stirred for twelve hours. To the reaction mixture was added ice water 50 ml. The resulting mixture was extracted with ethyl acetate. The organic layer was washed with water and was dried over anhydrous magnesium sulfate, and was then concentrated under reduced pressure. The resulting residue was subjected to a silica gel column chromatography to give cyclopropyl-(4-hydroxy-3-methyl-phenyl)-ethanone 8.2 g.

Cyclopropyl-(4-hydroxy-3-methyl-phenyl)-ethanone

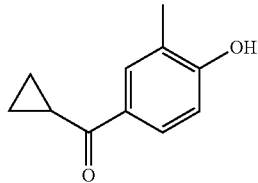

$^1$H-NMR (CDCl$_3$) δ: 7.85 (1H, d, J=2.17 Hz), 7.80 (1H, dd, J=8.45, 2.17 Hz), 6.84 (1H, d, J=8.45 Hz), 6.15 (1H, br s), 2.68-2.61 (1H, m), 2.30 (3H, s), 1.25-1.20 (2H, m), 1.04-0.98 (2H, m).

Reference Preparation Example 89

At room temperature, to a mixture of 1-(4-methoxy-3-methylphenyl)-ethanone (described in Reference Preparation example 48) and tetrahydrofuran 200 ml was added diethyl carbonate 16.1 g, 55% sodium hydride 6.2 g, dibenzo-18-crown-6 0.05 g and ethanol 3 mL, and the resulting mixture was stirred with heating under reflux for eight hours. To the reaction mixture was added water, and the resulting mixture was acidified with 10% aqueous hydrochloric acid solution and was extracted with ethyl acetate. The organic layer was washed with water and was dried over anhydrous magnesium sulfate, and was then concentrated under reduced pressure. The resulting residue was subjected to a silica gel column chromatography to give 3-(4-methoxy-3-methyl-phenyl)-3-oxo-propionic acid ethyl ester 14.8 g.

3-(4-methoxy-3-methyl-phenyl)-3-oxo-propionic acid ethyl ester

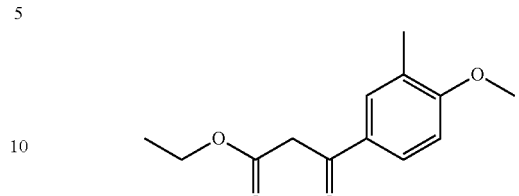

$^1$H-NMR (CDCl$_3$) δ: 7.81 (1H, dd, J=8.5, 2.4 Hz), 7.76-7.76 (1H, m), 6.86 (1H, d, J=8.5 Hz), 4.21 (2H, q, J=7.1 Hz), 3.93 (2H, s), 3.90 (3H, s), 2.24 (3H, s), 1.26 (3H, t, J=7.1 Hz).

Reference Preparation Example 90

At room temperature, to a mixture of 3-(4-methoxy-3-methyl-phenyl)-3-oxo-propionic acid ethyl ester (described in Reference Preparation example 89) 14.8 g and toluene 100 ml was added N-methyl hydrazine 29 g, and the resulting mixture was stirred for twelve hours. The toluene was distilled off. At room temperature, to the reaction mixture was added water 100 ml and the resulting mixture was acidified with 10% aqueous hydrochloric acid solution and was stirred for three hours. The precipitates were filtered and were washed with water 400 ml and ethyl acetate 500 ml, and then were dried under reduced pressure to give 5-hydroxy-3-(4-methoxy-3-methyl-phenyl)-1-methyl-1H-pyrazole 9.3 g.

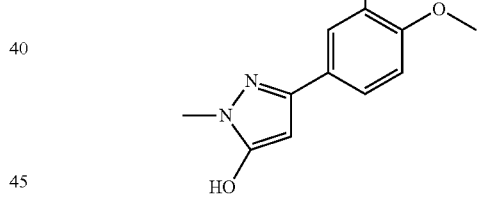

$^1$H-NMR (DMSO-D$_6$) δ: 7.58-7.56 (2H, m), 6.97 (1H, d, J=8.9 Hz), 5.90 (1H, s), 3.81 (3H, s), 3.60 (3H, 2.18 (3H, s).

Reference Preparation Example 91

At 0° C., to phosphorus oxychloride 56 g was added N,N-dimethylformamide 4.0 g and the resulting mixture was stirred for a half hour. Thereto was added 5-hydroxy-3-(4-methoxy-3-methyl-phenyl)-1-methyl-1H-pyrazole (described in Reference preparation example 90) 9.3 g. The resulting mixture was stirred for seven hours and the reaction solvent was distilled off under reduced pressure. To the reaction mixture was added ice water 100 ml and the resulting mixture was extracted with ethyl acetate. The organic layer was washed with water and was dried over anhydrous magnesium sulfate, and was then concentrated under reduced pressure. The resulting residue was subjected to a silica gel column chromatography to give 5-chloro-4-formyl-3-(4-methoxy-3-methyl-phenyl)-1-methyl-1H-pyrazole 6.3 g.

5-chloro-4-formyl-3-(4-methoxy-3-methyl-phenyl)-1-methyl-1H-pyrazole

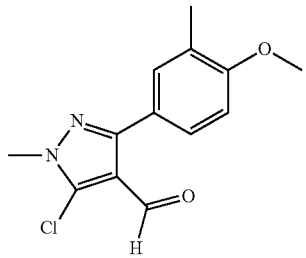

$^1$H-NMR (CDCl$_3$) δ: 9.93 (1H, s), 7.55 (1H, dd, J=8.5, 2.2 Hz), 7.51 (1H, s), 6.90 (1H, d, J=8.5 Hz), 3.92 (3H, s), 3.88 (3H, s), 2.27 (3H, s).

Reference Preparation Example 92

At 0° C., a mixture of 5-chloro-4-formyl-3-(4-methoxy-3-methyl-phenyl)-1-methyl-1H-pyrazole (described in Reference Preparation example 91) 0.3 g and trifluoroacetic acid 10 ml was added trimethylsilane 0.27 g. The resulting mixture was stirred at room temperature for three hours, and thereto was added water 5 ml. The resulting mixture was extracted with ethyl acetate. The organic layer was washed with water and was dried over anhydrous magnesium sulfate, and was then concentrated under reduced pressure. The resulting residue was subjected to a silica gel column chromatography to give 5-chloro-3-(4-methoxy-3-methyl-phenyl)-1,4-dimethyl-1H-pyrazole 0.28 g.

5-chloro-3-(4-methoxy-3-methyl-phenyl)-1,4-dimethyl-1H-pyrazole

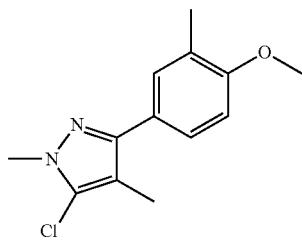

$^1$H-NMR (DMSO-D$_6$) δ: 7.42-7.40 (2H, m), 6.98 (1H, d, J=9.2 Hz), 3.81 (3H, s), 3.80 (3H, s), 2.19 (3H, s), 2.11 (3H, s).

Reference Preparation Example 93

A mixture of 1-(4-hydroxy-3-methyl-phenyl)-ethanone 10 g, isopropyl iodide 13.6 g, potassium carbonate 18.4 g and acetone 250 ml was stirred with heating under reflux for twelve hours. The reaction mixture was filtered and the resulting filtrate was concentrated under reduced pressure, and the resulting residue was subjected to a silica gel column chromatography to give 1-(4-isopropoxy-3-methyl-phenyl)-ethanone 9.5 g.

1-(4-isopropoxy-3-methyl-phenyl)-ethanone

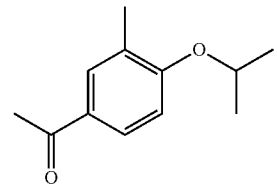

$^1$H-NMR (CDCl$_3$) δ: 7.80-7.78 (2H, m), 6.84 (1H, d, J=8.2 Hz), 4.69-4.60 (1H, m), 2.54 (3H, s), 2.23 (3H, s), 1.37 (6H, d, J=6.0 Hz).

Reference Preparation Example 94

At room temperature, to a mixture of 1-(4-isopropoxy-3-methyl-phenyl)-ethanone (described in Reference Preparation example 93) 9.4 g and tetrahydrofuran 150 ml was added diethyl carbonate 11.6 g, 55% sodium hydride 4.5 g, dibenzo-18-crown-6 0.04 g and ethanol 3 mL, and the resulting mixture was stirred with heating under reflux for nine hours. To the reaction mixture was added water, and the resulting mixture was acidified with 10% aqueous hydrochloric acid solution and was extracted with ethyl acetate. The organic layer was washed with water and was dried over anhydrous magnesium sulfate, and was then concentrated under reduced pressure. The resulting residue was subjected to a silica gel column chromatography to give 3-(4-isopropoxy-3-methyl-phenyl)-3-oxo-propionic acid ethyl ester 12.1 g.

3-(4-isopropoxy-3-methyl-phenyl)-3-oxo-propionic acid ethyl ester

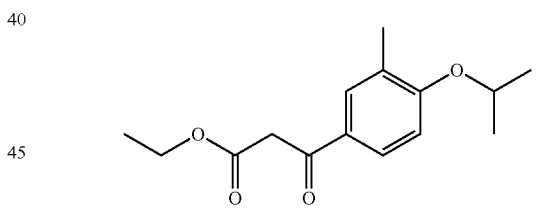

$^1$H-NMR (CDCl$_3$) δ: 7.79-7.76 (2H, m), 6.85-6.83 (1H, m), 4.68-4.62 (1H, m), 4.21 (2H, q, J=7.2 Hz), 3.93 (2H, s), 2.22 (3H, s), 1.37 (6H, d, J=6.0 Hz), 1.26 (3H, t, J=7.1 Hz).

Reference Preparation Example 95

At room temperature, to a mixture of 3-(4-isopropoxy-3-methyl-phenyl)-3-oxo-propionic acid ethyl ester (described in Reference Preparation example 94) 12.1 g and toluene 100 ml was added N-methyl hydrazine 21 g, and the resulting mixture was stirred for twelve hours. The toluene was distilled off under reduced pressure. At room temperature, to the reaction mixture was added water 100 ml and the resulting mixture was acidified with 10% aqueous hydrochloric acid solution and was stirred for three hours. The precipitates were filtered and were washed with water 400 ml and ethyl acetate 500 ml, and then were dried under reduced pressure to give 5-hydroxy-3-(4-isopropoxy-3-methyl-phenyl)-1-methyl-1H-pyrazole 9.5 g.

5-hydroxy-3-(4-isopropoxy-3-methyl-phenyl)-1-methyl-1H-pyrazole

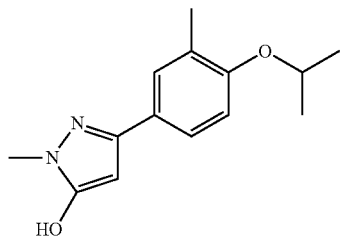 [SMILES: Cc1cc(-c2cc(O)n(C)n2)ccc1OC(C)C]

¹H-NMR (DMSO-D$_6$) δ: 7.58-7.54 (2H, m), 7.01-6.98 (1H, m), 5.95 (1H, s), 4.66-4.60 (1H, m), 3.62 (3H, s), 2.16 (3H, s), 1.28 (6H, d, J=5.1 Hz).

Reference Preparation Example 96

At 0° C., to phosphorus oxychloride 43 g was added N,N-dimethylformamide 3.2 g and the resulting mixture was stirred for a half hour. Thereto was added 5-hydroxy-3-(4-isopropoxy-3-methyl-phenyl)-1-methyl-1H-pyrazole (described in Reference preparation example 95) 8.3 g. The resulting mixture was stirred at 100° C. for ten hours and the reaction solvent was distilled off under reduced pressure. To the reaction mixture was added ice water 100 ml and the resulting mixture was extracted with ethyl acetate. The organic layer was washed with water and were dried over anhydrous magnesium sulfate, and was then concentrated under reduced pressure. The resulting residue was subjected to a silica gel column chromatography to give 5-chloro-4-formyl-3-(4-isopropoxy-3-methyl-phenyl)-1-methyl-1H-pyrazole 5.1 g and 2-methyl-4-(5-chloro-4-formyl-1-methyl-1H-pyrazol-3-yl)-phenol 0.6 g.

5-chloro-4-formyl-3-(4-isopropoxy-3-methyl-phenyl)-1-methyl-1H-pyrazole

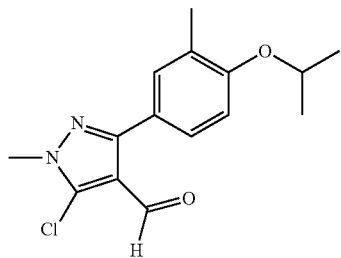 [SMILES: Cc1cc(-c2nn(C)c(Cl)c2C=O)ccc1OC(C)C]

¹H-NMR (CDCl$_3$) δ: 9.93 (1H, s), 7.52-7.50 (2H, m), 6.91-6.89 (1H, m), 4.63-4.54 (1H, m), 3.92 (3H, s), 2.25 (3H, s), 1.36 (6H, d, J=6.0 Hz).

2-methyl-4-(5-chloro-4-formyl-1-methyl-1H-pyrazol-3-yl)-phenol

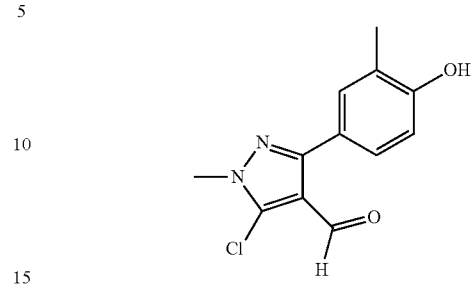

¹H-NMR (CDCl$_3$) δ: 9.92 (1H, s), 7.52-7.51 (1H, m), 7.47 (1H, dd, J=8.2, 2.3 Hz), 6.85 (1H, d, J=8.2 Hz), 4.95 (1H, s), 3.93 (3H, s), 2.30 (3H, s).

Reference Preparation Example 97

At room temperature, to a mixture of 5-chloro-4-formyl-3-(4-isopropoxy-3-methyl-phenyl)-1-methyl-1H-pyrazole (described in Reference Preparation example 96) 4.8 g and tetrahydrofuran 100 ml was added methanol 0.6 g and 55% sodium hydride 0.8 g, and the resulting mixture was stirred for three hours. To the reaction mixture was added water 50 ml, and the resulting mixture was extracted with ethyl acetate. The organic layer was washed with water and was dried over anhydrous magnesium sulfate, and was then concentrated under reduced pressure. The resulting residue was subjected to a silica gel column chromatography to give 4-formyl-3-(4-isopropoxy-3-methyl-phenyl)-5-methoxy-1-methyl-1H-pyrazole 4.5 g.

4-formyl-3-(4-isopropoxy-3-methyl-phenyl)-5-methoxy-1-methyl-1H-pyrazole

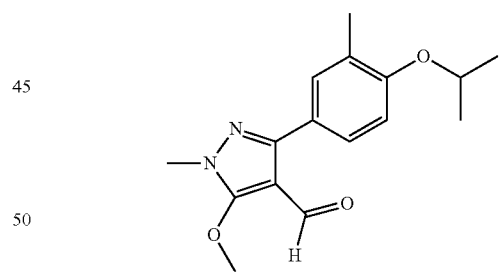

¹H-NMR (CDCl$_3$) δ: 9.75 (1H, s), 7.39 (1H, d, J=1.9 Hz), 7.35 (1H, dd, J=8.3, 2.3 Hz), 6.90 (1H, d, J=8.5 Hz), 4.63-4.54 (1H, m), 4.30 (3H, s), 3.71 (3H, s), 2.24 (3H, s), 1.36 (6H, d, J=6.0 Hz).

Reference Preparation Example 98

At 0° C., a mixture of 4-formyl-3-(4-isopropoxy-3-methyl-phenyl)-5-methoxy-1-methyl-1H-pyrazole (described in Reference Preparation example 97) 4.2 g and trifluoroacetic acid 20 ml was added trimethylsilane 4.2 g. The resulting mixture was stirred at room temperature for six hours, and the solvent was distilled off under reduced pressure, and thereto was added water 10 ml. The resulting mixture was extracted with ethyl acetate. The organic layer was washed with water and was dried over anhydrous magnesium sulfate, and was then concentrated under reduced pressure. The resulting residue was subjected to a silica gel column chromatography to give 1,4-dimethyl-3-(4-isopropoxy-3-methyl-phenyl)-5-methoxy-1H-pyrazole 3.8 g.

1,4-dimethyl-3-(4-isopropoxy-3-methyl-phenyl)-5-methoxy-1H-pyrazole

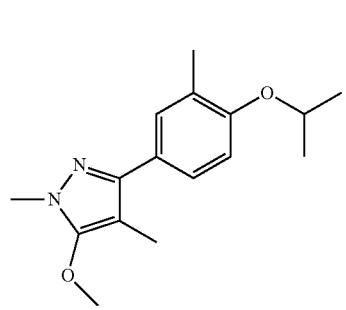

$^1$H-NMR (CDCl$_3$) δ: 7.43 (1H, dd, J=2.1, 0.7 Hz), 7.37-7.34 (1H, m), 6.86 (1H, d, J=8.5 Hz), 4.57-4.51 (1H, m), 3.93 (3H, s), 3.71 (3H, s), 2.24 (3H, s), 2.14 (3H, s), 1.35 (6H, d, J=6.0 Hz).

Reference Preparation Example 99

A mixture of 1,4-dimethyl-3-(4-isopropoxy-3-methyl-phenyl)-5-methoxy-1H-pyrazole (described in Reference Preparation example 98) 7.4 g and 30% aqueous sulfurinc acid solution 100 ml was stirred with heating under reflux for fifteen hours. Next, the following work-up treatments was carried out. The reaction mixture was cooled to 0° C., and the resulting precipitates were filtered and were washed with cool water to give some solids. Again, the filtrate were concentrated under reduced pressure to about a half volume and were cooled to 0° C., and the resulting precipitates were filtered and were washed with cool water to give some solids. These work-up treatments were carried out four times and the resulting all solids were dried under reduced pressure to give 4-(1,4-dimethyl-5-methoxy-1H-pyrazol-3-yl)-2-methyl-phenol 6.4 g.

4-(1,4-dimethyl-5-methoxy-1H-pyrazol-3-yl)-2-methyl-phenol

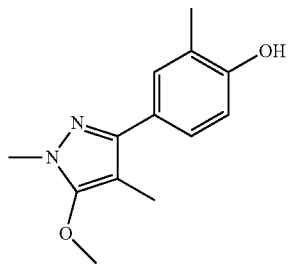 [SMILES: COc1c(C)c(-c2ccc(O)c(C)c2)nn1C]

$^1$H-NMR (DMSO-D$_6$) δ: 9.33 (1H, s), 7.29 (1H, s), 7.20 (1H, d, J=8.2 Hz), 6.79 (1H, d, J=8.2 Hz), 3.87 (3H, s), 3.60 (3H, s), 2.14 (3H, s), 2.04 (3H, s).

Reference Preparation Example 100

A similar reaction to Reference Preparation example 97 using ethanol instead of methanol gave 5-ethoxy-4-formyl-3-(4-isopropoxy-3-methyl-phenyl)-1-methyl-1H-pyrazole.

5-ethoxy-4-formyl-3-(4-isopropoxy-3-methyl-phenyl)-1-methyl-1H-pyrazole

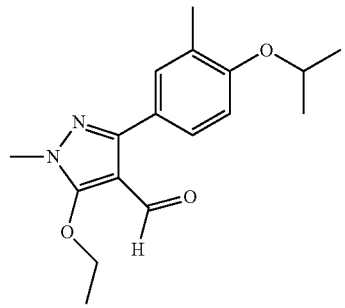 [SMILES: CCOc1c(C=O)c(-c2ccc(OC(C)C)c(C)c2)nn1C]

$^1$H-NMR (CDCl$_3$) δ: 9.74 (1H, s), 7.39 (1H, d, J=1.8 Hz), 7.35 (1H, dd, J=8.2, 2.3 Hz), 6.89 (1H, d, J=8.5 Hz), 4.63 (2H, q, J=7.1 Hz), 4.61-4.55 (1H, m), 3.72 (3H, s), 2.24 (3H, s), 1.44 (3H, t, J=7.1 Hz), 1.36 (6H, d, J=6.0 Hz).

Reference Preparation Example 101

A similar reaction to Reference Preparation example 97 using 5-ethoxy-4-formyl-3-(4-isopropoxy-3-methyl-phenyl)-1-methyl-1H-pyrazole (described in Reference Preparation example 100) instead of 4-formyl-3-(4-isopropoxy-3-methyl-phenyl)-5-methoxy-1-methyl-1H-pyrazole gave 1,4-dimethyl-5-ethoxy-3-(4-isopropoxy-3-methyl-phenyl)-1H-pyrazole.

1,4-dimethyl-5-ethoxy-3-(4-isopropoxy-3-methyl-phenyl)-1H-pyrazole

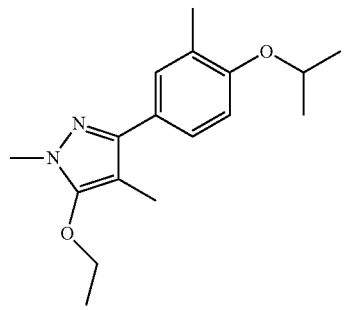 [SMILES: CCOc1c(C)c(-c2ccc(OC(C)C)c(C)c2)nn1C]

$^1$H-NMR (CDCl$_3$) δ: 7.43 (1H, d, J=1.6 Hz), 7.38-7.35 (1H, m), 6.86 (1H, d, J=8.5 Hz), 4.57-4.51 (1H, m), 4.14 (2H, q, J=7.0 Hz), 3.71 (3H, s), 2.24 (3H, s), 2.12 (3H, s), 1.41 (3H, t, J=7.0 Hz), 1.35 (6H, d, J=6.0 Hz).

Reference Preparation Example 102

A similar reaction to Reference Preparation example 99 using 1,4-dimethyl-5-ethoxy-3-(4-isopropoxy-3-methyl-phenyl)-1H-pyrazole (described in Reference Preparation example 101) instead of 1,4-dimethyl-3-(4-isopropoxy-3-methyl-phenyl)-5-methoxy-1H-pyrazole gave 4-(1,4-dimethyl-5-ethoxy-1H-pyrazol-3-yl)-2-methyl-phenol.

4-(1,4-dimethyl-5-ethoxy-1H-pyrazol-3-yl)-2-methyl-phenol

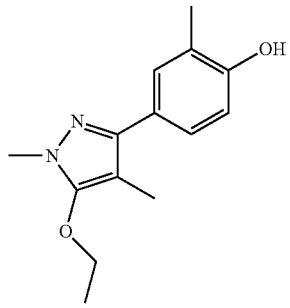 [SMILES: CCOc1c(C)c(-c2ccc(O)c(C)c2)nn1C]

¹H-NMR (DMSO-D₆) δ: 7.32 (1H, d, J=1.4 Hz), 7.23 (1H, dd, J=8.2, 2.3 Hz), 6.84 (1H, d, J=8.2 Hz), 4.18 (2H, q, J=7.0 Hz), 3.65 (3H, s), 2.15 (3H, s), 2.06 (3H, s), 1.34 (3H, t, J=7.0 Hz).

Reference Preparation Example 103

At room temperature, to a mixture of 5-chloro-4-formyl-3-(4-isopropoxy-3-methyl-phenyl)-1-methyl-1H-pyrazole (described in Reference Preparation example 96) 10 g and tetrahydrofuran 100 ml was added sodium thiomethoxide 2.9 g and the resulting mixture was stirred for eight hours. To the reaction mixture was added water 50 mL and the resulting mixture was extracted with ethyl acetate. The organic layer was washed with water and was dried over anhydrous magnesium sulfate, and was then concentrated under reduced pressure. The resulting residue was subjected to a silica gel column chromatography to give 4-formyl-3-(4-isopropoxy-3-methyl-phenyl)-5-methylthio-1H-pyrazole 10.4 g.

4-formyl-3-(4-isopropoxy-3-methyl-phenyl)-5-methylthio-1H-pyrazole

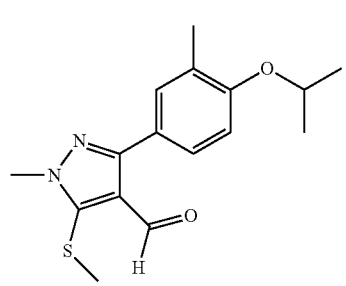 [SMILES: CSc1c(C=O)c(-c2ccc(OC(C)C)c(C)c2)nn1C]

¹H-NMR (CDCl₃) δ: 10.02 (1H, s), 7.50-7.48 (2H, m), 6.91-6.89 (1H, m), 4.62-4.56 (1H, m), 4.02 (3H, s), 2.54 (3H, s), 2.25 (3H, s), 1.36 (6H, d, J=6.0 Hz).

Reference Preparation Example 104

A similar reaction to Reference Preparation example 98 using 4-formyl-3-(4-isopropoxy-3-methyl-phenyl)-5-methylthio-1H-pyrazole (described in Reference Preparation example 103) instead of 4-formyl-3-(4-isopropoxy-3-methyl-phenyl)-5-methoxy-1-methyl-1H-pyrazole gave 1,4-dimethyl-3-(4-isopropoxy-3-methyl-phenyl)-5-methylthio-1H-pyrazole.

1,4-dimethyl-3-(4-isopropoxy-3-methyl-phenyl)-5-methylthio-1H-pyrazole

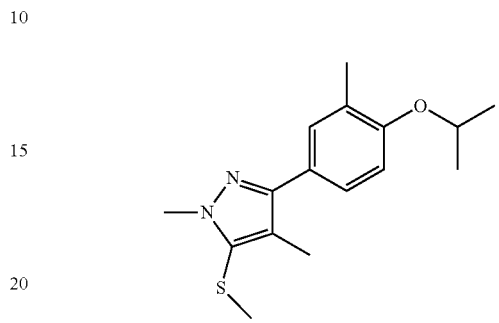

¹H-NMR (CDCl₃) δ: 7.45 (1H, dd, J=2.2, 0.6 Hz), 7.39 (1H, dd, J=8.5, 2.3 Hz), 6.87 (1H, d, J=8.5 Hz), 4.58-4.52 (1H, m), 3.99 (3H, s), 2.27 (3H, s), 2.26 (3H, s), 2.24 (3H, s), 1.35 (6H, d, J=6.2 Hz).

Reference Preparation Example 105

A mixture of 1,4-dimethyl-3-(4-isopropoxy-3-methyl-phenyl)-5-methylthio-1H-pyrazole (described in Reference Preparation example 104) 8.9 g and 30% aqueous sulfuric acid solution 120 ml was stirred with heating under reflux for twenty hours. The reaction mixture was cooled to 0° C. and thereto was added ice water 50 ml. The resulting precipitates were filtered and were washed with cool water and hexane, and were concentrated under reduced pressure to give 4-(1,4-dimethyl-5-methylthio-1H-pyrazol-3-yl)-2-methyl-phenol 7.3 g.

4-(1,4-dimethyl-5-methylthio-1H-pyrazol-3-yl)-2-methyl-phenol

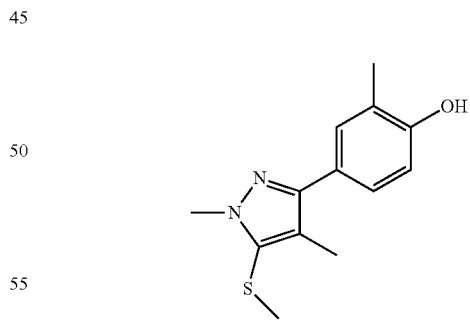

¹H-NMR (CDCl₃) δ: 7.44 (1H, d, J=1.6 Hz), 7.33 (1H, dd, J=8.3, 2.2 Hz), 6.80 (1H, d, J=8.2 Hz), 3.99 (3H, s), 2.28 (3H, s), 2.27 (3H, s), 2.26 (3H, s).

Reference Preparation Example 106

At room temperature, to a mixture of 3-butyl-pentane-2,4-dione 7 g and ethanol 70 ml was added hydrazine one hydrate 3.3 g and the resulting mixture was stirred for twelve hours. The reaction mixture was subjected to a silica gel column chromatography to give 4-butyl-3,5-dimethyl-1H-pyrazole 7 g.

4-butyl-3,5-dimethyl-1H-pyrazole

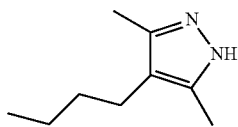

¹H-NMR (CDCl₃) δ: 2.33 (2H, t, J=7.5 Hz), 2.20 (3H, s), 2.20 (3H, s), 1.46-1.37 (2H, m), 1.36-1.27 (2H, m), 0.91 (3H, t, J=7.2 Hz).

Reference Preparation Example 107

A similar reaction to Reference Preparation example 33 using 4-butyl-3,5-dimethyl-1H-pyrazole (described in Reference Preparation example 106) instead of 3,4,5-trimethyl-1H-pyrazole gave 4-butyl-1-(4-methoxy-3-methyl-phenyl)-3,5-dimethyl-1H-pyrazole.

4-butyl-1-(4-methoxy-3-methyl-phenyl)-3,5-dimethyl-1H-pyrazole

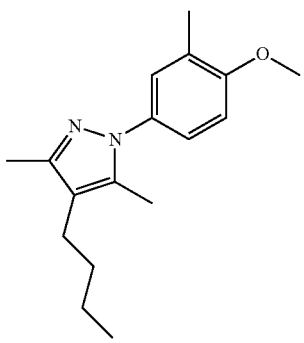

¹H-NMR (CDCl₃) δ: 7.19 (1H, d, J=2.4 Hz), 7.15 (1H, dd, J=8.7, 2.7 Hz), 6.84 (1H, d, J=8.7 Hz), 3.86 (3H, s), 2.38 (2H, t, J=7.5 Hz), 2.25 (3H, s), 2.24 (3H, s), 2.16 (3H, s), 1.50-1.43 (2H, m), 1.36 (2H, td, J=14.6, 7.3 Hz), 0.94 (3H, t, J=7.1 Hz).

Reference Preparation Example 108

A similar reaction to Reference Preparation example 29 using 4-butyl-1-(4-methoxy-3-methyl-phenyl)-3,5-dimethyl-1H-pyrazole (described in Reference Preparation example 107) instead of 3-(4-methoxy-3-methyl-phenyl)-1-methyl-1H-pyrazole gave 4-(4-butyl-3,5-dimethyl-pyrazol-1-yl)-2-methyl-phenol.

4-(4-butyl-3,5-dimethyl-pyrazol-1-yl)-2-methyl-phenol

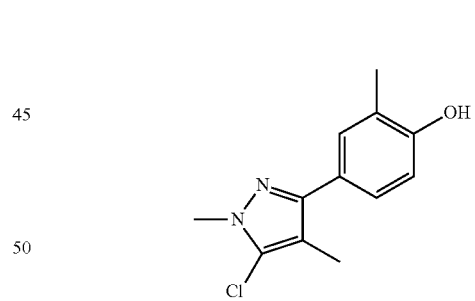

¹H-NMR (DMSO-D₆) δ: 7.18 (1H, d, J=2.7 Hz), 7.09 (1H, dd, J=8.7, 2.7 Hz), 6.86 (1H, d, J=8.5 Hz), 2.37 (2H, t, J=7.2 Hz), 2.17 (3H, s), 2.16 (3H, s), 2.14 (3H, s), 1.45-1.37 (2H, m), 1.36-1.27 (2H, m), 0.91 (3H, t, J=7.2 Hz).

Reference Preparation Example 109

A mixture of 5-chloro-3-(4-methoxy-3-methyl-phenyl)-1,4-dimethyl-1H-pyrazole (described in Reference Preparation example 92) 0.4 g, 47% hydrobromic acid 3 ml and acetic acid 3 ml was stirred with heating under reflux for fifteen hours. The solvent was distilled off and to the resulting residues was added ethyl acetate 20 ml, and the resulting mixture was stirred at room temperature for one hour. The precipitates were filtered and were washed with hexane, and were concentrated under reduced pressure to give 4-(5-chloro-1,4-dimethyl-1H-pyrazol-3-yl)-2-methyl-phenol 0.3 g.

4-(5-chloro-1,4-dimethyl-1H-pyrazol-3-yl)-2-methyl-phenol

¹H-NMR (DMSO-D₆) δ: 7.33 (1H, s), 7.24 (1H, d, J=8.2 Hz), 6.83 (1H, d, J=8.2 Hz), 3.78 (3H, s), 2.15 (3H, 2.09 (3H,

Reference Preparation Example 110

At room temperature, to mixture of 5-hydroxy-3-(4-isopropoxy-3-methyl-phenyl)-1-methyl-1H-pyrazole (described in Reference Preparation example 95) 9.5 g, and N,N-dimethylformamide 70 ml was added 55%-sodium hydride 2.5 g and was stirred for one hour, and thereto was then added dimethyl sulfate 9.7 g and stirred at 100° C. for 12 hours. Thereto was added water 50 ml and the resulting mixture was extracted with ethyl acetate. The organic layer was washed with water, and was dried over anhydrous magnesium sulfate and was then concentrated under reduced pressure. The resulting residue was subjected to a silica gel column chromatography to give 3-(4-isopropoxy-3-methyl-phenyl)-5-methoxy-1-methyl-1H-pyrazole 5.8 g.

3-(4-isopropoxy-3-methyl-phenyl)-5-methoxy-1-methyl-1H-pyrazole

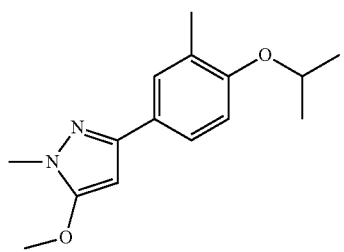 [SMILES: COc1cc(-c2ccc(OC(C)C)c(C)c2)nn1C]

$^1$H-NMR (CDCl$_3$) δ: 7.55 (1H, dd, J=2.3, 0.7 Hz), 7.49-7.47 (1H, m), 6.84 (1H, d, J=8.5 Hz), 5.75 (1H, s), 4.56-4.50 (1H, m), 3.92 (3H, s), 3.66 (3H, s), 2.23 (3H, s), 1.35 (3H, s), 1.33 (3H, s).

Reference Preparation Example 111

At room temperature, a mixture of 3-(4-isopropoxy-3-methyl-phenyl)-5-methoxy-1-methyl-1H-pyrazole (described in Reference Preparation example 110) 5.8 g, N-chlorosuccinimide 3.3 g and chloroform 70 ml was stirred for 14 hours. Thereto was added water 50 ml and the resulting mixture was extracted with chloroform. The organic layer was washed with water, and was dried over anhydrous magnesium sulfate and was then concentrated under reduced pressure. The resulting residue was subjected to a silica gel column chromatography to give 4-Chloro-3-(4-isopropoxy-3-methyl-phenyl)-5-methoxy-1-methyl-1H-pyrazole 5.6 g.

4-Chloro-3-(4-isopropoxy-3-methyl-phenyl)-5-methoxy-1-methyl-1H-pyrazole

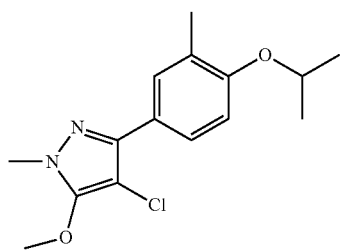 [SMILES: COc1c(Cl)c(-c2ccc(OC(C)C)c(C)c2)nn1C]

$^1$H-NMR (CDCl$_3$) δ: 7.62-7.59 (2H, m), 6.87 (1H, d, J=9.1 Hz), 4.59-4.53 (1H, m), 4.11 (3H, s), 3.70 (3H, s), 2.24 (3H, s), 1.36 (3H, s), 1.34 (3H, s).

Reference Preparation Example 112

A mixture of 4-chloro-3-(4-isopropoxy-3-methyl-phenyl)-5-methoxy-1-methyl-1H-pyrazole (described in Reference Preparation example 111) 5.6 g and 30% aqueous sulfuric acid solution 60 ml was stirred with heating under reflux for 20 hours. Thereto was added ice water 10 ml and the resulting mixture was extracted with ethyl acetate. The organic layer was washed with water, and was dried over anhydrous magnesium sulfate and was then concentrated under reduced pressure. The resulting residue was subjected to a silica gel column chromatography to give 4-(4-Chloro-5-methoxy-1-methyl-1H-pyrazol-3-yl)-2-methyl-phenol 1.2 g.

4-(4-Chloro-5-methoxy-1-methyl-1H-pyrazol-3-yl)-2-methyl-phenol

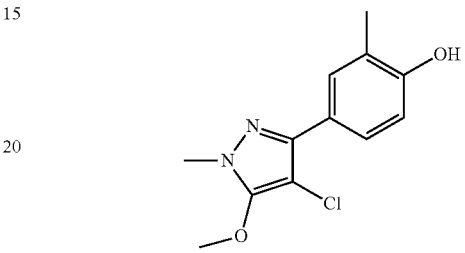

$^1$H-NMR (CDCl$_3$) δ: 7.59 (1H, d, J=2.0 Hz), 7.55 (1H, dd, J=8.4, 2.0 Hz), 6.80 (1H, d, J=8.5 Hz), 5.06 (1H, s), 4.11 (3H, s), 3.70 (3H, s), 2.28 (3H, s).

Reference Preparation Example 113

At 0° C., to a mixture of o-cresol 10 g and chloroform 100 ml was added propionyl chloride 10 g and triethylamine 28 g. The resulting mixture was raised to room temperature and was stirred for two hours. Then the reaction mixture was extracted with chloroform and the organic layer was washed with water and was dried over anhydrous magnesium sulfate, and was then concentrated under reduced pressure. The resulting residue was subjected to a silica gel column chromatography to give propionic acid o-tolyl ester 14 g.

Propionic Acid O-Tolyl Ester

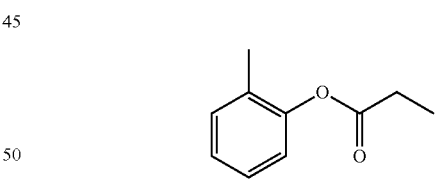

$^1$H-NMR (CDCl$_3$) δ: 7.24-7.18 (2H, m), 7.15-7.11 (1H, m), 7.01-6.99 (1H, m), 2.61 (2H, q, J=7.6 Hz), 2.17 (3H, s), 1.29 (3H, t, J=7.6 Hz).

Reference Preparation Example 114

At 0° C., to a mixture of nitromethane 150 ml and propionic acid o-tolyl ester (described in Reference Preparation example 113) 14 g was added aluminum trichloride 30 g. The resulting mixture was heated to 50° C. and was stirred for twelve hours. To the reaction mixture was added ice water 200 ml and the resulting mixture was extracted with ethyl acetate. The organic layer was washed with water and was dried over anhydrous magnesium sulfate, and was then concentrated under reduced pressure. The resulting residue was subjected to a silica gel column chromatography to give 1-(4-hydroxy-3-methyl-phenyl)-propane-1-one 8.8 g.

1-(4-hydroxy-3-methyl-phenyl)-propane-1-one

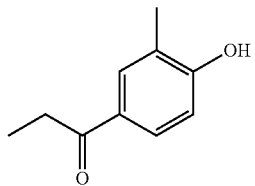

$^1$H-NMR (CDCl$_3$) δ: 7.80 (1H, d, J=1.9 Hz), 7.75 (1H, dd, J=8.5, 2.2 Hz), 6.86 (1H, d, J=8.5 Hz), 6.65 (1H, s), 2.96 (2H, q, J=7.2 Hz), 2.30 (3H, s), 1.22 (3H, td, J=7.3, 1.3 Hz).

Reference Preparation Example 115

At 0° C., to a mixture of 1-[3-cyclopropyl-2-(2-methyl-4-propionyl-phenoxymethyl)-phenyl]-4-methyl-1,4-dihydro-tetrazol-5-one (Present compound 47) 7 g, ethyl oxalate 5.2 g and N,N-dimethylformamide 150 ml was added potassium tert-butoxide 4 g and the resulting mixture was stirred for three hours. To the reaction mixture was added water, and was acidified with 10% hydrochloric acid solution and was extracted with ethyl acetate. The organic layer was washed with water and was dried over anhydrous magnesium sulfate, and was then concentrated under reduced pressure. The resulting residue was subjected to a silica gel column chromatography to give 4-{4-[2-Cyclopropyl-6-(4-methyl-5-oxo-4,5-dihydro-tetrazol-1-yl)-benzyloxy]-3-methyl-phenyl}-3-methyl-2,4-dioxo-butyric acid ethyl ester 5.5 g.

4-{4-[2-Cyclopropyl-6-(4-methyl-5-oxo-4,5-dihydro-tetrazol-1-yl)-benzyloxy]-3-methyl-phenyl}-3-methyl-2,4-dioxo-butyric acid ethyl ester

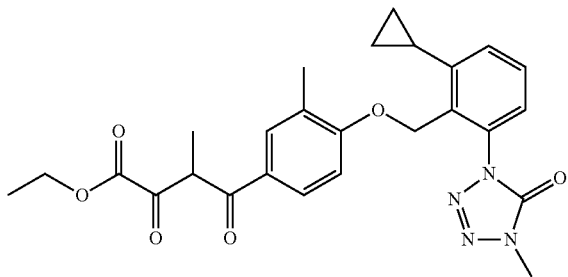 [SMILES: CCOC(=O)C(=O)C(C)C(=O)c1ccc(OCc2c(C3CC3)cccc2-n2nnn(C)c2=O)c(C)c1]

$^1$H-NMR (CDCl$_3$) δ: 7.84 (1H, dd, J=8.6, 2.2 Hz), 7.77-7.77 (1H, m), 7.46 (1H, t, J=7.9 Hz), 7.29 (2H, d, J=8.0 Hz), 6.97 (1H, d, J=8.5 Hz), 5.35 (2H, s), 5.01 (1H, q, J=7.1 Hz), 4.27 (2H, q, J=7.2 Hz), 3.62 (3H, s), 2.12-2.07 (4H, m), 1.45 (3H, d, J=7.1 Hz), 1.31 (3H, t, J=7.1 Hz), 1.03-0.98 (2H, m), 0.80-0.76 (2H, m).

Reference Preparation Example 116

At room temperature, the mixture of 5-{4-[2-Cyclopropyl-6-(4-methyl-5-oxo-4,5-dihydro-tetrazol-1-yl)-benzyloxy]-3-methyl-phenyl}-2,4-dimethyl-2H-pyrazole-3-carboxylic acid ethyl ester (Present compound 48) 1.4 g, tetrahydrofuran 40 ml, methanol 10 ml, water 10 ml and lithium hydroxide 0.2 g was stirred for twelve hours. The resulting mixture was concentrated under reduced pressure and was acidified with 10% hydrochloric acid solution and the mixture was extracted with ethyl acetate. The organic layer was washed with water and was dried over anhydrous magnesium sulfate, and was then concentrated under reduced pressure to give 5-{4-[2-Cyclopropyl-6-(4-methyl-5-oxo-4,5-dihydro-tetrazol-1-yl)-benzyloxy]-3-methyl-phenyl}-2,4-dimethyl-2H-pyrazole-3-carboxylic acid 1.3 g.

5-{4-[2-Cyclopropyl-6-(4-methyl-5-oxo-4,5-dihydro-tetrazol-1-yl)-benzyloxy]-3-methyl-phenyl}-2,4-dimethyl-2H-pyrazole-3-carboxylic acid

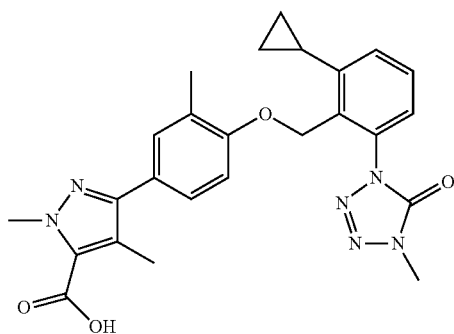 [SMILES: Cc1cc(-c2nn(C)c(C(=O)O)c2C)ccc1OCc1c(C2CC2)cccc1-n1nnn(C)c1=O]

$^1$H-NMR (CDCl$_3$) δ: 7.44 (1H, t, J=7.9 Hz), 7.39-7.33 (2H, m), 7.28 (1H, d, J=8.0 Hz), 7.20 (1H, d, J=7.8 Hz), 6.95 (1H, d, J=8.2 Hz), 5.30 (2H, s), 4.20 (3H, s), 3.63 (3H, s), 2.41 (3H, s), 2.19-2.10 (4H, m), 1.05-0.97 (2H, m), 0.79-0.72 (2H, m).

Reference Preparation Example 117

At room temperature, to the mixture of 5-{4-[2-Cyclopropyl-6-(4-methyl-5-oxo-4,5-dihydro-tetrazol-1-yl)-benzyloxy]-3-methyl-phenyl}-2,4-dimethyl-2H-pyrazole-3-carboxylic acid (described in Reference Preparation example 116) and tetrahydrofuran 50 ml was added oxalyl dichloride 0.5 g and N,N-dimethylformamide 0.1 ml. The mixture was stirred for two hours and concentrated under reduced pressure to give 5-{4-[2-Cyclopropyl-6-(4-methyl-5-oxo-4,5-dihydro-tetrazol-1-yl)-benzyloxy]-3-methyl-phenyl}-2,4-dim ethyl-2H-pyrazole-3-carbonylchloride 1.3 g.

5-{4-[2-Cyclopropyl-6-(4-methyl-5-oxo-4,5-dihydro-tetrazol-1-yl)-benzyloxy]-3-methyl-phenyl}-2,4-dimethyl-2H-pyrazole-3-carbonylchloride

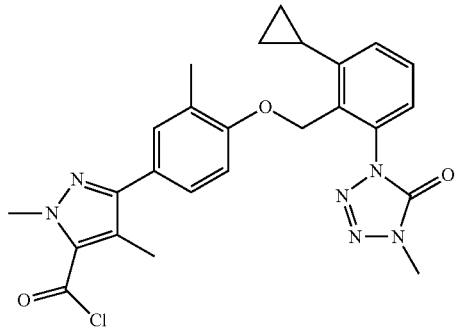 [SMILES: Cc1cc(-c2nn(C)c(C(=O)Cl)c2C)ccc1OCc1c(C2CC2)cccc1-n1nnn(C)c1=O]

$^1$H-NMR (CDCl$_3$) δ: 7.47-7.42 (1H, m), 7.30-7.27 (3H, m), 7.20 (1H, d, J=7.9 Hz), 6.96 (1H, d, J=8.3 Hz), 5.30 (2H, s), 4.15 (3H, s), 3.63 (3H, s), 2.48 (3H, s), 2.17-2.11 (4H, m), 1.04-0.98 (2H, m), 0.79-0.73 (2H, m).

Reference Preparation Example 118

At room temperature, a mixture of 1-{3-cyclopropyl-2-[2-methyl-4-(3,5-dimethyl-4-formyl-pyrazol-1-yl)-phenoxymethyl]-phenyl}-4-methyl-1,4-dihydrotetrazole-5-one (Present compound 51) 1.7 g, chloroform 20 ml, hydroxylamine hydrochloride salt 0.3 g and pyridine 0.9 g was stirred for twelve hours. To the resulting mixture was added water 20 ml, and the mixture was extracted with chloroform. The organic layer was washed with water and was dried over anhydrous magnesium sulfate, and then was concentrated under reduced pressure. The resulting residue was subjected to a silica gel column chromatography to give 1-{4-[2-Cyclopropyl-6-(4-methyl-5-oxo-4,5-dihydro-tetrazol-1-yl)-benzyloxy]-3-methyl-phenyl}-3,5-dimethyl-1H-pyrazole-4-carbaldehyde oxime 1.4 g.

1-{4-[2-Cyclopropyl-6-(4-methyl-5-oxo-4,5-dihydro-tetrazol-1-yl)-benzyloxy]-3-methyl-phenyl}-3,5-dimethyl-1H-pyrazole-4-carbaldehyde oxime

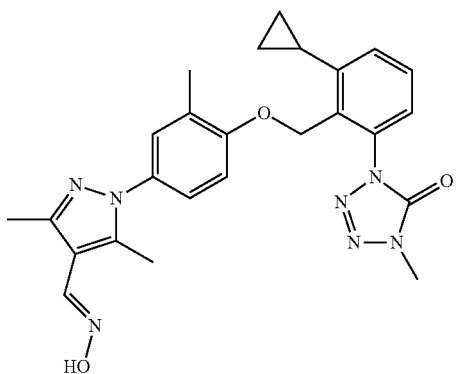 [SMILES: Cc1cc(-n2nc(C)c(/C=N/O)c2C)ccc1OCc1c(C2CC2)cccc1-n1nnn(C)c1=O]

$^1$H-NMR (CDCl$_3$) δ: 8.14 (1H, s), 7.59 (1H, s), 7.46-7.42 (1H, m), 7.28 (2H, d, J=7.8 Hz), 7.15-7.11 (2H, m), 6.92 (1H, d, J=8.5 Hz), 5.29 (2H, s), 3.63 (3H, s), 2.38 (3H, s), 2.34 (3H, s), 2.14-2.08 (4H, m), 1.02-0.97 (2H, m), 0.79-0.75 (2H, m).

According to the above-mentioned processes, the following compounds can be prepared:
Compounds EP1A-001~EP1A-1023, EP1B-001~EP1B-1023, EP1C-001~EP1C-1023, EP1D-001~EP1D-1023, EP1E-001~EP1E-1023, EP1F-001~EP1F-1023, EP1G-001~EP1G-1023, EP1H-001~EP1H-1023, EP1I-001~EP1I-1023, EP1J-001~EP1J-1023, EP2A-001~EP2A-1023, EP2B-001~EP2B-1023, EP2C-001~EP2C-1023, EP2D-001~EP2D-1023, EP2E-001~EP2E-1023, EP2F-001~EP2F-1023, EP2G-001~EP2G-1023, EP2H-001~EP2H-1023, EP2I-001~EP2I-1023, EP2J-001~EP2J-1023, EP3A-001~EP3A-1023, EP3B-001~EP3B-1023, EP3C-001~EP3C-1023, EP3D-001~EP3D-1023, EP3E-001~EP3E-1023, EP3F-001~EP3F-1023, EP3G-001~EP3G-1023, EP3H-001~EP3H-1023, EP3I-001~EP3I-1023, EP3J-001~EP3J-1023, EP4A-001~EP4A-1023, EP4B-001~EP4B-1023, EP4C-001~EP4C-1023, EP4D-001~EP4D-1023, EP4E-001~EP4E-1023, EP4F-001~EP4F-1023, EP4G-001~EP4G-1023, EP4H-001~EP4H-1023, EP4I-001~EP4I-1023, EP4J-001~EP4J-1023, EP5A-001~EP5A-1023, EP5B-001~EP5B-1023, EP5C-001~EP5C-1023, EP5D-001~EP5D-1023, EP5E-001~EP5E-1023, EP5F-001~EP5F-1023, EP5G-001~EP5G-1023, EP5H-001~EP5H-1023, EP5I-001~EP5I-1023 and EP5J-001~EP5J-1023.

Compounds EP1A-001~EP1A-1023 represent compounds represented by a formula:

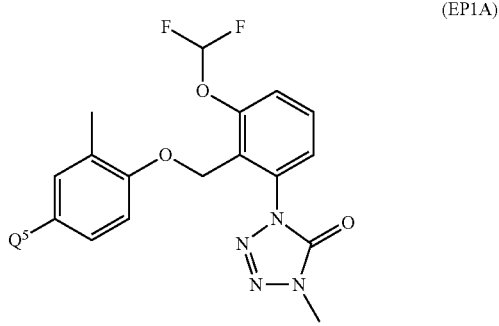

(EP1A)

[in the formula (EP1A), $Q^5$ represents a substituent corresponding to each of substituents Nos. 1 to 1023 indicated in Table 1 to Table 54 as below-mentioned];

Compounds EP1B-001~EP1B-1023 represent compounds represented by a formula:

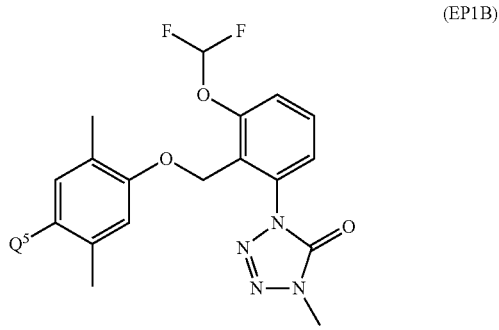

(EP1B)

[in the formula (EP1B), $Q^5$ represents a substituent corresponding to each of substituents Nos. 1 to 1023 indicated in Table 1 to Table 54 as below-mentioned];

Compounds EP1C-001~EP1C-1023 represent compounds represented by a formula:

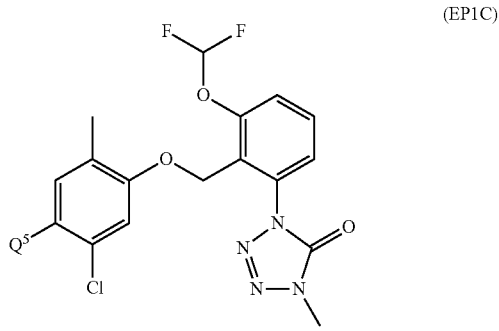

(EP1C)

[in the formula (EP1C), $Q^5$ represents a substituent corresponding to each of substituents Nos. 1 to 1023 indicated in Table 1 to Table 54 as below-mentioned];

Compounds EP1D-001~EP1D-1023 represent compounds represented by a formula:

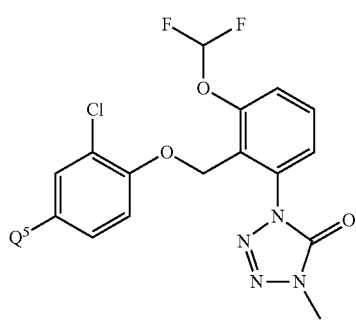

(EP1D)

[in the formula (EP1D), $Q^5$ represents a substituent corresponding to each of substituents Nos. 1 to 1023 indicated in Table 1 to Table 54 as below-mentioned];

Compounds EP1E-001~EP1E-1023 represent compounds represented by a formula:

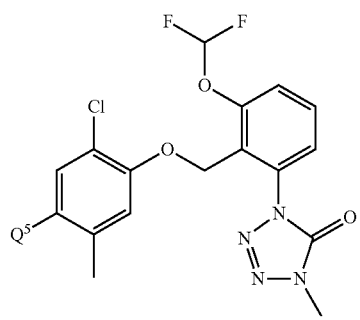

(EP1E)

[in the formula (EP1E), $Q^5$ represents a substituent corresponding to each of substituents Nos. 1 to 1023 indicated in Table 1 to Table 54 as below-mentioned];

Compounds EP1F-001~EP1F-1023 represent compounds represented by a formula:

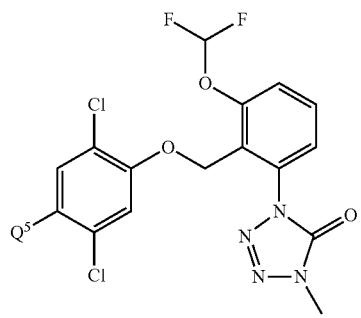

(EP1F)

[in the formula (EP1F), $Q^5$ represents a substituent corresponding to each of substituents Nos. 1 to 1023 indicated in Table 1 to Table 54 as below-mentioned];

Compounds EP1G-001~EP1G-1023 represent compounds represented by a formula:

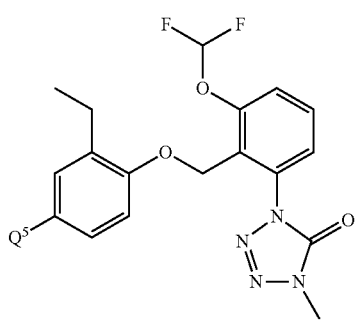

(EP1G)

[in the formula (EP1G), $Q^5$ represents a substituent corresponding to each of substituents Nos. 1 to 1023 indicated in Table 1 to Table 54 as below-mentioned];

Compounds EP1H-001~EP1H-1023 represent compounds represented by a formula:

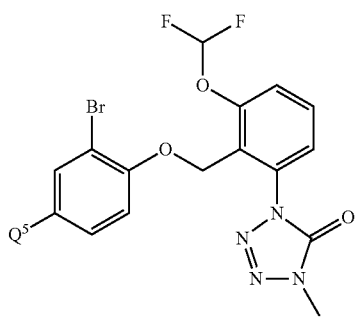

(EP1H)

[in the formula (EP1H), $Q^5$ represents a substituent corresponding to each of substituents Nos. 1 to 1023 indicated in Table 1 to Table 54 as below-mentioned];

Compounds EP1I-001~EP1I-1023 represent compounds represented by a formula:

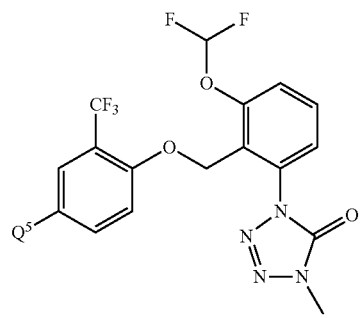

(EP1I)

[in the formula (EP1I), $Q^5$ represents a substituent corresponding to each of substituents Nos. 1 to 1023 indicated in Table 1 to Table 54 as below-mentioned];

Compounds EP1J-001~EP1J-1023 represent compounds represented by a formula:

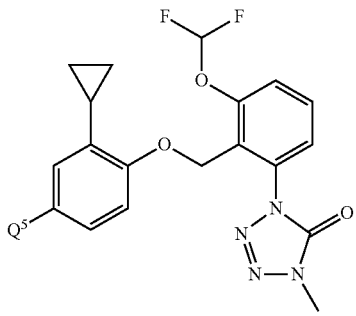

(EP1J)

[in the formula (EP1J), $Q^5$ represents a substituent corresponding to each of substituents Nos. 1 to 1023 indicated in Table 1 to Table 54 as below-mentioned];

Compounds EP2A-001~EP2A-1023 represent compounds represented by a formula:

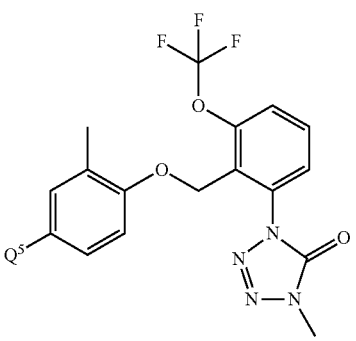

(EP2A)

[in the formula (EP2A), $Q^5$ represents a substituent corresponding to each of substituents Nos. 1 to 1023 indicated in Table 1 to Table 54 as below-mentioned];

Compounds EP2B-001~EP2B-1023 represent compounds represented by a formula:

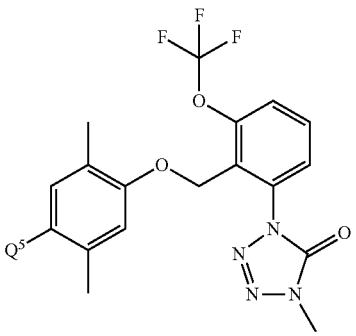

(EP2B)

[in the formula (EP2B), $Q^5$ represents a substituent corresponding to each of substituents Nos. 1 to 1023 indicated in Table 1 to Table 54 as below-mentioned];

Compounds EP2C-001~EP2C-1023 represent compounds represented by a formula:

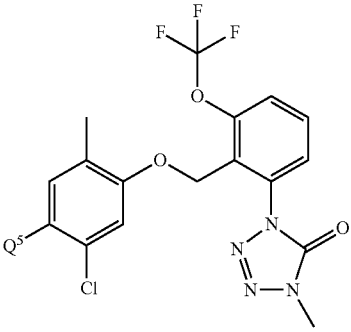

(EP2C)

[in the formula (EP2C), $Q^5$ represents a substituent corresponding to each of substituents Nos. 1 to 1023 indicated in Table 1 to Table 54 as below-mentioned];

Compounds EP2D-001~EP2D-1023 represent compounds represented by a formula:

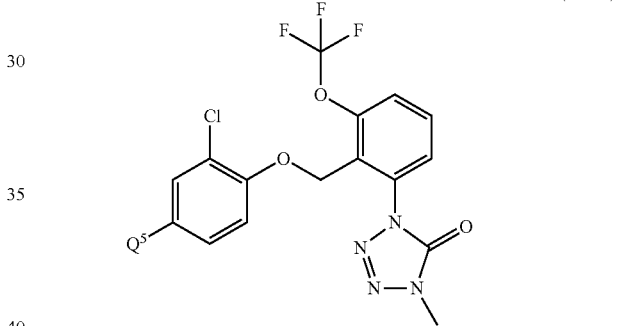

(EP2D)

[in the formula (EP2D), $Q^5$ represents a substituent corresponding to each of substituents Nos. 1 to 1023 indicated in Table 1 to Table 54 as below-mentioned];

Compounds EP2E-001~EP2E-1023 represent compounds represented by a formula:

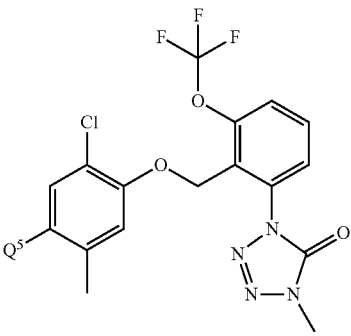

(EP2E)

[in the formula (EP2E), $Q^5$ represents a substituent corresponding to each of substituents Nos. 1 to 1023 indicated in Table 1 to Table 54 as below-mentioned];

Compounds EP2F-001~EP2F-1023 represent compounds represented by a formula:

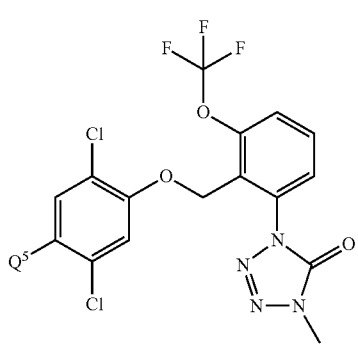
(EP2F)

[in the formula (EP2F), Q⁵ represents a substituent corresponding to each of substituents Nos. 1 to 1023 indicated in Table 1 to Table 54 as below-mentioned];

Compounds EP2G-001~EP2G-1023 represent compounds represented by a formula:

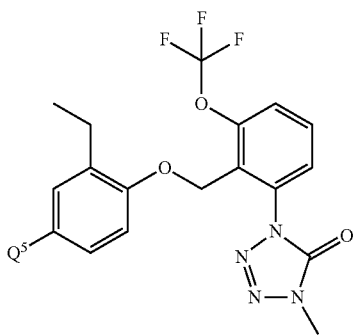
(EP2G)

[in the formula (EP2G), Q⁵ represents a substituent corresponding to each of substituents Nos. 1 to 1023 indicated in Table 1 to Table 54 as below-mentioned];

Compounds EP2H-001~EP2H-1023 represent compounds represented by a formula:

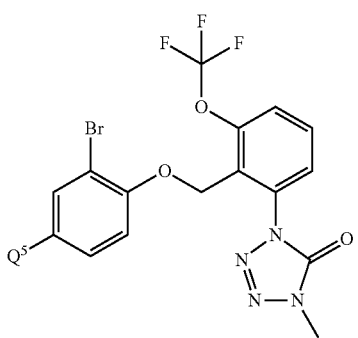
(EP2H)

[in the formula (EP2H), Q⁵ represents a substituent corresponding to each of substituents Nos. 1 to 1023 indicated in Table 1 to Table 54 as below-mentioned];

Compounds EP2I-001~EP2I-1023 represent compounds represented by a formula:

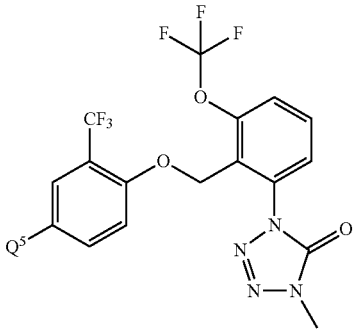
(EP2I)

[in the formula (EP2I), Q⁵ represents a substituent corresponding to each of substituents Nos. 1 to 1023 indicated in Table 1 to Table 54 as below-mentioned];

Compounds EP2J-001~EP2J-1023 represent compounds represented by a formula:

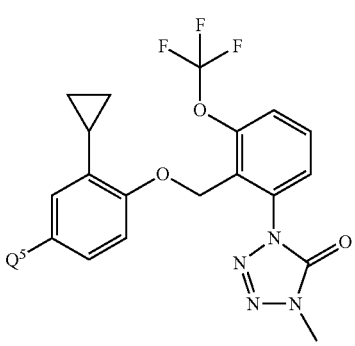
(EP2J)

[in the formula (EP2J), Q⁵ represents a substituent corresponding to each of substituents Nos. 1 to 1023 indicated in Table 1 to Table 54 as below-mentioned];

Compounds EP3A-001~EP3A-1023 represent compounds represented by a formula:

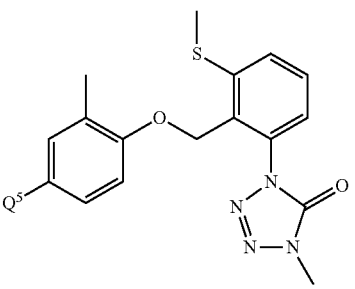
(EP3A)

[in the formula (EP3A), Q⁵ represents a substituent corresponding to each of substituents Nos. 1 to 1023 indicated in Table 1 to Table 54 as below-mentioned];

Compounds EP3B-001~EP3B-1023 represent compounds represented by a formula:

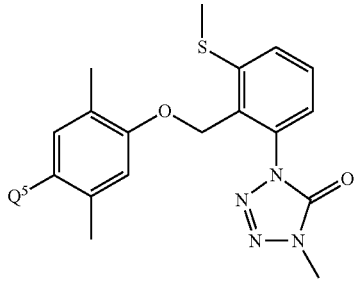

(EP3B)

[in the formula (EP3B), $Q^5$ represents a substituent corresponding to each of substituents Nos. 1 to 1023 indicated in Table 1 to Table 54 as below-mentioned];

Compounds EP3C-001~EP3C-1023 represent compounds represented by a formula:

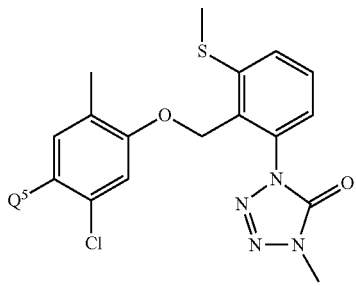

(EP3C)

[in the formula (EP3C), $Q^5$ represents a substituent corresponding to each of substituents Nos. 1 to 1023 indicated in Table 1 to Table 54 as below-mentioned];

Compounds EP3D-001~EP3D-1023 represent compounds represented by a formula:

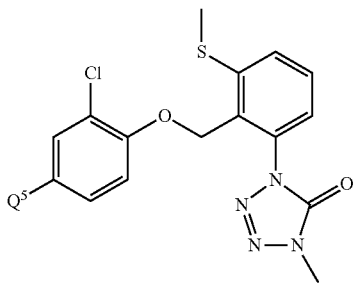

(EP3D)

[in the formula (EP3D), $Q^5$ represents a substituent corresponding to each of substituents Nos. 1 to 1023 indicated in Table 1 to Table 54 as below-mentioned];

Compounds EP3E-001~EP3E-1023 represent compounds represented by a formula:

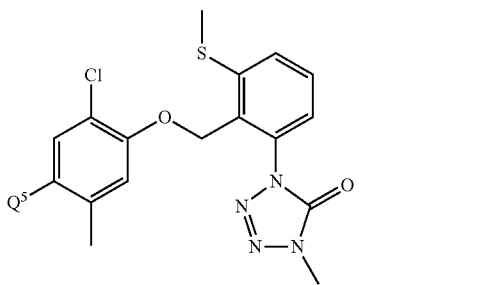

(EP3E)

[in the formula (EP3E), $Q^5$ represents a substituent corresponding to each of substituents Nos. 1 to 1023 indicated in Table 1 to Table 54 as below-mentioned];

Compounds EP3F-001~EP3F-1023 represent compounds represented by a formula:

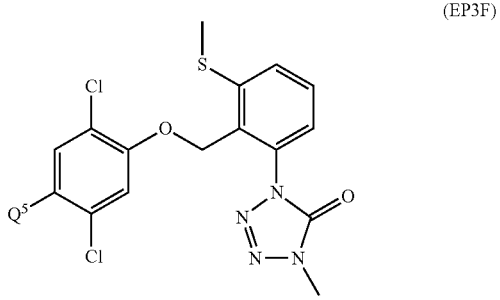

(EP3F)

[in the formula (EP3F), $Q^5$ represents a substituent corresponding to each of substituents Nos. 1 to 1023 indicated in Table 1 to Table 54 as below-mentioned];

Compounds EP3G-001~EP3G-1023 represent compounds represented by a formula:

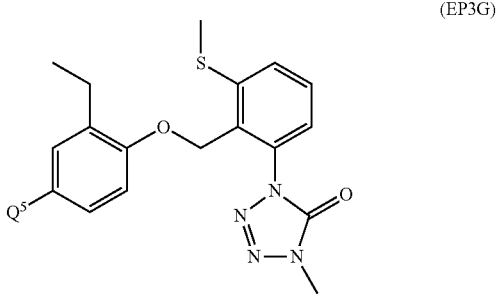

(EP3G)

[in the formula (EP3G), $Q^5$ represents a substituent corresponding to each of substituents Nos. 1 to 1023 indicated in Table 1 to Table 54 as below-mentioned];

Compounds EP3H-001~EP3H-1023 represent compounds represented by a formula:

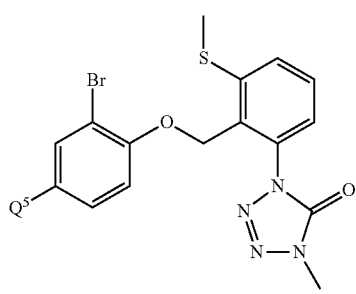

(EP3H)

[in the formula (EP3H), $Q^5$ represents a substituent corresponding to each of substituents Nos. 1 to 1023 indicated in Table 1 to Table 54 as below-mentioned];

Compounds EP3I-001~EP3I-1023 represent compounds represented by a formula:

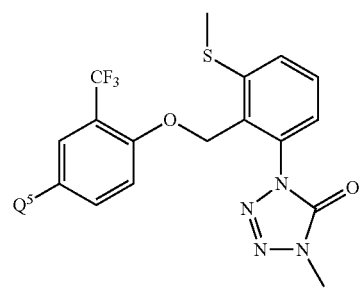

(EP3I)

[in the formula (EP3I), $Q^5$ represents a substituent corresponding to each of substituents Nos. 1 to 1023 indicated in Table 1 to Table 54 as below-mentioned];

Compounds EP3J-001~EP3J-1023 represent compounds represented by a formula:

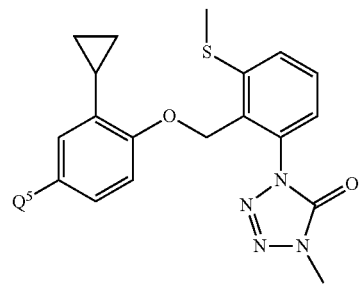

(EP3J)

[in the formula (EP3J), $Q^5$ represents a substituent corresponding to each of substituents Nos. 1 to 1023 indicated in Table 1 to Table 54 as below-mentioned];

Compounds EP4A-001~EP4A-1023 represent compounds represented by a formula:

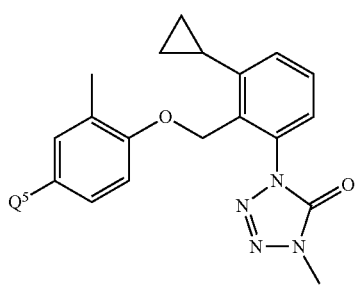

(EP4A)

[in the formula (EP4A), $Q^5$ represents a substituent corresponding to each of substituents Nos. 1 to 1023 indicated in Table 1 to Table 54 as below-mentioned];

Compounds EP4B-001~EP4B-1023 represent compounds represented by a formula:

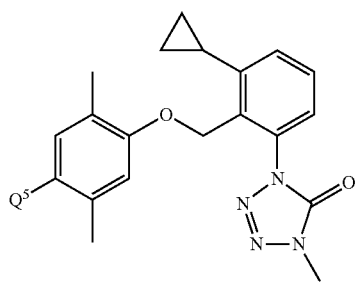

(EP4B)

[in the formula (EP4B), $Q^5$ represents a substituent corresponding to each of substituents Nos. 1 to 1023 indicated in Table 1 to Table 54 as below-mentioned];

Compounds EP4C-001~EP4C-1023 represent compounds represented by a formula:

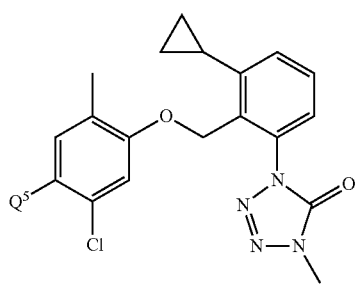

(EP4C)

[in the formula (EP4C), $Q^5$ represents a substituent corresponding to each of substituents Nos. 1 to 1023 indicated in Table 1 to Table 54 as below-mentioned];

Compounds EP4D-001~EP4D-1023 represent compounds represented by a formula:

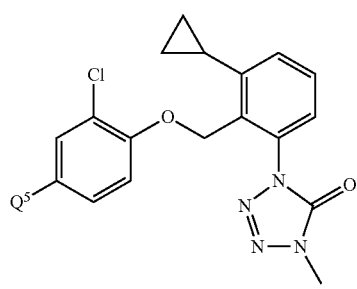

(EP4D)

[in the formula (EP4D), $Q^5$ represents a substituent corresponding to each of substituents Nos. 1 to 1023 indicated in Table 1 to Table 54 as below-mentioned];

Compounds EP4E-001~EP4E-1023 represent compounds represented by a formula:

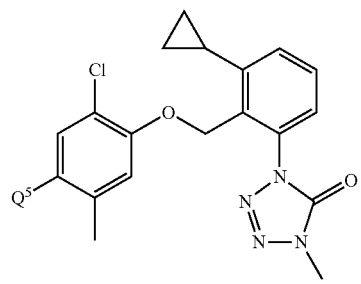

(EP4E)

[in the formula (EP4E), $Q^5$ represents a substituent corresponding to each of substituents Nos. 1 to 1023 indicated in Table 1 to Table 54 as below-mentioned];

Compounds EP4F-001~EP4F-1023 represent compounds represented by a formula:

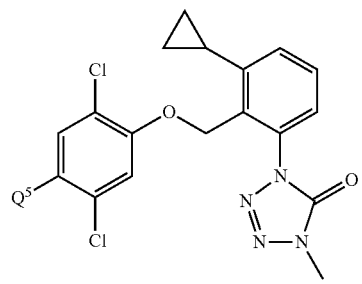

(EP4F)

[in the formula (EP4F), $Q^5$ represents a substituent corresponding to each of substituents Nos. 1 to 1023 indicated in Table 1 to Table 54 as below-mentioned];

Compounds EP4G-001~EP4G-1023 represent compounds represented by a formula:

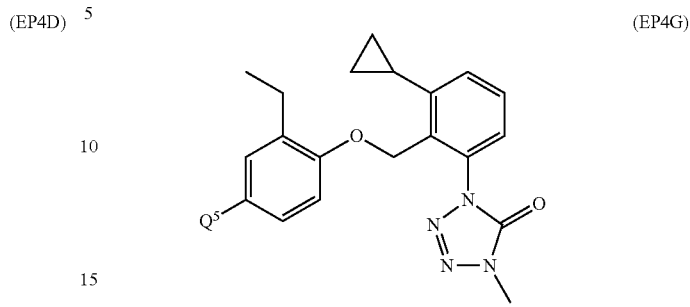

(EP4G)

[in the formula (EP4G), $Q^5$ represents a substituent corresponding to each of substituents Nos. 1 to 1023 indicated in Table 1 to Table 54 as below-mentioned];

Compounds EP4H-001~EP4H-1023 represent compounds represented by a formula:

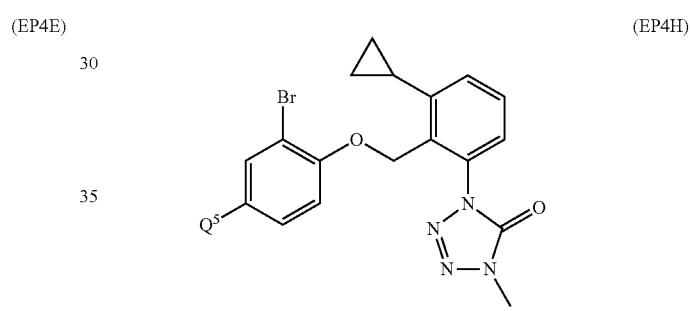

(EP4H)

[in the formula (EP4H), $Q^5$ represents a substituent corresponding to each of substituents Nos. 1 to 1023 indicated in Table 1 to Table 54 as below-mentioned];

Compounds EP4I-001~EP4I-1023 represent compounds represented by a formula:

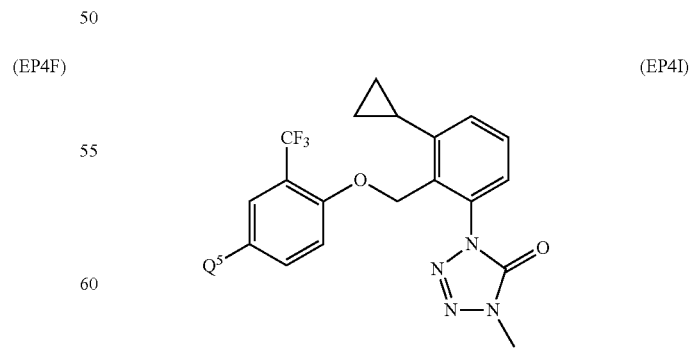

(EP4I)

[in the formula (EP4I), $Q^5$ represents a substituent corresponding to each of substituents Nos. 1 to 1023 indicated in Table 1 to Table 54 as below-mentioned];

Compounds EP4J-001~EP4J-1023 represent compounds represented by a formula:

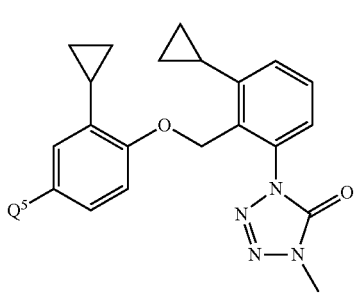

(EP4J)

[in the formula (EP4J), $Q^5$ represents a substituent corresponding to each of substituents Nos. 1 to 1023 indicated in Table 1 to Table 54 as below-mentioned];

Compounds EP5A-001~EP5A-1023 represent compounds represented by a formula:

(EP5A)

[in the formula (EP5A), $Q^5$ represents a substituent corresponding to each of substituents Nos. 1 to 1023 indicated in Table 1 to Table 54 as below-mentioned];

Compounds EP5B-001~EP5B-1023 represent compounds represented by a formula:

(EP5B)

[in the formula (EP5B), $Q^5$ represents a substituent corresponding to each of substituents Nos. 1 to 1023 indicated in Table 1 to Table 54 as below-mentioned];

Compounds EP5C-001~EP5C-1023 represent compounds represented by a formula:

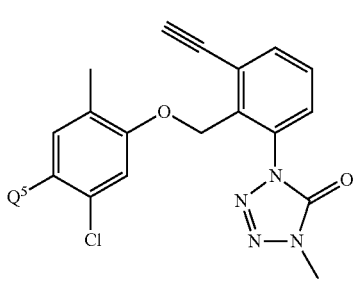

(EP5C)

[in the formula (EP5C), $Q^5$ represents a substituent corresponding to each of substituents Nos. 1 to 1023 indicated in Table 1 to Table 54 as below-mentioned];

Compounds EP5D-001~EP5D-1023 represent compounds represented by a formula:

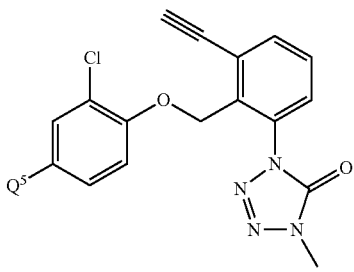

(EP5D)

[in the formula (EP5D), $Q^5$ represents a substituent corresponding to each of substituents Nos. 1 to 1023 indicated in Table 1 to Table 54 as below-mentioned];

Compounds EP5E-001~EP5E-1023 represent compounds represented by a formula:

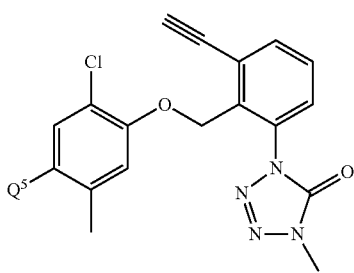

(EP5E)

[in the formula (EP5E), $Q^5$ represents a substituent corresponding to each of substituents Nos. 1 to 1023 indicated in Table 1 to Table 54 as below-mentioned];

Compounds EP5F-001~EP5F-1023 represent compounds represented by a formula:

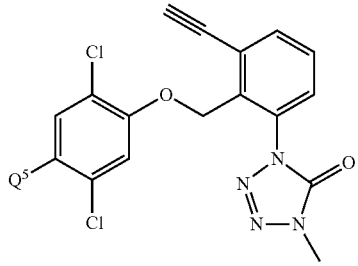

(EP5F)

[in the formula (EP5F), $Q^5$ represents a substituent corresponding to each of substituents Nos. 1 to 1023 indicated in Table 1 to Table 54 as below-mentioned];

Compounds EP5G-001~EP5G-1023 represent compounds represented by a formula:

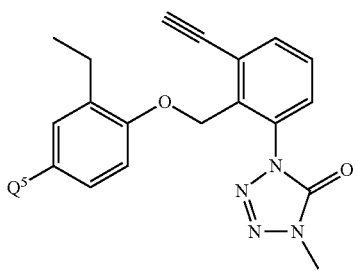

(EP5G)

[in the formula (EP5G), $Q^5$ represents a substituent corresponding to each of substituents Nos. 1 to 1023 indicated in Table 1 to Table 54 as below-mentioned];

Compounds EP5H-001~EP5H-1023 represent compounds represented by a formula:

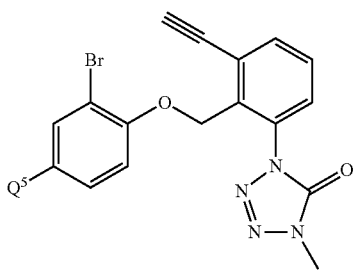

(EP5H)

[in the formula (EP5H), $Q^5$ represents a substituent corresponding to each of substituents Nos. 1 to 1023 indicated in Table 1 to Table 54 as below-mentioned];

Compounds EP5I-001~EP5I-1023 represent compounds represented by a formula:

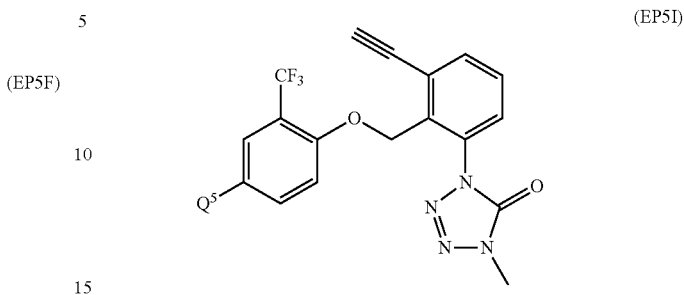

(EP5I)

[in the formula (EP5I), $Q^5$ represents a substituent corresponding to each of substituents Nos. 1 to 1023 indicated in Table 1 to Table 54 as below-mentioned]; and Compounds EP5J-001~EP5J-1023 represent compounds represented by a formula:

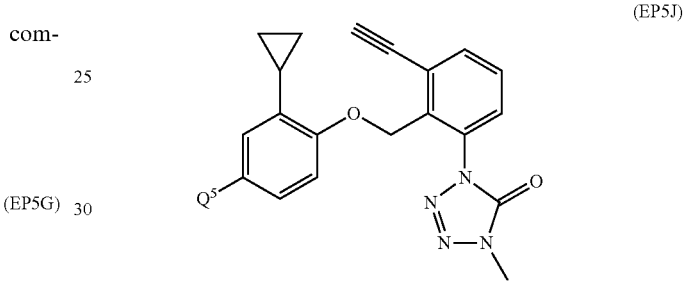

(EP5J)

[in the formula (EP5J), $Q^5$ represents a substituent corresponding to each of substituents Nos. 1 to 1023 indicated in Table 1 to Table 54 as below-mentioned].

TABLE 1

| substituents Nos. | $Q^5$ |
|---|---|
| 1 | pyrazol-1-yl group |
| 2 | 4-fluoro-pyrazol-1-yl group |
| 3 | 4-chloro-pyrazol-1-yl group |
| 4 | 4-bromo-pyrazol-1-yl group |
| 5 | 4-methyl-pyrazol-1-yl group |
| 6 | 4-ethyl-pyrazol-1-yl group |
| 7 | 4-propyl-pyrazol-1-yl group |
| 8 | 4-isopropyl-pyrazol-1-yl group |
| 9 | 4-cyclopropyl-pyrazol-1-yl group |
| 10 | 4-difluoromethyl-pyrazol-1-yl group |
| 11 | 4-cyano-pyrazol-1-yl group |
| 12 | 4-ethynyl-pyrazol-1-yl group |
| 13 | 4-propynyl-pyrazol-1-yl group |
| 14 | 5-methyl-pyrazol-1-yl group |
| 15 | 4-fluoro-5-methyl-pyrazol-1-yl group |
| 16 | 4-chloro-5-methyl-pyrazol-1-yl group |
| 17 | 4-bromo-5-methyl-pyrazol-1-yl group |
| 18 | 4,5-dimethylpyrazol-1-yl group |
| 19 | 4-ethyl-5-methyl-pyrazol-1-yl group |
| 20 | 5-methyl-4-propyl-pyrazol-1-yl group |
| 21 | 4-isopropyl-5-methyl-pyrazol-1-yl group |
| 22 | 4-cyclopropyl-5-methyl-pyrazol-1-yl group |
| 23 | 4-difluoromethyl-5-methyl-pyrazol-1-yl group |
| 24 | 4-cyano-5-methyl-pyrazol-1-yl group |
| 25 | 4-ethynyl-5-methyl-pyrazol-1-yl group |
| 26 | 5-methyl-4-propynyl-pyrazol-1-yl group |
| 27 | 5-ethylpyrazol-1-yl group |
| 28 | 4-fluoro-5-ethylpyrazol-1-yl group |
| 29 | 4-chloro-5-ethylpyrazol-1-yl group |

TABLE 2

| substituents Nos. | Q⁵ |
|---|---|
| 30 | 4-bromo-5-ethyl-pyrazol-1-yl group |
| 31 | 5-ethyl-4-methyl-pyrazol-1-yl group |
| 32 | 4,5-diethyl-pyrazol-1-yl group |
| 33 | 4,5,6,7-tetrahydro-indazol-1-yl group |
| 34 | 3-methyl-4,5,6,7-tetrahydro-indazol-1-yl group |
| 35 | 4,5,6,7-tetrahydro-indazol-2-yl group |
| 36 | 3-methyl-4,5,6,7-tetrahydro-indazol-2-yl group |
| 37 | 1,4,5,6-tetrahydro-cyclopentapyrazol-1-yl group |
| 38 | 3-methyl-4,5,6,7-tetrahydro-indazol-2-yl group |
| 39 | 3-methyl-pyrazol-1-yl group |
| 40 | 4-fluoro-3-methyl-pyrazol-1-yl group |
| 41 | 4-chloro-3-methyl-pyrazol-1-yl group |
| 42 | 4-bromo-3-methyl-pyrazol-1-yl group |
| 43 | 3,4-dimethyl-pyrazol-1-yl group |
| 44 | 4-ethyl-3-methyl-pyrazol-1-yl group |
| 45 | 4-propyl-3-methyl-pyrazol-1-yl group |
| 46 | 4-isopropyl-3-methyl-pyrazol-1-yl group |
| 47 | 4-cyclopropyl-3-methyl-pyrazol-1-yl group |
| 48 | 4-difluoromethyl-3-methyl-pyrazol-1-yl group |
| 49 | 3-methyl-4-trifluoromethyl-pyrazol-1-yl group |
| 50 | 4-cyano-3-methyl-pyrazol-1-yl group |
| 51 | 4-ethynyl-3-methylpyrazol-1-yl group |
| 52 | 3-methyl-4-propynyl-pyrazol-1-yl group |
| 53 | 3,5-dimethyl-pyrazol-1-yl group |
| 54 | 4-fluoro-3,5-dimethyl-pyrazol-1-yl group |
| 55 | 4-chloro-3,5-dimethyl-pyrazol-1-yl group |
| 56 | 4-bromo-3,5-dimethyl-pyrazol-1-yl group |
| 57 | 3,4,5-trimethyl-pyrazol-1-yl group |
| 58 | 4-ethyl-3,5-dimethyl-pyrazol-1-yl group |

TABLE 3

| substituents Nos. | Q⁵ |
|---|---|
| 59 | 3,5-dimethyl-4-propyl-pyrazol-1-yl group |
| 60 | 3,5-dimethyl-4-isopropyl-pyrazol-1-yl group |
| 61 | 3,5-dimethyl-4-cyclopropyl-pyrazol-1-yl group |
| 62 | 4-difluoromethyl-3,5-dimethyl-pyrazol-1-yl group |
| 63 | 4-cyano-3,5-dimethyl-pyrazol-1-yl group |
| 64 | 4-ethynyl-3,5-dimethyl-pyrazol-1-yl group |
| 65 | 3,5-dimethyl-4-propynyl-pyrazol-1-yl group |
| 66 | 5-ethyl-3-methyl-pyrazol-1-yl group |
| 67 | 5-ethyl-4-fluoro-3-methyl-pyrazol-1-yl group |
| 68 | 4-chloro-5-ethyl-3-methyl-pyrazol-1-yl group |
| 69 | 4-bromo-5-ethyl-3-methyl-pyrazol-1-yl group |
| 70 | 3,4-dimethyl-5-ethyl-pyrazol-1-yl group |
| 71 | 4,5-diethyl-3-methyl-pyrazol-1-yl group |
| 72 | 5-ethyl-4-propyl-3-methyl-pyrazol-1-yl group |
| 73 | 5-ethyl-4-isopropyl-3-methyl-pyrazol-1-yl group |
| 74 | 5-ethyl-4-cyclopropyl-3-methyl-pyrazol-1-yl group |
| 75 | 5-ethyl-4-difluoromethyl-3-methyl-pyrazol-1-yl group |
| 76 | 4-cyano-5-ethyl-3-methyl-pyrazol-1-yl group |
| 77 | 5-ethyl-4-ethynyl-3-methyl-pyrazol-1-yl group |
| 78 | 5-ethyl-3-methyl-4-propynyl-pyrazol-1-yl group |
| 79 | 3,5-dimethyl-4-methoxy-pyrazol-1-yl group |
| 80 | 4-ethoxy-3,5-dimethyl-pyrazol-1-yl group |
| 81 | 3,5-dimethyl-4-(2-propynyloxy)-pyrazol-1-yl group |
| 82 | 3,5-dimethyl-4-trifluoromethyl-pyrazol-1-yl group |
| 83 | 3-ethyl-pyrazol-1-yl group |
| 84 | 4-fluoro-3-ethyl-pyrazol-1-yl group |
| 85 | 4-chloro-3-ethyl-pyrazol-1-yl group |
| 86 | 4-bromo-3-ethyl-pyrazol-1-yl group |
| 87 | 3-ethyl-4-methyl-pyrazol-1-yl group |

TABLE 4

| substituents Nos. | Q⁵ |
|---|---|
| 88 | 3,4-diethylpyrazol-1-yl group |
| 89 | 3-ethyl-4-propyl-pyrazol-1-yl group |
| 90 | 3-ethyl-4-isopropyl-pyrazol-1-yl group |
| 91 | 4-cyclopropyl-3-ethylpyrazol-1-yl group |
| 92 | 3-ethyl-4-difluoromethyl-pyrazol-1-yl group |
| 93 | 4-cyano-3-ethylpyrazol-1-yl group |
| 94 | 3-ethyl-4-ethynyl-pyrazol-1-yl group |
| 95 | 3-ethyl-4-propynyl-pyrazol-1-yl group |
| 96 | 3-ethyl-5-methyl-pyrazol-1-yl group |
| 97 | 3-ethyl-4-fluoro-5-methyl-pyrazol-1-yl group |
| 98 | 4-chloro-3-ethyl-5-methyl-pyrazol-1-yl group |
| 99 | 4-bromo-3-ethyl-5-methyl-pyrazol-1-yl group |
| 100 | 3-ethyl-4,5-dimethyl-pyrazol-1-yl group |
| 101 | 3,4-diethyl-5-methyl-pyrazol-1-yl group |
| 102 | 3-ethyl-5-methyl-4-propyl-pyrazol-1-yl group |
| 103 | 3-ethyl-4-isopropyl-5-methyl-pyrazol-1-yl group |

TABLE 5

| substituents Nos. | Q⁵ |
|---|---|
| 104 | 4-difluoromethyl-3-ethyl-5-methyl-pyrazol-1-yl group |
| 105 | 3-ethyl-5-methyl-4-trifluoromethyl-pyrazol-1-yl group |
| 106 | 3-ethyl-4-ethynyl-5-methyl-pyrazol-1-yl group |
| 107 | 3-ethyl-5-methyl-4-propynyl-pyrazol-1-yl group |
| 108 | 3-cyclopropyl-pyrazol-1-yl group |
| 109 | 3-cyclopropyl-4-fluoro-pyrazol-1-yl group |
| 110 | 4-chloro-3-cyclopropyl-pyrazol-1-yl group |
| 111 | 4-bromo-3-cyclopropyl-pyrazol-1-yl group |
| 112 | 3-cyclopropyl-4-methyl-pyrazol-1-yl group |
| 113 | 3-cyclopropyl-4-ethyl-pyrazol-1-yl group |
| 114 | 3-cyclopropyl-4-propyl-pyrazol-1-yl group |
| 115 | 3,5-dimethyl-4-(2-propynyloxy)-1-yl group |
| 116 | 3,5-dimethyl-4-(2-butynyloxy)-1-yl group |

TABLE 6

| substituents Nos. | Q⁵ |
|---|---|
| 117 | 3-cyclopropyl-4-isopropyl-pyrazol-1-yl group |
| 118 | 3,5-dicyclopropyl-pyrazol-1-yl group |
| 119 | 3-cyclopropyl-4-difluoromethyl-pyrazol-1-yl group |
| 120 | 3-cyclopropyl-4-trifluoromethyl-pyrazol-1-yl group |
| 121 | 3-cyclopropyl-4-ethynyl-pyrazol-1-yl group |
| 122 | 3-cyclopropyl-4-propynyl-pyrazol-1-yl group |
| 123 | 3-cyclopropyl-5-methyl-pyrazol-1-yl group |
| 124 | 3-cyclopropyl-4-fluoro-5-methyl-pyrazol-1-yl group |
| 125 | 4-chloro-3-cyclopropyl-5-methyl-pyrazol-1-yl group |
| 126 | 4-bromo-3-cyclopropyl-5-methyl-pyrazol-1-yl group |
| 127 | 3-cyclopropyl-4,5-dimethylpyrazol-1-yl group |
| 128 | 3-cyclopropyl-4-ethyl-5-methyl-pyrazol-1-yl group |
| 129 | 3-cyclopropyl-4-propyl-5-methyl-pyrazol-1-yl group |
| 130 | 3-cyclopropyl-4-isopropyl-5-methyl-pyrazol-1-yl group |
| 131 | 3,5-dicyclopropyl-4-methyl-pyrazol-1-yl |

TABLE 7

| substituents Nos. | $Q^5$ |
|---|---|
| 132 | 3-cyclopropyl-4-difluoromethyl-5-methyl-pyrazol-1-yl group |
| 133 | 3-cyclopropyl-4-trifluoromethy-5-methyl-pyrazol-1-yl group |
| 134 | 3-cyclopropyl-4-ethynyl-5-methyl-pyrazol-1-yl group |
| 135 | 3-cyclopropyl-4-propynyl-5-methyl-pyrazol-1-yl group |
| 136 | 3-difluoromethyl-pyrazol-1-yl group |
| 137 | 3-difluoromethyl-4-methyl-pyrazol-1-yl group |
| 138 | 3-difluoromethyl-4-ethyl-pyrazol-1-yl group |
| 139 | 3-difluoromethyl-4-propyl-pyrazol-1-yl group |
| 140 | 3-difluoromethyl-4-isopropyl-pyrazol-1-yl group |
| 141 | 3-difluoromethyl-4-cyclopropyl-pyrazol-1-yl group |
| 142 | 3-difluoromethyl-4-ethynyl-pyrazol-1-yl group |
| 143 | 3-difluoromethyl-4-propynyl-pyrazol-1-yl group |
| 144 | 3-difluoromethyl-4-isobutyl-pyrazol-1-yl group |
| 145 | 3-difluoromethyl-4-fluoro-pyrazol-1-yl group |

TABLE 8

| substituents Nos. | $Q^5$ |
|---|---|
| 146 | 4-chloro-3-difluoromethyl-pyrazol-1-yl group |
| 147 | 4-bromo-3-difluoromethyl-pyrazol-1-yl group |
| 148 | 3-trifluoromethyl-pyrazol-1-yl group |
| 149 | 4-fluoro-3-trifluoromethyl-pyrazol-1-yl group |
| 150 | 4-chloro-3-trifluoromethyl-pyrazol-1-yl group |
| 151 | 4-bromo-3-trifluoromethyl-pyrazol-1-yl group |
| 152 | 4-methyl-3-trifluoromethyl-pyrazol-1-yl group |
| 153 | 4-ethyl-3-trifluoromethyl-pyrazol-1-yl group |
| 154 | 4-propyl-3-trifluoromethyl-pyrazol-1-yl group |
| 155 | 4-isopropyl-3-trifluoromethyl-pyrazol-1-yl group |
| 156 | 4-cyclopropyl-3-trifluoromethyl-pyrazol-1-yl group |
| 157 | 4-difluoromethyl-3-trifluoromethyl-pyrazol-1-yl group |
| 158 | 3,4-bis-trifluoromethyl-pyrazol-1-yl group |
| 159 | 4-ethynyl-3-trifluoromethyl-pyrazol-1-yl group |

TABLE 9

| substituents Nos. | $Q^5$ |
|---|---|
| 160 | 4-propynyl-3-trifluoromethyl-pyrazol-1-yl group |
| 161 | 3,5-dimethyl-4-trifluoromethyl-pyrazol-1-yl group |
| 162 | 3-propyl-pyrazol-1-yl group |
| 163 | 3-propyl-4-methyl-pyrazol-1-yl group |
| 164 | 3-propyl-4,5-dimethyl-pyrazol-1-yl group |
| 165 | 3-isopropyl-pyrazol-1-yl group |
| 166 | 3-isopropyl-4-methyl-pyrazol-1-yl group |
| 167 | 3-isopropyl-4,5-dimethyl-pyrazol-1-yl group |
| 168 | 3-tert-butyl-pyrazol-1-yl group |
| 169 | 4-methyl-3-tert-butyl-pyrazol-1-yl group |
| 170 | 4,5-dimethyl-3-tert-butyl-pyrazol-1-yl group |
| 171 | 5-methyl-3-propyl-pyrazol-1-yl group |
| 172 | 3-isopropyl-5-methyl-pyrazol-1-yl group |
| 173 | 5-methyl-3-tert-butyl-pyrazol-1-yl group |
| 174 | 3-ethyl-4-methoxy-5-methyl-pyrazol-1-yl group |

TABLE 10

| substituents Nos. | $Q^5$ |
|---|---|
| 175 | 1-methyl-1H-pyrazol-3-yl group |
| 176 | 1-ethyl-1H-pyrazol-3-yl group |
| 177 | 1-isopropyl-1H-pyrazol-3-yl group |
| 178 | 1-difluoroethyl-1H-pyrazol-3-yl group |
| 179 | 1-(2-propyny)-1H-pyrazol-3-yl group |
| 180 | 1-(2-butynyl)-1H-pyrazol-3-yl group |
| 181 | 1-cyclopropylmethyl-1H-pyrazol-3-yl group |
| 182 | 1-trifluoroethyl-1H-pyrazol-3-yl group |
| 183 | 1-propyl-1H-pyrazol-3-yl group |
| 184 | 1-butyl-1H-pyrazol-3-yl group |
| 185 | 1-isobutyl-1H-pyrazol-3-yl group |
| 186 | 1-(3-methylbutyl)-1H-pyrazol-3-yl group |
| 187 | 1-(4-methyl-pentyl)-1H-pyrazol-3-yl group |
| 188 | 1,4-dimethyl-1H-pyrazol-3-yl group |
| 189 | 1-ethyl-4-methyl-1H-pyrazol-3-yl group |

TABLE 11

| substituents Nos. | $Q^5$ |
|---|---|
| 190 | 1-isopropyl-4-methyl-1H-pyrazol-3-yl group |
| 191 | 1-(2,2-difluoroethyl)-4-methyl-1H-pyrazol-3-yl group |
| 192 | 1-(2-propynyl)-4-methyl-1H-pyrazol-3-yl group |
| 193 | 1-(2-butynyl)-4-methyl-1H-pyrazol-3-yl group |
| 194 | 1-cyclopropylmethyl-4-methyl-1H-pyrazol-3-yl group |
| 195 | 1-(2,2,2-trifluoroethyl)-4-methyl-1H-pyrazol-3-yl group |
| 196 | 4-methyl-1-propyl-1H-pyrazol-3-yl group |
| 197 | 1-butyl-4-methyl-1H-pyrazol-3-yl group |
| 198 | 1-isobutyl-4-methyl-1H-pyrazol-3-yl group |
| 199 | 1-(3-methylbutyl)-4-methyl-1H-pyrazol-3-yl group |
| 200 | 1-(4-methyl-pentyl)-4-methyl-1H-pyrazol-3-yl group |
| 201 | 5-ethyl-1-methyl-1H-pyrazol-3-yl group |
| 202 | 4-ethyl-1-isopropyl-1H-pyrazol-3-yl group |
| 203 | 4-ethyl-1-(2,2-difluoroethyl)-1H-pyrazol-3-yl group |

TABLE 12

| substituents Nos. | $Q^5$ |
|---|---|
| 204 | 4-ethyl-1-(2-propynyl)-1H-pyrazol-3-yl group |
| 205 | 1-(2-butynyl)-4-ethyl-1H-pyrazol-3-yl group |
| 206 | 4-ethyl-1-(2,2,2-trifluoroethyl)-1H-pyrazol-3-yl group |
| 207 | 4-ethyl-1-(2,2-difluoroethyl)-1H-pyrazol-3-yl group |
| 208 | 4-ethyl-1-propyl-1H-pyrazol-3-yl group |
| 209 | 1-butyl-4-ethyl-1H-pyrazol-3-yl group |
| 210 | 4-ethyl-1-isobutyllE-1H-pyrazol-3-yl group |
| 211 | 4-ethyl-1-(3-methylbutyl)-1H-pyrazol-3-yl group |
| 212 | 4-ethyl-1-(4-methyl-pentyl)-1H-pyrazol-3-yl group |
| 213 | 4-fluoro-1-methyl-1H-pyrazol-3-yl group |
| 214 | 1-ethyl-4-fluoro-1H-pyrazol-3-yl group |
| 215 | 4-fluoro-1-isopropyl-1H-pyrazol-3-yl group |
| 216 | 4-fluoro-1-(2,2-difluoroethyl)-1H-pyrazol-3-yl group |
| 217 | 4-fluoro-1-(2-propynyl)-1H-pyrazol-3-yl group |
| 218 | 1-(2-butynyl)-4-fluoro-1H-pyrazol-3-yl group |

TABLE 13

| substituents Nos. | $Q^5$ |
|---|---|
| 219 | 1-cyclopropylmethyl-4-fluoro-1H-pyrazol-3-yl group |
| 220 | 4-fluoro-1-(2,2,2-trifluoroethyl)-1H-pyrazol-3-yl group |
| 221 | 4-fluoro-1-propyl-1H-pyrazol-3-yl group |
| 222 | 1-butyl-4-fluoro-1H-pyrazol-3-yl group |
| 223 | 4-fluoro-1-isobutyl-1H-pyrazol-3-yl group |
| 224 | 4-fluoro-1-(3-methylbutyl)-1H-pyrazol-3-yl group |
| 225 | 4-fluoro-1-(4-methyl-pentyl)-1H-pyrazol-3-yl group |
| 226 | 4-chloro-1-methyl-1H-pyrazol-3-yl group |
| 227 | 4-chloro-1-ethyl-1H-pyrazol-3-yl group |
| 228 | 4-chloro-1-isopropyl-1H-pyrazol-3-yl group |
| 229 | 4-chloro-1-cyclopropylmethyl-1H-pyrazol-3-yl group |
| 230 | 4-chloro-1-(2,2,2-trifluoroethyl)-1H-pyrazol-3-yl group |
| 231 | 4-chloro-1-propyl-1H-pyrazol-3-yl group |
| 232 | 1-butyl-4-chloro-1H-pyrazol-3-yl group |

TABLE 14

| substituents Nos. | $Q^5$ |
|---|---|
| 233 | 4-chloro-1-isobutyl-1H-pyrazol-3-yl group |
| 234 | 4-chloro-1-(3-methylbutyl)-1H-pyrazol-3-yl group |
| 235 | 4-chloro-1-(4-methyl-pentyl)-1H-pyrazol-3-yl group |
| 236 | 1,4-diethyl-1H-pyrazol-3-yl |
| 237 | 4-bromo-1-methyl-1H-pyrazol-3-yl group |
| 238 | 4-bromo-1-ethyl-1H-pyrazol-3-yl group |
| 239 | 4-bromo-1-isopropyl-1H-pyrazol-3-yl group |
| 240 | 4-bromo-1-(2,2-difluoroethyl)-1H-pyrazol-3-yl group |
| 241 | 4-bromo-1-(2-propynyl)-1H-pyrazol-3-yl group |
| 242 | 4-bromo-1-(2-butynyl)-1H-pyrazol-3-yl group |
| 243 | 4-bromo-1-cyclopropylmethyl-1H-pyrazol-3-yl group |
| 244 | 4-bromo-1-(2,2,2-trifluoroethyl)-1H-pyrazol-3-yl group |
| 245 | 4-bromo-1-propyl-1H-pyrazol-3-yl group |
| 246 | 4-bromo-1-butyl-1H-pyrazol-3-yl group |
| 247 | 4-bromo-1-isobutyl-1H-pyrazol-3-yl group |

TABLE 15

| substituents Nos. | $Q^5$ |
|---|---|
| 248 | 4-bromo-1-(3-methylbutyl)-1H-pyrazol-3-yl group |
| 249 | 4-bromo-1-(4-methyl-pentyl)-1H-pyrazol-3-yl group |
| 250 | 1,5-dimethyl-1H-pyrazol-3-yl group |
| 251 | 1-ethyl-5-methyl-1H-pyrazol-3-yl group |
| 252 | 1-isopropyl-5-methyl-1H-pyrazol-3-yl group |
| 253 | 1-(2,2-difluoroethyl)-5-methyl-1H-pyrazol-3-yl group |
| 254 | 5-methyl-1-(2-propynyl)-1H-pyrazol-3-yl group |
| 255 | 1-(2-butynyl)-5-methyl-1H-pyrazol-3-yl group |
| 256 | 1-cyclopropylmethyl-5-methyl-1H-pyrazol-3-yl group |
| 257 | 5-methyl-1-(2,2,2-trifluoroethyl)-1H-pyrazol-3-yl group |
| 258 | 5-methyl-1-propyl-1H-pyrazol-3-yl group |
| 259 | 1-butyl-5-methyl-1H-pyrazol-3-yl group |

TABLE 15-continued

| substituents Nos. | $Q^5$ |
|---|---|
| 260 | 1-isobutyl-5-methyl-1H-pyrazol-3-yl group |
| 261 | 1-(3-methylbutyl)-5-methyl-1H-pyrazol-3-yl group |

TABLE 16

| substituents Nos. | $Q^5$ |
|---|---|
| 262 | 1-(4-methyl-pentyl)-5-methyl-1H-pyrazol-3-yl group |
| 263 | 1,4,5-trimethyl-1H-pyrazol-3-yl group |
| 264 | 1-ethyl-4,5-dimethyl-1H-pyrazol-3-yl group |
| 265 | 4,5-dimethyl-1-isopropyl-1H-pyrazol-3-yl group |
| 266 | 1-(2,2-difluoroethyl)-4,5-dimethyl-1H-pyrazol-3-yl group |
| 267 | 4,5-dimethyl-1-(2-propynyl)-1H-pyrazol-3-yl group |
| 268 | 1-(2-butynyl)-4,5-dimethyl-1H-pyrazol-3-yl group |
| 269 | 1-cyclopropylmethyl-4,5-dimethyl-1H-pyrazol-3-yl group |
| 270 | 4,5-dimethyl-1-(2,2,2-trifluoroethyl)-1H-pyrazol-3-yl group |
| 271 | 4,5-dimethyl-1-propyl-1H-pyrazol-3-yl group |
| 272 | 1-butyl-4,5-dimethyl-1H-pyrazol-3-yl group |
| 273 | 4,5-dimethyl-1-isobutyl-1H-pyrazol-3-yl group |
| 274 | 4,5-dimethyl-1-(3-methylbutyl)-1H-pyrazol-3-yl group |
| 275 | 4,5-dimethyl-1-(4-methyl-pentyl)-1H-pyrazol-3-yl group |
| 276 | 4-ethyl-1,5-dimethyl-1H-pyrazol-3-yl group |

TABLE 17

| substituents Nos. | $Q^5$ |
|---|---|
| 277 | 1,4-diethyl-5-methyl-1H-pyrazol-3-yl group |
| 278 | 1-isopropyl-4-ethyl-5-methyl-1H-pyrazol-3-yl group |
| 279 | 4-ethyl-1-(2,2-difluoroethyl)-5-methyl-1H-pyrazol-3-yl group |
| 280 | 4-ethyl-5-methyl-1-(2-propynyl)-1H-pyrazol-3-yl group |
| 281 | 1-(2-butynyl)-4-ethyl-5-methyl-1H-pyrazol-3-yl group |
| 282 | 1-cyclopropylmethyl-4-ethyl-5-methyl-1H-pyrazol-3-yl group |
| 283 | 4-ethyl-1-(2,2,2-trifluoroethyl)-5-methyl-1H-pyrazol-3-yl group |
| 284 | 4-ethyl-1-propyl-5-methyl-1H-pyrazol-3-yl group |
| 285 | 1-butyl-4-ethyl-5-methyl-1H-pyrazol-3-yl group |
| 286 | 4-ethyl-1-isobutyl-5-methyl-1H-pyrazol-3-yl group |
| 287 | 4-ethyl-1-(3-methylbutyl)-5-methyl-1H-pyrazol-3-yl group |
| 288 | 4-ethyl-1-(4-methyl-pentyl)-5-methyl-1H-pyrazol-3-yl group |
| 289 | 4-fluoro-1,5-dimethyl-1H-pyrazol-3-yl group |
| 290 | 1-ethyl-4-fluoro-5-methyl-1H-pyrazol-3-yl group |

TABLE 18

| substituents Nos. | $Q^5$ |
|---|---|
| 291 | 4-fluoro-1-isopropyl-5-methyl-1H-pyrazol-3-yl group |
| 292 | 1-(2,2-difluoroethyl)-4-fluoro5-methyl-1H-pyrazol-3-yl group |

TABLE 18-continued

| substituents Nos. | Q⁵ |
|---|---|
| 293 | 4-fluoro-5-methyl-1-(2-propynyl)-1H-pyrazol-3-yl group |
| 294 | 1-(2-butynyl)-4-fluoro-5-methyl-1H-pyrazol-3-yl group |
| 295 | 1-cyclopropylmethyl-4-fluoro-5-methyl-1H-pyrazol-3-yl group |
| 296 | 1-(2,2,2-trifluoroethyl)-4-fluoro5-methyl-1H-pyrazol-3-yl group |
| 297 | 1-propyl-4-fluoro-5-methyl-1H-pyrazol-3-yl group |
| 298 | 1-butyl-4-fluoro-5-methyl-1H-pyrazol-3-yl group |
| 299 | 1-isobutyl-4-fluoro-5-methyl-1H-pyrazol-3-yl group |
| 300 | 4-fluoro-1-(3-methylbutyl)-5-methyl-1H-pyrazol-3-yl group |
| 301 | 4-fluoro-1-(4-methyl-pentyl)-5-methyl-1H-pyrazol-3-yl group |
| 302 | 4-chloro-1,5-dimethyl-1H-pyrazol-3-yl group |
| 303 | 4-chloro-1-ethyl-5-methyl-1H-pyrazol-3-yl group |
| 304 | 4-chloro-1-isopropyl-5-methyl-1H-pyrazol-3-yl group |
| 305 | 4-chloro-1-(2,2-difluoroethyl)-5-methyl-1H-pyrazol-3-yl group |

TABLE 19

| substituents Nos. | Q⁵ |
|---|---|
| 306 | 4-chloro-5-methyl-1-(2-propynyl)-1H-pyrazol-3-yl group |
| 307 | 1-(2-butynyl)-4-chloro-5-methyl-1H-pyrazol-3-yl group |
| 308 | 4-chloro-1-cyclopropylmethyl-5-methyl-1H-pyrazol-3-yl group |
| 309 | 4-chloro-1-(2,2,2-trifluoroethyl)-5-methyl-1H-pyrazol-3-yl group |
| 310 | 4-chloro-5-methyl-1-propyl-1H-pyrazol-3-yl group |
| 311 | 1-butyl-4-chloro-5-methyl-1H-pyrazol-3-yl group |
| 312 | 4-chloro-1-isobutyl-5-methyl-1H-pyrazol-3-yl group |
| 313 | 4-chloro-1-(3-methylbutyl)-5-methyl-1H-pyrazol-3-yl group |
| 314 | 4-chloro-1-(4-methyl-pentyl)-5-methyl-1H-pyrazol-3-yl group |
| 315 | 4-bromo-1,5-dimethyl-1H-pyrazol-3-yl group |
| 316 | 4-bromo-1-ethyl-5-methyl-1H-pyrazol-3-yl group |
| 317 | 4-bromo-1-isopropyl-5-methyl-1H-pyrazol-3-yl group |
| 318 | 4-bromo-1-(2,2-difluoroethyl)-5-methyl-1H-pyrazol-3-yl group |
| 319 | 4-bromo-5-methyl-1-(2-propynyl)-1H-pyrazol-3-yl group |

TABLE 20

| substituents Nos. | Q⁵ |
|---|---|
| 320 | 4-bromo-1-(2-butynyl)-5-methyl-1H-pyrazol-3-yl group |
| 321 | 4-bromo-1-cyclopropylmethyl-5-methyl-1H-pyrazol-3-yl group |
| 322 | 4-bromo-5-methyl-1-(2,2,2-trifluoroethyl)-1H-pyrazol-3-yl group |
| 323 | 4-bromo-5-methyl-1-propyl-1H-pyrazol-3-yl group |
| 324 | 4-bromo-1-butyl-5-methyl-1H-pyrazol-3-yl group |
| 325 | 4-bromo-1-isobutyl-5-methyl-1H-pyrazol-3-yl group |
| 326 | 4-bromo-1-(3-methylbutyl)-5-methyl-1H-pyrazol-3-yl group |

TABLE 20-continued

| substituents Nos. | Q⁵ |
|---|---|
| 327 | 4-bromo-1-(4-methyl-pentyl)-5-methyl-1H-pyrazol-3-yl group |
| 328 | 5-ethyl-1-methyl-1H-pyrazol-3-yl group |
| 329 | 1,5-diethyl-1H-pyrazol-3-yl group |
| 330 | 5-ethyl-1-isopropyl-1H-pyrazol-3-yl group |
| 331 | 5-ethyl-1-(2,2-difluoroethyl)-1H-pyrazol-3-yl group |
| 332 | 5-ethyl-1-(2-propynyl)-1H-pyrazol-3-yl group |
| 333 | 1-(2-butynyl)-5-ethyl-1H-pyrazol-3-yl group |
| 334 | 1-cyclopropylmethyl-5-ethyl-1H-pyrazol-3-yl group |
| 335 | 1-(2,2,2-trifluoroethyl)-5-ethyl-1H-pyrazol-3-yl group |

TABLE 21

| substituents Nos. | Q⁵ |
|---|---|
| 336 | 5-ethyl-1-propyl-1H-pyrazol-3-yl group |
| 337 | 1-butyl-5-ethyl-1H-pyrazol-3-yl group |
| 338 | 5-ethyl-1-isobutyl-1H-pyrazol-3-yl group |
| 339 | 5-ethyl-1-(3-methylbutyl)-1H-pyrazol-3-yl group |
| 340 | 5-ethyl-1-(4-methyl-pentyl)-1H-pyrazol-3-yl group |
| 341 | 5-ethyl-1,4-dimethyl-1H-pyrazol-3-yl group |
| 342 | 1,5-diethyl-4-methyl-1H-pyrazol-3-yl group |
| 343 | 5-ethyl-1-isopropyl4-methyl-1H-pyrazol-3-yl group |
| 344 | 5-ethyl-1-(2,2-difluoroethyl)-4-methyl-1H-pyrazol-3-yl group |
| 345 | 5-ethyl-1-(2-propynyl)-4-methyl-1H-pyrazol-3-yl group |
| 346 | 1-(2-butynyl)-5-ethyl-4-methyl-1H-pyrazol-3-yl group |
| 347 | 1-cyclopropylmethyl-5-ethyl-4-methyl-1H-pyrazol-3-yl group |
| 348 | 5-ethyl-4-methyl-1-(2,2,2-trifluoroethyl)-1H-pyrazol-3-yl group |

TABLE 22

| substituents Nos. | Q⁵ |
|---|---|
| 349 | 5-ethyl4-methyl-1-propyl-1H-pyrazol-3-yl group |
| 350 | 1-butyl-5-ethyl4-methyl-1H-pyrazol-3-yl group |
| 351 | 5-ethyl-1-isobutyl-4-methyl-1H-pyrazol-3-yl group |
| 352 | 5-ethyl-1-(3-methylbutyl)-4-methyl-1H-pyrazol-3-yl group |
| 353 | 5-ethyl-1-(4-methyl-pentyl)-4-methyl-1H-pyrazol-3-yl group |
| 354 | 4,5-diethyl-1-methyl-1H-pyrazol-3-yl group |
| 355 | 1,4,5-triethyl-1H-pyrazol-3-yl group |
| 356 | 4,5-diethyl-1-isopropyl-1H-pyrazol-3-yl group |
| 357 | 4,5-diethyl-1-(2,2-difluoroethyl)-1H-pyrazol-3-yl group |
| 358 | 4,5-diethyl-1-(2-propynyl)-1H-pyrazol-3-yl group |
| 359 | 1-(2-butynyl)-4,5-diethyl-1H-pyrazol-3-yl group |
| 360 | 1-cyclopropylmethyl-4,5-diethyl-1H-pyrazol-3-yl group |
| 361 | 4,5-diethyl-1-(2,2,2-trifluoroethyl)-1H-pyrazol-3-yl group |
| 362 | 4,5-diethyl-1-propyl-1H-pyrazol-3-yl group |
| 363 | 1-butyl-4,5-diethyl-1H-pyrazol-3-yl group |

TABLE 23

| substituents Nos. | Q⁵ |
|---|---|
| 364 | 4,5-diethyl-1-pentyl-1H-pyrazol-3-yl group |
| 365 | 4,5-diethyl-1-isobutyl-1H-pyrazol-3-yl group |
| 366 | 4,5-diethyl-1-(3-methyl-butyl)-1H-pyrazol-3-yl group |
| 367 | 4,5-diethyl-1-(4-methyl-pentyl)-1H-pyrazol-3-yl group |
| 368 | 5-ethyl-4-fluoro-1-methyl-1H-pyrazol-3-yl group |
| 369 | 1,5-ethyl-4-fluoro-1H-pyrazol-3-yl group |
| 370 | 5-ethyl-4-fluoro-1-isopropyl-1H-pyrazol-3-yl group |
| 371 | 1-(2,2-difluoroethyl)-5-ethyl-4-fluoro-1H-pyrazol-3-yl group |
| 372 | 5-ethyl-4-fluoro-1-(2-propynyl)-1H-pyrazol-3-yl group |
| 373 | 1-(2-butynyl)-5-ethyl-4-fluoro-1H-pyrazol-3-yl group |
| 374 | 1-cyclopropylmethyl-5-ethyl-4-fluoro-1H-pyrazol-3-yl group |
| 375 | 5-ethyl-4-fluoro-1-(2,2,2-trifluoroethyl)-1H-pyrazol-3-yl group |
| 376 | 5-ethyl-4-fluoro-1-propyl-1H-pyrazol-3-yl group |
| 377 | 1-butyl-5-ethyl-4-fluoro-1H-pyrazol-3-yl group |

TABLE 24

| substituents Nos. | Q⁵ |
|---|---|
| 378 | 5-ethyl-4-fluoro-1-pentyl-1H-pyrazol-3-yl group |
| 379 | 5-ethyl-4-fluoro-1-isobutyl-1H-pyrazol-3-yl group |
| 380 | 5-ethyl-4-fluoro-(3-methylbutyl)-1H-pyrazol-3-yl group |
| 381 | 5-ethyl-4-fluoro(4-methyl-penty)-1H-pyrazol-3-yl group |
| 382 | 4-bromo-5-ethyl-1-methyl-1H-pyrazol-3-yl group |
| 383 | 4-bromo-5-ethyl-1-ethyl-1H-pyrazol-3-yl group |
| 384 | 4-bromo-5-ethyl-1-isopropyl-1H-pyrazol-3-yl group |
| 385 | 4-bromo-1-(2,2-difluoroethyl)-5-ethyl-1H-pyrazol-3-yl group |
| 386 | 4-bromo-5-ethyl-1-(2-propynyl)-1H-pyrazol-3-yl group |
| 387 | 4-bromo-1-(2-butynyl)-5-ethyl-1H-pyrazol-3-yl group |
| 388 | 4-bromo-1-cyclopropylmethyl-5-ethyl-1H-pyrazol-3-yl group |
| 389 | 4-bromo-1-5-ethyl-(2,2,2-trifluoroethyl)-1H-pyrazol-3-yl group |
| 390 | 4-bromo-5-ethyl-1-propyl-1H-pyrazol-3-yl group |
| 391 | 4-bromo-1-butyl-5-ethyl-1H-pyrazol-3-yl group |
| 392 | 4-bromo-5-ethyl-1-pentyl-1H-pyrazol-3-yl group |

TABLE 25

| substituents Nos. | Q⁵ |
|---|---|
| 393 | 4-bromo-5-ethyl-1-isobutyl-1H-pyrazol-3-yl group |
| 394 | 4-bromo-5-ethyl-(3-methylbutyl)-1H-pyrazol-3-yl group |
| 395 | 4-bromo-5-ethyl-(4-methyl-pentyl)-1H-pyrazol-3-yl group |
| 396 | 5-cyclopropyl-1-methyl-1H-pyrazol-3-yl group |

TABLE 25-continued

| substituents Nos. | Q⁵ |
|---|---|
| 397 | 5-cyclopropyl-1-ethyl-1H-pyrazol-3-yl group |
| 398 | 5-cyclopropyl-1-isopropyl-1H-pyrazol-3-yl group |
| 399 | 5-cyclopropyl-1-(2,2-difluoroethyl)-1H-pyrazol-3-yl group |
| 400 | 5-cyclopropyl-1-(2-propynyl)-1H-pyrazol-3-yl group |
| 401 | 1-(2-butynyl)-5-cyclopropyl-1H-pyrazol-3-yl group |
| 402 | 1-cyclopropylmethyl-5-cyclopropyl-1H-pyrazol-3-yl group |
| 403 | 5-cyclopropyl-1-(2,2,2-trifluoroethyl)-1H-pyrazol-3-yl group |
| 404 | 5-cyclopropyl-1-propyl-1H-pyrazol-3-yl group |
| 405 | 1-butyl-5-cyclopropyl-1H-pyrazol-3-yl group |
| 406 | 5-cyclopropyl-1-pentyl-1H-pyrazol-3-yl group |

TABLE 26

| substituents Nos. | Q⁵ |
|---|---|
| 407 | 5-cyclopropyl-1-isobutyl-1H-pyrazol-3-yl group |
| 408 | 5-cyclopropyl-1-(3-methylbutyl)-1H-pyrazol-3-yl group |
| 409 | 5-cyclopropyl-1-(4-methyl-pentyl)-1H-pyrazol-3-yl group |
| 410 | 5-cyclopropyl-1,4-dimethyl-1H-pyrazol-3-yl group |
| 411 | 5-cyclopropyl-1-ethyl-4-methyl-1H-pyrazol-3-yl group |
| 412 | 5-cyclopropyl-1-isopropyl-4-methyl-1H-pyrazol-3-yl group |
| 413 | 5-cyclopropyl-1-(2,2-difluoroethyl)-4-methyl-1H-pyrazol-3-yl group |
| 414 | 5-cyclopropyl-4-methyl-1-(2-propynyl)-1H-pyrazol-3-yl group |
| 415 | 1-(2-butynyl)-5-cyclopropyl-4-methyl-1H-pyrazol-3-yl group |
| 416 | 1-cyclopropylmethyl-5-cyclopropyl-4-methyl-1H-pyrazol-3-yl group |
| 417 | 5-cyclopropyl-1-(2,2,2-trifluoroethyl)-4-methyl-1H-pyrazol-3-yl group |
| 418 | 5-cyclopropyl-4-methyl-1-propyl-1H-pyrazol-3-yl group |
| 419 | 1-butyl-5-cyclopropyl-4-methyl-1H-pyrazol-3-yl group |
| 420 | 5-cyclopropyl-4-methyl-1-pentyl-1H-pyrazol-3-yl group |
| 421 | 5-cyclopropyl-1-isobutyl-4-methyl-1H-pyrazol-3-yl group |

TABLE 27

| substituents Nos. | Q⁵ |
|---|---|
| 422 | 5-cyclopropyl-4-methyl-1-(3-methylbutyl)-1H-pyrazol-3-yl group |
| 423 | 5-cyclopropyl-4-methyl-1-(4-methyl-pentyl)-1H-pyrazol-3-yl group |
| 424 | 5-cyclopropyl-4-fluoro-1-methyl-1H-pyrazol-3-yl group |
| 425 | 5-cyclopropyl-4-fluoro-1-ethyl-1H-pyrazol-3-yl group |
| 426 | 5-cyclopropyl-4-fluoro-1-isopropyl-1H-pyrazol-3-yl group |
| 427 | 5-cyclopropyl-4-fluoro-1-(2,2-difluoroethyl)-1H-pyrazol-3-yl group |
| 428 | 5-cyclopropyl-4-fluoro-1-(2-propynyl)-1H-pyrazol-3-yl group |

TABLE 27-continued

| substituents Nos. | Q⁵ |
|---|---|
| 429 | 1-(2-butynyl)-5-cyclopropyl-4-fluoro-1H-pyrazol-3-yl group |
| 430 | 5-cyclopropyl-1-cyclopropylmethyl-4-fluoro-1H-pyrazol-3-yl group |
| 431 | 5-cyclopropyl-4-fluoro-1-(2,2,2-trifluoroethyl)-1H-pyrazol-3-yl group |
| 432 | 5-cyclopropyl-4-fluoro-1-propyl-1H-pyrazol-3-yl group |
| 433 | 1-butyl-5-cyclopropyl-4-fluoro-1H-pyrazol-3-yl group |
| 434 | 5-cyclopropyl-4-fluoro-1-pentyl-1H-pyrazol-3-yl group |
| 435 | 5-cyclopropyl-4-fluoro-1-isobutyl-1H-pyrazol-3-yl group |

TABLE 28

| substituents Nos. | Q⁵ |
|---|---|
| 436 | 5-cyclopropyl-4-fluoro-1-(3-methylbutyl)-1H-pyrazol-3-yl group |
| 437 | 5-cyclopropyl-4-fluoro-1-(4-methyl-pentyl)-1H-pyrazol-3-yl group |
| 438 | 4-chloro-5-cyclopropyl-1-methyl-1H-pyrazol-3-yl group |
| 439 | 4-chloro-5-cyclopropyl-1-ethyl-1H-pyrazol-3-yl group |
| 440 | 4-chloro-5-cyclopropyl-1-isopropyl-1H-pyrazol-3-yl group |
| 441 | 4-chloro-5-cyclopropyl-1-(2,2-difluoroethyl)-1H-pyrazol-3-yl group |
| 442 | 4-chloro-5-cyclopropyl-1-(2-propynyl)-1H-pyrazol-3-yl group |
| 443 | 1-(2-butynyl)-4-chloro-5-cyclopropyl-1H-pyrazol-3-yl group |
| 444 | 4-chloro-1-cyclopropylmethyl-5-cyclopropyl-1H-pyrazol-3-yl group |
| 445 | 4-chloro-5-cyclopropyl-1-(2,2,2-trifluoroethyl)-1H-pyrazol-3-yl group |
| 446 | 4-chloro-5-cyclopropyl-1-propyl-1H-pyrazol-3-yl group |
| 447 | 4-chloro-5-cyclopropyl-1-butyl-1H-pyrazol-3-yl group |
| 448 | 4-chloro-5-cyclopropyl-1-pentyl-1H-pyrazol-3-yl group |
| 449 | 4-chloro-5-cyclopropyl-1-isobutyl-1H-pyrazol-3-yl group |

TABLE 29

| substituents Nos. | Q⁵ |
|---|---|
| 450 | 4-bromo-5-cyclopropyl-1-methyl-1H-pyrazol-3-yl group |
| 451 | 4-bromo-5-cyclopropyl-1-ethyl-1H-pyrazol-3-yl group |
| 452 | 4-bromo-5-cyclopropyl-1-isopropyl-1H-pyrazol-3-yl group |
| 453 | 4-bromo-5-cyclopropyl-1-(2,2-difluoroethyl)-1H-pyrazol-3-yl group |
| 454 | 4-bromo-5-cyclopropyl-1-(2-propynyl)-1H-pyrazol-3-yl group |
| 455 | 4-bromo-1-(2-butynyl)-5-cyclopropyl-1H-pyrazol-3-yl group |
| 456 | 4-bromo-1-cyclopropyl-methyl-5-cyclopropyl-1H-pyrazol-3-yl group |
| 457 | 4-bromo-5-cyclopropyl-1-(2,2,2-trifluoroethyl)-1H-pyrazol-3-yl group |
| 458 | 4-bromo-5-cyclopropyl-1-propyl-1H-pyrazol-3-yl group |

TABLE 29-continued

| substituents Nos. | Q⁵ |
|---|---|
| 459 | 4-bromo-1-butyl-5-cyclopropyl-1H-pyrazol-3-yl group |
| 460 | 4-bromo-5-cyclopropyl-1-pentyl-1H-pyrazol-3-yl group |
| 461 | 4-bromo-5-cyclopropyl-1-isobutyl-1H-pyrazol-3-yl group |
| 462 | 5-isopropyl-1-methyl-1H-pyrazol-3-yl group |
| 463 | 1-ethyl-5-isopropyl-1H-pyrazol-3-yl group |
| 464 | 1,5-diisopropyl-1H-pyrazol-3-yl group |

TABLE 30

| substituents Nos. | Q⁵ |
|---|---|
| 465 | 1-(2,2-difluoroethyl)-5-isopropyl-1H-pyrazol-3-yl group |
| 466 | 5-isopropyl-1-(2-propynyl)-1H-pyrazol-3-yl group |
| 467 | 1-(2-butynyl)-5-isopropyl-1H-pyrazol-3-yl group |
| 468 | 1-cyclopropylmethyl-5-isopropyl-1H-pyrazol-3-yl group |
| 469 | 5-isopropyl-1-(2,2,2-trifluoroethyl)-1H-pyrazol-3-yl group |
| 470 | 5-isopropyl-1-propyl-1H-pyrazol-3-yl group |
| 471 | 1-butyl-5-isopropyl-1H-pyrazol-3-yl group |
| 472 | 5-isopropyl-1-pentyl-1H-pyrazol-3-yl group |
| 473 | 1-isobutyl-5-isopropyl-1H-pyrazol-3-yl group |
| 474 | 5-isopropyl-1-(3-methylbutyl)-1H-pyrazol-3-yl group |
| 475 | 5-isopropyl-1-(4-methyl-pentyl)-1H-pyrazol-3-yl group |
| 476 | 1,4-dimethyl-5-isopropyl-1H-pyrazol-3-yl group |
| 477 | 1-ethyl-5-isopropyl-4-methyl-1H-pyrazol-3-yl group |
| 478 | 1,5-diisopropyl-4-methyl-1H-pyrazol-3-yl group |
| 479 | 1-(2,2-difluoroethy)-5-isopropyl4-methyl-1H-pyrazol-3-yl group |

TABLE 31

| substituents Nos. | Q⁵ |
|---|---|
| 480 | 5-isopropyl-4-methyl-1-(2-propynyl)-1H-pyrazol-3-yl group |
| 481 | 1-(2-butynyl)-5-isopropyl-4-methyl-1H-pyrazol-3-yl group |
| 482 | 1-cyclopropylmethyl-5-isopropyl-4-methyl-1H-pyrazol-3-yl group |
| 483 | 5-isopropyl-4-methyl-1-(2,2,2-trifluoroethyl)-1H-pyrazol-3-yl group |
| 484 | 5-isopropyl-l-propyl-4-methyl-1H-pyrazol-3-yl group |
| 485 | 1-butyl-5-isopropyl-4-methyl-1H-pyrazol-3-yl group |
| 486 | 5-isopropyl-4-methyl-1-pentyl-1H-pyrazol-3-yl group |
| 487 | 5-isopropyl-4-methyl-1-isobutyl-1H-pyrazol-3-yl group |
| 488 | 5-isopropyl-1-(3-methylbutyl)-4-methy-1H-pyrazol-3-yl group |
| 489 | 5-isopropyl-4-methyl-1-(4-methyl-pentyl)-1H-pyrazol-3-yl group |
| 490 | 4-fluoro-5-isopropyl-1-methyl-1H-pyrazol-3-yl group |

TABLE 31-continued

| substituents Nos. | $Q^5$ |
|---|---|
| 491 | 4-fluoro-5-isopropyl-1-ethyl-1H-pyrazol-3-yl group |
| 492 | 4-fluoro-1,5-diisopropyl-1H-pyrazol-3-yl group |
| 493 | 4-fluoro-5-isopropyl-1-(2,2-difluoroethyl)-1H-pyrazol-3-yl group |

TABLE 32

| substituents Nos. | $Q^5$ |
|---|---|
| 494 | 4-fluoro-5-isopropyl-1-(2-propynyl)-1H-pyrazol-3-yl group |
| 495 | 4-fluoro-5-isopropyl-1-(2-butynyl)-1H-pyrazol-3-yl group |
| 496 | 4-fluoro-5-isopropyl-1-cyclopropylmethyl-1H-pyrazol-3-yl group |
| 497 | 4-fluoro-5-isopropyl-1-(2,2,2-trifluoroethyl)-1H-pyrazol-3-yl group |
| 498 | 4-fluoro-5-isopropyl-1-propyl-1H-pyrazol-3-yl group |
| 499 | 4-fluoro-5-isopropyl-1-butyl-1H-pyrazol-3-yl group |
| 500 | 4-fluoro-5-isopropyl-1-pentyl-1H-pyrazol-3-yl group |
| 501 | 4-fluoro-5-isopropyl-1-isobutyl-1H-pyrazol-3-yl group |
| 502 | 4-fluoro-5-isopropyl-1-(3-methylbutyl)-1H-pyrazol-3-yl group |
| 503 | 4-fluoro-5-isopropyl-1-(4-methyl-pentyl)-1H-pyrazol-3-yl group |
| 504 | 4-chloro-5-isopropyl-1-methyl-1H-pyrazol-3-yl group |
| 505 | 4-chloro-5-isopropyl-1-ethyl-1H-pyrazol-3-yl group |
| 506 | 4-chloro-1,5-diisopropyl-1H-pyrazol-3-yl group |
| 507 | 4-chloro-1-(2,2-difluoroethyl)-5-isopropyl-1H-pyrazol-3-yl group |
| 508 | 4-chloro-5-isopropyl-1-(2-propynyl)-1H-pyrazol-3-yl group |

TABLE 33

| substituents Nos. | $Q^5$ |
|---|---|
| 509 | 1-(2-butynyl)-4-chloro-5-isopropyl-1H-pyrazol-3-yl group |
| 510 | 4-chloro-5-isopropyl-1-cyclopropylmethyl-1H-pyrazol-3-yl group |
| 511 | 4-chloro-5-isopropyl-1-(2,2,2-trifluoroethyl)-1H-pyrazol-3-yl group |
| 512 | 4-chloro-5-isopropyl-1-propyl-1H-pyrazol-3-yl group |
| 513 | 4-chloro-5-isopropyl-1-butyl-1H-pyrazol-3-yl group |
| 514 | 4-chloro-5-isopropyl-1-pentyl-1H-pyrazol-3-yl group |
| 515 | 4-chloro-5-isopropyl-1-isobutyl-1H-pyrazol-3-yl group |
| 516 | 4-chloro-5-isopropyl-1-(3-methylbutyl)-1H-pyrazol-3-yl group |
| 517 | 4-chloro-5-isopropyl-1-(4-methyl-pentyl)-1H-pyrazol-3-yl group |
| 518 | 4-bromo-5-isopropyl-1-methyl-1H-pyrazol-3-yl group |
| 519 | 4-bromo-1-ethyl-5-isopropyl-1H-pyrazol-3-yl group |

TABLE 33-continued

| substituents Nos. | $Q^5$ |
|---|---|
| 520 | 4-bromo-1,5-diisopropyl-1H-pyrazol-3-yl group |
| 521 | 4-bromo-1-(2,2-difluoroethyl)-5-isopropyl-1H-pyrazol-3-yl group |
| 522 | 4-bromo-5-isopropyl-1-(2-propynyl)-1H-pyrazol-3-yl group |

TABLE 34

| substituents Nos. | $Q^5$ |
|---|---|
| 523 | 4-bromo-1-(2-butynyl)-5-isopropyl-1H-pyrazol-3-yl group |
| 524 | 4-bromo-1-cyclopropylmethyl-5-isopropyl-1H-pyrazol-3-yl group |
| 525 | 4-bromo-5-isopropyl-1-(2,2,2-trifluoroethyl)-1H-pyrazol-3-yl group |
| 526 | 4-bromo-5-isopropyl-1-propyl-1H-pyrazol-3-yl group |
| 527 | 4-bromo-1-butyl-5-isopropyl-1H-pyrazol-3-yl group |
| 528 | 4-bromo-5-isopropyl-1-pentyl-1H-pyrazol-3-yl group |
| 529 | 4-bromo-5-isopropyl-1-isobutyl-1H-pyrazol-3-yl group |
| 530 | 4-bromo-5-isopropyl-1-(3-methylbutyl)-1H-pyrazol-3-yl group |
| 531 | 4-bromo-5-isopropyl-1-(4-methyl-pentyl)-1H-pyrazol-3-yl group |
| 532 | 5-methoxy-1-methyl-1H-pyrazol-3-yl group |
| 533 | 1-ethyl-5-methoxy-1H-pyrazol-3-yl group |
| 534 | 5-methoxy-1-isopropyl-1H-pyrazol-3-yl group |
| 535 | 1-(2,2-difluoroethyl)-5-methoxy-1H-pyrazol-3-yl group |
| 536 | 5-methoxy-1-(2-propynyl)-1H-pyrazol-3-yl group |
| 537 | 1-(2-butynyl)-5-methoxy-1H-pyrazol-3-yl group |

TABLE 35

| substituents Nos. | $Q^5$ |
|---|---|
| 538 | 1-cyclopropylmethyl-5-methoxy-1H-pyrazol-3-yl group |
| 539 | 1,4-dimethyl-5-methoxy-1H-pyrazol-3-yl group |
| 540 | 1-ethyl-5-methoxy-4-methyl-1H-pyrazol-3-yl group |
| 541 | 5-methoxy-1-isopropyl-4-methyl-1H-pyrazol-3-yl group |
| 542 | 1-(2,2-difluoroethyl)-5-methoxy4-methyl-1H-pyrazol-3-yl group |
| 543 | 5-methoxy-1-(2-propynyl)-4-methyl-1H-pyrazol-3-yl group |
| 544 | 1-(2-2-butynyl)-5-methoxy-4-methyl-1H-pyrazol-3-yl group |
| 545 | 1-cyclopropylmethyl-5-methoxy-4-methyl-1H-pyrazol-3-yl group |
| 546 | 4-fluoro-5-methoxy-1-methyl-1H-pyrazol-3-yl group |
| 547 | 4-fluoro-5-methoxy-1-ethyl-1H-pyrazol-3-yl group |
| 548 | 4-fluoro-5-methoxy-1-isopropyl-1H-pyrazol-3-yl group |
| 549 | 1-(2, 2-difluoroethyl)-4-fluoro-5-methoxy-1H-pyrazol-3-yl group |
| 550 | 4-fluoro-5-methoxy-1-(2-propynyl)-1H-pyrazol-3-yl group |
| 551 | 1-(2-butynyl)-4-fluoro-5-methoxy-1H-pyrazol-3-yl group |

TABLE 36

| substituents Nos. | Q⁵ |
|---|---|
| 552 | 1-cyclopropylmethyl-4-fluoro-5-methoxy-1H-pyrazol-3-yl group |
| 553 | 4-chloro-5-methoxy-1-methyl-1H-pyrazol-3-yl group |
| 554 | 4-chloro-5-methoxy-1-ethyl-1H-pyrazol-3-yl group |
| 555 | 4,5-dichloro-1-ethyl-1H-pyrazol-3-yl group |
| 556 | 4-chloro-1-ethyl-5-trifluoromethyl-1H-pyrazol-3-yl group |
| 557 | 1-ethyl-5-trifluoromethyl-1H-pyrazol-3-yl group |
| 558 | 1-ethyl-4-methyl-5-trifluoromethyl-1H-pyrazol-3-yl group |
| 559 | 5-chloro-1-ethyl-1H-pyrazol-3-yl group |
| 560 | 5-chloro-1-ethyl4-methyl-1H-pyrazol-3-yl group |
| 561 | 4,5-dichloro-1-methyl-1H-pyrazol-3-yl group |
| 562 | 4-chloro-1-methyl-5-trifluoromethyl-1H-pyrazol-3-yl group |
| 563 | 1-methyl-5-trifluoromethyl-1H-pyrazol-3-yl group |
| 564 | 1,4-dimethyl-5-trifluoromethyl-1H-pyrazol-3-yl group |

TABLE 37

| substituents Nos. | Q⁵ |
|---|---|
| 565 | 5-chloro-1-methyl-1H-pyrazol-3-yl group |
| 566 | 5-chloro-1,4-dimethyl-1H-pyrazol-3-yl group |
| 567 | 5,6-dihydro-4H-pyrolo[1,2-b]pyrazol-2-yl group |
| 568 | 4,5,6,7-tetrahydro-pyrazolo[1,2-a]pyridin-2-yl group |
| 569 | 5,6-dihydro-3-methyl-4H-pyrolo[1,2-b]pyrazol-2-yl group |
| 570 | 4,5,6,7-3-methyl-tetrahydro-pyrazolo[1,2-a]pyridin-2-ylgroup |
| 571 | 1-methyl-1H-pyrazol-4-yl group |
| 572 | 1,5-dimethyl-1H-pyrazol-4-yl group |
| 573 | 1-ethyl-1H-pyrazol-4-yl group |
| 574 | 1-ethyl-5-methyl-1H-pyrazol-4-yl group |
| 575 | 1,3-dimethyl-1H-pyrazol-4-yl group |
| 576 | 1,3,5-trimethyl-1H-pyrazol-4-yl group |
| 577 | 1-ethyl-3-methyl-1H-pyrazol-4-yl group |
| 578 | 3,5-dimethyl-1-ethyl-1H-pyrazol-4-yl group |
| 579 | 1-(2-propynyl)-1H-pyrazol-4-yl group |
| 580 | 5-methyl-1-(2-propynyl)-1H-pyrazol-4-yl group |

TABLE 38

| substituents Nos. | Q⁵ |
|---|---|
| 581 | 3-methyl-1-(2-propynyl)-1H-pyrazol-4-yl group |
| 582 | 3,5-dimethyl-1-(2-propynyl)-1H-pyrazol-4-yl group |
| 583 | 1-cyclopropylmethyl-1H-pyrazol-4-yl group |
| 584 | 1-cyclopropylmethyl-3-methyl-1H-pyrazol-4-yl group |
| 585 | 1-cyclopropylmethyl-5-methyl-1H-pyrazol-4-yl group |
| 586 | 1-cyclopropylmethyl-3,5-dimethyl-1H-pyrazol-4-yl group |
| 587 | 1-(2,2-difluoroethyl)-1H-pyrazol-4-yl group |
| 588 | 1-(2,2-difluoroethyl)-3-methyl-1H-pyrazol-4-yl group |
| 589 | 1-(2,2-difluoroethyl)-5-methyl-1H-pyrazol-4-yl group |
| 590 | 1-(2, 2-difluoroethyl)-3, 5-dimethyl-1H-pyrazol-4-yl group |

TABLE 38-continued

| substituents Nos. | Q⁵ |
|---|---|
| 591 | 1-methyl-1H-pyrazol-5-yl group |
| 592 | 1,4-dimethyl-1H-pyrazol-5-yl group |
| 593 | 4-fluoro-1-methyl-1H-pyrazol-5-yl group |
| 594 | 4-chloro-1-methyl-1H-pyrazol-5-yl group |
| 595 | 4-bromo-1-methyl-1H-pyrazol-5-yl group |
| 596 | 1-ethyl-1H-pyrazol-5-yl group |
| 597 | 1-ethyl-4-methyl-1H-pyrazol-5-yl group |
| 598 | 1-ethyl-4-fluoro-1H-pyrazol-5-yl group |
| 599 | 4-chloro-1-ethyl-1H-pyrazol-5-yl group |
| 600 | 4-bromo-1-ethyl-1H-pyrazol-5-yl group |
| 601 | 1-propyl-1H-pyrazol-5-yl group |
| 602 | 4-methyl-1-propyl-1H-pyrazol-5-yl group |
| 603 | 4-fluoro-1-propyl-1H-pyrazol-5-yl group |
| 604 | 4-chloro-1-propyl-1H-pyrazol-5-yl group |
| 605 | 4-bromo-1-propyl-1H-pyrazol-5-yl group |
| 606 | 1-butyl-1H-pyrazol-5-yl group |
| 607 | 1-butyl-4-methyl-1H-pyrazol-5-yl group |
| 608 | 1-butyl-4-fluoro-1H-pyrazol-5-yl group |
| 609 | 1-butyl-4-chloro-1H-pyrazol-5-yl group |

TABLE 39

| substituents Nos. | Q⁵ |
|---|---|
| 610 | 1-butyl-4-bromo-1H-pyrazol-5-yl group |
| 611 | 1,3-dimethyl-1H-pyrazol-5-yl group |
| 612 | 1,3,4-trimethyl-1H-pyrazol-5-yl group |
| 613 | 1,3-dimethyl-4-fluoro-1H-pyrazol-5-yl group |
| 614 | 4-chloro-1,3-dimethyl-1H-pyrazol-5-yl group |
| 615 | 4-bromo-1,3-dimethyl-1H-pyrazol-5-yl group |
| 616 | 1-ethyl-3-methyl-1H-pyrazol-5-yl group |
| 617 | 3,4-dimethyl-1-ethyl-1H-pyrazol-5-yl group |
| 618 | 1-ethyl-4-fluoro-3-methyl-1H-pyrazol-5-yl group |
| 619 | 4-chloro-1-ethyl-3-methyl-1H-pyrazol-5-yl group |
| 620 | 4-bromo-1-ethyl-3-methyl-1H-pyrazol-5-yl group |
| 621 | 3-methyl-1-propyl-1H-pyrazol-5-yl group |
| 622 | 3,4-dimethyl-1-propyl-1H-pyrazol-5-yl group |
| 623 | 3,4-dimethyl-4-fluoro-1-propyl-1H-pyrazol-5-yl group |
| 624 | 4-chloro-3,4-dimethyl-1-propyl-1H-pyrazol-5-yl group |

TABLE 40

| substituents Nos. | Q⁵ |
|---|---|
| 625 | 4-bromo-3,4-dimethyl-1-propyl-1H-pyrazol-5-yl group |
| 626 | 1-butyl-3-methyl-1H-pyrazol-5-yl group |
| 627 | 1-butyl-3,4-dimethyl-1H-pyrazol-5-yl group |
| 628 | 1-butyl-4-fluoro3,4-dimethyl-1H-pyrazol-5-yl group |
| 629 | 1-butyl-4-chloro-3,4-dimethyl-1H-pyrazol-5-yl group |
| 630 | 1-butyl-4-bromo-3,4-dimethyl-1H-pyrazol-5-yl group |
| 631 | 3-ethyl-1-methyl-1H-pyrazol-5-yl group |
| 632 | 1,4-dimethyl-3-ethyl-1H-pyrazol-5-yl group |
| 633 | 3-ethyl-4-fluoro-1-methyl-1H-pyrazol-5-yl group |
| 634 | 4-chloro-3-ethyl-1-methyl-1H-pyrazol-5-yl group |
| 635 | 4-bromo-3-ethyl-1-methyl-1H-pyrazol-5-yl group |

TABLE 40-continued

| substituents Nos. | Q⁵ |
|---|---|
| 636 | 1,3-diethyl-1H-pyrazol-5-yl group |
| 637 | 1,3-diethyl-4-methyl-1H-pyrazol-5-yl group |
| 638 | 1,3-diethyl-4-fluoro-1H-pyrazol-5-yl group |

TABLE 41

| substituents Nos. | Q⁵ |
|---|---|
| 639 | 4-chloro-1,3-diethyl-1H-pyrazol-5-yl group |
| 640 | 4-bromo-1,3-diethyl-1H-pyrazol-5-yl group |
| 641 | 4-fluoro-1,3-diethyl-1H-pyrazol-5-yl group |
| 642 | 3-ethyl-1-propyl-1H-pyrazol-5-yl group |
| 643 | 3-ethyl-4-methyl-1-propyl-1H-pyrazol-5-yl group |
| 644 | 4-fluoro-3-ethyl-1-propyl-1H-pyrazol-5-yl group |
| 645 | 4-chloro-3-ethyl-1-propyl-1H-pyrazol-5-yl group |
| 646 | 4-bromo-3-ethyl-1-propyl-1H-pyrazol-5-yl group |
| 647 | 1-butyl-3-ethyl-1H-pyrazol-5-yl group |
| 648 | 1-butyl-3-ethyl-4-methyl-1H-pyrazol-5-yl group |
| 649 | 1-butyl-3-ethyl-4-fluoro-1H-pyrazol-5-yl group |
| 650 | 1-butyl-4-chloro-3-ethyl-1H-pyrazol-5-yl group |
| 651 | 4-bromo-1-butyl-3-ethyl-1H-pyrazol-5-yl group |
| 652 | 1-(2-propynyl)-1H-pyrazol-5-yl group |
| 653 | 4-methyl-1-(2-propynyl)-1H-pyrazol-5-yl group |
| 654 | 3-methyl-1-(2-propynyl)-1H-pyrazol-5-yl group |
| 655 | 3,4-dimethyl-1-(2-propynyl)-1H-pyrazol-5-yl group |
| 656 | 1-cyclopropylmethyl-1H-pyrazol-5-yl group |
| 657 | 1-cyclopropylmethyl-4-methyl-1H-pyrazol-5-yl group |
| 658 | 1-cyclopropylmethyl-3-methyl-1H-pyrazol-5-yl group |
| 659 | 1-cyclopropylmethyl-3,4-dimethyl-1H-pyrazol-5-yl group |
| 660 | 1-(2-butynyl)-1H-pyrazol-5-yl group |

TABLE 42

| substituents Nos. | Q⁵ |
|---|---|
| 661 | 1,5-dimethyl-4-iodo-1H-pyrazol-3-yl group |
| 662 | 4-cyano-1,5-dimethyl-1H-pyrazol-3-yl group |
| 663 | 5-ethyl-1-methyl-4-iodo-1H-pyrazol-3-yl group |
| 664 | 4-cyano-5-ethyl-1-methyl-1H-pyrazol-3-yl group |
| 665 | 1,5-diethyl-4-iodo-1H-pyrazol-3-yl group |
| 666 | 4-cyano-1,5-diethyl-1H-pyrazol-3-yl group |
| 667 | 1,4-dimethyl-5-ethoxy-1H-pyrazol-3-yl group |
| 668 | 4-ethyl-1-methyl-5-ethoxy-1H-pyrazol-3-yl group |
| 669 | 1-ethyl-4-methyl-5-ethoxy-1H-pyrazol-3-yl group |
| 670 | 1,4-dimethyl-5-methylthio-1H-pyrazol-3-yl group |
| 671 | 1,4-dimethyl-5-ethylthio-1H-pyrazol-3-yl group |
| 672 | 1,4-diethyl-5-methylthio-1H-pyrazol-3-yl group |
| 673 | 5-cyano-1,4-dimethyl-1H-pyrazol-3-yl group |
| 674 | 5-cyano-1,4-diethyl-1H-pyrazol-3-yl group |
| 675 | 5-cyano-4-ethyl-1-methyl-1H-pyrazol-3-yl group |
| 676 | 5-cyano-1-ethyl-4-methyl-1H-pyrazol-3-yl group |

TABLE 42-continued

| substituents Nos. | Q⁵ |
|---|---|
| 677 | 3-chloro-1,3-dimethyl-1H-pyrazol-3-5yl |
| 678 | 1,3-dimethyl-3-methoxy-1H-pyrazol-3-5yl |
| 679 | 3-cyano-1,3-dimethyl-1H-pyrazol-3-5yl |
| 680 | 4-chloro-3-cyano-1-methyl-1H-pyrazol-3-5-yl |

TABLE 43

| substituents Nos. | Q⁵ |
|---|---|
| 681 | 5-fluoro-1-methyl-1H-pyrazol-3-yl group |
| 682 | 5-bromo-1-methyl-1H-pyrazol-3-yl group |
| 683 | 5-ethoxy-1-methyl-1H-pyrazol-3-yl group |
| 684 | 5-cyano-1-methyl-1H-pyrazol-3-yl group |
| 685 | 5-difluoromethyl-1-methyl-1H-pyrazol-3-yl group |
| 686 | 4,5-difluoro-1-methyl-1H-pyrazol-3-yl group |
| 687 | 5-chloro-4-fluoro-1-methyl-1H-pyrazol-3-yl group |
| 688 | 5-bromo-4-fluoro-1-methyl-1H-pyrazol-3-yl group |
| 689 | 5-ethoxy-4-fluoro-1-methyl-1H-pyrazol-3-yl group |
| 690 | 5-cyano-4-fluoro-1-methyl-1H-pyrazol-3-yl group |
| 691 | 5-difluoromethyl-4-fluoro-1-methyl-1H-pyrazol-3-yl group |
| 692 | 5-trifluoromethyl-4-fluoro-1-methyl-1H-pyrazol-3-yl group |
| 693 | 4-chloro-5-fluoro-1-methyl-1H-pyrazol-3-yl group |
| 694 | 5-bromo-4-chloro-1-methyl-1H-pyrazol-3-yl group |
| 695 | 4-chloro-5-ethyl-1-methyl-1H-pyrazol-3-yl group |
| 696 | 4-chloro-5-ethoxy-1-methyl-1H-pyrazol-3-yl group |
| 697 | 4-chloro-5-cyano-1-methyl-1H-pyrazol-3-yl group |
| 698 | 4-chloro-5-difluoromethyl-1-methyl-1H-pyrazol-3-yl group |
| 699 | 4-bromo-5-fluoro-1-methyl-1H-pyrazol-3-yl group |
| 700 | 4-bromo-5-chloro-1-methyl-1H-pyrazol-3-yl group |
| 701 | 4,5-dibromo-1-methyl-1H-pyrazol-3-yl group |
| 702 | 4-bromo-5-methoxy-1-methyl-1H-pyrazol-3-yl group |
| 703 | 4-bromo-5-ethoxy-1-methyl-1H-pyrazol-3-yl group |
| 704 | 4-bromo-5-cyano-1-methyl-1H-pyrazol-3-yl group |
| 705 | 4-bromo-5-difluoromethyl-1-methyl-1H-pyrazol-3-yl group |
| 706 | 4-bromo-5-trifluoromethyl-1-methyl-1H-pyrazol-3-yl group |
| 707 | 5-fluoro-1,4-dimethyl-1H-pyrazol-3-yl group |
| 708 | 5-bromo-1,4-dimethyl-1H-pyrazol-3-yl group |
| 709 | 5-ethoxy-1,4-dimethyl-1H-pyrazol-3-yl group |

TABLE 44

| substituents Nos. | Q⁵ |
|---|---|
| 710 | 5-cyclopropyl-1,4-dimethyl-1H-pyrazol-3-yl group |
| 711 | 5-difluoromethyl-1,4-dimethyl-1H-pyrazol-3-yl group |
| 712 | 4-ethyl-5-fluoro-1-methyl-1H-pyrazol-3-yl group |
| 713 | 4-ethyl-5-chloro-1-methyl-1H-pyrazol-3-yl group |
| 714 | 5-bromo-4-ethyl-1-methyl-1H-pyrazol-3-yl group |
| 715 | 4-ethyl-5-methoxy-1-methyl-1H-pyrazol-3-yl group |

TABLE 44-continued

| substituents Nos. | $Q^5$ |
|---|---|
| 716 | 5-cyclopropyl-4-ethyl-1-methyl-1H-pyrazol-3-yl group |
| 717 | 4-ethyl-5-difluoromethyl-1-methyl-1H-pyrazol-3-yl group |
| 718 | 4-ethyl-5-trifluoromethyl-1-methyl-1H-pyrazol-3-yl group |
| 719 | 4-methoxy-1-methyl-1H-pyrazol-3-yl group |
| 720 | 5-fluoro-4-methoxy-1-methyl-1H-pyrazol-3-yl group |
| 721 | 5-chloro-4-methoxy-1-methyl-1H-pyrazol-3-yl group |
| 722 | 5-bromo-4-methoxy-1-methyl-1H-pyrazol-3-yl group |
| 723 | 4-methoxy-1,5-dimethyl-1H-pyrazol-3-yl group |
| 724 | 5-ethyl-4-methoxy-1-methyl-1H-pyrazol-3-yl group |
| 725 | 4,5-dimethoxy-1-methyl-1H-pyrazol-3-yl group |
| 726 | 5-ethoxy-4-methoxy-1-methyl-1H-pyrazol-3-yl group |
| 727 | 5-cyano-4-methoxy-1-methyl-1H-pyrazol-3-yl group |
| 728 | 5-cyclopropyl-4-methoxy-1-methyl-1H-pyrazol-3-yl group |
| 729 | 5-difluoromethyl-4-methoxy-1-methyl-1H-pyrazol-3-yl group |
| 730 | 5-trifluoromethyl-4-methoxy-1-methyl-1H-pyrazol-3-yl group |
| 731 | 4-ethoxy-1-methyl-1H-pyrazol-3-yl group |
| 732 | 5-fluoro-4-ethoxy-1-methyl-1H-pyrazol-3-yl group |
| 733 | 5-chloro-4-ethoxy-1-methyl-1H-pyrazol-3-yl group |
| 734 | 5-bromo-4-ethoxy-1-methyl-1H-pyrazol-3-yl group |
| 735 | 4-ethoxy-1,5-dimethyl-1H-pyrazol-3-yl group |
| 736 | 5-ethyl-4-ethoxy-1-methyl-1H-pyrazol-3-yl group |
| 737 | 4-ethoxy-5-methoxy-1-methyl-1H-pyrazol-3-yl group |
| 738 | 4,5-diethoxy-1-methyl-1H-pyrazol-3-yl group |

TABLE 45

| substituents Nos. | $Q^5$ |
|---|---|
| 739 | 5-cyano-4-ethoxy-1-methyl-1H-pyrazol-3-yl group |
| 740 | 5-cyclopropyl-4-ethoxy-1-methyl-1H-pyrazol-3-yl group |
| 741 | 5-difluoromethyl-4-ethoxy-1-methyl-1H-pyrazol-3-yl group |
| 742 | 5-trifluoromethyl-4-ethoxy-1-methyl-1H-pyrazol-3-yl group |
| 743 | 4-cyano-1-methyl-1H-pyrazol-3-yl group |
| 744 | 4-cyano-5-fluoro-1-methyl-1H-pyrazol-3-yl group |
| 745 | 4-cyano-5-chloro-1-methyl-1H-pyrazol-3-yl group |
| 746 | 5-bromo-4-cyano-1-methyl-1H-pyrazol-3-yl group |
| 747 | 4-cyano-5-methoxy-1-methyl-1H-pyrazol-3-yl group |
| 748 | 4-cyano-5-ethoxy-1-methyl-1H-pyrazol-3-yl group |
| 749 | 4,5-dicyano-1-methyl-1H-pyrazol-3-yl group |
| 750 | 4-cyano-5-cyclopropyl-1-methyl-1H-pyrazol-3-yl group |
| 751 | 4-cyano-5-difluoromethyl-1-methyl-1H-pyrazol-3-yl group |
| 752 | 4-cyano-1-methyl-5-trifluoromethyl-1H-pyrazol-3-yl group |
| 753 | 4-difluoromethyl-1 methyl-1H-pyrazol-3-yl group |
| 754 | 5-fluoro-4-difluoromethyl-1-methyl-1H-pyrazol-3-yl group |
| 755 | 5-chloro-4-difluoromethyl-1-methyl-1H-pyrazol-3-yl group |
| 756 | 5-bromo-4-difluoromethyl-1-methyl-1H-pyrazol-3-yl group |
| 757 | 4-difluoromethyl-1,5-dimethyl-1H-pyrazol-3-yl group |
| 758 | 5-ethyl-4-difluoromethyl-1-methyl-1H-pyrazol-3-yl group |
| 759 | 4-difluoromethyl-5-methoxy-1-methyl-1H-pyrazol-3-yl group |
| 760 | 5-ethoxy-4-difluoromethyl-1-methyl-1H-pyrazol-3-yl group |
| 761 | 5-cyano-4-difluoromethyl-1-methyl-1H-pyrazol-3-yl group |
| 762 | 5-cyclopropyl-4-difluoromethyl-1-methyl-1H-pyrazol-3-yl group |

TABLE 45-continued

| substituents Nos. | $Q^5$ |
|---|---|
| 763 | 4,5-bis(difluoromethyl)-1-methyl-1H-pyrazol-3-yl group |
| 764 | 4-difluoromethyl-1-methyl-5-trifluoromethyl-1H-pyrazol-3-yl group |
| 765 | 1-methyl-4-trifluoromethyl-1H-pyrazol-3-yl group |
| 766 | 5-fluoro-1-methyl-4-trifluoromethyl-1H-pyrazol-3-yl group |
| 767 | 5-chloro-1-methyl-4-trifluoromethyl-1H-pyrazol-3-yl group |

TABLE 46

| substituents Nos. | $Q^5$ |
|---|---|
| 768 | 5-bromo-1-methyl-4-trifluoromethyl-1H-pyrazol-3-yl group |
| 769 | 1,5-dimethyl-4-trifluoromethyl-1H-pyrazol-3-yl group |
| 770 | 5-ethyl-1-methyl-4-trifluoromethyl-1H-pyrazol-3-yl group |
| 771 | 5-methoxy-1-methyl-4-trifluoromethyl-1H-pyrazol-3-yl group |
| 772 | 5-ethoxy-1-methyl-4-trifluoromethyl-1H-pyrazol-3-yl group |
| 773 | 5-cyano-1-methyl-4-trifluoromethyl-1H-pyrazol-3-yl group |
| 774 | 5-cyclopropyl-1-methyl-4-trifluoromethyl-1H-pyrazol-3-yl group |
| 775 | 5-difluoromethyl-1-methyl-4-trifluoromethyl-1H-pyrazol-3-yl group |
| 776 | 1-methyl-4,5-bis(trifluoromethyl)-1H-pyrazol-3-yl group |
| 777 | 1-ethyl-5-fluoro-1H-pyrazol-3-yl group |
| 778 | 5-bromo-1-ethyl-1H-pyrazol-3-yl group |
| 779 | 5-cyano-1-ethyl-1H-pyrazol-3-yl group |
| 780 | 1-ethyl-5-difluoromethyl-1H-pyrazol-3-yl group |
| 781 | 1-ethyl-4,5-difluoro-1H-pyrazol-3-yl group |
| 782 | 1-ethyl-4-chloro-1H-pyrazol-3-yl group |
| 783 | 1-ethyl-5-bromo-4-fluoro-1H-pyrazol-3-yl group |
| 784 | 1-ethyl-5-cyano-4-fluoro-1H-pyrazol-3-yl group |
| 785 | 1-ethyl-5-difluoromethyl-4-fluoro-1H-pyrazol-3-yl group |
| 786 | 1-ethyl-5-trifluoromethyl-4-fluoro-1H-pyrazol-3-yl group |
| 787 | 4-chloro-1-ethyl-5-fluoro-1H-pyrazol-3-yl group |
| 788 | 5-bromo-4-chloro-1-ethyl-1H-pyrazol-3-yl group |
| 789 | 4-chloro-1,5-diethyl-1H-pyrazol-3-yl group |
| 790 | 1-ethyl-5-cyano-4-chloro-1H-pyrazol-3-yl group |
| 791 | 1-ethyl-4-chloro-5-difluoro-1H-pyrazol-3-yl group |
| 792 | 4-bromo-1-ethyl-5-fluoro-1H-pyrazol-3-yl group |
| 793 | 4-bromo-1-ethyl-5-chloro-1H-pyrazol-3-yl group |
| 794 | 4-bromo-1-ethyl-5-methoxy-1H-pyrazol-3-yl group |
| 795 | 4-bromo-5-cyano-1-ethyl-1H-pyrazol-3-yl group |
| 796 | 5-fluoro-1-ethyl-4-methyl-1H-pyrazol-3-yl group |

TABLE 47

| substituents Nos. | $Q^5$ |
|---|---|
| 797 | 5-bromo-1-ethyl-4-methyl-1H-pyrazol-3-yl group |
| 798 | 5-cyclopropyl-1-ethyl-4-methyl-1H-pyrazol-3-yl group |
| 799 | 1-ethyl-5-difluoromethyl-4-methyl-1H-pyrazol-3-yl group |
| 800 | 1,4-diethyl-1H-pyrazol-3-yl group |
| 801 | 1,4-diethyl-5-fluoro-1H-pyrazol-3-yl group |
| 802 | 1,4-diethyl-5-chloro-1H-pyrazol-3-yl group |
| 803 | 1,4-diethyl-5-methoxy-1-methyl-1H-pyrazol-3-yl group |
| 804 | 4-methoxy-1-ethyl-1H-pyrazol-3-yl group |

TABLE 47-continued

| substituents Nos. | $Q^5$ |
|---|---|
| 805 | 5-fluoro-1-ethyl-4-methoxy-1H-pyrazol-3-yl group |
| 806 | 5-chloro-1-ethyl-4-methoxy-1H-pyrazol-3-yl group |
| 807 | 5-bromo-1-ethyl-4-methoxy-1H-pyrazol-3-yl group |
| 808 | 1-ethyl-5-methoxy-4-methyl-1H-pyrazol-3-yl group |
| 809 | 1,5-diethyl-4-methoxy-1H-pyrazol-3-yl group |
| 810 | 1-ethyl-4,5-dimethoxy-1H-pyrazol-3-yl group |
| 811 | 1-ethyl-5-cyano-4-methoxy-1H-pyrazol-3-yl group |
| 812 | 5-cyclopropyl-1-ethyl-4-methoxy-1H-pyrazol-3-yl group |
| 813 | 1-ethyl-5-difluoromethyl-4-methoxy-1H-pyrazol-3-yl group |
| 814 | 1-ethyl-4-methoxy-5-trifluoromethyl-1H-pyrazol-3-yl group |
| 815 | 4-cyano-1-ethyl-1H-pyrazol-3-yl group |
| 816 | 4-cyano-5-fluoro-1-ethyl-1H-pyrazol-3-yl group |
| 817 | 4-cyano-5 chloro-1-ethyl-1H-pyrazol-3-yl group |
| 818 | 5-bromo-4-cyano-1-ethyl-1H-pyrazol-3-yl group |
| 819 | 4-cyano-1-ethyl-5-methoxy-1H-pyrazol-3-yl group |
| 820 | 4,5-dicyano-1-ethyl-1H-pyrazol-3-yl group |
| 821 | 4-cyano-5-cyclopropyl-1-ethyl-1H-pyrazol-3-yl group |
| 822 | 4-cyano-5-difluoromethyl-1-ethyl-1H-pyrazol-3-yl group |
| 823 | 4-cyano-1-ethylpyrazol-5-trifluoromethyl-1H-pyrazol-3-yl group |
| 824 | 4-difluoromethyl-1-ethyl-1H-pyrazol-3-yl group |
| 825 | 5-fluoro-4-difluoromethyl-1-ethyl-1H-pyrazol-3-yl group |

TABLE 48

| substituents Nos. | $Q^5$ |
|---|---|
| 826 | 5-chloro-4-difluoromethyl-1-ethyl-1H-pyrazol-3-yl group |
| 827 | 4-difluoromethyl-1-ethyl-4-methyl-1H-pyrazol-3-yl group |
| 828 | 4-difluoromethyl-1-ethyl-5-methoxy-1H-pyrazol-3-yl group |
| 829 | 5-cyano-4-difluoromethyl-1-ethyl-1H-pyrazol-3-yl group |
| 830 | 1-ethyl-4-trifluoromethyl-1H-pyrazol-3-yl group |
| 831 | 5-fluoro-1-ethyl-4-trifluoromethyl-1H-pyrazol-3-yl group |
| 832 | 5-chloro-1-ethyl-4-trifluoromethyl-1H-pyrazol-3-yl group |
| 833 | 1-ethyl-4-trifluoromethyl-5-methyl-1H-pyrazol-3-yl group |
| 834 | 1-ethyl-4-trifluoromethyl-5-methoxy-1H-pyrazol-3-yl group |
| 835 | 5-cyano-1-ethyl-4-trifluoromethyl-1H-pyrazol-3-yl group |
| 836 | 4-methoxy-5-methylpyrazol-1-yl group |
| 837 | 4-ethoxy-5-methylpyrazol-1-yl group |
| 838 | 4-cyclopropyl-5-methylpyrazol-1-yl group |
| 839 | 4-trifluoromethyl-5-methylpyrazol-1-yl group |
| 840 | 4-bromo-3-methylpyrazol-1-yl group |
| 841 | 4-ethyl-3-methylpyrazol-1-yl group |
| 842 | 4-methoxy-3-methylpyrazol-1-yl group |
| 843 | 4-ethoxy-3-methylpyrazol-1-yl group |
| 844 | 4-cyclopropyl-3-methylpyrazol-1-yl group |
| 845 | 5-fluoro-3-methylpyrazol-1-yl group |
| 846 | 4,5-difluoro-3-methylpyrazol-1-yl group |
| 847 | 4-chloro-5-fluoro-3-methylpyrazol-1-yl group |
| 848 | 4-bromo-5-fluoro-3-methylpyrazol-1-yl group |
| 849 | 5-fluoro-3,4-dimethylpyrazol-1-yl group |
| 850 | 4-ethyl-5-fluoro-3-methylpyrazol-1-yl group |
| 851 | 5-fluoro-4-methoxy-3-methylpyrazol-1-yl group |
| 852 | 4-ethoxy-5-fluoro-3-methylpyrazol-1-yl group |
| 853 | 4-cyano-5-fluoro-3-methylpyrazol-1-yl group |
| 854 | 4-cyclopropyl-5-fluoro-3-methylpyrazol-1-yl group |

TABLE 49

| substituents Nos. | $Q^5$ |
|---|---|
| 855 | 4-difluoromethyl-5-fluoro-3-methylpyrazol-1-yl group |
| 856 | 4-trifluoromethyl-5-fluoro-3-methylpyrazol-1-yl group |
| 857 | 5-chloro-3-methylpyrazol-1-yl group |
| 858 | 5-chloro-4-fluoro-3-methylpyrazol-1-yl group |
| 859 | 4,5-dichloro-3-methylpyrazol-1-yl group |
| 860 | 4-bromo-5-chloro-3-methylpyrazol-1-yl group |
| 861 | 5-chloro-3,4-dimethylpyrazol-1-yl group |
| 862 | 5-chloro-4-ethyl-3-methylpyrazol-1-yl group |
| 863 | 5-chloro-4-methoxy-3-methylpyrazol-1-yl group |
| 864 | 5-chloro-4-ethoxy-3-methylpyrazol-1-yl group |
| 865 | 5-chloro-4-cyano-3-methylpyrazol-1-yl group |
| 866 | 5-chloro-4-cyclopropyl-3-methylpyrazol-1-yl group |
| 867 | 5-chloro-4-difluoromethyl-3-methylpyrazol-1-yl group |
| 868 | 5-chloro-4-trifluoromethyl-3-methylpyrazol-1-yl group |
| 869 | 5-bromo-3-methylpyrazol-1-yl group |
| 870 | 5-bromo-4-fluoro-3-methylpyrazol-1-yl group |
| 871 | 5-bromo-4-chloro-3-methylpyrazol-1-yl group |
| 872 | 4,5-dibromo-3-methylpyrazol-1-yl group |
| 873 | 5-bromo-3,4-dimethylpyrazol-1-yl group |
| 874 | 5-bromo-4-ethyl-3-methylpyrazol-1-yl group |
| 875 | 5-bromo-4-methoxy-3-methylpyrazol-1-yl group |
| 876 | 5-bromo-4-ethoxy-3-methylpyrazol-1-yl group |
| 877 | 5-bromo-4-cyano-3-methylpyrazol-1-yl group |
| 878 | 5-bromo-4-cyclopropyl-3-methylpyrazol-1-yl group |
| 879 | 5-bromo-4-difluoromethyl-3-methylpyrazol-1-yl group |
| 880 | 5-bromo-4-trifluoromethyl-3-methylpyrazol-1-yl group |
| 881 | 3,5-dimethylpyrazol-1-yl group |
| 882 | 5-ethyl-4-fluoro-3-methylpyrazol-1-yl group |
| 883 | 5-ethyl-4-methoxy-3-methylpyrazol-1-yl group |

TABLE 50

| substituents Nos. | $Q^5$ |
|---|---|
| 884 | 4-ethoxy-5-ethyl-3-methylpyrazol-1-yl group |
| 885 | 5-trifluoromethyl-4-methoxy-3-methylpyrazol-1-yl group |
| 886 | 5 methoxy-3-methylpyrazol-1-yl group |
| 887 | 4-fluoro-5-methoxy-3-methylpyrazol-1-yl group |
| 888 | 4-chloro-5-methoxy-3-methylpyrazol-1-yl group |
| 889 | 4-bromo-5-methoxy-3-methylpyrazol-1-yl group |
| 890 | 4-ethyl-5-methoxy-3-methylpyrazol-1-yl group |
| 891 | 4,5-dimethoxy-3-methylpyrazol-1-yl group |
| 892 | 4-ethyle-5-methoxy-3-methylpyrazol-1-yl group |
| 893 | 4-ethoxy-5-methoxy-3-methylpyrazol-1-yl group |
| 894 | 4-cyano-5-methoxy-3-methylpyrazol-1-yl group |
| 895 | 4-cyclopropyl-5-methoxy-3-methylpyrazol-1-yl group |
| 896 | 4-difluoromethy-5-methoxy-3-methylpyrazol-1-yl group |
| 897 | 5-methoxy-3-methyl-4-trifluoromethypyrazol-1-yl group |
| 898 | 5-ethoxy-3-methylpyrazol-1-yl group |
| 899 | 5-ethoxy-4-fluoro-3-methylpyrazol-1-yl group |
| 900 | 5-ethoxy-4-chloro-3-methylpyrazol-1-yl group |
| 901 | 5 ethoxy-4-bromo3-methylpyrazol-1-yl group |
| 902 | 5-ethoxy-3,4-dimethylpyrazol-1-yl group |
| 903 | 5-ethoxy-4-ethyl-3-methylpyrazol-1-yl group |
| 904 | 5-ethoxy-4-methoxy-3-methylpyrazol-1-yl group |
| 905 | 4,5-diethoxy-3-methylpyrazol-1-yl group |
| 906 | 4-cyano-5-ethoxy-3-methylpyrazol-1-yl group |
| 907 | 4-cyclopropyl-5-ethoxy-3-methylpyrazol-1-yl group |
| 908 | 4-difluoromethyl-5-ethoxy-3-methylpyrazol-1-yl group |
| 909 | 5-ethoxy-4-trifluoromethyl-3-methylpyrazol-1-yl group |
| 910 | 5-cyano-3-methylpyrazol-1-yl group |

TABLE 50-continued

| substituents Nos. | $Q^5$ |
|---|---|
| 911 | 5-cyano-4-fluoro-3-methylpyrazol-1-yl group |
| 912 | 5-cyano-4-chloro-3-methylpyrazol-1-yl group |

TABLE 51

| substituents Nos. | $Q^5$ |
|---|---|
| 913 | 5-cyano-4-bromo-3-methylpyrazol-1-yl group |
| 914 | 5-cyano-3,4-dimethylpyrazol-1-yl group |
| 915 | 5-cyano-4-ethyl-3-methylpyrazol-1-yl group |
| 916 | 5-cyano-4-methoxy-3-methylpyrazol-1-yl group |
| 917 | 5-cyano-4-ethoxy-3-methylpyrazol-1-yl group |
| 918 | 4,5-dicyano-3-methylpyrazol-1-yl group |
| 919 | 5-cyano-4-cyclopropyl-3-methylpyrazol-1-yl group |
| 920 | 5-cyano-4-difluoromethyl-3-methylpyrazol-1-yl group |
| 921 | 5-cyano-4-trifluoromethyl-3-methylpyrazol-1-yl group |
| 922 | 5-difluoromethyl-3-methylpyrazol-1-yl group |
| 923 | 5-difluoromethyl-4-fluoro-3-methylpyrazol-1-yl group |
| 924 | 4-chloro-5-difluoromethyl-3-methylpyrazol-1-yl group |
| 925 | 4-bromo-5-difluoromethyl-3-methylpyrazol-1-yl group |
| 926 | 5-difluoromethyl-3,4-dimethylpyrazol-1-yl group |
| 927 | 4-ethyl-5-difluoromethyl-3-methylpyrazol-1-yl group |
| 928 | 5-difluoromethyl-4-methoxy-3-methylpyrazol-1-yl group |
| 929 | 4-ethoxy-5-difluoromethyl-3-methylpyrazol-1-yl group |
| 930 | 4-cyano-5-difluoromethyl-3-methylpyrazol-1-yl group |
| 931 | 4-cyclopropyl-5-difluoromethyl-3-methylpyrazol-1-yl group |
| 932 | 4,5-bis(difluoromethyl)-3-methylpyrazol-1-yl group |
| 933 | 5-difluoromethyl-3-methyl-4-trifluoromethylpyrazol-1-yl group |
| 934 | 3-methyl-5-trifluoromethylpyrazol-1-yl group |
| 935 | 4-fluoro-3-methyl-5-trifluoromethypyrazol-1-yl group |
| 936 | 4-chloro-3-methyl-5-trifluoromethypyrazol-1-yl group |
| 937 | 4-bromo-3-methyl-5-trifluoromethylpyrazol-1-yl group |
| 938 | 3,4-dimethyl-5-trifluoromethylpyrazol-1-yl group |
| 939 | 4-ethyl-3-methyl-5-trifluoromethylpyrazol-1-yl group |
| 940 | 4-methoxy-3-methyl-5-trifluoromethylpyrazol-1-yl group |
| 941 | 4-ethoxy-3-methyl-5-trifluoromethylpyrazol-1-yl group |

TABLE 52

| substituents Nos. | $Q^5$ |
|---|---|
| 942 | 4-cyano-3-methyl-5-trifluoromethylpyrazol-1-yl group |
| 943 | 4-cyclopropyl-3-methyl-5-trifluoromethylpyrazol-1-yl group |
| 944 | 4-difluoromethyl-3-methyl-5-trifluoromethylpyrazol-1-yl group |
| 945 | 4,5-bis(trifluoromethyl)-3-methylpyrazol-1-yl group |
| 946 | 3-ethyl-4-ethoxy-5-methylpyrazol-1-yl group |
| 947 | 3-ethyl-4-cyano-5-methylpyrazol-1-yl group |
| 948 | 3-ethyl-4-cyclopropyl-5-methylpyrazol-1-yl group |

TABLE 52-continued

| substituents Nos. | $Q^5$ |
|---|---|
| 949 | 3-fluoro-5-methylpyrazol-1-yl group |
| 950 | 3,4-difluoro-5-methylpyrazol-1-yl group |
| 951 | 4-chloro-3-fluoro-5-methylpyrazol-1-yl group |
| 952 | 4-bromo-3-fluoro-5-methylpyrazol-1-yl group |
| 953 | 3-fluoro-4,5-dimethylpyrazol-1-yl group |
| 954 | 4-ethyl-3-fluoro-5-methylpyrazol-1-yl group |
| 955 | 3-fluoro-4-methoxy-5-methylpyrazol-1-yl group |
| 956 | 4-ethoxy-3-fluoro-5-methylpyrazol-1-yl group |
| 957 | 4-cyano-3-fluoro-5-methylpyrazol-1-yl group |
| 958 | 4-cyclopropyl-3-fluoro-5-methylpyrazol-1-yl group |
| 959 | 4-difluoromethyl-3-fluoro-5-methylpyrazol-1-yl group |
| 960 | 3-fluoro-5-methyl-4-trifluoromethylpyrazol-1-yl group |
| 961 | 3-chloro-5-methylpyrazol-1-yl group |
| 962 | 3-chloro-4-fluoro-5-methylpyrazol-1-yl group |
| 963 | 3,4-dichloro-5-methylpyrazol-1-yl group |
| 964 | 4-bromo-3-chloro-5-methylpyrazol-1-yl group |
| 965 | 3-chloro-4,5-dimethylpyrazol-1-yl group |
| 966 | 3-chloro-4-ethyl-5-methylpyrazol-1-yl group |
| 967 | 3-chloro-4-methoxy-5-methylpyrazol-1-yl group |
| 968 | 3-chloro-4-ethoxy-5-methylpyrazol-1-yl group |
| 969 | 3-chloro-4-cyano-5-methylpyrazol-1-yl group |
| 970 | 3-chloro-4-cyclopropyl-5-methylpyrazol-1-yl group |

TABLE 53

| substituents Nos. | $Q^5$ |
|---|---|
| 971 | 3-chloro-4-difluoromethyl-5-methylpyrazol-1-yl group |
| 972 | 3-chloro-5-methyl-4-trifluoromethylpyrazol-1-yl group |
| 973 | 3-methoxy-5-methylpyrazol-1-yl group |
| 974 | 4-fluoro-3-methoxy-5-methylpyrazol-1-yl group |
| 975 | 4-chloro-3-methoxy-5-methylpyrazol-1-yl group |
| 976 | 4-bromo-3-methoxy-5-methylpyrazol-1-yl group |
| 977 | 3-methoxy-4,5-dimethylpyrazol-1-yl group |
| 978 | 4-ethyl-3-methoxy-5-methylpyrazol-1-yl group |
| 979 | 3,4-dimethoxy-5-methylpyrazol-1-yl group |
| 980 | 4-ethoxy-3-methoxy-5-methylpyrazol-1-yl group |
| 981 | 4-cyano-3 methoxy-5-methylpyrazol-1-yl group |
| 982 | 4-cyclopropyl-3-methoxy-5-methylpyrazol-1-yl group |
| 983 | 4-difluoromethyl-3-methoxy-5-methylpyrazol-1-yl group |
| 984 | 5-methyl-3-methoxy-4-trifluoromethylpyrazol-1-yl group |
| 985 | 3-cyano-5-methylpyrazol-1-yl group |
| 986 | 3-cyano-4-fluoro-5-methylpyrazol-1-yl group |
| 987 | 4-chloro-3-cyano-5-methylpyrazol-1-yl group |
| 988 | 4-bromo-3-cyano-5-methylpyrazol-1-yl group |
| 989 | 3-cyano-4,5-dimethylpyrazol-1-yl group |
| 990 | 3-cyano-4-ethyl-5-methylpyrazol-1-yl group |
| 991 | 3-cyano-4-methoxy-5-methylpyrazol-1-yl group |
| 992 | 3-cyano-4-ethoxy-5-methylpyrazol-1-yl group |
| 993 | 3,4-dicyano-5-methylpyrazol-1-yl group |
| 994 | 3-cyano-4-cyclopropyl-5-methylpyrazol-1-yl group |
| 995 | 3-cyano-4-difluoromethyl-5-methylpyrazol-1-yl group |
| 996 | 3-cyano-5-methyl-4-trifluoromethylpyrazol-1-yl group |
| 997 | 3-cyclopropyl-4-methoxy-5-methylpyrazol-1-yl group |
| 998 | 3-cyclopropyl-4-ethoxy-5-methylpyrazol-1-yl group |
| 999 | 3-cyclopropyl-4-cyano-5-methylpyrazol-1-yl group |

TABLE 54

| substituents Nos. | Q⁵ |
|---|---|
| 1000 | 3-difluoromethyl-5-methylpyrazol-1-yl group |
| 1001 | 4-fluoromethyl-3-difluoro-5-methylpyrazol-1-yl group |
| 1002 | 4-chloro-3-difluoromethyl-5-methylpyrazol-1-yl group |
| 1003 | 4-bromo-3-difluoromethyl-5-methylpyrazol-1-yl group |
| 1004 | 3-difluoromethyl-4,5-dimethylpyrazol-1-yl group |
| 1005 | 3-difluoromethyl-4-ethyl-5-methylpyrazol-1-yl group |
| 1006 | 3-difluoromethyl-4-methoxy-5-methylpyrazol-1-yl group |
| 1007 | 3-difluoromethyl-4-ethoxy-5-methylpyrazol-1-yl group |
| 1008 | 3-difluoromethyl-4-cyano-5-methylpyrazol-1-yl group |
| 1009 | 3-difluoromethyl-4-cyclopropyl-5-methylpyrazol-1-yl group |
| 1010 | 4-difuruoromethyl-5-methylpyrazol-1-yl group |
| 1011 | 5-methyl-4-trifluoromethylpyrazol-1-yl group |
| 1012 | 5-methyl-3-trifluoromethylpyrazol-1-yl group |
| 1013 | 4-fluoro-5-methyl-3-trifluoromethylpyrazol-1-yl group |
| 1014 | 4-chloro-5-methyl-3-trifluoromethylpyrazol-1-yl group |
| 1015 | 4-bromo-5-methyl-3trifluoromethylpyrazol-1-yl group |
| 1016 | 4,5-dimethyl-3-trifluoromethylpyrazol-1-yl group |
| 1017 | 4-ethyl-5-methyl-3-trifluoromethylpyrazol-1-yl group |
| 1018 | 4-methoxy-5-methyl-3-trifluoromethylpyrazol-1-yl group |
| 1019 | 4-ethoxy-5-methyl-3-trifluoromethylpyrazol-1-yl group |
| 1020 | 4-cyano-5-methyl-3-trifluoromethylpyrazol-1-yl group |
| 1021 | 4-cyclopropyl-5-methyl-3-trifluoromethylpyrazol-1-yl group |
| 1022 | 4-difluoro-5-methyl-3-trifluoromethylpyrazol-1-yl group |
| 1023 | 5-methyl-3,4-bis(trifluoromethyl)pyrazol-1-yl group |

According to the above-mentioned processes, the following compounds can be prepared:
Compounds EB1A-001~EB1A-20, EB1B-001~EB1B-20, EB1C-001~EB1C-20, EB1D-001~EB1D-20, EB1E-001~EB1E-20, EB2A-001~EB2A-20, EB2B-001~EB2B-20, EB2C-001~EB2C-20, EB3A-001~EB3A-20, EB3B-001~EB3B-20, EB3C-001~EB3C-20, EB4A-001~EB4A-20, EB4B-001~EB4B-20, EB5A-001~EB5A-20, EB5B-001~EB5B-20 and EB5C-001~EB5C-20.

Compounds EB1A-001~EB1A-20 represent Compounds represented by a formula:

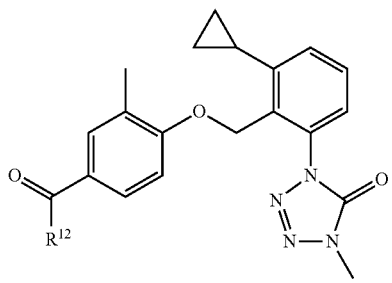

(EB1A)

[in the formula (EB1A), $R^{12}$ represents a substituent corresponding to each of substituents Nos. 1 to 20 indicated in Table B1 as below-mentioned];

Compounds EB1B-001~EB1B-20 represent Compounds represented by a formula:

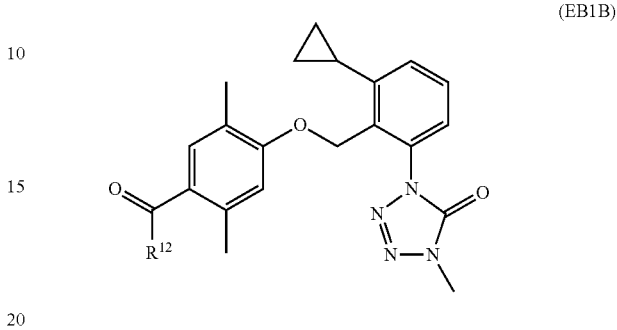

(EB1B)

[in the formula (EB1B), $R^{12}$ represents a substituent corresponding to each of substituents Nos. 1 to 20 indicated in Table B1 as below-mentioned];

Compounds EB1C-001~EB1C-20 represent Compounds represented by a formula:

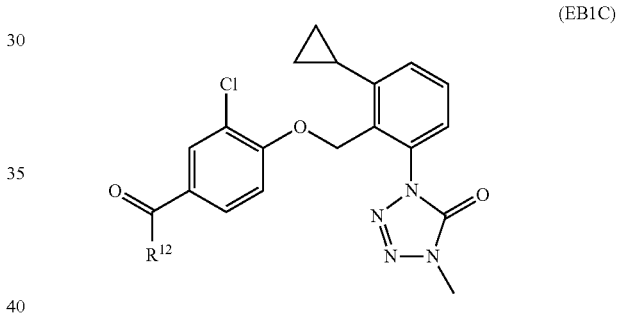

(EB1C)

[in the formula (EB1C), $R^{12}$ represents a substituent corresponding to each of substituents Nos. 1 to 20 indicated in Table B1 as below-mentioned];

Compounds EB1D-001~EB1D-20 represent Compounds represented by a formula:

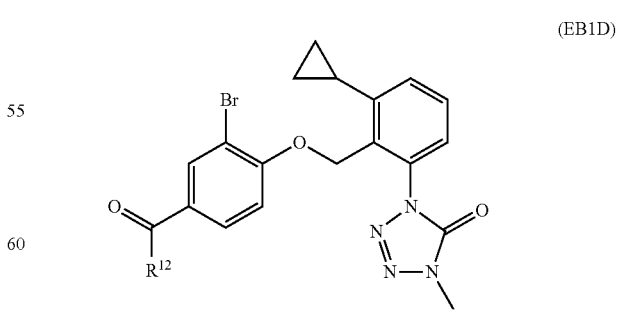

(EB1D)

[in the formula (EB1D), $R^{12}$ represents a substituent corresponding to each of substituents Nos. 1 to 20 indicated in Table B1 as below-mentioned];

Compounds EB1E-001~EB1E-20 represent Compounds represented by a formula:

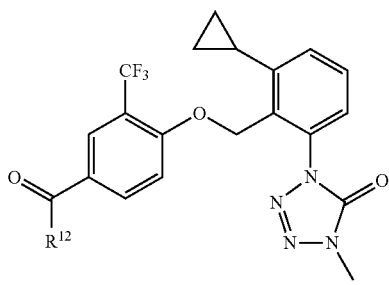

(EB1E)

[in the formula (EB1E), $R^{12}$ represents a substituent corresponding to each of substituents Nos. 1 to 20 indicated in Table B1 as below-mentioned];

Compounds EB2A-001~EB2A-20 represent Compounds represented by a formula:

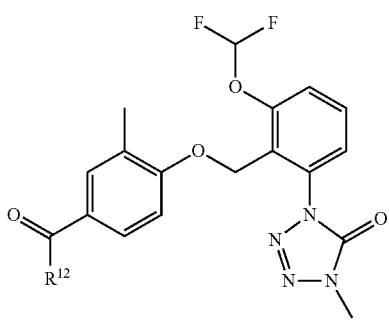

(EB2A)

[in the formula (EB2A), $R^{12}$ represents a substituent corresponding to each of substituents Nos. 1 to 20 indicated in Table B1 as below-mentioned];

Compounds EB2B-001~EB2B-20 represent Compounds represented by a formula:

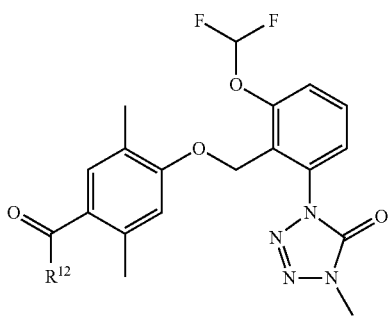

(EB2B)

[in the formula (EB2B), $R^{12}$ represents a substituent corresponding to each of substituents Nos. 1 to 20 indicated in Table B1 as below-mentioned];

Compounds EB2C-001~EB2C-20 represent Compounds represented by a formula:

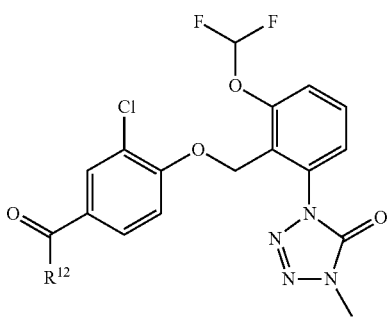

(EB2C)

[in the formula (EB2C), $R^{12}$ represents a substituent corresponding to each of substituents Nos. 1 to 20 indicated in Table B1 as below-mentioned];

Compounds EB3A-001~EB3A-20 represent Compounds represented by a formula:

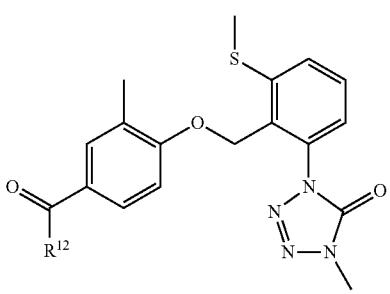

(EB3A)

[in the formula (EB3A), $R^{12}$ represents a substituent corresponding to each of substituents Nos. 1 to 20 indicated in Table B1 as below-mentioned];

Compounds EB3B-001~EB3B-20 represent Compounds represented by a formula:

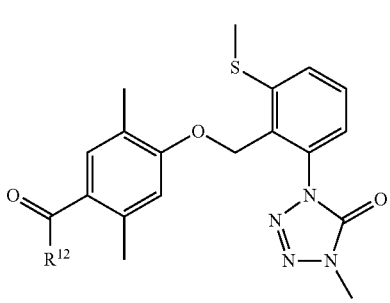

(EB3B)

[in the formula (EB3B), $R^{12}$ represents a substituent corresponding to each of substituents Nos. 1 to 20 indicated in Table B1 as below-mentioned];

Compounds EB3C-001~EB3C-20 represent Compounds represented by a formula:

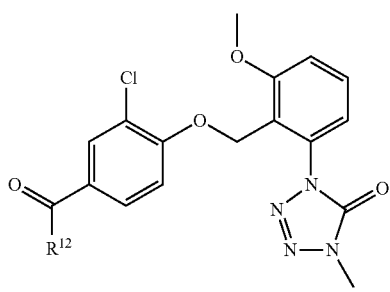

(EB3C)

[in the formula (EB3C), R$^{12}$ represents a substituent corresponding to each of substituents Nos. 1 to 20 indicated in Table B1 as below-mentioned];

Compounds EB4A-001~EB4A-20 represent Compounds represented by a formula:

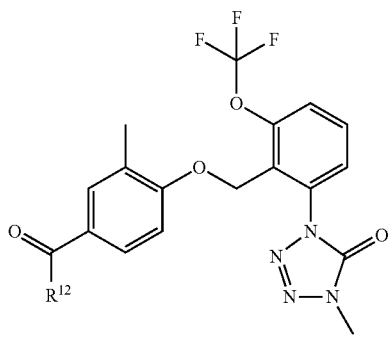

(EB4A)

[in the formula (EB4A), R$^{12}$ represents a substituent corresponding to each of substituents Nos. 1 to 20 indicated in Table B1 as below-mentioned];

Compounds EB4B-001~EB4B-20 represent Compounds represented by a formula:

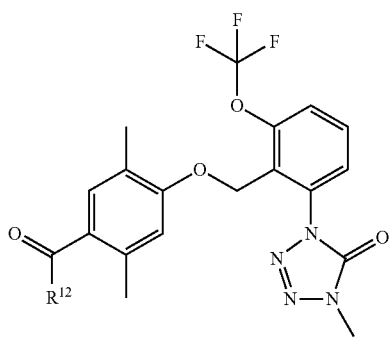

(EB4B)

[in the formula (EB4B), R$^{12}$ represents a substituent corresponding to each of substituents Nos. 1 to 20 indicated in Table B1 as below-mentioned];

Compounds EB5A-001~EB5A-20 represent Compounds represented by a formula:

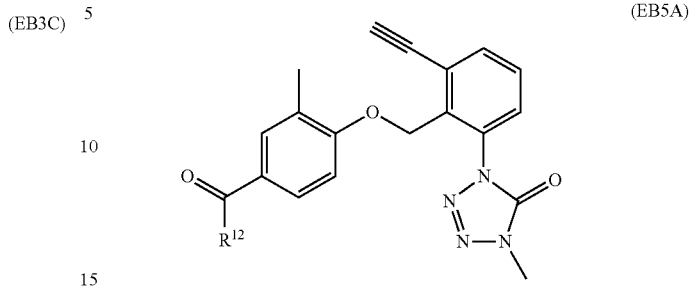

(EB5A)

[in the formula (EB5A), R$^{12}$ represents a substituent corresponding to each of substituents Nos. 1 to 20 indicated in Table B1 as below-mentioned];

Compounds EB5B-001~EB5B-20 represent Compounds represented by a formula:

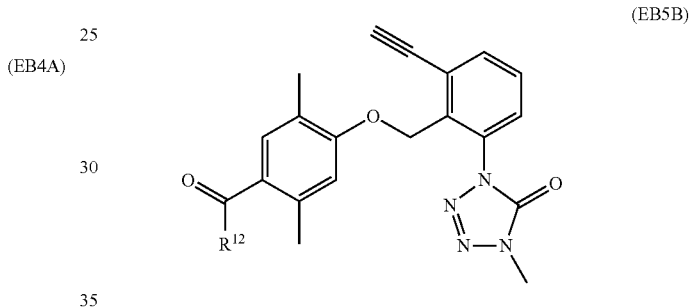

(EB5B)

[in the formula (EB5B), R$^{12}$ represents a substituent corresponding to each of substituents Nos. 1 to 20 indicated in Table B1 as below-mentioned]; and Compounds EB5C-001~EB5C-20 represent Compounds represented by a formula:

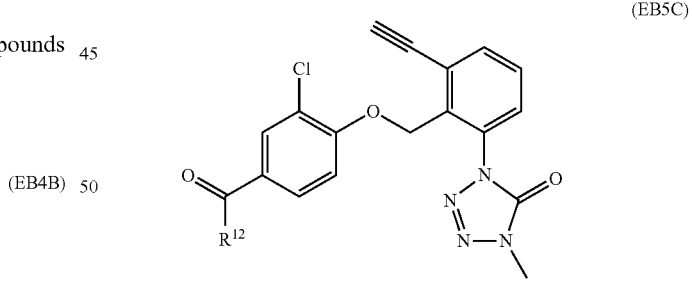

(EB5C)

[in the formula (EB5C), R$^{12}$ represents a substituent corresponding to each of substituents Nos. 1 to 20 indicated in Table B1 as below-mentioned].

TABLE B1

| substituents Nos. | R$^{12}$ |
|---|---|
| 1 | methyl group |
| 2 | ethyl group |
| 3 | propyl group |
| 4 | butyl group |

TABLE B1-continued

| substituents Nos. | $R^{12}$ |
|---|---|
| 5 | pentyl group |
| 6 | hexyl group |
| 7 | isopropyl group |
| 8 | tert-butyl group |
| 9 | isobutyl group |
| 10 | trifluoromethyl group |
| 11 | trichloromethyl group |
| 12 | 2.2-difluoroethyl group |
| 13 | cyclopropyl group |
| 14 | cyclobutyl group |
| 15 | cyclohexyl group |
| 16 | 1-fluoro-cyclopropyl group |
| 17 | 1-chloro-cyclopropyl group |
| 18 | 2,2-difluoro-cyclopropyl group |
| 19 | 2,2,3,3-tetrafluoro-cyclopropyl group |
| 20 | 1,2,2,3,3-pentafluoro-cyclopropyl group |

Next, the Formulation examples are shown below. In the Examples, the term "part(s)" means part(s) by weight unless otherwise specified.

Formulation Example 1

Fifty (50) parts of any one of the present Compounds 1 to 53, 3 parts of calcium lignosulfonate, 2 parts of magnesium lauryl sulfate and 45 parts of synthetic hydrated silicon dioxide are well mixed while grinding to obtain a formulation.

Formulation Example 2

Twenty (20) parts of any one of the present Compounds to 53, 1.5 parts of sorbitan trioleate are mixed with 28.5 parts of an aqueous solution containing 2 parts of polyvinyl alcohol, and the mixture is then finely-ground by a wet grinding method. To this mixture is then added 40 parts of an aqueous solution containing 0.05 parts of xanthane gum and 0.1 parts of magnesium aluminium silicate, and 10 parts of propylene glycol is further added thereto. The mixture is stirred to obtain a formulation.

Formulation Example 3

Two (2) parts of any one of the present Compounds 1 to 53, 88 parts of kaolin clay and 10 parts of talc are mixed-grinding to obtain a formulation.

Formulation Example 4

Five (5) parts of any one of the present Compounds 1 to 53, 14 parts of polyoxyethylene styryl phenyl ether, 6 parts of calcium dodecylbenzene sulfonate and 75 parts of xylene are mixed-grinding to obtain a formulation.

Formulation Example 5

Two (2) parts of any one of the present Compounds 1 to 53, one part of synthetic hydrated silicon dioxide, 2 parts of calcium lignosulfonate, 30 parts of bentonite and 65 parts of kaolin clay are mixed-grinding and thereto is added water and the mixture is well kneaded and is then granulated and dried to obtain a formulation.

Formulation Example 6

Ten (10) parts of any one of the present Compounds 1 to 53, 35 parts of white carbon containing 50 parts of ammonium polyoxyethylene alkyl ether sulfate, and 55 parts of water are mixed, and the mixture is then finely-ground by a wet grinding method to obtain a formulation.

Next, Test examples are used to show an efficacy of the present Compounds on controlling plant diseases.

Here the controlling effects were evaluated by visually observing a lesion area on the tested plants and followed by comparing the lesion area of the plants treated with the present Compounds with a lesion area of the untreated plants.

Test Example 1

A plastic pot was filled with soil and thereto rice (cv; Nipponbare) seeds were sown and the plants were grown in a greenhouse for twenty days. Thereafter, each of the present Compounds 2, 3, 6, 15, 17 and 24 was made to a formulation according to the above-mentioned Formulation examples and was then diluted with water so as to make a predetermined concentration (500 ppm). The dilutions were sprayed to foliar parts so as to adhere adequately on the leaves of the above-mentioned rice. After spraying the dilutions, the plants were air-dried and were placed at 24° C. during daytime and 20° C. during nighttime under a high humidity for 6 days while the above-mentioned spraying-treated rice were contacted rice seedlings (cv; Nipponbare) infected by rice blast fungi (Magnaporthe grisea), and a lesion area was observed. As a result, every of the lesion areas in plants treated with the present Compounds 2, 3, 6, 15, 17 and 24 showed 30% or less compared to the lesion area in an untreated plants.

Test Example 2

A plastic pot was filled with soil and thereto wheat (cv; Shirogane) seeds were sown and the plants were grown in a greenhouse for 9 days. Thereafter, each of the present Compounds 1, 2, 4, 5, 6, 7, 10, 11, 12, 13, 14, 15, 18, 21, 22, 23, 24 and 25 was made to a formulation according to the above-mentioned Formulation examples and was then diluted with water so as to make a predetermined concentration (500 ppm). The dilutions were sprayed to foliar parts so as to adhere adequately on the leaves of the above-mentioned wheat. After spraying dilutions, the plants were air-dried and were placed at 20° C. under lighting for 5 days. The spores of wheat rust fungi (Puccinia recondita) were sprinkling-inoculated. After inoculation, the plants were placed under a dark and humid condition at 23° C. for 1 day and were then cultivated at 20° C. under lighting for 8 days and a lesion area was observed. As a result, every of the lesion areas in plants treated with the present Compounds 1, 2, 4, 5, 6, 7, 10, 11, 12, 13, 14, 15, 18, 21, 22, 23, 24 and 25 showed 30% or less compared to the lesion area in an untreated plants.

Test Example 3

A plastic pot was filled with soil and thereto barley (cv; Mikamo Golden) seeds were sown and the plants were grown in a greenhouse for 7 days. Thereafter, each of the present Compounds 1, 2, 3, 4, 5, 6, 7, 8, 9, 10, 11, 12, 13, 14, 15, 16, 17, 18, 21, 22, 23, 24 and 25 was made to a formulation according to the above-mentioned Formulation examples and was then diluted with water so as to make a predetermined concentration (500 ppm). The dilutions were sprayed to foliar parts so as to adhere adequately on the leaves of the above-mentioned barley. After spraying the dilutions, the plants were air-dried and after 2 days, an aqueous suspension of the spores of barley net blotch fungi (*Pyrenophora teres*) was spraying-inoculated. After inoculation, the plants were placed at 23° C. during daytime and 20° C. during nighttime under a high humidity for 3 days and were then cultivated in the greenhouse for 7 days, and a lesion area was observed. As a result, every of the lesion areas in plants treated with the present Compounds 1, 2, 3, 4, 5, 6, 7, 8, 9, 10, 11, 12, 13, 14, 15, 16, 17, 18, 21, 22, 23, 24 and 25 showed 30% or less compared to the lesion area in an untreated plants.

Test Example 4

A plastic pot was filled with soil and thereto Kidney bean (cv; Nagauzurasaitou) seeds were sown and the plants were grown in a greenhouse for 8 days. Either of the present Compounds 1, 2, 3, 4, 6, 7, 8, 9, 10, 11, 12, 13, 14, 15, 16, 17, 18, 24, 37 and 39 was made to a formulation according to the above-mentioned Formulation examples and was then diluted with water so as to make a predetermined concentration (500 ppm). The dilutions were sprayed to foliar parts so as to adhere adequately on the leaves of the above-mentioned kidney bean. After spraying the dilutions, the plants were air-dried and a PDA medium containing hyphae of kidney bean *sclerotinia* rot fungi (*Sclerotinia sclerotiorum*) was placed on the leaves of the kidney bean. After inoculation, all kidney beans were placed under a high humidity during only night and after four days, and a lesion area was observed. As a result, every of the lesion areas in plants treated with either the present Compounds 1, 2, 3, 4, 6, 7, 8, 9, 10, 11, 12, 13, 14, 15, 16, 17, 18, 24, 37 and 39 showed 30% or less compared to the lesion area in an untreated plants.

Test Example 5

A plastic pot was filled with soil and thereto wheat (cv; Apogee) seeds were sown and the plants were grown in a greenhouse for 10 days. Each of the present Compounds 1, 2, 3, 4, 6, 7, 8, 9, 10, 11, 12, 13, 14, 15, 16, 17, 18, 22, 23, 24 and 25 was made to a formulation according to the above-mentioned Formulation examples and was then diluted with water so as to make a predetermined concentration (500 ppm). The dilutions were sprayed to foliar parts so as to adhere adequately on the leaves of the above-mentioned wheat. After spraying the dilutions, the plants were air-dried and after 4 days, an aqueous suspension of the spores of wheat leaf blotch fungi (*Septoria tritici*) was spraying-inoculated. After inoculation, the plants were placed at 18° C. under a high humidity for 3 days and then under lighting for 14 to 18 days, and a lesion area was observed. As a result, every of the lesion areas in plants treated with the present Compounds 1, 2, 3, 4, 6, 7, 8, 9, 10, 11, 12, 13, 14, 15, 16, 17, 18, 22, 23, 24 and 25 showed 30% or less compared to the lesion area in an untreated plants.

Test Example 6

A plastic pot was filled with soils and thereto cucumber (cv; Sagamihanjiro) seeds were sown and the plants were grown in a greenhouse for 12 days. Each of the present Compounds 1, 2, 3, 4, 6, 7, 8, 9, 10, 11, 12, 13, 14, 15, 16, 17, 18, 22, 23, 24, 37 and 39 was made to a formulation according to the above-mentioned Formulation examples and was then diluted with water so as to make a predetermined concentration (500 ppm). The dilutions were sprayed to foliar parts so as to adhere adequately on the leaves of the above-mentioned cucumber. After spraying the dilutions, the plants were air-dried and the spores of powdery mildew fungi (*Sphaerotheca fuliginea*) were sprinkling-inoculated. The plants were placed in a greenhouse of 24° C. during daytime and 20° C. during nighttime for 8 days, and a lesion area was observed. As a result, every of the lesion areas in plants treated with the present Compounds 1, 2, 3, 4, 6, 7, 8, 9, 10, 11, 12, 13, 14, 15, 16, 17, 18, 22, 23, 24, 37 and 39 showed 30% or less compared to the lesion area in an untreated plants.

Test Example 7

A plastic pot was filled with soils and thereto rice (cv; Nipponbare) seeds were sown and the plants were grown in a greenhouse for twenty days. Thereafter, each of the present Compounds 1, 6, 7, 10, 11, 12, 13, 14, 15, 18, 20, 21, 24, 25, 28, 33, 34, 36, 37, 42, 43, 44, 45 and 46 was made to a formulation according to the above-mentioned Formulation examples and was then diluted with water so as to make a predetermined concentration (200 ppm). The dilutions were sprayed to foliar parts so as to adhere adequately on the leaves of the above-mentioned rice. After spraying the dilutions, the plants were air-dried and were placed at 24° C. during daytime and 20° C. during nighttime under a high humidity for 6 days while the above-mentioned spraying-treated rice were contacted rice seedlings (cv; Nipponbare) infected by rice blast fungi (*Magnaporthe grisea*), and a lesion area was observed. As a result, every of the lesion areas in plants treated with the present Compounds 1, 6, 7, 10, 11, 12, 13, 14, 15, 18, 20, 21, 24, 25, 28, 33, 34, 36, 37, 42, 43, 44, 45 and 46 showed 30% or less compared to the lesion area in an untreated plants.

Test Example 8

A plastic pot was filled with soil and thereto wheat (cv; Shirogane) seeds were sown and the plants were grown in a greenhouse for 9 days. Thereafter, each of the present Compounds 2, 3, 4, 5, 6, 7, 9, 10, 12, 13, 14, 15, 17, 18, 20, 25, 28, 33, 34, 35, 36, 37, 39, 41, 42, 43, 44, 45 and 46 was made to a formulation according to the above-mentioned Formulation examples and was then diluted with water so as to make a predetermined concentration (200 ppm). The dilutions were sprayed to foliar parts so as to adhere adequately on the leaves of the above-mentioned wheat. After spraying the dilutions, the plants were air-dried and were placed at 20° C. under lighting for 5 days. The spores of wheat rust fungi (*Puccinia recondita*) were sprinkling-inoculated. After inoculation, the plants were placed under a dark and humid condition at 23° C. for 1 day and were then cultivated at 20° C. under lighting for 8 days and a lesion area was observed. As a result, every of the lesion areas in plants treated with the present Compounds 2, 3, 4, 5, 6, 7, 9, 10, 12, 13, 14, 15, 17, 18, 20, 25, 28, 33, 34, 35, 36, 37, 39, 41, 42, 43, 44, 45 and 46 showed 30% or less compared to the lesion area in an untreated plants.

Test Example 9

A plastic pot was filled with soil and thereto barley (cv; Mikamo Golden) seeds were sown and the plants were grown in a greenhouse for 7 days. Thereafter, each of the present Compounds 2, 3, 4, 5, 6, 7, 8, 9, 10, 12, 13, 14, 15, 16, 18, 21, 25, 28, 33, 34, 35, 36, 37, 39, 41, 42, 43, 44, 46 and 52 was made to a formulation according to the above-mentioned Formulation examples and was then diluted with water so as to make a predetermined concentration (200 ppm). The dilutions were sprayed to foliar parts so as to adhere adequately on the leaves of the above-mentioned barley. After spraying the dilutions, the plants were air-dried and after 2 days, an aqueous suspension of the spores of barley net blotch fungi (*Pyrenophora teres*) was spraying-inoculated. After inoculation, the plants were placed at 23° C. during daytime and 20° C. during nighttime under a high humidity for 3 days and were then cultivated in the greenhouse for 7 days, and a lesion area was observed. As a result, every of the lesion areas in plants treated with the present Compounds 2, 3, 4, 5, 6, 7, 8, 9, 10, 12, 13, 14, 15, 16, 18, 21, 25, 28, 33, 34, 35, 36, 37, 39, 41, 42, 43, 44, 46 and 52 showed 30% or less compared to the lesion area in an untreated plants.

Test Example 10

A plastic pot was filled with soil and thereto Kidney bean (cv; Nagauzurasaitou) seeds were sown and the plants were grown in a greenhouse for 8 days. Either of the present Compounds 2, 3, 4, 6, 7, 8, 9, 10, 12, 13, 14, 15, 16, 18, 21, 22, 23, 25, 28, 34, 35, 36 and 45 was made to a formulation according to the above-mentioned Formulation examples and was then diluted with water so as to make a predetermined concentration (200 ppm). The dilutions were sprayed to foliar parts so as to adhere adequately on the leaves of the above-mentioned kidney bean. After spraying the dilutions, the plants were air-dried and a PDA medium containing hyphae of kidney bean *sclerotinia* rot fungi (*Sclerotinia sclerotiorum*) was placed on the leaves of the kidney bean. After inoculation, all kidney beans were placed under a high humidity during only night and after four days, and a lesion area was observed. As a result, every of the lesion areas in plants treated with either the present Compounds 2, 3, 4, 6, 7, 8, 9, 10, 12, 13, 14, 15, 16, 18, 21, 22, 23, 25, 28, 34, 35, 36 and 45 showed 30% or less compared to the lesion area in an untreated plants.

Test Example 11

A plastic pot was filled with soil and thereto wheat (cv; Apogee) seeds were sown and the plants were grown in a greenhouse for 10 days. Each of the present Compounds 2, 3, 4, 6, 7, 8, 9, 10, 12, 13, 14, 15, 16, 18, 21, 25, 28, 34, 35, 36, 37, 39, 41, 42, 44, 45, 46 and 52 was made to a formulation according to the above-mentioned Formulation examples and was then diluted with water so as to make a predetermined concentration (200 ppm). The dilutions were sprayed to foliar parts so as to adhere adequately on the leaves of the above-mentioned wheat. After spraying the dilutions, the plants were air-dried and after 4 days, an aqueous suspension of the spores of wheat leaf blotch fungi (*Septoria tritici*) was spraying-inoculated. After inoculation, the plants were placed at 18° C. under a high humidity for 3 days and then under lighting for 14 to 18 days, and a lesion area was observed. As a result, every of the lesion areas in plants treated with the present Compounds 2, 3, 4, 6, 7, 8, 9, 10, 12, 13, 14, 15, 16, 18, 21, 25, 28, 34, 35, 36, 37, 39, 41, 42, 44, 45, 46 and 52 showed 30% or less compared to the lesion area in an untreated plants.

Test Example 12

A plastic pot was filled with soil and thereto cucumber (cv; Sagamihanjiro) seeds were sown and the plants were grown in a greenhouse for 12 days. Each of the present Compounds 2, 3, 4, 6, 7, 8, 9, 10, 12, 13, 14, 15, 16, 18, 20, 25, 28, 34, 35, 36, 39, 41, 42, 43, 44, 45 and was made to a formulation according to the above-mentioned Formulation examples and was then diluted with water so as to make a predetermined concentration (200 ppm). The dilutions were sprayed to foliar parts so as to adhere adequately on the leaves of the above-mentioned cucumber. After spraying the dilutions, the plants were air-dried and the spores of powdery mildew fungi (*Sphaerotheca fuliginea*) were sprinkling-inoculated. The plants were placed in a greenhouse of 24° C. during daytime and 20° C. during nighttime for 8 days, and a lesion area was observed. As a result, every of the lesion areas in plants treated with the present Compounds 2, 3, 4, 6, 7, 8, 9, 10, 12, 13, 14, 15, 16, 18, 20, 25, 28, 34, 35, 36, 39, 41, 42, 43, 44, 45 and 46 showed 30% or less compared to the lesion area in an untreated plants.

Test Example 13

A plastic pot was filled with soil and thereto soybean (cv: Kurosengoku) seeds were sown and the plants were grown in a greenhouse for 13 days. Each of the present Compounds 2, 5, 6, 7, 11, 12, 13, 14, 15, 18, 21, 22, 24, 25, 28, 34, 36, 37, 39, 43, 44, 45 and 46 was made to a formulation according to the above-mentioned Formulation examples and was then diluted with water so as to make a predetermined concentration (200 ppm). The dilutions were sprayed to foliar parts so as to adhere adequately on the leaves of the above-mentioned soybean. After spraying the dilutions, the plants were air-dried and after 2 days, an aqueous suspension of the spores of soybean rust fungi (*phakopsora pachyrhizi*) was spraying-inoculated. After inoculation, the plants were placed in a greenhouse of 23° C. during daytime and 20° C. during nighttime under a high humidity for 3 days and were then cultivated in the greenhouse for 14 days, and a lesion area was observed. As a result, every of the lesion areas in plants treated with the present Compounds 2, 5, 6, 7, 11, 12, 13, 14, 15, 18, 21, 22, 24, 25, 28, 34, 36, 37, 39, 43, 44, 45 and 46 showed 30% or less compared to the lesion area in an untreated plants.

Test Example 14

A plastic pot was filled with soil and thereto barley (cv; Mikamo Golden) seeds were sown and the plants were grown in a greenhouse for 7 days. Each of the present Compounds 1, 2, 3, 4, 6, 7, 9, 10, 11, 12, 13, 14, 15, 16, 17, 18, 20, 21, 22, 23, 24, 25, 28, 34, 35, 36, 39, 41, 42, 44, 43, 44, 45, 46 and 52 was made to a formulation according to the above-mentioned Formulation examples and was then diluted with water so as to make a predetermined concentration (200 ppm). The dilutions were sprayed to foliar parts so as to adhere adequately on the leaves of the above-mentioned barley. After spraying the dilutions, the plants were air-dried and after 2 days, an aqueous suspension of the spores of barley leaf blotch fungi (*Rhynchosporium secalis*) was spraying-inoculated. After inoculation, the plants were placed in a greenhouse of 23° C. during daytime and 20° C. during nighttime under a high humidity for 3 days and were then cultivated in the greenhouse for 7 days, and a lesion area was observed. As a result, every of the lesion areas in plants treated with the present Compounds 1, 2, 3, 4, 6, 7, 9, 10, 11, 12, 13, 14, 15, 16, 17, 18, 20, 21, 22, 23, 24, 25, 28, 34, 35, 36, 39, 41, 42, 44, 43, 44, 45, 46 and 52 showed 30% or less compared to the lesion area in an untreated plants.

Test Example 15

A plastic pot was filled with soil and thereto tomato (cv; Patio) seeds were sown and the plants were grown in a greenhouse for 20 days. The present compounds 6 and 7 were made to a formulation according to the above-mentioned Formulation examples and was then diluted with water so as to make a predetermined concentration (500 ppm). The dilutions were sprayed to foliar parts so as to adhere adequately on the leaves of the above-mentioned tomato. After the plants were air-dried to such an extent that the dilutions were dried, an aqueous suspension of the spores of tomato late blight fungi (*Phytophthora infestans*) was spraying-inoculated. After inoculation, the plants were at first placed at 23° C. under a high humidity for 1 day and were then cultivated in the greenhouse for 4 days, and a lesion area was observed. As a result, every of the lesion areas in plants treated with the present compounds 6 and 7 showed 30% or less compared to the lesion area in untreated plants.

Test Example 16

A plastic pot was filled with soils and thereto cucumber (cv; Sagamihanjiro) seeds were sown and the plants were grown in a greenhouse for 19 days. Each of the present Compounds 35, 37, 39, 42, 43 and 44 was made to a formulation according to the above-mentioned Formulation examples and was then diluted with water so as to make a predetermined concentration (200 ppm). The dilutions were sprayed to foliar parts so as to adhere adequately on the leaves of the above-mentioned cucumber. After spraying the dilutions, the plants were air-dried and after 1 day, an aqueous suspension of the spores of cucumber target spot fungi (*Corynespora cassiicola*) was spaying-inoculated. After an inoculation, the plants were placed at 24° C. during daytime and 20° C. during nighttime under a high humidity for 7 days, and a lesion area was observed. As a result, every of the lesion areas in plants treated with the present Compounds 35, 37, 39, 42, 43 and 44 showed 30% or less compared to the lesion area in an untreated plants.

Test Example 17

A plastic pot was filled with soil and thereto cucumber (cv; Sagamihanjiro) seeds were sown and the plants were grown in a greenhouse for 19 days. Each of the present Compounds 13, 14, 18, 22, 23, 24, 25, 28, 33, 34, 35, 36, 39, 41, 42, 43, 44, 45 and 46 was made to a formulation according to the above-mentioned Formulation examples and was then diluted with water so as to make a predetermined concentration (200 ppm). The dilutions were sprayed to foliar parts so as to adhere adequately on the leaves of the above-mentioned cucumber. After spraying the dilutions, the plants were air-dried and after 1 day, an aqueous suspension of the spores of cucumber anthracnose fungi (*Colletotrichum lagenarium*) was spraying-inoculated. After an inoculation, the plants were placed firstly at 23° C. under a high humidity for 1 day and were then cultivated in a greenhouse of 24° C. during daytime and 20° C. during nighttime for 6 days, and a lesion area was observed. As a result, every of the lesion areas in plants treated with the present Compounds 13, 14, 18, 22, 23, 24, 25, 28, 33, 34, 35, 36, 39, 41, 42, 43, 44, 45 and 46 showed 30% or less compared to the lesion area in an untreated plants.

Comparative Test Example

A plastic pot was filled with soils and thereto was seeded wheat (cv; Shirogane) and the plants were grown in a greenhouse for 9 days. A control compound, 1-{2-[2-chloro-4-(3,5-dimethyl-pyrazol-1-yl)-phenoxymethyl]-phenyl}-4-methyl-1,4-dihydrotetrazole-5-one was made to a formulation according to the above-mentioned Formulation example 2 and was then diluted with water so as to make a predetermined concentration (500 ppm). The dilutions were sprayed to foliar parts so as to adhere adequately on the leaves of the above-mentioned wheat. After spraying the dilutions, the plants were air-dried and were then cultivated at 20° C. under lighting for 5 days. The spores of wheat rust fungi (*Puccinia recondita*) were sprinkling-inoculated. After inoculation, the plants were placed under a dark and humid condition at 23° C. for 1 day and were then cultivated at 20° C. under lighting for 8 days and a lesion area was observed. As a result, the lesion area in plants treated with the control compound, 1-{2-[2-chloro-4-(3,5-dimethyl-pyrazol-1-yl)-phenoxymethyl]-phenyl}-4-methyl-1,4-dihydrotetrazole-5-one showed 70% or more compared to the lesion area in an untreated plants.

The invention claimed is:
1. A tetrazolinone compound of formula (1):

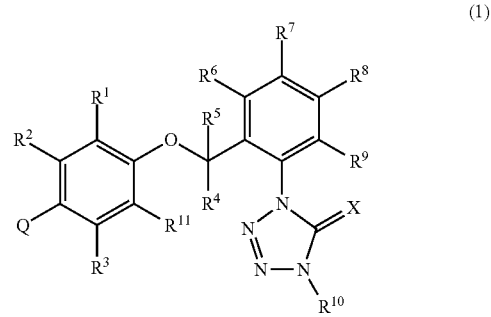

wherein
Q represents a group selected from the following group:
Q1:

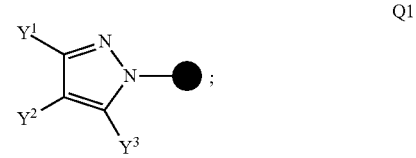

$R^1$, $R^2$, $R^3$ and $R^{11}$ represent independently of each other a hydrogen atom, a halogen atom, a cyano group, a nitro group, an amino group, a hydroxy group, a thiol group, a C2-C6 alkenyl group, a C2-C6 haloalkenyl group, a C2-C6 alkynyl group, a C2-C6 haloalkynyl group, a C1-C6 alkoxy group, a C1-C6 haloalkoxy group, a C1-C8 alkylamino group, a C1-C8 haloalkylamino group, a C1-C6 alkylthio group, a C1-C6 haloalkylthio group, a C1-C6 alkylsulfinyl group, a C1-C6 haloalkylsulfinyl group, a C1-C6 alkylsulfonyl group, a C1-C6 haloalkylsulfonyl group, a pentafluorosulfanyl group, a C3-C9 trialkylsilyl group, a C2-C6 alkylcarbonyl group, a C2-C6 alkoxycarbonyl group, a C2-C8 alkylaminocarbonyl group, a C1-C6 alkyl group optionally having one or more groups selected from Group $P^1$ or a C3-C6 cycloalkyl group optionally having one or more groups selected from Group $P^1$;
$R^4$ and $R^5$ represent independently of each other a hydrogen atom, a halogen atom or a C1-C3 alkyl group;

$R^6$ represents a C3-C6 cycloalkyl group, a C2-C4 alkynyl group, a C2-C4 haloalkynyl group, a C1-C4 haloalkoxy group, a C1-C4 alkythio group, a C1-C4 alkylsulfinyl group, a C1-C4 alkylsulfonyl group, a C1-C4 haloalkylthio group, a C1-C4 haloalkylsulfinyl group, a C1-C4 haloalkylsulfonyl group, a C1-C6 alkylamino group, a C1-C6 haloalkylamino group or a C3-C6 halocycloalkyl group;

$R^7$, $R^8$ and $R^9$ represent independently of each other a hydrogen atom, a halogen atom, a C1-C3 alkyl group, a C1-C3 haloalkyl group, a C2-C3 alkenyl group, a C2-C3 haloalkenyl group or a C1-C3 alkoxy group;

$R^{10}$ represents a C1-C3 alkyl group, a C1-C3 haloalkyl group, a C2-C3 alkenyl group, a C2-C3 haloalkenyl group, a C2-C3 alkynyl group, a C2-C3 haloalkynyl group, a C3-C5 cycloalkyl group or a C3-C5 halocycloalkyl group;

X represents an oxygen atom or a sulfur atom;

$Y^1$, $Y^2$, and $Y^3$ represent independently of each other a hydrogen atom, a halogen atom, a cyano group, a nitro group, an amino group, a hydroxy group, a thiol group, an aldehyde group, a C2-C6 alkenyl group, a C2-C6 haloalkenyl group, a C2-C6 alkynyl group, a C2-C6 haloalkynyl group, a C1-C6 alkoxy group, a C1-C6 haloalkoxy group, a C3-C6 alkenyloxy group, a C3-C6 haloalkenyloxy group, a C3-C6 alkynyloxy group, a C3-C6 haloalkynyloxy group, a C3-C6 alkenylthio group, a C3-C6 alkynylthio group, a C3-C6 haloalkenylthio group, a C3-C6 haloalkynylthio group, a C1-C8 alkylamino group, a C1-C8 haloalkylamino group, a C1-C6 alkylthio group, a C1-C6 haloalkylthio group, a C1-C6 alkylsulfinyl group, a C1-C6 haloalkylsulfinyl group, a C1-C6 alkylsulfonyl group, a C1-C6 haloakylsulfonyl group, a C2-C8 alkylaminosulfonyl group, a pentaflurosulfanyl group, a C3-C9 trialkylsilyl group, a C2-C6 alkylcarbonyl group, a C2-C6 alkoxycarbonyl group, an aminocarbonyl group, a C2-C8 alkylaminocarbonyl group, a C1-C6 alkyl group optionally having one or more groups selected from Group $P^1$ or a C3-C6 cycloalkyl group optionally having one or more groups selected from Group $P^1$; or $Y^1$ and $Y^2$ may combine each other together with the carbon atom to which they are attached to form a five-, six- or seven-membered saturated ring, said saturated ring may optionally contain one or more oxygen atoms or sulfur atoms as the ring-constituent atom, and the saturated ring may optionally have one or more substituents selected from Group $P^1$; or $Y^2$ and $Y^3$ may combine each other together with the carbon atom to which they are attached to form a five-, six- or seven-membered saturated ring, said saturated ring may optionally contain one or more oxygen atoms or sulfur atoms as the ring-constituent atom, and the saturated ring may optionally have one or more substituents selected from Group $P^1$; and Group $P^1$: a group consisting of a halogen atom, a cyano group, a C3-C6 cycloalkyl group, a C3-C6 halocycloalkyl group, a C1-C4 alkoxy group, a C1-C4 haloalkoxy group, a C1-C4 alkylthio group or a C1-C4 haloalkylthio group.

2. The tetrazolinone compound according to claim 1, wherein $R^1$ represents a C1-C3 alkyl group, a halogen atom, a C1-C3 haloalkyl group, a C2-C3 alkynyl group, a C2-C3 haloalkynyl group, a C3-C5 cycloalkyl group, a C3-C5 halocycloalkyl group, a C1-C3 alkoxy group or a C1-C3 haloalkoxy group;

$R^2$, $R^4$, $R^5$, $R^7$, $R^8$, $R^9$ and $R^{11}$ represent a hydrogen atom;

$R^3$ represents a hydrogen atom, a halogen atom, a C1-C3 alkyl group or a C1-C3 haloalkyl group;

$R^6$ represents a C3-C6 cycloalkyl group, a C2-C4 alkynyl group, a C2-C4 haloalkynyl group, a C1-C4 haloalkoxy group, a C1-C4 alkythio group, a C1-C4 haloalkylthio group or a C3-C6 halocycloalkyl group;

$R^{10}$ represents a methyl group; and

X represents an oxygen atom.

3. The tetrazolinone compound according to claim 1, wherein $Y^1$ and $Y^2$ may combine each other together with the carbon atom to which they are attached to form a five- or six-membered saturated ring;

$Y^2$ and $Y^3$ may combine each other together with the carbon atom to which they are attached to form a five- or six-membered saturated ring;

when each of $Y^1$, $Y^2$ and $Y^3$ does not form the five- or six-membered saturated ring, $Y^1$ represents a hydrogen atom, a C1-C6 alkyl group, a C1-C6 haloalkyl group, a C3-C6 cycloalkyl group or a C3-C6 halocycloalkyl group;

$Y^2$ represents a hydrogen atom, a halogen atom, a C1-C6 alkyl group, a C1-C6 haloalkyl group, a C2-C6 alkynyl group, a C1-C6 alkoxy group, a C1-C6 haloalkoxy group, a C3-C6 cycloalkyl group or a C3-C6 halocycloalkyl group;

$Y^3$ represents a hydrogen atom, a C1-C4 alkyl group or a C1-C4 haloalkyl group.

4. The tetrazolinone compound according to claim 1, wherein $Y^1$ and $Y^2$ connect to each other to represent —CH$_2$—CH$_2$—CH$_2$—CH$_2$—, which combines together with the carbon atoms to which $Y^1$ and $Y^2$ are attached to form a six-membered ring;

$Y^2$ and $Y^3$ connect to each other to represent —CH$_2$—CH$_2$—CH$_2$—CH$_2$—, which combines together with the carbon atoms to which $Y^2$ and $Y^3$ are attached to form a six-membered ring;

when each of $Y^1$, $Y^2$ and $Y^3$ does not form the six-membered saturated ring, $Y^1$ represents a hydrogen atom, a C1-C3 alkyl group, a C1-C3 haloalkyl group or a cyclopropyl group;

$Y^2$ represents a hydrogen atom, a C1-C3 alkyl group, a C1-C3 haloalkyl group, a cyano group or a C1-C3 alkoxy group; and $Y^3$ represents a hydrogen atom or a methyl group.

5. The tetrazolinone compound according to claim 1, wherein $R^1$ represents a methyl group, an ethyl group, a chlorine atom, a bromine atom or a trifluoromethyl group;

$R^3$ represents a hydrogen atom or a methyl group; and $R^6$ represents a cyclopropyl group, an ethynyl group, a difluoromethoxy group or a methylthio group.

6. An agent for controlling pests comprising the tetrazolinone compound according to claim 1.

7. A method for controlling pests comprising applying an effective amount of the tetrazolinone compound according to claim 1 to plant or soil.

* * * * *